US012630842B2

(12) United States Patent
Nonnenmacher et al.

(10) Patent No.: US 12,630,842 B2
(45) **Date of Patent: *May 19, 2026**

(54) REDIRECTION OF TROPISM OF AAV CAPSIDS

(71) Applicant: VOYAGER THERAPEUTICS, INC., Lexington, MA (US)

(72) Inventors: Mathieu E. Nonnenmacher, Boston, MA (US); Jinzhao Hou, Lexington, MA (US); Wei Wang, Lexington, MA (US); Matthew Child, Ashland, MA (US); Shaoyong Li, Hopkinton, MA (US)

(73) Assignee: VOYAGER THERAPEUTICS, INC., Lexington, MA (US)

( * ) Notice: Subject to any disclaimer, the term of this patent is extended or adjusted under 35 U.S.C. 154(b) by 688 days.

This patent is subject to a terminal disclaimer.

(21) Appl. No.: 17/924,800

(22) PCT Filed: Mar. 31, 2021

(86) PCT No.: PCT/US2021/025061
§ 371 (c)(1),
(2) Date: Nov. 11, 2022

(87) PCT Pub. No.: WO2021/230987
PCT Pub. Date: Nov. 18, 2021

(65) Prior Publication Data
US 2023/0203102 A1     Jun. 29, 2023

Related U.S. Application Data

(60) Provisional application No. 63/122,300, filed on Dec. 7, 2020, provisional application No. 63/023,927, filed on May 13, 2020.

(51) Int. Cl.
*C12N 15/86* (2006.01)
*A61K 35/761* (2015.01)
(Continued)

(52) U.S. Cl.
CPC ............ *C12N 15/86* (2013.01); *A61K 35/761* (2013.01); *C07K 14/005* (2013.01); *C12N 7/00* (2013.01); *C12N 2750/14122* (2013.01)

(58) Field of Classification Search
CPC .... A61K 35/761; C07K 14/005; C12N 15/86; C12N 2750/14122; C12N 2750/14143;
(Continued)

(56) References Cited

U.S. PATENT DOCUMENTS 9,409,953 B2     8/2016 Asokan et al.
9,585,971 B2     3/2017 Deverman et al.
(Continued)

FOREIGN PATENT DOCUMENTS

CN     106032540 A     10/2016
CN     106884014 A     6/2017
(Continued)

OTHER PUBLICATIONS

Abeliovich, A. et al. "Gene Therapy for Parkinson's Disease Associated with GBA1 Mutations." Journal of Parkinson's Disease vol. 11,s2 (2021): S183-S188.
(Continued)

*Primary Examiner* — Thomas J. Visone
*Assistant Examiner* — Marlene V Buckmaster
(74) *Attorney, Agent, or Firm* — K&L Gates LLP

(57) ABSTRACT

The disclosure relates to compositions, methods, and processes for the preparation, use, and/or formulation of adeno-
(Continued)

Orthogonal Evolution of Loop8-7mer Library associated virus capsid proteins, wherein the capsid proteins comprise targeting peptide inserts tor enhanced tropism to a target tissue.

25 Claims, 45 Drawing Sheets

Specification includes a Sequence Listing.

(51) Int. Cl.
    *C07K 14/005*        (2006.01)
    *C12N 7/00*          (2006.01)

(58) Field of Classification Search
    CPC .... C12N 2750/14145; C12N 2830/008; C12N
                             7/00; C40B 40/08
    See application file for complete search history.

(56) References Cited

U.S. PATENT DOCUMENTS

| | | | |
|---|---|---|---|
| 9,644,205 | B2 | 5/2017 | Brunicardi et al. |
| 9,938,541 | B2 | 4/2018 | Nishie et al. |
| 10,081,659 | B2 | 9/2018 | Chiorini et al. |
| 10,265,417 | B2 | 4/2019 | Wilson et al. |
| 10,485,993 | B2 | 11/2019 | Goer et al. |
| 10,695,441 | B2 | 6/2020 | Wilson et al. |
| 10,973,928 | B2 | 4/2021 | Wilson et al. |
| 11,149,256 | B2 | 10/2021 | Gradinaru et al. |
| 11,459,558 | B2 | 10/2022 | Nakai et al. |
| 11,572,637 | B2 | 2/2023 | Nakai et al. |
| 11,821,009 | B2 | 11/2023 | Crystal et al. |
| 11,859,200 | B2 | 1/2024 | Nonnenmacher et al. |
| 11,981,967 | B2 | 5/2024 | McGovern et al. |
| 12,084,653 | B2 | 9/2024 | Nakai et al. |
| 12,084,654 | B2 | 9/2024 | Nakai et al. |
| 12,296,025 | B2 | 5/2025 | Nonnenmacher et al. |
| 12,419,969 | B2 | 9/2025 | Nonnenmacher et al. |
| 12,467,046 | B2 | 11/2025 | Nonnenmacher et al. |
| 12,577,588 | B2 | 3/2026 | Nonnenmacher et al. |
| 2004/0132042 | A1 | 7/2004 | Frankard et al. |
| 2005/0148076 | A1 | 7/2005 | Allen |
| 2010/0186103 | A1 | 7/2010 | Gao et al. |
| 2013/0035472 | A1 | 2/2013 | Horlick et al. |
| 2013/0296409 | A1 | 11/2013 | Miller et al. |
| 2016/0333375 | A1 | 11/2016 | Chen |
| 2017/0166926 | A1 | 6/2017 | Deverman et al. |
| 2017/0204144 | A1 | 7/2017 | Deverman et al. |
| 2018/0230186 | A1 | 8/2018 | Deverman et al. |
| 2018/0265571 | A1 | 9/2018 | Esteves et al. |
| 2020/0165576 | A1 | 5/2020 | Gradinaru et al. |
| 2020/0237799 | A1 | 7/2020 | Sah et al. |
| 2020/0239912 | A1 | 7/2020 | Sah et al. |
| 2020/0316221 | A1 | 10/2020 | Gao et al. |
| 2021/0163985 | A1 | 6/2021 | Sah et al. |
| 2021/0207167 | A1 | 7/2021 | Hou et al. |
| 2021/0214749 | A1 | 7/2021 | Hou et al. |
| 2021/0230632 | A1 | 7/2021 | Sah et al. |
| 2021/0269825 | A1 | 9/2021 | Chamberlain |
| 2021/0277418 | A1 | 9/2021 | Sah et al. |
| 2021/0371470 | A1 | 12/2021 | Murlidharan et al. |
| 2021/0380969 | A1 | 12/2021 | Nonnenmacher et al. |
| 2021/0393713 | A1 | 12/2021 | Hordeaux et al. |
| 2021/0395776 | A1 | 12/2021 | Patzke et al. |
| 2022/0042044 | A1 | 2/2022 | Nonnenmacher et al. |
| 2022/0064675 | A1 | 3/2022 | McCoy et al. |
| 2022/0186256 | A1 | 6/2022 | Danos et al. |
| 2023/0054144 | A1 | 2/2023 | Fyffe-Maricich et al. |
| 2023/0119163 | A1 | 4/2023 | Nakai et al. |
| 2023/0131352 | A1 | 4/2023 | Nonnenmacher et al. |
| 2023/0193315 | A1 | 6/2023 | Nakai et al. |
| 2023/0265453 | A1 | 8/2023 | Xue et al. |
| 2024/0141377 | A1 | 5/2024 | Nguyen et al. |
| 2024/0200097 | A1 | 6/2024 | Nonnenmacher et al. |
| 2024/0374756 | A1 | 11/2024 | Nonnenmacher et al. |
| 2024/0391988 | A1 | 11/2024 | Liu et al. |
| 2025/0001012 | A1 | 1/2025 | Nonnenmacher et al. |
| 2025/0011372 | A1 | 1/2025 | Nonnenmacher et al. |
| 2025/0034559 | A1 | 1/2025 | Nonnenmacher et al. |
| 2025/0049955 | A1 | 2/2025 | Nonnenmacher et al. |
| 2025/0161485 | A1 | 5/2025 | Nonnenmacher et al. |
| 2025/0215453 | A1 | 7/2025 | Nonnenmacher et al. |
| 2025/0228967 | A1 | 7/2025 | Nonnenmacher et al. |
| 2025/0295809 | A1 | 9/2025 | Laks et al. |

FOREIGN PATENT DOCUMENTS

| | | |
|---|---|---|
| CN | 108330147 A | 7/2018 |
| WO | 2004096993 A2 | 11/2004 |
| WO | 2005033321 A2 | 4/2005 |
| WO | 2010138263 A2 | 12/2010 |
| WO | 2011133890 A1 | 10/2011 |
| WO | 2012109570 A1 | 8/2012 |
| WO | 2012145601 A2 | 10/2012 |
| WO | 2015038958 A1 | 3/2015 |
| WO | 2015121501 A1 | 8/2015 |
| WO | 2015164757 A1 | 10/2015 |
| WO | 2016065001 A1 | 4/2016 |
| WO | 2016073693 A2 | 5/2016 |
| WO | 2016081811 A1 | 5/2016 |
| WO | 2016126857 A1 | 8/2016 |
| WO | 2016164642 A1 | 10/2016 |
| WO | 2017058892 A2 | 4/2017 |
| WO | 2017100671 A1 | 6/2017 |
| WO | 2017143100 A1 | 8/2017 |
| WO | 2017189963 A1 | 11/2017 |
| WO | 2018022905 A2 | 2/2018 |
| WO | 2018035213 A1 | 2/2018 |
| WO | 2018071831 A1 | 4/2018 |
| WO | 2018119330 A2 | 6/2018 |
| WO | 2018204797 A1 | 11/2018 |
| WO | 2018226785 A1 | 12/2018 |
| WO | 2019006043 A1 | 1/2019 |
| WO | 2019006418 A2 | 1/2019 |
| WO | 2019028306 A2 | 2/2019 |
| WO | 2019060454 A2 | 3/2019 |
| WO | 2019068854 A1 | 4/2019 |
| WO | 2019169132 A1 | 9/2019 |
| WO | 2019213668 A1 | 11/2019 |
| WO | 2019216932 A1 | 11/2019 |
| WO | 2019222329 A1 | 11/2019 |
| WO | 2019222441 A1 | 11/2019 |
| WO | 2019222444 A2 | 11/2019 |
| WO | 2020014471 A1 | 1/2020 |
| WO | 2020028751 A2 | 2/2020 |
| WO | 2020068990 A1 | 4/2020 |
| WO | 2020069461 A1 | 4/2020 |
| WO | 2020072683 A1 | 4/2020 |
| WO | 2020077165 A1 | 4/2020 |
| WO | 2020154324 A1 | 7/2020 |
| WO | 2020160337 A1 | 8/2020 |
| WO | 2020160508 A1 | 8/2020 |
| WO | 2020191300 A1 | 9/2020 |
| WO | 2020193799 A1 | 10/2020 |
| WO | 2020205889 A1 | 10/2020 |
| WO | 2020206189 A1 | 10/2020 |
| WO | 2020210655 A1 | 10/2020 |
| WO | 2020219933 A1 | 10/2020 |
| WO | 2020219988 A2 | 10/2020 |
| WO | 2020223276 A1 | 11/2020 |
| WO | 2020223280 A1 | 11/2020 |
| WO | 2021025995 A1 | 2/2021 |
| WO | 2021073568 A1 | 4/2021 |
| WO | 2021113512 A1 | 6/2021 |
| WO | 2021202651 A1 | 10/2021 |
| WO | 2021211753 A1 | 10/2021 |
| WO | 2021216456 A2 | 10/2021 |
| WO | 2021222831 A2 | 11/2021 |
| WO | 2021226008 A1 | 11/2021 |
| WO | 2021230987 A1 | 11/2021 |
| WO | 2021242909 A1 | 12/2021 |

(56) References Cited

FOREIGN PATENT DOCUMENTS

| WO | 2022026409 A1 | 2/2022 |
|---|---|---|
| WO | 2022040527 A2 | 2/2022 |
| WO | 2022076750 A2 | 4/2022 |
| WO | 2022098699 A1 | 5/2022 |
| WO | 2022187548 A1 | 9/2022 |
| WO | 2022/221400 A2 | 10/2022 |
| WO | 2022/221404 A2 | 10/2022 |
| WO | 2022/221420 A2 | 10/2022 |
| WO | 2022/221421 A2 | 10/2022 |
| WO | 2022226263 A1 | 10/2022 |
| WO | 2022/235702 A1 | 11/2022 |
| WO | 2023/004416 A1 | 1/2023 |
| WO | 2023278305 A1 | 1/2023 |
| WO | 2023/044306 A1 | 3/2023 |
| WO | 2023/049710 A1 | 3/2023 |
| WO | 2023044483 A2 | 3/2023 |
| WO | 2023060269 A1 | 4/2023 |
| WO | 2023/091934 A1 | 5/2023 |
| WO | 2023073071 A1 | 5/2023 |
| WO | 2023081648 A1 | 5/2023 |
| WO | 2023091948 A1 | 5/2023 |
| WO | 2023091949 A2 | 5/2023 |
| WO | 2023092002 A2 | 5/2023 |
| WO | 2023092004 A1 | 5/2023 |
| WO | 2023154693 A1 | 8/2023 |
| WO | 2023/168333 A1 | 9/2023 |
| WO | 2023/183582 A2 | 9/2023 |
| WO | 2023/183583 A2 | 9/2023 |
| WO | 2023201207 A1 | 10/2023 |
| WO | 2023/215546 A2 | 11/2023 |
| WO | 2023/225508 A2 | 11/2023 |
| WO | 2023220695 A2 | 11/2023 |
| WO | 2023/244919 A1 | 12/2023 |
| WO | 2023/244920 A2 | 12/2023 |
| WO | 2023235791 A1 | 12/2023 |
| WO | 2023240236 A1 | 12/2023 |
| WO | 2023250388 A1 | 12/2023 |
| WO | 2024006741 A1 | 1/2024 |
| WO | 2024011112 A1 | 1/2024 |
| WO | 2024030976 A2 | 2/2024 |
| WO | 2024059739 A1 | 3/2024 |
| WO | 2024/086628 A2 | 4/2024 |
| WO | 2024086747 A1 | 4/2024 |
| WO | 2024/092164 A1 | 5/2024 |
| WO | 2024100633 A1 | 5/2024 |
| WO | 2024191778 A1 | 9/2024 |
| WO | 2024226761 A2 | 10/2024 |
| WO | 2024226790 A1 | 10/2024 |
| WO | 2024228943 A1 | 11/2024 |
| WO | 2024229125 A2 | 11/2024 |
| WO | 2024229161 A1 | 11/2024 |
| WO | 2024229163 A1 | 11/2024 |
| WO | 2024229164 A2 | 11/2024 |
| WO | 2024229167 A1 | 11/2024 |
| WO | 2024229173 A2 | 11/2024 |
| WO | 2024229389 A1 | 11/2024 |
| WO | 2024229425 A1 | 11/2024 |
| WO | 2024238579 A2 | 11/2024 |
| WO | 2024238684 A1 | 11/2024 |
| WO | 2025038430 A1 | 2/2025 |
| WO | 2025038795 A1 | 2/2025 |
| WO | 2025038796 A1 | 2/2025 |
| WO | 2025038800 A1 | 2/2025 |
| WO | 2025038802 A1 | 2/2025 |
| WO | 2025038805 A1 | 2/2025 |
| WO | 2025122530 A1 | 6/2025 |
| WO | 2025122531 A1 | 6/2025 |
| WO | 2025122532 A1 | 6/2025 |
| WO | 2025122536 A1 | 6/2025 |
| WO | 2025122543 A1 | 6/2025 |
| WO | 2025122548 A1 | 6/2025 |
| WO | 2025122634 A1 | 6/2025 |
| WO | 2025122644 A1 | 6/2025 |
| WO | 2025147436 A1 | 7/2025 |
| WO | 2025235734 A2 | 11/2025 |

OTHER PUBLICATIONS

Adachi et al. "A new recombinant adeno-associated virus (AAV)-based random peptide display library system: infection-defective AAV1.9-3 as a novel detargeted platform for vector evolution," Gene Therapy and Regulation (2010) vol. 5, pp. 31-55.

Adachi et al., "Drawing a high-resolution functional map of adeno-associated virus capsid by massively parallel sequencing," Nature Communications (2014) vol. 5, article 3075, 14 pages.

Albright et al. "Modulation of sialic acid dependence influences the central nervous system transduction profile of adeno-associated viruses," Journal of Virology, 2019, vol. 93, Issue 11, pp. 1-15.

Anonymous: "capsid associated protein VP80 [Spodoptera littoralis nucleopolyhedrovirus]—Protein—NCBI", (Feb. 15, 2013), pp. 1-1, Retrieved from the Internet: URL:https://www.ncbi.nlm.nih.gov/protein/AGE89944 [retrieved on Mar. 6, 2023].

Anonymous: "toxin-antitoxin system YwqK family antitoxin [*Campylobacter* sp. CCUG 57310]—Protein—NCBI", (Jun. 7, 2020), Retrieved from the Internet: URL:https://www.ncbi.nlm.nih.gov/protein/WP_173030534 [retrieved on Mar. 7, 2023].

Bryant et al. "Deep diversification of an AAV capsid protein by machine learning," Nature Biotechnology, 2021, vol. 39, pp. 691-696.

Challis et al. "Systemic AAV vectors for widespread and targeted gene delivery in rodents," Nature Protocols (2019) vol. 14, pp. 379-414.

Chen et al. "Efficient Gene Delivery and Expression in Pancreas and Pancreatic Tumors by Capsid-Optimized AAV8 Vectors," Human Gene Therapy Methods (2017) vol. 28, No. 1, pp. 49-59.

Chen et al. "Targeting the Rodent Peripheral Nervous System Efficiently and with Greater Specificity through Intravenous Delivery of AAV Capsids Evolved by Multiplexed-CREATE," Molecular Therapy (2020) vol. 28, No. 4S1, pp. 252-253, Abstract 571.

Choi et al., "AAV Hybrid Serotypes: Improved Vectors for Gene Delivery," Current Gene Therapy (2005) vol. 5, No. 3, pp. 209-210.

Davidsson et al. "A systematic capsid evolution approach performed in vivo for the design of AAV vectors with tailored properties and tropism," PNAS, 2019, vol. 116, No. 52, pp. 27053-27062.

Deverman et al. "Cre-dependent selection yields AAV variants for widespread gene transfer to the adult brain," Nat Biotechnol. (2016) vol. 34, No. 2, pp. 204-209.

Dimattia et al., "Structural Insight into the Unique Properties of Adeno-Associated Virus Serotype 9," J Virol (2012) vol. 86, No. 12, pp. 6947-6958.

Fischell, J.M. and Fishman, P.S. "A Multifaceted Approach to Optimizing AAV Delivery to the Brain for the Treatment of Neurodegenerative Diseases." Frontiers in Neuroscience vol. 15, article 747726 (2021).

Flytzanis et al. "Broad gene expression throughout the mouse and marmoset brain after intravenous delivery of engineered AAV capsids," bioRxiv Preprint Server (2020) Doi: https://doi.org/10.1101/2020.06.16.152975, 21 pages.

Gao, G. et al. "Clades of Adeno-associated viruses are widely disseminated in human tissues," Journal of Virology vol. 78, 12 (2004): 6381-8.

Gessler et al., "Intravenous infusion of AAV for widespread gene delivery to the nervous system," Methods Mol. Biol., 2019, vol. 1950, pp. 143-163.

Goertsen et al. "AAV capsid variants with brain-wide transgene expression and decreased liver targeting after intravenous delivery in mouse and marmoset," Nature Neuroscience, 2022, vol. 25, pp. 106-115.

Goertsen et al. "Transduction Profiles of Engineered Adeno-Associated Viral Capsids in Mouse and Marmoset," Molecular Therapy (2020) vol. 28, No. 4S1, pp. 269-270, Abstract 609.

Hanlon et al. "Selection of an efficient AAV vector for robust CNS transgene expression," Molecular Therapy: Methods & Clinical Development, 2019, vol. 15, pp. 320-332.

Huang et al. "Cell Type-Specific TRAnscriptionDependent Directed Evolution (TRADE) Identifies Novel AAV Capsids Capable of

(56) References Cited

OTHER PUBLICATIONS

Enhanced Neuronal Transduction in Mice and Non-Human Primates," Molecular Therapy (2019) vol. 27, No. 4S1, pp. 24-25, Abstract 44.

Huang et al. "Delivering genes across the blood-brain barrier: LY6A, a novel cellular receptor for AAV-PHP.B capsids," PLOS One (2019) vol. 14, No. 11, e0225206, pp. 1-17.

International Search Report and Written Opinion for International Application No. PCT/US2021/025061 dated Sep. 20, 2021.

International Search Report and Written Opinion for International Patent Application No. PCT/US2021/025072 dated Jul. 26, 2021.

International Search Report and Written Opinion from International Patent Application No. PCT/US2019/054345 dated Jan. 24, 2020.

International Search Report and Written Opinion in International Patent Application No. PCT/US2022/079060 dated Mar. 6, 2023.

International Search Report and Written Opinion in International Patent Application No. PCT/US2022/079963 dated May 9, 2023.

International Search Report and Written Opinion in International Patent Application No. PCT/US2022/080035 dated Apr. 3, 2023.

International Search Report and Written Opinion in International Patent Application No. PCT/US2022/080040 dated Mar. 1, 2023.

International Search Report and Written Opinion of International Patent Application No. PCT/US2022/079964 dated Jun. 9, 2023.

Invitation to Pay Additional Fees and Partial Search Report from International Application No. PCT/US2021/025061 dated Jul. 27, 2021.

Ising, C. et al. "AAV-mediated expression of anti-tau scFvs decreases tau accumulation in a mouse model of auopathy." The Journal of Experimental Medicine vol. 214, 5 (2017): 1227-1238.

Kienle et al. "Secrets to finding the ideal mate: New insights into parameters that govern successful Adeno-associated virus (AAV) vector evolution," Dissertation, University Heidelberg (2014) pp. 1-194.

Kotterman et al. "4D-C102, a novel muscle-tropic AAV variant demonstrates superior gene delivery in cardiac and skeletal muscle tissues versus wild-type AAV in human cells and non-human primates.".

Kotterman et al. "Engineering adeno-associated viruses for clinical gene therapy," Nature Reviews Genetics (2014) vol. 15, pp. 445-451.

Kotterman et al., "Directed evolution of AAV targeting lung epithelia using aerosol delivery identifies 4D-A101, a variant demonstrating robust gene delivery in non-human primates" Abstract 1336, 31 pages.

Kumar et al. "Evolution and Investigation of Engineered AAV Capsids Exhibiting Enhanced Transduction of the Central Nervous System with or without Murine Strain Specificity," Molecular Therapy (2020) vol. 28, No. 4S1, pp. 11-12, Abstract 22.

Kumar et al. "Multiplexed Cre-dependent selection yields systemic AAVs for targeting distinct brain cell types," Nature Methods (2020) vol. 17, No. 5, pp. 541-550.

Li et al. "A Novel AAV Capsid with a Potential of Crossing NHP Blood-Brain Barrier," Molecular Therapy (2020) vol. 28, No. 4S1, pp. 253, Abstract 572.

Liu, W. et al. "AAV Gene Delivery of the Anti-Tau Antibody PHF1 Reduces Brain Tau Pathology in P301L Mice," Molecular Therapy vol. 23, Supplement 1 (2015): S237, Abstract 596.

Liu, W. et al. "Efficacy of a vectorized anti-tau antibody using systemic dosing of a blood brain barrier penetrant AAV capsid in mouse models of tauopathies." Alzheimer's & Dementia vol. 17, No. S9 (2021): e053341.

Marsic et al. "High-accuracy biodistribution analysis of adeno-associated virus variants by double barcode sequencing," Molecular Therapy—Methods & Clinical Development (2015) vol. 2, 15041.

Marsic, D. et al. "Vector design Tour de Force: integrating combinatorial and rational approaches to derive novel adeno-associated virus variants." Molecular Therapy : The Journal of the American Society of Gene Therapy vol. 22,11 (2014): 1900-9.

Nonnenmacher et al. "Rapid evolution of blood-brain barrier-penetrating AAV capsids by RNA-driven biopanning," Molecular Therapy (2021) vol. 20, pp. 366-378.

Nonnenmacher et al. "RNA-Driven Evolution of AAV Capsid Libraries Identifies Variants with High Transduction Efficiency in Non-Human Primate Central Nervous System," Molecular Therapy (2021) vol. 29, No. 4S1, pp. 25-26, Abstract 51.

Nonnenmacher et al. "Targeted In Vivo Biopanning of AAV Capsid Libraries Using Cell Type-Specific RNA Expression," Molecular Therapy (2019) vol. 27, No. 4S1, p. 27, Abstract 48.

Nonnenmacher et al., "Dose-response evaluation of 9P801, an engineered AAV capsid with high BBB penetration and CNS transduction in non-human primates," ESGCT 29th Annual Congress In collaboration with BSGCT Edinburgh, UK Oct. 11-14, 2022 Abstract P015.Human Gene Therapy.Dec. 2022.

Nonnenmacher. "RNA-driven Evolution of AAV Capsid Libraries Identifies Variants with High Transduction Efficiency in Non-Human Primate Central Nervous System," American Society of Cell + Gene Therapy Annual Meeting, 2021, 17 pages.

Ogden et al. "Comprehensive AAV capsid fitness landscape reveals a viral gene and enables machine-guided design," Science, 2019, 366(6469), pp. 1139-1143.

Adachi, M. et al. "A segment of the Mecp2 promoter is sufficient to drive expression in neurons." Human Molecular Genetics vol. 14,23 (2005): 3709-22.

Afione, S. et al. "Identification and mutagenesis of the adeno-associated virus 5 sialic acid binding region." Journal of Virology vol. 89,3 (2015): 1660-72.

Almeida, C F et al. "Promising AAV.U7snRNAs vectors targeting DMPK improve DM1 hallmarks in patient-derived cell lines." Frontiers in Cell and Developmental Biology vol. 11 1181040. Jun. 15, 2023.

Bremel, R. et al. "Bioinformatic Processes for Determination of Peptide Binding", GS_PROT_ALERT:WO20130401421 Mar. 2013 (Mar. 21, 2013), retrieved from WO2013040142, Database Accession No. GS_PROT_ALERT:WO2013040142.974324.

Buning, H. & Srivastava, A. "Capsid Modifications for Targeting and Improving the Efficacy of AAV Vectors." Molecular Therapy—Methods & Clinical Development vol. 12 (2019): 248-265.

Child, M.A. et al. "High-resolution Quantitative Analysis of Multiple AAV Capsids in Rodent and Primate Models Using Multiplexed Reporter Protein Tagging Platform." Voyager Therapeutics. ASGCT 27th Annual Meeting 2024, May 7-11, 2024, Baltimore, MD, USA.

Choudhury, S. et al. "Peptide Grafting Yields Novel AAV Vectors Capable of Enhanced Neuronal Transduction in Adult Mouse Brain." Molecular Therapy vol. 22, Supplement 1 (2014): S109-S110, Abstract 285.

Chung, C. et al. "Development of AAV-GBA1 Gene Replacement Therapy via Single-IV-Delivery with a Blood Brain Barrier Penetrant AAV Capsid." Molecular Therapy vol. 31 No 4S1, Apr. 2023, Abstract 695.

Chung, C. et al. "Development of AAV-GBA1 Gene Replacement Therapy via Single-IV-Delivery with a Blood Brain Barrier Penetrant AAV Capsid." Voyager Therapeutics. ASGCT—Annual Meeting 2023, May 16-May 20, 2023, Los Angeles, CA, USA (#695).

Govindasamy, L. et al. "Structural insights into adeno-associated virus serotype 5." Journal of Virology vol. 87,20 (2013): 11187-99.

Grannan, M.D. et al. "Intravenous Delivery of AAV Gene Therapy for the Treatment of SOD1-ALS Provides Broad SOD1 Lowering in NHP." Molecular Therapy, vol. 32 No. 4S1 (2024): 769-770, Abstract 1647.

Grannan, M.D. et al. "Intravenous Delivery of AAV Gene Therapy for the Treatment of SOD1-ALS Provides Broad SOD1 Lowering in NHP." Voyager Therapeutics. ASGCT 27th Annual Meeting 2024, May 7-11, 2024, Baltimore, MD, USA.

Gray, S.J. et al. "Optimizing promoters for recombinant adeno-associated virus-mediated gene expression in the peripheral and central nervous system using self-complementary vectors." Human Gene Therapy vol. 22,9 (2011): 1143-53.

Hida, K. et al. "Sites in the AAV5 capsid tolerant to deletions and tandem duplications." Archives of Biochemistry and Biophysics vol. 496,1 (2010): 1-8.

(56)         References Cited

OTHER PUBLICATIONS

Hoffman, B. et al. "Identification and Characterization of a Highly Conserved Cell Surface Receptor Utilized by Engineered BBB-Penetrant AAV Capsids with Enhanced Brain Tropism in Non-Human Primates and Mice." Voyager Therapeutics. ASGCT 27th Annual Meeting 2024, May 7-11, 2024, Baltimore, MD, USA.

Hoffman, B. et al. "Identification and Characterization of a Highly Conserved Cell Surface Receptor Utilized by Engineered BBB-Penetrant AAV Capsids with Enhanced Brain Tropism in Non-Human Primates and Mice." Molecular Therapy, vol. 32 No. 4S1 (2024): 475, Abstract 975.

Hoffman, B. et al. "Identification of a cell surface receptor utilized by an engineered BBB-penetrant capsid family with enhanced brain tropism in non-human primates and mice." Human Gene Therapy vol. 33: A2-A212 (Dec. 2022), A32, Abstract P024.

Hoffman, B.A. et al. "Discovery and Characterization of Novel Cross-Species BBB-Penetrant Capsids." Voyager Therapeutics. ASGCT 26th Annual Meeting 2023, May 16-20, 2023, Los Angeles, CA, USA.

Hoffman, B.A. et al. "Identification of a Cell Surface Receptor Utilized by an Engineered BBB-Penetrant Capsid Family with Enhanced Brain Tropism in Non-Human Primates and Mice." Voyager Therapeutics. ESGCT—29th Congress, Oct. 11-14, 2022, Edinburgh, Scotland, UK.

Ibe, M.et al. "Role of strong anchor residues in the effective binding of 10-mer and 11-mer peptides to HLA-A*2402 molecules," Immunogenetics vol. 44, 4, (1996): 233-241.

International Search Report and Written Opinion in International Patent Application No. PCT/US2023/062101 dated Jul. 24, 2023.

International Search Report and Written Opinion in International Patent Application No. PCT/US2023/067749 dated Sep. 29, 2023.

International Search Report and Written Opinion in International Patent Application No. PCT/US2023/069146 dated Nov. 9, 2023.

International Search Report and Written Opinion in International Patent Application No. PCT/US2023/069621 dated Oct. 16, 2023.

International Search Report and Written Opinion in International Patent Application No. PCT/US2024/041668 dated Dec. 3, 2024.

International Search Report and Written Opinion in International Patent Application No. PCT/US2024/042395 dated Dec. 2, 2024.

International Search Report and Written Opinion in International Patent Application No. PCT/US2024/042397 dated Dec. 3, 2024.

International Search Report and Written Opinion in International Patent Application No. PCT/US2024/042405 dated Dec. 2, 2024.

International Search Report and Written Opinion in International Patent Application No. PCT/US2024/042407 dated Dec. 2, 2024.

International Search Report and Written Opinion in International Patent Application No. PCT/US2024/042411 dated Dec. 2, 2024.

International Search Report and Written Opinion in International Patent Application No. PCT/US2024/058328 dated Mar. 12, 2025.

International Search Report and Written Opinion in International Patent Application No. PCT/US2024/058329 dated Mar. 3, 2025.

International Search Report and Written Opinion in International Patent Application No. PCT/US2024/058330 dated Mar. 12, 2025.

International Search Report and Written Opinion in International Patent Application No. PCT/US2024/058339 dated Mar. 12, 2025.

International Search Report and Written Opinion in International Patent Application No. PCT/US2024/058351 dated Mar. 12, 2025.

International Search Report and Written Opinion in International Patent Application No. PCT/US2024/058361 dated Mar. 12, 2025.

International Search Report and Written Opinion in International Patent Application No. PCT/US2024/058486 dated Mar. 12, 2025.

International Search Report and Written Opinion in International Patent Application No. PCT/US2024/058500 dated Mar. 12, 2025.

International Search Report and Written Opinion in International Patent Application No. PCT/US2024/062267 dated Jun. 10, 2025.

Ishan, S. et al. "Establishment of a Predictive Transcytosis Model to Recapitulate Capsid-Receptor Interaction and Phenotype of BBB-penetrant AAV Variant." Voyager Therapeutics. ASGCT 27th Annual Meeting 2024, May 7-11, 2024, Baltimore, MD, USA.

Jose, A. et al. "High-Resolution Structural Characterization of a New Adeno-associated Virus Serotype 5 Antibody Epitope toward Engineering Antibody-Resistant Recombinant Gene Delivery Vectors." Journal of Virology vol. 93,1 e01394-18. Dec. 10, 2018.

Khalid, A. et al. "Evaluation of Cross-species Expression Across Four Species and Cellular Tropism of VCAP-102, an Engineered Blood-brain Barrier-penetrating AAV Derived Capsid from TRACER Platform Screens." Voyager Therapeutics. ASGCT 27th Annual Meeting 2024, May 7-11, 2024, Baltimore, MD, USA.

Khalid, H. et al. "Evaluation of Cross-Species Expression Across Four Species and Cellular Tropism of VCAP-102, an Engineered Blood-Brain Barrier-Penetrating AAV." Molecular Therapy, vol. 32 No. 4S1 (2024): 685, Abstract 1452.

Kotchey, N. M. et al. "A potential role of distinctively delayed blood clearance of recombinant adeno-associated virus serotype 9 in robust cardiac transduction." Molecular Therapy : The Journal of the American Society of Gene Therapy vol. 19,6 (2011): 1079-89.

Kotterman et al., "Directed evolution of AAV targeting lung epithelia using aerosol delivery identifies 4D-A101, a variant demonstrating robust gene delivery in non-human primates.".

Lin, J. et al. "An Evolved AAV Variant with Enhanced Brain and Spinal Cord Tropism and Translation across Primate Species," Molecular Therapy vol. 31 No. 4S1, Apr. 2023, Abstract 1393.

Lin, J. et al. "An Evolved AAV Variant with Enhanced Brain and Spinal Cord Tropism and Translation across Primate Species." Voyager Therapeutics. ASGCT Annual Meeting 2023, May 16-May 20, 2023, Los Angeles, CA, USA, (#1393).

Manikandan, Ceera et al. "Viral vector: potential therapeutic for glioblastoma multiforme." Cancer Gene Therapy vol. 27,5 (2020): 270-279.

Maura, D. et al. "Discovery of Tracer Aav Capsids Escaping Pre-Existing Neutralizing Antibodies." Molecular Therapy, vol. 32 No. 4S1 (2024): 475, Abstract 973.

Maura, D. et al. "Discovery of TRACER AAV Capsids Escaping Pre-existing Neutralizing Antibodies." Voyager Therapeutics. ASGCT 27th Annual Meeting 2024, May 7-11, 2024, Baltimore, MD, USA.

Maura, D. et al. "Stepwise Evolution of the AAV5-Derived Capsid VCAP-100 Identifies Novel Variants with Improved CNS Transduction and Liver Detargeting Following Systemic Injection," Molecular Therapy vol. 31 No. 4S1, Apr. 2023, Abstract 464.

Maura, D. et al. "Stepwise evolution of the AAV5-derived capsid VCAP-100 identifies novel variants with improved CNS transduction and liver detargeting following systemic injection." Voyager Therapeutics. ASGCT Annual Meeting 2023, May 16-May 20, 2023, Los Angeles, CA, USA, (#464).

Medici, G. et al., "Expression of a Secretable, Cell-Penetrating CDKL5 Protein Enhances the Efficacy of AAC Vector-Mediated Gene Therapy for CDKL5 Deficiency Disorder," Dec. 17, 2021 (Dec. 17, 2021), p. 1-25, Retrieved from the Internet: URL:https://www.biorxiv.org/content/10.1101/2021.07.26.453746v2.full.pdf.

Moyer, T. "Continued directed evolution of VCAP-101 and VCAP-102 identifies second generation capsids with increased brain tropism in non-human primates and mice (#119)." Voyager Therapeutics. ASGCT 27th Annual Meeting. ASGCT 27th Annual Meeting 2024, May 7-11, 2024, Baltimore, MD, USA. Breaking Barriers to the CNS via AAV Capsid Engineering, Wednesday May 8, 2024.

Moyer, T. "Directed Evolution of AAV9 Peptide Display Libraries Identifies a Family of Cross- Species Variants With Enhanced Brain Tropism in Non-Human Primates and Mice Following Systemic Administration." Voyager Therapeutics. SGCT 2022—Novel AAV Capsids for the Brain, Eye, and Kidney, May 19, 2022.

Moyer, T. "Directed Evolution of an AAV9 Library Identifies a Capsid Variant with Enhanced Brain Tropism and Liver Detargeting in Non-Human Primates and Mice Following Systemic Administration." Voyager Therapeutics. AAV Engineering for CNS Targeting, Thursday, May 18, 2023, Abstract #105.

Moyer, T. et al. "Continued Directed Evolution of VCAP-101 and VCAP-102 Identifies Second Generation Capsid Variants with Increased Brain Tropism and in Non-Human Primates and Mice." Molecular Therapy, vol. 32 No. 4S1 (2024): 64, Abstract 119.

Moyer, T. et al. "Directed Evolution of AAV9 Peptide Display Libraries Identifies a Family of Cross-Species Variants with Enhanced

(56)                    References Cited

OTHER PUBLICATIONS

Brain Tropism in Non-Human Primates and Mice Following Systemic Administration." Molecular Therapy, vol. 30 No. 4S1 (2022): 556, Abstract 1198.

Moyer, T. et al. "Directed Evolution of an AAV9 Library Identifies a Capsid Variant with Enhanced Brain Tropism and Liver De-Targeting in Non-Human Primates and Mice Following Systemic Administration." Molecular Therapy, vol. 31 No. 4S1 (2023): 57, Abstract 105.

Moyer, T.C. et al. "Highly conserved brain vascular receptor ALPL mediates transport of engineered viral vectors across the blood-brain barrier," bioRxiv 2024.03.12.584703.

Nonnenmacher, M. "Iterative Evolution of Cross-Species BBB-Penetrant Capsids." Voyager Therapeutics. In Vivo Gene Therapy & Genome Editing Summit, Oct. 30-Nov. 2, 2023, Miami, FL, USA, talk was on Oct. 31, 2023.

Nonnenmacher, M. "TracerTM capsid discovery platform." Voyager Therapeutics. In Vivo Gene Therapy & Genome Editing Summit, Oct. 31-Nov. 2, 2022, Miami, FL, USA.

Nonnenmacher, M. et al. "Directed Evolution of an AAV5 Capsid Library Identifies a Variant with Enhanced Transduction in Non-Human Primate and Rodent Brain Following Systemic Administration," Molecular Therapy vol. 30 No. 4S1, Apr. 2022, Abstract 129.

Nonnenmacher, M. et al. "Directed Evolution of an AAV5 Capsid Library Identifies a Variant with Enhanced Transduction in Non-Human Primate and Rodent Brain Following Systemic Administration." Voyager Therapeutics. ASGCT 2022 Annual Meeting, May 16-19, 2022, Washington, DC, USA (#129).

Puglisi, M. et al. "Targeting astrocytes by non-invasive viral vectors and probing the influence of age and inducibile expression of the reprogramming factors in vivo." Presented at Cell State Conversions, Cold Spring Harbor Laboratory, New York, USA, Oct. 10-14, 2023.

Qian, R. et al. "Directed Evolution of AAV Serotype 5 for Increased Hepatocyte Transduction and Retained Low Humoral Seroreactivity." Molecular Therapy. Methods & Clinical Development vol. 20 122-132. Oct. 20, 2020.

Qiao, C. et al. "Liver-specific microRNA-122 target sequences incorporated in AAV vectors efficiently inhibits transgene expression in the liver." Gene Therapy vol. 18,4 (2011): 403-10.

Rees, H. A. and Liu, D. R. "Base editing: precision chemistry on the genome and transcriptome of living cells." Nature Reviews. Genetics vol. 19,12 (2018): 770-788.

Reid, C A. "Dependoparvovirus AAV5 VP3 capsid protein fragment (560-594)." Nov. 26, 2020, Database Accession No. BIK62852.

Ren, X. et al. "Establishment of a Predictive Transcytosis Model to Recapitulate Capsid-Receptor Interaction and Phenotype of BBB Penetrant AAV Variants." Molecular Therapy, vol. 32 No. 4S1 (2024): 476, Abstract 976.

Shah, I. et al. "Establishment of a Predictive Transcytosis Model to Recapitulate Capsid-Receptor Interaction and Phenotype of BBB-penetrant AAV Variant." Voyager Therapeutics. ASGCT 27th Annual Meeting 2024, May 7-11, 2024, Baltimore, MD, USA.

Walters, R. W. et al. "Structure of adeno-associated virus serotype 5." Journal of Virology vol. 78,7 (2004): 3361-71.

Wang, Y. et al. "Directed evolution of adeno-associated virus 5 capsid enables specific liver tropism." Molecular Therapy. Nucleic Acids, vol. 28, (2022):293-306.

Xu, Guangxue et al. "Structural basis for the neurotropic AAV9 and the engineered AAVPHP.eB recognition with cellular receptors." Molecular Therapy. Methods & Clinical Development vol. 26 (2022):52-60.

Ye, Chaoyang et al. "Efficient expression of the adeno-associated virus type 5 p41 capsid gene promoter in 293 cells does not require Rep." Journal of Virology vol. 80, 13 (2006): 6559-67.

Yin, Z. et al., "Research Advances on Increasing the Transduction Efficiency of Recombinant Adeno-associated Viral Vectors." Biotechnology Bulletin vol. 31, 9 (2015): 49-59.

Zhang, X. et al. "Blood-brain barrier shuttle peptides enhance AAV transduction in the brain after systemic administration." Biomaterials vol. 176 (2018): 71-83.

Pekrun et al. "Screening of Barcoded Capsid Shuffled AAV Libraries Results in the Selection of Capsids with Enhanced Transduction Efficiency for Human Islets," Molecular Therapy (2019) vol. 26, No. 5S1, pp. 41, Abstract 82.

Song et al. "Strong Alpha Cell Preference of the AAV Strains That Best Transduce Human Pancreatic Islets in Vitro," Molecular Therapy (2017) vol. 25, No. 5S1, pp. 47, Abstract 98.

Stanton, A. C. et al. "Systemic administration of novel engineered AAV capsids facilitates enhanced transgene expression in the macaque CNS." Med vol. 4,1 (2023): 31-50.e8. Epub: Nov. 22, 2022.

Stoica, L. and Sena-Esteves, M. "Adeno Associated Viral Vector Delivered RNAi for Gene Therapy of SOD1 Amyotrophic Lateral Sclerosis." Frontiers in Molecular Neuroscience vol. 9 article 56 (2016).

Voyager Therapeutics, "Intravenous Delivery of Novel AAV Capsids", Oct. 20, 2017, Retrieved from the Internet: URL:https://www.voyagertherapeutics.com/wp-content/uploads/2017/10/ESGCT_slides.pdf [retrieved on Oct. 9, 2019].

Wang et al. "Adeno-associated virus vector as a platform for gene therapy delivery," Nat Rev Drug Discov., 2019, vol. 18, 5, pp. 358-378.

Yan et al., "Two-Amino Acid Molecular Switch in an Epithelial Morphogen That Regulates Binding to Two Distinct Receptors," Science (2000) vol. 290, pp. 523-527.

Diprimio, N. et al. "Surface loop dynamics in adeno-associated virus capsid assembly." Journal of Virology vol. 82,11 (2008): 5178-89.

Hordeaux, J. et al. "The GPI-Linked Protein LY6A Drives AAV-PHP.B Transport across the Blood-Brain Barrier." Molecular Therapy : The Journal of the American Society of Gene Therapy vol. 27,5 (2019): 912-921.

International Search Report and Written Opinion in International Patent Application No. PCT/US2024/026263 dated Oct. 14, 2024.

International Search Report and Written Opinion in International Patent Application No. PCT/US2024/027834 dated Oct. 15, 2024.

International Search Report and Written Opinion in International Patent Application No. PCT/US2025/028361 dated Nov. 6, 2025.

Leib, D. E. et al. "Optimized AAV capsids for basal ganglia diseases show robust potency and distribution." bioRxiv preprint DOI: 10.1101/2024.05.02.532211; this version posted May 5, 2024, URL:https://www.biorxiv.org/content/10.1101/2024.05.02.592211v1.full.pdf.

Liu, W. et al. "Vectored Intracerebral Immunization with the Anti-Tau Monoclonal Antibody PHF1 Markedly Reduces Tau Pathology in Mutant Tau Transgenic Mice." The Journal of Neuroscience : The Official Journal of the Society for Neuroscience vol. 36,49 (2016): 12425-12435.

Li, D. et al. "Transduction and Expression Characteristics of Adeno-Associated Viruses in the Central Nervous System." Journal of Brain and Nervous Diseases, vol. 24, 5 (2016): 322-327.

Varadi, K. et al. "Novel random peptide libraries displayed on AAV serotype 9 for selection of endothelial cell-directed gene transfer vectors." Gene Therapy, vol. 19, 8 (2012): 800-9.

P3-Blind Loop8-7mer Library

Orthogonal Evolution of Loop8-7mer Library

High-Throughput Screening by NGS

FIG. 4

AAV9:            TNHQSAQA-------QAQT

AAV9-589:       TNHQSAQAXXXXXXQAQT

AAV9-588:       TNHQSAQXXXXXXAQAQT

AAV9-split:     TNHQSXXXAVXXXAQAQT

Sensory cortex

Thalamus

NHP #1 (RT-ddPCR folds)

Relative normalized expression

Frontal cortex
Sensory cortex
Motor cortex
Putamen
Thalamus
Cerebellar cortex

TTD-002　TTD-003　TTD-004　TTD-005　AAV9

Dentate Nucleus

TTD-001 – NHP#2

TTD-001 – NHP#1

AAV9

Cerebellar Cortex

AAV9    TTD-001 – NHP#1    TTD-001 – NHP#2

Cortex

AAV9    TTD-001 – NHP#1    TTD-001 – NHP#2

DRG

TTD-004 – 10x

TTD-004 – 20x

DRG

AAV9 – 10x

AAV9 – 20x

Heart

TTD-001

TTD-004

AAV9

Heart: Left Ventricle

TTD-001 TTD-004

AAV9

Heart: Right Ventricle

TTD-001                          TTD-004

AAV9

REDIRECTION OF TROPISM OF AAV CAPSIDS

RELATED APPLICATIONS

This application is a U.S. National Phase Application under 35 U.S.C. § 371 of International Application No. PCT/US2021/025061, filed Mar. 31, 2021, which claims priority to U.S. Provisional Application 63/023,927 filed on May 13, 2020, and U.S. Provisional Application 63/122,300 filed on Dec. 7, 2020, the entire contents of which are hereby incorporated by reference.

REFERENCE TO THE SEQUENCE LISTING

The present application is being filed along with a Sequence Listing in electronic format. The Sequence Listing is provided as a file entitled 2057_1119PCT_SL, created on Mar. 31, 2021 which is 7,087,883 bytes in size. The information in the electronic format of the sequence listing is incorporated herein by reference in its entirety.

FIELD OF THE DISCLOSURE

The disclosure relates to compositions, methods, and processes for the preparation, use, and/or formulation of adeno-associated virus capsid proteins, wherein the capsid proteins comprise peptides, e.g., targeting peptide inserts, for enhanced tropism to a target cell or tissue.

BACKGROUND

Gene delivery to the adult central nervous system (CNS) remains a significant challenge in gene therapy. Engineered adeno-associated virus (AAV) capsids with improved brain tropism represent an attractive solution to the limitations of CNS delivery.

AAV-derived vectors are promising tools for clinical gene transfer because of their non-pathogenic nature, their low immunogenic profile, low rate of integration into the host genome and long-term transgene expression in non-dividing cells. However, the transduction efficiency of AAV natural variants in certain organs is too low for clinical applications, and capsid neutralization by pre-existing neutralizing antibodies may prevent treatment of a large proportion of patients. For these reasons, considerable efforts have been devoted to obtaining novel capsid variants with enhanced properties. Of many approaches tested so far, significant advances have resulted from directed evolution of AAV capsids using in vitro or in vivo selection of capsid variants created by capsid sequence randomization using either error-prone PCR, shuffling of various parent serotypes, or insertion of fully randomized short peptides at defined positions.

Attempts at providing AAV capsids with improved properties, e.g., improved tropism to a target cell or tissue upon systemic administration, have met with limited success. As such, there is a need for improved methods of producing AAV capsids and resulting AAV capsids for delivery of a payload of interest to a target cell or tissue, e.g., a CNS cell or tissue, or a muscle cell or tissue.

SUMMARY OF THE DISCLOSURE

The present disclosure pertains at least in part, to compositions and methods for the production and use of an AAV particle comprising an AAV capsid polypeptide, e.g., an AAV capsid variant. In some embodiments, the AAV capsid variant has an enhanced tropism for a tissue or a cell, e.g., a CNS tissue, a CNS cell, a muscle tissue, or a muscle cell. Said tropism can be useful for delivery of a payload, e.g., a payload described herein to a cell or tissue, for the treatment of a disorder, e.g., a neurological or a neurodegenerative disorder, a muscular or a neuromuscular disorder, or a neuro-oncological disorder.

Accordingly, in one aspect, the present disclosure provides an AAV capsid polypeptide, e.g., an AAV capsid variant, comprising: the amino acid sequence of any of SEQ ID NO: 1725-3622 or 3648-3659; an amino acid sequence comprising no more than four modifications, e.g., substitutions, relative to the amino acid sequence of any of SEQ ID NO: 1725-3622 or 3648-3659; or at least 3, 4, 5, 6, 7, 8, or 9 consecutive amino acids from the amino acid sequence of any of SEQ ID NO: 1725-3622 or 3648-3659. In some embodiments, the amino acid sequence is present in loop VIII. In some embodiments, the amino acid sequence is present immediately subsequent to position 586, 588, or 589, relative to a reference sequence numbered according to the amino acid sequence of SEQ ID NO: 138. In some embodiments, the AAV capsid variant comprises the amino acid sequence of any one of SEQ ID NOs: 3636-3647, or an amino acid sequence with at least 80% (e.g., at least about 85, 90, 95, 96, 97, 98, or 99%) sequence identity thereto.

In another aspect, the present disclosure provides an AAV capsid polypeptide, e.g., an AAV capsid variant, comprising: a parental amino acid sequence having an insert, wherein the insert comprises the amino acid sequence of any of SEQ ID NO: 1725-3622 or 3648-3659; an amino acid sequence comprising no more than four modifications, e.g., substitutions, relative to the amino acid sequence of any of SEQ ID NO: 1725-3622 or 3648-3659; or at least 3, 4, 5, 6, 7, 8, or 9 consecutive amino acids from the amino acid sequence of any of SEQ ID NO: 1725-3622 or 3648-3659. In some embodiments, the parental sequence comprises an amino acid sequence comprising at least one, two, or three modifications but no more than 30, 20 or 10 modifications, e.g., substitutions, to the amino acid sequence of SEQ ID NO: 138; and/or the amino acid sequence of SEQ ID NO: 138, or an amino acid sequence substantially identical (e.g., having at least 70%, 75%, 80%, 85%, 90%, 92%, 95%, 97%, 98%, or 99% sequence identity) thereto. In some embodiments, the insert is present in, e.g., inserted into, loop VIII of the parental amino acid sequence. In some embodiments, the insert is present, e.g., inserted, immediately subsequent to position 586, 588, or 589 of the parental sequence. In some embodiments, the AAV capsid variant further comprises a deletion at position 587 and/or a deletion at position 588 of the parental amino acid sequence.

In another aspect, the present disclosure provides a peptide, e.g., a targeting peptide, comprising: at least the amino acid sequence of any of SEQ ID NO: 1725-3622 or 3648-3659; an amino acid sequence comprising no more than four modifications, e.g., substitutions, relative to the amino acid sequence of any of SEQ ID NO: 1725-3622 or 3648-3659; or 3, 4, 5, 6, 7, 8, or 9 consecutive amino acids from the amino acid sequence of any of SEQ ID NO: 1725-3622 or 3648-3659. In some embodiments, the peptide is encoded by the nucleotide sequence of any one of SEQ ID NOs: 3660-3671, or a nucleic acid sequence substantially identical (e.g., having at least 70%, 75%, 80%, 85%, 90%, 92%, 95%, 97%, 98%, or 99% sequence identity) thereto; or a nucleotide sequence comprising at least one, two, three, four, five, six, or seven modifications but no more than ten modifications of the nucleotide sequences of any of SEQ ID NOs: 3660-3671. In some embodiments, the nucleotide sequence encoding the peptide comprises the nucleotide sequence of any one of SEQ ID NOs: 3660-3671, or a nucleic acid sequence substantially identical (e.g., having at least 70%, 75%, 80%, 85%, 90%, 92%, 95%, 97%, 98%, or 99% sequence identity) thereto, or a nucleotide sequence comprising at least one, two, three, four, five, six, or seven modifications but no more than ten modifications of the nucleotide sequences of any of SEQ ID NOs: 3660-3671.

In yet another aspect, the present disclosure provides a polynucleotide encoding an AAV capsid polypeptide, e.g., an AAV capsid variant, wherein the AAV capsid variant comprises the amino acid sequence of any of SEQ ID NO: 1725-3622 or 3648-3659; an amino acid sequence comprising no more than four modifications, e.g., substitutions, relative to the amino acid sequence of any of SEQ ID NO: 1725-3622 or 3648-3659; or at least 3, 4, 5, 6, 7, 8, or 9 consecutive amino acids from the amino acid sequence of any of SEQ ID NO: 1725-3622 or 3648-3659. In some embodiments, the polynucleotide comprises the nucleotide sequence of any one of SEQ ID NOS: 3623-3635, or a nucleotide sequence with at least 80% (e.g., at least about 85, 90, 95, 96, 97, 98, or 99%) sequence identity thereto.

In yet another aspect, the present disclosure provides an AAV particle comprising an AAV capsid polypeptide, e.g., an AAV capsid variant, described herein. In some embodiments, the AAV particle comprises a nucleic acid sequence encoding a payload. In some embodiments, the AAV particle further comprises a viral genome comprising a promoter operably linked to the nucleic acid encoding the payload.

In yet another aspect, the present disclosure provides a method of making an AAV particle comprising an AAV capsid polypeptide, e.g., an AAV capsid variant, described herein. The method comprises providing a host cell comprising a viral genome and incubating the host cell under conditions suitable to enclose the viral genome in the AAV capsid variant, e.g., an AAV capsid variant described herein, thereby making the AAV particle.

In yet another aspect, the present disclosure provides a method of delivering a payload to a cell or tissue (e.g., a CNS cell, a CNS tissue, a muscle cell, or a muscle tissue). The method comprising administering an effective amount of an AAV particle comprising an AAV capsid variant described herein.

In yet another aspect, the present disclosure provides a method of treating a subject having or diagnosed with having neurological, e.g., a neurodegenerative, disorder. The method comprising administering an effective amount of an AAV particle comprising an AAV capsid variant described herein.

In yet another aspect, the present disclosure provides a method of treating a subject having or diagnosed with having a muscular disorder or a neuromuscular disorder. The method comprising administering an effective amount of an AAV particle comprising an AAV capsid variant described herein.

In yet another aspect, the present disclosure provides a method of treating a subject having or diagnosed with having a neuro-oncological disorder. The method comprising administering an effective amount of an AAV particle comprising an AAV capsid variant described herein.

The present disclosure presents an AAV capsid protein comprising a parental amino acid sequence selected from any of SEQ ID NO: 1-1724, which may have inserted therein at least one peptide selected from any member of SEQ ID NO: 1725-3622.

In certain embodiments, the inserted peptide is selected from SEQ ID NO: 1725-3622 and is inserted into the parental amino acid sequence.

In certain embodiments, the peptide is inserted at any amino acid position between amino acids 586-592, inclusive of the parental amino acid sequence. In such embodiments, the peptide may be inserted between amino acids 588-589 of the parental amino acid sequence.

In some embodiments, the parental amino acid sequence may be SEQ ID NO: 138 or SEQ ID NO: 11.

The present disclosure also presents a peptide comprising an amino acid sequence selected from the group consisting of SEQ ID NO: 1725-3622.

In other aspects, the disclosure presents an AAV particle comprising an AAV capsid protein disclosed herein and a viral genome. In such aspects, the viral genome may comprise a nucleic acid sequence that encodes a payload. In some embodiments, the payload may be an RNAi agent, which may consist of dsRNA, siRNA, shRNA, pre-miRNA, pri-miRNA, miRNA, miRNA precursor, stRNA, lncRNA, piRNA, or snoRNA.

In additional aspects, the payload may be a peptide, polypeptide, antibody or antibody fragment.

The present disclosure also presents a pharmaceutical composition comprising the AAV particle and a pharmaceutically acceptable excipient, as well as a method of treating a disease in a subject by administering the pharmaceutical composition said subject.

Those skilled in the art will recognize or be able to ascertain using no more than routine experimentation, many equivalents to the specific embodiments of the invention described herein. Such equivalents are intended to be encompassed by the following enumerated embodiments.

ENUMERATED EMBODIMENTS

1. An AAV capsid polypeptide, e.g., an AAV capsid variant, comprising:
   (a) the amino acid sequence of any of SEQ ID NO: 1725-3622 or 3648-3659;
   (b) at least 3, 4, 5, 6, 7, 8, or 9 consecutive amino acids from the amino acid sequence of any of SEQ ID NO: 1725-3622 or 3648-3659; or
   (c) an amino acid sequence comprising no more than four modifications, e.g., substitutions, relative to the amino acid sequence of any of SEQ ID NO: 1725-3622 or 3648-3659.

2. An AAV capsid polypeptide, e.g., an AAV capsid variant, comprising:
   (a) the amino acid sequence of any of SEQ ID NO: 3648-3659;
   (b) at least 3, 4, 5, 6, 7, 8, or 9 consecutive amino acids from the amino acid sequence of any of SEQ ID NO: 3648-3659; or
   (c) an amino acid sequence comprising no more than four modifications, e.g., substitutions, relative to the amino acid sequence of any of SEQ ID NO: 3648-3659.

3. The AAV capsid polypeptide, e.g., the AAV capsid variant, of embodiment 1 or 2, which comprises at least 3, 4, 5, 6, 7, 8, or 9 consecutive amino acids from the amino acid sequence of any of SEQ ID NO: 3648-3659.

4. The AAV capsid polypeptide, e.g., the AAV capsid variant, of any one of embodiments 1-3, wherein the 3 consecutive amino acids comprise PLN.

5. The AAV capsid polypeptide, e.g., the AAV capsid variant, of any one of embodiments 1-4, wherein the 4 consecutive amino acids comprise PLNG (SEQ ID NO: 3678).

6. The AAV capsid polypeptide, e.g., the AAV capsid variant, of any one of the preceding embodiments, wherein the 5 consecutive amino acids comprise PLNGA (SEQ ID NO: 3679).

7. The AAV capsid polypeptide, e.g., the AAV capsid variant, of any one of the preceding embodiments, wherein the 6 consecutive amino acids comprise PLNGAV (SEQ ID NO: 3680).

8. The AAV capsid polypeptide, e.g., the AAV capsid variant, of any one of the preceding embodiments, wherein the 7 consecutive amino acids comprise PLNGAVH (SEQ ID NO: 3681).

9. The AAV capsid polypeptide, e.g., the AAV capsid variant, of any one of the preceding embodiments, wherein the 8 consecutive amino acids comprise PLNGAVHL (SEQ ID NO: 3682).

10. The AAV capsid polypeptide, e.g., the AAV capsid variant, of any one of the preceding embodiments, wherein the 9 consecutive amino acids comprise PLNGAVHLY (SEQ ID NO: 3648).

11. The AAV capsid polypeptide, e.g., the AAV capsid variant, of any one of embodiments 1-3, wherein the 3 consecutive amino acids comprise YST.

12. The AAV capsid polypeptide, e.g., the AAV capsid variant, of any one of embodiments 1-3 or 11, wherein the 4 consecutive amino acids comprise YSTD (SEQ ID NO: 3690).

13. The AAV capsid polypeptide, e.g., the AAV capsid variant, of any one of embodiments 1-3 or 11-12, wherein the 5 consecutive amino acids comprise YSTDE (SEQ ID NO: 3691) or YSTDV (SEQ ID NO: 3700).

14. The AAV capsid polypeptide, e.g., the AAV capsid variant, of any one of embodiments 1-3 or 11-13, wherein the 6 consecutive amino acids comprise YSTDER (SEQ ID NO: 3692) or YSTDVR (SEQ ID NO: 3701).

15. The AAV capsid polypeptide, e.g., the AAV capsid variant, of any one of embodiments 1-3, wherein the 3 consecutive amino acids comprise IVM.

16. The AAV capsid polypeptide, e.g., the AAV capsid variant, of any one of embodiments 1-3 or 15, wherein the 4 consecutive amino acids comprise IVMN (SEQ ID NO: 3693).

17. The AAV capsid polypeptide, e.g., the AAV capsid variant, of any one of embodiments 1-3 or 15-16, wherein the 5 consecutive amino acids comprise IVMNS (SEQ ID NO: 3694).

18. The AAV capsid polypeptide, e.g., the AAV capsid variant, of any one of embodiments 1-3 or 15-17, wherein the 6 consecutive amino acids comprise IVMNSL (SEQ ID NO: 3695).

19. The AAV capsid polypeptide, e.g., the AAV capsid variant, of any one of embodiments 1-3 or 15-18, wherein the 7 consecutive amino acids comprise IVMNSLK (SEQ ID NO: 3651).

20. The AAV capsid polypeptide, e.g., the AAV capsid variant of any one of embodiments 1-19, which comprises an amino acid sequence comprising at least one, two, or three but no more than four modifications, e.g., substitutions, relative to the amino acid sequence of any of SEQ ID NO: 3648-3659.

21. The AAV capsid polypeptide, e.g., the AAV capsid variant, of any one of embodiments 1-10 or 20, comprising the amino acid sequence of PLNGAVHLY (SEQ ID NO:

3648), or an amino acid sequence having at least one, two, or three but no more than four modifications, e.g., substitutions, relative to the amino acid sequence of PLN-GAVHLY (SEQ ID NO: 3648), optionally, wherein position 7 is H.

22. The AAV capsid polypeptide, e.g., the AAV capsid variant, of any one of embodiments 1-3 or 20, comprising the amino acid sequence of RDSPKGW (SEQ ID NO: 3649), or an amino acid sequence having at least one, two, or three modifications but no more than four modifications, e.g., substitutions, relative to the amino acid sequence of RDSPKGW (SEQ ID NO: 3649).

23. The AAV capsid polypeptide, e.g., the AAV capsid variant, of any one of embodiments 1-3 or 15-20, comprising the amino acid sequence of IVMNSLK (SEQ ID NO: 3651), or an amino acid sequence having at least one, two, or three modifications but no more than four modifications, e.g., substitutions, relative to the amino acid sequence of IVMNSLK (SEQ ID NO: 3651).

24. The AAV capsid polypeptide, e.g., the AAV capsid variant, of any one of embodiments 1-3, 11-14, or 20, comprising the amino acid sequence of YSTDVRM (SEQ ID NO: 3650), or an amino acid sequence having at least one, two, or three modifications but no more than four modifications, e.g., substitutions, relative to the amino acid sequence of YSTDVRM (SEQ ID NO: 3650).

25. The AAV capsid polypeptide, e.g., the AAV capsid variant, of any one of embodiments 1-3 or 20, comprising the amino acid sequence of RESPRGL (SEQ ID NO: 3652), or a sequence having at least one, two, or three modifications but no more than four modifications, e.g., substitutions, relative to the amino acid sequence of RESPRGL (SEQ ID NO: 3652).

26. The AAV capsid polypeptide, e.g., the AAV capsid variant, of any one of the preceding embodiments, which comprises the amino acid sequence of any of SEQ ID NO: 3648-3659.

27. The AAV capsid polypeptide, e.g., the AAV capsid variant, of any one of embodiments 1-26, comprising:

(i) an amino acid sequence encoded by the nucleotide sequence of any one of SEQ ID NOS: 3660-3671, or a nucleotide sequence substantially identical (e.g., having at least 70%, 75%, 80%, 85%, 90%, 92%, 95%, 97%, 98%, or 99% sequence identity) thereto; or (ii) an amino acid sequence encoded by a nucleotide sequence comprising at least one, two, three, four, five, six, or seven modifications but no more than ten modifications of the nucleotide sequence of any of SEQ ID NOs: 3660-3671.

28. The AAV capsid polypeptide, e.g., the AAV capsid variant, of any one of embodiments 1-27, wherein the nucleotide sequence encoding the AAV capsid variant comprises:

(i) the nucleotide sequence of any one of SEQ ID NOs: 3660-3671, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of any of SEQ ID NOS: 3660-3671.

29. The AAV capsid polypeptide, e.g., the AAV capsid variant, of any one of embodiments 1-10, 20-21, or 26-28, comprising an amino acid sequence encoded by:

(i) the nucleotide sequence of SEQ ID NO: 3660, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3660.

30. The AAV capsid polypeptide, e.g., the AAV capsid variant, of any one of embodiments 1-10, 20-21, or 26-29, wherein the nucleotide sequence encoding the AAV capsid variant comprises:

(i) the nucleotide sequence of SEQ ID NO: 3660, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3660.

31. The AAV capsid polypeptide, e.g., the AAV capsid variant, of any one of embodiments 1-3, 20, 22, or 26-28, comprising an amino acid sequence encoded by:

(i) the nucleotide sequence of SEQ ID NO: 3661, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3661.

32. The AAV capsid polypeptide, e.g., the AAV capsid variant, of any one of embodiments 1-3, 20, 22, 26-28, or 31, wherein the nucleotide sequence encoding the AAV capsid variant comprises:

(i) the nucleotide sequence of SEQ ID NO: 3661, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3661.

33. The AAV capsid polypeptide, e.g., the AAV capsid variant, of any one of embodiments 1-3, 11-14, 20, 24, or 26-28, comprising an amino acid sequence encoded by:

(i) the nucleotide sequence of SEQ ID NO: 3662, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3662.

34. The AAV capsid polypeptide, e.g., the AAV capsid variant, of any one of embodiments 1-3, 11-14, 20, 24, 26-28, or 33, wherein the nucleotide sequence encoding the AAV capsid variant comprises:

(i) the nucleotide sequence of SEQ ID NO: 3662, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3662.

35. The AAV capsid polypeptide, e.g., the AAV capsid variant, of any one of embodiments 1-3, 15-20, 23, or 26-28, comprising an amino acid sequence encoded by:

(i) the nucleotide sequence of SEQ ID NO: 3663, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3663.

36. The AAV capsid polypeptide, e.g., the AAV capsid variant, of any one of embodiments 1-3, 15-20, 23, 26-28, or 35, wherein the nucleotide sequence encoding the AAV capsid variant comprises:

(i) the nucleotide sequence of SEQ ID NO: 3663, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3663.

37. The AAV capsid polypeptide, e.g., the AAV capsid variant, of any one of embodiments 1-3, 20, or 25-28, comprising an amino acid sequence encoded by:

(i) the nucleotide sequence of SEQ ID NO: 3664, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3664.

38. The AAV capsid polypeptide, e.g., the AAV capsid variant, of any one of embodiments 1-3, 20, 25-28, or 37, wherein the nucleotide encoding the AAV capsid variant comprises:

(i) the nucleotide sequence of SEQ ID NO: 3664, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3664.

39. The AAV capsid polypeptide, e.g., the AAV capsid variant, of any one of the preceding embodiments, wherein the amino acid sequence is present in loop VIII.

40. The AAV capsid polypeptide, e.g., the AAV capsid variant, of any one of embodiments 1-10, 20-21, 26-30, or 39, wherein the amino acid sequence is present immediately subsequent to position 586, relative to a reference sequence numbered according to the amino acid sequence of SEQ ID NO: 138.

41. The AAV capsid polypeptide, e.g., the AAV capsid variant, of any one of embodiments 1-3, 15-20, 23, 26-28, 35-36, or 39, wherein the amino acid sequence is present immediately subsequent to position 588, relative to a reference sequence numbered according to the amino acid sequence of SEQ ID NO: 138.

42. The AAV capsid polypeptide, e.g., the AAV capsid variant, of any one of embodiments 1-3, 11-14, 20, 22, 24-28, 31-34, 37-38, or 39 wherein the amino acid sequence is present immediately subsequent to position 589, relative to a reference sequence numbered according to the amino acid sequence of SEQ ID NO: 138.

43. The AAV capsid polypeptide, e.g., the AAV capsid variant of any one of embodiments 1-42, which comprises an amino acid residue other than "A" at position 587 and/or an amino acid residue other than "Q" at position 588, numbered according to SEQ ID NO: 138.

44. The AAV capsid polypeptide, e.g., the AAV capsid variant, of any one of embodiments 1-10, 20-21, 26-30, 39-40, or 43, comprising the amino acid sequence of PLN-GAVHLY (SEQ ID NO: 3648), wherein the amino acid sequence of PLNGAVHLY (SEQ ID NO: 3648) is present immediately subsequent to position 586, relative to a reference sequence numbered according to the amino acid sequence of SEQ ID NO: 138.

45. The AAV capsid polypeptide, e.g., the AAV capsid variant, of any one of embodiments 1-3, 20, 26-28, 39-40, or 43, comprising the amino acid sequence of GGTLAVVSL (SEQ ID NO: 3654), wherein the amino acid sequence of GGTLAVVSL (SEQ ID NO: 3654) is present immediately subsequent to position 586, relative to a reference sequence numbered according to the amino acid sequence of SEQ ID NO: 138.

46. The AAV capsid polypeptide, e.g., the AAV capsid variant, of any one of embodiments 1-3, 15-20, 23, 26-28, 35-36, 39, or 41, comprising the amino acid sequence of IVMNSLK (SEQ ID NO: 3651), wherein the amino acid sequence of IVMNSLK (SEQ ID NO: 3651) is present immediately subsequent to position 588, relative to a reference sequence numbered according to the amino acid sequence of SEQ ID NO: 138.

47. The AAV capsid polypeptide, e.g., the AAV capsid variant, of any one of embodiments 1-3, 11-14, 20, 22, 24-28, 31-34, 37-38, 39, or 42, comprising the amino acid sequence of any of SEQ ID NOs: 3649, 3650, 3652, 3653, or 3655-3659, wherein the amino acid sequence of any of the aforesaid sequences is present immediately subsequent to position 589, relative to a reference sequence numbered according to the amino acid sequence of SEQ ID NO: 138.

48. The AAV capsid polypeptide, e.g., the AAV capsid variant, of any one of the preceding embodiments, which further comprises the amino acid substitution of K449R, numbered according to SEQ ID NO: 138.

49. The AAV capsid polypeptide, e.g., the AAV capsid variant, of any one of the preceding embodiments, which further comprises a modification, e.g., an insertion, substitution, and/or deletion, in loop I, II, IV and/or VI.

50. The AAV capsid polypeptide, e.g., the AAV capsid variant, of any one of the preceding embodiments, which comprises an amino acid sequence having at least one, two or three modifications but not more than 30, 20 or 10 modifications of the amino acid sequence of SEQ ID NO: 138.

51. The AAV capsid polypeptide, e.g., the AAV capsid variant, of any one of the preceding embodiments, which comprises the amino acid sequence of SEQ ID NO: 138, or an amino acid sequence with at least 80% (e.g., at least about 85, 90, 95, 96, 97, 98, or 99%) sequence identity thereto.

52. The AAV capsid polypeptide, e.g., the AAV capsid variant, of any one of the preceding embodiments, which comprises the amino acid sequence of SEQ ID NO: 138.

53. The AAV capsid polypeptide, e.g., the AAV capsid variant, of any one of the preceding embodiments, which comprises an amino acid sequence encoded by the nucleotide sequence of SEQ ID NO: 137, or a sequence with at least 80% (e.g., at least about 85, 90, 95, 96, 97, 98, or 99%) sequence identity thereto.

54. The AAV capsid polypeptide, e.g., the AAV capsid variant, of any one of the preceding embodiments, wherein the nucleotide sequence encoding the capsid variant comprises the nucleotide sequence of SEQ ID NO: 137, or a sequence with at least 80% (e.g., at least about 85, 90, 95, 96, 97, 98, or 99%) sequence identity thereto.

55. The AAV capsid polypeptide, e.g., the AAV capsid variant, of any one of the preceding embodiments, which comprises a VP1 protein, a VP2 protein, a VP3 protein, or a combination thereof.

56. The AAV capsid polypeptide, e.g., the AAV capsid variant, of any one of the preceding embodiments, which comprises the amino acid sequence corresponding to positions 138-743, e.g., a VP2, of any one of SEQ ID NOs: 3636-3647, or a sequence with at least 80% (e.g., at least about 85, 90, 95, 96, 97, 98, or 99%) sequence identity thereto.

57. The AAV capsid polypeptide, e.g., the AAV capsid variant, of any one of the preceding embodiments, which comprises the amino acid sequence corresponding to positions 203-743, e.g., a VP3, of any one of SEQ ID NOs: 3636-3647, or a sequence with at least 80% (e.g., at least about 85, 90, 95, 96, 97, 98, or 99%) sequence identity thereto.

58. The AAV capsid polypeptide, e.g., the AAV capsid variant, of any one of the preceding embodiments, which comprises the amino acid sequence of any one of SEQ ID NOs: 3636-3647, or an amino acid sequence with at least 80% (e.g., at least about 85, 90, 95, 96, 97, 98, or 99%) sequence identity thereto.

59. The AAV capsid polypeptide, e.g., the AAV capsid variant, of any one of the preceding embodiments, which comprises an amino acid sequence having at least one, two or three modifications, but not more than 30, 20 or 10 modifications of the amino acid sequence of any one of SEQ ID NOs: 3636-3647.

60. The AAV capsid polypeptide, e.g., the AAV capsid variant, of any one of the preceding embodiments, which comprises an amino acid sequence encoded by the nucleotide sequence of any one of SEQ ID NOs: 3623-3635, or a nucleotide sequence with at least 80% (e.g., at least about 85, 90, 95, 96, 97, 98, or 99%) sequence identity thereto.

61. The AAV capsid polypeptide, e.g., the AAV capsid variant, of any one of the preceding embodiments, wherein the nucleotide sequence encoding the capsid variant comprises the nucleotide sequence of any one of SEQ ID NOs: 3623-3635, or a nucleotide sequence with at least 80% (e.g., at least about 85, 90, 95, 96, 97, 98, or 99%) sequence identity thereto.

62. The AAV capsid polypeptide, e.g., the AAV capsid variant, of any one of embodiments 1-10, 20-21, 26-30, 39-40, 43-44, or 48-61, wherein the nucleotide sequence encoding the capsid variant comprises the nucleotide sequence of SEQ ID NO: 3623, or a nucleotide sequence with at least 80% (e.g., at least about 85, 90, 95, 96, 97, 98, or 99%) sequence identity thereto.

63. The AAV capsid polypeptide, e.g., the AAV capsid variant, of any one of embodiments 1-3, 15-20, 23, 26-28, 35-36, 39, 41, 46, or 48-61, wherein the nucleotide sequence encoding the capsid variant comprises the nucleotide sequence of SEQ ID NO: 3627, or a nucleotide sequence with at least 80% (e.g., at least about 85, 90, 95, 96, 97, 98, or 99%) sequence identity thereto.

64. The AAV capsid polypeptide, e.g., the AAV capsid variant, of any one of the preceding embodiments, wherein the nucleotide sequence encoding the capsid variant is codon optimized.

65. An AAV capsid polypeptide, e.g., an AAV capsid variant, comprising the amino acid sequence of any one of embodiments 1-10, 20-21, 26-30, 39-40, 43-44, 48-62, or 64, and further comprising an amino acid sequence at least 95% identical to SEQ ID NO: 3636.

66. An AAV capsid polypeptide, e.g., an AAV capsid variant, comprising the amino acid sequence of SEQ ID NO: 3636.

67. An AAV capsid polypeptide, e.g., an AAV capsid variant, comprising the amino acid sequence of any one of embodiments 1-3, 20, 22, 26-28, 31-32, 39, 42, 47-61, or 64, and further comprising an amino acid sequence at least 95% identical to SEQ ID NO: 3637.

68. An AAV capsid polypeptide, e.g., an AAV capsid variant, comprising the amino acid sequence of SEQ ID NO: 3637.

69. An AAV capsid polypeptide, e.g., an AAV capsid variant, comprising the amino acid sequence of any one of embodiments 1-3, 11-12, 20, 24, 26-28, 33-34, 39, 42, 47-61, or 64, and further comprising an amino acid sequence at least 95% identical to SEQ ID NO: 3638.

70. An AAV capsid polypeptide, e.g., an AAV capsid variant, comprising the amino acid sequence of SEQ ID NO: 3638.

71. An AAV capsid polypeptide, e.g., an AAV capsid variant, comprising the amino acid sequence of any one of embodiments 1-3, 15-20, 23, 26-28, 35-36, 39, 41, 46, 48-61, or 63-64, and further comprising an amino acid sequence at least 95% identical to SEQ ID NO: 3639.

72. An AAV capsid polypeptide, e.g., an AAV capsid variant, comprising the amino acid sequence of SEQ ID NO: 3639.

73. An AAV capsid polypeptide, e.g., an AAV capsid variant, comprising the amino acid sequence of any one of embodiments 1-3, 20, 25-28, 37-39, 42, 47-61, or 64, and further comprising an amino acid sequence at least 95% identical to SEQ ID NO: 3640.

74. An AAV capsid polypeptide, e.g., an AAV capsid variant, comprising the amino acid sequence of SEQ ID NO: 3640.

75. An AAV capsid polypeptide, e.g., an AAV capsid variant, comprising the amino acid sequence of SEQ ID NO: 3641.

76. An AAV capsid polypeptide, e.g., an AAV capsid variant, comprising the amino acid sequence of SEQ ID NO: 3642.

77. An AAV capsid polypeptide, e.g., an AAV capsid variant, comprising the amino acid sequence of SEQ ID NO: 3643.

78. An AAV capsid polypeptide, e.g., an AAV capsid variant, comprising the amino acid sequence of SEQ ID NO: 3644.

79. An AAV capsid polypeptide, e.g., an AAV capsid variant, comprising the amino acid sequence of SEQ ID NO: 3645.

80. An AAV capsid polypeptide, e.g., an AAV capsid variant, comprising the amino acid sequence of SEQ ID NO: 3646.

81. An AAV capsid polypeptide, e.g., an AAV capsid variant, comprising the amino acid sequence of SEQ ID NO: 3647.

82. An AAV capsid polypeptide, e.g., an AAV capsid variant, comprising an amino acid sequence encoded by the nucleotide sequence of any one of SEQ ID NOs: 3623-3635, or a nucleotide sequence at least 95% identical thereto.

83. An AAV capsid polypeptide, e.g., an AAV capsid variant, comprising a parental amino acid sequence having an insert, e.g., a targeting peptide, wherein the insert comprises:

(a) the amino acid sequence of any of SEQ ID NO: 1725-3622 or 3648-3659;

(b) at least 3, 4, 5, 6, 7, 8, or 9 consecutive amino acids from the amino acid sequence of any of SEQ ID NO: 1725-3622 or 3648-3659; or (c) an amino acid sequence comprising no more than four modifications, e.g., substitutions, relative to the amino acid sequence of any of SEQ ID NO: 1725-3622 or 3648-3659.

84. The AAV capsid polypeptide, e.g., the AAV capsid variant, of embodiment 83, wherein the parental sequence comprises:

(i) the amino acid sequence of SEQ ID NO: 138, or an amino acid sequence substantially identical (e.g., having at least 70%, 75%, 80%, 85%, 90%, 92%, 95%, 97%, 98%, or 99% sequence identity) thereto; and/or (ii) an amino acid sequence comprising at least one, two, or three modifications but no more than 30, 20 or 10 modifications, e.g., substitutions, to the amino acid sequence of SEQ ID NO: 138.

85. The AAV capsid polypeptide, e.g., the AAV capsid variant, of embodiment 83 or 84, wherein the parental sequence further comprises a substitution at position K449, e.g., a K449R substitution.

86. The AAV capsid polypeptide, e.g., the AAV capsid variant, of any one of embodiments 83-85, wherein the parental sequence comprises an amino acid sequence encoded by the nucleotide sequence of SEQ ID NO: 137, or a nucleotide sequence substantially identical (e.g., having at least 70%, 75%, 80%, 85%, 90%, 92%, 95%, 97%, 98%, or 99% sequence identity) thereto.

87. The AAV capsid polypeptide, e.g., the AAV capsid variant, of any one of embodiments 83-86, wherein the nucleotide sequence encoding the parental sequence comprises the nucleotide sequence of SEQ ID NO: 137, or a nucleotide sequence substantially identical (e.g., having at least 70%, 75%, 80%, 85%, 90%, 92%, 95%, 97%, 98%, or 99% sequence identity) thereto.

88. The AAV capsid polypeptide, e.g., the AAV capsid variant, of any one of embodiments 83-87, wherein the parental sequence comprises:

(i) the amino acid sequence of SEQ ID NO: 11 or an amino acid sequence substantially identical (e.g., having at least 70%, 75%, 80%, 85%, 90%, 92%, 95%, 97%, 98%, or 99% sequence identity) thereto; and/or (ii) an amino acid sequence comprising at least one, two, or three modifications but no more than 30, 20 or 10 modifications, e.g., substitutions, to the amino acid sequence of SEQ ID NO: 11; optionally, provided that position 449 of SEQ ID NO: 11 is not K, e.g., is R.

89. The AAV capsid polypeptide, e.g., the AAV capsid variant, of any one of embodiments 83-88, wherein the insert comprises the amino acid sequence of PLNGAVHLY (SEQ ID NO: 3648).

90. The AAV capsid polypeptide, e.g., the AAV capsid variant, of any one of embodiments 83-88, wherein the insert comprises the amino acid sequence of GGTLAVVSL (SEQ ID NO: 3654).

91. The AAV capsid polypeptide, e.g., the AAV capsid variant, of any one of embodiments 83-88, wherein the insert comprises the amino acid sequence of IVMNSLK (SEQ ID NO: 3651).

92. The AAV capsid polypeptide, e.g., the AAV capsid variant, of any one of embodiments 83-88, wherein the insert comprises an amino acid sequence chosen from RDSPKGW (SEQ ID NO: 3649), YSTDVRM (SEQ ID NO:

3650), RESPRGL (SEQ ID NO: 3652), SENDTRA (SEQ ID NO: 3653), YGLPKGP (SEQ ID NO: 3655) or STGTLRL (SEQ ID NO: 3656).

93. The AAV capsid polypeptide, e.g., the AAV capsid variant, of any one of embodiments 83-92, wherein the insert is present in loop VIII of the parental amino acid sequence.

94. The AAV capsid polypeptide, e.g., the AAV capsid variant, of any one of embodiments 83-90 or 93, wherein the insert is present immediately subsequent to position 586 in the parental amino acid sequence.

95. The AAV capsid polypeptide, e.g., the AAV capsid variant, of any one of embodiments 83-89 or 93-94, wherein the insert comprises the amino acid sequence of PLN-GAVHLY (SEQ ID NO: 3648) and is inserted immediately subsequent to position 586 of the parental amino acid sequence.

96. The AAV capsid polypeptide, e.g., the AAV capsid variant, of any one of embodiments 83-88, 90, or 93-94, wherein the insert comprises the amino acid sequence of GGTLAVVSL (SEQ ID NO: 3654) and is inserted immediately subsequent to position 586 of the parental amino acid sequence.

97. The AAV capsid polypeptide, e.g., the AAV capsid variant, of any one of embodiments 83-90, 93-96, which comprises an amino acid other than "A" at position 587 and/or an amino acid other than "Q" at position 588 of the parental sequence.

98. The AAV capsid polypeptide, e.g., the AAV capsid variant, of any one of embodiments 83-90 or 93-97, further comprising a deletion of amino acid "A" at position 587 and/or a deletion of amino acid "Q" at position 588 of the parental amino acid sequence.

99. The AAV capsid polypeptide, e.g., the AAV capsid variant, of any one of embodiments 83-89, 93-95, or 97-98, comprising:
   (i) an insert comprising the amino acid sequence of PLNGAVHLY (SEQ ID NO: 3648), which is inserted immediately subsequent to position 586 of the parental amino acid sequence; and
   (ii) a deletion of the amino acids "AQ" at positions 587 and 588 of the parental amino acid sequence.

100. The AAV capsid polypeptide, e.g., the AAV capsid variant, of any one of embodiments 83-88, 90, 93-94, or 96-98, comprising:
   (i) an insert comprising the amino acid sequence of GGTLAVVSL (SEQ ID NO: 3654), which is inserted immediately subsequent to position 586 of the parental amino acid sequence; and
   (ii) a deletion of the amino acids "AQ" at positions 587 and 588 of the parental amino acid sequence.

101. The AAV capsid polypeptide, e.g., the AAV capsid variant, of any one of embodiments 83-88, 91, or 93, wherein the insert is inserted immediately subsequent to position 588 in the parental amino acid sequence.

102. The AAV capsid polypeptide, e.g., the AAV capsid variant, of any one of embodiments 83-88, 91, 93, or 101, wherein the insert comprises the amino acid sequence of IVMNSLK (SEQ ID NO: 3651) and is inserted immediately subsequent to position 588 of the parental amino acid sequence.

103. The AAV capsid polypeptide, e.g., the AAV capsid variant, of embodiment 83-88, or 92-93, wherein the insert is inserted immediately subsequent to position 589 in the parental amino acid sequence.

104. The AAV capsid polypeptide, e.g., the AAV capsid variant, of any one of embodiments 83-88, 92-93, or 103, wherein the insert comprises an amino acid sequence chosen from RDSPKGW (SEQ ID NO: 3649), YSTDVRM (SEQ ID NO: 3650), RESPRGL (SEQ ID NO: 3652), SENDTRA (SEQ ID NO: 3653), YGLPKGP (SEQ ID NO: 3655) or STGTLRL (SEQ ID NO: 3656) and is inserted immediately subsequent to position 589 of the parental amino acid sequence.

105. The AAV capsid polypeptide, e.g., the AAV capsid variant, of any one of the preceding embodiments, which does not comprise an insert sequence present immediately subsequent to position 586, 588, or 589 numbered relative to SEQ ID NO: 138, having at least 5 consecutive amino acids corresponding to positions 586 to 594 numbered relative to SEQ ID NO: 138, of any of SEQ ID NOs: 1-1724, e.g., as described in Table 6.

106. The AAV capsid polypeptide, e.g., the AAV capsid variant, of any one of the preceding embodiments, which does not comprise the amino acid sequence of TLAVPFK (SEQ ID NO: 1262) present immediately subsequent to position 588, numbered according to SEQ ID NO: 138.

107. The AAV capsid polypeptide, e.g., the AAV capsid variant, of any one of the preceding embodiments, which has an increased tropism for a CNS cell or tissue, e.g., a brain cell, brain tissue, spinal cord cell, or spinal cord tissue, relative to the tropism of a reference sequence comprising the amino acid sequence of SEQ ID NO: 138.

108. The AAV capsid polypeptide, e.g., the AAV capsid variant, of any one of embodiments 1-12, 15-44, 46-74, 82-89, 91-95, 97-99, 101-107, which transduces a brain region, e.g., selected from dentate nucleus, cerebellar cortex, cerebral cortex, brain stem, hippocampus, thalamus and putamen, optionally wherein the level of transduction is at least 5, 10, 50, 100, 200, 500, 1,000, 2,000, 5,000, or 10,000-fold greater as compared to a reference sequence of SEQ ID NO: 138, e.g., when measured by an assay, e.g., an immunohistochemistry assay, a qRT-PCR, or a RT-ddPCR assay, e.g., as described in Example 5.

109. The AAV capsid polypeptide, e.g., the AAV capsid variant, of any one of the preceding embodiments, which is enriched at least about 5, 6, 7, 8, 9, or 10-fold, in the brain compared to a reference sequence of SEQ ID NO: 138, e.g., when measured by an assay as described in Example 4.

110. The AAV capsid polypeptide, e.g., the AAV capsid variant, of any one of embodiments 1-14, 20-22, 24-34, 39-40, 42-44, 47-62, 64-70, 79-80, 82-89, 92-95, 97-99, or 103-109, which is enriched at least about 20, 30, 40, or 50-fold in the brain compared to a reference sequence of SEQ ID NO: 138, e.g., when measured by an assay as described in Example 4.

111. The AAV capsid polypeptide, e.g., the AAV capsid variant, of any one of embodiments 1-10, 20-22, 26-32, 39-40, 42-44, 47-62, 64-68, 82-89, 92-95, 97-99, or 103-110, which is enriched at least about 100, 200, 300, or 400-fold in the brain compared to a reference sequence of SEQ ID NO: 138, e.g., when measured by an assay as described in Example 4.

112. The AAV capsid polypeptide, e.g., the AAV capsid variant, of any one of embodiments 1-10, 20-21, 26-30, 39-40, 43-44, 48-62, 64-66, 82-89, 93-95, 97-99, or 105-111, which delivers an increased level of viral genomes to a brain region, optionally wherein the level of viral genomes is increased by at least 5, 10, 20, 30, 40 or 50-fold, as compared to a reference sequence of SEQ ID NO: 138, e.g., when measured by an assay, e.g., a qRT-PCR or a RT-ddPCR assay (e.g., as described in Example 5).

113. The AAV capsid polypeptide, e.g., the AAV capsid variant, of any one of embodiments 1-12, 15-44, 46-74, 82-89, 91-95, 97-99, 101-112, which delivers an increased level of a payload to a brain region, optionally wherein the level of the payload is increased by at least 5, 10, 50, 100, 200, 500, 1,000, 2,000, 5,000, or 10,000-fold, as compared to a reference sequence of SEQ ID NO: 138, e.g., when measured by an assay, e.g., a qRT-PCR or a RT-ddPCR assay (e.g., as described in Example 5).

114. The AAV capsid polypeptide, e.g., the AAV capsid variant, of embodiment 113, wherein the brain region comprises a frontal cortex, sensory cortex, motor cortex, putamen, thalamus, cerebellar cortex, dentate nucleus, caudate, and/or hippocampus.

115. The AAV capsid polypeptide, e.g., the AAV capsid variant, of any one of embodiments 1-12, 15-44, 46-74, 82-89, 91-95, 97-99, 101-114, which delivers an increased level of a payload to a spinal cord region, optionally wherein the level of the payload is increased by at least 10, 20, 50, 100, 200, 300, 400, 500, 600, 700, 800 or 900-fold, as compared to a reference sequence of SEQ ID NO: 138, e.g., when measured by an assay, e.g., a qRT-PCR assay (e.g., as described in Example 5).

116. The AAV capsid polypeptide, e.g., the AAV capsid variant, of embodiment 115, wherein the spinal cord region comprises a cervical, thoracic, and/or lumbar region.

117. The AAV capsid polypeptide, e.g., the AAV capsid variant, of any one of embodiments 1-3, 15-20, 23, 26-28, 35-36, 39, 41, 46, 48-61, 63-64, 71-72, 83-88, 91, 93, 101-102, 105-109, or 113-116, which shows preferential transduction in a brain region relative to the transduction in the dorsal root ganglia (DRG).

118. The AAV capsid polypeptide, e.g., the AAV capsid variant, of any one of embodiments 1-10, 20-21, 26-30, 39-40, 43-44, 48-62, 64-66, 82-89, 93-95, 97-99, or 105-116, wherein the capsid variant:

(i) is enriched at least about 300, or 400-fold in the brain compared to a reference sequence of SEQ ID NO: 138, e.g., when measured by an assay as described in Example 4;

(ii) transduces a brain region, e.g., selected from dentate nucleus, cerebellar cortex, cerebral cortex, brain stem, hippocampus, thalamus and putamen, wherein the level of transduction is at least 500, 1,000, 2,000, 5,000, or 10,000-fold greater as compared to a reference sequence of SEQ ID NO: 138, e.g., when measured by an assay, e.g., an immunohistochemistry assay, a qRT-PCR, or a RT-ddPCR assay, e.g., as described in Example 5;

(iii) delivers an increased level of a payload to a brain region, optionally wherein the level of the payload is increased by at least 500, 1,000, 2,000, 5,000, or 10,000-fold, as compared to a reference sequence of SEQ ID NO: 138, e.g., when measured by an assay, e.g., a qRT-PCR or a RT-ddPCR assay (e.g., as described in Example 5), optionally wherein the brain region comprises a frontal cortex, sensory cortex, motor cortex, putamen, thalamus, cerebellar cortex, dentate nucleus, caudate, and/or hippocampus;

(iv) delivers an increased level of a payload to a spinal cord region, optionally wherein the level of the payload is increased by at least 50, 100, 200, 300, 400, 500, 600, 700, 800 or 900-fold, as compared to a reference sequence of SEQ ID NO: 138, e.g., when measured by an assay, e.g., a qRT-PCR assay (e.g., as described in Example 5), optionally wherein the spinal cord region comprises a cervical, thoracic, and/or lumbar region; and/or

(v) delivers an increased level of viral genomes to a brain region, optionally wherein the level of viral genomes is increased by at least 5, 10, 20, 30, 40 or 50-fold, as compared to a reference sequence of SEQ ID NO: 138, e.g., when measured by an assay, e.g., a qRT-PCR or a RT-ddPCR assay (e.g., as described in Example 5), optionally wherein the brain region comprises a frontal cortex, sensory cortex, motor cortex, putamen, thalamus, cerebellar cortex, dentate nucleus, caudate, and/or hippocampus.

119. An AAV capsid polypeptide, e.g., an AAV capsid variant comprising: (a) the amino acid sequence of PLNGAVHLY (SEQ ID NO: 3648); (b) an amino acid sequence comprising at least one, two, or three modifications but no more than four modifications, e.g., substitutions, relative to the amino acid sequence of PLNGAVHLY (SEQ ID NO: 3648); or (c) at least 3, 4, 5, 6, 7, 8, or 9 consecutive amino acids from the amino acid sequence of PLNGAVHLY (SEQ ID NO: 3648); and wherein the capsid variant:

(i) is enriched at least about 300 or 400-fold in the brain compared to a reference sequence of SEQ ID NO: 138, e.g., when measured by an assay as described in Example 4;

(ii) transduces a brain region, e.g., selected from dentate nucleus, cerebellar cortex, cerebral cortex, brain stem, hippocampus, thalamus and putamen, wherein the level of transduction is at least 500, 1,000, 2,000, 5,000, or 10,000-fold greater as compared to a reference sequence of SEQ ID NO: 138, e.g., when measured by an assay, e.g., an immunohistochemistry assay, a qRT-PCR, or a RT-ddPCR assay, e.g., as described in Example 5;

(iii) delivers an increased level of a payload to a brain region, optionally wherein the level of the payload is increased by at least 500, 1,000, 2,000, 5,000, or 10,000-fold, as compared to a reference sequence of SEQ ID NO: 138, e.g., when measured by an assay, e.g., a qRT-PCR or a RT-ddPCR assay (e.g., as described in Example 5), optionally wherein the brain region comprises a frontal cortex, sensory cortex, motor cortex, putamen, thalamus, cerebellar cortex, dentate nucleus, caudate, and/or hippocampus;

(iv) delivers an increased level of a payload to a spinal cord region, optionally wherein the level of the payload is increased by at least 50, 100, 200, 300, 400, 500, 600, 700, 800 or 900-fold, as compared to a reference sequence of SEQ ID NO: 138, e.g., when measured by an assay, e.g., a qRT-PCR assay (e.g., as described in Example 5), optionally wherein the spinal cord region comprises a cervical, thoracic, and/or lumbar region; and/or (v) delivers an increased level of viral genomes to a brain region, optionally wherein the level of viral genomes is increased by at least 5, 10, 20, 30, 40 or 50-fold, as compared to a reference sequence of SEQ ID NO: 138, e.g., when measured by an assay, e.g., a qRT-PCR or a RT-ddPCR assay (e.g., as described in Example 5), optionally wherein the brain region comprises a frontal cortex, sensory cortex, motor cortex, putamen, thalamus, cerebellar cortex, dentate nucleus, caudate, and/or hippocampus.

120. The AAV capsid polypeptide, e.g., the AAV capsid variant, of any one of embodiments 1-3, 15-20, 23, 26-28, 35-36, 39, 41, 46, 48-61, 63-64, 71-72, 83-88, 91, 93, 101-102, 105-109, or 113-117, wherein the AAV capsid variant has an increased tropism for a muscle cell or tissue, e.g., a heart tissue, relative to the tropism of a reference sequence comprising the amino acid sequence of SEQ ID NO: 138.

121. The AAV capsid polypeptide, e.g., the AAV capsid variant, of any one of embodiments 1-3, 15-20, 23, 26-28, 35-36, 39, 41, 46, 48-61, 63-64, 71-72, 83-88, 91, 93, 101-102, 105-109, 113-117, or 120, which delivers an increased level of a payload to a muscle region, optionally wherein the level of the payload is increased by at least 10, 15, 20, 30, or 40-fold, as compared to a reference sequence of SEQ ID NO: 138, e.g., when measured by an assay, e.g., an IHC assay or a RT-ddPCR assay (e.g., as described in Example 5).

122. The AAV capsid polypeptide, e.g., the AAV capsid variant, of embodiment 120 or 121, wherein the muscle region comprises a heart muscle, quadriceps muscle, and/or a diaphragm muscle region.

123. The AAV capsid polypeptide, e.g., the AAV capsid variant, of any one of embodiments 120-122, wherein the muscle region comprises a heart muscle region, e.g., a heart atrium muscle region or a heart ventricle muscle region.

124. The AAV capsid polypeptide, e.g., the AAV capsid variant, of any one of the preceding embodiments, which is isolated, e.g., recombinant.

125. A polynucleotide encoding the polypeptide, e.g., the AAV capsid variant of any one of embodiments 1-124.

126. The polynucleotide of embodiment 125, which comprises:
- (i) a nucleotide sequence comprising at least one, two, three, four, five, six, or seven modifications but no more than ten modifications of the nucleotide sequences of any of SEQ ID NOS: 3660-3671; or
- (ii) the nucleotide sequence of any one of SEQ ID NOs: 3660-3671, or nucleotide sequence substantially identical (e.g., having at least 70%, 75%, 80%, 85%, 90%, 92%, 95%, 97%, 98%, or 99% sequence identity) thereto.

127. The polynucleotide of embodiment 125 or 126, which comprises the nucleotide sequence of any one of SEQ ID NOs: 3623-3635, or a nucleotide sequence with at least 80% (e.g., at least about 85, 90, 95, 96, 97, 98, or 99%) sequence identity thereto.

128. The polynucleotide of any one of embodiments 125-127, which comprises a nucleotide sequence that is codon optimized.

129. A peptide, e.g., a targeting peptide, comprising:
- (a) the amino acid sequence of any of SEQ ID NO: 1725-3622 or 3648-3659;
- (b) an amino acid sequence comprising no more than four modifications, e.g., substitutions, relative to the amino acid sequence of any of SEQ ID NO: 1725-3622 or 3648-3659; or
- (c) at least 3, 4, 5, 6, 7, 8, or 9 consecutive amino acids from the amino acid sequence of any of SEQ ID NO: 1725-3622 or 3648-3659.

130. A peptide, e.g., a targeting peptide, comprising the amino acid sequence of any one of embodiments 1-106.

131. A peptide, e.g., a targeting peptide, comprising:
- (i) the amino acid sequence of PLNGAVHLY (SEQ ID NO: 3648);
- (ii) an amino acid sequence comprising at least one, two, or three modifications but no more than four modifications, e.g., substitutions, relative to the amino acid sequence of PLNGAVHLY (SEQ ID NO: 3648); or
- (iii) at least 3, 4, 5, 6, 7, 8, or 9 consecutive amino acids from the amino acid sequence of PLNGAVHLY (SEQ ID NO: 3648).

132. A peptide, e.g., a targeting peptide, encoded by:
- (i) the nucleotide sequence of SEQ ID NO: 3660 or a nucleotide sequence substantially identical (e.g., having at least 70%, 75%, 80%, 85%, 90%, 92%, 95%, 97%, 98%, or 99% sequence identity) thereto; or
- (ii) a nucleotide sequence comprising at least one, two, three, four, five, six, or seven modifications but no more than ten modifications of the nucleotide sequence of SEQ ID NO: 3660.

133. A peptide, e.g., a targeting peptide, wherein the nucleotide sequence encoding the peptide comprises:
- (i) the nucleotide sequence of SEQ ID NO: 3660 or a nucleotide sequence substantially identical (e.g., having at least 70%, 75%, 80%, 85%, 90%, 92%, 95%, 97%, 98%, or 99% sequence identity) thereto; or
- (ii) a nucleotide sequence comprising at least one, two, three, four, five, six, or seven modifications but no more than ten modifications of the nucleotide sequence of SEQ ID NO: 3660.

134. A peptide, e.g., a targeting peptide, comprising:
- (i) the amino acid sequence of IVMNSLK (SEQ ID NO: 3651);
- (ii) an amino acid sequence comprising at least one, two, or three modifications but no more than four modifications, e.g., substitutions, relative to the amino acid sequence of IVMNSLK (SEQ ID NO: 3651); or
- (iii) at least 3, 4, 5, 6, 7, 8, or 9 consecutive amino acids from the amino acid sequence of IVMNSLK (SEQ ID NO: 3651).

135. A peptide, e.g., a targeting peptide, encoded by:
- (i) the nucleotide sequence of SEQ ID NO: 3663, or a nucleotide sequence substantially identical (e.g., having at least 70%, 75%, 80%, 85%, 90%, 92%, 95%, 97%, 98%, or 99% sequence identity) thereto; or
- (ii) a nucleotide sequence comprising at least one, two, three, four, five, six, or seven modifications but no more than ten modifications of the nucleotide sequence of SEQ ID NO: 3663.

136. A peptide, e.g., a targeting peptide, wherein the nucleotide sequence encoding the peptide comprises:
- (i) the nucleotide sequence of SEQ ID NO: 3663, or a nucleotide sequence substantially identical (e.g., having at least 70%, 75%, 80%, 85%, 90%, 92%, 95%, 97%, 98%, or 99% sequence identity) thereto; or
- (ii) a nucleotide sequence comprising at least one, two, three, four, five, six, or seven modifications but no more than ten modifications of the nucleotide sequence of SEQ ID NO: 3663.

137. A peptide, e.g., a targeting peptide, comprising:
- (i) the amino acid sequence of RDSPKGW (SEQ ID NO: 3649);
- (ii) an amino acid sequence comprising at least one, two, or three modifications but no more than four modifications, e.g., substitutions, relative to the amino acid sequence of RDSPKGW (SEQ ID NO: 3649); or
- (iii) at least 3, 4, 5, 6, 7, 8, or 9 consecutive amino acids from the amino acid sequence of RDSPKGW (SEQ ID NO: 3649).

138. A peptide, e.g., a targeting peptide, encoded by:
- (i) the nucleotide sequence of SEQ ID NO: 3661, or a nucleotide sequence substantially identical (e.g., having at least 70%, 75%, 80%, 85%, 90%, 92%, 95%, 97%, 98%, or 99% sequence identity) thereto; or
- (ii) a nucleotide sequence comprising at least one, two, three, four, five, six, or seven modifications but no more than ten modifications of the nucleotide sequence of SEQ ID NO: 3661.

139. A peptide, e.g., a targeting peptide, wherein the nucleotide sequence encoding the peptide comprises:

(i) the nucleotide sequence of SEQ ID NO: 3661, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3661.

140. A peptide, e.g., a targeting peptide, comprising:

(i) the amino acid sequence of YSTDVRM (SEQ ID NO: 3650);

(ii) an amino acid sequence comprising at least one, two, or three modifications but no more than four modifications, e.g., substitutions, relative to the amino acid sequence of YSTDVRM (SEQ ID NO: 3650); or (iii) at least 3, 4, 5, 6, 7, 8, or 9 consecutive amino acids from the amino acid sequence of YSTDVRM (SEQ ID NO: 3650).

141. A peptide, e.g., a targeting peptide, encoded by:

(i) the nucleotide sequence of SEQ ID NO: 3662, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3662.

142. A peptide, e.g., a targeting peptide, wherein the nucleotide sequence encoding the peptide comprises:

(i) the nucleotide sequence of SEQ ID NO: 3662, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3662.

143. A peptide, e.g., a targeting peptide, comprising:

(i) the amino acid sequence of RESPRGL (SEQ ID NO: 3652);

(ii) an amino acid sequence comprising at least one, two, or three modifications but no more than four modifications, e.g., substitutions, relative to the amino acid sequence of RESPRGL (SEQ ID NO: 3652); or (iii) at least 3, 4, 5, 6, 7, 8, or 9 consecutive amino acids from the amino acid sequence of RESPRGL (SEQ ID NO: 3652).

144. A peptide, e.g., a targeting peptide, encoded by:

(i) the nucleotide sequence of SEQ ID NO: 3664, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3664.

145. A peptide, e.g., a targeting peptide, wherein the nucleotide sequence encoding the peptide comprises:

(i) the nucleotide sequence of SEQ ID NO: 3664, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3664.

146. An AAV capsid polypeptide, e.g., an AAV capsid variant, comprising the peptide, e.g., targeting peptide, of any one of embodiments 129-145.

147. A polynucleotide encoding the peptide, e.g., targeting peptide, of any one of embodiments 129-145.

148. A polynucleotide encoding an AAV capsid polypeptide, e.g., an AAV capsid variant comprising:

(a) the amino acid sequence of any of SEQ ID NO: 1725-3622 or 3648-3659;

(b) an amino acid sequence comprising no more than four modifications, e.g., substitutions, relative to the amino acid sequence of any of SEQ ID NO: 1725-3622 or 3648-3659; or (c) at least 3, 4, 5, 6, 7, 8, or 9 consecutive amino acids from the amino acid sequence of any of SEQ ID NO: 1725-3622 or 3648-3659;

optionally wherein the amino acid sequence of (a), (b), and/or (c) is present immediately subsequent to position 586, 588, or 589, relative to a reference sequence numbered according to the amino acid sequence of SEQ ID NO: 138.

149. A polynucleotide encoding an AAV capsid polypeptide, e.g., an AAV capsid variant, wherein the AAV capsid variant comprises:

(i) the amino acid sequence of PLNGAVHLY (SEQ ID NO: 3648);

(ii) an amino acid sequence comprising at least one, two, or three modifications but no more than four modifications, e.g., substitutions, relative to the amino acid sequence of PLNGAVHLY (SEQ ID NO: 3648); or (iii) at least 3, 4, 5, 6, 7, 8, or 9 consecutive amino acids from the amino acid sequence of PLNGAVHLY (SEQ ID NO: 3648);

optionally wherein the amino acid sequence of (i), (ii), and/or (iii) is present immediately subsequent to position 586, relative to a reference sequence numbered according to the amino acid sequence of SEQ ID NO: 138.

150. The polynucleotide of embodiment 149, which comprises:

(i) the nucleotide sequence of SEQ ID NO: 3660 or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3660.

151. A polynucleotide encoding an AAV capsid polypeptide, e.g., an AAV capsid variant, wherein the AAV capsid variant comprises:

(i) the amino acid sequence of IVMNSLK (SEQ ID NO: 3651);

(ii) an amino acid sequence comprising at least one, two, or three modifications but no more than four modifications, e.g., substitutions, relative to the amino acid sequence of IVMNSLK (SEQ ID NO: 3651); or (iii) at least 3, 4, 5, 6, 7, 8, or 9 consecutive amino acids from the amino acid sequence of IVMNSLK (SEQ ID NO: 3651);

optionally wherein the amino acid sequence of (i), (ii), and/or (iii) is present immediately subsequent to position 588, relative to a reference sequence numbered according to the amino acid sequence of SEQ ID NO: 138.

152. The polynucleotide of embodiment 151, which comprises:

(i) the nucleotide sequence of SEQ ID NO: 3663, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3663.

153. A polynucleotide encoding an AAV capsid polypeptide, e.g., an AAV capsid variant, wherein the AAV capsid variant comprises:

(i) the amino acid sequence of RDSPKGW (SEQ ID NO: 3649);

(ii) an amino acid sequence comprising at least one, two, or three modifications but no more than four modifications, e.g., substitutions, relative to the amino acid sequence of RDSPKGW (SEQ ID NO: 3649); or (iii) at least 3, 4, 5, 6, 7, 8, or 9 consecutive amino acids from the amino acid sequence of RDSPKGW (SEQ ID NO: 3649);

optionally wherein the amino acid sequence of (i), (ii), and/or (iii) is present immediately subsequent to position 589, relative to a reference sequence numbered according to the amino acid sequence of SEQ ID NO: 138.

154. The polynucleotide of embodiment 153, which comprises:

(i) the nucleotide sequence of SEQ ID NO: 3661, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3661.

155. A polynucleotide encoding an AAV capsid polypeptide, e.g., an AAV capsid variant, wherein the AAV capsid variant comprises:

(i) the amino acid sequence of YSTDVRM (SEQ ID NO: 3650);

(ii) an amino acid sequence comprising at least one, two, or three modifications but no more than four modifications, e.g., substitutions, relative to the amino acid sequence of YSTDVRM (SEQ ID NO: 3650); or (iii) at least 3, 4, 5, 6, 7, 8, or 9 consecutive amino acids from the amino acid sequence of YSTDVRM (SEQ ID NO: 3650);

optionally wherein the amino acid sequence of (i), (ii), and/or (iii) is present immediately subsequent to position 589, relative to a reference sequence numbered according to the amino acid sequence of SEQ ID NO: 138.

156. The polynucleotide of embodiment 155, which comprises:

(i) the nucleotide sequence of SEQ ID NO: 3662, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3662.

157. A polynucleotide encoding an AAV capsid polypeptide, e.g., an AAV capsid variant, wherein the AAV capsid variant comprises:

(i) the amino acid sequence of RESPRGL (SEQ ID NO: 3652);

(ii) an amino acid sequence comprising at least one, two, or three modifications but no more than four modifications, e.g., substitutions, relative to the amino acid sequence of RESPRGL (SEQ ID NO: 3652); or (iii) at least 3, 4, 5, 6, 7, 8, or 9 consecutive amino acids from the amino acid sequence of RESPRGL (SEQ ID NO: 3652);

optionally wherein the amino acid sequence of (i), (ii), and/or (iii) is present immediately subsequent to position 589, relative to a reference sequence numbered according to the amino acid sequence of SEQ ID NO: 138.

158. The polynucleotide of embodiment 157, which comprises:

(i) the nucleotide sequence of SEQ ID NO: 3664, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven modifications but no more than ten modifications of the nucleotide sequence of SEQ ID NO: 3664.

159. The polynucleotide of any one of embodiments 147-158, wherein the AAV capsid variant comprises:

(i) the amino acid sequence of any one of SEQ ID NOs: 3636-3647, or an amino acid sequence with at least 80% (e.g., at least about 85, 90, 95, 96, 97, 98, or 99%) sequence identity thereto; or (ii) an amino acid sequence having at least one, two or three modifications but not more than 30, 20 or 10 modifications of the amino acid sequence of any one of SEQ ID NOs: 3636-3647.

160. The polynucleotide of any one of embodiments 147-159, comprising the nucleotide sequence of any one of SEQ ID NOs: 3623-3635, or a nucleotide sequence with at least 80% (e.g., at least about 85, 90, 95, 96, 97, 98, or 99%) sequence identity thereto.

161. The polynucleotide, peptide, or AAV capsid polypeptide, e.g., AAV capsid variant, of any one of embodiments 125-160, which is isolated, e.g., recombinant.

162. An AAV particle comprising the AAV capsid polypeptide, e.g., the AAV capsid variant, of any one of embodiments 1-124 or 146.

163. The AAV particle of embodiment 162, which comprises a nucleotide sequence encoding a payload.

164. The AAV particle of embodiment 163, wherein the encoded payload comprises a therapeutic protein or functional variant thereof; an antibody or antibody fragment; an enzyme; a component of a gene editing system; an RNAi agent (e.g., a dsRNA, siRNA, shRNA, pre-miRNA, pri-miRNA, miRNA, stRNA, lncRNA, piRNA, or snoRNA); or a combination thereof.

165. The AAV particle of embodiment 164, wherein the therapeutic protein or functional variant thereof, e.g., a recombinant protein, is associated with (e.g., aberrantly expressed in) a neurological or neurodegenerative disorder, a muscular or neuromuscular disorder, or a neuro-oncological disorder.

166. The AAV particle of embodiment 164 or 165, the therapeutic protein or functional variant thereof is chosen from apolipoprotein E (APOE) (e.g., ApoE2, ApoE3 and/or ApoE4); human survival of motor neuron (SMN) 1 or SMN2; glucocerebrosidase (GBA1); aromatic L-amino acid decarboxylase (AADC); aspartoacylase (ASPA); tripeptidyl peptidase I (CLN2); beta-galactosidase (GLB1); N-sulpho-glucosamine sulphohydrolase (SGSH); N-acetyl-alpha-glu-cosaminidase (NAGLU); iduronate 2-sulfatase (IDS); intra-cellular cholesterol transporter (NPC1); gigaxonin (GAN); or a combination thereof.

167. The AAV particle of embodiment 164, wherein the antibody or antibody binding fragment binds to:

(i) a CNS related target, e.g. an antigen associated with a neurological or neurodegenerative disorder, e.g., β-amyloid, APOE, tau, SOD1, TDP-43, huntingtin (HTT), and/or synuclein;

(ii) a muscular or neuromuscular related target, e.g., an antigen associated with a muscular or neuromuscular disorder; or (iii) a neuro-oncology related target, e.g., an antigen associated with a neuro-oncological disorder, e.g., HER2, or EGFR (e.g., EGFRvIII).

168. The AAV particle of embodiment 164, wherein the enzyme comprises a meganuclease, a zinc finger nuclease, a TALEN, a recombinase, integrase, a base editor, a Cas9, or a fragment thereof.

169. The AAV particle of embodiment 164, wherein the component of a gene editing system comprises one or more components of a CRISPR-Cas system.

170. The AAV particle of embodiment 164 or 169, wherein the one or more components of the CRISPR-Cas system comprises a Cas9, e.g., a Cas9 ortholog or a Cpf1, and a single guide RNA (sgRNA), optionally wherein:

(i) the sgRNA is located upstream (5') of the cas9 enzyme; or (ii) the sgRNA is located downstream (3') of the cas9 enzyme.

171. The AAV particle of embodiment 164, wherein the RNAi agent (e.g., a dsRNA, siRNA, shRNA, pre-miRNA, pri-miRNA, miRNA, stRNA, lncRNA, piRNA, or snoRNA), modulates, e.g., inhibits, expression of, a CNS related gene, mRNA, and/or protein.

172. The AAV particle of embodiment 171, wherein the CNS related gene is chosen from SOD1, MAPT, APOE, HTT, C9ORF72, TDP-43, APP, BACE, SNCA, ATXN1, ATXN3, ATXN7, SCNIA-SCN5A, SCN8A-SCN11A, or a combination thereof.

173. The AAV particle of any one of embodiments 162-172, which comprises a viral genome comprising a promoter operably linked to the nucleic acid sequence encoding the payload.

174. The AAV particle of embodiment 173, wherein the promoter is chosen from human elongation factor 1α-sub-unit (EF1α), cytomegalovirus (CMV) immediate-early enhancer and/or promoter, chicken β-actin (CBA) and its derivative CAG, β glucuronidase (GUSB), or ubiquitin C (UBC), neuron-specific enolase (NSE), platelet-derived growth factor (PDGF), platelet-derived growth factor B-chain (PDGF-β), intercellular adhesion molecule 2 (ICAM-2), synapsin (Syn), methyl-CpG binding protein 2 (MeCP2), Ca2+/calmodulin-dependent protein kinase II (CaMKII), metabotropic glutamate receptor 2 (mGluR2), neurofilament light (NFL) or heavy (NFH), β-globin mini-gene nβ2, preproenkephalin (PPE), enkephalin (Enk) and excitatory amino acid transporter 2 (EAAT2), glial fibrillary acidic protein (GFAP), myelin basic protein (MBP), a car-diovascular promoter (e.g., aMHC, cTnT, and CMV-MLC2k), a liver promoter (e.g., hAAT, TBG), a skeletal muscle promoter (e.g., desmin, MCK, C512) or a fragment, e.g., a truncation, or a functional variant thereof.

175. The AAV particle of any one of embodiments 173 or 174, wherein the viral genome further comprises a polyA signal sequence.

176. The AAV particle of any one of embodiments 173-175, wherein the viral genome further comprises an inverted terminal repeat (ITR) sequence.

177. The AAV particle of any one of embodiments 173-176, wherein the viral genome comprises an ITR sequence positioned 5' relative to the encoded payload.

178. The AAV particle of any one of embodiments 173-177, wherein the viral genome comprises an ITR sequence positioned 3' relative to the encoded payload.

179. The AAV particle of any one of embodiments 173-178, wherein the viral genome comprises an ITR sequence positioned 5' relative to the encoded payload and an ITR sequence positioned 3' relative to the encoded payload.

180. The AAV particle of any one of embodiments 173-179, wherein the viral genome further comprises an enhancer, a Kozak sequence, an intron region, and/or an exon region.

181. The AAV particle of any one of embodiments 173-180, wherein the viral genome further comprises a miR binding site, e.g., a miR binding site that modulates, e.g., reduces, expression of the payload encoded by the viral genome in a cell or tissue where the corresponding miRNA is expressed.

182. The AAV particle of any one of embodiments 173-181, wherein the viral genome comprises at least 1-5 copies of a miR binding site, e.g., at least 1, 2, 3, 4, or 5 copies.

183. The AAV particle of any one of embodiments 173-182, wherein the viral genome comprises at least 3 copies of a miR binding site, optionally wherein all three copies comprise the same miR binding site, or at least one, two, or all of the copies comprise a different miR binding site.

184. The AAV particle of any one of embodiments 173-182, wherein the viral genome comprises at least 4 copies of a miR binding site, optionally wherein all four copies comprise the same miR binding site, or at least one, two, three, or all of the copies comprise a different miR binding site.

185. The AAV particle of any one of embodiments 181-184, wherein the miR binding site comprises a miR122 binding site, a miR 183 binding site, a miR-142-3p, or a combination thereof, optionally wherein:

(i) the miR122 binding site comprises the nucleotide sequence of SEQ ID NO: 3672, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, but no more than ten modifi-cations of SEQ ID NO: 3672;

(ii) the miR 183 binding site comprises the nucleotide sequence of SEQ ID NO: 3675, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, but no more than ten modifi-cations of SEQ ID NO: 3675; and/or (iii) the miR-142-3p binding site comprises the nucleotide sequence of SEQ ID NO: 3674, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, but no more than ten modifications of SEQ ID NO: 3674.

186. The AAV particle of any one of embodiments 173-185, wherein the viral genome is single stranded.

187. The AAV particle of any one of embodiments 173-186, wherein the viral genome further comprises a nucleotide sequence encoding a Rep protein, e.g., a non-structural protein, wherein the Rep protein comprises a Rep78 protein, a Rep68, Rep52 protein, and/or a Rep40 protein.

188. The AAV particle of embodiment 187, wherein the Rep78 protein, the Rep68 protein, the Rep52 protein, and/or the Rep40 protein are encoded by at least one Rep gene.

189. The AAV particle of any one of embodiments 173-188, wherein the viral genome further comprises a nucleic acid sequence encoding the AAV capsid variant of any one of embodiments 1-124 or 146.

190. The AAV particle of any one of embodiments, 162-189, which is isolated, e.g., recombinant.

191. A polypeptide comprising a parental amino acid sequence of any of SEQ ID NO: 1-1724, having inserted therein one or more targeting peptide inserts, said targeting peptide inserts comprising individually a contiguous amino acid sequence region of 2-9 amino acids selected from any of the targeting peptides of SEQ ID NO: 1725-3622.

192. The polypeptide of embodiment 191, wherein the polypeptide has a first targeting peptide insert, said first targeting peptide insert having a contiguous amino acid region of at least 5 amino acids selected from any of the targeting peptides of SEQ ID NO: 1725-3622.

193. An AAV capsid comprising VP1, VP2 and VP3 proteins, wherein each of said VP1, VP2 and VP3 proteins comprises a polypeptide of any of those of embodiment 191 or 192.

194. The polypeptide of embodiment 191, wherein the parental amino acid sequence is SEQ ID NO: 138.

195. The polypeptide of embodiment 194, wherein the parental amino acid sequence has the substitution, K449R.

196. The polypeptide of embodiment 194 or 195, wherein said first targeting peptide insert comprises the amino acid sequence PLNGAVHLY (SEQ ID NO: 3648) which is inserted immediately after amino acid 586 of the parental amino acid sequence.

197. The polypeptide of embodiment 196, further comprising a deletion of the amino acids "AQ" at positions 587-588 of the parental amino acid sequence.

198. The polypeptide of embodiment 194 or 195, wherein said first targeting peptide insert comprises the amino acid sequence GGTLAVVSL (SEQ ID NO: 3654) which is inserted immediately after amino acid 586 of the parental amino acid sequence.

199. The polypeptide of embodiment 198, further comprising a deletion of the amino acids "AQ" at positions 587-588 of the parental amino acid sequence.

200. The polypeptide of embodiment 194 or 195, wherein said first targeting peptide insert comprises a 7 amino acid sequence selected from RDSPKGW (SEQ ID NO: 3649), YSTDVRM (SEQ ID NO: 3650), RESPRGL (SEQ ID NO: 3652), SENDTRA (SEQ ID NO: 3653), YGLPKGP (SEQ ID NO: 3655) or STGTLRL (SEQ ID NO: 3656) which is inserted immediately after amino acid 589 of the parental amino acid sequence.

201. The polypeptide of embodiment 194 or 195, wherein said first targeting peptide insert comprises a 7 amino acid sequence IVMNSLK (SEQ ID NO: 3651) which is inserted immediately after amino acid 588 of the parental amino acid sequence.

202. The polypeptide of embodiment 191, wherein the parental amino acid sequence is SEQ ID NO: 5.

203. The polypeptide of embodiment 202, wherein the parental amino acid sequence has the substitution, K449R.

204. An AAV capsid comprising VP1, VP2 and VP3 proteins, wherein each of said VP1, VP2 and VP3 proteins comprises a polypeptide of any of those of embodiments 194-203.

205. A polynucleotide encoding the polypeptides or capsid proteins of any of embodiments 191-204.

206. The polynucleotide of embodiment 205, which is DNA and the DNA sequence is codon optimized.

207. An AAV particle comprising a capsid of any of embodiments 193 or 205 and a vector genome encoding a therapeutic payload.

208. The AAV particle of embodiment 207, wherein the therapeutic payload is a gene of interest.

209. The AAV particle of embodiment 208, wherein the therapeutic payload encodes a therapeutic RNA.

210. An AAV VP1 capsid selected from the group consisting of any of SEQ ID NO: 3636-3647.

211. A polynucleotide encoding any of the AAV VP1 capsid proteins of embodiment 210.

212. A vector comprising a polynucleotide encoding the AAV capsid variant of any one of embodiments 1-124 or 146, the polynucleotide of any one of embodiments 126-128, 147-161, 205-206, or 211, a polynucleotide encoding the peptide, e.g., targeting peptide, of any one of embodiments 129-145 or 161, or a polynucleotide encoding the polypeptide of any one of embodiments 191-192 or 194-203.

213. A cell, e.g., a host cell, comprising the AAV capsid variant of any one of embodiments 1-124 or 146, the polynucleotide of any one of embodiments 126-128, 147-161, 205-206, or 211, the peptide of any one of embodiments 129-145 or 161, the polypeptide of any one of embodiments 191-192 or 194-203, the AAV particle of any one of embodiments 162-190 or 207-209, or the vector of embodiment 212.

214. The cell of embodiment 213, wherein the cell is a mammalian cell or an insect cell.

215. The cell of embodiment 213 or 214, wherein the cell is a cell of a brain region or a spinal cord region, optionally a cell of the frontal cortex, sensory cortex, motor cortex, caudate, dentate nucleus, cerebellar cortex, cerebral cortex, brain stem, hippocampus, thalamus, putamen, cervical spinal cord region, thoracic spinal cord region, and/or lumbar spinal cord region.

216. The cell of embodiment 213 or 214, wherein the cell is a neuron, a sensory neuron, a motor neuron, an astrocyte, or a muscle cell (e.g., a cell of the heart, diaphragm, or quadriceps).

217. A method of making an AAV particle, comprising
(i) providing a host cell comprising a viral genome; and
(ii) incubating the host cell under conditions suitable to enclose the viral genome in the AAV capsid variant of any one of embodiments 1-124 or 146 or an AAV capsid variant encoded by the polynucleotide of any one of embodiments 125-128 or 147-161;
thereby making the AAV particle.

218. The method of embodiment 217, further comprising, prior to step (i), introducing a first nucleic acid molecule comprising the viral genome into the host cell.

219. The method of embodiment 217 or 218, wherein the host cell comprises a second nucleic acid encoding the capsid variant.

220. The method of any one of embodiments 217-219, wherein the second nucleic acid molecule is introduced into the host cell prior to, concurrently with, or after the first nucleic acid molecule.

221. A pharmaceutical composition comprising the AAV particle of any one of embodiments 162-190, an AAV particle comprising the capsid variant of any one of embodiments 1-124 or 146, an AAV particle comprising the peptide of any one of embodiments 129-145 or 161, or an AAV particle comprising the polypeptide of any one of embodiments 191-192 or 194-203, and a pharmaceutically acceptable excipient.

222. A method of delivering a payload to a cell or tissue (e.g., a CNS cell, a CNS tissue, a muscle cell, or a muscle tissue), comprising administering an effective amount of the pharmaceutical composition of embodiment 221, the AAV particle of any one of embodiments 162-190, an AAV particle comprising the capsid variant of any one of embodiments 1-124 or 146, an AAV particle comprising the peptide of any one of embodiments 129-145 or 161, or an AAV particle comprising the polypeptide of any one of embodiments 191-192 or 194-203.

223. The method of embodiment 222, wherein the cell is a cell of a brain region or a spinal cord region, optionally a cell of the frontal cortex, sensory cortex, motor cortex, caudate, dentate nucleus, cerebellar cortex, cerebral cortex, brain stem, hippocampus, thalamus, putamen, cervical spinal cord region, thoracic spinal cord region, and/or lumbar spinal cord region.

224. The method of embodiment 222 or 223, wherein the cell is a neuron, a sensory neuron, a motor neuron, an astrocyte, or a muscle cell (e.g., a cell of the heart, diaphragm, or quadriceps).

225. The method of any one of embodiments 222-224, wherein the cell or tissue is within a subject.

226. The method of embodiment 225, wherein the subject has, has been diagnosed with having, or is at risk of having a neurological, e.g., a neurodegenerative disorder.

227. The method of embodiment 225, wherein the subject has, has been diagnosed with having, or is at risk of having a muscular disorder or a neuromuscular disorder.

228. The method of embodiment 225, wherein the subject has, has been diagnosed with having, or is at risk of having a neuro-oncological disorder.

229. A method of treating a subject having or diagnosed with having a neurological disorder, e.g., a neurodegenerative disorder, comprising administering to the subject an effective amount of the pharmaceutical composition of embodiment 221, the AAV particle of any one of embodiments 162-190, an AAV particle comprising the capsid variant of any one of embodiments 1-124 or 146, an AAV particle comprising the peptide of any one of embodiments 129-145 or 161, or an AAV particle comprising the polypeptide of any one of embodiments 191-192 or 194-203.

230. A method of treating a subject having or diagnosed with having a muscular disorder or a neuromuscular disorder, comprising administering to the subject an effective amount of the pharmaceutical composition of embodiment 221, the AAV particle of any one of embodiments 162-190, an AAV particle comprising the capsid variant of any one of embodiments 1-124 or 146, an AAV particle comprising the peptide of any one of embodiments 129-145 or 161, or an AAV particle comprising the polypeptide of any one of embodiments 191-192 or 194-203.

231. A method of treating a subject having or diagnosed with having a neuro-oncological disorder, comprising administering to the subject an effective amount of the pharmaceutical composition of embodiment 221, the AAV particle of any one of embodiments 162-190, an AAV particle comprising the capsid variant of any one of embodiments 1-124 or 146, an AAV particle comprising the peptide of any one of embodiments 129-145 or 161, or an AAV particle comprising the polypeptide of any one of embodiments 191-192 or 194-203.

232. The method of any one of embodiments 229-231, where treating comprises prevention of progression of the disease or disorder in the subject.

233. The method of embodiment 225-232, wherein the subject is a human.

234. The method of any one of embodiments 225-233, wherein the AAV particle is administered to the subject intramuscularly, intravenously, intracerebrally, intrathecally, intracerebroventricularly, via intraparenchymal administration, or via intra-cisterna magna injection (ICM).

235. The method of any one of embodiments 225-233, wherein the AAV particle is administered to the subject via focused ultrasound (FUS), e.g., coupled with the intravenous administration of microbubbles (FUS-MB), or MRI-guided FUS coupled with intravenous administration.

236. The method of any one of embodiments 225-235, wherein the AAV particle is administered to the subject intravenously.

237. The method of any one of embodiments 222-236, wherein administration of the AAV particle results in a decreased presence, level, and/or activity of a gene, mRNA, protein, or combination thereof.

238. The method of any one of embodiments 222-148, wherein administration of the AAV particle results in an increased presence, level, and/or activity of a gene, mRNA, protein, or a combination thereof.

239. The pharmaceutical composition of embodiment 221, the AAV particle of any one of embodiments 162-190, an AAV particle comprising the capsid variant of any one of embodiments 1-124 or 146, an AAV particle comprising the polypeptide of any one of embodiments 129-145 or 161, or an AAV particle comprising the polypeptide of any one of embodiments 191-192 or 194-203, for use in a method of delivering a payload to a cell or tissue.

240. The pharmaceutical composition of embodiment 221, the AAV particle of any one of embodiments 162-190, an AAV particle comprising the capsid variant of any one of embodiments 1-124 or 196, an AAV particle comprising the polypeptide of any one of embodiments 129-145 or 161, or an AAV particle comprising the polypeptide of any one of embodiments 191-192 or 194-203, for use in a method of treating a neurological disorder, neurodegenerative, disorder, muscular disorder, neuromuscular disorder, or a neuro-oncological disorder.

241. The pharmaceutical composition of embodiment 221, the AAV particle of any one of embodiments 162-190, an AAV particle comprising the capsid variant of any one of embodiments 1-124 or 146, an AAV particle comprising the peptide of any one of embodiments 129-145 or 161, or an AAV particle comprising the polypeptide of any one of embodiments 191-192 or 194-203, for use in the manufacture of a medicament.

242. Use of the pharmaceutical composition of embodiment 221, the AAV particle of any one of embodiments 162-190, an AAV particle comprising the capsid variant of any one of embodiments 1-124 or 146, an AAV particle comprising the peptide of any one of embodiments 129-145 or 161, or an AAV particle comprising the polypeptide of any one of embodiments 191-192 or 194-203 in the manufacture of a medicament for treating a neurological disorder, a neurodegenerative disorder, a muscular disorder, a neuro-muscular disorder, or a neuro-oncological disorder.

BRIEF DESCRIPTION OF THE DRAWINGS

The foregoing and other objects, features, and advantages will be apparent from the following description of particular embodiments of the disclosure, as illustrated in the accompanying drawings. The drawings are not necessarily to scale, emphasis instead being placed upon illustrating the principles of various embodiments of the disclosure.

FIG. 4 provides a diagram of an exemplary TRACER™ AAV library design (SEQ ID NO: 3696-3699).

Figure 17B:
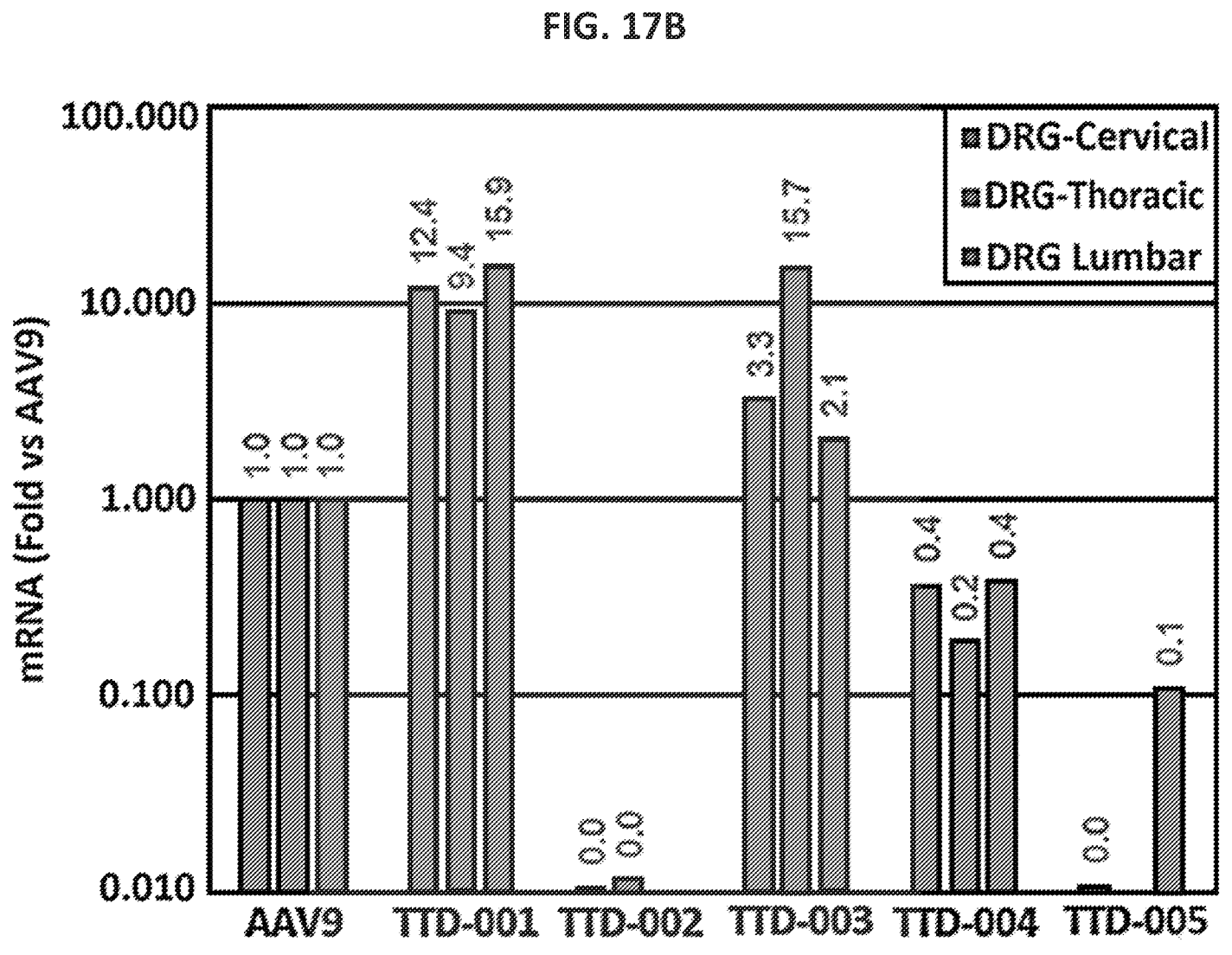

FIG. 17A and FIG. 17B show spinal cord (FIG. 17A) and DRG (FIG. 17B) mRNA expression as fold over AAV9.

Figure 18A:
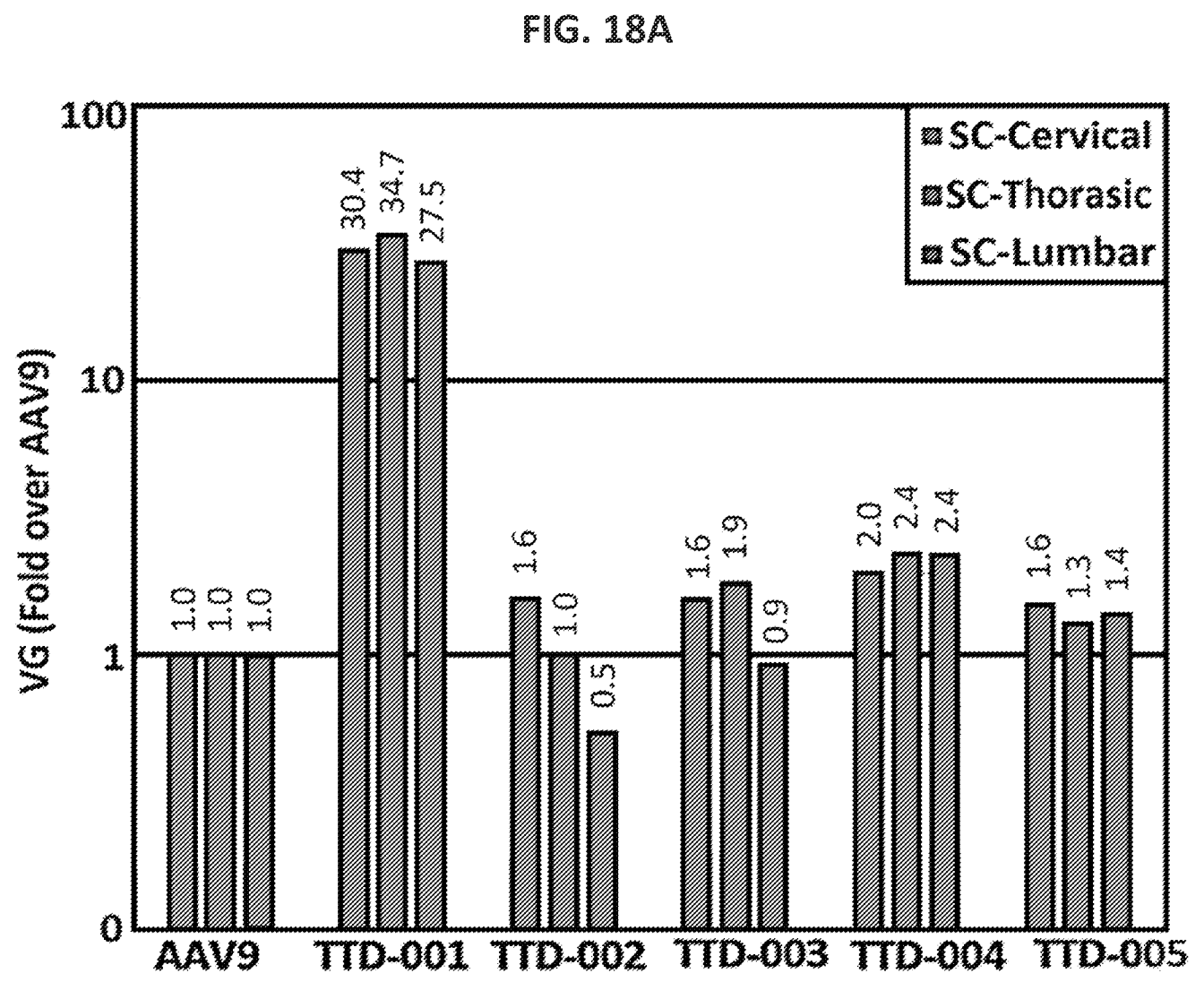

FIG. 18A and FIG. 18B show spinal cord (FIG. 18A) and DRG (FIG. 18B) viral genome biodistribution as fold over AAV9.

Figure 19A:
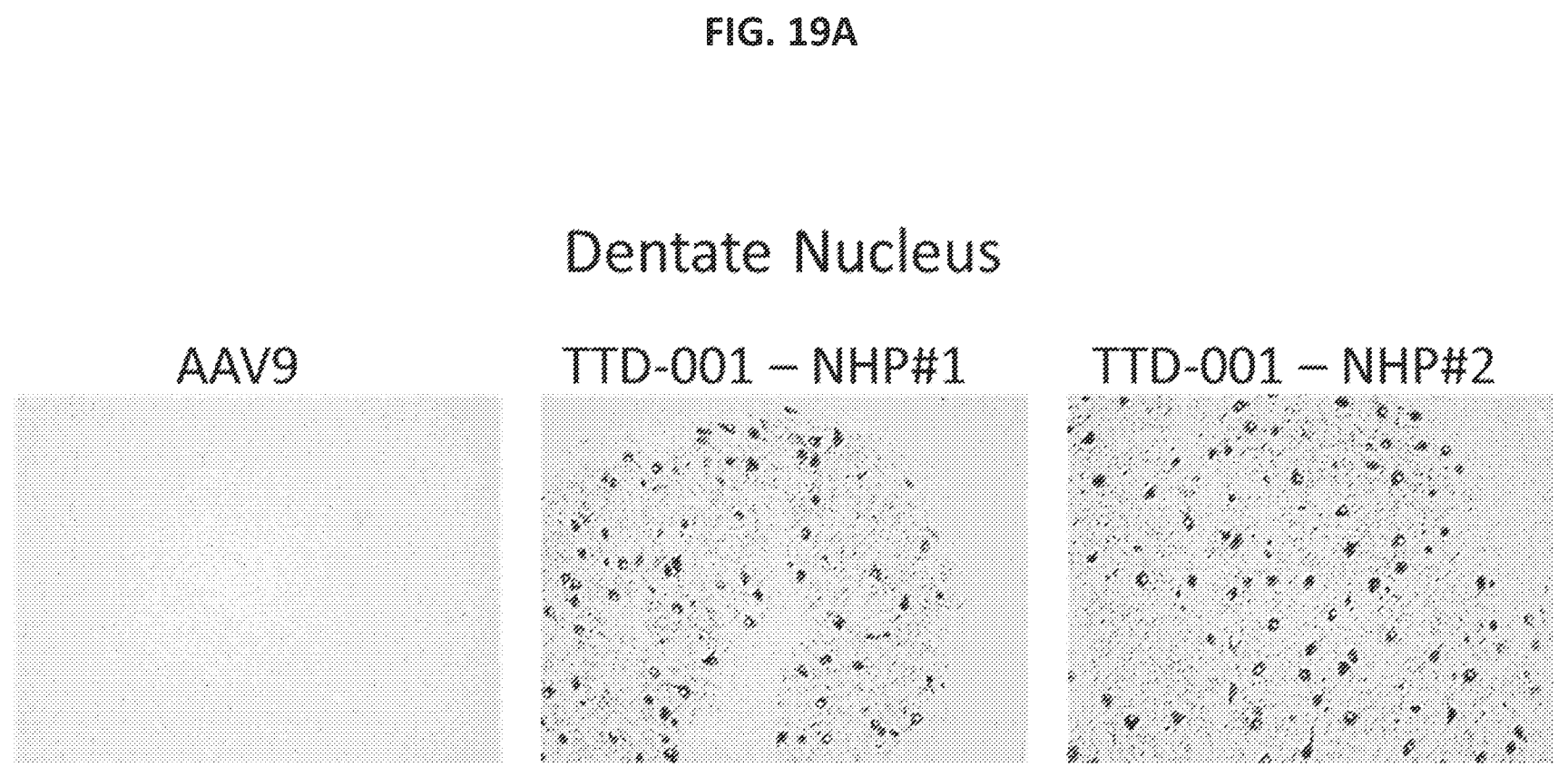

FIG. 19A, FIG. 19B, FIG. 19C, FIG. 19D, and FIG. 19E show images of the brain transduction profile for TTD-001 and AAV9 as determined by immunohistochemical analyses of the dentate nucleus (FIG. 19A), cerebellar cortex (FIG. 19B), cortex (FIG. 19C), brain stem, hippocampus, thalamus and putamen (FIG. 19D) and dorsal root ganglion (FIG. 19E).

FIG. 22A provides a series of global images of the heart muscle, FIG. 22B provides a series of images of the left ventricle of the heart, and FIG. 22C provides a series of images of the right ventricle of the heart. For each series of images in FIGS. 22A-22C, the top left panel shows staining following administration of AAV particles comprising a TTD-001 capsid variant, the top right panel shows staining following administration of AAV particles comprising a TTD-004 capsid variant, and the bottom panel shows staining following administration of AAV particles comprising a wild-type AAV9 control capsid variant.

DETAILED DESCRIPTION OF THE DISCLOSURE

Figure 1A:
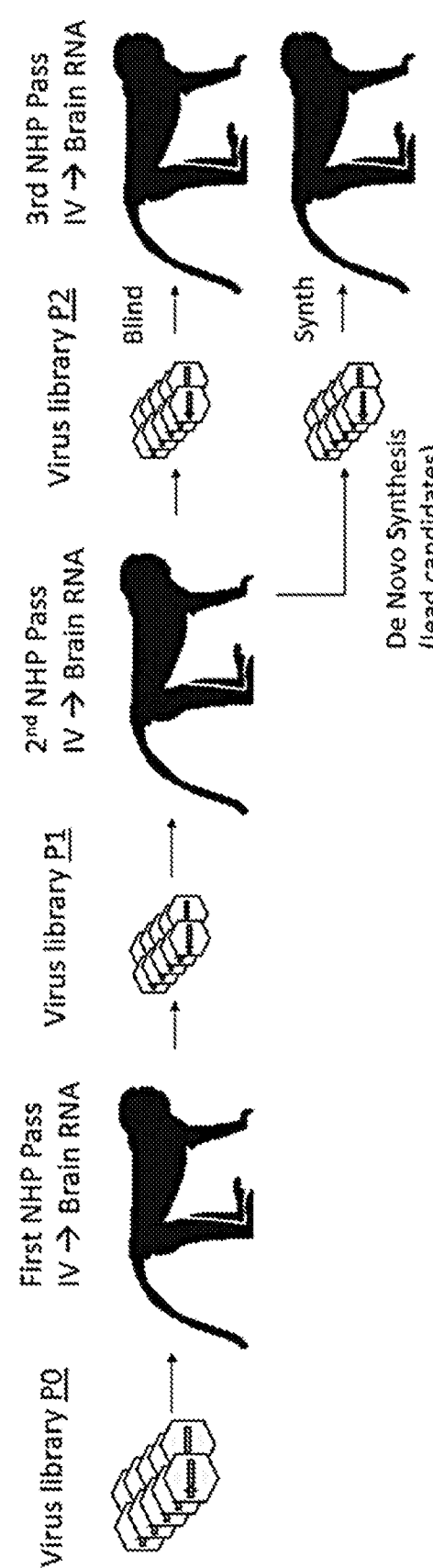
FIG. 1A and FIG. 1B provide diagrams of identification and design of non-human primate (NHP) TRACER™ AAV capsid libraries.

The details of one or more embodiments of the disclosure are set forth in the accompanying description below. Although any materials and methods similar or equivalent to those described herein can be used in the practice or testing of the present disclosure, the preferred materials and methods are now described. Other features, objects and advantages of the disclosure will be apparent from the description. In the description, the singular forms also include the plural unless the context clearly dictates otherwise. Unless defined otherwise, all technical and scientific terms used herein have the same meaning as commonly understood by one of ordinary skill in the art to which this disclosure belongs. In the case of conflict, the present description will control. Certain terms are defined in the Definition section and throughout.

Described herein, inter alia, are compositions comprising an AAV capsid polypeptide, e.g., an AAV capsid variant, e.g., an AAV capsid variant described herein, and methods of making and using the same. Generally, the AAV capsid variant has enhanced tropism for a cell or tissue, e.g., for the delivery of a payload to said cell or tissue, for example a CNS tissue, a CNS cell, a muscle cell, or a muscle tissue.

As demonstrated in the Examples herein below, certain AAV capsid variants described herein show multiple advantages over wild-type AAV9, including (i) increased penetrance through the blood brain barrier following intravenous administration, (ii) wider distribution throughout the multiple brain regions, e.g., frontal cortex, sensory cortex, motor cortex, putamen, thalamus, cerebellar cortex, dentate nucleus, caudate, and/or hippocampus, and/or (iii) elevated payload expression in multiple brain regions. Without wishing to be being bound by theory, it is believed that these advantages may be due, in part, to the dissemination of the AAV capsid variants through the brain vasculature. In some embodiments, the AAV capsids described herein enhance the delivery of a payload to multiple regions of the brain including for example, the frontal cortex, sensory cortex, motor cortex, putamen, thalamus, cerebellar cortex, dentate nucleus, caudate, and/or hippocampus.

According to the present disclosure, AAV particles with enhanced tropism for a target tissue (e.g., CNS) are provided, as well as associated processes for their targeting, preparation, formulation and use. Peptides, e.g., targeting peptides, and nucleic acid sequences encoding the peptides, e.g., targeting peptides, are also provided. These peptides, e.g., targeting peptides, may be inserted into an AAV capsid protein sequence to alter tropism to a particular cell-type, tissue, organ or organism, in vivo, ex vivo or in vitro.

Several approaches have been used previously to produce AAV capsids with enhanced tropism for a cell or tissue, e.g., a CNS cell or tissue. One approach used co-infection of cultured cells (Grimm et al., 2008, the contents of which are herein incorporated by reference in its entirety) or in situ animal tissue (Lisowski et al., 2014, the contents of which are herein incorporated by reference in its entirety) with adenovirus, in order to trigger exponential replication of infectious AAV DNA. Another approach involved the use of cell-specific CRE transgenic mice (Deverman et al., 2016. the contents of which are herein incorporated by reference in its entirety) allowing viral DNA recombination specifically in astrocytes, followed by recovery of CRE-recombined capsid variants. Both approaches have had limited success.

The transgenic CRE system used by Deverman et al. (2016) has limited tractable in other animal species and AAV variants selected by directed evolution in mouse tissue do not show similar properties in large animals. Previously described transduction-specific approaches are not amenable to large animal studies because: 1) many tissues of interest (e.g. CNS) are not readily accessible to adenovirus co-infection, 2) the specific adenovirus tropism itself would bias the library distribution, and 3) large animals are typically not amenable to transgenesis or genetic engineering to express CRE recombinase in defined cell types.

To address these limitations, a broadly-applicable functional AAV capsid library screening platform for cell type-specific biopanning in non-transgenic animals has been developed and is described in the appended Examples. In the TRACER™ (Tropism Redirection of AAV by Cell type-specific Expression of RNA) platform system, the capsid gene is placed under the control of a cell type-specific promoter to drive capsid mRNA expression in the absence of helper virus co-infection. Without wishing to be bound by theory, it is believed that this RNA-driven screen increases the selective pressure in favor of capsid variants which transduce a specific cell type. The TRACER™ platform allows for generation of AAV capsid libraries whereby specific recovery and subcloning of capsid mRNA expressed in transduced cells is achieved with no need for transgenic animals or helper virus co-infection. Without wishing to be bound by theory, it is believed that since mRNA transcription is a hallmark of full transduction, the methods disclosed herein allow identification of fully infectious AAV capsid mutants, and in addition to its higher stringency, this method allows identification of capsids with high tropism for particular cell types using libraries designed to express CAP mRNA under the control of any cell-specific promoter such as, but not limited to, synapsin-1 promoter (neurons), GFAP promoter (astrocytes), TBG promoter (liver), CAMK promoter (skeletal muscle), MYH6 promoter (cardiomyocytes). Described herein are novel AAV capsid variants generated using the TRACER™ method which demonstrate enhance tropism in for example a CNS cell, a CNS tissue, a muscle cell, or a muscle tissue.

The AAV particles and payloads of the disclosure may be delivered to one or more target cells, tissues, organs, or organisms. In some embodiments, the AAV particles of the disclosure demonstrate enhanced tropism for a target cell type, tissue or organ. As a non-limiting example, the AAV particle may have enhanced tropism for cells and tissues of the central or peripheral nervous systems (CNS and PNS, respectively), or cells and tissues of a muscle. The AAV particles of the disclosure may, in addition, or alternatively, have decreased tropism for an undesired target cell-type, tissue or organ.

In some embodiments, an AAV comprises a small non-enveloped icosahedral capsid virus of the Parvoviridae family and is characterized by a single stranded DNA viral genome. Parvoviridae family viruses consist of two subfamilies: Parvovirinae, which infect vertebrates, and Densovirinae, which infect invertebrates. The Parvoviridae family comprises the Dependovirus genus which includes AAV, capable of replication in vertebrate hosts including, but not limited to, human, primate, bovine, canine, equine, and ovine species.

The parvoviruses and other members of the Parvoviridae family are generally described in Kenneth I. Berns, "Parvoviridae: The Viruses and Their Replication," Chapter 69 in FIELDS VIROLOGY (3d Ed. 1996), the contents of which are incorporated by reference in their entirety.

In some embodiments, AAV are used as a biological tool due to a relatively simple structure, their ability to infect a wide range of cells (including quiescent and dividing cells) without integration into the host genome and without replicating, and their relatively benign immunogenic profile. The genome of the virus may be manipulated to contain a minimum of components for the assembly of a functional recombinant virus, or viral particle, which is loaded with or engineered to target a particular tissue and express or deliver a desired payload.

In some embodiments, the AAV, is a naturally occurring (e.g., wild-type) AAV or a recombinant AAV. In some embodiments, the wild-type AAV vector genome is a linear, single-stranded DNA (ssDNA) molecule approximately 5,000 nucleotides (nt) in length. In some embodiments, inverted terminal repeats (ITRs) cap the viral genome at both the 5' and the 3' end, providing origins of replication for the viral genome. In some embodiments, an AAV viral genome typically comprises two ITR sequences. These ITRs have a characteristic T-shaped hairpin structure defined by a self-complementary region (145 nt in wild-type AAV) at the 5' and 3' ends of the ssDNA which form an energetically stable double stranded region. The double stranded hairpin structures comprise multiple functions including, but not limited to, acting as an origin for DNA replication by functioning as primers for the endogenous DNA polymerase complex of the host viral replication cell.

In some embodiments, the wild-type AAV viral genome further comprises nucleotide sequences for two open reading frames, one for the four non-structural Rep proteins (Rep78, Rep68, Rep52, Rep40, encoded by Rep genes) and one for the three capsid, or structural, proteins (VP1, VP2, VP3, encoded by capsid genes or Cap genes). The Rep proteins are used for replication and packaging, while the capsid proteins are assembled to create the protein shell of the AAV, or AAV capsid polypeptide, e.g., an AAV capsid variant. Alternative splicing and alternate initiation codons and promoters result in the generation of four different Rep proteins from a single open reading frame and the generation of three capsid proteins from a single open reading frame. Though it varies by AAV serotype, as a non-limiting example, for AAV9/hu. 14 (SEQ ID NO: 123 of U.S. Pat. No. 7,906,111, the contents of which are herein incorporated by reference in their entirety) VP1 refers to amino acids 1-736, VP2 refers to amino acids 138-736, and VP3 refers to amino acids 203-736. In some embodiments, for any one of the amino acid sequences of SEQ ID NOs: 3636-3647, VP1 comprises amino acids 1-743, VP2 comprises amino acids 138-743, and VP3 comprises amino acids 203-743. In other words, VP1 is the full-length capsid sequence, while VP2 and VP3 are shorter components of the whole. As a result, changes in the sequence in the VP3 region, are also changes to VP1 and VP2, however, the percent difference as compared to the parent sequence will be greatest for VP3 since it is the shortest sequence of the three. Though described here in relation to the amino acid sequence, the nucleic acid sequence encoding these proteins can be similarly described. Together, the three capsid proteins assemble to create the AAV capsid protein. While not wishing to be bound by theory, the AAV capsid protein typically comprises a molar ratio of 1:1:10 of VP1:VP2:VP3.

AAV vectors of the present disclosure may be produced recombinantly and may be based on adeno-associated virus (AAV) parent or reference sequences. In addition to single stranded AAV viral genomes (e.g., ssAAVs), the present disclosure also provides for self-complementary AAV (scAAVs) viral genomes. scAAV vector genomes contain DNA strands which anneal together to form double stranded DNA. By skipping second strand synthesis, scAAVs allow for rapid expression in the transduced cell. In some embodiments, the AAV particle of the present disclosure is an scAAV. In some embodiments, the AAV particle of the present disclosure is an ssAAV.

Methods for producing and/or modifying AAV particles are disclosed in the art such as pseudotyped AAV vectors (PCT Patent Publication Nos. WO200028004; WO200123001; WO2004112727; WO2005005610; and WO2005072364, the content of each of which is incorporated herein by reference in its entirety).

As described herein, the AAV particles of the disclosure comprising an AAV capsid polypeptide, e.g., an AAV capsid variant, and a viral genome, have enhanced tropism for a cell-type or a tissue, e.g., a CNS cell-type, region, or tissue, or a muscle cell-type or tissue. In some embodiments, the AAV particles of the disclosure comprising a capsid with an inserted peptide, e.g., a targeting peptide, and a viral genome, may have enhanced tropism for a cell-type, region, or tissue of the human CNS or a muscle.

Peptides, e.g., Targeting Peptides

Disclosed herein are peptides, e.g., targeting peptides, and associated AAV particles comprising an AAV capsid polypeptide, e.g., an AAV capsid variant, with a peptide, e.g., targeting peptide insert, for enhanced or improved transduction of a target tissue (e.g., cells of the CNS or PNS). In some, embodiments, the peptide, e.g., targeting peptide, is an isolated, e.g., recombinant, peptide, e.g., targeting peptide. In some embodiments, the nucleic acid encoding the peptide, e.g., targeting peptide, is an isolated, e.g., recombinant nucleic acid.

In some embodiments, the peptide, e.g., targeting peptide, may direct an AAV particle to a cell, region, or tissue of the CNS. The cell of the CNS may be, but is not limited to, neurons (e.g., excitatory, inhibitory, motor, sensory, autonomic, sympathetic, parasympathetic, Purkinje, Betz, etc.), glial cells (e.g., microglia, astrocytes, oligodendrocytes) and/or supporting cells of the brain such as immune cells (e.g., T cells). The tissue of the CNS may be, but is not limited to, the cortex (e.g., frontal, parietal, occipital, temporal), thalamus, hypothalamus, striatum, putamen, caudate nucleus, hippocampus, entorhinal cortex, basal ganglia, or deep cerebellar nuclei.

In some embodiments, the peptide, e.g., targeting peptide, may direct an AAV particle to a cell, region, or tissue of the PNS. The cell or tissue of the PNS may be, but is not limited to, a dorsal root ganglion (DRG).

In some embodiments, the peptide, e.g., targeting peptide, may direct an AAV particle to the CNS (e.g., the cortex) after intravenous administration. In some embodiments, the peptide, e.g., targeting peptide, may direct an AAV particle to the CNS (e.g., the cortex) following focused ultrasound (FUS), e.g., coupled with the intravenous administration of microbubbles (FUS-MB), or MRI-guided FUS coupled with intravenous administration.

In some embodiments, the peptide, e.g., targeting peptide, may direct an AAV particle to the PNS (e.g., DRG) after intravenous administration. In some embodiments, the peptide, e.g., targeting peptide, may direct an AAV particle to the PNS (e.g., DRG) following focused ultrasound (FUS), e.g., coupled with the intravenous administration of microbubbles (FUS-MB), or MRI-guided FUS coupled with intravenous administration.

In some embodiments, the peptide, e.g., targeting peptide, may direct an AAV particle to a cell, region, or tissue of a muscle. In some embodiments, the muscle is a heart muscle. In some embodiments, the peptide, e.g., targeting peptide, may direct an AAV particle to a muscle cell, region, or tissue after intravenous administration.

A peptide, e.g., a targeting peptide, may vary in length. In some embodiments, the peptide, e.g., targeting peptide, is about 3 to about 20 amino acids in length. As non-limiting examples, the targeting peptide may be 3, 4, 5, 6, 7, 8, 9, 10, 11, 12, 13, 14, 15, 16, 17, 18, 19, 20 or 3-5, 3-8, 3-10, 3-12, 3-15, 3-18, 3-20, 5-10, 5-15, 5-20, 10-12, 10-15, 10-20, 12-20, or 15-20 amino acids in length. In some embodiments, a peptide comprises about 6 to 12 amino acids in length, e.g., about 9 amino acids in length. In some embodiments, a peptide comprises about 5 to 10 amino acids in length, e.g., about 7 amino acids in length.

A peptide, e.g., a targeting peptide, may be contiguous (or continuous) or noncontiguous (or not continuous), or split, or divided across two or more amino acid sequences by intervening amino acid sequences that may vary in length. The contiguous peptide, e.g., targeting peptide, may vary in length. As non-limiting examples, the contiguous peptide, e.g., targeting peptide, may be 3, 4, 5, 6, 7, 8, 9, 10, 11, 12, 13, 14, 15, 16, 17, 18, 19, 20 or 3-5, 3-8, 3-10, 3-12, 3-15, 3-18, 3-20, 5-10, 5-15, 5-20, 10-12, 10-15, 10-20, 12-20, or 15-20 amino acids in length. The noncontiguous, or split, peptide, e.g., targeting peptide, may vary in length. As non-limiting examples, the noncontiguous, or split, peptide, e.g., targeting peptide, may be 3, 4, 5, 6, 7, 8, 9, 10, 11, 12, 13, 14, 15, 16, 17, 18, 19, 20 or 3-5, 3-8, 3-10, 3-12, 3-15, 3-18, 3-20, 5-10, 5-15, 5-20, 10-12, 10-15, 10-20, 12-20, or 15-20 amino acids in length. The intervening amino acid sequence may vary in length. As non-limiting examples, the intervening peptide, e.g., targeting peptide, may be 3, 4, 5, 6, 7, 8, 9, 10, 11, 12, 13, 14, 15, 16, 17, 18, 19, 20 or 3-5, 3-8, 3-10, 3-12, 3-15, 3-18, 3-20, 5-10, 5-15, 5-20, 10-12, 10-15, 10-20, 12-20, or 15-20 amino acids in length.

In some embodiments, a peptide, e.g., a targeting peptide, of the present disclosure may be identified and/or designed by any sliding window algorithm known in the art.

In some embodiments, a peptide, e.g., a targeting peptide, and associated AAV particle (e.g., an AAV particle comprising an AAV capsid polypeptide, e.g., an AAV capsid variant) may be identified from libraries of AAV capsid polypeptides, e.g., AAV capsid variants. In some embodiments, the peptide, e.g., targeting peptide, may be a 5-10 amino acid sequence, e.g., a 6-10 amino acid sequence, a 6-9 amino acid sequence, a 7-10 amino acid sequence, a 7-9 amino acid sequence, an 8-10 amino acid sequence, a 7 amino acid sequence, an 8 amino acid sequence, or a 9 amino acid sequence. In some embodiments, the peptide, e.g., targeting peptide, may be a 5 amino acid sequence (5-mer). In some embodiments, the peptide, e.g. targeting peptide, may be a 6 amino acid sequence (6-mer). In some embodiments, the peptide, e.g., targeting peptide, may be a 7 amino acid sequence (7-mer). In some embodiments, the peptide, e.g., targeting peptide, may be a 9 amino acid sequence (9-mer). In some embodiments, the peptides, e.g., targeting peptides, may also differ in their method of creation or design, with non-limiting examples including, random peptide selection, site saturation mutagenesis, and/or optimization of a particular region of the peptide (e.g., flanking regions or central core).

In some embodiments, a peptide library, e.g., a targeting peptide library, comprises targeting peptides of 7 amino acids (7-mer) in length randomly generated by PCR.

In some embodiments, a peptide, e.g., a targeting peptide, library comprises peptides, e.g., targeting peptides, with 3 mutated amino acids. In some embodiments, these 3 mutated amino acids are consecutive, or contiguous, amino acids. In another embodiment, these 3 mutated amino acids are not consecutive, or noncontiguous, or split, amino acids. In some embodiments, the peptide, e.g., targeting peptide, is a 5-mer. In some embodiments, the peptide, e.g., targeting peptide, is a 6-mer. In some embodiments, the parent peptide, e.g., targeting peptide, is a 7-mer. In another embodiment, the parent peptide is a 9-mer.

In some embodiments, a peptide, e.g. a targeting peptide, library comprises 7-mer peptides, e.g., targeting peptides, wherein the amino acids of the peptide, e.g., targeting peptide, and/or the flanking sequences are evolved through site saturation mutagenesis of 3 consecutive amino acids. In some embodiments, NNK (N=any base; K=G or T) codons are used to generate the site saturated mutation sequences.

AAV particles comprising capsid proteins with a peptide, e.g., a targeting peptide, insert (e.g., an AAV capsid variant) are generated and viral genomes encoding a reporter (e.g., GFP) encapsulated within. These AAV particles (or AAV capsid library) comprising AAV capsid variants are then administered to a transgenic rodent (e.g. mouse) by intravenous delivery to the tail vein. Administration of these capsid libraries to cre-expressing mice results in expression of the reporter payload in the target tissue, due to the expression of Cre.

In some embodiments, AAV capsid mRNA expression may be modulated, e.g., under the control of, or driven by, a cell-type specific promoter. Such capsids, which may comprise peptide, e.g., targeting peptide, inserts and viral genomes encoding a reporter encapsulated within, may be administered, e.g., by intravenous delivery to the tail vein, to a non-transgenic rodent (e.g. mouse), such as but not limited to a C57BL/6 mouse, a BALB/C mouse and a rat. Administration of such capsid libraries to a non-transgenic rodent may result in the expression of the reporter payload in the target tissue, due to the cell-type specific promoter.

In some embodiments, AAV capsid mRNA expression may be under the control of, or driven by, a cell-type specific promoter. Such capsids, which may comprise a peptides, e.g., targeting peptide inserts, and viral genomes encoding a reporter encapsulated within, may be administered, e.g., by intravenous delivery to the saphenous vein, to a non-human primate, such as but not limited to a cynomolgus macaque and a rhesus macaque. Administration of such capsid libraries to a non-human primate may result in the expression of the reporter payload in the target tissue, due to the cell-type specific promoter In some embodiments, AAV particles comprising capsid proteins with peptide, e.g., targeting peptide, inserts may hereinafter also be referred to as peptide display capsid libraries.

AAV particles and/or viral genomes may be recovered from the target tissue for identification of peptides, e.g., targeting peptides, and associated AAV particles that are enriched, indicating enhanced transduction of target tissue. Standard methods in the art, such as, but not limited to next generation sequencing (NGS), viral genome quantification, biochemical assays, immunohistochemistry and/or imaging of target tissue samples may be used to determine enrichment.

A target tissue may be any cell, tissue or organ of a subject. As non-limiting examples, samples may be collected from brain, spinal cord, dorsal root ganglia and associated roots, liver, heart, gastrocnemius muscle, soleus muscle, pancreas, kidney, spleen, lung, adrenal glands, stomach, sciatic nerve, saphenous nerve, thyroid gland, eyes (with or without optic nerve), pituitary gland, skeletal muscle (rectus femoris), colon, duodenum, ileum, jejunum, skin of the leg, superior cervical ganglia, urinary bladder, ovaries, uterus, prostate gland, testes, and/or any sites identified as having a lesion, or being of interest.

In some embodiments a peptide, e.g., a targeting peptide, may comprise a sequence as set forth in Table 1. In some embodiments a peptide, e.g., a targeting peptide, may comprise a sequence as set forth in Table 2. In some embodiments, the peptide, e.g., targeting peptide, comprises an amino acid sequence of any one of peptide 1, 2, 3, 4, 5, 6, 7, 8, 9, 10, 11, or 12. e.g., as described in Table 2. In some embodiments, the peptide. e.g., targeting peptide, is isolated, e.g., recombinant.

TABLE 1

Exemplary Peptide Sequences, e.g., Targeting Peptides

| Peptide Sequence | SEQ ID NO: |
|---|---|
| PLNGAVHLYA | 1725 |
| AQARDSPKGW | 1726 |
| LTNGAVRDRP | 1727 |
| VQAFTHDSRG | 1728 |
| AQAYSTDVRM | 1729 |
| AQAYSTDVRI | 1730 |
| AQAFTAAERM | 1731 |
| AQTHLQIGVA | 1732 |
| AQSNAVLSLA | 1733 |
| AQAYSTDERM | 1734 |
| AQAYSTDVRL | 1735 |
| AQATVSTLRM | 1736 |
| AQAYSTDERK | 1737 |
| AQAYSTDMRM | 1738 |

TABLE 1-continued

| Exemplary Peptide Sequences, e.g., Targeting Peptides | |
| --- | --- |
| Peptide Sequence | SEQ ID NO: |
| VVNGAVLHVA | 1739 |
| AQAYSTDVTM | 1740 |
| AQAHLQIGVA | 1741 |
| FLDPAVSSKA | 1742 |
| AQAYVSTLRM | 1743 |
| AQAQTGPPLK | 1744 |
| EQASRLPTPG | 1745 |
| AQASVSTMRM | 1746 |
| TDYSAVRLGA | 1747 |
| TQAYSTDVRM | 1748 |
| AQALPSNERL | 1749 |
| AQAYSTDVRT | 1750 |
| AQSSLPEMVA | 1751 |
| AQAGEQSTRL | 1752 |
| AQASNDVGRA | 1753 |
| AQATFTASEY | 1754 |
| AKAHAGTIYS | 1755 |
| AQARTIDQCC | 1756 |
| AQEYNSNPKA | 1757 |
| AQVVDNSTHA | 1758 |
| AQATLSVPLK | 1759 |
| AQIVMNSLKA | 1760 |
| AQATMSQTMA | 1761 |
| AQALTQDERW | 1762 |
| AQAQLSTLRP | 1763 |
| AQVVMGISVA | 1764 |
| AQAYTTDVRM | 1765 |
| AQHIDSMRPP | 1766 |
| AQASTGTLRL | 1767 |
| AQHRALDYYA | 1768 |
| AQARESPRGL | 1769 |
| AQALLAGTRV | 1770 |
| TKIQAVPWNA | 1771 |
| AQASLSSTRP | 1772 |
| AQAMGSRSDQ | 1773 |
| AQAAQGTYRG | 1774 |

TABLE 1-continued

| Exemplary Peptide Sequences, e.g., Targeting Peptides | |
| --- | --- |
| Peptide Sequence | SEQ ID NO: |
| SQENAVFSKA | 1775 |
| AQALSLSTRP | 1776 |
| AQAAAGTLRD | 1777 |
| AQASRLPTPG | 1778 |
| AQAGSLSERG | 1779 |
| AQSKGDGFTA | 1780 |
| GAGTAVTATA | 1781 |
| AQAQGSSSVG | 1782 |
| AQAYSTDARM | 1783 |
| ERAHAVTGLA | 1784 |
| AQAYGLPKGP | 1785 |
| AQAYSTEVRM | 1786 |
| AQAGVSTALH | 1787 |
| AQSYSTDVRM | 1788 |
| AQPLMSHTDA | 1789 |
| AQAAALASRP | 1790 |
| AQAAITSTIS | 1791 |
| AQPANDGLRA | 1792 |
| AQDYSTDVRM | 1793 |
| AQATLGYSTA | 1794 |
| AQATLGTIRV | 1795 |
| AQAGASDMVH | 1796 |
| AQAVSGTVRS | 1797 |
| GGTLAVVSLA | 1798 |
| AQAYSADVRM | 1799 |
| AQAFAMPKGL | 1800 |
| AQALVSTSRP | 1801 |
| AQASFQQAST | 1802 |
| AQAMTGNDRS | 1803 |
| AQASTQSPPG | 1804 |
| NARSAVESLA | 1805 |
| AQITVSHTTA | 1806 |
| AQALAGYDKA | 1807 |
| AQSTSHDTRA | 1808 |
| AQAIQDRTVV | 1809 |
| AQSKTTLTLA | 1810 |
| AQASMGTVRL | 1811 |

TABLE 1-continued

Exemplary Peptide Sequences,
e.g., Targeting Peptides

| Peptide Sequence | SEQ ID NO: |
|---|---|
| AQHSDTLTRA | 1812 |
| AQKEMYTSVA | 1813 |
| AQASPSQPLL | 1814 |
| AQAYAGTIYS | 1815 |
| AQARSLEPVI | 1816 |
| TQAGVSTAVH | 1817 |
| AQNTLSLSLA | 1818 |
| AQAYVSSVKM | 1819 |
| AQAATSPRLG | 1820 |
| GYLTAVQPQA | 1821 |
| LNNLAVGMTA | 1822 |
| AQTVSVHVRA | 1823 |
| AQINGLVTTA | 1824 |
| AQAAITTTIS | 1825 |
| AQASTFVTTI | 1826 |
| AQALYDNVPL | 1827 |
| AQAAAGTWKG | 1828 |
| AQATTGTLRS | 1829 |
| GQYAADSSYA | 1830 |
| AQAGIATVRT | 1831 |
| AQALGHELRA | 1832 |
| AQAREAIPQG | 1833 |
| AQAMSGTLRM | 1834 |
| AQAVDRVRPP | 1835 |
| AQAPVNNDRG | 1836 |
| AQAQQVAGTM | 1837 |
| AQAEPRDTRA | 1838 |
| AQRLSEQGVA | 1839 |
| AQASEGIQLS | 1840 |
| AQRQGPDPLA | 1841 |
| AQVTLGSAKA | 1842 |
| AQAGASLGLA | 1843 |
| AQAFTQDERW | 1844 |
| AQASQTTVRS | 1845 |
| AQARVSSNGV | 1846 |
| AQGPLSGLRA | 1847 |

TABLE 1-continued

Exemplary Peptide Sequences,
e.g., Targeting Peptides

| Peptide Sequence | SEQ ID NO: |
|---|---|
| AQAYGGQSLG | 1848 |
| AQANLGTVRQ | 1849 |
| AQARSDTRGL | 1850 |
| AQAGSDGPRL | 1851 |
| TDGAAVVMRA | 1852 |
| SGITAVPLHA | 1853 |
| AQAAAVGHLP | 1854 |
| AQRVEPKWIA | 1855 |
| AQAVASSPYA | 1856 |
| TQYGAVEGQD | 1857 |
| AQAKSHTLEG | 1858 |
| AQTHLQIVVA | 1859 |
| AQKNEHGMLA | 1860 |
| AQITVSHTRA | 1861 |
| AQARLAPKGL | 1862 |
| KTPGAVSTTA | 1863 |
| AQAFSGTIKS | 1864 |
| PLNGAVNLYA | 1865 |
| AQALTQDERC | 1866 |
| AQATAQVQRS | 1867 |
| AQTPALINLA | 1868 |
| AQASDRSPLL | 1869 |
| AQITVSHTMA | 1870 |
| AQATGTHLMG | 1871 |
| LDGGAVVVTA | 1872 |
| LTNGAVRDRA | 1873 |
| AQARGSDLRD | 1874 |
| AQATFGTQRI | 1875 |
| AQALPQTNRP | 1876 |
| AQARSNDPVL | 1877 |
| AQAYLAVQNG | 1878 |
| AQATQSTLRP | 1879 |
| AQALGGFGPQ | 1880 |
| LVGQAVGSRA | 1881 |
| AQSIANVVVA | 1882 |
| AQASPSVSRP | 1883 |
| AQTVVVSTTA | 1884 |

TABLE 1-continued

Exemplary Peptide Sequences,
e.g., Targeting Peptides

| Peptide Sequence | SEQ ID NO: |
| --- | --- |
| VKEQAVSVMA | 1885 |
| AQQATGTFRA | 1886 |
| AQAQGSSSGG | 1887 |
| AQAHAVGPQG | 1888 |
| AQRLETKETA | 1889 |
| AQLAQGIGVA | 1890 |
| AQAVQSSFTI | 1891 |
| AQATYTASEY | 1892 |
| AQTSSQNLKA | 1893 |
| AQLVPSVAMA | 1894 |
| AQASPSAFAG | 1895 |
| AQALALVSAS | 1896 |
| AQASVGTTYT | 1897 |
| AQARVSSSGT | 1898 |
| NSMGAVLGAA | 1899 |
| AQHTDTLTRA | 1900 |
| AQPNLQPRGA | 1901 |
| AQADRHSSIV | 1902 |
| SPSVAVPSQA | 1903 |
| AQPGIVSTIA | 1904 |
| AQAQHSVGLP | 1905 |
| AQTNSGAILA | 1906 |
| AQDSYDVGRA | 1907 |
| EQAQGSSSVG | 1908 |
| AQAGVSTAVQ | 1909 |
| AQARDMLPLQ | 1910 |
| AQAMVGTLRG | 1911 |
| AQPNVVSTLA | 1912 |
| AQAGHVVTSD | 1913 |
| AQAYTTDERM | 1914 |
| TAVSAVQVMA | 1915 |
| AQAAAGTLRV | 1916 |
| VSNEAVHARA | 1917 |
| AQVLPQSLSA | 1918 |
| AQASVSTLRM | 1919 |
| AQAGLLLSVA | 1920 |

TABLE 1-continued

Exemplary Peptide Sequences,
e.g., Targeting Peptides

| Peptide Sequence | SEQ ID NO: |
| --- | --- |
| AQANLVTGPL | 1921 |
| AQASQHSSMA | 1922 |
| GYSSAVSSVA | 1923 |
| AQVGVSPAVA | 1924 |
| DGTLAVPFKA | 1925 |
| AQAPPTSTAM | 1926 |
| AQATPANVRG | 1927 |
| AQAGSSNFLS | 1928 |
| AQLLAQDIRA | 1929 |
| AQPSSDGYRA | 1930 |
| AQALIGTLRT | 1931 |
| SVHGAVGILA | 1932 |
| AQPYVVSGAA | 1933 |
| AQWTHNITAA | 1934 |
| PTNAAVRTNA | 1935 |
| AHAYSTDVRM | 1936 |
| PLAAAVGMKA | 1937 |
| AQARDNSVML | 1938 |
| AQAQFPRNGG | 1939 |
| GALNAVNGVA | 1940 |
| AQASHQQGVP | 1941 |
| SYQSAVVPQA | 1942 |
| AQSIMGTIRA | 1943 |
| AQAYVSQAQG | 1944 |
| AQATGNQAHF | 1945 |
| AQVTVGTPIA | 1946 |
| AQAQTSTFRG | 1947 |
| SVHMAVTVSA | 1948 |
| AQAQSTLNLG | 1949 |
| AQDQTGPPLK | 1950 |
| HLAHAVSTAA | 1951 |
| AQALARDSSF | 1952 |
| AQLLSGTLKA | 1953 |
| AQASLLPTPG | 1954 |
| AQPMAGQSTA | 1955 |
| AQARSLEPDI | 1956 |
| AQFVTGNQDA | 1957 |

TABLE 1-continued

Exemplary Peptide Sequences,
e.g., Targeting Peptides

| Peptide Sequence | SEQ ID NO: |
| --- | --- |
| AQATFKTSVP | 1958 |
| LNARAVEGPA | 1959 |
| AQALPNSGRP | 1960 |
| AQALNGSPEA | 1961 |
| AQATSLHPLP | 1962 |
| AQAVQPPLKN | 1963 |
| AQAMLSGTRI | 1964 |
| AQHVDLASKA | 1965 |
| AQASFATMRP | 1966 |
| AQAMPLNARS | 1967 |
| AQALVGQMRG | 1968 |
| VVNGAVLHLA | 1969 |
| AQAQTAPPLK | 1970 |
| AQGHGDLHRA | 1971 |
| AQAADRSPVH | 1972 |
| GALNAVTGVA | 1973 |
| AQAERMASLG | 1974 |
| AQAPPTTTRL | 1975 |
| AQAAVGQTLA | 1976 |
| AQSLGTGMHA | 1977 |
| AQSLGSPALA | 1978 |
| AQASVSVTRP | 1979 |
| AQATMSHTMA | 1980 |
| AQAVQSLTVG | 1981 |
| AQSQTGTYRA | 1982 |
| AQSLASVYAA | 1983 |
| STKLAVHEQA | 1984 |
| AQSHLFPTPA | 1985 |
| AQGTWSSSEA | 1986 |
| AQTPQGLTKA | 1987 |
| AQVSLGTQYA | 1988 |
| AQDSRLPTPG | 1989 |
| ASIQAVGVKA | 1990 |
| AQATMSEQRL | 1991 |
| TAQAAVQGMA | 1992 |
| AQAFNAAERM | 1993 |

TABLE 1-continued

Exemplary Peptide Sequences,
e.g., Targeting Peptides

| Peptide Sequence | SEQ ID NO: |
| --- | --- |
| AQINFLSGVA | 1994 |
| PQHLAVSSEA | 1995 |
| AQALGNFPAV | 1996 |
| AQANASTVRV | 1997 |
| AQRIVDLTTA | 1998 |
| VRQVAVEGVA | 1999 |
| AQAPASSQKL | 2000 |
| AQQIDSMRPA | 2001 |
| AQAHGTSSLF | 2002 |
| AQVNSGIALA | 2003 |
| AQLHLAETRA | 2004 |
| AQALTHDERW | 2005 |
| NTVRAVIMEA | 2006 |
| AQAYVAGSRP | 2007 |
| AQDRAFVVSA | 2008 |
| AQAQEKQVFS | 2009 |
| AQACVSTAVH | 2010 |
| AQAFTHDSRG | 2011 |
| AQASHQGTVG | 2012 |
| AQAVLVTEQG | 2013 |
| AQAVVSTAVH | 2014 |
| AQATSRETKG | 2015 |
| YQQPAVSSRA | 2016 |
| AQANMGLSLS | 2017 |
| AQWTSSMSEA | 2018 |
| AQASISIMST | 2019 |
| AQASVAPLTC | 2020 |
| AQLVTVEKQA | 2021 |
| AQAATAGEKL | 2022 |
| AQALSHGPGG | 2023 |
| AQSNAHIEIA | 2024 |
| AQARSSSTGI | 2025 |
| AQAVGGDVTR | 2026 |
| AQAPRTVYQG | 2027 |
| AQALHNLGPA | 2028 |
| VRMGAVSDNA | 2029 |
| AQAFRTSQFT | 2030 |

TABLE 1-continued

Exemplary Peptide Sequences,
e.g., Targeting Peptides

| Peptide Sequence | SEQ ID NO: |
|---|---|
| AQSSATMQRA | 2031 |
| AQTLAETYRA | 2032 |
| AQANGSIVLN | 2033 |
| AQARVADQLP | 2034 |
| AQAVKQGLYE | 2035 |
| AQAFSDGLKS | 2036 |
| AQVSVTPVKA | 2037 |
| VNGRAVSMMA | 2038 |
| SLVGAVAQMA | 2039 |
| AQARVSPVGL | 2040 |
| AQSNTILILA | 2041 |
| AQTSTEHLRA | 2042 |
| AQAGMGINLP | 2043 |
| AQANAHSLTL | 2044 |
| AQARFTTIEM | 2045 |
| AQLGYQEVKA | 2046 |
| AQAGQHASVF | 2047 |
| AQATGSNPRG | 2048 |
| AQAPVSPSIP | 2049 |
| AQTTLGVGTA | 2050 |
| AQASHLVSLA | 2051 |
| AQAPLTGLSV | 2052 |
| AQVSTSTLRA | 2053 |
| AQVQLGTLKA | 2054 |
| AQAHVSVSER | 2055 |
| AQLLLSGQTA | 2056 |
| TTSSAVLTPA | 2057 |
| AQFGADTVNA | 2058 |
| AQTFSSDNLA | 2059 |
| AQIHPANSRA | 2060 |
| AQSIGQFPVA | 2061 |
| AQVISPENLA | 2062 |
| AQALSAISAT | 2063 |
| AQAGVSASQM | 2064 |
| AQASTKTPLP | 2065 |
| AQAPPSTTAM | 2066 |

TABLE 1-continued

Exemplary Peptide Sequences,
e.g., Targeting Peptides

| Peptide Sequence | SEQ ID NO: |
|---|---|
| AQAVSSDRMH | 2067 |
| AQAGSVTMRL | 2068 |
| AQAVLLGGAV | 2069 |
| AQAQRDMVTT | 2070 |
| AQAHHGSSLG | 2071 |
| VLSSAVGQRA | 2072 |
| AQAAGSVLLG | 2073 |
| AQAYPTDVRM | 2074 |
| AQWSRDAQSA | 2075 |
| AQQGLDMGRA | 2076 |
| AQAAQNHALV | 2077 |
| AQRSQIVEVA | 2078 |
| AQMSDVSGRA | 2079 |
| AKALTQDERW | 2080 |
| AQAVSSSTLT | 2081 |
| AQPSRLPTPG | 2082 |
| RTSTAVLDFA | 2083 |
| AQDLSSSIRA | 2084 |
| AQLLDGLTSA | 2085 |
| AQALIGLSKP | 2086 |
| AQASGTVRPP | 2087 |
| AQLLDTRYKA | 2088 |
| AQAPNTSFTA | 2089 |
| AQTHLQIGVD | 2090 |
| AQRLDTSQVA | 2091 |
| AQRTQDTLSA | 2092 |
| AQADIQSHAL | 2093 |
| PNMNAVGIKA | 2094 |
| AQAGVSTAVH | 2095 |
| AQASGKTFIG | 2096 |
| AQAGVQSTRL | 2097 |
| AQAQGAYPLV | 2098 |
| AQPYSTDVRM | 2099 |
| SSSVAVVTLA | 2100 |
| AQTYNGLNKA | 2101 |
| AQASVSKLRM | 2102 |
| AQRGSENEKA | 2103 |

47

TABLE 1-continued

TABLE 1-continued

Exemplary Peptide Sequences,
e.g., Targeting Peptides

Exemplary Peptide Sequences,
e.g., Targeting Peptides

| Peptide Sequence | SEQ ID NO: |
|---|---|
| PITNAVLKTA | 2104 |
| TNSYAVSSPA | 2105 |
| PYQTAVAGAA | 2106 |
| GPALAVLGRA | 2107 |
| LSISAVPAKA | 2108 |
| AQTLGPLPHA | 2109 |
| AQAQQPLAHV | 2110 |
| AQTDGAWSKA | 2111 |
| AQALSGPPSI | 2112 |
| AQASSPSTRG | 2113 |
| AQASLASNRP | 2114 |
| AQNMALSTVA | 2115 |
| AQHSDTMTRA | 2116 |
| AQAMPRYPPL | 2117 |
| AQHIDSMSPA | 2118 |
| AQALPGTSRV | 2119 |
| AQAKSTQDVQ | 2120 |
| AQPLVSASKA | 2121 |
| AQAMSGTLRK | 2122 |
| AQTLILGAHA | 2123 |
| AQAGQARSQG | 2124 |
| AQRKDLSLVA | 2125 |
| AQALSAPMSL | 2126 |
| TNSLAVGMRA | 2127 |
| AQAPIGTVRP | 2128 |
| FIQAAVSSSA | 2129 |
| AQAEKPTHLL | 2130 |
| AQALSGDTTR | 2131 |
| AQAYIASGGT | 2132 |
| QLNQAVGTLA | 2133 |
| AQASGALDRP | 2134 |
| AQAQDTALRA | 2135 |
| AQAQAGMARG | 2136 |
| AQAQGSSAVG | 2137 |
| AQLLRDIGPA | 2138 |
| VDRGAVTQMA | 2139 |

| Peptide Sequence | SEQ ID NO: |
|---|---|
| AQAVNVSKGS | 2140 |
| SVNTAVESLA | 2141 |
| AQARLPHTSS | 2142 |
| AQRNGSEVVA | 2143 |
| AQATDRVDRP | 2144 |
| AQASLSRERT | 2145 |
| AQAYSTHVRM | 2146 |
| AQHLSAGPTA | 2147 |
| LNGGAVSLRA | 2148 |
| AQAYGVSSVT | 2149 |
| AQFGSAVQLA | 2150 |
| AQAPPTSTRL | 2151 |
| AQVSTNWPKA | 2152 |
| AQTSTDLSRA | 2153 |
| AQAHSTDVRM | 2154 |
| AQATLTGHVS | 2155 |
| AQATTQGALT | 2156 |
| AQAAKASDRT | 2157 |
| AQGNEHGGRA | 2158 |
| AQALSTSLLL | 2159 |
| AQASLGSTYL | 2160 |
| AQAFSTVGAV | 2161 |
| AQLNGLVTTA | 2162 |
| AQASVRTLRM | 2163 |
| AQATMSRPWQ | 2164 |
| AQSSLPAMVA | 2165 |
| RETVAVGQYA | 2166 |
| AQAFGSEGRS | 2167 |
| SSGTAVEHRA | 2168 |
| FGTNAVIPRA | 2169 |
| AQAGQARSLG | 2170 |
| AQSFSSDNMA | 2171 |
| AQMNGLTGKA | 2172 |
| AQQNGKQHLA | 2173 |
| AQHIDSIRPA | 2174 |
| AQAADRLSTL | 2175 |
| AQFGLKDIRA | 2176 |

TABLE 1-continued

Exemplary Peptide Sequences,
e.g., Targeting Peptides

| Peptide Sequence | SEQ ID NO: |
| --- | --- |
| AQAHQGGATL | 2177 |
| AQATYNSPKP | 2178 |
| AQAMSNMLRN | 2179 |
| VPISAVMSTA | 2180 |
| AQHSLGNTVA | 2181 |
| AQATSALSRL | 2182 |
| AQADRQTFPV | 2183 |
| AQAVNSMSIG | 2184 |
| AQALAIVSKN | 2185 |
| AQGQLQERFA | 2186 |
| AQFNGASAHA | 2187 |
| AQLGGQSPVA | 2188 |
| AQANGAYTDN | 2189 |
| AQNLSSSEPA | 2190 |
| AQSAIVLTTA | 2191 |
| ITRSAVPDVA | 2192 |
| GALKAVTGVA | 2193 |
| AQAVGQDYLR | 2194 |
| AQVTLNTPLA | 2195 |
| AQALTQDDRW | 2196 |
| AQAYSTNVRM | 2197 |
| AQAVAAPASL | 2198 |
| AQANPVSIMS | 2199 |
| AQASMQAVKD | 2200 |
| AQAVGGHSVA | 2201 |
| AQAVAASTRL | 2202 |
| GGTHAVSSFA | 2203 |
| AQAADSSGFR | 2204 |
| AQQSHVPQTA | 2205 |
| AQARVGNTNV | 2206 |
| AQTVSYSDLA | 2207 |
| AQAEHGLARS | 2208 |
| AQASNYPVAA | 2209 |
| VLLSAVGMAA | 2210 |
| AQALSGQNRG | 2211 |
| AQAWGQETRQ | 2212 |

TABLE 1-continued

Exemplary Peptide Sequences,
e.g., Targeting Peptides

| Peptide Sequence | SEQ ID NO: |
| --- | --- |
| AQGYSTDVRM | 2213 |
| AQAGSVMSRE | 2214 |
| AQAGSLSARG | 2215 |
| AQATALAPKS | 2216 |
| AQAIRQNGSS | 2217 |
| AQLQDNLQLA | 2218 |
| AKAYSTDVRM | 2219 |
| AQSVDRTLLA | 2220 |
| AQAGQNSRLP | 2221 |
| AQTNLQPRGA | 2222 |
| PNTIAVGQRA | 2223 |
| AQAHATLSLS | 2224 |
| NHLRAVGSPA | 2225 |
| AQETDRNLRA | 2226 |
| AQARAETSGS | 2227 |
| AQHRELDSYA | 2228 |
| AQRHTSDVLA | 2229 |
| AQVGQTSSWA | 2230 |
| AQANSAALLM | 2231 |
| AQAIIERTAT | 2232 |
| AQSSRYEEKA | 2233 |
| QATQAVNPRA | 2234 |
| AQASYSVSVG | 2235 |
| AQQGHTVNNA | 2236 |
| AQASLPISTR | 2237 |
| AQHIDSMRPT | 2238 |
| AQAQDTENMR | 2239 |
| RTGAAVTGAA | 2240 |
| AQASSVRGMG | 2241 |
| AQPGIESTIA | 2242 |
| AQHVDLDSKA | 2243 |
| AQATTVPALG | 2244 |
| AQVNPTPQKA | 2245 |
| AQAGYISSAS | 2246 |
| AQTLILGDPA | 2247 |
| AQAASGLTMM | 2248 |
| AQALERPPSG | 2249 |

TABLE 1-continued

Exemplary Peptide Sequences,
e.g., Targeting Peptides

| Peptide Sequence | SEQ ID NO: |
|---|---|
| TTYDAVHSKA | 2250 |
| AQAMLDSANG | 2251 |
| AQAMHQTDKF | 2252 |
| KSTVAVQSVA | 2253 |
| AQATAGTL1G | 2254 |
| GLKSAVTHVA | 2255 |
| AQAHSAYQGA | 2256 |
| AQSFSSDNLA | 2257 |
| AQLNMAASVA | 2258 |
| AQFSQAYNAA | 2259 |
| AQHLTAGLRA | 2260 |
| AQAHTVSPHL | 2261 |
| GILGAVLPRA | 2262 |
| AQHNSSSLLA | 2263 |
| AQAPQVAGTM | 2264 |
| AQHQDSRPMA | 2265 |
| AQRFQETGLA | 2266 |
| AQLTVSHTRA | 2267 |
| AQANLRTTMG | 2268 |
| AQAGLRDPRM | 2269 |
| AQHLLHGTAA | 2270 |
| RNQGAVASLA | 2271 |
| AQAGSSSVTW | 2272 |
| AQPHLQIGVA | 2273 |
| AQANSGAVLA | 2274 |
| AQLLGDAVKA | 2275 |
| SSGNAVSSLA | 2276 |
| AQVSVTMALA | 2277 |
| AQYHTRGFAA | 2278 |
| AQSTTKGTLA | 2279 |
| AQAQPPSARY | 2280 |
| AQAGLQGTAA | 2281 |
| AQPQGSSTFA | 2282 |
| TQYRAVEGQA | 2283 |
| AQA1STQLAG | 2284 |
| AQLGSNISHA | 2285 |

TABLE 1-continued

Exemplary Peptide Sequences,
e.g., Targeting Peptides

| Peptide Sequence | SEQ ID NO: |
|---|---|
| AQTGLSGTVA | 2286 |
| AQRVDSSGRA | 2287 |
| AQAGLALNPN | 2288 |
| AQFYSDNSLA | 2289 |
| AQAVGAPQRL | 2290 |
| AQASYDDGRA | 2291 |
| SSFAAVATAA | 2292 |
| AQSTLSMPLA | 2293 |
| AQASLHAPRP | 2294 |
| HAVAAVSYPA | 2295 |
| AQTSPVMVQA | 2296 |
| AQADITSTIS | 2297 |
| AQAAGVAMLY | 2298 |
| AQASVSTLRK | 2299 |
| MDLKAVSSRA | 2300 |
| AQASLSTLRM | 2301 |
| AQPRSPLPMA | 2302 |
| GQYADVSSYA | 2303 |
| LVGGAVVVPA | 2304 |
| AQAQSARPLA | 2305 |
| AQSLHPSTTA | 2306 |
| AQFQTDLSRA | 2307 |
| RTELAVGLSA | 2308 |
| AQVVDNSPLA | 2309 |
| AQAVSSDSMH | 2310 |
| AQASPALHTL | 2311 |
| GQYAAVASYA | 2312 |
| AQLWQSRVDA | 2313 |
| GTFSAVQSTA | 2314 |
| AQAILSTIEV | 2315 |
| AQNVVSTLRA | 2316 |
| AQAMLAVSPG | 2317 |
| AQATDSLVAR | 2318 |
| AQASPQSSHG | 2319 |
| AQATPVHDTL | 2320 |
| LRSSAVGTAA | 2321 |
| MGRGAVLDTA | 2322 |

53

TABLE 1-continued

Exemplary Peptide Sequences,
e.g., Targeting Peptides

| Peptide Sequence | SEQ ID NO: |
|---|---|
| AQSHLIPTPA | 2323 |
| AQAVIKAPIN | 2324 |
| AQKIAPAFLA | 2325 |
| AGNVAVLPHA | 2326 |
| AQSLGTGLHD | 2327 |
| AQAHAMSSRP | 2328 |
| AQQGKFDMRA | 2329 |
| AQALSGDGTR | 2330 |
| AQTHLQIAVA | 2331 |
| AQRTQGSSWA | 2332 |
| AIGSAVDLRA | 2333 |
| AQAQLASGTL | 2334 |
| AQALVSAGAL | 2335 |
| AQATESVPLK | 2336 |
| AQVYNSNPKA | 2337 |
| AQRTTYPSSA | 2338 |
| AQAMFQQAST | 2339 |
| AQPDALVIRA | 2340 |
| AQARDISMRG | 2341 |
| AQMSFGSTLA | 2342 |
| RLLSAVDQQA | 2343 |
| AQTTRSIENA | 2344 |
| AQVSDFSSRA | 2345 |
| AQAHSRVNTE | 2346 |
| AQAYSTDLRM | 2347 |
| AQALNGSAYS | 2348 |
| TQYGAVEAQA | 2349 |
| AQAHAGTIYS | 2350 |
| AQDPHSMRPA | 2351 |
| AQASANIHSS | 2352 |
| AQASLQAVSM | 2353 |
| AQSSHPAMVA | 2354 |
| AQANLQPRGA | 2355 |
| AQAVGSSPRG | 2356 |
| AQTSAPSALA | 2357 |
| AQAVQLQNRG | 2358 |

54

TABLE 1-continued

Exemplary Peptide Sequences,
e.g., Targeting Peptides

| Peptide Sequence | SEQ ID NO: |
|---|---|
| AQAQGSGMVS | 2359 |
| AQAYPSSKSG | 2360 |
| AQAVSDYGRG | 2361 |
| AQMSLGATRA | 2362 |
| AQAFLNSASA | 2363 |
| AQALPSNARL | 2364 |
| AQANVSVRRE | 2365 |
| AQAGASVMVH | 2366 |
| AQSLAKDQSA | 2367 |
| AQILSALSSA | 2368 |
| AQSVHLSLAA | 2369 |
| AQALSASSFL | 2370 |
| AQTSQLNQTA | 2371 |
| AQSNLFPTPA | 2372 |
| AQAHGRSFDT | 2373 |
| AQLGSNTILA | 2374 |
| AQASMNSAKA | 2375 |
| AQRQAVEQSA | 2376 |
| AQASTGTLRH | 2377 |
| AQGPTYPNVA | 2378 |
| AQAGPTTSKA | 2379 |
| AQATTYRGMA | 2380 |
| AQVTNRGMPA | 2381 |
| AQAISGQAAW | 2382 |
| AQAFRGEDKG | 2383 |
| AQQSMPRFVA | 2384 |
| AQAGVKSTRL | 2385 |
| AQATGSILLA | 2386 |
| AQASGHSSFS | 2387 |
| AQTANDGLRA | 2388 |
| AQASQLALLA | 2389 |
| AQLVDRVPRA | 2390 |
| AQHSNGYVHA | 2391 |
| AQAAPSSSDS | 2392 |
| AQAMQRSSSA | 2393 |
| AQAASGRPTC | 2394 |
| AQPRPGDSRA | 2395 |

TABLE 1-continued

Exemplary Peptide Sequences,
e.g., Targeting Peptides

| Peptide Sequence | SEQ ID NO: |
|---|---|
| AQRDRANGIA | 2396 |
| AQVLAISLSA | 2397 |
| AQAGMRDPRM | 2398 |
| AQASSNSSRA | 2399 |
| MHRDAVSGVA | 2400 |
| AQAEMKNMPP | 2401 |
| AQSGSLLASA | 2402 |
| AQAFASQSRG | 2403 |
| AQALHLPTLQ | 2404 |
| AQAKTGGMNT | 2405 |
| ISLNAVSGKA | 2406 |
| AQGVHGHYVA | 2407 |
| AQAYSKDVRM | 2408 |
| VPSIAVSSHA | 2409 |
| AQSSRHDDLA | 2410 |
| AQANGSGSRG | 2411 |
| AQVGIADRRA | 2412 |
| AQARGMESML | 2413 |
| AQAGVSTAGH | 2414 |
| AQVSTRNLIA | 2415 |
| AQAVPRLTAG | 2416 |
| AQRHMELQEA | 2417 |
| SQSRAVVWEA | 2418 |
| QSHTAVSSLA | 2419 |
| AKASVSTLRM | 2420 |
| AQASGSSQWA | 2421 |
| AQPNAQYMKA | 2422 |
| AQAMGTGSSL | 2423 |
| AQAFSTSQLT | 2424 |
| AQAKDQSQRL | 2425 |
| AQVGGNGSRA | 2426 |
| AQANGASRAV | 2427 |
| QVNKAVLDFA | 2428 |
| AQETLSSTRA | 2429 |
| GVYGAVHSSA | 2430 |
| AQTITIENVA | 2431 |

56

TABLE 1-continued

Exemplary Peptide Sequences,
e.g., Targeting Peptides

| Peptide Sequence | SEQ ID NO: |
|---|---|
| AQALMKIADG | 2432 |
| AQANVSLQAA | 2433 |
| AQSTTSHLRA | 2434 |
| AQLSNLVSVA | 2435 |
| AQANSTPTRQ | 2436 |
| AQQRGDRAAA | 2437 |
| AQARLGQSVG | 2438 |
| AQQLTYGSSA | 2439 |
| AQPAEKQYSA | 2440 |
| AQAMPRSRGD | 2441 |
| AQGLSGRALA | 2442 |
| AQARVTAVDA | 2443 |
| AQVGVSTAVA | 2444 |
| AQTGVTSAQA | 2445 |
| AQALVTSSEK | 2446 |
| AQASPHSSMA | 2447 |
| AQALTQDEMW | 2448 |
| AQAFSTQQRL | 2449 |
| AQAGSQVTQA | 2450 |
| AQQSTLALKA | 2451 |
| AQALNGSHAA | 2452 |
| AQATEGHLRS | 2453 |
| AQPMANMLMA | 2454 |
| PSTSAVSQKA | 2455 |
| AQAPPSSTEM | 2456 |
| AQRERVDLAA | 2457 |
| AQASVTLPRT | 2458 |
| AQAYPSSSKA | 2459 |
| AQAHSGSAIP | 2460 |
| AQSPSQSLKA | 2461 |
| AQATPPATSP | 2462 |
| CLGAAVNQCA | 2463 |
| VLGQAVRDKA | 2464 |
| AQAQKANNVG | 2465 |
| AQTLLPVNGA | 2466 |
| AQAHGTIQRG | 2467 |
| TVYTAVGVSA | 2468 |

57

TABLE 1-continued

Exemplary Peptide Sequences,
e.g., Targeting Peptides

| Peptide Sequence | SEQ ID NO: |
|---|---|
| LGRGAVLDMA | 2469 |
| AQANVRSDQM | 2470 |
| AQARDSQKGW | 2471 |
| AQTPGSRSAA | 2472 |
| AQALPSNARQ | 2473 |
| AQASATSVVH | 2474 |
| AQINLGTMRA | 2475 |
| AQVYNNTSAA | 2476 |
| AQASANLTRG | 2477 |
| AQLRTDYTRA | 2478 |
| AQAYSTDVKM | 2479 |
| AQTSQLYQPA | 2480 |
| AQALTQEERW | 2481 |
| LPNGAVRDRA | 2482 |
| VTGSAVAGIA | 2483 |
| AQAFSTDVRM | 2484 |
| AQAHGPTSGV | 2485 |
| AQAGVGLPIA | 2486 |
| AQVNSGQARA | 2487 |
| AQAQTGPPMK | 2488 |
| AQARLAPVAC | 2489 |
| LSIGAVASMA | 2490 |
| AQAQDLGVMR | 2491 |
| PTGLAVTSPA | 2492 |
| AQSASTSWSA | 2493 |
| AQNGSNVRNA | 2494 |
| AQASISSSAT | 2495 |
| AQNSHAHLAA | 2496 |
| AQAVGVKQFF | 2497 |
| AQAHLSPTHA | 2498 |
| AQPAYGSSYA | 2499 |
| AQAHQARSGS | 2500 |
| AQAHTSPTQR | 2501 |
| AQAATPSSSR | 2502 |
| AQAHNSYPKV | 2503 |
| AQSSLGSSLA | 2504 |

58

TABLE 1-continued

Exemplary Peptide Sequences,
e.g., Targeting Peptides

| Peptide Sequence | SEQ ID NO: |
|---|---|
| AQALSRSNVG | 2505 |
| AQASLSSLSG | 2506 |
| AQHGSSEFTA | 2507 |
| AQSALVAGVA | 2508 |
| AQASSSSLRP | 2509 |
| AQTARDTGFA | 2510 |
| KSVQAVRDPA | 2511 |
| AQAGSHSSVS | 2512 |
| VRAHAVTGLA | 2513 |
| ASHTAVGEFA | 2514 |
| AQIRSEWRDA | 2515 |
| AQQLARVSGA | 2516 |
| AQAAITSTNS | 2517 |
| AQARDAVQLP | 2518 |
| AQAKELVSTS | 2519 |
| AQGIAETLSA | 2520 |
| AQLGSGFSTA | 2521 |
| AQNAKELERA | 2522 |
| AQTHLQNGVA | 2523 |
| SGNLAVGTPA | 2524 |
| AQPSPGTSVA | 2525 |
| AQSSAAAGRA | 2526 |
| AQAGISAAIM | 2527 |
| AQALGYHQTG | 2528 |
| NAGQAVAARA | 2529 |
| AQPFGGSGYA | 2530 |
| AQAGSPSRLC | 2531 |
| AQARTIGTIA | 2532 |
| AQVVSVSSRA | 2533 |
| AQAGQARSMG | 2534 |
| AQATRGVTAG | 2535 |
| AQQSNGYGRA | 2536 |
| AQASLAPLKS | 2537 |
| AQPGANHNGA | 2538 |
| LGRGAVPDTA | 2539 |
| AQHFQTASLA | 2540 |
| AQAPAGHHTR | 2541 |

TABLE 1-continued

Exemplary Peptide Sequences,
e.g., Targeting Peptides

| Peptide Sequence | SEQ ID NO: |
|---|---|
| AQPSVQNSMA | 2542 |
| AQAKLSGHVS | 2543 |
| AQFGTSSPSA | 2544 |
| AQASHISSVR | 2545 |
| AQALSRNGIG | 2546 |
| AQASAQVQRS | 2547 |
| AQGGPHLQAA | 2548 |
| AQAQSDSAFR | 2549 |
| AQTYSTDVRM | 2550 |
| LARGAVLDTA | 2551 |
| AQASPHTLRS | 2552 |
| AQHSDTQTRA | 2553 |
| AQATPSPSAS | 2554 |
| AQNQVTYSKA | 2555 |
| AQHTSVVYGA | 2556 |
| AQAQVSQMSH | 2557 |
| SFLRAVKNDA | 2558 |
| AQAYSTDVGM | 2559 |
| AKTPALINLA | 2560 |
| VSTAAVSSAA | 2561 |
| AQAPITSTIS | 2562 |
| AQTNLQTRGA | 2563 |
| AQATRLPTPG | 2564 |
| PQHLAVSSAA | 2565 |
| AQASPHPSRP | 2566 |
| AQAQPAGQRG | 2567 |
| AQPQRQGVQA | 2568 |
| AQHVAGSSNA | 2569 |
| AQVPIQMGVA | 2570 |
| AQATVSVPLK | 2571 |
| AQISVSHTRA | 2572 |
| SLVGPVAQMA | 2573 |
| AQPRLNLTEA | 2574 |
| AQASQEYSRL | 2575 |
| AQKSLAFDSA | 2576 |
| AQALGHSHHC | 2577 |

TABLE 1-continued

Exemplary Peptide Sequences,
e.g., Targeting Peptides

| Peptide Sequence | SEQ ID NO: |
|---|---|
| AQAAQTGRPI | 2578 |
| AQASGTSVRQ | 2579 |
| AQAMGTASYC | 2580 |
| AQISHNHPQA | 2581 |
| AQAYSTYVRM | 2582 |
| AQVGKLDIRA | 2583 |
| AQLKQGGINA | 2584 |
| AQASAHFREP | 2585 |
| AQALDTVISA | 2586 |
| GAGTAVGNIA | 2587 |
| AQANGSATYA | 2588 |
| AQTQLAQQKA | 2589 |
| AQYVTTVSPA | 2590 |
| SQFSAVTVTA | 2591 |
| AQAASDSFRY | 2592 |
| AQASPASVTR | 2593 |
| AQARDSGMFL | 2594 |
| AQSKTTLTLS | 2595 |
| AQLVQESLSA | 2596 |
| AQAALKSLAG | 2597 |
| AQAVPNQGQK | 2598 |
| AQALSRSSLG | 2599 |
| AQAGSVMSRV | 2600 |
| AQMATVTPMA | 2601 |
| AQARTASGID | 2602 |
| SHSSAVSHPA | 2603 |
| AQADRMRTTA | 2604 |
| AQNAQNRALA | 2605 |
| AQAASNAYSS | 2606 |
| AQATFQQAST | 2607 |
| AQVYTISTPA | 2608 |
| AQTVIAVGVA | 2609 |
| LARGAVPPTA | 2610 |
| AQMLQTSVLA | 2611 |
| AQARQVSPLL | 2612 |
| AQAGQMSNAR | 2613 |
| AQTPALIKLA | 2614 |

61

TABLE 1-continued

Exemplary Peptide Sequences,
e.g., Targeting Peptides

| Peptide Sequence | SEQ ID NO: |
|---|---|
| AQAYTTDVRK | 2615 |
| VVKGAVLHVA | 2616 |
| AQDTVSVPLK | 2617 |
| AQKGAPSLQA | 2618 |
| AQASYDVGRA | 2619 |
| AQGPLSGMRA | 2620 |
| AQALGTSVPA | 2621 |
| AQVNKGASTA | 2622 |
| AQLTRTSPVA | 2623 |
| AQADAALRFS | 2624 |
| AQVQLVVSPA | 2625 |
| AQAYSSDVRM | 2626 |
| AQARSGLSLP | 2627 |
| AQNGHKFTAA | 2628 |
| AQGLSSATKA | 2629 |
| AQGTWSTVKA | 2630 |
| AQASGVGGRI | 2631 |
| AQTSYPAQKA | 2632 |
| AQNAVPTHSA | 2633 |
| AQSYPEITRA | 2634 |
| AQTGLSTSSA | 2635 |
| AQYDTHNFAA | 2636 |
| AQAVLSSVIQ | 2637 |
| AQDSAVALMA | 2638 |
| AQATGKGALP | 2639 |
| AQNSRSGHDA | 2640 |
| AQAFQKEPSV | 2641 |
| AQAGSTSGKM | 2642 |
| AQRDQAHSQA | 2643 |
| AQAASALSGR | 2644 |
| AQARHSSLLP | 2645 |
| AQGPGTSYLA | 2646 |
| FLAPAVSSKA | 2647 |
| AQAGPQCSSC | 2648 |
| AQALTQHERW | 2649 |
| AQAIRSSERV | 2650 |

62

TABLE 1-continued

Exemplary Peptide Sequences,
e.g., Targeting Peptides

| Peptide Sequence | SEQ ID NO: |
|---|---|
| AQAVHSSSVY | 2651 |
| AQSSRTALAA | 2652 |
| AQITFSHTRA | 2653 |
| AQALTLSGGL | 2654 |
| AQAGKTLSVL | 2655 |
| AQASRSNLDN | 2656 |
| AQGSLSTHTA | 2657 |
| AQQSVAYNVA | 2658 |
| AQHTLRLSSA | 2659 |
| AQAGGTPNKL | 2660 |
| AQAFQSLTLA | 2661 |
| AQAVALSHQE | 2662 |
| AQMLASGIPA | 2663 |
| AQNRALDSYA | 2664 |
| AQASGSTTRN | 2665 |
| AQARGDGYVA | 2666 |
| DARVAVLDFA | 2667 |
| AQAVASQVSR | 2668 |
| AQARGPSPAT | 2669 |
| AQHRALDSYD | 2670 |
| AQLIDSTSRA | 2671 |
| AQAQTLSRGS | 2672 |
| AQFRSAITSA | 2673 |
| AQANMTKQSL | 2674 |
| AQNAGSTSRA | 2675 |
| VLGSAVTGRA | 2676 |
| AQPMLQSSSA | 2677 |
| AQLGTPSLSA | 2678 |
| AQATAHTGVP | 2679 |
| AQAVGRDNRL | 2680 |
| AQATSASVWA | 2681 |
| AQAGSEASLR | 2682 |
| AQANQNRTAF | 2683 |
| AQASAQVKRS | 2684 |
| AQATSGVHHP | 2685 |
| AQTHMQIGVA | 2686 |
| AQSHIFPTPA | 2687 |

TABLE 1-continued

Exemplary Peptide Sequences,
e.g., Targeting Peptides

| Peptide Sequence | SEQ ID NO: |
|---|---|
| AQLFHTGSPA | 2688 |
| LASRAVVGTA | 2689 |
| AQALLRVGVG | 2690 |
| AQITLPSGTA | 2691 |
| AQAEKSLGRQ | 2692 |
| AQTSNTTTRA | 2693 |
| AQAHTQASYM | 2694 |
| AQERGASSSA | 2695 |
| AQATPSSTAM | 2696 |
| AQSTVNRTYA | 2697 |
| AQAGHGPSTR | 2698 |
| AQLSLVPLQA | 2699 |
| AQLHSPIPSA | 2700 |
| AQSLARDGLA | 2701 |
| AQAPPSSPAM | 2702 |
| TQYGAVERQA | 2703 |
| AQAGQARSLA | 2704 |
| AQPVGRVPPA | 2705 |
| AQAREQRGPV | 2706 |
| AQKTSLLWEA | 2707 |
| AQGSGKNLIA | 2708 |
| AQASEGHQLS | 2709 |
| AQALHAGHHP | 2710 |
| AQSKRDDPSA | 2711 |
| AQTSRELRMA | 2712 |
| AQALPASGAR | 2713 |
| AQSNALLSLA | 2714 |
| AQASPVVGVS | 2715 |
| AQARGDSYMA | 2716 |
| AQAGASSLTV | 2717 |
| AQALRPVNGT | 2718 |
| AQVRSGPTLA | 2719 |
| AQFPPLSRSA | 2720 |
| AQVARGTVQA | 2721 |
| AQTSTQSPPG | 2722 |
| AQARDGMNVR | 2723 |

TABLE 1-continued

Exemplary Peptide Sequences,
e.g., Targeting Peptides

| Peptide Sequence | SEQ ID NO: |
|---|---|
| AQAVSRNVVV | 2724 |
| AQHTATRSVA | 2725 |
| AQAVREDGHA | 2726 |
| TNSSAVAASA | 2727 |
| AQATFQLAST | 2728 |
| AQAHHQQTSL | 2729 |
| AQGQHAHMMA | 2730 |
| AQATSSLHVL | 2731 |
| AQAPNSGLAM | 2732 |
| SASRAVLDFA | 2733 |
| AQARGEQRFV | 2734 |
| AQTHLQIRVA | 2735 |
| AQAPPSSKAM | 2736 |
| AQIVSKAMPA | 7737 |
| AQASVRNNPS | 2738 |
| AQAESRVAAL | 2739 |
| LTNGAVRDRT | 2740 |
| AQGRLAGSLA | 2741 |
| AQAGQDSARR | 2742 |
| AQAASRLGAV | 2743 |
| AQALARGMAS | 2744 |
| AQASRGLSMG | 2745 |
| AQAQASSYGS | 2746 |
| AKASRLPTPG | 2747 |
| AQSLSRASTA | 2748 |
| AQASTFVQTI | 2749 |
| AQASSKVVAA | 2750 |
| AQAYRNGEAA | 2751 |
| AQAYSTGVRM | 2752 |
| AQAVSSRSMG | 2753 |
| AQARGGLATP | 2754 |
| AQAGHSGVRA | 2755 |
| AQPSYHGGAA | 2756 |
| AQRVNQVSTA | 2757 |
| AQAAFQQAST | 2758 |
| AQAVPGSPRA | 2759 |
| AQLSLSPLAA | 2760 |

TABLE 1-continued

Exemplary Peptide Sequences,
e.g., Targeting Peptides

| Peptide Sequence | SEQ ID NO: |
| --- | --- |
| AQANMTVRVS | 2761 |
| AQATRSSGDP | 2762 |
| AQVASNATRA | 2763 |
| AQTNQQPRGA | 2764 |
| AQRLQNDHLA | 2765 |
| AQAPVQLGRP | 2766 |
| AQRQGPDTLA | 2767 |
| AQHTLSNHMA | 2768 |
| AQLSGMVNRA | 2769 |
| AQDRQVSSRA | 2770 |
| AQRQLSTSLA | 2771 |
| AQQRPTVSFA | 2772 |
| AQAKPHSQLD | 2773 |
| AQAGRVNHPP | 2774 |
| AQAINSQSMR | 2775 |
| AQYSTAVMSA | 2776 |
| SQARAVERSA | 2777 |
| AQAYKSSSVG | 2778 |
| AQASTPGLYP | 2779 |
| AQSRTSMLAA | 2780 |
| AQLFSSNMPA | 2781 |
| AQAYCTDVRM | 2782 |
| AQTMSRGFVA | 2783 |
| AQALNGYPAA | 2784 |
| AQAQTGHPLK | 2785 |
| AQASSNSQYR | 2786 |
| AQAAIKSTIS | 2787 |
| AQSTLNLRPA | 2788 |
| AQATLSPGSG | 2789 |
| AQANGSGTGR | 2790 |
| STSLAVAGRA | 2791 |
| AQASNLSAYR | 2792 |
| AQASRQVLVA | 2793 |
| NEVRAVFFEA | 2794 |
| AKAQGSSSVG | 2795 |
| ARGSAVQSQA | 2796 |

TABLE 1-continued

Exemplary Peptide Sequences,
e.g., Targeting Peptides

| Peptide Sequence | SEQ ID NO: |
| --- | --- |
| AVRVAVSSSA | 2797 |
| AQAFSTSQFK | 2798 |
| AQGTSSQRTA | 2799 |
| AQATMSQTIA | 2800 |
| AQSANRSTLA | 2801 |
| AQRDLAHSKA | 2802 |
| AQASKVGLYA | 2803 |
| AQAYYTDVRM | 2804 |
| AQAGLRDPRA | 2805 |
| AQAFSQATGA | 2806 |
| AQVAGMSVRA | 2807 |
| AQAGQSSFTI | 2808 |
| AQKEMRSQGA | 2809 |
| AQNYSSGVRA | 2810 |
| AQITVSYTRA | 2811 |
| AQAQQPRSSI | 2812 |
| WTSGAVPGKA | 2813 |
| AQFKPSQVIA | 2814 |
| RQGQAVGSSA | 2815 |
| AQSISPHYAA | 2816 |
| AQARSLNEYK | 2817 |
| AQAASSRLMA | 2818 |
| AQAYSTDGRM | 2819 |
| AQASVPRVMG | 2820 |
| AQGQMPRYPA | 2821 |
| AQASSGMKPC | 2822 |
| AQPLRSSLSA | 2823 |
| AQNSASQSQA | 2824 |
| AQGHLSGLRA | 2825 |
| AQRAQSGVAA | 2826 |
| AQANPRLQDK | 2827 |
| AQAPRTATLG | 2828 |
| AQRTASLSQA | 2829 |
| AQGNPGLLRA | 2830 |
| MSSHAVGNRA | 2831 |
| AQLAPKASPA | 2832 |
| AQTTQGRERA | 2833 |

TABLE 1-continued

Exemplary Peptide Sequences,
e.g., Targeting Peptides

| Peptide Sequence | SEQ ID NO: |
|---|---|
| AQASGKSTSS | 2834 |
| AQAPHQHSMK | 2835 |
| GKLGAVVAQA | 2836 |
| AQAFQKVQSV | 2837 |
| AQTVAQSRVA | 2838 |
| AQAPPSQTSR | 2839 |
| AQAGVGYSSK | 2840 |
| AQMGSPSSKA | 2841 |
| QSSRAVLDFA | 2842 |
| AQARQTLDFG | 2843 |
| AQSIRSASQA | 2844 |
| AQFLSPKVTA | 2845 |
| AQAAGSGHTR | 2846 |
| VSSSAVIVGT | 2847 |
| AQAYSTDVMM | 2848 |
| AQALIGTNPR | 2849 |
| AQVMPSPSRA | 2850 |
| AQITVSHTRS | 2851 |
| AQGPHSGLRA | 2852 |
| AQANGRVQVT | 2853 |
| AQAMPRTASV | 2854 |
| AQVSTKWPKS | 2855 |
| AQAMPRYPGE | 2856 |
| AQAATTPMSR | 2857 |
| AQARGDHFSI | 2858 |
| AQAKTNTSHA | 2859 |
| AQNTPRINQA | 2860 |
| AQATVALPRG | 2861 |
| AQGSKVGLNA | 2862 |
| AQAHQNLRGA | 2863 |
| AQIVSTLQHA | 2864 |
| AQTGSSLSRA | 2865 |
| AQVRTALASA | 2866 |
| AQAYSTVVRM | 2867 |
| AQQMPRIVPA | 2868 |
| AQALTQYERW | 2869 |

TABLE 1-continued

Exemplary Peptide Sequences,
e.g., Targeting Peptides

| Peptide Sequence | SEQ ID NO: |
|---|---|
| AQASRQPPAQ | 2870 |
| AQAYYTDERM | 2871 |
| TQITVSHTRA | 2872 |
| AQASSGTRSA | 2873 |
| AQAKVSVPLK | 2874 |
| TQYGAVEGQA | 2875 |
| AQANSTSSTR | 2876 |
| AAGTAVTATA | 2877 |
| AQAAPPHRLS | 2878 |
| AQMMPRMPPA | 2879 |
| AQTHLQIWVA | 2880 |
| AQTNLKPRGA | 2881 |
| AQTNLQIGVA | 2882 |
| ILAPAVSSKA | 2883 |
| AQAHKVLDFG | 2884 |
| AQAYSTDVSM | 2885 |
| AQAYSTDVWM | 2886 |
| AQAGMPRGPS | 2887 |
| AQHLPALKMA | 2888 |
| AQAIGLNESA | 2889 |
| AQTQLQIGVA | 2890 |
| AQAYSPDVRM | 2891 |
| AQANSTDERM | 2892 |
| HATVAVQGAA | 2893 |
| AQACSTDVRM | 2894 |
| AQIKSLTSVA | 2895 |
| EQAYSTDVRM | 2896 |
| AQANSTDVRM | 2897 |
| AQAMPRTPGV | 2898 |
| GEGTAVTATA | 2899 |
| PTNAAVRTKA | 2900 |
| AQTHLQIGEA | 2901 |
| AQADSTDVRM | 2902 |
| VTFAAVTDKA | 2903 |
| AQAYYTDVRK | 2904 |
| EQTHLQIGVA | 2905 |
| AQAYSTDVRV | 2906 |

69

TABLE 1-continued

| Exemplary Peptide Sequences, e.g., Targeting Peptides | |
| --- | --- |
| Peptide Sequence | SEQ ID NO: |
| AQQFQTQNAA | 2907 |
| AQITVSHTSA | 2908 |
| AQLGRMQYAA | 2909 |
| AVRVADSSSA | 2910 |
| AQIQTDLSRA | 2911 |
| AQAYFTDVRM | 2912 |
| AQAYSTDVRK | 2913 |
| TQAHAGTIYS | 2914 |
| AQARSLEPVN | 2915 |
| AQAYVSQGMS | 2916 |
| EQALTQDERW | 2917 |
| AQAGLSTAVH | 2918 |
| AQAGLSDPRM | 2919 |
| PTNAADRTNA | 2920 |
| AQAPQVEGTM | 2921 |
| AQAFTPAERM | 2922 |
| AQGPLYGLRA | 2923 |
| AQTNLQQRGA | 2924 |
| AQPRFNLTQA | 2925 |
| AQAYSMDVRM | 2926 |
| AQLGGQSQVA | 2927 |
| AQGSKDGLYA | 2928 |
| ALAYSTDVRM | 2929 |
| AKSKTTLTLA | 2930 |
| EQAFTAAERM | 2931 |
| AQDSVSTLRM | 2932 |
| AQVYSTDVRM | 2933 |
| AQGNMLVKDA | 2934 |
| AQARSLEQVI | 2935 |
| AQAFSTSQFT | 2936 |
| LTYGAVRDRA | 2937 |
| AQSLGTGLHA | 2938 |
| AQAAITSTIT | 2939 |
| GALNADTGVA | 2940 |
| AQRLKNDHLA | 2941 |
| VQAYSTDVRM | 2942 |

70

TABLE 1-continued

| Exemplary Peptide Sequences, e.g., Targeting Peptides | |
| --- | --- |
| Peptide Sequence | SEQ ID NO: |
| SVHGAVGIMA | 2943 |
| AQTSQLYQNA | 2944 |
| AQARSMEPVI | 2945 |
| SQAYSTDVRM | 2946 |
| AQRLQNDNLA | 2947 |
| AQEVDNSTLA | 2948 |
| VSTEAVSSAA | 2949 |
| AQASPLPTPG | 2950 |
| AQARRLEPVI | 2951 |
| AQAQTGTPLK | 2952 |
| AQSKTTFTLA | 2953 |
| AQTTFQQAST | 2954 |
| AQLSTSGLLA | 2955 |
| AQASGALDRT | 2956 |
| AQTVSVHDRA | 2957 |
| AQSKTTLTLP | 2958 |
| AQATFQQASS | 2959 |
| AQAKGSRSDQ | 2960 |
| AQAANTSTIS | 2961 |
| SVNTAVASLA | 2962 |
| AQAPPSSTAM | 2963 |
| LTNGSVRDRA | 2964 |
| AQRQGPDPMA | 2965 |
| AQARSLEPLI | 2966 |
| AQAGRMSQSG | 2967 |
| AQTLMSHTDA | 2968 |
| AQAPGMGAPL | 2969 |
| GAGPAVTATA | 2970 |
| AQAQPGPPLK | 2971 |
| AQLIDSMRPA | 2972 |
| AQAQTGPPQK | 2973 |
| AQARVAVKLP | 2974 |
| AQARTNNSSG | 2975 |
| AQARSLAPVI | 2976 |
| AKAFTAAERM | 2977 |
| AQNVDLASKA | 2978 |
| AQARTIDKCC | 2979 |

TABLE 1-continued

Exemplary Peptide Sequences,
e.g., Targeting Peptides

| Peptide Sequence | SEQ ID NO: |
|---|---|
| AQAPPSSTAK | 2980 |
| AQSNSVLSLA | 2981 |
| AQTLILGATA | 2982 |
| AKATMSQTMA | 2983 |
| AQAQTGPPLQ | 2984 |
| AQPGIVSTID | 2985 |
| AQHRALDSNA | 2986 |
| QTNAAVRTNA | 2987 |
| AQAPQVAGTK | 2988 |
| AQHGFTDSSA | 2989 |
| EQTPALINLA | 2990 |
| SVNTDVASLA | 2991 |
| AQAHPSSTAM | 2992 |
| AQYISDTYRA | 2993 |
| AQHIDSMRPA | 2994 |
| AQTSGQDERA | 2995 |
| AQAGDAAVRY | 2996 |
| AQAGRYESGN | 2997 |
| AQSMQSRSEA | 2998 |
| AQRLQNDHMA | 2999 |
| AQPVSVHVRA | 3000 |
| AQASEGLKLS | 3001 |
| AQLYVSSSVA | 3002 |
| AQATGVSQQM | 3003 |
| AQAPSKELFM | 3004 |
| AQAAITRTIS | 3005 |
| GLKSAVTHAA | 3006 |
| AQALGVTQSP | 3007 |
| AQAPSHLVPV | 3008 |
| AQARVAVQLQ | 3009 |
| AQAGSRLALE | 3010 |
| AQYGAVEGQA | 3011 |
| AQHSNKQVMA | 3012 |
| AQATFQQAGT | 3013 |
| AQAPTSSTAM | 3014 |
| AQHQDSRTLA | 3015 |

TABLE 1-continued

Exemplary Peptide Sequences,
e.g., Targeting Peptides

| Peptide Sequence | SEQ ID NO: |
|---|---|
| AQAQRPMTSV | 3016 |
| AQAHARQMTV | 3017 |
| AKAFSTSQFT | 3018 |
| AQATPRQASH | 3019 |
| AQAAGSLRLG | 3020 |
| AQAQSRQLAM | 3021 |
| AQAMPGPMSR | 3022 |
| AQAPPRSTAM | 3023 |
| AQAAITSTIR | 3024 |
| AQALRGAALP | 3025 |
| AQASVQGISR | 3026 |
| AQAMMSRQSV | 3027 |
| AQARQSPLSG | 3028 |
| AQAGNVASTR | 3029 |
| AGRVAVNLVA | 3030 |
| AHSYAVTSTA | 3031 |
| AISGAVYSPA | 3032 |
| AKAGQSSFTI | 3033 |
| ALKHAVDVLA | 3034 |
| ALNKPRINQA | 3035 |
| ALNTPRINKA | 3036 |
| AQAAPVQSGV | 3037 |
| AQAAQSSFTI | 3038 |
| AQAARHSTTG | 3039 |
| AQAARIAQAS | 3040 |
| AQAARSTVYT | 3041 |
| AQAARTAPGL | 3042 |
| AQAARTSAVS | 3043 |
| AQAARYVTGV | 3044 |
| AQAASFLTAD | 3045 |
| AQAASGGSFT | 3046 |
| AQAASMRDHT | 3047 |
| AQAASVRQAR | 3048 |
| AQAAVDTTYR | 3049 |
| AQADCKFVVV | 3050 |
| AQADPSYRAN | 3051 |
| AQADRMVLRS | 3052 |

TABLE 1-continued

Exemplary Peptide Sequences,
e.g., Targeting Peptides

| Peptide Sequence | SEQ ID NO: |
|---|---|
| AQADRPMVHR | 3053 |
| AQADTGASMQ | 3054 |
| AQAEGNGHWR | 3055 |
| AQAELQSGIR | 3056 |
| AQAEMRSSSR | 3057 |
| AQAESFLTAV | 3058 |
| AQAETRSGLS | 3059 |
| AQAFITSQFT | 3060 |
| AQAFLPMGGA | 3061 |
| AQAFRGASAL | 3062 |
| AQAFSSTHSR | 3063 |
| AQAFSTTQFT | 3064 |
| AQAGCSKELR | 3065 |
| AQAGDIRLSL | 3066 |
| AQAGDSRQGS | 3067 |
| AQAGGLHGVA | 3068 |
| AQAGHRTPGP | 3069 |
| AQAGHVVTYV | 3070 |
| AQAGLRDPSM | 3071 |
| AQAGLSQVIQ | 3072 |
| AQAGNSYSQR | 3073 |
| AQAGRGTIMA | 3074 |
| AQAGRLSKSG | 3075 |
| AQAGRLSQSG | 3076 |
| AQAGRLYQSG | 3077 |
| AQAGRPAFPW | 3078 |
| AQAGRQDLFS | 3079 |
| AQAGRSDSSL | 3080 |
| AQAGRTMNWS | 3081 |
| AQAGRVEVHL | 3082 |
| AQAGSSVSRA | 3083 |
| AQAGSTGGSA | 3084 |
| AQAGTRSMLA | 3085 |
| AQAGTSTPRW | 3086 |
| AQAGVNLRAL | 3087 |
| AQAHDRLPSG | 3088 |

TABLE 1-continued

Exemplary Peptide Sequences,
e.g., Targeting Peptides

| Peptide Sequence | SEQ ID NO: |
|---|---|
| AQAHNAGVPD | 3089 |
| AQAHNSDRAR | 3090 |
| AQAHRGEVGQ | 3091 |
| AQAHRHISGP | 3092 |
| AQAHSRSMSQ | 3093 |
| AQAHSVNTAS | 3094 |
| AQAHTSTVLC | 3095 |
| AQAIALHRPS | 3096 |
| AQAICLSPDR | 3097 |
| AQAIEGRYPR | 3098 |
| AQAIPSPYSV | 3099 |
| AQAIRGAVQA | 3100 |
| AQAKSSPLSV | 3101 |
| AQAKSSSPTL | 3102 |
| AQAKTASSPP | 3103 |
| AQALATLPAM | 3104 |
| AQALEHTSPR | 3105 |
| AQALGGFRSE | 3106 |
| AQALGHQGQL | 3107 |
| AQALIPMVRG | 3108 |
| AQALQASRPP | 3109 |
| AQALQPFSFH | 3110 |
| AQALQQPQSR | 3111 |
| AQALRASAPR | 3112 |
| AQALVGSRGQ | 3113 |
| AQALYQHHSI | 3114 |
| AQALYRQSET | 3115 |
| AQAMASSLLA | 3116 |
| AQAMGPVGKC | 3117 |
| AQAMGRESYN | 3118 |
| AQAMGSNERY | 3119 |
| AQAMGTADRA | 3120 |
| AQAMITTVHS | 3121 |
| AQAMPRLRDA | 3122 |
| AQAMRSLSAA | 3123 |
| AQAMSRLGTA | 3124 |
| AQAMSRTVMP | 3125 |

TABLE 1-continued

Exemplary Peptide Sequences,
e.g., Targeting Peptides

| Peptide Sequence | SEQ ID NO: |
|---|---|
| AQANCLSPDR | 3126 |
| AQANFPFGGP | 3127 |
| AQANGRDVRT | 3128 |
| AQANKDEGMG | 3129 |
| AQANLQQSSG | 3130 |
| AQANLQRSSA | 3131 |
| AQANQVRSPL | 3132 |
| AQANSSLSSR | 3133 |
| AQAPGQGSQT | 3134 |
| AQAPHRGLYT | 3135 |
| AQAPHSSTAM | 3136 |
| AQAPKVLDWG | 3137 |
| AQAPMSRLAQ | 3138 |
| AQAPMTSGVQ | 3139 |
| AQAPNNGVQK | 3140 |
| AQAPQTRPGR | 3141 |
| AQAPREHPSR | 3142 |
| AQAPRTPDLR | 3143 |
| AQAPSSDRVH | 3144 |
| AQAPSSQEAR | 3145 |
| AQAPSSSYMR | 3146 |
| AQAPTSASRA | 3147 |
| AQAPTSCLAT | 3148 |
| AQAPYTPSSF | 3149 |
| AQAQGAYREM | 3150 |
| AQAQKSPQFR | 3151 |
| AQAQLGTSSP | 3152 |
| AQAQPNYASV | 3153 |
| AQAQRGLHAV | 3154 |
| AQAQSQSWSS | 3155 |
| AQAQTRPPLK | 3156 |
| AQAQTSRAMD | 3157 |
| AQAQVSQMSL | 3158 |
| AQARAAHMAQ | 3159 |
| AQARAAVPSK | 3160 |
| AQARAQGHSY | 3161 |

TABLE 1-continued

Exemplary Peptide Sequences,
e.g., Targeting Peptides

| Peptide Sequence | SEQ ID NO: |
|---|---|
| AQARASYNSM | 3162 |
| AQARATLGST | 3163 |
| AQARDASGVA | 3164 |
| AQARDRMMIN | 3165 |
| AQARDRMMYN | 3166 |
| AQAREQNVSS | 3167 |
| AQARFPSVYA | 3168 |
| AQARFTTNEL | 3169 |
| AQARGDMFAW | 3170 |
| AQARGDSGVS | 3171 |
| AQARGLAEVE | 3172 |
| AQARGNNLYT | 3173 |
| AQARGSPMSR | 3174 |
| AQARGTQTAE | 3175 |
| AQARGTTTAE | 3176 |
| AQARIDHGRC | 3177 |
| AQARITTDMS | 3178 |
| AQARLPMLVG | 3179 |
| AQARMPVVFG | 3180 |
| AQARNGLMIM | 3181 |
| AQARPPLGRL | 3182 |
| AQARPTGFTL | 3183 |
| AQARQSSFTI | 3184 |
| AQARSGVASL | 3185 |
| AQARSLEPGI | 3186 |
| AQARSPVVEK | 3187 |
| AQARSSDRGS | 3188 |
| AQARTIDQSC | 3189 |
| AQARTPLGYQ | 3190 |
| AQARTTSFVA | 3191 |
| AQARVDVQLP | 3192 |
| AQARVQIEKH | 3193 |
| AQASAKPLIE | 3194 |
| AQASARMPSS | 3195 |
| AQASAVRMAR | 3196 |
| AQASDPPRSS | 3197 |
| AQASDRVSRG | 3198 |

TABLE 1-continued

Exemplary Peptide Sequences,
e.g., Targeting Peptides

| Peptide Sequence | SEQ ID NO: |
|---|---|
| AQASGIAAGA | 3199 |
| AQASGYTSVS | 3200 |
| AQASHSTLGT | 3201 |
| AQASLKILSL | 3202 |
| AQASLQILSL | 3203 |
| AQASLQILTL | 3204 |
| AQASLQIMSL | 3205 |
| AQASMQILSL | 3206 |
| AQASNRLDRP | 3207 |
| AQASQAQPKS | 3208 |
| AQASRESPTR | 3209 |
| AQASRIHSCC | 3210 |
| AQASRNLSAG | 3211 |
| AQASRTSPPL | 3212 |
| AQASSKSACQ | 3213 |
| AQASSRVSSF | 3214 |
| AQASSTSISK | 3215 |
| AQASVSGRAL | 3216 |
| AQASVSRSLL | 3217 |
| AQASYKPSLM | 3218 |
| AQASYQPSLM | 3219 |
| AQASYQTSLM | 3220 |
| AQATALLHQM | 3221 |
| AQATCQQAST | 3222 |
| AQATFLQAST | 3223 |
| AQATFQQTST | 3224 |
| AQATFSKGIV | 3225 |
| AQATGSDSRR | 3226 |
| AQATGSSGLS | 3227 |
| AQATLGKPSV | 3228 |
| AQATLPMLTR | 3229 |
| AQATRLSAAL | 3230 |
| AQATRQAHPS | 3231 |
| AQATRSDTIP | 3232 |
| AQATRSNGGV | 3233 |
| AQATSGRPVC | 3234 |

TABLE 1-continued

Exemplary Peptide Sequences,
e.g., Targeting Peptides

| Peptide Sequence | SEQ ID NO: |
|---|---|
| AQATSGSSSQ | 3235 |
| AQATTIQSAA | 3236 |
| AQATTRATLS | 3237 |
| AQATTSNTRA | 3238 |
| AQATVPLFWL | 3239 |
| AQAVAMSPHA | 3240 |
| AQAVEVGATR | 3241 |
| AQAVGIQKLL | 3242 |
| AQAVITSRAP | 3243 |
| AQAVLPIALG | 3244 |
| AQAVRASTSL | 3245 |
| AQAVRLPAFV | 3246 |
| AQAVRSGVIK | 3247 |
| AQAVSGRLST | 3248 |
| AQAVVGRSVP | 3249 |
| AQAVVTRSPP | 3250 |
| AQAWPLASQS | 3251 |
| AQAWQSNMER | 3252 |
| AQAYGPLNTL | 3253 |
| AQAYHPSMKV | 3254 |
| AQAYKAPYGA | 3255 |
| AQAYNQTSRL | 3256 |
| AQAYNTHSPT | 3257 |
| AQAYQKVPSV | 3258 |
| AQAYTSQLNS | 3259 |
| AQCGSLCRTA | 3260 |
| AQDFSTSQFT | 3261 |
| AQDFTAAERM | 3262 |
| AQDHVQRSSA | 3263 |
| AQDKKSWPPA | 3264 |
| AQDLVTPSRA | 3265 |
| AQDRCTFVEA | 3266 |
| AQDRNNTRVA | 3267 |
| AQDRQLLWEA | 3268 |
| AQDTKTIGWA | 3269 |
| AQELRGSKTA | 3270 |
| AQESGMPMDA | 3271 |

TABLE 1-continued

Exemplary Peptide Sequences,
e.g., Targeting Peptides

| Peptide Sequence | SEQ ID NO: |
|---|---|
| AQFESDIYSA | 3272 |
| AQFMSVSRSP | 3273 |
| AQFMSVYRSP | 3274 |
| AQFSPRVTGA | 3275 |
| AQFSREPTRA | 3276 |
| AQFTSFPSSA | 3277 |
| AQGFAPTKLA | 3278 |
| AQGHVGLPYA | 3279 |
| AQGLYDAKVA | 3280 |
| AQGMFGAQNA | 3281 |
| AQGMFNSSSA | 3282 |
| AQGMTNHASA | 3283 |
| AQGNGSRITA | 3284 |
| AQGPGSRISA | 3285 |
| AQGPSNTRAA | 3286 |
| AQGQEFMNFA | 3287 |
| AQGRGANYMA | 3288 |
| AQGRGDVVSA | 3289 |
| AQGRQSSLAA | 3290 |
| AQGRQTDRVA | 3291 |
| AQGSGPRYMA | 3292 |
| AQGSKVGLYD | 3293 |
| AQGSKVGMYA | 3294 |
| AQGSNVRSYA | 3295 |
| AQGSVRSPLA | 3296 |
| AQGTMGHHLA | 3297 |
| AQGVRTMVTA | 3298 |
| AQHIASMRPA | 3299 |
| AQHIDSMRLA | 3300 |
| AQHQASLGTA | 3301 |
| AQIDRAYPLA | 3302 |
| AQIDRAYTLA | 3303 |
| AQIDREYPLA | 3304 |
| AQILHAKLAA | 3305 |
| AQILRVANSA | 3306 |
| AQIPGRPWDA | 3307 |

TABLE 1-continued

Exemplary Peptide Sequences,
e.g., Targeting Peptides

| Peptide Sequence | SEQ ID NO: |
|---|---|
| AQIPSGVANA | 3308 |
| AQIRIPYSSA | 3309 |
| AQISGMTSRA | 3310 |
| AQISRPLGSA | 3311 |
| AQKANVTGRA | 3312 |
| AQKELVAPHA | 3313 |
| AQKFAFVSAA | 3314 |
| AQKIAPHWSA | 3315 |
| AQKSDRHPQA | 3316 |
| AQKSWPQTVA | 3317 |
| AQKTTFPSSA | 3318 |
| AQLALKKTAA | 3319 |
| AQLDLTIGRA | 3320 |
| AQLDTMQGKA | 3321 |
| AQLERQYSGA | 3322 |
| AQLFQVFRQA | 3323 |
| AQLGDSTLKA | 3324 |
| AQLGLKLRPA | 3325 |
| AQLGLSDRRA | 3326 |
| AQLGQWSAGA | 3327 |
| AQLHLNSKSA | 3328 |
| AQLIGGSGSA | 3329 |
| AQLKHSNDKA | 3330 |
| AQLKNSPWDA | 3331 |
| AQLLHGESVA | 3332 |
| AQLLSSRAAA | 3333 |
| AQLMHSARVA | 3334 |
| AQLMPPMGRA | 3335 |
| AQLPNTLSMA | 3336 |
| AQLRTIRIAA | 3337 |
| AQLSREYNSA | 3338 |
| AQLSRVMASA | 3339 |
| AQLSSSLRSA | 3340 |
| AQLTPGYKTA | 3341 |
| AQLVTFVPEA | 3342 |
| AQLVTPNPVA | 3343 |
| AQMASLLPEA | 3344 |

81

TABLE 1-continued

Exemplary Peptide Sequences,
e.g., Targeting Peptides

| Peptide Sequence | SEQ ID NO: |
|---|---|
| AQMASLLQEA | 3345 |
| AQMASLLTEA | 3346 |
| AQMAYLLPEA | 3347 |
| AQMDRVTSPA | 3348 |
| AQMDSLLPEA | 3349 |
| AQMGGLLLSA | 3350 |
| AQMHGPGSNA | 3351 |
| AQMNAFNTHA | 3352 |
| AQMRSAYPAA | 3353 |
| AQMSRTRLPA | 3354 |
| AQMTYSQPKA | 3355 |
| AQNGKILVPA | 3356 |
| AQNRSLPHQA | 3357 |
| AQNSANTTCA | 3358 |
| AQPGIPFHGA | 3359 |
| AQPGQSFPAA | 3360 |
| AQPGYHLTSA | 3361 |
| AQPLRMGNIA | 3362 |
| AQPSGITALA | 3363 |
| AQPTRLVGGA | 3364 |
| AQPVRNDRLA | 3365 |
| AQQEKSSTPA | 3366 |
| AQQLVALPFA | 3367 |
| AQQPSRAAQA | 3368 |
| AQQPSYISTA | 3369 |
| AQQSANTMAA | 3370 |
| AQQSFPRATA | 3371 |
| AQQSPVAVRA | 3372 |
| AQQTTSWSEA | 3373 |
| AQQTTVRTDA | 3374 |
| AQQVQFRFEA | 3375 |
| AQRALNKSDA | 3376 |
| AQRDLAHTQA | 3377 |
| AQRDLEHSQA | 3378 |
| AQRDRDARSA | 3379 |
| AQREFTPMDA | 3380 |

82

TABLE 1-continued

Exemplary Peptide Sequences,
e.g., Targeting Peptides

| Peptide Sequence | SEQ ID NO: |
|---|---|
| AQRGFPASTA | 3381 |
| AQRGYDLSPA | 3382 |
| AQRGYDLSTA | 3383 |
| AQRGYENEKA | 3384 |
| AQRHLELKEA | 3385 |
| AQRLAVQAKA | 3386 |
| AQRLHSSATA | 3387 |
| AQRLRQQEDA | 3388 |
| AQRLSGQSSA | 3389 |
| AQRNSYLSDA | 3390 |
| AQRQAVAQSA | 3391 |
| AQRQGPDLLA | 3392 |
| AQRRGDQGQA | 3393 |
| AQRSASGIQA | 3394 |
| AQRSGSPQPA | 3395 |
| AQRSIMKGQA | 3396 |
| AQRSIMQGKA | 3397 |
| AQRSLASVTA | 3398 |
| AQRSYPSTSA | 3399 |
| AQRTSDLLQA | 3400 |
| AQRTSSMSEA | 3401 |
| AQRYLGNSLA | 3402 |
| AQRYTNQVPA | 3403 |
| AQRYVNNSAA | 3404 |
| AQSFSSEQLA | 3405 |
| AQSGIRDARA | 3406 |
| AQSGKSIAGA | 3407 |
| AQSGNHFGKA | 3408 |
| AQSGRVVTLA | 3409 |
| AQSIQYLDYA | 3410 |
| AQSIQYSHTA | 3411 |
| AQSISGVAMA | 3412 |
| AQSKSAITWA | 3413 |
| AQSKTSASQA | 3414 |
| AQSLAKDLSA | 3415 |
| AQSLGTGLQA | 3416 |
| AQSLQHLDWA | 3417 |

TABLE 1-continued

Exemplary Peptide Sequences,
e.g., Targeting Peptides

| Peptide Sequence | SEQ ID NO: |
|---|---|
| AQSMDWPPSA | 3418 |
| AQSMPNSPMA | 3419 |
| AQSMSARGLA | 3420 |
| AQSNLSYARA | 3421 |
| AQSNSYLDSA | 3422 |
| AQSQAVAQSA | 3423 |
| AQSQLFGLRA | 3424 |
| AQSQLVGLRA | 3425 |
| AQSQSGTAWA | 3426 |
| AQSRGQDKAA | 3427 |
| AQSRMLPTSA | 3428 |
| AQSRVLSHQA | 3429 |
| AQSSMSRLVA | 3430 |
| AQSTLTVLPA | 3431 |
| AQSVQYSTSA | 3432 |
| AQSWVGPAVA | 3433 |
| AQSYASSYAA | 3434 |
| AQTKSFSSAA | 3435 |
| AQTLARPRIA | 3436 |
| AQTLPFISSA | 3437 |
| AQTMGGQYSA | 3438 |
| AQTMSGSMVA | 3439 |
| AQTMVSARPA | 3440 |
| AQTNLNFNLA | 3441 |
| AQTPAFINLA | 3442 |
| AQTPRQLASA | 3443 |
| AQTQQSSGWA | 3444 |
| AQTQSIDPSA | 3445 |
| AQTQVPSGAA | 3446 |
| AQTRGDSVGA | 3447 |
| AQTSQMYQTA | 3448 |
| AQTSVMEQRA | 3449 |
| AQTVETHMRA | 3450 |
| AQTVSVHVSA | 3451 |
| AQTVYQQAPA | 3452 |
| AQVGAYADVA | 3453 |

TABLE 1-continued

Exemplary Peptide Sequences,
e.g., Targeting Peptides

| Peptide Sequence | SEQ ID NO: |
|---|---|
| AQVIGNSSAA | 3454 |
| AQVLRAQSQA | 3455 |
| AQVLRMKGIA | 3456 |
| AQVPRYMRPA | 3457 |
| AQVPSVRSSA | 3458 |
| AQVQYLNSHA | 3459 |
| AQVREFRLTA | 3460 |
| AQVSRHVTSA | 3461 |
| AQVTRSLLSA | 3462 |
| AQVVKNSSVA | 3463 |
| AQVVVLTTAA | 3464 |
| AQVVYSEGRA | 3465 |
| AQWGKSDLTA | 3466 |
| AQWPQFMSAA | 3467 |
| AQWQMKQVSA | 3468 |
| AQYGAAPGVA | 3469 |
| AQYKGFEKVA | 3470 |
| AQYKSGGLTA | 3471 |
| AQYMQGALHA | 3472 |
| AQYPSQTVTA | 3473 |
| AQYSAHVSQA | 3474 |
| AQYSLAGSSA | 3475 |
| AQYSLGQATA | 3476 |
| AQYVRSPRKA | 3477 |
| ARAYSTDVRM | 3478 |
| ARVRADSHLA | 3479 |
| ASLSAVAAVA | 3480 |
| AVTRAVQNSA | 3481 |
| CPAAAVLAAA | 3482 |
| DDSRAVGLRA | 3483 |
| DRQPAVHMTA | 3484 |
| EGAFAVLPYA | 3485 |
| EQAFSTSQFT | 3486 |
| ETFNAVRNSA | 3487 |
| FAGSAVMTMA | 3488 |
| FALPAVPGSA | 3489 |
| FLAPAVSTKA | 3490 |

TABLE 1-continued

Exemplary Peptide Sequences,
e.g., Targeting Peptides

| Peptide Sequence | SEQ ID NO: |
| --- | --- |
| FRSVAVENVA | 3491 |
| FRYNAVGEGA | 3492 |
| FSLPAVPNIA | 3493 |
| FVSNAVQGKA | 3494 |
| FVTSAVTEPA | 3495 |
| GALNAVTGVD | 3496 |
| GASRAVVLSA | 3497 |
| GDHRAVAARA | 3498 |
| GDNFAVSGMA | 3499 |
| GGGHAVVLAA | 3500 |
| GGGHAVVQAA | 3501 |
| GGGNAVVLAA | 3502 |
| GLSSAVIAQA | 3503 |
| GMDRAVQTQA | 3504 |
| GNLSAVIIQA | 3505 |
| GPAMAVVGVA | 3506 |
| GPRQAVAGIA | 3507 |
| GQYAAVSSYA | 3508 |
| GRGHAVVLAA | 3509 |
| GRRQAVHSEA | 3510 |
| GSGSAVVTQA | 3511 |
| GTRSAVAALA | 3512 |
| GTSYAVGGQA | 3513 |
| HAQLAVVGEA | 3514 |
| HSPAAVGLQA | 3515 |
| HTATAVGLQA | 3516 |
| IASLAVSQVA | 3517 |
| ISGHAVSTAA | 3518 |
| KQYGAVEGQA | 3519 |
| KSSAAVHATA | 3520 |
| LAAVAVQSPA | 3521 |
| LAENAVKLMA | 3522 |
| LDSRAVLSSA | 3523 |
| LGRGAVLDSA | 3524 |
| LGRGAVLDTA | 3525 |
| LGRGAVLDTV | 3526 |

TABLE 1-continued

Exemplary Peptide Sequences,
e.g., Targeting Peptides

| Peptide Sequence | SEQ ID NO: |
| --- | --- |
| LGRGAVLGTA | 3527 |
| LGRGAVLVTA | 3528 |
| LGRGPVLDTA | 3529 |
| LGRGSVLDTA | 3530 |
| LGRGVVLDTA | 3531 |
| LLAPAVSSKA | 3532 |
| LLYPAVVLEA | 3533 |
| LRRGAVLDTA | 3534 |
| LSPGAVVTSA | 3535 |
| LTNGAGRDRA | 3536 |
| LTNGAIRDRA | 3537 |
| LTNGAVGDRA | 3538 |
| LTNGAVRDQA | 3539 |
| LTNGAVRGRA | 3540 |
| LVNSAVLRNA | 3541 |
| LVPSAVVSKA | 3542 |
| MAVKAVPWTA | 3543 |
| MGRSAVNPVA | 3544 |
| MPNRAVIDSA | 3545 |
| MRSRAVDPVA | 3546 |
| MSLHAVTHSA | 3547 |
| NASLAVSTAA | 3548 |
| NRSDAVRMVA | 3549 |
| NTERAVILEA | 3550 |
| NTRGAVGSAA | 3551 |
| NTVSAVILEA | 3552 |
| PAGSAVVSPA | 3553 |
| PFNSAVSSSA | 3554 |
| PSSYAVSHVA | 3555 |
| PTLTAVAHAA | 3556 |
| QGQAAVGIYA | 3557 |
| QLNRAVNSGA | 3558 |
| QMSRAVSDYA | 3559 |
| RDSMAVGNVA | 3560 |
| RFGSAVGLTA | 3561 |
| RIVNAVKAQA | 3562 |
| RLDQAVSTSA | 3563 |

TABLE 1-continued

Exemplary Peptide Sequences,
e.g., Targeting Peptides

| Peptide Sequence | SEQ ID NO: |
|---|---|
| RLLPAVSNDA | 3564 |
| RLSEAVSMTA | 3565 |
| RLSKAVAAGA | 3566 |
| RNDVAVVHTA | 3567 |
| RNSYAVSEAA | 3568 |
| RPSNAVSVHA | 3569 |
| RTGKAVDTVA | 3570 |
| RTPDAVHMLA | 3571 |
| SANLAVTLLA | 3572 |
| SAVRAVTWDA | 3573 |
| SEIGAVYGSA | 3574 |
| SGESAVVSVA | 3575 |
| SGLKAVGNPA | 3576 |
| SGLLAVSPPA | 3577 |
| SGSLAVGSMA | 3578 |
| SGTRAVSPSA | 3579 |
| SGYTAVASGA | 3580 |
| SLNAAVHSGA | 3581 |
| SLNTAVASLA | 3582 |
| SLSYAVDMRA | 3583 |
| SLVGALAQMA | 3584 |
| SLVGAVSQMA | 3585 |
| SMRQAVSQYA | 3586 |
| SQAHMQASVT | 3587 |
| SQNNAVVSYA | 3588 |
| SRSKAVSWEA | 3589 |
| SRYSAVPREA | 3590 |
| SSSPAVTRSA | 3591 |
| STESAVSDRA | 3592 |
| SVIGAVYGYA | 3593 |
| SVNKAVASLA | 3594 |
| SVNTAVASMA | 3595 |
| SVSKAVSLGA | 3596 |
| TARYAVAQQA | 3597 |
| TFRSAVELRA | 3598 |
| TFYSAVKLGA | 3599 |

TABLE 1-continued

Exemplary Peptide Sequences,
e.g., Targeting Peptides

| Peptide Sequence | SEQ ID NO: |
|---|---|
| TPIQAVRESA | 3600 |
| TQHIDSMRPA | 3601 |
| TQSKTTLTLA | 3602 |
| TQYGAVECQA | 3603 |
| TQYGAVEGRA | 3604 |
| TTALAVGDNA | 3605 |
| TVLSAVSGGA | 3606 |
| VAVHAVGSVA | 3607 |
| VDTRAVGHQA | 3608 |
| VGGAAVGTTA | 3609 |
| VKERAVSQSA | 3610 |
| VMNGAVRLLA | 3611 |
| VPGSAVIAAA | 3612 |
| VSTYAVSMQA | 3613 |
| VIGKAVTGVA | 3614 |
| VTRGAVEAHA | 3615 |
| VVESAVVGLA | 3616 |
| VVNVAVLHVA | 3617 |
| VVSSAVGRTA | 3618 |
| YLVGAVAQMA | 3619 |
| YNRTAVSSEA | 3620 |
| YRSTAVEGYA | 3621 |
| AQASFNDTRA | 3622 |

TABLE 2

Exemplary Peptide, e.g.,
Targeting Peptide Sequences

| Pep-tide | SEQ ID NO: | Amino Acid Sequence | SEQ ID NO: | Nucleotide Sequence |
|---|---|---|---|---|
| 1 | 3648 | PLNGAVH LY | 3660 | ccgcttaatggtgccgtccatct ttat |
| 2 | 3649 | RDSPKGW | 3661 | cgtgattctccgaaggggttggca |
| 3 | 3650 | YSTDVRM | 3662 | tattctacggatgtgaggatgca |
| 4 | 3651 | IVMNSLK | 3663 | attgttatgaattcgttgaaggc |
| 5 | 3652 | RESPRGL | 3664 | cgggagagtcctcgtgggctgca |
| 6 | 3653 | SFNDTRA | 3665 | agtttaatgatactagggctca |
| 7 | 3654 | GGTLAVV SL | 3666 | ggtggtacgttggccgtcgtgtc gctt |

TABLE 2-continued

Exemplary Peptide, e.g.,
Targeting Peptide Sequences

| Pep-tide | SEQ ID NO: | Amino Acid Sequence | SEQ ID NO: | Nucleotide Sequence |
|---|---|---|---|---|
| 8 | 3655 | YGLPKGP | 3667 | tatgggttgccgaagggtcct |
| 9 | 3656 | STGTLRL | 3668 | tcgactgggacgcttcggctt |
| 10 | 3657 | YSTDERM | 3669 | tattcgacggatgagaggatg |
| 11 | 3658 | YSTDERK | 3670 | tattcgacggatgagaggaag |
| 12 | 3659 | YVSSVKM | 3671 | tatgtttcgtctgttaagatg |

In some embodiments, the peptide, e.g., targeting peptide, comprises at least 3, 4, 5, 6, 7, 8, or 9 consecutive amino acids from the amino acid sequence of any of SEQ ID NO: 1725-3622. In some embodiments, the peptide comprises at least 3, 4, 5, 6, 7, 8, or 9 consecutive amino acids from the amino acid sequence of any of SEQ ID NO: 3648-3659.

In some embodiments, the 3 consecutive amino acids comprise PLN. In some embodiments, the 4 consecutive amino acids comprise PLNG (SEQ ID NO: 3678). In some embodiments, the 5 consecutive amino acids comprise PLNGA (SEQ ID NO: 3679). In some embodiments, the 6 consecutive amino acids comprise PLNGAV (SEQ ID NO: 3680). In some embodiments, the 7 consecutive amino acids comprise PLNGAVH (SEQ ID NO: 3681). In some embodiments, the 8 consecutive amino acids comprise PLNGAVHL (SEQ ID NO: 3682). In some embodiments, the 9 consecutive amino acids comprise PLNGAVHLY (SEQ ID NO: 3648).

In some embodiments, the four consecutive amino acids comprise NGAV (SEQ ID NO: 3683). In some embodiments, the four consecutive amino acids comprise GAVH (SEQ ID NO: 3684). In some embodiments, the five consecutive amino acids comprise NGAVH (SEQ ID NO: 3685). In some embodiments, the five consecutive amino acids comprise GAVHL (SEQ ID NO: 3686). In some embodiments, the five consecutive amino acids comprise AVHLY (SEQ ID NO: 3687). In some embodiments, the six consecutive amino acids comprise NGAVHL (SEQ ID NO: 3688). In some embodiments, the seven consecutive amino acids comprise NGAVHLY (SEQ ID NO: 3689).

In some embodiments, the 3 consecutive amino acids comprise YST. In some embodiments, the 4 consecutive amino acids comprise YSTD (SEQ ID NO: 3690). In some embodiments, the 5 consecutive amino acids comprise YSTDE (SEQ ID NO: 3691). In some embodiments, the 5 consecutive amino acids comprise YSTDV (SEQ ID NO: 3700). In some embodiments, the 6 consecutive amino acids comprise YSTDER (SEQ ID NO: 3692). In some embodiments, the 6 consecutive amino acids comprise YSTDVR (SEQ ID NO: 3701). In some embodiments, the 7 consecutive amino acids comprise YSTDERM (SEQ ID NO: 3657). In some embodiments, the 7 consecutive amino acids comprise YSTDERK (SEQ ID NO: 3658). In some embodiments, the 7 consecutive amino acids comprise YSTDVRM (SEQ ID NO: 3650).

In some embodiments, the 3 consecutive amino acids comprise IVM. In some embodiments, the 4 consecutive amino acids comprise IVMN (SEQ ID NO: 3693). In some embodiments, the 5 consecutive amino acids comprise IVMNS (SEQ ID NO: 3694). In some embodiments, the 6 consecutive amino acids comprise IVMNSL (SEQ ID NO: 3695). In some embodiments, the 7 consecutive amino acids comprise IVMNSLK (SEQ ID NO: 3651).

In some embodiments, the peptide, e.g., targeting peptide, comprises an amino acid sequence comprising at least one, two, or three but no more than four modifications, e.g., substitutions, relative to the amino acid sequence of any of SEQ ID NO: 1725-3622. In some embodiments, the peptide, e.g., targeting peptide, comprises an amino acid sequence comprising at least one, two, or three but no more than four modifications, e.g., substitutions, relative to the amino acid sequence of any of SEQ ID NO: 3648-3659.

In some embodiments, the peptide, e.g., targeting peptide comprises the amino acid sequence of PLNGAVHLY (SEQ ID NO: 3648), or an amino acid sequence having at least one, two, or three but no more than four modifications, e.g., substitutions, relative to the amino acid sequence of PLNGAVHLY (SEQ ID NO: 3648), optionally wherein position 7 is H.

In some embodiments, the peptide, e.g., targeting peptide comprises the amino acid sequence of RDSPKGW (SEQ ID NO: 3649), or an amino acid sequence having at least one, two, or three modifications but no more than four modifications, e.g., substitutions, relative to the amino acid sequence of RDSPKGW (SEQ ID NO: 3649).

In some embodiments, the peptide, e.g., targeting peptide comprises the amino acid sequence of IVMNSLK (SEQ ID NO: 3651), or an amino acid sequence having at least one, two, or three modifications but no more than four modifications, e.g., substitutions, relative to the amino acid sequence of IVMNSLK (SEQ ID NO: 3651).

In some embodiments, the peptide, e.g., targeting peptide comprises the amino acid sequence of YSTDVRM (SEQ ID NO: 3650), or an amino acid sequence having at least one, two, or three modifications but no more than four modifications, e.g., substitutions, relative to the amino acid sequence of YSTDVRM (SEQ ID NO: 3650).

In some embodiments, the peptide, e.g., targeting peptide comprises the amino acid sequence of RESPRGL (SEQ ID NO: 3652), or a sequence having at least one, two, or three modifications but no more than four modifications, e.g., substitutions, relative to the amino acid sequence of RESPRGL (SEQ ID NO: 3652).

In some embodiments, the peptide, e.g., targeting peptide comprises the amino acid sequence of any of SEQ ID NO: 1725-3622. In some embodiments, the peptide comprises the amino acid sequence of any of SEQ ID NO: 3648-3659.

In some embodiments, the peptide, e.g., targeting peptide, may comprise an amino acid sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of the sequences shown in Table 1 or Table 2.

In some embodiments, the peptide, e.g., targeting peptide, comprises the amino acid sequence of SEQ ID NO: 3648. In some embodiments, the peptide, e.g., targeting peptide, comprises the amino acid sequence of SEQ ID NO: 3649. In some embodiments, the peptide, e.g., targeting peptide, comprises the amino acid sequence of SEQ ID NO: 3650. In some embodiments, the peptide, e.g., targeting peptide, comprises the amino acid sequence of SEQ ID NO: 3651. In some embodiments, the peptide, e.g., targeting peptide, comprises the amino acid sequence of SEQ ID NO: 3652. In some embodiments, the peptide, e.g., targeting peptide, comprises the amino acid sequence of SEQ ID NO: 3653. In some embodiments, the peptide, e.g., targeting peptide, comprises the amino acid sequence of SEQ ID NO: 3654. In some embodiments, the peptide, e.g., targeting peptide, comprises the amino acid sequence of SEQ ID NO: 3655. In some embodiments, the peptide, e.g., targeting peptide, comprises the amino acid sequence of SEQ ID NO: 3656. In some embodiments, the peptide, e.g., targeting peptide, comprises the amino acid sequence of SEQ ID NO: 3657. In some embodiments, the peptide, e.g., targeting peptide, comprises the amino acid sequence of SEQ ID NO: 3658. In some embodiments, the peptide, e.g., targeting peptide, comprises the amino acid sequence of SEQ ID NO: 3659.

In some embodiments, the peptide, e.g., targeting peptide, may comprise SEQ ID NO: 1725. In some embodiments, the peptide, e.g., targeting peptide, may comprise SEQ ID NO: 1726. In some embodiments, the peptide, e.g., targeting peptide, may comprise SEQ ID NO: 1729. In some embodiments, the peptide, e.g., targeting peptide, may comprise SEQ ID NO: 1760. In some embodiments, the peptide, e.g., targeting peptide, may comprise SEQ ID NO: 1769. In some embodiments, the peptide, e.g., targeting peptide, may comprise SEQ ID NO: 3622. In some embodiments, the peptide, e.g., targeting peptide, may comprise SEQ ID NO: 1798. In some embodiments, the peptide, e.g., targeting peptide, may comprise SEQ ID NO: 1785. In some embodiments, the peptide, e.g., targeting peptide, may comprise SEQ ID NO: 1767. In some embodiments, the peptide, e.g., targeting peptide, may comprise SEQ ID NO: 1734. In some embodiments, the peptide, e.g., targeting peptide, may comprise SEQ ID NO: 1737. In some embodiments, the peptide, e.g., targeting peptide, may comprise SEQ ID NO: 1819.

In some embodiments, a peptide, e.g., targeting peptide, may comprise 4 or more contiguous amino acids of any of the peptides, e.g., targeting peptides, disclosed herein. In some embodiments the peptide, e.g., targeting peptide, may comprise 4 contiguous amino acids of any of the sequences as set forth in Table 1 or Table 2. In some embodiments the peptide, e.g., targeting peptide, may comprise 5 contiguous amino acids of any of the sequences as set forth in Table 1 or 2. In some embodiments the peptide, e.g., targeting peptide, may comprise 6 contiguous amino acids of any of the sequences as set forth in Table 1 or 2.

In some embodiments, the peptide, e.g., targeting peptide, comprises an amino acid sequence encoded by a nucleotide sequence described herein, e.g., a nucleotide sequence of Table 2. In some embodiments, the peptide comprises an amino acid sequence encoded by a nucleotide sequence comprising at least one, two, three, four, five, six, or seven modifications but no more than ten modifications of the nucleotide sequences of any of SEQ ID NOs: 3660-3671. In some embodiments, the peptide comprises an amino acid sequence encoded by the nucleotide sequence of any one of SEQ ID NOs: 3660-3671, or a nucleotide sequence substantially identical (e.g., having at least 70%, 75%, 80%, 85%, 90%, 92%, 95%, 97%, 98%, or 99% sequence identity) thereto.

In some embodiments, the peptide, e.g., targeting peptide comprises an amino acid sequence encoded by a nucleotide sequence comprising at least one, two, three, four, five, six, or seven modifications but no more than ten modifications of the nucleotide sequence of SEQ ID NO: 3660. In some embodiments, the peptide comprises an amino acid sequence encoded by the nucleotide sequence of SEQ ID NO: 3660, or a nucleotide sequence substantially identical (e.g., having at least 70%, 75%, 80%, 85%, 90%, 92%, 95%, 97%, 98%, or 99% sequence identity) thereto.

In some embodiments, the peptide, e.g., targeting peptide, comprises an amino acid sequence encoded by a nucleotide sequence comprising at least one, two, three, four, five, six, or seven modifications but no more than ten modifications of the nucleotide sequence of SEQ ID NO: 3663. In some embodiments, the peptide comprises an amino acid sequence encoded by the nucleotide sequence of SEQ ID NO: 3663, or a nucleotide sequence substantially identical (e.g., having at least 70%, 75%, 80%, 85%, 90%, 92%, 95%, 97%, 98%, or 99% sequence identity) thereto.

In some embodiments, the nucleotide sequence encoding a peptide, e.g., targeting peptide, described herein e.g., peptide 1-12, comprises a nucleotide sequence described herein, e.g., as described in Table 2. In some embodiments, the nucleic acid sequence encoding a peptide described herein comprises the nucleotide sequence of any of SEQ ID NOs: 3660-3671, or a nucleotide sequence substantially identical (e.g., having at least 70%, 75%, 80%, 85%, 90%, 92%, 95%, 97%, 98%, or 99% sequence identity) thereto. In some embodiments, the nucleic acid sequence encoding a peptide described herein comprises a nucleotide sequence comprising at least one, two, three, four, five, six, or seven modifications but no more than ten modifications of the nucleotide sequences of any of SEQ ID NOs: 3660-3671. In some embodiments, the nucleotide sequence encoding a peptide, e.g., targeting peptide, described herein is isolated, e.g., recombinant.

In some embodiments the nucleotide sequence encoding a peptide, e.g., targeting peptide, described herein comprises a nucleotide sequence comprising at least one, two, three, four, five, six, or seven modifications but no more than ten modifications of the nucleotide sequence of SEQ ID NO: 3660. In some embodiments the nucleic acid sequence encoding a peptide described herein comprises a nucleotide sequence comprising the nucleotide sequence of SEQ ID NO: 3660, or a nucleotide sequence substantially identical (e.g., having at least 70%, 75%, 80%, 85%, 90%, 92%, 95%, 97%, 98%, or 99% sequence identity) thereto.

In some embodiments, the nucleic acid encoding a peptide described herein comprises a nucleotide sequence comprising at least one, two, three, four, five, six, or seven modifications but no more than ten modifications of the nucleotide sequence of SEQ ID NO: 3663. In some embodiments the nucleic acid encoding a peptide described herein comprises a nucleotide sequence comprising the nucleotide sequence of SEQ ID NO: 3663, or a nucleotide sequence substantially identical (e.g., having at least 70%, 75%, 80%, 85%, 90%, 92%, 95%, 97%, 98%, or 99% sequence identity) thereto.

In some embodiments, an AAV particle of the disclosure comprises an AAV capsid, e.g., and AAV capsid variant, with a peptide, e.g., targeting peptide, insert (e.g., an AAV capsid variant), wherein the peptide, e.g., targeting peptide, has an amino acid sequence as set forth in any of Table 1 or Table 2.

In some embodiments, an AAV particle of the disclosure comprises an AAV capsid polypeptide, e.g., an AAV capsid variant, with a peptide, e.g., targeting peptide, insert (e.g., an AAV capsid variant), wherein the peptide has an amino acid having at least one, two, or three modifications but no more than four modifications, e.g., substitutions, relative to the amino acid sequence in any of Table 1 or Table 2.

In some embodiments, the AAV particle of the disclosure comprises an AAV capsid polypeptide, e.g., an AAV capsid variant, with a peptide, e.g., targeting peptide, insert (e.g., an AAV capsid variant), wherein the peptide, e.g., targeting peptide, has an amino acid sequence comprising at least 3, 4, 5, 6, 7, 8, or 9 contiguous amino acids of any of the sequences as set forth in any of Table 1 or 2.

In some embodiments, the AAV particle of the disclosure comprises an AAV capsid, e.g., an AAV capsid variant, with a peptide, e.g., a targeting peptide, insert (e.g., an AAV capsid variant), wherein the peptide, e.g., targeting peptide, has an amino acid sequence substantially identical thereto (e.g., having at least 70%, 75%, 80%, 85%, 90%, 92%, 95%, 97%, 98%, or 99% sequence identity) to any of the sequences as set forth in any of Table 1 or 2.

In some embodiments, the peptide, e.g., targeting peptide, may include the amino acid at position 1 to the amino acid at position 2 of SEQ ID NO: 1725-3622 or 3648-3659. In some embodiments, the peptide, e.g., targeting peptide, may include the amino acid at position 1 to the amino acid at position 3 of SEQ ID NO: 1725-3622 or 3648-3659. In some embodiments, the peptide, e.g., targeting peptide, may include the amino acid at position 2 to the amino acid at position 3 of SEQ ID NO: 1725-3622 or 3648-3659. In some embodiments, the peptide, e.g., targeting peptide, may include the amino acid at position 1 to the amino acid at position 4 of SEQ ID NO: 1725-3622 or 3648-3659. In some embodiments, the peptide, e.g., targeting peptide may include the amino acid at position 2 to the amino acid at position 4 of SEQ ID NO: 1725-3622 or 3648-3659. In some embodiments, the peptide, e.g., targeting peptide may include the amino acid at position 3 to the amino acid at position 4 of SEQ ID NO: 1725-3622 or 3648-3659. In some embodiments, the peptide, e.g., targeting peptide, may include the amino acid at position 1 to the amino acid at position 5 of SEQ ID NO: 1725-3622 or 3648-3659. In some embodiments, the peptide, e.g., targeting peptide, may include the amino acid at position 2 to the amino acid at position 5 of SEQ ID NO: 1725-3622 or 3648-3659. In some embodiments, the peptide, e.g., targeting peptide, may include the amino acid at position 3 to the amino acid at position 5 of SEQ ID NO: 1725-3622 or 3648-3659. In some embodiments, the peptide, e.g., targeting peptide, may include the amino acid at position 4 to the amino acid at position 5 of SEQ ID NO: 1725-3622 or 3648-3659. In some embodiments, the peptide, e.g., targeting peptide, may include the amino acid at position 1 to the amino acid at position 6 of SEQ ID NO: 1725-3622 or 3648-3659. In some embodiments, the peptide, e.g., targeting peptide, may include the amino acid at position 2 to the amino acid at position 6 of SEQ ID NO: 1725-3622 or 3648-3659. In some embodiments, the peptide, e.g., targeting peptide, may include the amino acid at position 3 to the amino acid at position 6 of SEQ ID NO: 1725-3622 or 3648-3659. In some embodiments, the peptide, e.g., targeting peptide, may include the amino acid at position 4 to the amino acid at position 6 of SEQ ID NO: 1725-3622 or 3648-3659. In some embodiments, the peptide, e.g., targeting peptide, may include the amino acid at position 5 to the amino acid at position 6 of SEQ ID NO: 1725-3622 or 3648-3659. In some embodiments, the peptide, e.g., targeting peptide, may include the amino acid at position 1 to the amino acid at position 7 of SEQ ID NO: 1725-3622 or 3648-3659. In some embodiments, the peptide, e.g., targeting peptide, may include the amino acid at position 2 to the amino acid at position 7 of SEQ ID NO: 1725-3622 or 3648-3659. In some embodiments, the peptide, e.g., targeting peptide, may include the amino acid at position 3 to the amino acid at position 7 of SEQ ID NO: 1725-3622 or 3648-3659. In some embodiments, the peptide, e.g., targeting peptide, may include the amino acid at position 4 to the amino acid at position 7 of SEQ ID NO: 1725-3622 or 3648-3659. In some embodiments, the peptide, e.g., targeting peptide, may include the amino acid at position 5 to the amino acid at position 7 of SEQ ID NO: 1725-3622 or 3648-3659. In some embodiments, the peptide, e.g., targeting peptide, may include the amino acid at position 6 to the amino acid at position 7 of SEQ ID NO: 1725-3622 or 3648-3659. In some embodiments, the peptide, e.g., targeting peptide, may include the amino acid at position 1 to the amino acid at position 8 of SEQ ID NO: 1725-3622 or 3648-3659. In some embodiments, the peptide, e.g., targeting peptide, may include the amino acid at position 2 to the amino acid at position 8 of SEQ ID NO: 1725-3622 or 3648-3659. In some embodiments, the peptide, e.g., targeting peptide, may include the amino acid at position 3 to the amino acid at position 8 of SEQ ID NO: 1725-3622 or 3648-3659. In some embodiments, the peptide, e.g., targeting peptide, may include the amino acid at position 4 to the amino acid at position 8 of SEQ ID NO: 1725-3622 or 3648-3659. In some embodiments, the peptide, e.g., targeting peptide, may include the amino acid at position 5 to the amino acid at position 8 of SEQ ID NO: 1725-3622 or 3648-3659. In some embodiments, the peptide, e.g., targeting peptide, may include the amino acid at position 6 to the amino acid at position 8 of SEQ ID NO: 1725-3622 or 3648-3659. In some embodiments, the peptide, e.g., targeting peptide, may include the amino acid at position 7 to the amino acid at position 8 of SEQ ID NO: 1725-3622 or 3648-3659. In some embodiments, the peptide, e.g., targeting peptide, may include the amino acid at position 1 to the amino acid at position 9 of SEQ ID NO: 1725-3622 or 3648-3659. In some embodiments, the peptide, e.g., targeting peptide, may include the amino acid at position 2 to the amino acid at position 9 of SEQ ID NO: 1725-3622 or 3648-3659. In some embodiments, the peptide, e.g., targeting peptide, may include the amino acid at position 3 to the amino acid at position 9 of SEQ ID NO: 1725-3622 or 3648-3659. In some embodiments, the peptide, e.g., targeting peptide, may include the amino acid at position 4 to the amino acid at position 9 of SEQ ID NO: 1725-3622 or 3648-3659. In some embodiments, the peptide, e.g., targeting peptide, may include the amino acid at position 5 to the amino acid at position 9 of SEQ ID NO: 1725-3622 or 3648-3659. In some embodiments, the peptide, e.g., targeting peptide, may include the amino acid at position 6 to the amino acid at position 9 of SEQ ID NO: 1725-3622 or 3648-3659. In some embodiments, the peptide, e.g., targeting peptide, may include the amino acid at position 7 to the amino acid at position 9 of SEQ ID NO: 1725-3622 or 3648-3659. In some embodiments, the peptide, e.g., targeting peptide, may include the amino acid at position 8 to the amino acid at position 9 of SEQ ID NO: 1725-3622 or 3648-3659. In some embodiments, the peptide, e.g., targeting peptide, may include the amino acid at position 1 to the amino acid at position 10 of SEQ ID NO: 1725-3622. In some embodiments, the peptide, e.g., targeting peptide, may include the amino acid at position 2 to the amino acid at position 10 of SEQ ID NO: 1725-3622. In some embodiments, the peptide, e.g., targeting peptide, may include the amino acid at position 3 to the amino acid at position 10 of SEQ ID NO: 1725-3622. In some embodiments, the peptide, e.g., targeting peptide, may include the amino acid at position 4 to the amino acid at position 10 of SEQ ID NO: 1725-3622. In some embodiments, the peptide, e.g., targeting peptide, may include the amino acid at position 5 to the amino acid at position 10 of SEQ ID NO: 1725-3622. In some embodiments, the peptide, e.g., targeting peptide, may include the amino acid at position 6 to the amino acid at position 10 of SEQ ID NO: 1725-3622. In some embodiments, the peptide, e.g., targeting peptide, may include the amino acid at position 7 to the amino acid at position 10 of SEQ ID NO: 1725-3622. In some embodiments, the peptide, e.g., targeting peptide, may include the amino acid at position 8 to the amino acid at position 10 of SEQ ID NO: 1725-3622. In some embodiments, the peptide, e.g., targeting peptide, may include the amino acid at position 9 to the amino acid at position 10 of SEQ ID NO: 1725-3622.

The present disclosure also provides a nucleic acid or polynucleotide encoding any of the above described peptides, e.g., targeting peptides, and AAV capsid polypeptides, e.g., AAV capsid variants, AAV particles, vectors, and cells comprising the same.

In some embodiments, an insertion of a peptide, e.g., targeting peptide, into a parent AAV capsid, e.g., a parental sequence, results in a combination insertion/replacement as compared to the parent amino acid sequence. In some embodiments, all the amino acids of a peptide, e.g., targeting peptide, are inserted into the parent AAV capsid sequence. In some embodiments, one amino acid of the peptide, e.g., targeting peptide, replaces one amino acid in the parent AAV capsid while the remaining amino acids of the peptide, e.g., targeting peptide, are inserted into the parent AAV capsid sequence. In some embodiments, two amino acids of the peptide, e.g., targeting peptide, replace two amino acids in the parent AAV capsid while the remaining amino acids of the peptide, e.g., targeting peptide, are inserted into the parent AAV capsid sequence. In some embodiments, three amino acids of the peptide, e.g., targeting peptide, replace three amino acids in the parent AAV capsid while the remaining amino acids of the peptide, e.g., targeting peptide, are inserted into the parent AAV capsid sequence. In some embodiments, four amino acids of the peptide, e.g., targeting peptide, replace four amino acids in the parent AAV capsid while the remaining amino acids of the peptide, e.g., targeting peptide, are inserted into the parent AAV capsid sequence. In some embodiments, five amino acids of the peptide, e.g., targeting peptide, replace five amino acids in the parent AAV capsid while the remaining amino acids of the peptide, e.g., targeting peptide, are inserted into the parent AAV capsid sequence. In some embodiments, six amino acids of the peptide, e.g., targeting peptide, replace six amino acids in the parent AAV capsid while the remaining amino acids of the peptide, e.g., targeting peptide, are inserted into the parent AAV capsid sequence. In some embodiments, seven amino acids of the peptide, e.g., targeting peptide, replace seven amino acids in the parent AAV capsid while the remaining amino acids of the peptide, e.g., targeting peptide, are inserted into the parent AAV capsid sequence. In some embodiments, eight amino acids of the peptide, e.g., targeting peptide, replace eight amino acids in the parent AAV capsid while the remaining amino acids of the peptide, e.g., targeting peptide, are inserted into the parent AAV capsid sequence. In some embodiments, nine amino acids of the peptide, e.g., targeting peptide, replace nine amino acids in the parent AAV capsid while the remaining amino acids of the peptide, e.g., targeting peptide, are inserted into the parent AAV capsid sequence.

In some embodiments, one amino acid of the peptide, e.g., targeting peptide, is inserted into the parent AAV capsid, e.g., parental sequence, while the remaining amino acids of the peptide. e.g., targeting peptide, replace corresponding amino acids in the parent AAV capsid sequence. In some embodiments, two amino acids of the peptide, e.g., targeting peptide, are inserted into the parent AAV capsid while the remaining amino acids of the peptide, e.g., targeting peptide, replace corresponding amino acids in the parent AAV capsid sequence. In some embodiments, three amino acids of the peptide, e.g., targeting peptide, are inserted into the parent AAV capsid while the remaining amino acids of the peptide, e.g., targeting peptide, replace corresponding amino acids in the parent AAV capsid sequence. In some embodiments, four amino acids of the peptide, e.g., targeting peptide, are inserted into the parent AAV capsid while the remaining amino acids of the peptide, e.g., targeting peptide, replace corresponding amino acids in the parent AAV capsid sequence. In some embodiments, five amino acids of the peptide, e.g., targeting peptide, are inserted into the parent AAV capsid while the remaining amino acids of the peptide, e.g., targeting peptide, replace corresponding amino acids in the parent AAV capsid sequence. In some embodiments, six amino acids of the peptide, e.g., targeting peptide, are inserted into the parent AAV capsid while the remaining amino acids of the peptide, e.g., targeting peptide, replace corresponding amino acids in the parent AAV capsid sequence. In some embodiments, seven amino acids of the peptide, e.g., targeting peptide, are inserted into the parent AAV capsid while the remaining amino acids of the peptide, e.g., targeting peptide, replace corresponding amino acids in the parent AAV capsid sequence. In some embodiments, eight amino acids of the peptide, e.g., targeting peptide, are inserted into the parent AAV capsid while the remaining amino acids of the peptide, e.g., targeting peptide, replace corresponding amino acids in the parent AAV capsid sequence. In some embodiments, nine amino acids of the peptide, e.g., targeting peptide, are inserted into the parent AAV capsid while the remaining amino acids of the peptide, e.g., targeting peptide, replace corresponding amino acids in the parent AAV capsid sequence.

Figure 4:
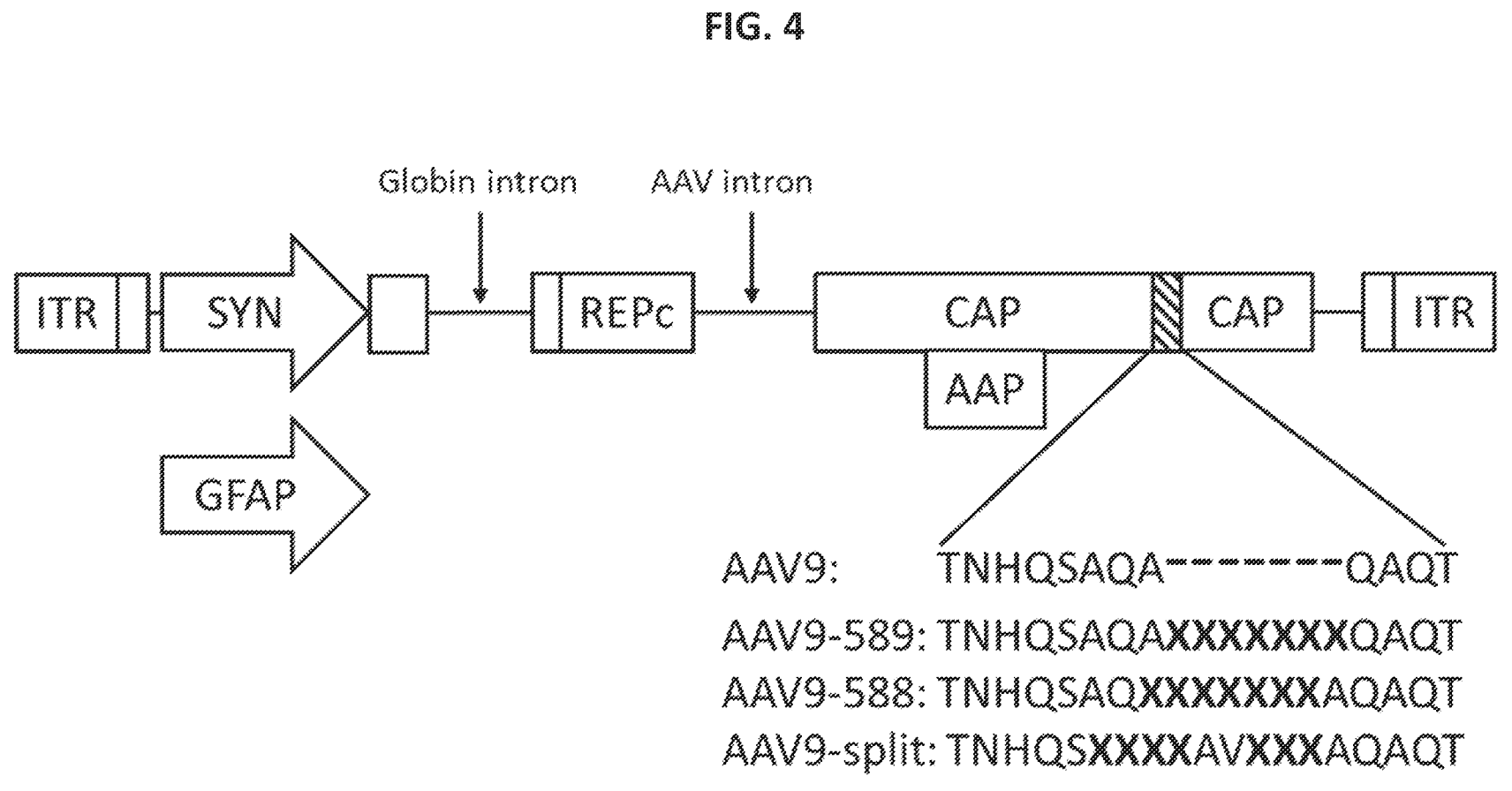

In some embodiments, certain amino acids of the peptide, e.g., targeting peptide, may be anchored and or retained as in the original parent AAV capsid sequence, e.g., parental sequence. In certain embodiments, these anchored amino acids are centrally located in the peptide, e.g., targeting peptide, resulting in a split insertion-anchor-insertion design. Similarly, as a non-limiting example, the insertion of a peptide, e.g., targeting peptide, may result in a split insertion-replacement-insertion design. As a non-limiting example, the insertion of a peptide, e.g., targeting peptide, into a parent AAV capsid sequence may result in a split replacement-insertion-replacement design. As a non-limiting example, a split design peptide, e.g., targeting peptide, may be as shown in FIG. 4 (e.g., TNHQSXXXXAVXXXAQAQT (SEQ ID NO: 3699)).

In some embodiments, an insertion of a peptide, e.g., targeting peptide, into the parent AAV capsid sequence, e.g., parental sequence, may result in the replacement or mutation of at least one amino acid of the parent AAV capsid. In certain embodiments, the first amino acid (N-terminal) of the peptide, e.g., targeting peptide, replaces an amino acid in the parent AAV capsid sequence. In certain embodiments, the first two amino acids (N-terminal) of the peptide, e.g., targeting peptide, replace two amino acids in the parent AAV capsid sequence. In certain embodiments, the first three amino acids (N-terminal) of the peptide, e.g., targeting peptide, replace three amino acids in the parent AAV capsid sequence. In certain embodiments, the first four amino acids (N-terminal) of the peptide, e.g., targeting peptide, replace four amino acids in the parent AAV capsid sequence. In certain embodiments, the first five amino acids (N-terminal) of the peptide, e.g., targeting peptide, replace five amino acids in the parent AAV capsid sequence. In certain embodiments, the first six amino acids (N-terminal) of the peptide, e.g., targeting peptide, replace six amino acids in the parent AAV capsid sequence. In certain embodiments, the first seven amino acids (N-terminal) of the peptide, e.g., targeting peptide, replace seven amino acids in the parent AAV capsid sequence. In certain embodiments, the first eight amino acids (N-terminal) of the peptide, e.g., targeting peptide, replace eight amino acids in the parent AAV capsid sequence. In certain embodiments, the first nine amino acids (N-terminal) of the peptide, e.g., targeting peptide, replace nine amino acids in the parent AAV capsid sequence. In certain embodiments, the first ten amino acids (N-terminal) of the peptide, e.g., targeting peptide, replace ten amino acids in the parent AAV capsid sequence.

In certain embodiments, the last amino acid (C-terminal) of the peptide, e.g., targeting peptide, replaces an amino acid in the parent AAV capsid sequence. In certain embodiments, the last two amino acids (C-terminal) of the peptide, e.g., targeting peptide, replace two amino acids in the parent AAV capsid sequence. In certain embodiments, the last three amino acids (C-terminal) of the peptide, e.g., targeting peptide, replace three amino acids in the parent AAV capsid sequence. In certain embodiments, the last four amino acids (C-terminal) of the peptide, e.g., targeting peptide, replace four amino acids in the parent AAV capsid sequence. In certain embodiments, the last five amino acids (C-terminal) of the peptide, e.g., targeting peptide, replace five amino acids in the parent AAV capsid sequence. In certain embodiments, the last six amino acids (C-terminal) of the peptide, e.g., targeting peptide, replace six amino acids in the parent AAV capsid sequence. In certain embodiments, the last seven amino acids (C-terminal) of the peptide, e.g., targeting peptide, replace seven amino acids in the parent AAV capsid sequence. In certain embodiments, the last eight amino acids (C-terminal) of the peptide, e.g., targeting peptide, replace eight amino acids in the parent AAV capsid sequence. In certain embodiments, the last nine amino acids (C-terminal) of the peptide, e.g., targeting peptide, replace nine amino acids in the parent AAV capsid sequence. In certain embodiments, the last ten amino acids (C-terminal) of the peptide, e.g., targeting peptide, replace ten amino acids in the parent AAV capsid sequence.

In certain embodiments, the first (N-terminal) and last (C-terminal) amino acids of the peptide, e.g., targeting peptide, may replace amino acids in the parent AAV capsid sequence, e.g., parental sequence. In certain embodiments, the first two (N-terminal) and last two (C-terminal) amino acids of the peptide, e.g., targeting peptide, may replace amino acids in the parent AAV capsid sequence. In certain embodiments, the first three (N-terminal) and last three (N-terminal) amino acids of the peptide, e.g., targeting peptide, may replace amino acids in the parent AAV capsid sequence. In certain embodiments, the replacements are asymmetrical in terms of N-terminal and C-terminal replacements and may be any combination of the any of the above.

In certain embodiments, one amino acid of the peptide, e.g., targeting peptide, replaces an amino acid in the parent AAV capsid sequence, e.g., parental sequence. In certain embodiments, two amino acids of the peptide, e.g., targeting peptide, replace two amino acids in the parent AAV capsid sequence. In certain embodiments, three amino acids of the peptide, e.g., targeting peptide, replace three amino acids in the parent AAV capsid sequence. In certain embodiments, four amino acids of the peptide, e.g., targeting peptide, replace four amino acids in the parent AAV capsid sequence. In certain embodiments, five amino acids of the peptide, e.g., targeting peptide, replace five amino acids in the parent AAV capsid sequence. In certain embodiments, six amino acids of the peptide, e.g., targeting peptide, replace six amino acids in the parent AAV capsid sequence. In certain embodiments, seven amino acids of the peptide, e.g., targeting peptide, replace seven amino acids in the parent AAV capsid sequence. In certain embodiments, eight amino acids of the peptide, e.g., targeting peptide, replace eight amino acids in the parent AAV capsid sequence. In certain embodiments, nine amino acids of the peptide, e.g., targeting peptide, replace nine amino acids in the parent AAV capsid sequence. In certain embodiments, ten amino acids of the peptide, e.g., targeting peptide, replace ten amino acids in the parent AAV capsid sequence. In certain embodiments, all amino acids of the peptide, e.g., targeting peptide, replace the same number of amino acids in the parent AAV capsid sequence.

In some embodiments, the AAV particle of the disclosure may comprise a polynucleotide encoding an AAV capsid polypeptide, e.g., an AAV capsid variant, wherein said polynucleotide further comprising a nucleic acid insert, e.g., a targeting nucleic acid insert, wherein the nucleic acid insert has a nucleotide sequence substantially comprising any of those as described in Hanlon et al., 2019 (Hanlon et al., Mol Ther Methods Clin Dev. 2019 Oct. 23; 15:320-332, the contents of which are herein incorporated by reference in its entirety). As a non-limiting the nucleic acid insert, e.g., targeting nucleic acid insert, has a nucleotide sequence substantially comprising AAV-S. As a non-limiting example, the targeting nucleic acid insert has a nucleotide sequence substantially comprising AAV-F.

The AAV particle of the disclosure comprising a nucleic acid insert, e.g., a targeting nucleic acid insert, may have a polynucleotide sequence encoding a capsid polypeptide with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more, identity to the parent capsid sequence.

The AAV particle of the disclosure comprising a peptide, e.g., a targeting peptide, insert, may have an amino acid sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more, identity to the parent capsid sequence.

AAV Capsid Polypeptide, e.g., AAV Capsid Variant

In some embodiments, a peptide, e.g., targeting peptide, is inserted, included or otherwise incorporated into a polypeptide. In some embodiments, such a polypeptide may be referred to as the "parental polypeptide" or "starting polypeptide" or "parental amino acid sequence" and such an insert may be referred to as "targeting peptide insert", "peptide insert" or "amino acid sequence insert". In some embodiments, an AAV capsid polypeptide, e.g., an AAV capsid variant described herein may comprise a peptide, e.g., targeting peptide, insert and a polypeptide, e.g., a larger polypeptide described herein. In some embodiments, the AAV capsid polypeptide, e.g., the AAV capsid variant has an amino acid sequence that is longer than the parent AAV capsid. In other embodiments, the AAV capsid polypeptide, e.g., the AAV capsid variant has an amino acid sequence that is the same length as the parent AAV capsid. In some embodiments, the AAV capsid polypeptide, e.g., the AAV capsid variant has an amino acid sequence that is shorter than the parent AAV capsid.

Where a peptide, e.g., targeting peptide, including sequences of 5-50 contiguous amino acids, is inserted into a parental polypeptide, the insertion may be between two amino acids in the parental polypeptide. Insertion may also be a split insertion whereby one contiguous portion of a peptide insert is inserted between a first set of two amino acids in the parental polypeptide and a second portion of the peptide is inserted between a second set of two amino acids in the parental polypeptide, e.g., a different site. Between this first site and second site, any number of amino acids of the parental polypeptide may be retained. In some embodiments, 1, 2, 3, 4, 5, 6, 7, 8, or 9 amino acids in the parental polypeptide may be retained between the first and second peptide insert.

In some embodiments, a peptide, e.g., targeting peptide, inserts may, in whole or in part, replace one or more amino acids in the parental polypeptide. For example, a peptide insert of 4 amino acids may be inserted immediately after position 586 in the parental polypeptide wherein the last two amino acids of the peptide insert replace the amino acids at positions 587 and 588 of the parental polypeptide. Consequently, the newly formed polypeptide will have increased in length by only two amino acids, e.g., 2 inserted and 2 substituted. In some embodiments, a combinatorial insert/substitutional (i/s) variant may comprise one or more amino acid inserts and one or more amino acid substitutions, e.g., each from 1 to 15 amino acids in length and from 1 to 15 in number.

A peptide, e.g., targeting peptide, may be stand-alone peptides or may be inserted into or conjugated to a parent sequence. In some embodiments, the peptides, e.g., targeting peptides, are inserted into the capsid protein of an AAV particle.

One or more peptides, e.g., targeting peptides, may be inserted into a parent AAV capsid sequence to generate the AAV particles of the disclosure.

A peptide, e.g., targeting peptide, may be inserted into a parent AAV capsid sequence in any location that results in fully functional AAV particles, e.g., an AAV particle comprising an AAV capsid polypeptide, e.g., an AAV capsid variant described herein. The peptide, e.g., targeting peptide may be inserted in VP1, VP2 and/or VP3. Numbering of the amino acid residues may differ across AAV serotypes. As used herein, amino acid positions of the parent AAV capsid sequence are described using AAV9 (SEQ ID NO: 138) as reference.

In some embodiments, the peptide, e.g., targeting peptide, is inserted in a hypervariable region of the AAV capsid sequence. Non-limiting examples of such hypervariable regions include Loop I, Loop II, Loop IV, Loop VI, and Loop VIII of the parent AAV capsid. While not wishing to be bound by theory, it is believed in some embodiments that these surface exposed loops, which may hereinafter also be referred to as surface loops, are typically unstructured and poorly conserved, making them suitable regions for insertion of peptides, e.g., targeting peptides.

In some embodiments, a peptide, e.g., targeting peptide, is inserted into Loop I. In another embodiment, the peptide, e.g., targeting peptide, is used to replace a portion, or all of Loop I. As a non-limiting example, addition of the peptide, e.g., targeting peptide, to the parent AAV capsid sequence may result in the replacement or mutation of at least one amino acid of the parent AAV capsid.

In some embodiments, a peptide, e.g., targeting peptide, is inserted into Loop II. In another embodiment, the targeting peptide is used to replace a portion, or all of Loop II. As a non-limiting example, addition of the targeting peptide to the parent AAV capsid sequence may result in the replacement or mutation of at least one amino acid of the parent AAV capsid.

In some embodiments, the peptide, e.g., targeting peptide, is inserted into Loop IV. In another embodiment, the peptide, e.g., targeting peptide, is used to replace a portion, or all of Loop IV. As a non-limiting example, addition of the peptide, e.g., targeting peptide, to the parent AAV capsid sequence may result in the replacement or mutation of at least one amino acid of the parent AAV capsid.

In some embodiments, the peptide, e.g., targeting peptide, is inserted into Loop VI. In another embodiment, the peptide, e.g., targeting peptide, is used to replace a portion, or all of Loop VI. As a non-limiting example, addition of the peptide, e.g., targeting peptide, to the parent AAV capsid sequence may result in the replacement or mutation of at least one amino acid of the parent AAV capsid.

In some embodiments, the peptide, e.g., targeting peptide, is inserted into Loop VIII. In another embodiment, the peptide, e.g., targeting peptide, is used to replace a portion, or all of Loop VIII. As a non-limiting example, addition of the peptide, e.g., targeting peptide, to the parent AAV capsid sequence may result in the replacement or mutation of at least one amino acid of the parent AAV capsid.

In some embodiments, more than one peptide, e.g., targeting peptide, is inserted into a parent AAV capsid sequence. As a non-limiting example, peptide, e.g., targeting peptide, may be inserted at both Loop IV and Loop VIII in the same parent AAV capsid sequence.

A peptide, e.g., targeting peptide, may be inserted at any amino acid position of the parent AAV capsid sequence, such as, but not limited to, between amino acids at positions 586-592, 588-589, 586-589, 452-458, 262-269, 464-473, 491-495, 546-557 and/or 659-668.

In some embodiments, the peptide, e.g., targeting peptide, is inserted into a parent AAV capsid sequence between amino acids at positions 588 and 589 (Loop VIII). In some embodiments, the parent AAV capsid is AAV9 (SEQ ID NO: 138). In some embodiments, the parent AAV capsid is K449R AAV9 (SEQ ID NO: 11).

In some embodiments, the peptide, e.g., targeting peptide, is inserted into a parent AAV capsid sequence between amino acids at positions 454, 455, 457, 458, 459, 460, and/or 461 (Loop IV).

In some embodiments, the peptide, e.g., targeting peptide, is inserted into a parent AAV capsid sequence between amino acids at positions 586, 587, 588, 589, and/or 590 (Loop VIII).

In some embodiments, the peptide, e.g., targeting peptide, is inserted into a parent AAV capsid sequence Loop IV. As a non-limiting example, the parent AAV capsid may be AAV5. As a non-limiting example, the parent AAV capsid may be AAV9. As a non-limiting example, the parent AAV capsid may be AAV9hu. 14 (SEQ ID NO: 137 or 138). As a non-limiting example, the parent AAV capsid may be AAV9 K449R (SEQ ID NO: 11). As a non-limiting example, the parent AAV capsid may be PHP.B (SEQ ID NO: 5 or 6). As a non-limiting example, the parent AAV capsid may be PHP.N (SEQ ID NO: 4). As a non-limiting example, the parent AAV capsid may be VOY101 (SEQ ID NO: 1 or 2). As a non-limiting example, the parent AAV capsid may be VOY201 (SEQ ID NO: 3 or 1724).

In some embodiments, the peptide, e.g., targeting peptide, are inserted into a parent AAV capsid sequence Loop VIII. As a non-limiting example, the parent AAV capsid may be AAV5. As a non-limiting example, the parent AAV capsid may be AAV9. As a non-limiting example, the parent AAV capsid may be AAV9hu.14 (SEQ ID NO: 137 or 138). As a non-limiting example, the parent AAV capsid may be AAV9 K449R (SEQ ID NO: 11). As a non-limiting example, the parent AAV capsid may be PHP.B (SEQ ID NO: 5 or 6). As a non-limiting example, the parent AAV capsid may be PHP.N (SEQ ID NO: 4). As a non-limiting example, the parent AAV capsid may be VOY101 (SEQ ID NO: 1 or 2). As a non-limiting example, the parent AAV capsid may be VOY201 (SEQ ID NO: 3 or 1724).

In some embodiments, the peptide, e.g., a targeting peptide, is present in loop VIII of an AAV capsid polypeptide, e.g., an AAV capsid variant. In some embodiments, the peptide of an AAV capsid variant described herein, is present immediately subsequent to position 586, relative to a reference sequence numbered according to the amino acid sequence of SEQ ID NO: 138. In some embodiments, the peptide of an AAV capsid variant described herein, is present immediately subsequent to position 588, relative to a reference sequence numbered according to the amino acid sequence of SEQ ID NO: 138. In some embodiments, the peptide of an AAV capsid variant described herein, is present immediately subsequent to position 589, relative to a reference sequence numbered according to the amino acid sequence of SEQ ID NO: 138.

In some embodiments, the peptide, e.g., targeting peptide, of an AAV capsid polypeptide, e.g., an AAV capsid variant described herein comprises the amino acid sequence of PLNGAVHLY (SEQ ID NO: 3648), wherein the amino acid sequence of PLNGAVHLY (SEQ ID NO: 3648) is present immediately subsequent to position 586, relative to a reference sequence numbered according to the amino acid sequence of SEQ ID NO: 138.

In some embodiments, the peptide, e.g., targeting peptide, of an AAV capsid polypeptide, e.g., an AAV capsid variant described herein comprises the amino acid sequence of GGTLAVVSL (SEQ ID NO: 3654), wherein the amino acid sequence of GGTLAVVSL (SEQ ID NO: 3654) is present immediately subsequent to position 586, relative to a reference sequence numbered according to the amino acid sequence of SEQ ID NO: 138.

In some embodiments, the peptide, e.g., targeting peptide, of an AAV capsid polypeptide, e.g., an AAV capsid variant, described herein comprises the amino acid sequence of IVMNSLK (SEQ ID NO: 3651), wherein the amino acid sequence of IVMNSLK (SEQ ID NO: 3651) is present immediately subsequent to position 588, relative to a reference sequence numbered according to the amino acid sequence of SEQ ID NO: 138.

In some embodiments, the peptide, e.g., targeting peptide, of an AAV capsid polypeptide, e.g., an AAV capsid variant, described herein comprises the amino acid sequence of any of SEQ ID NOs: 3649, 3650, 3652, 3653, or 3655-3659, wherein the amino acid sequence of any of the aforesaid sequences is present immediately subsequent to position 589, relative to a reference sequence numbered according to the amino acid sequence of SEQ ID NO: 138.

The peptide, e.g., targeting peptide, described herein may increase the transduction of an AAV particle of the disclosure (e.g., an AAV particle comprising an AAV capsid polypeptide, e.g., an AAV capsid variant) to a target tissue as compared to the parent AAV particle lacking a peptide, e.g., targeting peptide insert. In some embodiments, the peptide, e.g., targeting peptide increases the transduction of an AAV particle to a target tissue by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 300%, 400%, 500%, or more as compared to a parent AAV particle lacking a peptide, e.g., targeting peptide, insert.

In some embodiments, the peptide, e.g., targeting peptide, increases the transduction of an AAV particle (e.g., an AAV particle comprising an AAV capsid polypeptide, e.g., an AAV capsid variant) to a cell, region, or tissue of the CNS (e.g., a brain cell, brain tissue, brain region, spinal cord cell, spinal cord region, or spinal cord tissue) by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 300%, 400%, 500%, or more as compared to a parent AAV particle lacking a peptide, e.g., targeting peptide, insert. In some embodiments, the brain region comprises a frontal cortex, sensory cortex, motor cortex, putamen, thalamus, cerebellar cortex, dentate nucleus, caudate, and/or hippocampus. In some embodiments, the spinal cord region comprises a cervical, thoracic, and/or lumbar region.

In some embodiments, the peptide, e.g., targeting peptide, increases the transduction of an AAV particle (e.g., an AAV particle comprising an AAV capsid polypeptide, e.g., an AAV capsid variant) to a cell or tissue of the PNS by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 300%, 400%, 500%, or more as compared to a parent AAV particle lacking a peptide, e.g., targeting peptide, insert.

In some embodiments, the peptide, e.g., targeting peptide, increases the transduction of an AAV particle (e.g., an AAV particle comprising an AAV capsid polypeptide, e.g., an AAV capsid variant) to a cell or tissue of the DRG by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 300%, 400%, 500%, or more as compared to a parent AAV particle lacking a peptide, e.g., targeting peptide, insert.

In some embodiments, the peptide, e.g., targeting peptide, increases the transduction of an AAV particle (e.g., an AAV particle comprising an AAV capsid polypeptide, e.g., an AAV capsid variant) to a cell, region, or tissue of a muscle by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 300%, 400%, 500%, or more as compared to a parent AAV particle lacking a targeting peptide insert. In some embodiments, a muscle region may comprise a heart muscle, quadriceps muscle, and/or a diaphragm muscle region. In some embodiments, the muscle region comprises a heart muscle region, e.g., a heart atrium muscle region or a heart ventricle muscle region, In some embodiments, an AAV particle described herein comprises an AAV capsid polypeptide, e.g., an AAV capsid polypeptide, e.g., an AAV capsid variant. In some embodiments, the AAV capsid variant comprises a peptide, e.g., targeting peptide, sequence as described in Table 1 or 2.

In some embodiments, the AAV capsid polypeptide, e.g., the AAV capsid variant, comprises at least 3, 4, 5, 6, 7, 8, or 9 consecutive amino acids from the amino acid sequence of any of SEQ ID NO: 1725-3622. In some embodiments, the AAV capsid variant comprises at least 3, 4, 5, 6, 7, 8, or 9 consecutive amino acids from the amino acid sequence of any of SEQ ID NO: 3648-3659. In some embodiments, the amino acid sequence is present in loop VIII. In some embodiments, the amino acid sequence is present immediately subsequent to position 586, 588, or 589, relative to a reference sequence numbered according to the amino acid sequence of SEQ ID NO: 138.

In some embodiments, the 3 consecutive amino acids comprise PLN. In some embodiments, the 4 consecutive amino acids comprise PLNG (SEQ ID NO: 3678). In some embodiments, the 5 consecutive amino acids comprise PLNGA (SEQ ID NO: 3679). In some embodiments, the 6 consecutive amino acids comprise PLNGAV (SEQ ID NO: 3680). In some embodiments, the 7 consecutive amino acids comprise PLNGAVH (SEQ ID NO: 3681). In some embodiments, the 8 consecutive amino acids comprise PLNGAVHL (SEQ ID NO: 3682). In some embodiments, the 9 consecutive amino acids comprise PLNGAVHLY (SEQ ID NO: 3648).

In some embodiments, the 3 consecutive amino acids comprise YST. In some embodiments, the 4 consecutive amino acids comprise YSTD (SEQ ID NO: 3690). In some embodiments, the 5 consecutive amino acids comprise YSTDE (SEQ ID NO: 3691). In some embodiments, the 5 consecutive amino acids comprise YSTDV (SEQ ID NO: 3700). In some embodiments, the 6 consecutive amino acids comprise YSTDER (SEQ ID NO: 3692). In some embodiments, the 6 consecutive amino acids comprise YSTDVR (SEQ ID NO: 3701). In some embodiments, the 7 consecutive amino acids comprise YSTDERM (SEQ ID NO: 3657). In some embodiments, the 7 consecutive amino acids comprise YSTDERK (SEQ ID NO: 3658). In some embodiments, the 7 consecutive amino acids comprise YSTDVRM (SEQ ID NO: 3650).

In some embodiments, the 3 consecutive amino acids comprise IVM. In some embodiments, the 4 consecutive amino acids comprise IVMN (SEQ ID NO: 3693). In some embodiments, the 5 consecutive amino acids comprise IVMNS (SEQ ID NO: 3694). In some embodiments, the 6 consecutive amino acids comprise IVMNSL (SEQ ID NO: 3695). In some embodiments, the 7 consecutive amino acids comprise IVMNSLK (SEQ ID NO: 3651).

In some embodiments, the AAV capsid polypeptide, e.g., the AAV capsid variant, comprises an amino acid sequence comprising at least one, two, or three but no more than four modifications, e.g., substitutions, relative to the amino acid sequence of any of SEQ ID NO: 1725-3622. In some embodiments, the AAV capsid variant comprises an amino acid sequence comprising at least one, two, or three but no more than four modifications, e.g., substitutions, relative to the amino acid sequence of any of SEQ ID NO: 3648-3659. In some embodiments, the amino acid sequence is present in loop VIII. In some embodiments, the amino acid sequence is present immediately subsequent to position 586, 588, or 589, relative to a reference sequence numbered according to the amino acid sequence of SEQ ID NO: 138.

In some embodiments, the AAV capsid polypeptide, e.g., the AAV capsid variant, comprises the amino acid sequence of PLNGAVHLY (SEQ ID NO: 3648), or an amino acid sequence having at least one, two, or three but no more than four modifications, e.g., substitutions, relative to the amino acid sequence of PLNGAVHLY (SEQ ID NO: 3648), optionally wherein position 7 is H.

In some embodiments, the AAV capsid polypeptide, e.g., the AAV capsid variant, comprises the amino acid sequence of RDSPKGW (SEQ ID NO: 3649), or an amino acid sequence having at least one, two, or three modifications but no more than four modifications, e.g., substitutions, relative to the amino acid sequence of RDSPKGW (SEQ ID NO: 3649).

In some embodiments, the AAV capsid polypeptide, e.g. the AAV capsid variant, comprises the amino acid sequence of IVMNSLK (SEQ ID NO: 3651), or an amino acid sequence having at least one, two, or three modifications but no more than four modifications, e.g., substitutions, relative to the amino acid sequence of IVMNSLK (SEQ ID NO: 3651).

In some embodiments, the AAV capsid polypeptide, e.g. the AAV capsid variant, comprises the amino acid sequence of YSTDVRM (SEQ ID NO: 3650), or an amino acid sequence having at least one, two, or three modifications but no more than four modifications, e.g., substitutions, relative to the amino acid sequence of YSTDVRM (SEQ ID NO: 3650).

In some embodiments, the AAV capsid polypeptide, e.g., the AAV capsid variant, comprises the amino acid sequence of RESPRGL (SEQ ID NO: 3652), or a sequence having at least one, two, or three modifications but no more than four modifications, e.g., substitutions, relative to the amino acid sequence of RESPRGL (SEQ ID NO: 3652).

In some embodiments, the AAV capsid polypeptide, e.g., the AAV capsid variant, comprises the amino acid sequence of any of SEQ ID NO: 1725-3622. In some embodiments, the AAV capsid variant comprises the amino acid sequence of any of SEQ ID NO: 3648-3659. In some embodiments, the amino acid sequence is present in loop VIII of an AAV capsid variant described herein. In some embodiments, the amino acid sequence is present immediately subsequent to position 586, relative to a reference sequence numbered according to the amino acid sequence of SEQ ID NO: 138. In some embodiments, the amino acid sequence is present immediately subsequent to position 588, relative to a reference sequence numbered according to the amino acid sequence of SEQ ID NO: 138. In some embodiments, the amino acid sequence is present immediately subsequent to position 589, relative to a reference sequence numbered according to the amino acid sequence of SEQ ID NO: 138.

In some embodiments, the AAV capsid polypeptide, e.g., the AAV capsid variant (e.g., an AAV capsid variant described herein), comprises an amino acid sequence encoded by the nucleotide sequence of any one of SEQ ID NOs: 3660-3671, or a nucleotide sequence substantially identical (e.g., having at least 70%, 75%, 80%, 85%, 90%, 92%, 95%, 97%, 98%, or 99% sequence identity) thereto. In some embodiments, the AAV capsid, e.g., an AAV capsid variant described herein, comprises an amino acid sequence encoded by a nucleotide sequence comprising at least one, two, three, four, five, six, or seven modifications but no more than ten modifications of the nucleotide sequences of any of SEQ ID NOs: 3660-3671.

In some embodiments, the nucleotide sequence encoding the AAV capsid polypeptide, e.g., the AAV capsid variant (e.g., an AAV capsid variant described herein), comprises the nucleotide sequence of any one of SEQ ID NOs: 3660-3671, or a nucleotide sequence substantially identical (e.g., having at least 70%, 75%, 80%, 85%, 90%, 92%, 95%, 97%, 98%, or 99% sequence identity) thereto. In some embodiments, nucleic acid sequence encoding the AAV capsid variant, e.g., an AAV capsid variant described herein, comprises a nucleotide sequence comprising at least one, two, three, four, five, six, or seven modifications but no more than ten modifications of the nucleotide sequences of any of SEQ ID NOs: 3660-3671.

In some embodiments, the nucleotide sequence encoding the AAV capsid polypeptide, e.g., the AAV capsid variant (e.g., an AAV capsid variant described herein), comprises the nucleotide sequence of SEQ ID NO: 3660, or a nucleotide sequence substantially identical (e.g., having at least 70%, 75%, 80%, 85%, 90%, 92%, 95%, 97%, 98%, or 99% sequence identity) thereto. In some embodiments, the nucleic acid sequence encoding the AAV capsid variant comprises a nucleotide sequence comprising at least one, two, three, four, five, six, or seven modifications but no more than ten modifications of the nucleotide sequences of SEQ ID NO: 3660.

In some embodiments, the nucleotide sequence encoding the AAV capsid polypeptide, e.g., the AAV capsid variant (e.g., an AAV capsid variant described herein), comprises the nucleotide sequence of SEQ ID NO: 3663, or a nucleotide sequence substantially identical (e.g., having at least 70%, 75%, 80%, 85%, 90%, 92%, 95%, 97%, 98%, or 99% sequence identity) thereto. In some embodiments, the nucleic acid sequence encoding the AAV capsid variant comprises a nucleotide sequence comprising at least one, two, three, four, five, six, or seven modifications but no more than ten modifications of the nucleotide sequences of SEQ ID NO: 3663.

In some embodiments, the AAV capsid polypeptide, e.g., the AAV capsid variant, comprises an amino acid residue other than "A" at position 587 and/or an amino acid residue other than "Q" at position 588, numbered according to SEQ ID NO: 138.

In some embodiments, the AAV capsid polypeptide, e.g., the AAV capsid variant, comprises the amino acid sequence of PLNGAVHLY (SEQ ID NO: 3648) wherein the amino acid sequence of PLNGAVHLY (SEQ ID NO: 3648) is present immediately subsequent to position 586, relative to a reference sequence numbered according to the amino acid sequence of SEQ ID NO: 138.

In some embodiments, the polypeptide, e.g., the AAV capsid variant, comprises the amino acid sequence of GGT-LAVVSL (SEQ ID NO: 3654), wherein the amino acid sequence of GGTLAVVSL (SEQ ID NO: 3654) is present immediately subsequent to position 586, relative to a reference sequence numbered according to the amino acid sequence of SEQ ID NO: 138.

In some embodiments, the AAV capsid polypeptide, e.g., the AAV capsid variant, comprises the amino acid sequence of IVMNSLK (SEQ ID NO: 3651), wherein the amino acid sequence of IVMNSLK (SEQ ID NO: 3651) is present immediately subsequent to position 588, relative to a reference sequence numbered according to the amino acid sequence of SEQ ID NO: 138.

In some embodiments, the AAV capsid polypeptide, e.g., the AAV capsid variant, comprises the amino acid sequence of any of SEQ ID NOs: 3649, 3650, 3652, 3653, or 3655-3659, wherein the amino acid sequence of any of the aforesaid sequences is present immediately subsequent to position 589, relative to a reference sequence numbered according to the amino acid sequence of SEQ ID NO: 138.

In some embodiments, the AAV capsid polypeptide, e.g., the AAV capsid variant, further comprises a substitution at position K449, e.g., a K449R substitution, numbered according to SEQ ID NO: 138. In some embodiments, the AAV capsid variant further comprises a modification, e.g., an insertion, substitution, and/or deletion in loop I, II, IV, and/or VI.

In some embodiments, the AAV capsid polypeptide, e.g., the AAV capsid variant, further comprises an amino acid sequence having at least one, two or three modifications but not more than 30, 20 or 10 modifications of the amino acid sequence of SEQ ID NO: 138. In some embodiments, the AAV capsid variant further comprises the amino acid sequence of SEQ ID NO: 138, or an amino acid sequence with at least 80% (e.g., at least about 85, 90, 95, 96, 97, 98, or 99%) sequence identity thereto. In some embodiments, the AAV capsid variant further comprises an amino acid sequence encoded by the nucleotide sequence of SEQ ID NO: 137, or a sequence with at least 80% (e.g., at least about 85, 90, 95, 96, 97, 98, or 99%) sequence identity thereto.

In some embodiments, an AAV capsid polypeptide, e.g., an AAV capsid variant, of the present disclosure comprises a parental amino acid sequence having an insert, e.g., a peptide, e.g., a targeting peptide, wherein the insert comprises the amino acid sequence of any of SEQ ID NO: 1725-3622 or 3648-3659. In some embodiments, the insert comprises at least 3, 4, 5, 6, 7, 8, or 9 consecutive amino acids from the amino acid sequence of any of SEQ ID NO: 1725-3622 or 3648-3659. In some embodiments, the insert comprises an amino acid sequence comprising at least one, two, or three modifications, but no more than four modifications, e.g., substitutions, relative to the amino acid sequence of any of SEQ ID NO: 1725-3622 or 3648-3659.

In some embodiments, the parental sequence of an AAV capsid polypeptide, e.g., an AAV capsid variant, described herein comprises an amino acid sequence comprising at least one, two, or three modifications but no more than 30, 20 or 10 modifications, e.g., substitutions, to the amino acid sequence of SEQ ID NO: 138. In some embodiments, the parental sequence comprises the amino acid sequence of SEQ ID NO: 138, or an amino acid sequence substantially identical (e.g., having at least 70%, 75%, 80%, 85%, 90%, 92%, 95%, 97%, 98%, or 99% sequence identity) thereto. In some embodiments, the parental sequence further comprises a substitution at position K449, e.g., a K449R substitution. In some embodiments, the parental sequence comprises an amino acid sequence encoded by the nucleotide sequence of SEQ ID NO: 137, or a nucleotide sequence substantially identical (e.g., having at least 70%, 75%, 80%, 85%, 90%, 92%, 95%, 97%, 98%, or 99% sequence identity) thereto. In some embodiments, the polynucleotide encoding the parental sequence described herein comprises the nucleotide sequence of SEQ ID NO: 137, or a nucleotide sequence substantially identical (e.g., having at least 70%, 75%, 80%, 85%, 90%, 92%, 95%, 97%, 98%, or 99% sequence identity) thereto.

In some embodiments, the parental sequence of an AAV capsid polypeptide, e.g., an AAV capsid variant, described herein comprises an amino acid sequence comprising at least one, two, or three modifications but no more than 30, 20 or 10 modifications, e.g., substitutions, to the amino acid sequence of SEQ ID NO: 11, e.g., provided that position 449 of SEQ ID NO: 11 is not K, e.g., is R. In some embodiments, the parental sequence of an AAV capsid variant described herein comprises the amino acid sequence of SEQ ID NO: 11 or an amino acid sequence substantially identical (e.g., having at least 70%, 75%, 80%, 85%, 90%, 92%, 95%, 97%, 98%, or 99% sequence identity) thereto, e.g., provided that position 449 of SEQ ID NO: 11 is not K, e.g., is R.

In some embodiments, the insert of an AAV capsid variant is inserted into loop VIII of the parental amino acid sequence described herein. In some embodiments, the insert is inserted immediately subsequent to position 586, 588, or 589 in the parental amino acid sequence described herein.

In some embodiments, the AAV capsid variant further comprises an amino acid other than "A" at position 587 and/or an amino acid other than "Q" at position 588 of the parental sequence described herein. In some embodiments, the AAV capsid variant further comprises a deletion at position 587 and/or a deletion at position 588 of the parental amino acid sequence described herein. In some embodiments, the AAV capsid variant comprises a deletion of the amino acids "AQ" at positions 587-588 of the parental amino acid sequence described herein.

In some embodiment, the insert of an AAV capsid variant described herein comprises the amino acid sequence of PLNGAVHLY (SEQ ID NO: 3648). In some embodiments, the insert sequence of PLNGAVHLY (SEQ ID NO: 3648) is inserted immediately subsequent to position 586 of the parental amino acid sequence. In some embodiments, the AAV capsid variant further comprises a deletion of the amino acids "AQ" at positions 587-588 of the parental amino acid sequence. In some embodiments, the AAV capsid variant comprises an insert comprising the amino acid sequence of PLNGAVHLY (SEQ ID NO: 3648), which is inserted immediately subsequent to position 586 of the parental amino acid sequence and a deletion of the amino acids "AQ" at positions 587-588 of the parental amino acid sequence.

In some embodiments, the insert of an AAV capsid polypeptide, e.g., an AAV capsid variant, described herein comprises the amino acid sequence of GGTLAVVSL (SEQ ID NO: 3654). In some embodiments, the insert sequence of GGTLAVVSL (SEQ ID NO: 3654) is inserted immediately subsequent to position 586 of the parental amino acid sequence. In some embodiments, the AAV capsid variant further comprises a deletion of the amino acids "AQ" at positions 587-588 of the parental amino acid sequence. In some embodiments, the AAV capsid variant comprises an insert comprising the amino acid sequence of GGTLAVVSL (SEQ ID NO: 3654), which is inserted immediately subsequent to position 586 of the parental amino acid sequence and a deletion of the amino acids "AQ" at positions 587-588 of the parental amino acid sequence.

In some embodiments, the insert of an AAV capsid polypeptide, e.g., an AAV capsid variant, described herein comprises the amino acid sequence of IVMNSLK (SEQ ID NO: 3651). In some embodiments, the insert sequence of IVMNSLK (SEQ ID NO: 3651) is inserted immediately subsequent to position 588 of the parental amino acid sequence. In some embodiments, the AAV capsid variant comprises an insert comprising the amino acid sequence of IVMNSLK (SEQ ID NO: 3651), which is inserted immediately subsequent to position 589 of the parental amino acid sequence.

In some embodiments, the insert of an AAV capsid polypeptide, e.g., an AAV capsid variant, described herein comprises the amino acid sequence of RDSPKGW (SEQ ID NO: 3649), YSTDVRM (SEQ ID NO: 3650), RESPRGL (SEQ ID NO: 3652), SENDTRA (SEQ ID NO: 3653), YGLPKGP (SEQ ID NO: 3655) or STGTLRL (SEQ ID NO: 3656). In some embodiments, the insert sequence of RDSPKGW (SEQ ID NO: 3649), YSTDVRM (SEQ ID NO: 3650), RESPRGL (SEQ ID NO: 3652), SENDTRA (SEQ ID NO: 3653), YGLPKGP (SEQ ID NO: 3655) or STGTLRL (SEQ ID NO: 3656) is inserted immediately subsequent to position 589 of the parental amino acid sequence. In some embodiments, the AAV capsid variant comprises an insert comprising the amino acid sequence of RDSPKGW (SEQ ID NO: 3649), YSTDVRM (SEQ ID NO: 3650), RESPRGL (SEQ ID NO: 3652), SENDTRA (SEQ ID NO: 3653), YGLPKGP (SEQ ID NO: 3655) or STGTLRL (SEQ ID NO:

3656), which is inserted immediately subsequent to position 589 of the parental amino acid sequence.

In some embodiments, an AAV capsid polypeptide, e.g., an AAV capsid variant, of the present disclosure comprises an amino acid sequence as described herein, e.g. an amino acid sequence of an AAV capsid variant chosen from TTD-001, TTD-002, TTD-003, TTD-004, TTD-005, TTD-006, TTD-007, TTD-008, TTD-009, TTD-010, TTD-011, or TTD-012, e.g., as described in Tables 3 and 4.

In some embodiments, an AAV capsid polypeptide, e.g. the AAV capsid variant, comprises a VP1, VP2, and/or VP3 protein comprising an amino acid sequence described herein, e.g. an amino acid sequence of an AAV capsid variant chosen from TTD-001, TTD-002, TTD-003, TTD-004, TTD-005, TTD-006, TTD-007, TTD-008, TTD-009, TTD-010, TTD-011, or TTD-012, e.g., as described in Tables 3 and 4.

In some embodiments, an AAV capsid polypeptide, e.g., the AAV capsid variant, comprises an amino acid sequence encoded by a nucleotide sequence as described herein, e.g. a nucleotide sequence of an AAV capsid variant chosen from TTD-001, TTD-002, TTD-003, TTD-004, TTD-005, TTD-006, TTD-007, TTD-008, TTD-009, TTD-010, TTD-011, or TTD-012, e.g., as described in Tables 3 and 5.

In some embodiments, a polynucleotide encoding an AAV capsid polypeptide, e.g., an AAV capsid variant, of the present disclosure comprises a nucleotide sequence described herein, e.g. a nucleotide sequence of an AAV capsid variant chosen from TTD-001, TTD-002, TTD-003, TTD-004, TTD-005, TTD-006, TTD-007, TTD-008, TTD-009, TTD-010, TTD-011, or TTD-012, e.g., as described in Tables 3 and 5.

In some embodiments, insertion of a nucleic acid sequence, targeting nucleic acid sequence, or a peptide, e.g., targeting peptide, into a parent AAV sequence generates the non-limiting exemplary full length capsid sequences, e.g., an AAV capsid polypeptide, e.g., an AAV capsid variant, as described in Tables 3, 4 and 5.

TABLE 3

| Exemplary full length capsid sequences (VP1 with insert) | | | |
|---|---|---|---|
| Serotype | VP1 DNA SEQ ID NO: | VPA PRT SEQ ID NO: | Peptide PRT SEQ ID NO: | Peptide DNA SEQ ID NO: |
| TTD-001 | 3623 | 3636 | 1725 or 3648 | 3660 |
| TTD-002 | 3624 or 3625 | 3637 | 1726 or 3649 | 3661 |
| TTD-003 | 3626 | 3638 | 1729 or 3650 | 3662 |
| TTD-004 | 3627 | 3639 | 1760 or 3651 | 3663 |
| TTD-005 | 3628 | 3640 | 1769 or 3652 | 3664 |
| TTD-006 | 3629 | 3641 | 3622 or 3653 | 3665 |
| TTD-007 | 3630 | 3642 | 1798 or 3654 | 3666 |
| TTD-008 | 3631 | 3643 | 1785 or 3655 | 3667 |
| TTD-009 | 3632 | 3644 | 1767 or 3656 | 3668 |
| TTD-010 | 3633 | 3645 | 1734 or 3657 | 3669 |
| TTD-011 | 3634 | 3646 | 1737 or 3658 | 3670 |
| TTD-012 | 3635 | 3647 | 1819 or 3659 | 3671 |

TABLE 4

| | | |
|---|---|---|
| Exemplary fall length capsid amino acid sequences | | |

| Name and Annotation | SEQ ID NO: | Amino Acid Sequence |
|---|---|---|
| TTD-001<br>9mer peptide<br>underlined,<br>starts at<br>position 587<br>(immediately<br>subsequent to<br>position 586);<br>743 aa | 3636 | MAADGYLPDWLEDNLSEGIREWWALKPGAPQPKANQQHQDNARGLVLPG<br>YKYLGPGNGLDKGEPVNAADAAALEHDKAYDQQLKAGDNPYLKYNHADA<br>EFQERLKEDTSFGGNLGRAVFQAKKRLLEPLGLVEEAAKTAPGKKRPVE<br>QSPQEPDSSAGIGKSGAQPAKKRLNFGQTGDTESVPDPQPIGEPPAAPS<br>GVGSLTMASGGGAPVADNNEGADGVGSSSGNWHCDSQWLGDRVITTSTR<br>TWALPTYNNHLYKQISNSTSGGSSNDNAYFGYSTPWGYFDFNRFHCHFS<br>PRDWQRLINNNWGFRPKRLNFKLFNIQVKEVTDNNGVKTIANNLTSTVQ<br>VFTDSDYQLPYVLGSAHEGCLPPFPADVFMIPQYGYLTLNDGSQAVGRS<br>SFYCLEYFPSQMLRTGNNFQFSYEFENVPFHSSYAHSQSLDRLMNPLID<br>QYLYYLSKTINGSGQNQQTLKFSVAGPSNMAVQGRNYIPGPSYRQQRVS<br>TTVTQNNNSEFAWPGASSWALNGRNSLMNPGPAMASHKEGEDRFFPLSG<br>SLIFGKQGTGRDNVDADKVMITNEEEIKTTNPVATESYGQVATNHQSPL<br>NGAVHLYAQAQTGWVQNQGILPGMVWQDRDVYLQGPIWAKIPHTDGNFH<br>PSPLMGGFGMKHPPPQILIKNTPVPADPPTAFNKDKLNSFITQYSTGQV<br>SVEIEWELQKENSKRWNPEIQYTSNYYKSNNVEFAVNTEGVYSEPRPIG<br>TRYLTRNL |
| TTD-002<br>7mer peptide<br>underlined,<br>starts at<br>position 590<br>(immediately<br>subsequent to<br>position 589);<br>743 aa | 3637 | MAADGYLPDWLEDNLSEGIREWWALKPGAPQPKANQQHQDNARGLVLPG<br>YKYLGPGNGLDKGEPVNAADAAALEHDKAYDQQLKAGDNPYLKYNHADA<br>EFQERLKEDTSFGGNLGRAVFQAKKRLLEPLGLVEEAAKTAPGKKRPVE<br>QSPQEPDSSAGIGKSGAQPAKKRLNFGQTGDTESVPDPQPIGEPPAAPS<br>GVGSLTMASGGGAPVADNNEGADGVGSSSGNWHCDSQWLGDRVITTSTR<br>TWALPTYNNHLYKQISNSTSGGSSNDNAYFGYSTPWGYFDFNRFHCHFS<br>PRDWQRLINNNWGFRPKRLNFKLFNIQVKEVTDNNGVKTIANNLTSTVQ<br>VFTDSDYQLPYVLGSAHEGCLPPFPADVFMIPQYGYLTLNDGSQAVGRS<br>SFYCLEYFPSQMLRTGNNFQFSYEFENVPFHSSYAHSQSLDRLMNPLID<br>QYLYYLSKTINGSGQNQQTLKFSVAGPSNMAVQGRNYIPGPSYRQQRVS<br>TTVTQNNNSEFAWPGASSWALNGRNSLMNPGPAMASHKEGEDRFFPLSG<br>SLIFGKQGTGRDNVDADKVMITNEEEIKTTNPVATESYGQVATNHQSAQ<br>ARDSPKGWQAQTGWVQNQGILPGMVWQDRDVYLQGPIWAKIPHTDGNFH<br>PSPLMGGFGMKHPPPQILIKNTPVPADPPTAFNKDKLNSFITQYSTGQV<br>SVEIEWELQKENSKRWNPEIQYTSNYYKSNNVEFAVNTEGVYSEPRPIG<br>TRYLTRNL |
| TTD-003<br>7mer peptide<br>underlined,<br>starts at<br>position 590<br>(immediately<br>subsequent to<br>position 589);<br>743 aa | 3638 | MAADGYLPDWLEDNLSEGIREWWALKPGAPQPKANQQHQDNARGLVLPG<br>YKYLGPGNGLDKGEPVNAADAAALEHDKAYDQQLKAGDNPYLKYNHADA<br>EFQERLKEDTSFGGNLGRAVFQAKKRLLEPLGLVEEAAKTAPGKKRPVE<br>QSPQEPDSSAGIGKSGAQPAKKRLNFGQTGDTESVPDPQPIGEPPAAPS<br>GVGSLTMASGGGAPVADNNEGADGVGSSSGNWHCDSQWLGDRVITTSTR<br>TWALPTYNNHLYKQISNSTSGGSSNDNAYFGYSTPWGYFDFNRFHCHFS<br>PRDWQRLINNNWGFRPKRLNFKLFNIQVKEVTDNNGVKTIANNLTSTVQ<br>VFTDSDYQLPYVLGSAHEGCLPPFPADVFMIPQYGYLTLNDGSQAVGRS<br>SFYCLEYFPSQMLRTGNNFQFSYEFENVPFHSSYAHSQSLDRLMNPLID<br>QYLYYLSKTINGSGQNQQTLKFSVAGPSNMAVQGRNYIPGPSYRQQRVS<br>TTVTQNNNSEFAWPGASSWALNGRNSLMNPGPAMASHKEGEDRFFPLSG<br>SLIFGKQGTGRDNVDADKVMITNEEEIKTTNPVATESYGQVATNHQSAQ<br>AYSTDVRMQAQTGWVQNQGILPGMVWQDRDVYLQGPIWAKIPHTDGNFH<br>PSPLMGGFGMKHPPPQILIKNTPVPADPPTAFNKDKLNSFITQYSTGQV<br>SVEIEWELQKENSKRWNPEIQYTSNYYKSNNVEFAVNTEGVYSEPRPIG<br>TRYLTRNL |
| TTD-004<br>7mer peptide<br>underlined,<br>starts at<br>position 589<br>(immediately<br>subsequent to<br>position 588);<br>743 aa | 3639 | MAADGYLPDWLEDNLSEGIREWWALKPGAPQPKANQQHQDNARGLVLPG<br>YKYLGPGNGLDKGEPVNAADAAALEHDKAYDQQLKAGDNPYLKYNHADA<br>EFQERLKEDTSFGGNLGRAVFQAKKRLLEPLGLVEEAAKTAPGKKRPVE<br>QSPQEPDSSAGIGKSGAQPAKKRLNFGQTGDTESVPDPQPIGEPPAAPS<br>GVGSLTMASGGGAPVADNNEGADGVGSSSGNWECDSQWLGDRVITTSTR<br>TWALPTYNNHLYKQISNSTSGGSSNDNAYFGYSTPWGYFDFNRFHCHFS<br>PRDWQRLINNNWGFRPKRLNFKLFNIQVKEVTDNNGVKTIANNLTSTVQ<br>VFTDSDYQLPYVLGSAHEGCLPPFPADVFMIPQYGYLTLNDGSQAVGRS<br>SFYCLEYFPSQMLRTGNNFQFSYEFENVPFHSSYAHSQSLDRLMNPLID<br>QYLYYLSKTINGSGQNQQTLKFSVAGPSNMAVQGRNYIPGPSYRQQRVS<br>TTVTQNNNSEFAWPGASSWALNGRNSLMNPGPAMASHKEGEDRFFPLSG<br>SLIFGKQGTGRDNVDADKVMITNEEEIKTTNPVATESYGQVATNHQSAQ<br>IVMNSLKAQAQTGWVQNQGILPGMVWQDRDVYLQGPIWAKIPHTDGNFH<br>PSPLMGGFGMKHPPPQILIKNTPVPADPPTAFNKDKLNSFITQYSTGQV<br>SVEIEWELQKENSKRWNPEIQYTSNYYKSNNVEFAVNTEGVYSEPRPIG<br>TRYLTRNL |
| TTD-005<br>7mer peptide<br>underlined,<br>starts at<br>position 590<br>(immediately | 3640 | MAADGYLPDWLEDNLSEGIREWWALKPGAPQPKANQQHQDNARGLVLPG<br>YKYLGPGNGLDKGEPVNAADAAALEHDKAYDQQLKAGDNPYLKYNHADA<br>EFQERLKEDTSFGGNLGRAVFQAKKRLLEPLGLVEEAAKTAPGKKRPVE<br>QSPQEPDSSAGIGKSGAQPAKKRLNFGQTGDTESVPDPQPIGEPPAAPS<br>GVGSLTMASGGGAPVADNNEGADGVGSSSGNWHCDSQWLGDRVITTSTR<br>TWALPTYNNHLYKQISNSTSGGSSNDNAYFGYSTPWGYFDFNRFHCHFS |

TABLE 4-continued

Exemplary fall length capsid amino acid sequences

| Name and Annotation | SEQ ID NO: | Amino Acid Sequence |
|---|---|---|
| subsequent to position 589); 743 aa | | PRDWQRLINNNWGFRPKRLNFKLFNIQVKEVTDNNGVKTIANNLTSTVQ VFTDSDYQLPYVLGSAHEGCLPPFPADVFMIPQYGYLTLNDGSQAVGRS SFYCLEYFPSQMLRTGNNFQFSYEFENVPFHSSYAH3QSLDRLMNPLID QYLYYLSKTINGSGQNQQTLKFSVAGPSNMAVQGRNYIPGPSYRQQRVS TTVTQNNNSEFAWPGASSWALNGRNSLMNPGPAMASHKEGEDRFFPLSG SLIFGKQGTGRDNVDADKVMITNEEEIKTTNPVATESYGQVATNHQSAQ ARESPRGLQAQTGWVQNQGILPGMVWQDRDVYLQGPIWAKIPHTDGNFH PSPLMGGFGMKHPPPQILIKNTPVPADPPTAFNKDKLNSFITQYSTGQV SVEIEWELQKENSKRWNPEIQYTSNYYKSNNVEFAVNTEGVYSEPRPIG TRYLTRNL |
| TTD-006 7mer peptide underlined, starts at position 590 (immediately subsequent to 589); 743 aa | 3641 | MAADGYLPDWLEDNLSEGIREWWALKPGAPQPKANQQHQDNARGLVLPG YKYLGPGNGLDKGEPVNAADAAALEHDKAYDQQLKAGDNPYLKYNHADA EFQERLKEDTSFGGNLGRAVFQAKKRLLEPLGLVEEAAKTAPGKKRPVE QSPQEPDSSAGIGKSGAQPAKKRLNFGQTGDTESVPDPQPIGEPPAAPS GVGSLTMASGGGAPVADNNEGADGVG3SSGNWHCDSQWLGDRVTTTSTR TWALPTYNNHLYKQISNSTSGGSSNDNAYFGYSTPWGYFDFNRFHCHFS PRDWQRLINNNWGFRPKRLNFKLFNIQVKEVTDNNGVKTIANNLTSTVQ VFTDSDYOLPYVLGSAHEGCLPPFPADVFMIPQYGYLTLNDGSQAVGRS SFYCLEYFPSQMLRTGNNFQFSYEFENVPFHSSYAHSQSLDRLMNPL1D QYLYYLSKTINGSGQNQQTLKFSVAGPSNMAVQGRNYIPGPSYRQQRVS TTVTQNNNSEFAWPGASSWALNGRNSLMNPGPAMASHKEGEDRFFPLSG SLIFGKQGTGRDNVDADKVMITNEEEIKTTNPVATESYGQVATNHQSAQ ASFNDTRAQAQTGWVQNQGILPGMVWQDRDVYLQGPTWAKIPHTDGNFH PSPLMGGFGMKHPPPQILIKNTPVPADPPTAFNKDKLNSFITQYSTGQV SVEIEWELQKENSKRWNPEIQYTSNYYKSNNVEFAVNTEGVYSEPRPIG TRYLTRNL |
| TTD-007 9mer peptide underlined, starts at position 587 (immediately subsequent to position 586); 743 aa | 3642 | MAADGYLPDWLEDNLSEGIREWWALKPGAPQPKANQQHQDNARGLVLPG YKYLGPGNGLDKGEPVNAADAAALEHDKAYDQQLKAGDNPYLKYNHADA EFQERLKEDTSFGGNLGRAVFQAKKRLLEPLGLVEEAAKTAPGKKRPVE QSPQEPDSSAGIGKSGAQPAKKRLNFGQTGDTESVPDPQPIGEPPAAPS GVGSLTMASGGGAPVADNNEGADGVGS3SGNWHCDSQWLGDRVITTSTR TWALPTYNNHLYKQISNSTSGGSSNDNAYFGYSTPWGYFDFNRFHCHFS PRDWQRLINNNWGFRPKRLNFKLFNIQVKEVTDNNGVKTIANNLTSTVQ VFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLID QYLYYLSKTINGSGQNQQTLKFSVAGPSNMAVQGRNYIPGPSYRQQRVS TTVTQNNNSEFAWPGASSWALNGRNSLMNPGPAMASHKEGEDRFFPLSG SLIFGKQGTGRDNVDADKVM1TNEEEI KTTNPVATESYGQVATNHQSGG TLAVVSLAQAQTGWVQNQGILPGMVWQDRDVYLQGPIWAKIPHTDGNFH PSPLMGGFGMKHPPPOILIKNTPVPADPPTAFNKDKLNSFITQYSTGQV SVEIEWELQKENSKRWNPEIQYTSNYYKSNNVEFAVNTEGVYSEPRPIG TRYLTRNL |
| TTD-008 7mer peptide underlined, starts at position 590 (immediately subsequent to 589); 743 aa | 3643 | MAADGYLPDWLEDNLSEGIREWWALKPGAPQPKANQQHQDNARGLVLPG YKYLGPGNGLDKGEPVNAADAAALEHDKAYDQQLKAGDNPYLKYNHADA EFQERLKEDTSFGGNLGRAVFQAKKRLLEPLGLVEEAAKTAPGKKRPVE QSPQEPDSSAGIGKSGAQPAKKRLNFGQTGDTESVPDPQPIGEPPAAPS GVGSLTMASGGGAPVADNNEGADGVGSSSGNWECDSQWLGDRVITTSTR TWALPTYNNHLYKQISNSTSGGSSNDNAYFGYSTPWGYFDFNRFHCHFS PRDWQRLINNNWGFRPKRLNFKLFNIQVKEVTDNNGVKTIANNLTSTVQ VFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLID QYLYYLSKTINGSGQNQQTLKFSVAGPSNMAVQGRNYIPGPSYRQQRVS TTVTQNNNSEFAWPGASSWALNGRNSLMNPGPAMASHKEGEDRFFPLSG SLIFGKQGTGRDNVDADKVMITNEEEIKTTNPVATESYGQVATNHQSAQ AYGLPKGPQAQTGWVQNQGILPGMVWQDRDVYLQGPIWAKIPHTDGNFH PSPLMGGFGMKHPPPQILIKNTPVPADPPTAFNKDKLNSFITQYSTGQV SVEIEWELQKENSKRWNPEIQYTSNYYKSNNVEFAVNTEGVYSEPRPIG TRYLTRNL |
| TTD-009 7mer peptide underlined, starts at position 590 (immediately subsequent to 589); 743 aa | 3644 | MAADGYLPDWLEDNLSEGIREWWALKPGAPQPKANQQHQDNARGLVLPG YKYLGPGNGLDKGEPVNAADAAALEHDKAYDQQLKAGDNPYLKYNHADA EFQERLKEDTSFGGNLGRAVFQAKKRLLEPLGLVEEAAKTAPGKKRPVE QSPQEPDSSAGIGKSGAQPAKKRLNFGQTGDTESVPDPQPIGEPPAAPS GVGSLTMASGGGAPVADNNEGADGVGSSSGNWHCDSQWLGDRVITTSTR TWALPTYNNHLYKQISNSTSGGSSNDNAYFGYSTPWGYFDFNRFHCHFS PRDWQRLINNNWGFRPKRLNFKLFNIQVKEVTDNNGVKTIANNLTSTVQ VFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLID QYLYYLSKTTNGSGQNQQTLKFSVAGPSNMAVQGRNYIPGPSYRQQRVS TTVTQNNNSEFAWPGASSWALNGRNSLMNPGPAMASHKEGEDRFFPLSG SLIFGKQGTGRDNVDADKVMITNEEEIKTTNPVATESYGQVATNHQSAQ |

TABLE 4-continued

Exemplary fall length capsid amino acid sequences

| Name and Annotation | SEQ ID NO: | Amino Acid Sequence |
|---|---|---|
| | | ASTGTLRLQAQTGWVQNQGILPGMVWQDRDVYLQGPTWAKIPHTDGNFH PSPLMGGFGMKHPPPQILIKNTPVPADPPTAFNKDKLNSFITQYSTGQV SVEIEWELQKENSKRWNPEIQYTSNYYKSNNVEFAVNTEGVYSEPRPIG TRYLTRNL |
| TTD-010 7mer peptide underlined, starts at position 590 (immediately subsequent to 589); 743 aa | 3645 | MAADGYLPDWLEDNLSEGIREWWALKPGAPQPKANQQHQDNARGLVLPG YKYLGPGNGLDKGEPVNAADAAALEHDKAYDQQLKAGDNPYLKYNHADA EFQERLKEDTSFGGNLGRAVFQAKKRLLEPLGLVEEAAKTAPGKKRPVE QSPQEPDSSAGIGKSGAQPAKKRLNFGQTGDTESVPDPQPIGEPPAAPS GVGSLTMASGGGAPVADNNEGADGVGSSSGNWHCDSQWLGDRVITTSTR TWALPTYNNHLYKQISNSTSGGSSNDNAYFGYSTPWGYFDFNRFHCHFS PRDWQRLINNNWGFRPKRLNFKLFNIQVKEVTDNNGVKTIANNLTSTVQ VFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLID QYLYYLSKTINGSGQNQQTLKFSVAGPSNMAVQGRNYIPGPSYRQQRVS TTVTQNNSEFAWPGASSWALNGRNSLMNPGPAMASHKEGEDRFFPLSG SLIFGKQGTGRDNVDADKVMITNEEEIKTTNPVATESYGQVATNHQSAQ AYSTDERMQAQTGWVQNQGILPGMVWQDRDVYLQGPIWAKIPHTDGNFH PSPLMGGFGMKHPPPQILIKNTPVPADPPTAFNKDKLNSFITQYSTGQV SVEIEWELQKENSKRWNPEIQYTSNYYKSNNVEFAVNTEGVYSEPRPIG TRYLTRNL |
| TTD-011 7mer peptide underlined, starts at position 590 (immediately subsequent to 589); 743 aa | 3646 | MAADGYLPDWLEDNLSEGIREWWALKPGAPQPKANQQHQDNARGLVLPG YKYLGPGNGLDKGEPVNAADAAALEHDKAYDQQLKAGDNPYLKYNHADA EEQERLKEDTSEGGNLGRAVFQAKKRLLEPLGLVEEAAKTAPGKKRPVE QSPQEPDSSAGIGKSGAQPAKKRLNFGQTGDTESVPDPQPIGEPPAAPS GVGSLTMASGGGAPVADNNEGADGVGSSSGNWHCDSQWLGDRVITTSTR TWALPTYNNHLYKQISNSTSGGSSNDNAYFGYSTPWGYFDFNRFHCHFS PRDWQRLINNNWGFRPKRLNFKLFNIQVKEVTDNNGVKTIANNLTSTVQ VFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLID QYLYYLSKTINGSGQNQQTLKFSVAGPSNMAVQGRNYIPGPSYRQQRVS TTVTQNNSEFAWPGASSWALNGRNSLMNPGPAMASHKEGEDRFFPLSG SLIFGKQGTGRDNVDADKVMITNEEEIKTTNPVATESYGQVATNHQSAQ AYSTDERKQAQTGWVQNQGILPGMVWQDRDVYLQGPIWAKIPHTDGNFH PSPLMGGFGMKHPPPQILIKNTPVPADPPTAFNKDKLNSFITQYSTGQV SVEIEWELQKENSKRWNPEIQYTSNYYKSNNVEFAVNTEGVYSEPRPIG TRYLTRNL |
| TTD-012 mer peptide underlined, starts at position 590 (immediately subsequent to 589); 743 aa | 3647 | MAADGYLPDWLEDNLSEGIREWWALKPGAPQPKANQQHQDNARGLVLPG YKYLGPGNGLDKGEPVNAADAAALEHDKAYDQQLKAGDNPYLKYNHADA EEQERLKEDTSEGGNLGRAVFQAKKRLLEPLGLVEEAAKTAPGKKRPVE QSPQEPDSSAGIGKSGAQPAKKRLNFGQTGDTESVPDPQPIGEPPAAPS GVGSLTMASGGGAPVADNNEGADGVGSSSGNWHCDSQWLGDRVITTSTR TWALPTYNNHLYKQISNSTSGGSSNDNAYFGYSTPWGYFDFNRFHCHFS PRDWQRLINNNWGFRPKRLNFKLFNIQVKEVTDNNGVKTIANNLTSTVQ VPTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLID QYLYYLSKTINGSGQNQQTLKFSVAGPSNMAVQGRNYIPGPSYRQQRVS TTVTQNNSEFAWPGASSWALNGRNSLMNPGPAMASHKEGEDRFFPLSG SLIFGKQGTGRDNVDADKVMITNEEEIKTTNPVATESYGQVATNHQSAQ AYVSSVKMQAQTGWVQNQGILPGMVWQDRDVYLQGPIWAKIPHTDGNFH PSPLMGGFGMKHPPPQILIKNTPVPADPPTAFNKDKLNSFITQYSTGQV SVEIEWELQKENSKRWNPEIQYTSNYYKSNNVEFAVNTEGVYSEPKPIG TRYLTRNL |

TABLE 5

Exemplary full length capsid nucleic acid sequences

| Name and Annotation | SEQ ID NO: | NT Sequence |
|---|---|---|
| TTD-001 9mer peptide underlined | 3623 | atggctgccgatggttatcttccagattggctcgaggacaaccttagtgaaggaattcgcg agtggtgggctttgaaacctggagcccctcaacccaaggcaaatcaacaacatcaagacaa cgctcgaggtcttgtgcttccgggttacaaataccttggacccggcaacggactcgacaag gggagccggtcaacgcagcagacgcggcggccctcgagcacgacaaggcctacgaccagc agctcaaggccggagacaacccgtacctcaagtacaaccacgccgacgccgagttccagga gcggctcaaagaagatacgtcttttgggggcaacctcgggcgagcagtcttccaggccaaa aagaggcttcttgaacctcttggtctggttgaggaagcggctaagacggctcctggaaaga |

TABLE 5-continued

| | | |
|---|---|---|

Exemplary full length capsid nucleic acid sequences

| Name and Annotation | SEQ ID NO: | NT Sequence |
|---|---|---|
| | | agaggcctgtagagcagtctcctcaggaaccggactcctccgcgggtattggcaaatcggg<br>tgcacagcccgctaaaaagagactcaatttcggtcagactggcgacacagagtcagtccca<br>gaccctcaaccaatcggagaacctcccgcagcccctcaggtgtgggatctcttacaatgg<br>cttcaggtggtggcgcaccagtggcagacaataacgaaggtgccgatggagtgggtagttc<br>ctcgggaaattggcattgcgattcccaatggctgggggacagagtcatcaccaccagcacc<br>cgaacctgggccctgcccacctacaacaatcacctctacaagcaaatctccaacagcacat<br>ctggaggatcttcaaacgacaacgcctacttcggctacagcaccccctgggggtattttga<br>cttcaacagattccactgccacttctcaccacgtgactggcagcgactcatcaacaacaac<br>tggggattccggcctaagcgactcaacttcaagctcttcaacattcaggtcaaagaggtta<br>cggacaacaatggagtcaagaccatcgccaataaccttaccagcacggtccaggtcttcac<br>ggactcagactatcagctcccgtacgtgctcgggtcggctcacgagggctgcctcccgccg<br>ttcccagcggacgtttctcatgattcctcagtacgggtatctgacgcttaatgatggaagcc<br>aggccgtgggtcgttcgtcctttactgcctggaatatttcccgtcgcaaatgctaagaac<br>gg9taacaacttcca9ttca9ctacgagtttgagaacgtacctttccatagcagctacgct<br>cacagccaaagcctggaccgactaatgaatccactcatcgaccaatacttgtactatctct<br>caaagactattaacggttctggacagaatcaacaaacgctaaaattcagtgtggccggacc<br>cagcaacacggctgtccagggaagaaactacatacctggacccagctaccgacaacaacgt<br>gtctcaaccactgtgactcaaaacaacaacagcgaattgcttggcctggagcttcttctt<br>gggctctcaatgacgtaatagcttgatgaatcgtggacctgctatggccagccacaaaga<br>aggagaggaccgttctttcctttgtctggatctttaattttttggcaaacaaggasctgga<br>agagacaacgtggatgcggacaaagtcatgataaccaacgaagaagaaattaaaactacta<br>acacggtagcaacggagtcctatggacaagtggccacaaaccaccagagtccgcttaatgg<br>tgccgtccatctttatgctcaggcgcagaccggctgggttcaaaaccaaggaatacttccg<br>ggtatggtttggcaggacagagatgtgtacctgcaaggacccattgggccaaaattcctc<br>acacggacggcaactttcacccttctccgctgatgggagggtttggaatgaagcaccgcc<br>tcctcagatcctcatcaaaaacacacctgtacctgcCgatcctccaacggccttcaacaag<br>gacaagctgaactctttcatcacccagtattctactggccaagtcagcgtggagatcgagt<br>gggagctgcagaaggaaaacagcaagcgGtggaacccggagatccagtacacttccaacta<br>ttacaagtctaataatgttgaatttgctgttaatactgaaggtgtatatagtgaaccccgc<br>cccattggcaccagatacctgactcgtaatctgtaa |
| TTD-002<br>7mer peptide<br>underlined | 3624 | atggctgccgatggttatcttccagattggctcgaggacaaccttagtgaaggaattcgcg<br>agtggtgggcttugaaaccuggagccctcaacccaagocaaatcaacaacatcaagacaa<br>cgctcgaggtcttgtgcttccggggttacaaataccttggacccggcaacggactcgacaag<br>ggggagccggtcaacgcagcagacgcggcggccctcgagcacgacaaggcctacgaccagc<br>agctcaaggccggagacaacccgtacctcaagtacaaccacgccgacgccgagttccagga<br>gcggctcaaagaagatacgtcttttgggggcaacctcgggcgagcagtcttccaggccaaa<br>aagaggcttcttgaacctcttggtctggttgaggaagcggctaagacggctcctggaaaga<br>agaggcctgtagagcagtctcctcaggaaccggactcctccgcgggtattggcaaatcggg<br>tgcacagcccgctaaaaagagactcaatttcggtcagactggcgacacagagtcagtccca<br>gaccctcaaccaatcggagaacctcccgcagcccctcaggtgtgggatctcttacaatgg<br>cttcaggtggtggcgcaccagtggcagacaataacgaaggtgccgatggagtgggtagttc<br>ctcgggaaattggcattgcgattcccaatggctgggggacagagtcatcaccaccagcacc<br>cgaacctgggccctgcccacctacaacaatcacctctacaagcaaatctccaacagcacat<br>ctggaggatcttcaaatgacaacgcctacttcggctacagcacccccctgggggtattttga<br>cttcaacagattccactgccacttctcaccacgtgactggcagcgactcatcaacaacaac<br>tggggattccggcctaagcgactcaacttcaagctcttcaacattcaggtcazagaggtta<br>cggacaacaatggagtcaagaccatcgccaataaccttaccagcacggtccaggtcttcac<br>ggactcagactatcagctcccgtacgtgctcgggtcggctcacgagggctgcctcccgccg<br>ttcccagcggacgtttctcatgattcctcagtacgggtatctgacgcttaatgatggaagcc<br>aggccgtgggtcgttcgtcctttactgcctggaatatttcccgtcgcaaatgctaagaac<br>gggtaacaacttccagttcagctacgagtttgagaacgtacctttccatagcagctacgct<br>cacagccaaagcctggaccgactaatgaatccactcatcgaccaatacttgtactatctct<br>caaagactattaacggttctggacagaatcaacaaacgctaaaattcagtgtggccggacc<br>cagcaacatggctgtccagggaagaaactacatacctggacccagctacgacaacaacgt<br>gtctcaaccactgtgactcaaaacaacaacagcgaattgcttggcctggagcttcttctt<br>gggctctcaatgacgtaatagcttgatgaatcctggacctgctatggccagccacaaaga<br>aggagaggaccgtttctttcctttgtctggatctttaattttttggcaaacaaggaactgga<br>agagacaacgtggatgcggacaaagtcatgataaccaacgaagaagaaattaaaactacta<br>acccggtagcaacggagtcctatggacaagtggccacaaaccaccagagtgcacaggctcg<br>tgattctocgaagggttggcaggcgcagaccggctgggttcaaaaccaaggaatacttccg<br>ggtatggtttggcaggacagagatgtgtacctgcaaggacccattgggccaaaattcctc<br>acacggacggcaactttcacccttctccgctgatgggagggtttggaatgaagcaccgcc<br>tcctcagatcctcatcaaaaacacacctgtacctgcCgatcctccaacggccttcaacaag<br>gacaagctgaactctttcatcacccagtattctactggccaagtcagcgtggagatcgagt<br>gggagctgcagaaggaaaacagcaagcgGtggaacccggagatccagtacacttccaacta<br>ttacaagtctaataatgttgaatttgctgttaatactgaaggtgtatatagtgaaccccgc<br>cccattggcaccagatacctgactcgtaatctgtaa |
| | 3625 | atggctgccgatgottatcttccagattggctcgaggacaaccttagtgaaggaattcgcg<br>agtggcgggcttcgaaacctggagccctcaacccaaggcaaatcaacaacatcaagacaa<br>cgctcgaggtcttgtgcttccggggttacaaataccttggacccggcaacggactcgacaag<br>ggggagccggtcaacgcagcagacgcggcggccctcgagcacgacaaggcctacgaccagc<br>agctcaaggccggagacaacccgtacctcaagtacaaccacgccgacgccgagttccagga |

TABLE 5-continued

| Exemplary full length capsid nucleic acid sequences | | |
|---|---|---|
| Name and Annotation | SEQ ID NO: | NT Sequence |
| | | gcggctcaaagaagatacgtcttttgggggcaacctcgggcgagcagtcttccaggccaaa aagaggcttcttgaacctcttggtctggttgaggaagcggctaagacggctcctggaaaga agaggcctgtagagcagtctcctcaggaaccggactcctccgcgggtattggcaaatcggg tgcacagcccgctaaaaagagactcaatttcggtcagactggcgacacagagtcagtccca gaccctcaaccaatcggagaacctcccgcagcccctcaggtgtgggatctcttacaatgg cttcaggtggtggcgcaccagtggcagacaataacgaaggtgccgatggagtgggtagttc ctcgggaaattggcattgcgattcccaatggctgggggacagagtcatcaccaccagcacc cgaacctgggccctgcccacctacaacaatcacctctacaagcaaatctccaacagcacat ctggaggatcttcaaatgacaacgcctacttcggctacagcaccccctgggggtattttga cttcaacagattccactgccacttctcaccacgtgactggcagcgactcatcaacaacaac tggggattccggcctaagcgactcaacttcaagctcttcaacattcaggtcaaagaggtta cggacaacaatggagtcagaccatcgccaataaccttaccagcacggtccaggtctttcac ggactcagactatcagctcccgtacgtgctcgggtcggctcacgagggctgcctcccgccg ttcccagcggacgttttcatgattcctcagtacgggtatctgacgcttaatgatggaagcc aggccgtgggtcgttcgtccttttactgcctggaatatttcccgtcgcaaatgctaagaac gggtaacaacttccagttcagctacgagtttgagaacgtacctttccatagcagctacgct cacagccaaagcctggaccgactaatgaatccactcatcgaccaatacctgtactatctct caaaagactattaacggttctggacagaatcaacaaacgctaaaattcagtgtggccggacc cagcaacatggctgtccaggaagaaactacatacctggacccagctaccgacaacaacgt gtctcaaccactgtgactcaaaacaacaacagcgaatttgcttggcctggagcttcttctt gggctctcaatgacgtaatagcttgatgaatcctggacctgctatggccagccacaaaga aggagaggaccgtttctttcctttgtctggatctttaattttttggcaaacaaggaactgga agagacaacgtggatgcggacaaagtcatgataaccaacgaagaagaaattaaaactacta acccggtagcaacggagtcctatggacaagtggccacaaaccaccagagtgcacaggctcg tgattctccgaagggttggcaggcgcagaccggctgggttcaaaaccaaggaatacttccg ggtatggtttggcaggacagagatgtgtacctgcaaggacccatttgggccaaaattcctc acacggacggcaactttcacccttctccgctgatgggagggtttggaatgaagcacccgcc tcctcagatcctcatcaaaaacacacctgtacctgcggatcctccaacggccttcaacaag gacaagctgaactctttcatcacccagtattctactggccaagtcagcgtggagatcgagt gggagctgcagaaggaaaacagcaagcgctggaacccggagatccagtacacttccaacta ttacaagtctaataatgttgaatttgctgttaatactgaaggtgtatatagtgaaccccgc cccattggcaccagatacctgactcgtaatctgtaa |
| TTD-003 7mer peptide underlined | 3626 | atggctgccgatggttatcttccagattggctcgaggacaaccttagtgaaggaattcgcg agtggagggcttagaaaccaggagcccctcaacccaaggcaaatcaacaacatcaagacaa cgctcgaggtcttgtgcttccggggttacaaataccttggacccggcaacgggactcgacaag ggggagccggtcaacgcagcagacgcggcggccctcgagcacgacaaggcctacgaccagc agctcaaggccggagacaacccgtacctcaagtacaaccacgccgacgccgagttccagga gcggctcaaagaagatacgtcttttgggggcaacctcgggcgagcagtcttccaggccaaa aagaggcttcttgaacctcttggtctggttgaggaagcggctaagacggctcctggaaaga agaggcctgtagagcagtctcctcaggaaccggactcctccgcgggtattggcaaatcggg tgcacagcccgctaaaaagagactcaatttcggtcagactggcgacacagagtcagtccca gaccctcaaccaatcggagaacctcccgcagcccctcaggtgtgggatctcttacaatgg cttcaggtggtggcgcaccagtggcagacaataacgaaggtgccgatggagtgggtagttc ctcgggaaattggcattgcgattcccaatggctgggggacagagtcatcaccaccagcacc cgaacctgggccctgcccacctacaacaatcacctctacaagcaaatctccaacagcacat ctggaggatcttcaaatgacaacgcctacttcggctacagcaccccctgggggtattttga cttcaacagattccactgccacttctcaccacgtgactggcagcgactcatcaacaacaac tggggattccggcctaagcgactcaacttcaagctcttcaacattcaggtcaaagaggtta cggacaacaatggagtcagaccatcgccaataaccttaccagcacggtccaggtcttcac ggactcagactatcagctcccgtacgtgctcgggtcggctcacgagggctgcctcccgccg ttcccagcggacgttttcatgattcctcagtacgggtatctgacgcttaatgatggaagcc aggccgtgggtcgttcgtccttttactgcctggaatatttcccgtcgcaaatgctaagaac gggtaacaacttccagttcagctacgagtttgagaacgtacctttccatagcagctacgct cacagccaaagcctggaccgactaatgaatccactcatcgaccaatacatgtactatctct caaaagactattaacggttctggacagaatcaacaaacgctaaaattcagtgtggccggacc cagcaacatggctgtccaggaagaaactacatacctggacccagctaccgacaacaacgt gtctcaaccactgtgactcaaaacaacaacagcgaatttgcttggcctggagcttcttctt gggctctcaatgacgtaatagcttgatgaatcctggacctgctatggccagccacaaaga aggagaggaccgtttctttcctttgtctggatctttaattttttggcaaacaaggaactgga agagacaacgtggatgcggacaaagtcatgataaccaacgaagaagaaattaaaactacta acccggtagcaacggagtcctatggacaagtggccacaaaccaccagagtgcacaggctta ttctacggatgtgaggatgcaggcgcagaccggctgggttcaaaaccaaggaatacttccg ggtatggtttggcaggacagagatgtgtacctgcaaggacccatttgggccaaaattcctc acacggacggcaactttcacccttctccgctgatgggagggtttggaatgaagcacccgcc tcctcagatcctcatcaaaaacacacctgtacctgcCgatcctccaacggccttcaacaag gacaagctgaactctttcatcacccagtattctactggccaagtcagcgtggagatcgagt gggagctgcagaaggaaaacagcaagcGtggaacccggagatccagtacacttccaacta ttacaagtctaataatgttgsatttgctgttaatactgaaggtgtatatagtgaaccccgc cccattggcaccagatacctgactcgtaatctgtaa |
| TTD-004 7mer peptide underlined | 3627 | atggctgccgatggttatcttccagattggctcgaggacaaccttagtgaaggaattcgcg agtggtgggctttgaaacctggagcccctcaacccaaggcaaatcaacaacatcaagacaa cgctcgaggtcttgtgcttccggggttacaaataccttggacccggcaacggactcgacaag |

TABLE 5-continued

Exemplary full length capsid nucleic acid sequences

| Name and Annotation | SEQ ID NO: | NT Sequence |
|---|---|---| ggggagccggtcaacgcagcagacgcggcggccctcgagcacgacaaggcctacgaccagc
agctcaaggccggagacaacccgtacctcaagtacaaccacgccgacgccgagttccagga
gcggctcaaagaagatacgtcttttgggggcaacctcgggcgagcagtcttccaggccaaa
aagaggcttcttgaacctcttggtctggttgaggaagcggctaagacggctcctggaaaga
agaggcctgtagagcagtctcctcaggaaccggactcctccgcgggtattggcaaatcggg
tgcacagcccgctaaaaagagactcaatttcggtcagactggcgacacagagtcagtccca
gaccctcaaccaatcggagaacctcccgcagcccctcaggtgtgggatctcttacaatgg
cttcaggtggtggcgcaccagtggcagacaataacgaaggtgccgatggagtgggtagttc
ctcgggaaattggcattgcgattcccaatggctgggggacagagtcatcaccaccagcacc
cgaacctgggccctgcccacctacaacaatcacctctacaagcaaatctccaacagcacat
ctggaggatcttcaaatgacaacgcctacttcggctacagcacccctgggggtattttga
cttcaacagattccactgccacttctcaccacgtgactggcagcgactcatcaacaacaac
tggggattccggcctaagcgactcaacttcaagctcttcaacattcaggtcaaagaggtta
cggacaacaatggagtcaagaccatcgccaataaccttaccagcacggtccaggtcttcac
ggactcagactatcagctcccgtacgtgctcgggtcggctcacgagggctgcctcccgccg
ttcccagcggacgttttcatgattcctcagtacgggtatctgacgcttaatgatggaagcc
aggccgtgggtcgttcgtcctttttactgcctggaatatttcccgtcgcaaatgctaagaac
gg9taacaacttcca9ttca9ctacgagtttgagaacgtacctttccatagcagctacgct
cacagccaaagcctggaccgactaatgaatccactcatcgaccaatacttgtactatctct
caaagactattaacggttctggacagaatcaacaaacgctaaaattcagtgtggccggacc
cagcaacatggctgtccaggaagaaactacatacctggacccagctaccgacaacaacgt
gtctcaaccactgtgactcaaaacaacaacagcgaatttgcttggcctggagcttcttctt
gggctctcaatgacgactaatagcttgatgaatcctggacctgctatggccagccacaaaga
aggagaggaccgtttctttcctttgtctggatctttaattttttggcaaacaaggaactgga
agagacaacgtggatgcggacaaagtcatgataaccaacgaagaagaaattaaaactacta
acccggtagcaacggagtcctatggacaagtggccacaaaccaccagagtgcacag**attgt
tatgaattcgttgaaggc**tcaggcgcagaccggctgggttcaaaaccaaggaatacttccg
ggtatggtttggcaggacagagatgtgtacctgcaaggaccccatttgggccaaaattcctc
acacggacggcaactttcacccttctccgctgatgggagggtttggaatgaagcaccgcc
tcctcagatcctcatcaaaaacacacctgtacctgccgatcatccaacggccttcaacaag
gacaagctgaactctttcatcacccagtattctactggccaagtcagcgtggagatcgagt
gggagctgcagaaggaaaacagcaagcggtggaacccggagatccagtacacttccaacta
ttacaagtctaataatgttgaatttgctgttaatactgaaggtgtatatagtgaaccccgc
cccattggcaccagatacctgactcgtaatctgtaa

| TTD-005 7mer peptide underlined | 3628 | atggctgccgatggttatcttccagattggctcgaggacaaccttagtgaaggaattcgcg | agtggtgggctttgaaacctggagcccctcaacccaaggcaaatcaacaacatcaagacaa
cgctcgaggtcttgtgcttccgggttacaaataccttggacccggcaacggactcgacaag
ggggagccggtcaacgcagcagacgcggcggccctcgagcacgacaaggcctacgaccagc
agctcaaggccggagacaacccgtacctcaagtacaaccacgccgacgccgagttccagga
gcggctcaaagaagatacgtcttttgggggcaacctcgggcgagcagtcttccaggccaaa
aagaggcttcttgaacctcttggtctggttgaggaagcggctaagacggctcctggaaaga
agaggcctgtagagcagtctcctcaggaaccggactcctccgcgggtattggcaaatcggg
tgcacagcccgctaaaaagagactcaatttcggtcagactggcgacacagagtcagtccca
gaccctcaaccaatcggagaacctcccgcagcccctcaggtgtgggatctcttacaatgg
cttcaggtggtggcgcaccagtggcagacaataacgaaggtgccgatggagtgggtagttc
ctcgggaaattggcattgcgattcccaatggctgggggacagagtcatcaccaccagcacc
cgaacctgggccctgcccacctacaacaatcacctctacaagcaaatctccaacagcacat
ctggaggatcttcaaatgacaacgcctaccicggctacagcacccctgggggtattttga
cttcaacagattccactgccacttctcaccacgtgactggcagcgactcatcaacaacaac
tggggattccggcctaagcgactcaacttcaagctcttcaacattcaggtcaaagaggtta
cggacaacaatggagtcaagaccatcgccaataaccttaccagcacggtccaggtcttcac
ggactcagactatcagctcccgtacgtgctcgggtcggctcacgagggctgcctcccgccg
ttcccagcggacgttttcatgattcctcagtacgggtatctgacgcttaatgatggaagcc
aggccgtgggtcgttcgtcctttttactgcctggaatatttcccgtagcaaatgctaagaac
gggtaacaacttccagttcagctacgagtttgagaacgtacctttccatagcagctacgct
cccagccaaagcctggaccgactaatgaatccactcatcgaccaatacttgtactatctct
caaagactattaacggttctggacagaatcaacaaacgctaaaattcagtgtggccggacc
cagcaacatggctgtccaggaagaaactacatacctggacccagctacgacaacaacgt
gtctcaaccactgtgactcaaaacaacaacagcgaatttgcttggcctggagcttcttctt
gggctctcaatgacgactaatagcttgatgaatcctggacctgctatggccagccacaaaga
aggagaggaccgtttctttcctttgtctggatctttaattttttggcaaacaaggaactgga
agagacaacgtggatgcggacaaagtcatgataaccaacgaagaagaaattaaaactacta
acccggtagcaacggagtcctatggacaagtggccacaaaccaccagagtgcacaggct**cg
ggagagtcctcgtgggctgca**ggcgcagaccggctgggttcaaaaccaaggaatacttccg
ggtatggtttggcaggacagagatgtgtacctgcaaggaccccatttgggccaaaattcctc
acacggacggcaactttcacccttctccgctgatgggagggtttggaatgaagcaccgcc
tcctcagatcctcatcaaaaacacacctgtacctgccgatcctcCaacggccttcaacaag
gacaagctgaactctttcatcacccagtattctactggccaagtcagcgtggagatcgagt
gggagctgcagaaggaaaacagcaagcgGtggaacccggagatccagtacacttccaacta
ttacaagtctaataatgttgaatttgctgttaatactgaaggtgtatatagtgaaccccgc
cccattggcaccagatacctgactcgtaatctgtaa TABLE 5-continued Exemplary full length capsid nucleic acid sequences

| Name and Annotation | SEQ ID NO: | NT Sequence |
|---|---|---|
| TTD-006 7mer peptide underlined | 3629 | atggctgccgatggttatcttccagattggctcgaggacaaccttagtgaaggaattcgcg agtggtggggcttugaaaccuggagcccctcaacccaagcaaatcaacaacatcaagacaa cgctcgaggtcttgtgcttccggggttacaaataccttggacccggcaacggactcgacaag ggggagccggtcaacgcagcagacgcggcggccctcgagcacgacaaggcctacgaccagc agctcaaggccggagacaacccgtacctcaagtacaaccacgccgacgccgagttccagga gcggctcaaagaagatacgtcttttgggggcaacctcgggcgagcagtcttccaggccaaa aagaggcttcttgaacctcttggtctggttgaggaagcggctaagacggctcctggaaaga agaggcctgtagagcagtctcctcaggaaccggactcctccgcgggtattggcaaatcggg tgcacagcccgctaaaaagagactcaatttcggtcagactggcgacacagagtcagtccca gaccctcaaccaatcggagaacctcccgcagccccctcaggtgtgggatctcttacaatgg cttcaggtggtggcgcaccagtggcagacaataacgaaggtgccgatggagtgggtagttc ctcgggaaattggcattgcgattcccaatggctgggggacagagtcatcaccaccagcacc cgaacctgggccctgcccacctacaacaatcacctctacaagcaaatctccaacagcacat ctggaggatcttcaaatgacaacgcctacttcggctacagcacccccctgggggtgtttttga cttcaacagattccactgccacttctcaccacgtgactggcagcgactcatcaacaacaac tggggactccggcctaagcgactcaacttcaagctcttcaacattcaggtcaaagaggtta cggacaacaatggagtcaagaccatcgccaataaccttaccagcacggtccaggtcttcac ggactcagactatcagctcccgtacgtgctcgggtcggctcacgagggctgcctcccgccg ttcccagcggacgttttcatgattcctcagtacgggtatctgacgcttaatgatggaagcc aggccgtgggtcgttcgtccttttactgcctggaatatttcccgtcgcaaatgctaagaac gggtaacaacttccagttcagctacgagtttgagaacgtacctccccatagcagctacgct cacagccaaagcctggaccgactaatgaatccactcatcgaccaatacttgtactatctct caaagactattaacggttctggacagaatcaacaaacgctaaaattcagtgtggccggacc cagcaacatggctgtccaggaagaaactacatacctggacccagctaccgacaacaacgt gtctcaaccactgtgactcaaaacaacaacagcgaattgcttggcctggagcttcttcttt gggctctcaatggacgtaatagcttgatgaatcctggacctgctatggccagccacaaaga aggagaggaccgtttcttttcctttgtctggatctttaatttttggcaaacaaggaactgga agagacaacgtggatgcggacaaagtcatgataaccaacgaagaagaaattaaaactacta acccggtagcaacggagtcctatggacaagtggccacaaaccaccagagtgcacaggctag ttttaatgatactagggctcaggcgcagaccggctgggttcaaaaccaaggaatacttccg ggtatggtttggcaggacagagatgtgtacctgcaaggacccatttgggccaaaattcctc acacggacggcaacttteacccttctccgctgatgggagggtttggaatgaagcaccegcc tcctcagatcctcatcaaaaacacacctgtacctgcCgatcctccaacggccttcaacaag gacaagctgaactctttcatcacccagtattctactggccaagtcagcgtggagatcgagt gggagctgcagaaggaaaacagcaagcgGtggaacccggagatccagtacacttccaacta ttacaagtctaataatgttgaatttgctgttaatactgaaggtgtatatagtgaaccccgc cccattggcaccagatacctgactcgtaatctgtaa |
| TTD-007 9mer peptide underlined | 3630 | atggctgccgatggttatcttccagattggctcgaggscaaccttagtgaaggaattcgcg agtagtgggctttgaaacctggagcccctcaacccaaggcaaatcaacaacatcaagacaa cgctcgaggtcttgtgcttccggggttacaaataccttggacccggcaacggactcgacaag ggggagccggtcaacgcagcagacgcggcggccctcgagcacgacaaggcctacgaccagc agctcaaggccggagacaacccgtacctcaagtacaaccacgccgacgccgagttccagga gcggctcaaagaagatacgtcttttgggggcaacctcgggcgagcagtcttccaggccaaa aagaggcttcttgaacctcttggtctggttgaggaagcggctaagacggctcctggaaaga agaggcctgtagagcagtctcctcaggaaccggactcctccgcgggtattggcaaatcggg tgcacagcccgctaaaaagagactcaatttcggtcagactggcgacacagagtcagtccca gaccctcaaccaatcggagaacctcccgcagccccctcaggtgtgggatctcttacaatgg cttcaggtggtggcgcaccagtggcagacaataacgaaggtgccgatggagtgggtagttc ctcgggaaattggcattgcgattcccaatggctgggggacagagtcatcaccaccagcacc cgaacctgggccctgcccacctacaacaatcacctctacaagcaaatctccaacagcacat ctggaggatcttcaaatgacaacgcctacttcggctacagcacccccctgggggtgtttttga cttcaacagattccactgccacttctcaccacgtgactggcagcgactcatcaacaacaac tggggattccggcctaagcgactcaacttcaagctcttcaacattcaggtcaaagaggtta cggacaacaatggagucaagaccatcgccaataaccutaccagcacggtccaggtctucac ggactcagactatcagctcccgtacgtgctcgggtcggctcacgagggctgcctcccgccg ttcccagcggacgttttcatgattcctcagtacgggtatctgacgcttaatgatggaagcc aggccgtgggtcgttcgtcctuttactgcctggaatatttccgtcgcaaatgctaagaac gggtaacaacttccagttcagctacgagtttgagaacgtacctttccatagcagctacgct cacagccaaagcctggaccgactaatgaatccactcatcgaccaatacatgtactatctct caaagactattaacggttctggacagaatcaacaaacgctaaaattcagtgtggccggacc cagcaacatggctgtccaggaagaaactacatacctggacccagctaccgacaacaacgt gtctcaaccactgtgactcaaaacaacaacagcgaattgcttggcctggagcttcttcttt gggctctcaatggacgtaatagcttgatgaatcctggacctgctatggccagccacaaaga aggagaggaccgtttcttttcctttgtctggatctttaatttttggcaaacaaggaactgga agagacaacgtggatgcggacaaagtcatgataaccaacgaagaagaaattaaaactacta acccggtagcaacggagtcctatggacaagtggccacaaaccaccagagtggtggtacgtt ggccgtcgtgtcgcttgctcaggcgcagaccggctgggttcaaaaccaaggaatacttccg ggtatggtttggcaggacagagatgtgtacctgcaaggacccatttgggccaaaattcctc acacggacggcaactttcacccttctccgctgatgggagggtttggaatgaagcaccegcc tcctcagatcctcatcaaaaacacacctgtacctgcCgatcctccaacggccttcaacaag gacaagctgaactctttcatcacccagtattctactggccaagtcagcgtggagatcgagt gggagctgcagaaggaaaacagcaagcgGtggaacccggagatccagtacacttccaacta |

TABLE 5-continued

| Name and Annotation | SEQ ID NO: | NT Sequence |
|---|---|---|
| | | ttacaagtctaataatgttgaatttgctgttaatactgaaggtgtatatagtgaaccccgc<br>cccattggcaccagatacctgactcgtaatctgtaa |
| TTD-008<br>7mer peptide<br>underlined | 3631 | atggctgccgatggttatcttccagattggctcgaggacaaccttagtgaaggaattcgcg<br>agtggtgggctttgaaacctggagcccctcaacccaaggcaaatcaacaacatcaagacaa<br>cgctcgaggtcttgtgcttccgggttacaaataccttggacccggcaacggactcgacaag<br>ggggagccggtcaacgcagcagacgcggcggccctcgagcacgacaaggcctacgaccagc<br>agctcaaggccggagacaacccgtacctcaagtacaaccacgccgacgccgagttccagga<br>gcggctcaaagaagatacgtcttttgggggcaacctcgggcgagcagtcttccaggccaaa<br>aagaggcttcttgaacctcttggtctggttgaggaagcggctaagacggctcctggaaaga<br>agaggcctgtagagcagtctcctcaggaaccggactcctccgcgggtattggcaaatcggg<br>tgcacagcccgctaaaaagagactcaatttcggtcagactggcgacacagagtcagtccca<br>gaccctcaaccaatcggagaacctcccgcagcccctcaggtgtgggatctcttacaatgg<br>cttcaggtggtggcgcaccagtggcagacaataacgaaggtgccgatggagtgggtagttc<br>ctcgggaaattggcattgcgattcccaatggctgggggacagagtcatcaccaccagcacc<br>cgaacctgggccctgcccacctacaacaatcacctctacaagcaaatctccaacagcacat<br>ctggaggatcttcaaatgacaacgcctacttcggctacagcacccccctgggggtattttga<br>cttcaacagattccactgccacttctcaccacgtgactggcagcgactcatcaacaacaac<br>tggggattccggcctaagcgactcaacttcaagctcttcaacattcaggtcaaagaggtta<br>cggacaacaatggagtcaagaccatcgccaataaccttaccagcacggtccaggtcttcac<br>ggactcagactatcagctcccgtacgtgctcgggtcggctcacgagggctgcctcccgccg<br>ttcccagcggacgttttcatgattcctcagtacgggtatctgacgcttaatgatggaagcc<br>aggccgtgggtcgttcgtccttttactgcctggaatatttcccgtcgcaaatgctaagaac<br>gggtaacaacttccagatcagcaacgagtacgagaacgtacctttccatagcagctacgct<br>cacagccaaagcctggaccgactaatgaatccactcatcgaccaatacttgtactatctct<br>caaagactattaacggttctggacagaatcaacaaacgctaaaattcagtgtggccggacc<br>cagcaacatggctgtccaggaagaaactacatacctggacccagctaccgacaacaacgt<br>gtctcaaccactgtgactcaaaacaacaacagcgaatttgcttggcctggagcttcttctt<br>gggctctcaatggacgtaatagcttgatgaatcctggacctgctatggccagccacaaaga<br>aggagaggaccgtttctttcctttgtctggatctttaatttttggcaaacaaggaactgga<br>agagacaacgtggatgcggacaaagtcatgataaccaacgaagaagaaattaaaactacta<br>acccggtagcaacggagtcctatggacaagtggccacaaaccaccagagtgcacaggcta<br>tgggttgccgaaggtcctcaggcgcagaccggctgggttcaaaaccaaggaatacttccg<br>ggtatggtttggcaggacagagatgtgtacctgcaaggacccatttgggccaaaattcctc<br>acacggacggcaactttcaccttctccgctgatggggagggtttggaatgaagcacccgcc<br>tcctcagatcctcatcaaaaacacacctgtacctgcCgatcctccaacggccttcaacaag<br>gacaagctgaactctttcatcacccagtattctactggccaagtcagcgtggagatcgagt<br>gggagctgcagaaggaaaacagcaagcgGtggaacccggagatccagtacacttccaacta<br>ttacaagtctaataatgttgaatttgctgttaatactgaaggtgtatatagtgaaccccgc<br>cccattggcaccagatacctgactcgtaatctgtaa |
| TTD-009<br>7mer peptide<br>underlined | 3632 | atggctgccgatggttatcttccagattggctcgaggacaaccttagtgaaggaattcgcg<br>agtggtgggctttgaaacctggagcccctcaacccaaggcaaatcaacaacatcaagacaa<br>cgctcgaggtcttgtgcttccgggttacaaataccttggacccggcaacggactcgacaag<br>ggggagccggtcaacgcagcagacgcggcggccctcgagcacgacaaggcctacgaccagc<br>agctcaaggccggagacaacccgtacctcaagtacaaccacgccgacgccgagttccagga<br>gcggctcaaagaagatacgtcttttgggggcaacctcgggcgagcagtcttccaggccaaa<br>aagaggcttcttgaacctcttggtctggttgaggaagcggctaagacggctcctggaaaga<br>agaggcctgtagagcagtctcctcaggaaccggactcctccgcgggtattggcaaatcggg<br>tgcacagcccgctaaaaagagactcaatttcggtcagactggcgacacagagtcagtccca<br>gaccctcaaccaatcggagaacctcccgcagcccctcaggtgtgggatctcttacaatgg<br>cttcaggtggtggcgcaccagtggcagacaataacgaaggtgccgatggagtgggtagttc<br>ctcgggaaattggcattgcgattcccaatggctgggggacagagtcatcaccaccagcacc<br>cgaacctgggccctgcccacctacaacaatcacctctacaagcaaatctccaacagcacat<br>ctggaggatcttcaaatgacaacgcctacttcggctacagcacccccctgggggtattttga<br>cttcaacagattccactgccacttctcaccacgtgactggcagcgactcatcaacaacaac<br>tggggattccggcctaagcgactcaacttcaagctcttcaacattcaggtcaaagaggtta<br>cggacaacaatggagtcaagaccatcgccaataaccttaccagcacggtccaggtcttcac<br>ggactcagactatcagctcccgtacgtgctcgggtcggctcacgagggctgcctcccgccg<br>ttcccagcggacgttttcatgattcctcagtacgggtatctgacgcttaatgatggaagcc<br>aggccgtgggtcgttcgtccttttactgcctggaatatttcccgtcgcaaatgctaagaac<br>gggtaacaacttccagttcagctacgagtttgagaacgtacctttccatagcagctacgct<br>cacagccaaagcctggaccgactaatgaatccactcatcgaccaatacttgtactatctct<br>caaagactattaacggttctggacagaatcaacaaacgctaaaattcagtgtggccggacc<br>cagcaacatggctgtccaggaagaaactacatacctggacccagctaccgacaacaacgt<br>gtctcaaccactgtgactcaaaacaacaacagcgaatttgcttggcctggagcttcttctt<br>gggctctcaatggacgtaatagcttgatgaatcctggacctgctatggccagccacaaaga<br>aggagaggaccgtttctttcctttgtctggatctttaatttttggcaaacaaggaactgga<br>agagacaacgtggatgcggacaaagtcatgataaccaacgaagaagaaattaaaactacta<br>acccggtagcaacggagtcctatggacaagtggccacaaaccaccagagtgcacaggctc<br>gactgggacgattcggcttcaggcgcagaccggctgggttcaaaaccaaggaatacttccg<br>ggtatggtttggcaggacagagatgtgtacctgcaaggacccatttgggccaaaattcctc<br>acacggacggcaactttcaccttctccgctgatggggagggtttggaatgaagcacccgcc<br>tcctcagatcctcatcaaaaacacacctgtacctgcCgatcctccaacggccttcaacaag |

TABLE 5-continued

Exemplary full length capsid nucleic acid sequences

| Name and Annotation | SEQ ID NO: | NT Sequence |
|---|---|---|
| | | gacaagctgaactctttcatcacccagtattctactggccaagtcagcgtggagatcgagt gggagctgcagaaggaaaacagcaagcgGtggaacccggagatccagtacacttccaacta ttacaagtctaataatgttgaatttgctgttaatactgaaggtgtatatagtgaacccccgc cccattggcaccagatacctgactcgtaatctgtaa |
| TTD-010 7mer peptide underlined | 3633 | atggctgccgatggttatcttccagattggctcgaggacaaccttagtgaaggaattcgcg agtggtgggctttgaaacctggagcccctcaacccaaggcaaatcaacaacatcaagacaa cgctcgaggtcttgtgcttccgggttacaaataccttggacccggcaacggactcgacaag ggggagccggtcaacgcagcagacgcggcggccctcgagcacgacaaggcctacgaccagc agctcaaggccggagacaacccgtacctcaagtacaaccacgccgacgccgagttccagga gcggctcaaagaagatacgtcttttggggcaacctcgggcgagcagtcttccaggccaaa aagaggcttcttgaacctcttggtctggttgaggaagcggctaagacggctcctggaaaga agaggcctgtagagcagtctcctcaggaaccggactcctccgcgggtattggcaaatcggg tgcacagcccgctaaaaagagactcaatttcggtcagactggcgacacagagtcagtccca gaccctcaaccaatcggagaacctcccgcagcccccctcaggtgtgggatctcttacaatgg cttcaggtggtggcgcaccagtggcagacaataacgaaggtgccgatggagtgggtagttc ctcgggaaattggcattgcgattcccaatggctgggggacagagtcatcaccaccagcacc cgaacctgggccctgcccacctacaacaatcacctctacaagcaaatctccaacagcacat ctggaggatcttcaaacgacaacgcctacttcggctacagcaccccctgggggtatttttga cttcaacagattccactgccacttctcaccacgtgactggcagcgactcatcaacaacaac tggggattccggcctaagcgactcaacttcaagctcttcaacattcaggtcaaagaggtta cggacaacaatggagtcaagaccatcgccaataaccttaccagcacggtccaggtcttcac ggactcagactatcagctcccgtacgtgctcgggtcggctcacgagggctgcctcccgccg ttcccagcggacgttttcatgattcctcagtacgggtatctgacgcttaatgatggaagcc aggccgtgggtcgttcgtcctttttactgcctggaatatttcccgtcgcaaatgctaagaac gggtaacaacttccagttcdgcracgagtttgagaacgtacctttccatagcagctacgct cacagccaaagcctggaccgactaatgaatccactcatcgaccaatacttgtactatctct caaagactattaacggttctggacagaatcaacaaacgctaaaattcagtgtggccggacc cagcaacatggctgtccaggaagaaactacatacctggacccagctacogacaacaacgt gtctcaaccactgtgactcaaaacaacaacagcgaatttgcttggcctggagcttcttctt aggctctcaatggacgtaatagcttgatgaatcctggacctgctatggccagccacaaaga aggagaggaccgtttctttccttgtctggatctttaattttttggcaaacaaggaactgga agagacaacgtggatgcggacaaagtcatgataaccaacgaagaagaaattaaaactacta acccggtagcaacggagtcctatggacaagtggccacaaaccaccagagtgcgcaggcgta ttcgacggatgagaggatgcaggcgcagaccggctgggttcaaaaccaaggaatacttccg ggtatggtttggcaggacagagatgtgtacctgcaaggacccatttgggccaaaattcctc acacggacgcaactttcacccttctccgctgatgggagggtttggaatgaagcacccgcc tcctcagatcctcatcaaaaacacacctgtacctgccgatcctccaacggccttcaacaag gacaagctgaactctttcatcacccagtattctactggccaagtcagcgtggagatcgagt gggagctgcagaaggaaaacagcaagcggtggaacccggagatccagtacacttccaacta ttacaagtctaataatgttgaatttgctgttaatactgaaggtgtatatagtgaacccccgc cccattggcaccagatacctgactcgtaatctgtaa |
| TTD-011 7mer peptide underlined | 3634 | atggctgccgatggttatcttccagattggctcgaggacaaccttagtgaaggaattcgcg agtggcgggcttcgaaacccggagcccctcaacccaaggcaaatcaacaacatcaagacaa cgctcgaggtcttgtgcttccgggttacaaataccttggacccggcaacggactcgacaag ggggagccggtcaacgcagcagacgcggcggccctcgagcacgacaaggcctacgaccagc agctcaaggccggagacaacccgtacctcaagtacaaccacgccgacgccgagttccagga gcggctcaaagaagatacgtcttttggggcaacctcgggcgagcagtcttccaggccaaa aagaggcttcttgaacctcttggtctggttgaggaagcggctaagacggctcctggaaaga agaggcctgtagagcagtctcctcaggaaccggactcctccgcgggtattggcaaatcggg tgcacagcccgctaaaaagagactcaatttcggtcagactggcgacacagagtcagtccca gaccctcaaccaatcggagaacctcccgcagcccccctcaggtgtgggatctcttacaatgg cttcaggtggtggcgcaccagtggcagacaataacgaaggtgccgatggagtgggtagttc ctcgggaaattggcattgcgattcccaatggctgggggacagagtcatcaccaccagcacc cgaacctgggccctgcccacctacaacaatcacctctacaagcaaatctccaacagcacat ctggaggatcttcaaatgacaacgcctacttcggctacagcaccccctgggggtatttttga cttcaacagattccactgccacttctcaccacgtgactggcagcgactcatcaacaacaac tggggattccggcctaagcgactcaacttcaagctcttcaacattcaggtcaaagaggtta cggacaacaatggagtcaagaccatcgccaataaccttaccagcacggtccaggtcttcac ggactcagactatcagctcccgtacgtgctcgggtcggctcacgagggctgcctcccgccg ttcccagcggacgttttcatgattcctcagtacgggtatctgacgcttaatgatggaagcc aggccgtgggtcgttcgtcctttttactgcctggaatatttcccgtcgcaaatgctaagaac gggtaacaacttccagttcagctacgagtttgagaacgtacctttccatagcagctacgct cacagccaaagcctggaccgactaatgaatccactcatcgaccaatacttgtactatctct caaagactattaacggttctggacagaatcaacaaacgctaaaattcagtgtggccggacc cagcaacatggctgtccaggaagaaactacatacctggacccagctaccgacaacaacgt gtctcaaccactgtgactcaaaacaacaacagcgaatttgcttggcctggagcttcttctt gggctctcaatggacgtaatagcttgatgaatcctggacctgctatggccagccacaaaga aggagaggaccgtttctttccttgtctggatctttaattttttggcaaacaaggaactgga agagacaacgtggatgcggacaaagtcatgataaccaacgaagaagaaattaaaactacta acccggtagcaacggagtcctatggacaagtggccacaaaccaccagagtgcgcaggcgta ttcgacggatgagaggaagcaggcgcagaccggctgggttcaaaaccaaggaatacttccg ggtatggtttggcaggacagagatgtgtacctgcaaggacccatttgggccaaaattcctc |

TABLE 5-continued

| Exemplary full length capsid nucleic acid sequences | | |
| --- | --- | --- |
| Name and Annotation | SEQ ID NO: | NT Sequence |
| | | acacggacggcaactttcacccttctccgctgatgggagggtttggaatgaagcacccgcc tcctcagatcctcatcaaaaacacacctgtacctgcCgatcctccaacggccttcaacaag gacaagctgaactctttcatcacccagtattctactggccaagtcagcgtggagatcgagt gggagctgcagaaggaaaacagcaagcgGtggaacccggagatccagtacacttccaacta ttacaagtctaataatgttgaatttgctgttaatactgaaggtgtatatagtgaacccgc cccattggcaccagatacctgactcgtaatctgtaa |
| TTD-012 7mer peptide underlined | 3635 | atggctgccgatgcttatcttccagattggctcgaggacaaccttagtgaaggaattcgcg agtggtgggctttgaaacctggagcccctcaacccaagocaaatcaacaacatcaagacaa cgctcgaggtcttgtgcttccgggttacaaataccttggacccggcaacggactcgacaag ggggagccggtcaacgcagcagacgcggcggccctcgagcacgacaaggcctacgaccagc agctcaaggccggagacaacccgtacctcaagtacaaccacgccgacgccgagttccagga gcggctcaaagaagatacgtcttttgggggcaacctcgggcgagcagtcttccaggccaaa aagaggcttcttgaacctcttggtctggttgaggaagcggctaagacggctcctggaaaga agaggcctgtagagcagtctcctcaggaaccggactcctccgcgggtattggcaaatcggg tgcacagcccgctaaaaagagactcaatttcggtcagactggcgacacagagtcagtccca gaccctcaaccaatcggagaacctcccgcagcccctcaggtgtgggatctcttacaatgg cttcaggtggtggcgcaccagtggcagacaataacgaaggtgccgatggagtgggtagttc ctcgggaaattggcattgcgattcccaatggctgggggacagagtcatcaccaccagcacc cgaacctgggccctgcccacctacaacaatcacctctacaagcaaatctccaacagcacat ctggaggatcttcaaatgacaacgcctacttcggctacagcacccctggggtgtattttga cttcaacagattccactgccacttctcaccacgtgactggcagcgactcatcaacaacaac tggggactccggcctaagcgactcaacttcaagctcttcaacattcaggtcaaagaggtta cggacaacaatggagtcaagaccatcgccaataaccttaccagcacggtccaggtcttcac ggactcagactatcagctcccgtacgtgctcgggtcggctcacgagggctgcctcccgccg ttcccagcggacgtttttcatgattcctcagtacggtatctgacgcttaatgatggaagcc aggccgtgggtcgttcgtccttttactgcctggaatatttcccgtcgcaaatgctaagaac gggtaacaacttccagttcagctacgagtttgagaacgtacctttccatagcagctacgct cacagccaaagcctggaccgactaatgaatccactcatcgaccaatacttgtactatctct caaagactattaacggttctggacagaatcaacaaacgctaaaattcagtgtggccggacc cagcaacatggctgtccagggaagaaactacatacctggacccagctaccgacaacaacgt gtctcaaccactgtgactcaaaacaacaacagcgaatttgcttggcctggagcttcttctt gggctctcaatgacgtaatagcttgatgaatcctggacctgctatggccagccacacaaga aggagaggaccgtttctttcctttgtctggatctttaatttttggcaaacaaggaactgga agagacaacgtggatgcggacaaagtcatgataaccaacgaagaagaaattaaaactacta acccggtagcaacggagtcctatggacaagtggccacaaaccaccagagtgcacaggctta tgtttcgtctgttaagatgcaggcgcagaccggctgggttcaaaaccaaggaatacttccg ggtatggtttggcaggacagagatgtgtacctgcaaggacccatttgggccaaaattcctc acacggacggcaactttcacccttctccgctgatgggagggtttggaatgaagcacccgcc tcctcagatcctcatcaaaaacacacctgtacctgcCgatcctccaacggccttcaacaag gacaagctgaactctttcatcacccagtattctactggccaagtcagcgtggagatcgagt gggagctgcagaaggaaaacagcaagcgGtggaacccggagatccagtacacttccaacta ttacaagtctaataatgttgaatttgctgttaatactgaaggtgtatatagtgaacccgc cccattggcaccagatacctgactcgtaatctgtaa |

In some embodiments, the polynucleotide encoding an AAV capsid polypeptide, e.g., AAV capsid variant, described herein comprises the nucleotide sequence of any one of SEQ ID NOs: 3623-3635, or a nucleotide sequence with at least 80% (e.g., at least about 85, 90, 95, 96, 97, 98, or 99%) sequence identity thereto. In some embodiments, the polynucleotide encoding an AAV capsid variant described herein comprises the nucleotide sequence of SEQ ID NO: 3623, or a nucleotide sequence with at least 80% (e.g., at least about 85, 90, 95, 96, 97, 98, or 99%) sequence identity thereto. In some embodiments, the polynucleotide encoding an AAV capsid variant described herein comprises the nucleotide sequence of SEQ ID NO: 3627, or a nucleotide sequence with at least 80% (e.g., at least about 85, 90, 95, 96, 97, 98, or 99%) sequence identity thereto. In some embodiments, the nucleic acid sequence encoding an AAV capsid polypeptide, e.g., an AAV capsid variant, described herein is codon optimized.

In some embodiments, a polynucleotide encoding the AAV capsid polypeptide, e.g., the AAV capsid variant, (e.g., VP1) of an AAV particle may comprise a nucleic acid sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of those described herein or provided by any of SEQ ID NO: 3623-3635.

In some embodiments, a polynucleotide encoding an AAV capsid polypeptide, e.g., an AAV capsid variant, (e.g., VP1) may comprise a nucleic acid sequence having at least 80% identity to any of SEQ ID NO: 3623-3635. In some embodiments, a polynucleotide encoding an AAV capsid polypeptide, e.g., an AAV capsid variant, (e.g., VP1) may comprise a nucleic acid sequence having at least 85% identity to any of SEQ ID NO: 3623-3635. In some embodiments, a polynucleotide encoding an AAV capsid polypeptide, e.g., an AAV capsid variant, (e.g., VP1) is encoded by a nucleic acid sequence having at least 90% identity to any of SEQ ID NO: 3623-3635. In some embodiments, a polynucleotide encoding an AAV capsid polypeptide, e.g., an AAV capsid variant, (e.g., VP1) may comprise a nucleic acid sequence having at least 95% identity to any of SEQ ID NO: 3623-3635. In some embodiments, a polynucleotide encoding an AAV capsid polypeptide, e.g., an AAV capsid variant, (e.g., VP1) may comprise a nucleic acid sequence having at least 96% identity to any of SEQ ID NO: 3623-3635. In some embodiments, a polynucleotide encoding an AAV capsid polypeptide, e.g., an AAV capsid variant, (e.g., VP1) may comprise a nucleic acid sequence having at least 97% identity to any of SEQ ID NO: 3623-3635. In some embodiments, a polynucleotide encoding an AAV capsid polypeptide, e.g., an AAV capsid variant. (e.g., VP1) may comprise a nucleic acid sequence having at least 98% identity to any of SEQ ID NO: 3623-3635. In some embodiments, a polynucleotide encoding an AAV capsid polypeptide, e.g., an AAV capsid variant, (e.g., VP1) may comprise a nucleic acid sequence having at least 99% identity to any of SEQ ID NO: 3623-3635. In some embodiments, a polynucleotide encoding an AAV capsid polypeptide, e.g., an AAV capsid variant, (e.g., VP1) may comprise a nucleic acid sequence given by any of SEQ ID NO: 3623-3635.

In some embodiments, a polynucleotide encoding an AAV capsid polypeptide, e.g., an AAV capsid variant, may comprise a nucleic acid sequence having at least 80% identity to SEQ ID NO: 3623. In some embodiments, a polynucleotide encoding an AAV capsid polypeptide, e.g., an AAV capsid variant, may comprise a nucleic acid sequence having at least 85% identity to SEQ ID NO: 3623. In some embodiments, a polynucleotide encoding an AAV capsid polypeptide, e.g., an AAV capsid variant, may comprise a nucleic acid sequence having at least 90% identity to SEQ ID NO: 3623. In some embodiments, an AAV capsid polypeptide, e.g., an AAV capsid variant, may comprise a nucleic acid sequence having at least 95% identity to SEQ ID NO: 3623. In some embodiments, a polynucleotide encoding an AAV capsid polypeptide, e.g., an AAV capsid variant, may comprise a nucleic acid sequence having at least 96% identity to SEQ ID NO: 3623. In some embodiments, a polynucleotide encoding an AAV capsid polypeptide, e.g., an AAV capsid variant, may comprise a nucleic acid sequence having at least 97% identity to SEQ ID NO: 3623. In some embodiments, a polynucleotide encoding an AAV capsid polypeptide, e.g., an AAV capsid variant, may comprise a nucleic acid sequence having at least 98% identity to SEQ ID NO: 3623. In some embodiments, a polynucleotide encoding an AAV capsid polypeptide, e.g., an AAV capsid variant, may comprise a nucleic acid sequence having at least 99% identity to SEQ ID NO: 3623.

In some embodiments, a polynucleotide encoding an AAV capsid polypeptide, e.g., an AAV capsid variant, may have a nucleic acid sequence comprising SEQ ID NO: 3623.

In some embodiments, a polynucleotide encoding an AAV capsid polypeptide, e.g., an AAV capsid variant, may have a nucleic acid sequence consisting of SEQ ID NO: 3623.

In some embodiments, a polynucleotide encoding an AAV capsid polypeptide, e.g., an AAV capsid variant, may comprise a nucleic acid sequence having at least 80% identity to SEQ ID NO: 3624 or 3625. In some embodiments, a polynucleotide encoding an AAV capsid polypeptide, e.g., an AAV capsid variant, may comprise a nucleic acid sequence having at least 85% identity to SEQ ID NO: 3624 or 3625. In some embodiments, a polynucleotide encoding an AAV capsid polypeptide, e.g., an AAV capsid variant, may comprise a nucleic acid sequence having at least 90% identity to SEQ ID NO: 3624 or 3625. In some embodiments, a polynucleotide encoding an AAV capsid polypeptide, e.g., an AAV capsid variant, may comprise a nucleic acid sequence having at least 95% identity to SEQ ID NO: 3624 or 3625. In some embodiments, a polynucleotide encoding an AAV capsid polypeptide, e.g., an AAV capsid variant, may comprise a nucleic acid sequence having at least 96% identity to SEQ ID NO: 3624 or 3625. In some embodiments, a polynucleotide encoding an AAV capsid polypeptide, e.g., an AAV capsid variant, may comprise a nucleic acid sequence having at least 97% identity to SEQ ID NO: 3624 or 3625. In some embodiments, a polynucleotide encoding an AAV capsid polypeptide, e.g., an AAV capsid variant, may comprise a nucleic acid sequence having at least 98% identity to SEQ ID NO: 3624 or 3625. In some embodiments, a polynucleotide encoding an AAV capsid polypeptide, e.g., an AAV capsid variant, may comprise a nucleic acid sequence having at least 99% identity to SEQ ID NO: 3624 or 3625.

In some embodiments, a polynucleotide encoding an AAV capsid polypeptide, e.g., an AAV capsid variant, may have a nucleic acid sequence comprising SEQ ID NO: 3624 or 3625.

In some embodiments, a polynucleotide encoding an AAV capsid polypeptide, e.g., an AAV capsid variant, may have a nucleic acid sequence consisting of SEQ ID NO: 3624 or 3625.

In some embodiments, a polynucleotide encoding an AAV capsid polypeptide, e.g., an AAV capsid variant, may comprise a nucleic acid sequence having at least 80% identity to SEQ ID NO: 3626. In some embodiments, a polynucleotide encoding an AAV capsid polypeptide, e.g., an AAV capsid variant, may comprise a nucleic acid sequence having at least 85% identity to SEQ ID NO: 3626. In some embodiments, a polynucleotide encoding an AAV capsid polypeptide, e.g., an AAV capsid variant, may comprise a nucleic acid sequence having at least 90% identity to SEQ ID NO: 3626. In some embodiments, a polynucleotide encoding an AAV capsid polypeptide, e.g., an AAV capsid variant, may comprise a nucleic acid sequence having at least 95% identity to SEQ ID NO: 3626. In some embodiments, a polynucleotide encoding an AAV capsid polypeptide, e.g., an AAV capsid variant, may comprise a nucleic acid sequence having at least 96% identity to SEQ ID NO: 3626. In some embodiments, a polynucleotide encoding an AAV capsid polypeptide, e.g., an AAV capsid variant, may comprise a nucleic acid sequence having at least 97% identity to SEQ ID NO: 3626. In some embodiments, a polynucleotide encoding an AAV capsid polypeptide, e.g., an AAV capsid variant, may comprise a nucleic acid sequence having at least 98% identity to SEQ ID NO: 3626. In some embodiments, a polynucleotide encoding an AAV capsid polypeptide, e.g., an AAV capsid variant, may comprise a nucleic acid sequence having at least 99% identity to SEQ ID NO: 3626.

In some embodiments, a polynucleotide encoding an AAV capsid polypeptide, e.g., an AAV capsid variant, may have a nucleic acid sequence comprising SEQ ID NO: 3626.

In some embodiments, a polynucleotide encoding an AAV capsid polypeptide, e.g., an AAV capsid variant, may have a nucleic acid sequence consisting of SEQ ID NO: 3626.

In some embodiments, a polynucleotide encoding an AAV capsid polypeptide, e.g., an AAV capsid variant, may comprise a nucleic acid sequence having at least 80% identity to SEQ ID NO: 3627. In some embodiments, a polynucleotide encoding an AAV capsid polypeptide, e.g., an AAV capsid variant, may comprise a nucleic acid sequence having at least 85% identity to SEQ ID NO: 3627. In some embodiments, a polynucleotide encoding an AAV capsid polypeptide, e.g., an AAV capsid variant, may comprise a nucleic acid sequence having at least 90% identity to SEQ ID NO: 3627. In some embodiments, a polynucleotide encoding an AAV capsid polypeptide, e.g., an AAV capsid variant, may comprise a nucleic acid sequence having at least 95% identity to SEQ ID NO: 3627. In some embodiments, a polynucleotide encoding an AAV capsid polypeptide, e.g., an AAV capsid variant, may comprise a nucleic acid sequence having at least 96% identity to SEQ ID NO: 3627. In some embodiments, a polynucleotide encoding an AAV capsid polypeptide, e.g., an AAV capsid variant, may comprise a nucleic acid sequence having at least 97% identity to SEQ ID NO: 3627. In some embodiments, a polynucleotide encoding an AAV capsid polypeptide, e.g., an AAV capsid variant, may comprise a nucleic acid sequence having at least 98% identity to SEQ ID NO: 3627. In some embodiments, a polynucleotide encoding an AAV capsid polypeptide, e.g., an AAV capsid variant, may comprise a nucleic acid sequence having at least 99% identity to SEQ ID NO: 3627.

In some embodiments, a polynucleotide encoding an AAV capsid polypeptide, e.g., an AAV capsid variant, may have a nucleic acid sequence comprising SEQ ID NO: 3627.

In some embodiments, a polynucleotide encoding an AAV capsid polypeptide, e.g., an AAV capsid variant, may have a nucleic acid sequence consisting of SEQ ID NO: 3627.

In some embodiments, a polynucleotide encoding an AAV capsid polypeptide, e.g., an AAV capsid variant, may comprise a nucleic acid sequence having at least 80% identity to SEQ ID NO: 3628. In some embodiments, a polynucleotide encoding an AAV capsid polypeptide, e.g., an AAV capsid variant, may comprise a nucleic acid sequence having at least 85% identity to SEQ ID NO: 3628. In some embodiments, a polynucleotide encoding an AAV capsid polypeptide, e.g., an AAV capsid variant, may comprise a nucleic acid sequence having at least 90% identity to SEQ ID NO: 3628. In some embodiments, a polynucleotide encoding an AAV capsid polypeptide, e.g., an AAV capsid variant, may comprise a nucleic acid sequence having at least 95% identity to SEQ ID NO: 3628. In some embodiments, a polynucleotide encoding an AAV capsid polypeptide, e.g., an AAV capsid variant, may comprise a nucleic acid sequence having at least 96% identity to SEQ ID NO: 3628. In some embodiments, a polynucleotide encoding an AAV capsid polypeptide, e.g., an AAV capsid variant, may comprise a nucleic acid sequence having at least 97% identity to SEQ ID NO: 3628. In some embodiments, a polynucleotide encoding an AAV capsid polypeptide, e.g., an AAV capsid variant, may comprise a nucleic acid sequence having at least 98% identity to SEQ ID NO: 3628. In some embodiments, a polynucleotide encoding an AAV capsid polypeptide, e.g., an AAV capsid variant, may comprise a nucleic acid sequence having at least 99% identity to SEQ ID NO: 3628.

In some embodiments, a polynucleotide encoding an AAV capsid polypeptide, e.g., an AAV capsid variant, may have a nucleic acid sequence comprising SEQ ID NO: 3628.

In some embodiments, a polynucleotide encoding an AAV capsid polypeptide, e.g., an AAV capsid variant, may have a nucleic acid sequence consisting of SEQ ID NO: 3628.

In some embodiments, the AAV capsid polypeptide, e.g., the AAV capsid variant, comprises a VP2 protein comprising the amino acid sequence corresponding to positions 138-743, of any one of SEQ ID NOs: 3636-3647, or a sequence with at least 80% (e.g., at least about 85, 90, 95, 96, 97, 98, or 99%) sequence identity thereto. In some embodiments, the AAV capsid comprises a VP3 protein comprising the amino acid sequence corresponding to positions 203-743, of any one of SEQ ID NOs: 3636-3647, or a sequence with at least 80% (e.g., at least about 85, 90, 95, 96, 97, 98, or 99%) sequence identity thereto.

In some embodiments, the AAV capsid polypeptide, e.g., the AAV capsid variant, e.g., an AAV capsid variant described herein, comprises the amino acid sequence of any one of SEQ ID NOS: 3636-3647, or an amino acid sequence with at least 80% (e.g., at least about 85, 90, 95, 96, 97, 98, or 99%) sequence identity thereto. In some embodiments, the AAV capsid polypeptide, e.g., the AAV capsid variant, e.g., an AAV capsid variant described herein, comprises an amino acid sequence having at least one, two, or three modifications, but not more than 30, 20 or 10 modifications of the amino acid sequence of any one of SEQ ID NOs: 3636-3647.

In some embodiments, the AAV capsid polypeptide, e.g., AAV capsid variant, (e.g., VP1) of an AAV particle may comprise an amino acid sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of those described herein or provided as any of SEQ ID NO: 3636-3647.

In some embodiments, an AAV capsid polypeptide, e.g., AAV capsid variant, (e.g., VP1) may comprise an amino acid sequence having at least 80% identity to any of SEQ ID NO: 3636-3647. In some embodiments, an AAV capsid (e.g., VP1) may comprise an amino acid sequence having at least 85% identity to any of SEQ ID NO: 3636-3647. In some embodiments, an AAV capsid polypeptide, e.g., AAV capsid variant, (e.g., VP1) may comprise an amino acid sequence having at least 90% identity to any of SEQ ID NO: 3636-3647. In some embodiments, an AAV capsid polypeptide, e.g., AAV capsid variant, (e.g., VP1) may comprise an amino acid sequence having at least 95% identity to any of SEQ ID NO: 3636-3647. In some embodiments, an AAV capsid polypeptide, e.g., AAV capsid variant, (e.g., VP1) may comprise an amino acid sequence having at least 96% identity to any of SEQ ID NO: 3636-3647. In some embodiments, an AAV capsid polypeptide, e.g., AAV capsid variant, (e.g., VP1) may comprise an amino acid sequence having at least 97% identity to any of SEQ ID NO: 3636-3647. In some embodiments, an AAV capsid polypeptide, e.g., AAV capsid variant, (e.g., VP1) may comprise an amino acid sequence having at least 98% identity to any of SEQ ID NO: 3636-3647. In some embodiments, an AAV capsid polypeptide, e.g., AAV capsid variant, (e.g., VP1) may comprise an amino acid sequence having at least 99% identity to any of SEQ ID NO: 3636-3647. In some embodiments, an AAV capsid polypeptide, e.g., AAV capsid variant, (e.g., VP1) may have an amino acid sequence comprising any of SEQ ID NO: 3636-3647. In some embodiments, an AAV capsid polypeptide, e.g., AAV capsid variant, (e.g., VP1) may have an amino acid sequence consisting of any of SEQ ID NO: 3636-3647.

In some embodiments, an AAV capsid polypeptide, e.g., AAV capsid variant, may comprise an amino acid sequence having at least 80% identity to SEQ ID NO: 3636. In some embodiments, an AAV capsid polypeptide, e.g., AAV capsid variant, may comprise an amino acid sequence having at least 85% identity to SEQ ID NO: 3636. In some embodiments, an AAV capsid polypeptide, e.g., AAV capsid variant, may comprise an amino acid sequence having at least 90% identity to SEQ ID NO: 3636. In some embodiments, an AAV capsid polypeptide, e.g., AAV capsid variant, may comprise an amino acid sequence having at least 95% identity to SEQ ID NO: 3636. In some embodiments, an AAV capsid polypeptide, e.g., AAV capsid variant, may comprise an amino acid sequence having at least 96% identity to SEQ ID NO: 3636. In some embodiments, an AAV capsid polypeptide, e.g., AAV capsid variant, may comprise an amino acid sequence having at least 97% identity to SEQ ID NO: 3636. In some embodiments, an AAV capsid polypeptide, e.g., AAV capsid variant, may comprise an amino acid sequence having at least 98% identity to SEQ ID NO: 3636. In some embodiments, an AAV capsid polypeptide, e.g., AAV capsid variant, may comprise an amino acid sequence having at least 99% identity to SEQ ID NO: 3636.

In some embodiments, an AAV capsid polypeptide, e.g., AAV capsid variant, may have an amino acid sequence comprising SEQ ID NO: 3636. In some embodiments, the AAV capsid variant comprises the amino acid sequence of SEQ ID NO: 3636.

In some embodiments, an AAV capsid polypeptide, e.g., AAV capsid variant, may have an amino acid sequence consisting of SEQ ID NO: 3636.

In some embodiments, an AAV capsid polypeptide, e.g., AAV capsid variant, comprising an amino acid sequence given as SEQ ID NO: 3636 is encoded by a nucleic acid sequence comprising SEQ ID NO: 3623. In some embodiments, an AAV capsid polypeptide, e.g., AAV capsid variant, comprising an amino acid sequence given as SEQ ID NO: 3636 is encoded by a codon-optimized nucleic acid sequence having 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 3623.

In some embodiments, an AAV capsid polypeptide, e.g., AAV capsid variant, may comprise an amino acid sequence having at least 80% identity to SEQ ID NO: 3637. In some embodiments, an AAV capsid polypeptide, e.g., AAV capsid variant, may comprise an amino acid sequence having at least 85% identity to SEQ ID NO: 3637. In some embodiments, an AAV capsid polypeptide, e.g., AAV capsid variant, may comprise an amino acid sequence having at least 90% identity to SEQ ID NO: 3637. In some embodiments, an AAV capsid polypeptide, e.g., AAV capsid variant, may comprise an amino acid sequence having at least 95% identity to SEQ ID NO: 3637. In some embodiments, an AAV capsid polypeptide, e.g., AAV capsid variant, may comprise an amino acid sequence having at least 96% identity to SEQ ID NO: 3637. In some embodiments, an AAV capsid polypeptide, e.g., AAV capsid variant, may comprise an amino acid sequence having at least 97% identity to SEQ ID NO: 3637. In some embodiments, an AAV capsid polypeptide, e.g., AAV capsid variant, may comprise an amino acid sequence having at least 98% identity to SEQ ID NO: 3637. In some embodiments, an AAV capsid polypeptide, e.g., AAV capsid variant, may comprise an amino acid sequence having at least 99% identity to SEQ ID NO: 3637.

In some embodiments, an AAV capsid polypeptide, e.g., AAV capsid variant, may have an amino acid sequence comprising SEQ ID NO: 3637. In some embodiments, the AAV capsid variant comprises the amino acid sequence of SEQ ID NO: 3637.

In some embodiments, an AAV capsid polypeptide, e.g., AAV capsid variant, may have an amino acid sequence consisting of SEQ ID NO: 3637.

In some embodiments, an AAV capsid polypeptide, e.g., AAV capsid variant, comprising an amino acid sequence given as SEQ ID NO: 3637 is encoded by a nucleic acid sequence comprising SEQ ID NO: 3624 or 3625. In some embodiments, an AAV capsid polypeptide, e.g., AAV capsid variant, comprising an amino acid sequence given as SEQ ID NO: 3637 is encoded by a codon-optimized nucleic acid sequence having 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 3624 or 3625.

In some embodiments, an AAV capsid polypeptide, e.g., AAV capsid variant, may comprise an amino acid sequence having at least 80% identity to SEQ ID NO: 3638. In some embodiments, an AAV capsid polypeptide, e.g., AAV capsid variant, may comprise an amino acid sequence having at least 85% identity to SEQ ID NO: 3638. In some embodiments, an AAV capsid, e.g., AAV capsid variant, may comprise an amino acid sequence having at least 90% identity to SEQ ID NO: 3638. In some embodiments, an AAV capsid polypeptide, e.g., AAV capsid variant, may comprise an amino acid sequence having at least 95% identity to SEQ ID NO: 3638. In some embodiments, an AAV capsid polypeptide, e.g., AAV capsid variant, may comprise an amino acid sequence having at least 96% identity to SEQ ID NO: 3638. In some embodiments, an AAV capsid polypeptide, e.g., AAV capsid variant, may comprise an amino acid sequence having at least 97% identity to SEQ ID NO: 3638. In some embodiments, an AAV capsid polypeptide, e.g., AAV capsid variant, may comprise an amino acid sequence having at least 98% identity to SEQ ID NO: 3638. In some embodiments, an AAV capsid polypeptide, e.g., AAV capsid variant, may comprise an amino acid sequence having at least 99% identity to SEQ ID NO: 3638.

In some embodiments, an AAV capsid polypeptide, e.g., AAV capsid variant, may have an amino acid sequence comprising SEQ ID NO: 3638. In some embodiments, the AAV capsid variant comprises the amino acid sequence of SEQ ID NO: 3638.

In some embodiments, an AAV capsid polypeptide, e.g., AAV capsid variant, may have an amino acid sequence consisting of SEQ ID NO: 3638.

In some embodiments, an AAV capsid polypeptide, e.g., AAV capsid variant, comprising an amino acid sequence given as SEQ ID NO: 3638 is encoded by a nucleic acid sequence comprising SEQ ID NO: 3626. In some embodiments, an AAV capsid polypeptide, e.g., AAV capsid variant, comprising an amino acid sequence given as SEQ ID NO: 3638 is encoded by a codon-optimized nucleic acid sequence having 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 3626.

In some embodiments, an AAV capsid polypeptide, e.g., AAV capsid variant, may comprise an amino acid sequence having at least 80% identity to SEQ ID NO: 3639. In some embodiments, an AAV capsid polypeptide, e.g., AAV capsid variant, may comprise an amino acid sequence having at least 85% identity to SEQ ID NO: 3639. In some embodiments, an AAV capsid polypeptide, e.g., AAV capsid variant, may comprise an amino acid sequence having at least 90% identity to SEQ ID NO: 3639. In some embodiments, an AAV capsid polypeptide, e.g., AAV capsid variant, may comprise an amino acid sequence having at least 95% identity to SEQ ID NO: 3639. In some embodiments, an AAV capsid polypeptide, e.g., AAV capsid variant, may comprise an amino acid sequence having at least 96% identity to SEQ ID NO: 3639. In some embodiments, an AAV capsid polypeptide, e.g., AAV capsid variant, may comprise an amino acid sequence having at least 97% identity to SEQ ID NO: 3639. In some embodiments, an AAV capsid polypeptide, e.g., AAV capsid variant, may comprise an amino acid sequence having at least 98% identity to SEQ ID NO: 3639. In some embodiments, an AAV capsid polypeptide, e.g., AAV capsid variant, may comprise an amino acid sequence having at least 99% identity to SEQ ID NO: 3639.

In some embodiments, an AAV capsid polypeptide, e.g., AAV capsid variant, may have an amino acid sequence comprising SEQ ID NO: 3639. In some embodiments, the AAV capsid variant comprises the amino acid sequence of SEQ ID NO: 3639.

In some embodiments, an AAV capsid polypeptide, e.g., AAV capsid variant, may have an amino acid sequence consisting of SEQ ID NO: 3639.

In some embodiments, an AAV capsid polypeptide, e.g., AAV capsid variant, comprising an amino acid sequence given as SEQ ID NO: 3639 is encoded by a nucleic acid sequence comprising SEQ ID NO: 3627. In some embodiments, an AAV capsid polypeptide, e.g., AAV capsid variant, comprising an amino acid sequence given as SEQ ID NO: 3639 is encoded by a codon-optimized nucleic acid sequence having 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 3627.

In some embodiments, an AAV capsid polypeptide, e.g., AAV capsid variant, may comprise an amino acid sequence having at least 80% identity to SEQ ID NO: 3640. In some embodiments, an AAV capsid polypeptide, e.g., AAV capsid variant, may comprise an amino acid sequence having at least 85% identity to SEQ ID NO: 3640. In some embodiments, an AAV capsid polypeptide, e.g., AAV capsid variant, may comprise an amino acid sequence having at least 90% identity to SEQ ID NO: 3640. In some embodiments, an AAV capsid polypeptide, e.g., AAV capsid variant, may comprise an amino acid sequence having at least 95% identity to SEQ ID NO: 3640. In some embodiments, an AAV capsid polypeptide, e.g., AAV capsid variant, may comprise an amino acid sequence having at least 96% identity to SEQ ID NO: 3640. In some embodiments, an AAV capsid polypeptide, e.g., AAV capsid variant, may comprise an amino acid sequence having at least 97% identity to SEQ ID NO: 3640. In some embodiments, an AAV capsid polypeptide, e.g., AAV capsid variant, may comprise an amino acid sequence having at least 98% identity to SEQ ID NO: 3640. In some embodiments, an AAV capsid polypeptide, e.g., AAV capsid variant, may comprise an amino acid sequence having at least 99% identity to SEQ ID NO: 3640.

In some embodiments, an AAV capsid polypeptide, e.g., AAV capsid variant, may have an amino acid sequence comprising SEQ ID NO: 3640. In some embodiments, the AAV capsid variant comprises the amino acid sequence of SEQ ID NO: 3640.

In some embodiments, an AAV capsid polypeptide, e.g., AAV capsid variant, may have an amino acid sequence consisting of SEQ ID NO: 3640.

In some embodiments, an AAV capsid polypeptide, e.g., AAV capsid variant, comprising an amino acid sequence given as SEQ ID NO: 3640 is encoded by a nucleic acid sequence comprising SEQ ID NO: 3628. In some embodiments, an AAV capsid polypeptide, e.g., AAV capsid variant, comprising an amino acid sequence given as SEQ ID NO: 3640 is encoded by a codon-optimized nucleic acid sequence having 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 3628.

In some embodiments, an AAV capsid polypeptide, e.g., an AAV capsid variant, described herein has an increased tropism for a CNS cell or tissue, e.g., a brain cell, brain tissue, spinal cord cell, or spinal cord tissue, relative to the tropism of a reference sequence comprising the amino acid sequence of SEQ ID NO: 138.

In some embodiments, an AAV capsid polypeptide, e.g., an AAV capsid variant, described herein transduces a brain region, e.g., selected from dentate nucleus, cerebellar cortex, cerebral cortex, brain stem, hippocampus, thalamus and putamen. In some embodiments, the level of transduction of said brain region is at least 5, 10, 50, 100, 200, 500, 1,000, 2,000, 5,000, or 10,000-fold greater as compared to a reference sequence of SEQ ID NO: 138.

In some embodiments, an AAV capsid polypeptide, e.g., an AAV capsid variant, described herein is enriched at least about 5, 6, 7, 8, 9, or 10-fold, in the brain compared to a reference sequence of SEQ ID NO: 138. In some embodiments, an AAV capsid variant described herein is enriched at least about 20, 30, 40, or 50-fold in the brain compared to a reference sequence of SEQ ID NO: 138. In some embodiments, an AAV capsid variant described herein is enriched at least about 100, 200, 300, or 400-fold in the brain compared to a reference sequence of SEQ ID NO: 138.

In some embodiments, an AAV capsid polypeptide, e.g., an AAV capsid variant, described herein delivers an increased level of viral genomes to a brain region. In some embodiments, the level of viral genomes is increased by at least 5, 10, 20, 30, 40 or 50-fold, as compared to a reference sequence of SEQ ID NO: 138. In some embodiments, the brain region comprises a frontal cortex, sensory cortex, motor cortex, putamen, thalamus, cerebellar cortex, dentate nucleus, caudate, and/or hippocampus.

In some embodiments, an AAV capsid polypeptide, e.g., an AAV capsid variant, described herein delivers an increased level of a payload to a brain region. In some embodiments, the level of the payload is increased by at least 5, 10, 50, 100, 200, 500, 1,000, 2,000, 5,000, or 10,000-fold, as compared to a reference sequence of SEQ ID NO: 138. In some embodiments, the brain region comprises a frontal cortex, sensory cortex, motor cortex, putamen, thalamus, cerebellar cortex, dentate nucleus, caudate, and/or hippocampus.

In some embodiments, an AAV capsid polypeptide, e.g., an AAV capsid variant, described herein delivers an increased level of a payload to a spinal cord region. In some embodiments, the level of the payload is increased by at least 10, 20, 50, 100, 200, 300, 400, 500, 600, 700, 800 or 900-fold, as compared to a reference sequence of SEQ ID NO: 138. In some embodiments, the spinal cord region comprises a cervical, thoracic, and/or lumbar region.

In some embodiments, an AAV capsid polypeptide, e.g., an AAV capsid variant, described herein shows preferential transduction in a brain region relative to the transduction in the dorsal root ganglia (DRG).

In some embodiments, an AAV capsid polypeptide, e.g., an AAV capsid variant, described herein has an increased tropism for a muscle cell or tissue, e.g., a heart cell or tissue, relative to the tropism of a reference sequence comprising the amino acid sequence of SEQ ID NO: 138. In some embodiments, the AAV capsid variant delivers an increased level of a payload to a muscle region. In some embodiments, the payload is increased by at least 10, 15, 20, 30, or 40-fold, as compared to a reference sequence of SEQ ID NO: 138. In some embodiments, the muscle region comprises a heart muscle, quadriceps muscle, and/or a diaphragm muscle region. In some embodiments, the muscle region comprises a heart muscle region, e.g., a heart atrium muscle region or a heart ventricle muscle region.

In some embodiments, an, AAV capsid polypeptide, e.g., an AAV capsid variant, of the present disclosure is isolated, e.g., recombinant. In some embodiments, a polynucleotide encoding an AAV capsid polypeptide, e.g., an AAV capsid variant, of the present disclosure is isolated, e.g., recombinant.

In any of the DNA and RNA sequences referenced and/or described herein, the single letter symbol has the following description: A for adenine; C for cytosine; G for guanine; T for thymine; U for Uracil; W for weak bases such as adenine or thymine; S for strong nucleotides such as cytosine and guanine; M for amino nucleotides such as adenine and cytosine; K for keto nucleotides such as guanine and thymine; R for purines adenine and guanine; Y for pyrimidine cytosine and thymine; B for any base that is not A (e.g., cytosine, guanine, and thymine); D for any base that is not C (e.g., adenine, guanine, and thymine); H for any base that is not G (e.g., adenine, cytosine, and thymine); V for any base that is not T (e.g., adenine, cytosine, and guanine); N for any nucleotide (which is not a gap); and Z is for zero.

In any of the amino acid sequences referenced and/or described herein, the single letter symbol has the following description: G (Gly) for Glycine; A (Ala) for Alanine; L (Leu) for Leucine; M (Met) for Methionine; F (Phe) for Phenylalanine; W (Trp) for Tryptophan; K (Lys) for Lysine; Q (Gln) for Glutamine; E (Glu) for Glutamic Acid; S (Ser) for Serine; P (Pro) for Proline; V (Val) for Valine; I (Ile) for Isoleucine; C (Cys) for Cysteine; Y (Tyr) for Tyrosine; H (His) for Histidine; R (Arg) for Arginine; N (Asn) for Asparagine; D (Asp) for Aspartic Acid; T (Thr) for Threonine; B (Asx) for Aspartic acid or Asparagine; J (Xle) for Leucine or Isoleucine; O (Pyl) for Pyrrolysine; U (Sec) for Selenocysteine; X (Xaa) for any amino acid; and Z (Glx) for Glutamine or Glutamic acid.

Also provided herein are polynucleotide sequences encoding any of the AAV capsid variants described above and AAV particles, vectors, and cells comprising the same.

AAV Serotypes and Capsids

In some embodiments, an AAV particle of the present disclosure may comprise or be derived from any natural or recombinant AAV serotype. AAV serotypes may differ in characteristics such as, but not limited to, packaging, tropism, transduction and immunogenic profiles. While not wishing to be bound by theory, it is believed in some embodiments, that the AAV capsid protein, e.g., an AAV capsid variant, can modulate, e.g., direct, AAV particle tropism to a particular tissue.

In some embodiments, an AAV particle may have a capsid protein, e.g., an AAV capsid variant, and ITR sequences derived from the same parent serotype (e.g., AAV2 capsid and AAV2 ITRs). In another embodiment, the AAV particle may be a pseudo-typed AAV particle, wherein the capsid protein and ITR sequences are derived from different parent serotypes (e.g., AAV9 capsid and AAV2 ITRs; AAV2/9).

The AAV particles of the present disclosure may comprise an AAV capsid protein, e.g., an AAV capsid variant, with a peptide, e.g., targeting peptide, inserted into the parent sequence. The parent capsid or serotype may comprise or be derived from any natural or recombinant AAV serotype. As used herein, a "parent" sequence is a nucleotide or amino acid sequence into which a targeting sequence is inserted (e.g., a nucleotide insertion into nucleic acid sequence or amino acid sequence insertion into amino acid sequence).

In certain embodiments, the parent AAV capsid nucleotide sequence, e.g., a parental nucleic acid sequence, is as set forth in SEQ ID NO: 137. In some embodiments, the parent AAV capsid nucleotide sequence comprises the nucleic acid sequence of SEQ ID NO: 137, or a nucleic acid sequence substantially identical (e.g., having at least about 70%, 75%, 80%, 85%, 90%, 92%, 95%, 97%, 98%, or 99% sequence identity) at least thereto. In some embodiments, the parent AAV capsid amino acid sequence, e.g., the parental sequence, is encoded by the nucleic acid sequence of SEQ ID NO: 137, or a nucleic acid sequence substantially identical (e.g., having at least about 70%, 75%, 80%, 85%, 90%, 92%, 95%, 97%, 98%, or 99% sequence identity) at least thereto.

In some embodiments, the parent AAV capsid nucleotide sequence is a K449R variant of SEQ ID NO: 137, wherein the codon encoding a lysine (e.g., AAA or AAG) at position 449 in the amino acid sequence (nucleotides 1345-1347) is exchanged for one encoding an arginine (CGT, CGC, CGA, CGG, AGA, AGG). In some embodiments, the K449R variant has the same function as wild-type AAV9.

In some embodiments, the parent AAV capsid amino acid sequence, e.g., a parental amino acid sequence, is as set forth in SEQ ID NO: 138.

```
(SEQ ID NO: 138)
MAADGYLPDWLEDNLSEGIREWWALKPGAPQPKANQQHQDNARGLVLPGY

KYLGPGNGLDKGEPVNAADAAALEHDKAYDQQLKAGDNPYLKYNHADAEF

QERLKEDTSFGGNLGRAVFQAKKRLLEPLGLVEEAAKTAPGKKRPVEQSP

QEPDSSAGIGKSGAQPAKKRLNFGQTGDTESVPDPQPIGEPPAAPSGVGS

LTMASGGGAPVADNNEGADGVGSSSGNWHCDSQWLGDRVITTSTRTWALP

TYNNHLYKQISNSTSGGSSNDNAYFGYSTPWGYFDFNRFHCHFSPRDWQR

LINNNWGFRPKRLNFKLFNIQVKEVTDNNGVKTIANNLTSTVQVFTDSDY

QLPYVLGSAHEGCLPPFPADVFMIPQYGYLTLNDGSQAVGRSSFYCLEYF

PSQMLRTGNNFQFSYEFENVPFHSSYAHSQSLDRLMNPLIDQYLYYLSKT

INGSGQNQQTLKFSVAGPSNMAVQGRNYIPGPSYRQQRVSTTVTQNNNSE

FAWPGASSWALNGRNSLMNPGPAMASHKEGEDRFFPLSGSLIFGKQGTGR

DNVDADKVMITNEEEIKTTNPVATESYGQVATNHQSAQAQAQTGWVQNQG

ILPGMVWQDRDVYLQGPIWAKIPHTDGNFHPSPLMGGFGMKHPPPQILIK

NTPVPADPPTAFNKDKLNSFITQYSTGQVSVEIEWELQKENSKRWNPEIQ

YTSNYYKSNNVEFAVNTEGVYSEPRPIGTRYLTRNL
```

In some embodiments, the parental sequence comprises an amino acid sequence comprising at least one, two, or three modifications but no more than 30, 20, or 10 modifications, e.g., substitutions, relative to the amino acid sequence of SEQ ID NO: 138. In some embodiments, the parental sequence comprises the amino acid sequence of SEQ ID NO: 138, or an amino acid sequence substantially identical (e.g., having at least 70%, 75%, 80%, 85%, 90%, 92%, 95%, 97%, 98%, or 99% sequence identity) thereto. In some embodiments, the parental sequence comprises substitution at position K449, e.g., a K449R substitution.

In some embodiments, the parent AAV capsid amino acid sequence, e.g., a parental amino acid sequence, is as set forth in SEQ ID NO: 11. In some embodiments, the parental sequence comprises an amino acid sequence comprising at least one, two, or three modifications but no more than 30, 20, or 10 modifications, e.g., substitutions, relative to the amino acid sequence of SEQ ID NO: 11. In some embodiments, the parental sequence comprises the amino acid sequence of SEQ ID NO: 11 or an amino acid sequence substantially identical (e.g., having at least 70%, 75%, 80%, 85%, 90%, 92%, 95%, 97%, 98%, or 99% sequence identity) thereto.

In some embodiments, the AAV capsid polypeptide, e.g., AAV capsid variant, or the parent AAV capsid may be as described in Jackson et al (Frontiers in Molecular Neuroscience 9:154 (2016)), the contents of which are herein incorporated by reference in their entirety. In some embodiments, the AAV serotype of a parent AAV capsid described herein is PHP.B or AAV9. In some embodiments, the AAV serotype of a parent AAV capsid or AAV capsid variant is paired with a synapsin promoter to enhance neuronal transduction, as compared to when more ubiquitous promoters are used (e.g., CBA or CMV).

In some embodiments the AAV capsid polypeptide, e.g., AAV capsid variant, or the parent AAV capsid is AAV9, or a variant thereof. In some embodiments, the AAV9 capsid comprises the amino acid sequence SEQ ID NO: 138. In some embodiments, the AAV9 amino acid sequence is encoded by a nucleotide sequence comprising SEQ ID NO: 137. In some embodiments, the AAV9 capsid comprises an amino acid sequence at least 70% identical to SEQ ID NO: 138, such as, 70%, 75%, 80%, 85%, 90%, 91%, 92%, 93%, 94%, 95%, 96%, 97%, 98%, 99%, or greater than 99%. In some embodiments, the AAV9 capsid comprises a nucleotide sequence at least 70% identical to SEQ ID NO: 137, such as, 70%, 75%, 80%, 85%, 90%, 91%, 92%, 93%, 94%, 95%, 96%, 97%, 98%, 99%, or greater than 99%.

In some embodiments, the AAV capsid polypeptide, e.g., AAV capsid variant, or the parent AAV capsid is AAV9 K449R, or a variant thereof. In some embodiments, the AAV9 K449R capsid comprises the amino acid sequence SEQ ID NO: 11. In some embodiments, the AAV9 K449R capsid comprises an amino acid sequence at least 70% identical to SEQ ID NO: 11, such as, 70%, 75%, 80%, 85%, 90%, 91%, 92%, 93%, 94%, 95%, 96%, 97%, 98%, 99%, or greater than 99%.

In some embodiments, the AAV capsid polypeptide, e.g., AAV capsid variant, or the parent AAV capsid comprises an AAVDJ sequence. In some embodiments, the AAV capsid polypeptide, e.g., AAV capsid variant, or the parent AAV capsid comprises an AAVDJ8 sequence. In some embodiments, the AAV capsid polypeptide, e.g., AAV capsid variant, or the parent AAV capsid comprises an AAVrh10 sequence. In some embodiments, the AAV capsid polypeptide, e.g., AAV capsid variant, or the parent AAV capsid comprises an AAV1 sequence. In some embodiments, the AAV capsid polypeptide, e.g., AAV capsid variant, or the parent AAV capsid comprises AAVF7/HSC7 (SEQ ID NO: 8 and 27 of WO2016049230). In some embodiments, the AAV capsid polypeptide, e.g., AAV capsid variant, or the parent AAV capsid comprises AAVF15/HSC15 (SEQ ID NO: 16 and 33 of WO2016049230). In some embodiments, the AAV capsid polypeptide, e.g., AAV capsid variant, or the parent AAV capsid comprises AAVF17/HSC17 (SEQ ID NO: 13 and 35 of WO2016049230). In some embodiments, the AAV capsid polypeptide, e.g., AAV capsid variant, or the parent AAV capsid comprises an AAV5 sequence. As a non-limiting example, the AAV5 sequence is SEQ ID NO: 4 of U.S. Pat. No. 6,984,517, the contents of which are herein incorporated by reference in their entirety.

In some embodiments, the AAV capsid polypeptide, e.g., AAV capsid variant, allows for blood brain barrier penetration following intravenous administration. In some embodiments, the AAV capsid, e.g., AAV capsid variant, allows for blood brain barrier penetration following focused ultrasound (FUS), e.g., coupled with the intravenous administration of microbubbles (FUS-MB), or MRI-guided FUS coupled with intravenous administration. In some embodiments the AAV capsid, e.g., AAV capsid variant allows for increased distribution to a brain region. In some embodiments, the brain region comprises a frontal cortex, sensory cortex, motor cortex, caudate, dentate nucleus, cerebellar cortex, cerebral cortex, brain stem, hippocampus, thalamus, putamen, or a combination thereof. In some embodiments, the AAV capsid, e.g., AAV capsid variant allows for preferential transduction in a brain region relative to the transduction in the dorsal root ganglia (DRG).

In some embodiments the AAV capsid polypeptide, e.g., AAV capsid variant allows for increased distribution to a spinal cord region. In some embodiments, the spinal region comprises a cervical spinal cord region, thoracic spinal cord region, and/or lumbar spinal cord region.

In some embodiments, the AAV capsid polypeptide, e.g., AAV capsid variant, is suitable for intramuscular administration and/or transduction of muscle fibers. In some embodiments the AAV capsid polypeptide, e.g., AAV capsid variant, allows for increased distribution to a muscle region. In some embodiments, the muscle region comprises a heart muscle, quadriceps muscle, a diaphragm muscle region, or a combination thereof. In some embodiments, the muscle region comprises a heart muscle region, e.g., a heart atrium muscle region or a heart ventricle muscle region.

In some embodiments, one or more targeting sequence is inserted into a parent AAV capsid sequence or an AAV capsid polypeptide, e.g., AAV capsid variant, sequence. As a non-limiting example, one targeting sequence may be inserted into a parent AAV capsid sequence or an AAV capsid variant sequence. As a non-limiting example, two targeting sequences may be inserted into a parent AAV capsid sequence or an AAV capsid variant sequence. As a non-limiting example, three targeting sequences may be inserted into a parent AAV capsid sequence or an AAV capsid variant sequence. As a non-limiting example, more than three targeting sequences may be inserted into a parent AAV capsid sequence or an AAV capsid variant sequence.

In some embodiments, an AAV capsid polypeptide, e.g., an AAV capsid variant, described herein comprises a parental AAV capsid sequence having an insert, e.g., an amino acid sequence as described in Table 1 or 2. In some embodiments, the parental sequence may comprise at least 1, 2, 3 or more insert sequences.

While not wishing to be bound by theory, it is understood that a parent AAV capsid sequence or an AAV capsid polypeptide, e.g., an AAV capsid variant, comprises a VP1 region. In some embodiments, a parent AAV capsid sequence or an AAV capsid variant comprises a VP1, VP2 and/or VP3 region, or any combination thereof.

In some embodiments, the initiation codon for translation of the AAV VP1 capsid protein, e.g., a capsid variant, may be CTG, TTG, or GTG as described in U.S. Pat. No. 8,163,543, the contents of which are herein incorporated by reference in its entirety.

The present disclosure refers to structural capsid proteins (including VP1, VP2 and VP3) which are encoded by capsid (Cap) genes. These capsid proteins form an outer protein structural shell (e.g. capsid) of a viral vector such as AAV. VP capsid proteins synthesized from Cap polynucleotides generally include a methionine as the first amino acid in the peptide sequence (Met1), which is associated with the start codon (AUG or ATG) in the corresponding Cap nucleotide sequence. However, it is common for a first-methionine (Met1) residue or generally any first amino acid (AA1) to be cleaved off after or during polypeptide synthesis by protein processing enzymes such as Met-aminopeptidases. This "Met/AA-clipping" process often correlates with a corresponding acetylation of the second amino acid in the polypeptide sequence (e.g., alanine, valine, serine, threonine, etc.). Met-clipping commonly occurs with VP1 and VP3 capsid proteins but can also occur with VP2 capsid proteins.

Where the Met/AA-clipping is incomplete, a mixture of one or more (one, two or three) VP capsid proteins comprising the viral capsid may be produced, some of which may include a Met1/AA1 amino acid (Met+/AA+) and some of which may lack a Met1/AA1 amino acid as a result of Met/AA-clipping (Met−/AA−). For further discussion regarding Met/AA-clipping in capsid proteins, see Jin, et al. Direct Liquid Chromatography/Mass Spectrometry Analysis for Complete Characterization of Recombinant Adeno-Associated Virus Capsid Proteins. Hum Gene Ther Methods. 2017 Oct. 28 (5): 255-267; Hwang, et al. N-Terminal Acetylation of Cellular Proteins Creates Specific Degradation Signals. Science. 2010 Feb. 19. 327 (5968): 973-977; the contents of which are each incorporated herein by reference in its entirety.

According to the present disclosure, references to capsid proteins, e.g., AAV capsid variants, is not limited to either clipped (Met−/AA−) or unclipped (Met+/AA+) and may, in context, refer to independent capsid proteins, viral capsids comprised of a mixture of capsid proteins, and/or polynucleotide sequences (or fragments thereof) which encode, describe, produce or result in capsid proteins of the present disclosure. A direct reference to a capsid protein or capsid polypeptide (such as VP1, VP2 or VP2) may also comprise VP capsid proteins which include a Met1/AA1 amino acid (Met+/AA+) as well as corresponding VP capsid proteins which lack the Met1/AA1 amino acid as a result of Met/AA-clipping (Met−/AA−).

Further according to the present disclosure, a reference to a specific SEQ ID NO: (whether a protein or nucleic acid) which comprises or encodes, respectively, one or more capsid proteins which include a Met1/AA1 amino acid (Met+/AA+) should be understood to teach the VP capsid proteins which lack the Met1/AA1 amino acid as upon review of the sequence, it is readily apparent any sequence which merely lacks the first listed amino acid (whether or not Met1/AA1).

As a non-limiting example, reference to a VP1 polypeptide sequence which is 736 amino acids in length and which includes a "Met1" amino acid (Met+) encoded by the AUG/ATG start codon may also be understood to teach a VP1 polypeptide sequence which is 735 amino acids in length and which does not include the "Met1" amino acid (Met−) of the 736 amino acid Met+ sequence. As a second non-limiting example, reference to a VP1 polypeptide sequence which is 736 amino acids in length and which includes an "AA1" amino acid (AA1+) encoded by any NNN initiator codon may also be understood to teach a VP1 polypeptide sequence which is 735 amino acids in length and which does not include the "AA1" amino acid (AA1−) of the 736 amino acid AA1+ sequence.

References to viral capsids formed from VP capsid proteins (such as reference to specific AAV capsid serotypes), can incorporate VP capsid proteins which include a Met1/AA1 amino acid (Met+/AA1+), corresponding VP capsid proteins which lack the Met1/AA1 amino acid as a result of Met/AA1-clipping (Met−/AA1−), and combinations thereof (Met+/AA1+ and Met−/AA1−).

As a non-limiting example, an AAV capsid serotype can include VP1 (Met+/AA1+), VP1 (Met−/AA1−), or a combination of VP1 (Met+/AA1+) and VP1 (Met−/AA1−). An AAV capsid serotype can also include VP3 (Met+/AA1+), VP3 (Met−/AA1−), or a combination of VP3 (Met+/AA1+) and VP3 (Met−/AA1−); and can also include similar optional combinations of VP2 (Met+/AA1) and VP2 (Met−/AA1−).

Additional AAV Sequences

In some embodiments, the AAV capsid polypeptide, e.g., AAV capsid variant, comprises, or the parent AAV capsid is modified such that, immediately subsequent to position 586, 588, or 589 numbered relative to SEQ ID NO: 138, the AAV capsid variant or the parent AAV capsid polypeptide comprises at least 3, 4, 5, 6, 7, 8, or 9 consecutive amino acids of any of SEQ ID NOs: 1725-3622 or 3648-3659.

In some embodiments, the AAV capsid polypeptide, e.g., AAV capsid variant, or the parent AAV capsid described herein does not comprise an insert sequence present immediately subsequent to position 586, 588, or 589 numbered relative to SEQ ID NO: 138, having at least 5 consecutive amino acids corresponding to positions 586 to 594 numbered relative to SEQ ID NO: 138, of any of SEQ ID NOs: 1-1724, e.g., as described in Table 6.

In some embodiments, the AAV capsid polypeptide, e.g., AAV capsid variant, or the parent AAV capsid may comprise at a position other than 5 consecutive amino acids corresponding to positions 586 to 594 numbered relative to SEQ ID NO: 138, an amino acid sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of those described herein.

In any of the embodiments described herein, a position other than 5 consecutive amino acids corresponding to positions 586 to 594 numbered relative to SEQ ID NO: 138 can be identified by providing an alignment of a reference sequence and a query sequence, wherein the reference sequence is SEQ ID NO: 138, and identifying the residues corresponding to the positions in the query sequence that correspond to positions 586 to 594 in the reference sequence.

In some embodiments, the AAV capsid polypeptide, e.g., AAV capsid variant, or the parent AAV capsid may be encoded by a nucleic acid sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of those described herein, at a position other than 5 consecutive amino acids corresponding to positions 586 to 594 numbered relative to SEQ ID NO: 138.

In some embodiments, the AAV capsid polypeptide, e.g., AAV capsid variant, or the parent AAV capsid may be an AAV9, at a position other than 5 consecutive amino acids corresponding to positions 586 to 594 numbered relative to SEQ ID NO: 138. In some embodiments, In some embodiments, the AAV capsid polypeptide, e.g., AAV capsid variant, or the parent AAV capsid may be, at a position other than 5 consecutive amino acids corresponding to positions 586 to 594 numbered relative to SEQ ID NO: 138, an AAV9hu. 14 (SEQ ID NO: 137 or 138). In some embodiments, In some embodiments, the AAV capsid polypeptide, e.g., AAV capsid variant, or the parent AAV capsid may be, at a position other than 5 consecutive amino acids corresponding to positions 586 to 594 numbered relative to SEQ ID NO: 138, an AAV9 K449R (SEQ ID NO: 11). In some embodiments, the AAV capsid polypeptide, e.g., AAV capsid variant, or the parent AAV capsid may be, at a position other than 5 consecutive amino acids corresponding to positions 586 to 594 numbered relative to SEQ ID NO: 138, a PHP.B (SEQ ID NO: 5 or 6). In some embodiments, the AAV capsid polypeptide, e.g., AAV capsid variant, or the parent AAV capsid may be, at a position other than 5 consecutive amino acids corresponding to positions 586 to 594 numbered relative to SEQ ID NO: 138, a PHP.N (SEQ ID NO: 4). In some embodiments, the AAV capsid polypeptide, e.g., AAV capsid variant, or the parent AAV capsid may be, at a position other than 5 consecutive amino acids corresponding to positions 586 to 594 numbered relative to SEQ ID NO: 138, a VOY101 (SEQ ID NO: 1 or 2). In some embodiments, the AAV capsid polypeptide, e.g., AAV capsid variant, or the parent AAV capsid may be, at a position other than 5 consecutive amino acids corresponding to positions 586 to 594 numbered relative to SEQ ID NO: 138, a VOY201 (SEQ ID NO: 3 or 1724).

In some embodiments, the AAV capsid polypeptide, e.g., AAV capsid variant, or the parent AAV capsid may be, at a position other than 5 consecutive amino acids corresponding to positions 586 to 594 numbered relative to SEQ ID NO: 138, an AAV5.

In some embodiments, the AAV capsid polypeptide, e.g., AAV capsid variant, or the parent AAV capsid may be, at a position other than 5 consecutive amino acids corresponding to positions 586 to 594 numbered relative to SEQ ID NO: 138, selected from any of the following VOY101, VOY201, AAVPHP.B (PHP.B), AAVPHP.A (PHP.A), AAVG2B-26, AAVG2B-13, AAVTH1.1-32, AAVTH1.1-35, AAVPHP.B2 (PHP.B2), AAVPHP.B3 (PHP.B3), AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP. AAVPHP.B-SNP (3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3 (G2A3), AAVG2B4 (G2B4), AAVG2B5 (G2B5), PHP.S, AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9 K449R, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52.1/hu. 19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu. 12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu. 10, AAVhu. 11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AA Vhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AA Vhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu. 14/9, AAVhu.t 19, AAVrh.2, AAVrh.2R, AAVrh.8, AAVrh.8R, AAVrh.10, AAVrh.12, AAVrh.13, AAVrh. 13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AA VhEr2.4, AA VhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61

AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv1-1, AAV Clv1-10, AAV CLv1-2, AAV CLv-12, AAV CLv1-3, AAV CLv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, and/or AAVF9/HSC9 and variants thereof.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in United States Publication No. US20030138772, the contents of which are herein incorporated by reference in their entirety, such as, but not limited to, AAV1 (SEQ ID NO: 6 and 64 of US20030138772), AAV2 (SEQ ID NO: 7 and 70 of US20030138772), AAV3 (SEQ ID NO: 8 and 71 of US20030138772), AAV4 (SEQ ID NO: 63 of US20030138772), AAV5 (SEQ ID NO: 114 of US20030138772), AAV6 (SEQ ID NO: 65 of US20030138772), AAV7 (SEQ ID NO: 1-3 of US20030138772), AAV8 (SEQ ID NO: 4 and 95 of US20030138772), AAV9 (SEQ ID NO: 5 and 100 of US20030138772), AAV10 (SEQ ID NO: 117 of US20030138772), AAV11 (SEQ ID NO: 118 of US20030138772), AAV12 (SEQ ID NO: 119 of US20030138772), AAVrh10 (amino acids 1 to 738 of SEQ ID NO: 81 of US20030138772), AAV16.3 (US20030138772 SEQ ID NO: 10), AAV29.3/bb.1 (US20030138772 SEQ ID NO: 11), AAV29.4 (US20030138772 SEQ ID NO: 12), AAV29.5/bb.2 (US20030138772 SEQ ID NO: 13), AAV1.3 (US20030138772 SEQ ID NO: 14), AAV13.3 (US20030138772 SEQ ID NO: 15), AAV24.1 (US20030138772 SEQ ID NO: 16), AAV27.3 (US20030138772 SEQ ID NO: 17), AAV7.2 (US20030138772 SEQ ID NO: 18), AAVC1 (US20030138772 SEQ ID NO: 19), AAVC3 (US20030138772 SEQ ID NO: 20), AAVC5 (US20030138772 SEQ ID NO: 21), AAVF1 (US20030138772 SEQ ID NO: 22), AAVF3 (US20030138772 SEQ ID NO: 23), AAVF5 (US20030138772 SEQ ID NO: 24), AAVH6 (US20030138772 SEQ ID NO: 25), AAVH2 (US20030138772 SEQ ID NO: 26), AAV42-8 (US20030138772 SEQ ID NO: 27), AAV42-15 (US20030138772 SEQ ID NO: 28), AAV42-5b (US20030138772 SEQ ID NO: 29), AAV42-1b (US20030138772 SEQ ID NO: 30), AAV42-13 (US20030138772 SEQ ID NO: 31), AAV42-3a (US20030138772 SEQ ID NO: 32), AAV42-4 (US20030138772 SEQ ID NO: 33), AAV42-5a (US20030138772 SEQ ID NO: 34), AAV42-10 (US20030138772 SEQ ID NO: 35), AAV42-3b (US20030138772 SEQ ID NO: 36), AAV42-11 (US20030138772 SEQ ID NO: 37), AAV42-6b (US20030138772 SEQ ID NO: 38), AAV43-1 (US20030138772 SEQ ID NO: 39), AAV43-5 (US20030138772 SEQ ID NO: 40), AAV43-12 (US20030138772 SEQ ID NO: 41), AAV43-20 (US20030138772 SEQ ID NO: 42), AAV43-21 (US20030138772 SEQ ID NO: 43), AAV43-23 (US20030138772 SEQ ID NO: 44), AAV43-25 (US20030138772 SEQ ID NO: 45), AAV44.1 (US20030138772 SEQ ID NO: 46), AAV44.5 (US20030138772 SEQ ID NO: 47), AAV223.1 (US20030138772 SEQ ID NO: 48), AAV223.2 (US20030138772 SEQ ID NO: 49), AAV223.4 (US20030138772 SEQ ID NO: 50), AAV223.5 (US20030138772 SEQ ID NO: 51), AAV223.6 (US20030138772 SEQ ID NO: 52), AAV223.7 (US20030138772 SEQ ID NO: 53), AAVA3.4 (US20030138772 SEQ ID NO: 54), AAVA3.5 (US20030138772 SEQ ID NO: 55), AAVA3.7 (US20030138772 SEQ ID NO: 56), AAVA3.3 (US20030138772 SEQ ID NO: 57), AAV42.12 (US20030138772 SEQ ID NO: 58), AAV44.2 (US20030138772 SEQ ID NO: 59), AAV42-2 (US20030138772 SEQ ID NO: 9), or variants thereof.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in United States Publication No. US20150159173, the contents of which are herein incorporated by reference in their entirety, such as, but not limited to, AAV2 (SEQ ID NO: 7 and 23 of US20150159173), rh20 (SEQ ID NO: 1 of US20150159173), rh32/33 (SEQ ID NO: 2 of US20150159173), rh39 (SEQ ID NO: 3, 20 and 36 of US20150159173), rh46 (SEQ ID NO: 4 and 22 of US20150159173), rh73 (SEQ ID NO: 5 of US20150159173), rh74 (SEQ ID NO: 6 of US20150159173), AAV6.1 (SEQ ID NO: 29 of US20150159173), rh.8 (SEQ ID NO: 41 of US20150159173), rh.48.1 (SEQ ID NO: 44 of US20150159173), hu.44 (SEQ ID NO: 45 of US20150159173), hu.29 (SEQ ID NO: 42 of US20150159173), hu.48 (SEQ ID NO: 38 of US20150159173), rh54 (SEQ ID NO: 49 of US20150159173), AAV2 (SEQ ID NO: 7 of US20150159173), cy.5 (SEQ ID NO: 8 and 24 of US20150159173), rh. 10 (SEQ ID NO: 9 and 25 of US20150159173), rh. 13 (SEQ ID NO: 10 and 26 of US20150159173), AAV1 (SEQ ID NO: 11 and 27 of US20150159173), AAV3 (SEQ ID NO: 12 and 28 of US20150159173), AAV6 (SEQ ID NO: 13 and 29 of US20150159173), AAV7 (SEQ ID NO: 14 and 30 of US20150159173), AAV8 (SEQ ID NO: 15 and 31 of US20150159173), hu. 13 (SEQ ID NO: 16 and 32 of US20150159173), hu.26 (SEQ ID NO: 17 and 33 of US20150159173), hu.37 (SEQ ID NO: 18 and 34 of US20150159173), hu.53 (SEQ ID NO: 19 and 35 of US20150159173), rh.43 (SEQ ID NO: 21 and 37 of US20150159173), rh2 (SEQ ID NO: 39 of US20150159173), rh.37 (SEQ ID NO: 40 of US20150159173), rh.64 (SEQ ID NO: 43 of US20150159173), rh.48 (SEQ ID NO: 44 of US20150159173), ch.5 (SEQ ID NO 46 of US20150159173), rh.67 (SEQ ID NO: 47 of US20150159173), rh.58 (SEQ ID NO: 48 of US20150159173), or variants thereof including, but not limited to Cy5R1, Cy5R2, Cy5R3, Cy5R4, rh. 13R, rh.37R2, rh.2R, rh.8R, rh.48.1, rh.48.2, rh.48.1.2, hu.44R1, hu.44R2, hu.44R3, hu.29R, ch.5R1, rh64R1, rh64R2, AAV6.2, AAV6.1, AAV6.12, hu.48R1, hu.48R2, and hu.48R3.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in U.S. Pat. No. 7,198,951, the contents of which are herein incorporated by reference in their entirety, such as, but not limited to, AAV9 (SEQ ID NO: 1-3 of U.S. Pat. No. 7,198,951), AAV2 (SEQ ID NO: 4 of U.S. Pat. No. 7,198,951), AAV1 (SEQ ID NO: 5 of U.S. Pat. No. 7,198,951), AAV3 (SEQ ID NO: 6 of U.S. Pat. No. 7,198,951), and AAV8 (SEQ ID NO: 7 of U.S. Pat. No. 7,198,951).

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a mutation in the AAV9 sequence as described by N Pulicherla et al. (Molecular Therapy 19 (6): 1070-1078 (2011), herein incorporated by reference in its entirety), such as but not limited to, AAV9.9, AAV9.11, AAV9.13, AAV9.16, AAV9.24, AAV9.45, AAV9.47, AAV9.61, AAV9.68, AAV9.84.

In some embodiments, the AAV serotype, the parent AAV capsid polypeptide, or the AAV capsid variant may be or have, at a position other than 5 consecutive amino acids corresponding to positions 586 to 594 numbered relative to SEQ ID NO: 138, a sequence as described in U.S. Pat. No. 6,156,303, the contents of which are herein incorporated by reference in their entirety, such as, but not limited to, AAV3B (SEQ ID NO: 1 and 10 of U.S. Pat. No. 6,156,303), AAV6 (SEQ ID NO: 2, 7 and 11 of U.S. Pat. No. 6,156,303), AAV2 (SEQ ID NO: 3 and 8 of U.S. Pat. No. 6,156,303), AAV3A (SEQ ID NO: 4 and 9, of U.S. Pat. No. 6,156,303), or derivatives thereof.

In some embodiments, the AAV serotype, the parent AAV capsid polypeptide, or the AAV capsid variant may be or have, at a position other than 5 consecutive amino acids corresponding to positions 586 to 594 numbered relative to SEQ ID NO: 138, a sequence as described in United States Publication No. US20140359799, the contents of which are herein incorporated by reference in their entirety, such as, but not limited to, AAV8 (SEQ ID NO: 1 of US20140359799), AAVDJ (SEQ ID NO: 2 and 3 of US20140359799), or variants thereof.

In some embodiments, the AAV capsid polypeptide, e.g., AAV capsid variant, or the parent AAV capsid may be, at a position other than 5 consecutive amino acids corresponding to positions 586 to 594 numbered relative to SEQ ID NO: 138, a AAVDJ or a variant thereof, such as AAVDJ8 (or AAV-DJ8), as described by Grimm et al. (Journal of Virology 82 (12): 5887-5911 (2008), herein incorporated by reference in its entirety). In some embodiments, the amino acid sequence of AAVDJ8 may comprise two or more mutations in order to remove the heparin binding domain (HBD). In some embodiments, the AAV capsid polypeptide, e.g., AAV capsid variant, or the parent AAV capsid may comprise, at a position other than 5 consecutive amino acids corresponding to positions 586 to 594 numbered relative to SEQ ID NO: 138, the AAV-DJ sequence described as SEQ ID NO: 1 in U.S. Pat. No. 7,588,772, the contents of which are herein incorporated by reference in their entirety.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence of AAV4 as described in International Publication No. WO1998011244, the contents of which are herein incorporated by reference in their entirety, such as, but not limited to AAV4 (SEQ ID NO: 1-20 of WO1998011244).

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a mutation in the AAV2 sequence to generate AAV2G9 as described in International Publication No. WO2014144229 and herein incorporated by reference in its entirety.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in International Publication No. WO2005033321, the contents of which are herein incorporated by reference in their entirety, such as, but not limited to AAV3-3 (SEQ ID NO: 217 of WO2005033321), AAV1 (SEQ ID NO: 219 and 202 of WO2005033321), AAV106.1/hu.37 (SEQ ID No: 10 of WO2005033321), AAV114.3/hu.40 (SEQ ID No: 11 of WO2005033321), AAV127.2/hu.41 (SEQ ID NO: 6 and 8 of WO2005033321), AAV128.3/hu.44 (SEQ ID No: 81 of WO2005033321), AAV130.4/hu.48 (SEQ ID NO: 78 of WO2005033321), AAV145.1/hu.53 (SEQ ID No: 176 and 177 of WO2005033321), AAV145.6/hu.56 (SEQ ID NO: 168 and 192 of WO2005033321), AAV16.12/hu.11 (SEQ ID NO: 153 and 57 of WO2005033321), AAV16.8/hu. 10 (SEQ ID NO: 156 and 56 of WO2005033321), AAV161.10/hu.60 (SEQ ID No: 170 of WO2005033321), AAV161.6/hu.61 (SEQ ID No: 174 of WO2005033321), AAV1-7/rh.48 (SEQ ID NO: 32 of WO2005033321), AAV1-8/rh.49 (SEQ ID NOs: 103 and 25 of WO2005033321), AAV2 (SEQ ID NO:

211 and 221 of WO2005033321), AAV2-15/rh.62 (SEQ ID No: 33 and 114 of WO2005033321), AAV2-3/rh.61 (SEQ ID NO: 21 of WO2005033321), AAV2-4/rh.50 (SEQ ID No: 23 and 108 of WO2005033321), AAV2-5/rh.51 (SEQ ID NO: 104 and 22 of WO2005033321), AAV3.1/hu.6 (SEQ ID NO: 5 and 84 of WO2005033321), AAV3.1/hu.9 (SEQ ID NO: 155 and 58 of WO2005033321), AAV3-11/rh.53 (SEQ ID NO: 186 and 176 of WO2005033321), AAV3-3 (SEQ ID NO: 200 of WO2005033321), AAV33.12/hu. 17 (SEQ ID NO:4 of WO2005033321), AAV33.4/hu. 15 (SEQ ID No: 50 of WO2005033321), AAV33.8/hu.16 (SEQ ID No: 51 of WO2005033321), AAV3-9/rh.52 (SEQ ID NO: 96 and 18 of WO2005033321), AAV4-19/rh.55 (SEQ ID NO: 117 of WO2005033321), AAV4-4 (SEQ ID NO: 201 and 218 of WO2005033321), AAV4-9/rh.54 (SEQ ID NO: 116 of WO2005033321), AAV5 (SEQ ID NO: 199 and 216 of WO2005033321), AAV52.1/hu.20 (SEQ ID NO: 63 of WO2005033321), AAV52/hu. 19 (SEQ ID NO: 133 of WO2005033321), AAV5-22/rh.58 (SEQ ID No: 27 of WO2005033321), AAV5-3/rh.57 (SEQ ID NO: 105 of WO2005033321), AAV5-3/rh.57 (SEQ ID No: 26 of WO2005033321), AAV58.2/hu.25 (SEQ ID No: 49 of WO2005033321), AAV6 (SEQ ID NO: 203 and 220 of WO2005033321), AAV7 (SEQ ID NO: 222 and 213 of WO2005033321), AAV7.3/hu.7 (SEQ ID No: 55 of WO2005033321), AAV8 (SEQ ID NO: 223 and 214 of WO2005033321), AAVH-1/hu.1 (SEQ ID No: 46 of WO2005033321), AAVH-5/hu.3 (SEQ ID No: 44 of WO2005033321), AAVhu.1 (SEQ ID NO: 144 of WO2005033321), AAVhu. 10 (SEQ ID NO: 156 of WO2005033321), AAVhu.11 (SEQ ID NO: 153 of WO2005033321), AAVhu.12 (WO2005033321 SEQ ID NO: 59), AAVhu.13 (SEQ ID NO: 129 of WO2005033321), AAVhu.14/AAV9 (SEQ ID NO: 123 and 3 of WO2005033321), AAVhu. 15 (SEQ ID NO: 147 of WO2005033321), AAVhu.16 (SEQ ID NO: 148 of WO2005033321), AAVhu. 17 (SEQ ID NO: 83 of WO2005033321), AAVhu.18 (SEQ ID NO: 149 of WO2005033321), AAVhu. 19 (SEQ ID NO: 133 of WO2005033321), AAVhu.2 (SEQ ID NO: 143 of WO2005033321), AAVhu.20 (SEQ ID NO: 134 of WO2005033321), AAVhu.21 (SEQ ID NO: 135 of WO2005033321), AAVhu.22 (SEQ ID NO: 138 of WO2005033321), AAVhu.23.2 (SEQ ID NO: 137 of WO2005033321), AAVhu.24 (SEQ ID NO: 136 of WO2005033321), AAVhu.25 (SEQ ID NO: 146 of WO2005033321), AAVhu.27 (SEQ ID NO: 140 of WO2005033321), AAVhu.29 (SEQ ID NO: 132 of WO2005033321), AAVhu.3 (SEQ ID NO: 145 of WO2005033321), AAVhu.31 (SEQ ID NO: 121 of WO2005033321), AAVhu.32 (SEQ ID NO: 122 of WO2005033321), AAVhu.34 (SEQ ID NO: 125 of WO2005033321), AAVhu.35 (SEQ ID NO: 164 of WO2005033321), AAVhu.37 (SEQ ID NO: 88 of WO2005033321), AAVhu.39 (SEQ ID NO: 102 of WO2005033321), AAVhu.4 (SEQ ID NO: 141 of WO2005033321), AAVhu.40 (SEQ ID NO: 87 of WO2005033321), AAVhu.41 (SEQ ID NO: 91 of WO2005033321), AAVhu.42 (SEQ ID NO: 85 of WO2005033321), AAVhu.43 (SEQ ID NO: 160 of WO2005033321), AAVhu.44 (SEQ ID NO: 144 of WO2005033321), AAVhu.45 (SEQ ID NO: 127 of WO2005033321), AAVhu.46 (SEQ ID NO: 159 of WO2005033321), AAVhu.47 (SEQ ID NO: 128 of WO2005033321), AAVhu.48 (SEQ ID NO: 157 of WO2005033321), AAVhu.49 (SEQ ID NO: 189 of WO2005033321), AAVhu.51 (SEQ ID NO: 190 of WO2005033321), AAVhu.52 (SEQ ID NO: 191 of WO2005033321), AAVhu.53 (SEQ ID NO: 186 of WO2005033321), AAVhu.54 (SEQ ID NO: 188 of WO2005033321), AAVhu.55 (SEQ ID NO: 187 of WO2005033321), AAVhu.56 (SEQ ID NO: 192 of WO2005033321), AAVhu.57 (SEQ ID NO: 193 of WO2005033321), AAVhu.58 (SEQ ID NO: 194 of WO2005033321), AAVhu.6 (SEQ ID NO: 84 of WO2005033321), AAVhu.60 (SEQ ID NO: 184 of WO2005033321), AAVhu.61 (SEQ ID NO: 185 of WO2005033321), AAVhu.63 (SEQ ID NO: 195 of WO2005033321), AAVhu.64 (SEQ ID NO: 196 of WO2005033321), AAVhu.66 (SEQ ID NO: 197 of WO2005033321), AAVhu.67 (SEQ ID NO: 198 of WO2005033321), AAVhu.7 (SEQ ID NO: 150 of WO2005033321), AAVhu.8 (WO2005033321 SEQ ID NO: 12), AAVhu.9 (SEQ ID NO: 155 of WO2005033321), AAVLG-10/rh.40 (SEQ ID No: 14 of WO2005033321), AAVLG-4/rh.38 (SEQ ID NO: 86 of WO2005033321), AAVLG-4/rh.38 (SEQ ID No: 7 of WO2005033321), AAVN721-8/rh.43 (SEQ ID NO: 163 of WO2005033321), AAVN721-8/rh.43 (SEQ ID No: 43 of WO2005033321), AAVpi.1 (WO2005033321 SEQ ID NO: 28), AAVpi.2 (WO2005033321 SEQ ID NO: 30), AAVpi.3 (WO2005033321 SEQ ID NO: 29), AAVrh.38 (SEQ ID NO: 86 of WO2005033321), AAVrh.40 (SEQ ID NO: 92 of WO2005033321), AAVrh.43 (SEQ ID NO: 163 of WO2005033321), AAVrh.44 (WO2005033321 SEQ ID NO: 34), AAVrh.45 (WO2005033321 SEQ ID NO: 41), AAVrh.47 (WO2005033321 SEQ ID NO: 38), AAVrh.48 (SEQ ID NO: 115 of WO2005033321), AAVrh.49 (SEQ ID NO: 103 of WO2005033321), AAVrh.50 (SEQ ID NO: 108 of WO2005033321), AAVrh.51 (SEQ ID NO: 104 of WO2005033321), AAVrh.52 (SEQ ID NO: 96 of WO2005033321), AAVrh.53 (SEQ ID NO: 97 of WO2005033321), AAVrh.55 (WO2005033321 SEQ ID NO: 37), AAVrh.56 (SEQ ID NO: 152 of WO2005033321), AAVrh.57 (SEQ ID NO: 105 of WO2005033321), AAVrh.58 (SEQ ID NO: 106 of WO2005033321), AAVrh.59 (WO2005033321 SEQ ID NO: 42), AAVrh.60 (WO2005033321 SEQ ID NO: 31), AAVrh.61 (SEQ ID NO: 107 of WO2005033321), AAVrh.62 (SEQ ID NO: 114 of WO2005033321), AAVrh.64 (SEQ ID NO: 99 of WO2005033321), AAVrh.65 (WO2005033321 SEQ ID NO: 35), AAVrh.68 (WO2005033321 SEQ ID NO: 16), AAVrh.69 (WO2005033321 SEQ ID NO: 39), AAVrh.70 (WO2005033321 SEQ ID NO: 20), AAVrh.72 (WO2005033321 SEQ ID NO: 9), or variants thereof including, but not limited to, AAVcy.2, AAVcy.3, AAVcy.4, AAVcy.5, AAVcy.6, AAVrh. 12, AAVrh.17, AAVrh. 18, AAVrh. 19, AAVrh.21, AAVrh.22, AAVrh.23, AAVrh.24, AAVrh.25, AAVrh.25/42 15, AAVrh.31, AAVrh.32, AAVrh.33, AAVrh.34, AAVrh.35, AAVrh.36, AAVrh.37, AAVrh14. Non limiting examples of variants include SEQ ID NO: 13, 15, 17, 19, 24, 36, 40, 45, 47, 48, 51-54, 60-62, 64-77, 79, 80, 82, 89, 90, 93-95, 98, 100, 101, 109-113, 118-120, 124, 126, 131, 139, 142, 151,154, 158, 161, 162, 165-183, 202, 204-212, 215, 219, 224-236, of WO2005033321, the contents of which are herein incorporated by reference in their entirety.

In some embodiments, the AAV serotype, the parent AAV capsid polypeptide, or the AAV capsid variant may be or have, at a position other than 5 consecutive amino acids corresponding to positions 586 to 594 numbered relative to SEQ ID NO: 138, a sequence as described in International Publication No. WO2015168666, the contents of which are herein incorporated by reference in their entirety, such as, but not limited to, AAVrh8R (SEQ ID NO: 9 of WO2015168666), AAVrh8R A586R mutant (SEQ ID NO: 10 of WO2015168666), AAVrh8R R533A mutant (SEQ ID NO: 11 of WO2015168666), or variants thereof.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in U.S. Pat. No. 9,233,131, the contents of which are herein incorporated by reference in their entirety, such as, but not limited to, AAVhE1.1 (SEQ ID NO:44 of U.S. Pat. No. 9,233,131), AAVhEr1.5 (SEQ ID NO: 45 of U.S. Pat. No. 9,233,131), AAVhER1.14 (SEQ ID NO:46 of U.S. Pat. No. 9,233,131), AAVhEr1.8 (SEQ ID NO: 47 of U.S. Pat. No. 9,233,131), AAVhEr1.16 (SEQ ID NO:48 of U.S. Pat. No. 9,233,131), AAVhEr1.18 (SEQ ID NO:49 of U.S. Pat. No. 9,233,131), AAVhEr1.35 (SEQ ID NO:50 of U.S. Pat. No. 9,233,131), AAVhEr1.7 (SEQ ID NO:51 of U.S. Pat. No. 9,233,131), AAVhEr1.36 (SEQ ID NO:52 of U.S. Pat. No. 9,233,131), AAVhEr2.29 (SEQ ID NO:53 of U.S. Pat. No. 9,233,131), AAVhEr2.4 (SEQ ID NO:54 of U.S. Pat. No. 9,233,131), AAVhEr2.16 (SEQ ID NO:55 of U.S. Pat. No. 9,233,131), AAVhEr2.30 (SEQ ID NO:56 of U.S. Pat. No. 9,233,131), AAVhEr2.31 (SEQ ID NO:58 of U.S. Pat. No. 9,233,131), AAVhEr2.36 (SEQ ID NO:57 of U.S. Pat. No. 9,233,131), AAVhER1.23 (SEQ ID NO:53 of U.S. Pat. No. 9,233,131), AAVhEr3.1 (SEQ ID NO:59 of U.S. Pat. No. 9,233,131), AAV2.5T (SEQ ID NO:42 of U.S. Pat. No. 9,233,131), or variants thereof.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in United States Patent Publication No. US20150376607, the contents of which are herein incorporated by reference in their entirety, such as, but not limited to, AAV-PAEC (SEQ ID NO: 1 of US20150376607), AAV-LK01 (SEQ ID NO:2 of US20150376607), AAV-LK02 (SEQ ID NO:3 of US20150376607), AAV-LK03 (SEQ ID NO:4 of US20150376607), AAV-LK04 (SEQ ID NO:5 of US20150376607), AAV-LK05 (SEQ ID NO:6 of US20150376607), AAV-LK06 (SEQ ID NO:7 of US20150376607), AAV-LK07 (SEQ ID NO:8 of US20150376607), AAV-LK08 (SEQ ID NO:9 of US20150376607), AAV-LK09 (SEQ ID NO:10 of US20150376607), AAV-LK10 (SEQ ID NO:11 of US20150376607), AAV-LK11 (SEQ ID NO: 12 of US20150376607), AAV-LK12 (SEQ ID NO:13 of US20150376607), AAV-LK13 (SEQ ID NO:14 of US20150376607), AAV-LK14 (SEQ ID NO:15 of US20150376607), AAV-LK15 (SEQ ID NO:16 of US20150376607), AAV-LK16 (SEQ ID NO:17 of US20150376607), AAV-LK17 (SEQ ID NO:18 of US20150376607), AAV-LK18 (SEQ ID NO:19 of US20150376607), AAV-LK19 (SEQ ID NO:20 of US20150376607), AAV-PAEC2 (SEQ ID NO:21 of US20150376607), AAV-PAEC4 (SEQ ID NO:22 of US20150376607), AAV-PAEC6 (SEQ ID NO: 23 of US20150376607), AAV-PAEC7 (SEQ ID NO:24 of US20150376607), AAV-PAEC8 (SEQ ID NO: 25 of US20150376607), AAV-PAEC11 (SEQ ID NO:26 of US20150376607), AAV-PAEC12 (SEQ ID NO:27, of US20150376607), or variants thereof.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in U.S. Pat. No. 9,163,261, the contents of which are herein incorporated by reference in their entirety, such as, but not limited to, AAV-2-pre-miRNA-101 (SEQ ID NO: 1 U.S. Pat. No. 9,163,261), or variants thereof.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in United States Patent Publication No. US20150376240, the contents of which are herein incorporated by reference in their entirety, such as, but not limited to, AAV-8h (SEQ ID NO: 6 of US20150376240), AAV-8b (SEQ ID NO: 5 of US20150376240), AAV-h (SEQ ID NO: 2 of US20150376240), AAV-b (SEQ ID NO: 1 of US20150376240), or variants thereof.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in United States Patent Publication No. US20160017295, the contents of which are herein incorporated by reference in their entirety, such as, but not limited to, AAV SM 10-2 (SEQ ID NO: 22 of US20160017295), AAV Shuffle 100-1 (SEQ ID NO: 23 of US20160017295), AAV Shuffle 100-3 (SEQ ID NO: 24 of US20160017295), AAV Shuffle 100-7 (SEQ ID NO: 25 of US20160017295), AAV Shuffle 10-2 (SEQ ID NO: 34 of US20160017295), AAV Shuffle 10-6 (SEQ ID NO: 35 of US20160017295), AAV Shuffle 10-8 (SEQ ID NO: 36 of US20160017295), AAV Shuffle 100-2 (SEQ ID NO: 37 of US20160017295), AAV SM 10-1 (SEQ ID NO: 38 of US20160017295), AAV SM 10-8 (SEQ ID NO: 39 of US20160017295), AAV SM 100-3 (SEQ ID NO: 40 of US20160017295), AAV SM 100-10 (SEQ ID NO: 41 of US20160017295), or variants thereof.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in United States Patent Publication No. US20150238550, the contents of which are herein incorporated by reference in their entirety, such as, but not limited to, BNP61 AAV (SEQ ID NO: 1 of US20150238550), BNP62 AAV (SEQ ID NO: 3 of US20150238550), BNP63 AAV (SEQ ID NO: 4 of US20150238550), or variants thereof.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in United States Patent Publication No. US20150315612, the contents of which are herein incorporated by reference in their entirety, such as, but not limited to, AAVrh.50 (SEQ ID NO: 108 of US20150315612), AAVrh.43 (SEQ ID NO: 163 of US20150315612), AAVrh.62 (SEQ ID NO: 114 of US20150315612), AAVrh.48 (SEQ ID NO: 115 of US20150315612), AAVhu. 19 (SEQ ID NO: 133 of US20150315612), AAVhu.11 (SEQ ID NO: 153 of US20150315612), AAVhu.53 (SEQ ID NO: 186 of US20150315612), AAV4-8/rh.64 (SEQ ID No: 15 of US20150315612), AAVLG-9/hu.39 (SEQ ID No: 24 of US20150315612), AAV54.5/hu.23 (SEQ ID No: 60 of US20150315612), AAV54.2/hu.22 (SEQ ID No: 67 of US20150315612), AAV54.7/hu.24 (SEQ ID No: 66 of US20150315612), AAV54.1/hu.21 (SEQ ID No: 65 of US20150315612), AAV54.4R/hu.27 (SEQ ID No: 64 of US20150315612), AAV46.2/hu.28 (SEQ ID No: 68 of US20150315612), AAV46.6/hu.29 (SEQ ID No: 69 of US20150315612), AAV128.1/hu.43 (SEQ ID No: 80 of US20150315612), or variants thereof.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in International Publication No. WO2015121501, the contents of which are herein incorporated by reference in their entirety, such as, but not limited to, true type AAV (ttAAV) (SEQ ID NO: 2 of WO2015121501), "UPenn AAV10" (SEQ ID NO: 8 of WO2015121501), "Japanese AAV10" (SEQ ID NO: 9 of WO2015121501), or variants thereof.

According to the present disclosure, the AAV capsid polypeptide, e.g., AAV capsid variant, or the parent AAV capsid, may be selected or derived from a variety of species. In some embodiments, the AAV capsid polypeptide, e.g., AAV capsid variant, or the parent AAV capsid, may be, at a position other than 5 consecutive amino acids corresponding to positions 586 to 594 numbered relative to SEQ ID NO: 138, an avian AAV (AAAV). In some embodiments, the AAV serotype, the parent AAV capsid polypeptide, or the AAV capsid variant may be or have, at a position other than 5 consecutive amino acids corresponding to positions 586 to 594 numbered relative to SEQ ID NO: 138, a sequence as described in U.S. Pat. No. 9,238,800, the contents of which are herein incorporated by reference in their entirety, such as, but not limited to, AAAV (SEQ ID NO: 1, 2, 4, 6, 8, 10, 12, and 14 of U.S. Pat. No. 9,238,800), or variants thereof.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in U.S. Pat. No. 9,193,769, the contents of which are herein incorporated by reference in their entirety, such as, but not limited to, BAAV (SEQ ID NO: 1 and 6 of U.S. Pat. No. 9,193,769), or variants thereof. In some embodiments, the AAV serotype, the parent AAV capsid polypeptide, or the AAV capsid variant may be, at a position other than 5 consecutive amino acids corresponding to positions 586 to 594 numbered relative to SEQ ID NO: 138, a BAAV serotype comprising a sequence as described in U.S. Pat. No. 7,427,396, the contents of which are herein incorporated by reference in their entirety, such as, but not limited to, BAAV (SEQ ID NO: 5 and 6 of U.S. Pat. No. 7,427,396), or variants thereof.

In some embodiments, the AAV capsid polypeptide, e.g., AAV capsid variant, or the parent AAV capsid may be a caprine AAV. In some embodiments, the AAV serotype, the parent AAV capsid polypeptide, or the AAV capsid variant may be or have, at a position other than 5 consecutive amino acids corresponding to positions 586 to 594 numbered relative to SEQ ID NO: 138, may be a caprine AAV serotype comprising a sequence as described in U.S. Pat. No. 7,427, 396, the contents of which are herein incorporated by reference in their entirety, such as, but not limited to, caprine AAV (SEQ ID NO: 3 of U.S. Pat. No. 7,427,396), or variants thereof.

In other embodiments, the AAV capsid polypeptide, e.g., AAV capsid variant, or the parent AAV capsid may be engineered as a hybrid AAV from two or more serotypes, e.g., parental serotypes. In some embodiments, the AAV serotype, the parent AAV capsid polypeptide, or the AAV capsid variant may be, at a position other than 5 consecutive amino acids corresponding to positions 586 to 594 numbered relative to SEQ ID NO: 138, may be a AAV2G9, which comprises sequences from AAV2 and AAV9, e.g., wherein the AAV2G9 AAV serotype may be, or have, a sequence as described in United States Patent Publication No. US20160017005, the contents of which are herein incorporated by reference in its entirety.

In some embodiments, the AAV capsid polypeptide, e.g., AAV capsid variant, or the parent AAV capsid may be, at a position other than 5 consecutive amino acids corresponding to positions 586 to 594 numbered relative to SEQ ID NO: 138 a serotype generated by the AAV9 capsid library with mutations in amino acids 390-627 (VP1 numbering) as described by Pulicherla et al. (Molecular Therapy 19 (6): 1070-1078 (2011), the contents of which are herein incorporated by reference in their entirety. The serotype and corresponding nucleotide and amino acid substitutions may be, but is not limited to, AAV9.1 (G1594C; D532H), AAV6.2 (T1418A and T1436X; V473D and I479K), AAV9.3 (T1238A; F413Y), AAV9.4 (T1250C and A1617T; F417S), AAV9.5 (A1235G, A1314T, A1642G, C1760T; Q412R, T548A, A587V), AAV9.6 (T1231A; F411I), AAV9.9 (G1203A, G1785T; W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T; N512D), AAV9.35 (A1289T, T1450A, C1494T, A1515T, C1794A, G1816A; Q430L, Y484N, N98K, V606I), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G; G481R, W509R, L517V), 9.47 (G1241A, G1358A, A1669G, C1745T; S414N, G453D, K557E, T5821), AAV9.48 (C1445T, A1736T; P482L, Q579L), AAV9.50 (A1638T, C1683T, T1805A; Q546H, L602H), AAV9.53 (G1301A, A1405C, C1664T, G1811T; R134Q, S469R, A555V, G604V), AAV9.54 (C1531A, T1609A; L511I, L537M), AAV9.55 (T1605A; F535L), AAV9.58 (C1475T, C1579A; T4921, H527N), AAV.59 (T1336C; Y446H), AAV9.61 (A1493T; N4981), AAV9.64 (C1531A, A1617T; L511I), AAV9.65 (C1335T, T1530C, C1568A; A523D), AAV9.68 (C1510A; P504T), AAV9.80 (G1441A, G481R), AAV9.83 (C1402A, A1500T; P468T, E500D), AAV9.87 (T1464C, T1468C; S490P), AAV9.90 (A1196T; Y399F), AAV9.91 (T1316G, A1583T, C1782G, T1806C; L439R, K528I), AAV9.93 (A1273G, A1421G, A1638C, C1712T, G1732A, A1744T, A1832T; S425G, Q474R, Q546H, P571L, G578R, T582S, D611V), AAV9.94 (A1675T; M559L) and AAV9.95 (T1605A; F535L).

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in International Publication No. WO2016049230, the contents of which are herein incorporated by reference in their entirety, such as, but not limited to AAVF1/HSC1 (SEQ ID NO: 2 and 20 of WO2016049230), AAVF2/HSC2 (SEQ ID NO: 3 and 21 of WO2016049230), AAVF3/HSC3 (SEQ ID NO: 5 and 22 of WO2016049230), AAVF4/HSC4 (SEQ ID NO: 6 and 23 of WO2016049230), AAVF5/HSC5 (SEQ ID NO: 11 and 25 of WO2016049230), AAVF6/HSC6 (SEQ ID NO: 7 and 24 of WO2016049230), AAVF7/HSC7 (SEQ ID NO: 8 and 27 of WO2016049230), AAVF8/HSC8 (SEQ ID NO: 9 and 28 of WO2016049230), AAVF9/HSC9 (SEQ ID NO: 10 and 29 of WO2016049230), AAVF11/HSC11 (SEQ ID NO: 4 and 26 of WO2016049230), AAVF12/HSC12 (SEQ ID NO: 12 and 30 of WO2016049230), AAVF13/HSC13 (SEQ ID NO: 14 and 31 of WO2016049230), AAVF14/HSC14 (SEQ ID NO: 15 and 32 of WO2016049230), AAVF15/HSC15 (SEQ ID NO: 16 and 33 of WO2016049230), AAVF16/HSC16 (SEQ ID NO: 17 and 34 of WO2016049230), AAVF17/HSC17 (SEQ ID NO: 13 and 35 of WO2016049230), or variants or derivatives thereof.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in U.S. Pat. No. 8,734,809, the contents of which are herein incorporated by reference in their entirety, such as, but not limited to, AAV CBr-E1 (SEQ ID NO: 13 and 87 of U.S. Pat. No. 8,734,809), AAV CBr-E2 (SEQ ID NO: 14 and 88 of U.S. Pat. No. 8,734,809), AAV CBr-E3 (SEQ ID NO: 15 and 89 of U.S. Pat. No. 8,734,809), AAV CBr-E4 (SEQ ID NO: 16 and 90 of U.S. Pat. No. 8,734,809), AAV CBr-E5 (SEQ ID NO: 17 and 91 of U.S. Pat. No. 8,734,809), AAV CBr-e5 (SEQ ID NO: 18 and 92 of U.S. Pat. No. 8,734,809), AAV CBr-E6 (SEQ ID NO: 19 and 93 of U.S. Pat. No. 8,734,809), AAV CBr-E7 (SEQ ID NO: 20 and 94 of U.S. Pat. No. 8,734,809), AAV CBr-E8 (SEQ ID NO: 21 and 95 of U.S. Pat. No. 8,734,809), AAV CLv-D1 (SEQ ID NO: 22 and 96 of U.S. Pat. No. 8,734,809), AAV CLv-D2 (SEQ ID NO: 23 and 97 of U.S. Pat. No. 8,734,809), AAV CLv-D3 (SEQ ID NO: 24 and 98 of U.S. Pat. No. 8,734,809), AAV CLv-D4 (SEQ ID NO: 25 and 99 of U.S. Pat. No. 8,734,809), AAV CLv-D5 (SEQ ID NO: 26 and 100 of U.S. Pat. No. 8,734,809), AAV CLv-D6 (SEQ ID NO: 27 and 101 of U.S. Pat. No. 8,734, 809), AAV CLv-D7 (SEQ ID NO: 28 and 102 of U.S. Pat. No. 8,734,809), AAV CLv-D8 (SEQ ID NO: 29 and 103 of U.S. Pat. No. 8,734,809), AAV CLv-E1 (SEQ ID NO: 13 and 87 of U.S. Pat. No. 8,734,809), AAV CLv-R1 (SEQ ID NO: 30 and 104 of U.S. Pat. No. 8,734,809), AAV CLv-R2 (SEQ ID NO: 31 and 105 of U.S. Pat. No. 8,734,809), AAV CLv-R3 (SEQ ID NO: 32 and 106 of U.S. Pat. No. 8,734, 809), AAV CLv-R4 (SEQ ID NO: 33 and 107 of U.S. Pat. No. 8,734,809), AAV CLv-R5 (SEQ ID NO: 34 and 108 of U.S. Pat. No. 8,734,809), AAV CLv-R6 (SEQ ID NO: 35 and 109 of U.S. Pat. No. 8,734,809), AAV CLv-R7 (SEQ ID NO: 36 and 110 of U.S. Pat. No. 8,734,809), AAV CLv-R8 (SEQ ID NO: X and X of U.S. Pat. No. 8,734,809), AAV CLv-R9 (SEQ ID NO: X and X of U.S. Pat. No. 8,734,809), AAV CLg-F1 (SEQ ID NO: 39 and 113 of U.S. Pat. No. 8,734,809), AAV CLg-F2 (SEQ ID NO: 40 and 114 of U.S. Pat. No. 8,734,809), AAV CLg-F3 (SEQ ID NO: 41 and 115 of U.S. Pat. No. 8,734,809), AAV CLg-F4 (SEQ ID NO: 42 and 116 of U.S. Pat. No. 8,734,809), AAV CLg-F5 (SEQ ID NO: 43 and 117 of U.S. Pat. No. 8,734,809), AAV CLg-F6 (SEQ ID NO: 43 and 117 of U.S. Pat. No. 8,734,809), AAV CLg-F7 (SEQ ID NO: 44 and 118 of U.S. Pat. No. 8,734, 809), AAV CLg-F8 (SEQ ID NO: 43 and 117 of U.S. Pat. No. 8,734,809), AAV CSp-1 (SEQ ID NO: 45 and 119 of U.S. Pat. No. 8,734,809), AAV CSp-10 (SEQ ID NO: 46 and 120 of U.S. Pat. No. 8,734,809), AAV CSp-11 (SEQ ID NO: 47 and 121 of U.S. Pat. No. 8,734,809), AAV CSp-2 (SEQ ID NO: 48 and 122 of U.S. Pat. No. 8,734,809), AAV CSp-3 (SEQ ID NO: 49 and 123 of U.S. Pat. No. 8,734,809), AAV CSp-4 (SEQ ID NO: 50 and 124 of U.S. Pat. No. 8,734,809), AAV CSp-6 (SEQ ID NO: 51 and 125 of U.S. Pat. No. 8,734,809), AAV CSp-7 (SEQ ID NO: 52 and 126 of U.S. Pat. No. 8,734,809), AAV CSp-8 (SEQ ID NO: 53 and 127 of U.S. Pat. No. 8,734,809), AAV CSp-9 (SEQ ID NO: 54 and 128 of U.S. Pat. No. 8,734,809), AAV CHt-2 (SEQ ID NO: 55 and 129 of U.S. Pat. No. 8,734,809), AAV CHt-3 (SEQ ID NO: 56 and 130 of U.S. Pat. No. 8,734,809), AAV CKd-1 (SEQ ID NO: 57 and 131 of U.S. Pat. No. 8,734, 809), AAV CKd-10 (SEQ ID NO: 58 and 132 of U.S. Pat. No. 8,734,809), AAV CKd-2 (SEQ ID NO: 59 and 133 of U.S. Pat. No. 8,734,809), AAV CKd-3 (SEQ ID NO: 60 and 134 of U.S. Pat. No. 8,734,809), AAV CKd-4 (SEQ ID NO: 61 and 135 of U.S. Pat. No. 8,734,809), AAV CKd-6 (SEQ ID NO: 62 and 136 of U.S. Pat. No. 8,734,809), AAV CKd-7 (SEQ ID NO: 63 and 137 of U.S. Pat. No. 8,734,809), AAV CKd-8 (SEQ ID NO: 64 and 138 of U.S. Pat. No. 8,734, 809), AAV CLv-1 (SEQ ID NO: 35 and 139 of U.S. Pat. No. 8,734,809), AAV CLv-12 (SEQ ID NO: 66 and 140 of U.S. Pat. No. 8,734,809), AAV CLv-13 (SEQ ID NO: 67 and 141 of U.S. Pat. No. 8,734,809), AAV CLv-2 (SEQ ID NO: 68 and 142 of U.S. Pat. No. 8,734,809), AAV CLv-3 (SEQ ID NO: 69 and 143 of U.S. Pat. No. 8,734,809), AAV CLv-4 (SEQ ID NO: 70 and 144 of U.S. Pat. No. 8,734,809), AAV CLv-6 (SEQ ID NO: 71 and 145 of U.S. Pat. No. 8,734,809), AAV CLv-8 (SEQ ID NO: 72 and 146 of U.S. Pat. No. 8,734,809), AAV CKd-B1 (SEQ ID NO: 73 and 147 of U.S. Pat. No. 8,734,809), AAV CKd-B2 (SEQ ID NO: 74 and 148 of U.S. Pat. No. 8,734,809), AAV CKd-B3 (SEQ ID NO: 75 and 149 of U.S. Pat. No. 8,734,809), AAV CKd-B4 (SEQ ID NO: 76 and 150 of U.S. Pat. No. 8,734,809), AAV CKd-B5 (SEQ ID NO: 77 and 151 of U.S. Pat. No. 8,734,809), AAV CKd-B6 (SEQ ID NO: 78 and 152 of U.S. Pat. No. 8,734, 809), AAV CKd-B7 (SEQ ID NO: 79 and 153 of U.S. Pat. No. 8,734,809), AAV CKd-B8 (SEQ ID NO: 80 and 154 of U.S. Pat. No. 8,734,809), AAV CKd-H1 (SEQ ID NO: 81 and 155 of U.S. Pat. No. 8,734,809), AAV CKd-H2 (SEQ ID NO: 82 and 156 of U.S. Pat. No. 8,734,809), AAV CKd-H3 (SEQ ID NO: 83 and 157 of U.S. Pat. No. 8,734,809), AAV CKd-H4 (SEQ ID NO: 84 and 158 of U.S. Pat. No. 8,734, 809), AAV CKd-H5 (SEQ ID NO: 85 and 159 of U.S. Pat. No. 8,734,809), AAV CKd-H6 (SEQ ID NO: 77 and 151 of U.S. Pat. No. 8,734,809), AAV CHt-1 (SEQ ID NO: 86 and 160 of U.S. Pat. No. 8,734,809), AAV CLv1-1 (SEQ ID NO: 171 of U.S. Pat. No. 8,734,809), AAV CLv1-2 (SEQ ID NO: 172 of U.S. Pat. No. 8,734,809), AAV CLv1-3 (SEQ ID NO: 173 of U.S. Pat. No. 8,734,809), AAV CLv1-4 (SEQ ID NO: 174 of U.S. Pat. No. 8,734,809), AAV Clv1-7 (SEQ ID NO: 175 of U.S. Pat. No. 8,734,809), AAV Clv1-8 (SEQ ID NO: 176 of U.S. Pat. No. 8,734,809), AAV Clv1-9 (SEQ ID NO: 177 of U.S. Pat. No. 8,734,809), AAV Clv1-10 (SEQ ID NO: 178 of U.S. Pat. No. 8,734,809), AAV.VR-355 (SEQ ID NO: 181 of U.S. Pat. No. 8,734,809), AAV.hu.48R3 (SEQ ID NO: 183 of U.S. Pat. No. 8,734,809), or variants or derivatives thereof.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in International Publication No. WO2016065001, the contents of which are herein incorporated by reference in their entirety, such as, but not limited to AAV CHt-P2 (SEQ ID NO: 1 and 51 of WO2016065001), AAV CHt-P5 (SEQ ID NO: 2 and 52 of WO2016065001), AAV CHt-P9 (SEQ ID NO: 3 and 53 of WO2016065001), AAV CBr-7.1 (SEQ ID NO: 4 and 54 of WO2016065001), AAV CBr-7.2 (SEQ ID NO: 5 and 55 of WO2016065001), AAV CBr-7.3 (SEQ ID NO: 6 and 56 of WO2016065001), AAV CBr-7.4 (SEQ ID NO: 7 and 57 of WO2016065001), AAV CBr-7.5 (SEQ ID NO: 8 and 58 of WO2016065001), AAV CBr-7.7 (SEQ ID NO: 9 and 59 of WO2016065001), AAV CBr-7.8 (SEQ ID NO: 10 and 60 of WO2016065001), AAV CBr-7.10 (SEQ ID NO: 11 and 61 of WO2016065001), AAV CKd-N3 (SEQ ID NO: 12 and 62 of WO2016065001), AAV CKd-N4 (SEQ ID NO: 13 and 63 of WO2016065001), AAV CKd-N9 (SEQ ID NO: 14 and 64 of WO2016065001), AAV CLv-L4 (SEQ ID NO: 15 and 65 of WO2016065001), AAV CLv-L5 (SEQ ID NO: 16 and 66 of WO2016065001), AAV CLv-L6 (SEQ ID NO: 17 and 67 of WO2016065001), AAV CLv-K1 (SEQ ID NO: 18 and 68 of WO2016065001), AAV CLv-K3 (SEQ ID NO: 19 and 69 of WO2016065001), AAV CLv-K6 (SEQ ID NO: 20 and 70 of WO2016065001), AAV CLv-M1 (SEQ ID NO: 21 and 71 of WO2016065001), AAV CLv-M11 (SEQ ID NO: 22 and 72 of WO2016065001), AAV CLv-M2 (SEQ ID NO: 23 and 73 of WO2016065001), AAV CLv-M5 (SEQ ID NO: 24 and 74 of WO2016065001), AAV CLv-M6 (SEQ ID NO: 25 and 75 of WO2016065001), AAV CLv-M7 (SEQ ID NO: 26 and 76 of WO2016065001), AAV CLv-M8 (SEQ ID NO: 27 and 77 of WO2016065001), AAV CLv-M9 (SEQ ID NO: 28 and 78 of WO2016065001), AAV CHt-P1 (SEQ ID NO: 29 and 79 of WO2016065001), AAV CHt-P6 (SEQ ID NO: 30 and 80 of WO2016065001), AAV CHt-P8 (SEQ ID NO: 31 and 81 of WO2016065001), AAV CHt-6.1 (SEQ ID NO: 32 and 82 of WO2016065001), AAV CHt-6.10 (SEQ ID NO: 33 and 83 of WO2016065001), AAV CHt-6.5 (SEQ ID NO: 34 and 84 of WO2016065001), AAV CHt-6.6 (SEQ ID NO: 35 and 85 of WO2016065001), AAV CHt-6.7 (SEQ ID NO: 36 and 86 of WO2016065001), AAV CHt-6.8 (SEQ ID NO: 37 and 87 of WO2016065001), AAV CSp-8.10 (SEQ ID NO: 38 and 88 of WO2016065001), AAV CSp-8.2 (SEQ ID NO: 39 and 89 of WO2016065001), AAV CSp-8.4 (SEQ ID NO: 40 and 90 of WO2016065001), AAV CSp-8.5 (SEQ ID NO: 41 and 91 of WO2016065001), AAV CSp-8.6 (SEQ ID NO: 42 and 92 of WO2016065001), AAV CSp-8.7 (SEQ ID NO: 43 and 93 of WO2016065001), AAV CSp-8.8 (SEQ ID NO: 44 and 94 of WO2016065001), AAV CSp-8.9 (SEQ ID NO: 45 and 95 of WO2016065001), AAV CBr-B7.3 (SEQ ID NO: 46 and 96 of WO2016065001), AAV CBr-B7.4 (SEQ ID NO: 47 and 97 of WO2016065001), AAV3B (SEQ ID NO: 48 and 98 of WO2016065001), AAV4 (SEQ ID NO: 49 and 99 of WO2016065001), AAV5 (SEQ ID NO: 50 and 100 of WO2016065001), or variants or derivatives thereof.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a serotype selected from any of those found in Table 6.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence, fragment or variant thereof, of any of the sequences in Table 6.

In some embodiments, the AAV capsid polypeptide, e.g., AAV capsid variant, or the parent AAV capsid may be encoded by, at a position other than 5 consecutive amino acids corresponding to positions 586 to 594 numbered relative to SEQ ID NO: 138, a sequence, fragment or variant as described in Table 6.

TABLE 6

| Serotype | SEQ ID NO: | Reference Information |
|---|---|---|
| | | AAV Sequences |
| VOY101 | 1 | — |
| VOY101 | 2 | — |
| VOY201 | 3 | — |
| VOY201 | 1724 | — |
| PHP.N/PHP.B-DGT | 4 | WO2017100671 SEQ ID NO: 46 |
| AAVPHP.B or G2B-26 | 5 | WO2015038958 SEQ ID NO: 8 and 13 |
| AAVPHP.B | 6 | WO2015038958 SEQ ID NO: 9 |
| AAVG2B-13 | 7 | WO2015038958 SEQ ID NO: 12 |
| AAVTHL1-32 | 8 | WO2015038958 SEQ ID NO: 14 |
| AAVTH1.1-35 | 9 | WO2015038958 SEQ ID NO: 15 |
| PHP.S/G2A12 | 10 | WO2017100671 SEQ ID NO: 47 |
| AAV9/hu.14K449R | 11 | WO2017100671 SEQ ID NO: 45 |
| AAV1 | 12 | US20150159173 SEQ ID NO: 11, US20150315612 SEQ ID NO: 202 |
| AAV1 | 13 | US20160017295 SEQ ID NO: 1, US20030138772 SEQ ID NO: 64, US20150159173 SEQ ID NO: 27, US20150315612 SEQ ID NO: 219, U.S. Pat. No. 7,198,951 SEQ ID NO: 5 |
| AAV1 | 14 | US20030138772 SEQ ID NO: 6 |
| AAV1.3 | 15 | US20030138772 SEQ ID NO: 14 |
| AAV10 | 16 | US20030138772 SEQ ID NO: 117 |
| AAV10 | 17 | WO2015121501 SEQ ID NO: 9 |
| AAV10 | 18 | WO2015121501 SEQ ID NO: 8 |
| AAV11 | 19 | US20030138772 SEQ ID NO: 118 |
| AAV12 | 20 | US20030138772 SEQ ID NO: 119 |
| AAV2 | 21 | US20150159173 SEQ ID NO: 7, US20150315612 SEQ ID NO: 211 |
| AAV2 | 22 | US20030138772 SEQ ID NO: 70, US20150159173 SEQ ID NO: 23, US20150315612 SEQ ID NO: 221, US20160017295 SEQ ID NO: 2, U.S. Pat. No. 6,156,303 SEQ ID NO: 4, U.S. Pat. No. 7,198,951 SEQ ID NO: 4, WO2015121501 SEQ ID NO: 1 |
| AAV2 | 23 | U.S. Pat. No. 6,156,303 SEQ ID NO: 8 |
| AAV2 | 24 | US20030138772 SEQ ID NO: 7 |
| AAV2 | 25 | U.S. Pat. No. 6,156,303 SEQ ID NO: 3 |

TABLE 6-continued

| | | AAV Sequences |
|---|---|---|
| Serotype | SEQ ID NO: | Reference Information |
| AAV2.5T | 26 | U.S. Pat. No. 9,233,131 SEQ ID NO: 42 |
| AAV223.10 | 27 | US20030138772 SEQ ID NO: |
| AAV223.2 | 28 | US20030138772 SEQ ID NO: 49 |
| AAV223.2 | 29 | US20030138772 SEQ ID NO: 76 |
| AAV223.4 | 30 | US20030138772 SEQ ID NO: 50 |
| AAV223,4 | 31 | US20030138772 SEQ ID NO: 73 |
| AAV223.5 | 32 | US20030138772 SEQ ID NO: 51 |
| AAV223.5 | 33 | US20030138772 SEQ ID NO: 74 |
| AAV223.6 | 34 | US20030138772 SEQ ID NO: 52 |
| AAV223.6 | 35 | US20030138772 SEQ ID NO: 78 |
| AAV223.7 | 36 | US20030138772 SEQ ID NO: 53 |
| AAV223.7 | 37 | US20030138772 SEQ ID NO: 77 |
| AAV29.3 | 38 | US20030138772 SEQ ID NO: 82 |
| AAV29.4 | 39 | US20030138772 SEQ ID NO: 12 |
| AAV29.5 | 40 | US20030138772 SEQ ID NO: 83 |
| AAV29.5 (AAVbb.2) | 41 | US20030138772 SEQ ID NO: 13 |
| AAV3 | 42 | US20150159173 SEQ ID NO: 12 |
| AAV3 | 43 | US20030138772 SEQ ID NO: 71, US20150159173 SEQ ID NO: 28, US20160017295 SEQ ID NO: 3, U.S. Pat. No. 7,198,951 SEQ ID NO: 6 |
| AAV3 | 44 | US20030138772 SEQ ID NO: 8 |
| AAV3.3b | 45 | US20030138772 SEQ ID NO: 72 |
| AAV3-3 | 46 | US20150315612 SEQ ID NO: 200 |
| AAV3-3 | 47 | US20150315612 SEQIDNO. 217 |
| AAV3a | 48 | U.S. Pat. No. 6,156,303 SEQ ID NO: 5 |
| AAV3a | 49 | U.S. Pat. No. 6,156,303 SEQ ID NO: 9 |
| AAV3b | 50 | U.S. Pat. No. 6,156,303 SEQ ID NO: 6 |
| AAV3b | 51 | U.S. Pat. No. 6,156,303 SEQ ID NO: 10 |
| AAV3b | 52 | U.S. Pat. No. 6,156,303 SEQ ID NO: 1 |
| AAV4 | 53 | US20140348794 SEQ ID NO |
| AAV4 | 54 | US20140348794 SEQ ID NO: 5 |
| AAV4 | 55 | US20140348794 SEQ ID NO: 3 |
| AAV4 | 56 | US20140348794 SEQ ID NO: 14 |
| AAV4 | 57 | US20140348794 SEQ ID NO: 15 |
| AAV4 | 58 | US20140348794 SEQ ID NO: 19 |
| AAV4 | 59 | US20140348794 SEQ ID NO: 12 |
| AAV4 | 60 | US20140348794 SEQ ID NO: 13 |
| AAV4 | 61 | US20140348794 SEQ ID NO: 7 |
| AAV4 | 62 | US20140348794 SEQ ID NO: 8 |
| AAV4 | 63 | US20140348794 SEQ ID NO: 9 |
| AAV4 | 64 | US20140348794 SEQ ID NO: 2 |
| AAV4 | 65 | US20140348794 SEQ ID NO: 10 |
| AAV4 | 66 | US20140348794 SEQ ID NO: 11 |
| AAV4 | 67 | US20140348794 SEQ ID NO: 18 |
| AAV4 | 68 | US20030138772 SEQ ID NO: 63, US20160017295 SEQ ID NO: 4, US20140348794 SEQ ID NO: 4 |
| AAV4 | 69 | US20140348794 SEQ ID NO: 16 |
| AAV4 | 70 | US20140348794 SEQ ID NO: 20 |
| AAV4 | 71 | US20140348794 SEQ ID NO: 6 |
| AAV4 | 72 | US20140348794 SEQ ID NO: 1 |
| AAV42.2 | 73 | US20030138772 SEQ ID NO: 9 |
| AAV42.2 | 74 | US20030138772 SEQ ID NO: 102 |
| AAV42.3b | 75 | US20030138772 SEQ ID NO: 36 |
| AAV42.3B | 76 | US20030138772 SEQ ID NO: 107 |
| AAV42.4 | 77 | US20030138772 SEQ ID NO: 33 |
| AAV42.4 | 78 | US20030138772 SEQ ID NO: 88 |
| AAV42.8 | 79 | US20030138772 SEQ ID NO: 27 |
| AAV42.8 | 80 | US20030138772 SEQ ID NO: 85 |
| AAV43.1 | 83 | US20030138772 SEQ ID NO: 39 |
| AAV43.1 | 82 | US20030138772 SEQ ID NO: 92 |
| AAV43.12 | 83 | US20030138772 SEQ ID NO: 41 |
| AAV43.12 | 84 | US20030138772 SEQ ID NO: 93 |
| AAV43.20 | 85 | US20030138772 SEQ ID NO: 42 |
| AAV43.20 | 86 | US20030138772 SEQ ID NO: 99 |
| AAV43.21 | 87 | US20030138772 SEQ ID NO: 43 |
| AAV43.21 | 88 | US20030138772 SEQ ID NO: 96 |
| AAV43.23 | 89 | US20030138772 SEQ ID NO: 44 |
| AAV43.23 | 90 | US20030138772 SEQ ID NO: 98 |
| AAV43.25 | 91 | US20030138772 SEQ ID NO: 45 |
| AAV43.25 | 92 | US20030138772 SEQ ID NO: 97 |
| AAV43.5 | 93 | US20030138772 SEQ ID NO: 40 |
| AAV43.5 | 94 | US20030138772 SEQ ID NO: 94 |
| AAV4-4 | 95 | US20150315612 SEQ ID NO: 201 |
| AAV4-4 | 96 | US20150315612 SEQ ID NO: 218 |
| AAV44.1 | 97 | US20030138772 SEQ ID NO: 46 |

TABLE 6-continued

| | SEQ ID NO: | |
|---|---|---|
| Serotype | | Reference Information |
| AAV44.1 | 98 | US20030138772 SEQ ID NO: 79 |
| AAV44.5 | 99 | US20030138772 SEQ ID NO: 47 |
| AAV44.5 | 100 | US20030138772 SEQ ID NO: 80 |
| AAV4407 | 101 | US20150315612 SEQ ID NO: 90 |
| AAV5 | 102 | U.S. Pat. No. 7,427,396 SEQ ID NO: 1 |
| AAV5 | 103 | US20030138772 SEQ ID NO: 114 |
| AAV5 | 104 | US20160017295 SEQ ID NO: 5, U.S. Pat. No. 7,427,396 SEQ ID NO: 2. US20150315612 SEQ ID NO: 216 |
| AAV5 | 105 | US20150315612 SEQ ID NO: 199 |
| AAV6 | 106 | US20150159173 SEQ ID NO: 13 |
| AAV6 | 107 | US20030138772 SEQ ID NO: 65, US20150159173 SEQ ID NO. 29, US20160017295 SEQ ID NO: 6, U.S. Pat. No. 6,156,303 SEQ ID NO: 7 |
| AAV6 | 108 | U.S. Pat. No. 6,156,303 SEQ ID NO: 11 |
| AAV6 | 109 | U.S. Pat. No. 6,156,303 SEQ ID NO. 2 |
| AAV6 | 110 | US20150315612 SEQ ID NO: 203 |
| AAV6 | 111 | US20150315612 SEQ ID NO: 220 |
| AAV6.1 | 112 | US20150159173 |
| AAV6.12 | 113 | US20150159173 |
| AAV6.2 | 114 | US20150159173 |
| AAV7 | 115 | US20150159173 SEQ ID NO: 14 |
| AAV7 | 136 | US20150315612 SEQ ID NO: 183 |
| AAV7 | 117 | US20030138772 SEQ ID NO: 2, US20150159173 SEQ ID NO: 30, US20150315612 SEQ ID NO: 181, US20160017295 SEQ ID NO: 7 |
| AAV7 | 118 | US20030138772 SEQ ID NO: 3 |
| AAV7 | 119 | US20030138772 SEQ ID NO: 1, US20150315612 SEQ ID NO: 180 |
| AAV7 | 120 | US20150315612 SEQ ID NO: 213 |
| AAV7 | 121 | US20150315612 SEQ ID NO: 222 |
| AAV8 | 122 | US20150159173 SEQ ID NO: 15 |
| AAV8 | 123 | US20150376240 SEQ ID NO: 7 |
| AAV8 | 124 | US20030138772 SEQ ID NO: 4, US20150315612 SEQ ID NO: 182 |
| AAV8 | 125 | US20030138772 SEQ ID NO: 95, US20140359799 SEQ ID NO: 1, US20150159173 SEQ ID NO: 31, US20160017295 SEQ ID NO: 8, U.S. Pat. No. 7,198,951 SEQ ID NO: 7, US20150315612 SEQ ID NO: 223 |
| AAV8 | 126 | US20150376240 SEQ ID NO: 8 |
| AAV8 | 127 | US20150315612 SEQ ID NO: 214 |
| AAV-8b | 128 | US201503 76240 SEQ ID NO: 5 |
| AAV-8b | 129 | US20150376240 SEQ ID NO: 3 |
| AAV-8h | 130 | US20150376240 SEQ ID NO: 6 |
| AAV-8h | 131 | US20150376240 SEQ ID NO. 4 |
| AAV9 | 132 | US20030138772 SEQ ID NO: 5 |
| AAV9 | 133 | U.S. Pat. No. 7,198,951 SEQ ID NO. 1 |
| AAV9 | 134 | US20160017295 SEQ ID NO: 9 |
| AAV9 | 135 | US20030138772 SEQ ID NO: 100, U.S. Pat. No. 7,198,951 SEQ ID NO: 2 |
| AAV9 | 136 | U.S. Pat. No. 7,198,951 SEQ ID NO: 3 |
| AAV9 (AAVhu.14) | 137 | U.S. Pat. No. 7,906,111 SEQ ID NO: 3; WO2015038958 SEQ ID NO: 11 |
| AAV9 (AAVhu.14) | 138 | U.S. Pat. No. 7,906,111 SEQ ID NO: 123, WO2015038958 SEQ ID NO. 2 |
| AAVA3.1 | 139 | US20030138772 SEQ ID NO: 120 |
| AAVA3.3 | 140 | US20030138772 SEQ ID NO: 57 |
| AAVA3.3 | 141 | US20030138772 SEQ ID NO: 66 |
| AAVA3.4 | 142 | US20030138772 SEQ ID NO: 54 |
| AAVA3.4 | 143 | US20030138772 SEQ ID NO: 68 |
| AAVA3.5 | 144 | US20030138772 SEQ ID NO: 55 |
| AAVA3.5 | 145 | US20030138772 SEQ ID NO. 69 |
| AAVA3.7 | 146 | US20030138772 SEQ ID NO: 56 |
| AAVA35 | 147 | US20030138772 SEQ ID NO: 67 |
| AAV29.3 (AAVbb.1) | 148 | US20030138772 SEQ ID NO: 11 |
| AAVC2 | 149 | US20030138772 SEQ ID NO: 61 |
| AAVCh.5 | 150 | US20150159173 SEQ ID NO: 46, US20150315612 SEQ ID NO: 234 |
| AAVcy.2 (AAV13.3) | 151 | US20030138772 SEQ ID NO: 15 |
| AAV24.1 | 152 | US20030138772 SEQ ID NO: 101 |
| AAVcy.3 (AAV24.1) | 153 | US20030138772 SEQ ID NO: 16 |
| AAV27.3 | 154 | US20030138772 SEQ ID NO. 104 |
| AAVcy.4 (AAV27.3) | 155 | US20030138772 SEQ ID NO: 17 |
| AAVcy.5 | 156 | US20150315612 SEQ ID NO: 227 |
| AAV7.2 | 157 | US20030138772 SEQ ID NO: 103 |
| AAVcy.5 (AAV7.2) | 158 | US20030138772 SEQ ID NO: 18 |
| AAV16.3 | 159 | US20030138772 SEQ ID NO: 105 |
| AAVcy.6 (AAV16.3) | 160 | US20030138772 SEQ ID NO: 10 |
| AAVcy.5 | 161 | US20150159173 SEQ ID NO. 8 |
| AAVcy.5 | 162 | US20150159173 SEQ ID NO: 24 |
| AAVCy.5R1 | 163 | US20150159173 |

TABLE 6-continued

| | SEQ ID | |
|---|---|---|
| Serotype | NO: | Reference Information |
| AAVCy.5R2 | 164 | US20150159173 |
| AAVCy.5R3 | 165 | US20150159173 |
| AAVCy.5R4 | 166 | US20150159173 |
| AAVDJ | 167 | US20140359799 SEQ ID NO: 3, U.S. Pat. No. 7,588,772 SEQ ID NO: 2 |
| AAVDJ | 168 | US20140359799 SEQ ID NO. 2, U.S. Pat. No. 7,588,772 SEQ ID NO: 1 |
| AAVDJ-8 | 169 | U.S. Pat. No. 7,588,772; Grimm et al 2008 |
| AAVDJ-8 | 170 | U.S. Pat. No. 7,588,772; Grimm et al 2008 |
| AAVF5 | 171 | US20030138772. SEQ ID NO: 110 |
| AAVH2 | 172 | US20030138772 SEQ ID NO: 26 |
| AAVH6 | 173 | US20030138772 SEQ ID NO: 25 |
| AAVhE1.1 | 174 | U.S. Pat. No. 9,233,131 SEQ ID NO: 44 |
| AAVhEr1.14 | 175 | U.S. Pat. No. 9,233,131 SEQ ID NO: 46 |
| AAVhEr1.16 | 176 | U.S. Pat. No. 9,233,131 SEQ ID NO: 48 |
| AAVHEr.18 | 177 | U.S. Pat. No. 9,233,131 SEQ ID NO. 49 |
| A AVhEr1.23 (AAVhEr2.29) | 178 | U.S. Pat. No. 9,233,131 SEQ ID NO: 53 |
| AAVhEr1.35 | 179 | U.S. Pat. No. 9,233,131 SEQ ID NO: 50 |
| AAVhEr1.36 | 180 | U.S. Pat. No. 9,233,131 SEQ ID NO: 52. |
| AAVhEr1.5 | 181 | U.S. Pat. No. 9,233,131 SEQ ID NO: 45 |
| A AVhEr1.7 | 182 | U.S. Pat. No. 9,233,131 SEQ ID NO: 51 |
| A AVhEr1.8 | 183 | U.S. Pat. No. 9,233,131 SEQ ID NO: 47 |
| AAVHE:2.16 | 184 | U.S. Pat. No. 9,233,131 SEQ ID NO. 55 |
| AAVhEr2.30 | 185 | U.S. Pat. No. 9,233,131 SEQ ID NO: 56 |
| AAVhEr2.31 | 186 | U.S. Pat. No. 9,233,131 SEQ ID NO: 58 |
| AAVhEr2.36 | 187 | U.S. Pat. No. 9,233,131 SEQ ID NO: 57 |
| AAVhEr.4 | 188 | U.S. Pat. No. 9,233,131 SEQ ID NO: 54 |
| AAVHEr3.1 | 189 | U.S. Pat. No. 9,233,131 SEQ ID NO: 59 |
| AAVhu. 1 | 190 | US20150315612 SEQ ID NO |
| AAVhu I | 191 | US20150315612 SEQ ID NO: 144 |
| AAVhu.10 (AAV16.8) | 192 | US20150315612 SEQ ID NO: 56 |
| AAVhu.10 (AAV16.8) | 193 | US20150315612 SEQ ID NO: 156 |
| AAVhu.11 (AAV16.12) | 194 | US20150315612 SEQ ID NO: 57 |
| AAVhu.11 (AAV16.12) | 195 | US20150315612 SEQ ID NO: 153 |
| AAVhu.12 | 196 | US20150315612 SEQ ID NO: 59 |
| AAVhu.12 | 197 | US20150315612 SEQ ID NO: 154 |
| AAVhu.13 | 198 | US20150159173 SEQ ID NO: 16, US20150315612 SEQ ID NO: 71 |
| AAVhu.13 | 199 | US20150159173 SEQ ID NO: 32, US20150315612 SEQ ID NO: 129 |
| AAVhu.136.1 | 200 | US20150315612 SEQ ID NO: 165 |
| AAVhu.140.1 | 201 | US20150315612 SEQ ID NO: 166 |
| AAVhu.140.2 | 202 | US20150315612 SEQ ID NO: 167 |
| AAVhu.145.6 | 203 | US20150315612 SEQ ID No: 178 |
| AAVhu.15 | 204 | US20150315612 SEQ ID NO: 147 |
| AAVhu.15 (AAV33.4) | 205 | US20150315612 SEQ ID NO: 50 |
| AAVhu.156.1 | 206 | US20150315612 SEQ ID No 179 |
| AAVhu.16 | 207 | US20150315612 SEQ ID NO |
| AAVhu.16 (AAV33.8) | 208 | US20150315612 SEQ ID NO: 51 |
| AAVhu.17 | 209 | US20150315612 SEQ ID NO: 83 |
| AAVhu.17 (AAV33.12) | 210 | US20150315612 SEQ ID NO: 4 |
| AAVhu.172.1 | 211 | US20150315612 SEQ ID NO: 171 |
| AAVhu.172.2 | 212 | US20150315612 SEQ ID NO: 172 |
| AAVhu.173.4 | 213 | US20150315612 SEQ ID NO: 173 |
| AAVhu.173.8 | 214 | US20150315612 SEQ ID NO: 175 |
| AAVhu.18 | 215 | US20150315612 SEQ ID NO: 52 |
| AAVhu.18 | 216 | US20150315612 SEQ ID NO: 149 |
| AAVhu.19 | 217 | US20150315612 SEQ ID NO: 62 |
| AAVhu.19 | 218 | US20150315612 SEQ ID NO: 133 |
| AAVhu.2 | 219 | US20150315612 SEQ ID NO: 48 |
| AAVhu.2 | 220 | US20150315612 SEQ ID NO: 143 |
| AAVhu.20 | 221 | US20150315612 SEQ ID NO: 63 |
| AAVhu.20 | 222 | US20150315612 SEQ ID NO: 134 |
| AAVhu.21 | 223 | US20150315612 SEQ ID NO: 65 |
| AAVhu.21 | 224 | US20150315612 SEQ ID NO: 135 |
| AAVhu.22 | 225 | US20150315612 SEQ ID NO: 67 |
| AAVhu.22 | 226 | US20150315612 SEQ ID NO: 138 |
| AAVhu.23 | 227 | US20150315612 SEQ ID NO: 60 |
| AAVhu.23.2 | 228 | US20150315612 SEQ ID NO: 137 |
| AAVhu.24 | 229 | US20150315612 SEQ ID NO: 66 |
| AAVhu.24 | 230 | US20150315612 SEQ ID NO: 136 |
| AAVhu.25 | 231 | US20150315612 SEQ ID NO: 49 |
| AAVhu.25 | 232 | US20150315612 SEQ ID NO: 146 |
| AAVhu.26 | 233 | US20150159173 SEQ ID NO: 17, US20150315612 SEQ ID NO. 61 |
| AAVhu.26 | 234 | US20150159173 SEQ ID NO: 33, US20150315612 SEQ ID NO: 139 |
| AAVhu.27 | 235 | US20150315612 SEQ ID NO: 64 |

TABLE 6-continued

| | | AAV Sequences |
|---|---|---|
| Serotype | SEQ ID NO: | Reference Information |
| AAVhu.27 | 236 | US20150315612 SEQ ID NO: 140 |
| AAVhu.28 | 237 | US20150315612 SEQ ID NO: 68 |
| AAVhu.28 | 238 | US20150315612 SEQ ID NO: 130 |
| AAVhu.29 | 239 | US20150315612 SEQ ID NO: 69 |
| AAVhu.29 | 240 | US20150159173 SEQ ID NO: 42, US20150315612 SEQ ID NO: 132 |
| AAVhu.29 | 241 | US20150315612 SEQ ID NO: 225 |
| AAVhu.29R | 242 | US20150159173 |
| AAVhu.3 | 243 | US20150315612 SEQ ID NO: 44 |
| AAVhu.3 | 244 | US20150315612 SEQ ID NO: 145 |
| AAVhu.30 | 245 | US20150315612 SEQ ID NO: 70 |
| AAVhu.30 | 246 | US20150315612 SEQ ID NO: 131 |
| AAVhu.31 | 247 | US20150315612 SEQ ID NO: 1 |
| AAVhu.31 | 248 | US20150315612 SEQ ID NO: 121 |
| AAVhu.32 | 249 | US20150315612 SEQ ID NO: 2 |
| AAVhu.32 | 250 | US20150315612 SEQ ID NO: 122 |
| AAVhu.33 | 251 | US20150315612 SEQ ID NO: 75 |
| AAVhu.33 | 252 | US20150315612 SEQ ID NO: 124 |
| AAVhu.34 | 253 | US20150315612 SEQ ID NO. 72 |
| AAVhu.34 | 254 | US20150315612 SEQ ID NO: 125 |
| AAVhu.35 | 255 | US20150315612 SEQ ID NO: 73 |
| AAVhu.35 | 256 | US20150315612 SEQ ID NO: 164 |
| AAVhu.36 | 257 | US20150315612 SEQ ID NO: 74 |
| AAVhu.36 | 258 | US20150315612 SEQ ID NO: 126 |
| AAVhu.37 | 259 | US20150159173 SEQ ID NO: 34, US20150315612 SEQ ID NO: 88 |
| AAVhu.37 (AAV106.1) | 260 | US20150315612 SEQ ID NO: 10. US20150159173 SEQ ID NO: 18 |
| AAVhu.38 | 261 | US20150315612 SEQ ID NO: 161 |
| AAVhu.39 | 262 | US20150315612 SEQ ID NO: 102 |
| AAVhu.39 (AAVLG-9) | 263 | US20150315612 SEQ ID NO: 24 |
| AAVhu.4 | 264 | US20150315612 SEQ ID NO. 47 |
| AAVhu.4 | 265 | US20150315612 SEQ ID NO: 141 |
| AAVhu.40 | 266 | US20150315612 SEQ ID NO: 87 |
| AAVhu.40 (AAV114.3) | 267 | US20150315612 SEQ ID No: 11 |
| AAVhu.41 | 268 | US20150315612 SEQ ID NO: 91 |
| AAVhu.41 (AAV127.2) | 269 | US20150315612 SEQ ID NO: 6 |
| AAVhu.42 | 270 | US20150315612 SEQ ID NO: 85 |
| AAVhu.42 (AAV127.5) | 271 | US20150315612 SEQ ID NO. 8 |
| AAVhu.43 | 272 | US20150315612 SEQ ID NO: 160 |
| AAVhu.43 | 273 | US20150315612 SEQ ID NO: 236 |
| AAVhu.43 (AAV128.1) | 274 | US20150315612 SEQ ID NO: 80 |
| AAVhu.44 | 275 | US20150159173 SEQ ID NO: 45, US20150315612 SEQ ID NO: 158 |
| AAVhu.44 (AAV128.3) | 276 | US20150315612 SEQ ID NO. 81 |
| AAVhu.44R1 | 277 | US20150159173 |
| AAVhu.44R2 | 278 | US20150159173 |
| AAVhu.44R3 | 279 | US20150159173 |
| AAVhu.45 | 280 | US20150315612 SEQ ID NO: 76 |
| AAVhu.45 | 281 | US20150315612 SEQ ID NO: 127 |
| AAVhu.46 | 282 | US20150315612 SEQ ID NO: 82 |
| AAVhu.46 | 28.3 | US20150315612 SEQ ID NO: 159 |
| AAVhu.46 | 284 | US20150315612 SEQ ID NO: 224 |
| AAVhu.47 | 285 | US20150315612 SEQ ID NO: 77 |
| AAVhu.47 | 286 | US20150315612 SEQ ID NO: 128 |
| AAVhu.48 | 287 | US20150159173 SEQ ID NO. 38 |
| AAVhu.48 | 288 | US20150315612 SEQ ID NO: 157 |
| AAVhu.48 (AAV130.4) | 289 | US20150315612 SEQ ID NO: 78 |
| AAVhu.48R1 | 290 | US20150159173 |
| AAVhu.48R2 | 291 | US20150159173 |
| AAVhu.48R3 | 292 | US20150159173 |
| AAVhu.49 | 293 | US20150315612 SEQ ID NO: 209 |
| AAVhu.49 | 294 | US20150315612 SEQ ID NO: 189 |
| AAVhu.5 | 295 | US20150315612 SEQ ID NO: 45 |
| AAVhu.5 | 296 | US20150315612 SEQ ID NO: 142 |
| AAVhu.51 | 297 | US20150315612 SEQ ID NO: 208 |
| AAVhu.51 | 298 | US20150315612 SEQ ID NO: 190 |
| AAVhu.52 | 299 | US20150315612 S EQ ID NO 210 |
| AAVhu.52 | 300 | US20150315612 SEQ ID NO: 191 |
| AAVhu 53 | 301 | US20150159173 SEQ ID NO: 19 |
| AAVhu.53 | 302 | US20150159173 SEQ ID NO: 35 |
| AAVhu.53 (AAV145.1) | 303 | US20150315612 SEQ ID NO: 176 |
| AAVhu.54 | 304 | US20150315612 SEQ ID NO: 188 |
| AAVhu.54 (AAV145.5) | 305 | US20150315612 SEQ ID No: 177 |
| AAVhu.55 | 306 | US20150315612 SEQ ID NO: 187 |
| AAVhu.56 | 307 | US20150315612 SEQ ID NO: 205 |

TABLE 6-continued

| | | AAV Sequences |
|---|---|---|
| Serotype | SEQ ID NO: | Reference Information |
| AAVbu.56 (AAV145.6) | 308 | US20150315612 SEQ ID NO: 168 |
| AAVhu.56 (AAV145.6) | 309 | US20150315612 SEQ ID NO: 192 |
| AAVhu.57 | 310 | US20150315612 SEQ ID NO: 206 |
| AAVhu.57 | 311 | US20150315612 SEQ ID NO: 169 |
| AAVhu.57 | 312 | US20150315612 SEQ ID NO: 193 |
| AAVhu.58 | 313 | US20150315612 SEQ ID NO: 207 |
| AAVhu.58 | 314 | US20150315612 SEQ ID NO: 194 |
| AAVhu.6 (AAV3.1) | 315 | US20150315612 SEQ ID NO: 5 |
| AAVhu.6 (AAV3.1) | 316 | US20150315612 SEQ ID NO: 84 |
| AAVhu.60 | 317 | US20150315612 SEQ ID NO: 184 |
| AAVhu.60 (AAV161.10) | 318 | US20150315612 SEQ ID NO: 170 |
| AAVhu.61 | 339 | US20150315612 SEQ ID NO: 185 |
| AAVhu.61 (AAV161.6) | 320 | US20150315612 SEQ ID NO: 174 |
| AAVhu.63 | 321 | US20150315612 SEQ ID NO: 204 |
| AAVhu.63 | 322 | US20150315612 SEQ ID NO: 195 |
| AAVhu.64 | 323 | US20150315612 SEQ ID NO: 212 |
| AAVhu.64 | 324 | US20150315612 SEQ ID NO: 196 |
| AAVhu.66 | 325 | US20150315612 SEQ ID NO: 197 |
| AAVhu.67 | 326 | US20150315612 SEQ ID NO: 215 |
| AAVhu.67 | 327 | US20150315612 SEQ ID NO: 198 |
| AAVhu.7 | 328 | US20150315612 SEQ ID NO: 226 |
| AAVhu.7 | 329 | US20150315612 SEQ ID NO: 150 |
| AAVh.7 (AAV7.3) | 330 | US20150315612 SEQ ID NO: 55 |
| AAVhu.71 | 331 | US20150315612 SEQ ID NO: 79 |
| AAVhu.8 | 332 | US20150315612 SEQ ID NO: 53 |
| AAVhu.8 | 333 | US20150315612 SEQ ID NO: 12 |
| AAVhu.8 | 334 | US20150315612 SEQ ID NO: 151 |
| AAVhu.9 (AAV3.1) | 335 | US20150315612 SEQ ID NO: 58 |
| AAVhu.9 (AAV3.1) | 336 | US20150315612 SEQ ID NO: 155 |
| AAV-LK01 | 337 | US20150376607 SEQ ID NO: 2 |
| AAV-LK01 | 338 | US20150376607 SEQ ID NO: 29 |
| AAV-LK02 | 339 | US20150376607 SEQ ID NO: 3 |
| AAV-LK02 | 340 | US20150376607 SEQ ID NO: 30 |
| AAV-LK03 | 341 | US20150376607 SEQ ID NO: 4 |
| AAV-LK03 | 342 | WO2015121501 SEQ ID NO: 12, US20150376607 SEQ ID NO: 31 |
| AAV-LK04 | 343 | US20150376607 SEQ ID NO: 5 |
| AAV-LK04 | 344 | US20150376607 SEQ ID NO: 32 |
| AAV-LK05 | 345 | US20150376607 SEQ ID NO: 6 |
| AAV-LK05 | 346 | US20150376607 SEQ ID NO: 33 |
| AAV-LK06 | 347 | US20150376607 SEQ ID NO: 7 |
| AAV-LK06 | 348 | US20150376607 SEQ ID NO: 34 |
| AAV-LK07 | 349 | US20150376607 SEQ ID NO: 8 |
| AAV-LK07 | 350 | US20150376607 SEQ ID NO: 35 |
| AAV-LK08 | 351 | US20150376607 SEQ ID NO: 9 |
| AAV-LK08 | 352 | US20150376607 SEQ ID NO: 36 |
| AAV-LK09 | 353 | US20150376607 SEQ ID NO: 10 |
| AAV-LK09 | 354 | US20150376607 SEQ ID NO: 37 |
| AAV-LK10 | 355 | US20150376607 SEQ ID NO: 11 |
| AAV-LK10 | 356 | US20150376607 SEQ ID NO: 38 |
| AAV-LK11 | 357 | US20150376607 SEQ ID NO: 12 |
| AAV-LK11 | 358 | US20150376607 SEQ ID NO: 39 |
| AAV-LK12 | 359 | US20150376607 SEQ ID NO: 13 |
| AAV-LK12 | 360 | US20150376607 SEQ ID NO: 40 |
| AAV-LK13 | 361 | US20150376607 SEQ ID NO: 14 |
| AAV-LK13 | 362 | US20150376607 SEQ ID NO: 41 |
| AAV-LK14 | 363 | US20150376607 SEQ ID NO: 15 |
| AAV-LK14 | 364 | US20150376607 SEQ ID NO: 42 |
| AAV-LK15 | 365 | US20150376607 SEQ ID NO: 16 |
| AAV-LK15 | 366 | US20150376607 SEQ ID NO: 43 |
| AAV-LK16 | 367 | US20150376607 SEQ ID NO: 17 |
| AAV-LK16 | 368 | US20150376607 SEQ ID NO: 44 |
| AAV-LK17 | 369 | US20150376607 SEQ ID NO: 18 |
| AAV-LK17 | 370 | US20150376607 SEQ ID NO: 45 |
| AAV-LK8 | 371 | US20150376607 SEQ ID NO: 19 |
| AAV-LK18 | 372 | US20150376607 SEQ ID NO: 46 |
| AAV-LK19 | 373 | US20150376607 SEQ ID NO: 20 |
| AAV-LK19 | 374 | US20150376607 SEQ ID NO: 47 |
| AAV-PAEC | 375 | US20150376607 SEQ ID NO: 1 |
| AAV-PAEC | 376 | US20150376607 SEQ ID NO: 48 |
| AAV-PAEC11 | 377 | US20150376607 SEQ ID NO: 26 |
| AAV-PAEC11 | 378 | US20150376607 SEQ ID NO: 54 |
| AAV-PAEC12 | 379 | US20150376607 SEQ ID NO: 27 |
| AAV-PAEC12 | 380 | US20150376607 SEQ ID NO: 51 |
| AAV-PAEC13 | 381 | US20150376607 SEQ ID NO: 28 |

TABLE 6-continued

AAV Sequences

| Serotype | SEQ ID NO: | Reference Information |
|---|---|---|
| AAV-PAEC13 | 382 | US20150376607 SEQ ID NO: 49 |
| AAV-PAEC2 | 383 | US20150376607 SEQ ID NO: 21 |
| AAV-PAEC2 | 384 | US20150376607 SEQ ID NO: 56 |
| AAV-PAEC4 | 385 | US20150376607 SEQ ID NO: 22 |
| AAV-PAEC4 | 386 | US20150376607 SEQ ID NO: 55 |
| AAV-PAEC6 | 387 | US20150376607 SEQ ID NO: 23 |
| AAV-PAEC6 | 388 | US20150376607 SEQ ID NO: 52 |
| AAV-PAEC7 | 389 | US20150376607 SEQ ID NO: 24 |
| AAV-PAEC7 | 390 | US20150376607 SEQ ID NO: 53 |
| AAV-PAEC8 | 391 | US20150376607 SEQ ID NO: 25 |
| AAV-PAEC8 | 392 | US20150376607 SEQ ID NO: 50 |
| AAVpi.1 | 393 | US20150315612 SEQ ID NO: 28 |
| AAVpi.1 | 394 | US20150315612 SEQ ID NO: 93 |
| AAVpi.2 | 395 | US20150315612 SEQ ID NO: 30 |
| AAVpi.2 | 396 | US20150315612 SEQ ID NO: 95 |
| AAVpi.3 | 397 | US20150315612 SEQ ID NO: 29 |
| AAVpi.3 | 398 | US20150315612 SEQ ID NO: 94 |
| AAVrh.10 | 399 | US20150159173 SEQ ID NO: 9 |
| AAVrh.10 | 400 | US20150159173 SEQ ID NO: 25 |
| AAV44.2 | 401 | US20030138772 SEQ ID NO: 59 |
| AAVrh 10 (AAV44.2) | 402 | US20030138772 SEQ ID NO: 81 |
| AAV42.1B | 403 | US20030138772 SEQ ID NO: 90 |
| AAVrh.12 (AAV421b) | 404 | US20030138772 SEQ ID NO: 30 |
| AAVrh.13 | 405 | US20150159173 SEQ ID NO: 10 |
| AAVrh.13 | 406 | US20150159173 SEQ ID NO: 26 |
| AAVrh.13 | 407 | US20150315612 SEQ ID NO: 228 |
| AAVrh.13R | 408 | US20150159173 |
| AAV42.3A | 409 | US20030138772 SEQ ID NO: 87 |
| AAVrh.14 (AAV42.3a) | 410 | US20030138772 SEQ ID NO: 32 |
| AAV42.5A | 411 | US20030138772 SEQ ID NO: 89 |
| AAVrh.17 (AAV42Aa) | 412 | US20030138772 SEQ ID NO: 34 |
| AAV42.5B | 413 | US20030138772 SEQ ID NO: 91 |
| AAVrh.18 (AAV42.5b) | 414 | US20030138772 SEQ ID NO: 29 |
| AAV42.6B | 415 | US20030138772 SEQ ID NO: 112 |
| AAVrh.19 (AAV42.6b) | 416 | US20030138772 SEQ ID NO: 38 |
| AAVrh.2 | 417 | US20150159173 SEQ ID NO: 39 |
| AAVrh.2 | 418 | US20150315612 SEQ ID NO: 231 |
| AAVrh.20 | 419 | US20150159173 SEQ ID NO: 1 |
| AAV42.10 | 420 | US20030138772 SEQ ID NO: 106 |
| AAVrh.21 (AAV42.10) | 421 | US20030138772 SEQ ID NO: 35 |
| AAV42.11 | 422 | US20030138772 SEQ ID NO: 108 |
| AAVrh.22 (AAV42.11) | 423 | US20030138772 SEQ ID NO: 37 |
| AAV42.12 | 424 | US20030138772 SEQ ID NO: 113 |
| AAVrh.23 (AAV42.12) | 425 | US20030138772 SEQ ID NO: 58 |
| AAV42.13 | 426 | US20030138772 SEQ ID NO: 86 |
| AAVrh.24 (AAV42.13) | 427 | US20030138772 SEQ ID NO: 31 |
| AAV42.15 | 428 | US20030138772 SEQ ID NO: 84 |
| AAVrh.25 (AAV42.15) | 429 | US20030138772 SEQ ID NO: 28 |
| AAVrh.2R | 430 | US20150159173 |
| AAVrh.31 (AAV223.1) | 431 | US20030138772 SEQ ID NO: 48 |
| AAVC1 | 432 | US20030138772 SEQ ID NO: 60 |
| AAVrh.32 (AAVC1) | 433 | US20030138772 SEQ ID NO: 19 |
| AAVrh.32/33 | 434 | US20150159173 SEQ ID NO: 2 |
| AAVrh.33 (AAVC3) | 435 | US20030138772 SEQ ID NO: 20 |
| AAVC5 | 436 | US20030138772 SEQ ID NO: 62 |
| AAVrh.34 (AAVC5) | 437 | US20030138772 SEQ ID NO: 21 |
| AAVF1 | 438 | US20030138772 SEQ ID NO: 109 |
| AAVrh.35 (AAVF1) | 439 | US20030138772 SEQ ID NO: 22 |
| AAVF3 | 440 | US20030138772 SEQ ID NO: 111 |
| AAVrh.36 (AAVF3) | 441 | US20030138772 SEQ ID NO: 23 |
| AAVrh.37 | 442 | US20030138772 SEQ ID NO: 24 |
| AAVrh.37 | 443 | US20150159173 SEQ ID NO: 40 |
| AAVrh.37 | 444 | US20150315612 SEQ ID NO: 229 |
| AAVrh.37R2 | 445 | US20150159173 |
| AAVrh.38 (AAVLG-4) | 446 | US20150315612 SEQ ID NO: 7 |
| AAVrh.38 (AAVLG-4) | 447 | US20150315612 SEQ ID NO: 86 |
| AAVrh.39 | 448 | US20150159173 SEQ ID NO: 20, US20150315612 SEQ ID NO: 13 |
| AAVrh.39 | 449 | US20150159173 SEQ ID NO: 3, US20150159173 SEQ ID NO: 36, US20150315612 SEQ ID NO: 89 |
| AAVrh.40 | 450 | US20150315612 SEQ ID NO: 92 |
| AAVrh.40 (AAVLG-10) | 451 | US20150315612 SEQ ID No: 14 |
| AAVrh.43 (AAVN721-8) | 452 | US20150315612 SEQ ID NO: 43, US20150159173 SEQ ID NO: 21 |
| AAVrh.43 (AAVN721-8) | 453 | US20150315612 SEQ ID NO: 163, US20150159173 SEQ ID NO: 37 |

TABLE 6-continued

| | SEQ ID | |
|---|---|---|
| Serotype | NO: | Reference Information |
| AAVrh.44 | 454 | US20150315612 SEQ ID NO: 34 |
| AAVrh.44 | 455 | US20150315612 SEQ ID NO: 111 |
| AAVrh.45 | 456 | US20150315612 SEQ ID NO: 41 |
| AAVrh.45 | 457 | US20150315612 SEQ ID NO: 109 |
| AAVrh.46 | 458 | US20150159173 SEQ ID NO: 22, US20150315612 SEQ ID NO: 19 |
| AAVrh.46 | 459 | US20150159173 SEQ ID NO: 4, US20150315612 SEQ ID NO: 101 |
| AAVrh.47 | 460 | US20150315612 SEQ ID NO: 38 |
| AAVrh.47 | 461 | US20150315612 SEQ ID NO: 118 |
| AAVrh.48 | 462 | US20150159173 SEQ ID NO: 44, US20150315612 SEQ ID NO: 115 |
| AAVrh.48.1 | 463 | US20150159173 |
| AAVrh.48. 1.2 | 464 | US20150159173 |
| AAVrh.48.2 | 465 | US20150159173 |
| AAVrh.48 (AAVI-7) | 466 | US20150315612 SEQ ID NO: 32 |
| AAVrh.49 (AAV 1-8) | 467 | US20150315612 SEQ ID NO: 25 |
| AAVrh.49 (AAV 1-8) | 468 | US20150315612 SEQ ID NO: 103 |
| AAVrh.50 (AAV2-4) | 469 | US20150315612 SEQ ID NO: 23 |
| AAVrh.50 (AAV2-4) | 470 | US20150315612 SEQ ID NO: 108 |
| AAVrh.51 (AAV2-5) | 471 | US20150315612 SEQ ID No. 22 |
| AAVrh.51 (AAV2-5) | 472 | US20150315612 SEQ ID NO: 104 |
| AAVrh.52 (AAV3-9) | 473 | US20150315612 SEQ ID NO: 18 |
| AAVrh.52 (AAV3-9) | 474 | US20150315612 SEQ ID NO: 96 |
| AAVrh.53 | 475 | US20150315612 SEQ ID NO: 97 |
| AAVrh.53 (AAV3-11) | 476 | US20150315612 SEQ ID NO: 17 |
| AAVrh.53 (AAV3-11) | 477 | US20150315612 SEQ ID NO: 186 |
| AAVrh.54 | 478 | US20150315612 SEQ ID NO: 40 |
| AAVrh.54 | 479 | US20150159173 SEQ ID NO: 49, US20150315612 SEQ ID NO: 116 |
| AAVrh.55 | 480 | US20150315612 SEQ ID NO: 37 |
| AAVrh.55 (AAV4-19) | 481 | US20150315612 SEQ ID NO: 117 |
| AAVrh.56 | 482 | US20150315612 SEQ ID NO: 54 |
| AAVrh.56 | 483 | US20150315612 SEQ ID NO: 15.2 |
| AAVrh.57 | 484 | US20150315612 SEQ ID NO: 26 |
| AAVrh.57 | 485 | US20150315612 SEQ ID NO: 105 |
| AAVrh.58 | 486 | US20150315612 SEQ ID NO: 27 |
| AAVrh.58 | 487 | US20150159173 SEQ ID NO: 48, US20150315612 SEQ ID NO: 106 |
| AAVrh.58 | 488 | US20150315612 SEQ ID NO: 232 |
| AAVrh.59 | 489 | US20150315612 SEQ ID NO: 42 |
| AAVrh.59 | 490 | US20150315612 SEQ ID NO: 110 |
| AAVrh.60 | 491 | US20150315612 SEQ ID NO: 31 |
| AAVrh.60 | 492 | US20150315612 SEQ ID NO: 120 |
| AAVrh.61 | 493 | US20150315612 SEQ ID NO: 107 |
| AAVrh.61 (AAV2-3) | 494 | US20150315612 SEQ ID NO: 21 |
| AAVrh.62 (AAV2-15) | 495 | US20150315612 SEQ ID No: 3.3 |
| AAVrh.62 (AAV2-15) | 496 | US20150315612 SEQ ID NO: 114 |
| AAVrh.64 | 497 | US20150315612 SEQ ID No: 15 |
| AAVrh.64 | 498 | US20150159173 SEQ ID NO: 43, US20150315612 SEQ ID NO: 99 |
| AAVrh.64 | 499 | US20150315612 SEQ ID NO. 233 |
| AAVRh.64R1 | 500 | US20150159173 |
| AAVRh.64R2 | 501 | US20150159173 |
| AAVrh.65 | 502 | US20150315612 SEQ ID NO: 35 |
| AAVrh.65 | 503 | US20150315612 SEQ ID NO: 112 |
| AAVrh.67 | 504 | US20150315612 SEQ ID NO: 36 |
| AAVrh.67 | 505 | US20150315612 SEQ ID NO: 230 |
| AAVrh.67 | 506 | US20 150159173 SEQ ID NO: 47, US20150315612 SEQ ID NO: 113 |
| AAVrh.68 | 507 | US20150315612 SEQ ID NO: 16 |
| AAVrh.68 | 508 | US20150315612 SEQ ID NO: 100 |
| AAVrh.69 | 509 | US20150315612 SEQ ID NO: 39 |
| AAVrh.69 | 510 | US20 150315612 SEQ ID NO: 119 |
| AAVrh.70 | 511 | US20150315612 SEQ ID NO: 20 |
| AAVrh.70 | 512 | US20150315612 SEQ ID NO: 98 |
| AAVrh.71 | 513 | US201503 15612 SEQ ID NO: 162 |
| AAVrh.72 | 514 | US20150315612 SEQ ID NO: 9 |
| AAVrh.73 | 515 | US20150159173 SEQ ID NO: 5 |
| AAVrh.74 | 516 | US20150159173 SEQ ID NO: 6 |
| AAVrh.8 | 517 | US20150159173 SEQ ID NO: 41 |
| AAVrh.8 | 518 | US20150315612 SEQ ID NO. 235 |
| AAVrh.R | 519 | US20150159173, WO2015168666 SEQ ID NO: 9 |
| AAVrh.8R A586R mutant | 520 | WO2015168666 SEQ ID NO. 10 |
| AAVrh.8R R533A mutant | 521 | WO2015168666 SEQ ID NO: 11 |
| BAAV (bovine AAV) | 522 | U.S. Pat. No. 9,193,769 SEQ ID NO: 8 |
| BAAV (bovine AAV) | 523 | U.S. Pat. No. 9,193,769 SEQ ID NO: 10 |

TABLE 6-continued

| Serotype | SEQ ID NO: | Reference Information |
|---|---|---|
| | | AAV Sequences |
| BAAV (bovine AAV) | 524 | U.S. Pat. No. 9,193,769 SEQ ID NO: 4 |
| BAAV (bovine AAV) | 525 | U.S. Pat. No. 9,193,769 SEQ ID NO: 2 |
| BAAV (bovine AAV) | 526 | U.S. Pat. No. 9,193,769 SEQ ID NO: 6 |
| BAAV (bovine AAV) | 527 | U.S. Pat. No. 9,193,769 SEQ ID NO: 1 |
| BAAV (bovine AAV) | 528 | U.S. Pat. No. 9,193,769 SEQ ID NO: 5 |
| BAAV (bovine AAV) | 529 | U.S. Pat. No. 9,193,769 SEQ ID NO: 3 |
| BAAV (bovine AAV) | 530 | U.S. Pat. No. 9,193,769 SEQ ID NO: 11 |
| BAAV (bovine AAV) | 531 | U.S. Pat. No. 7,427,396 SEQ ID NO: 5 |
| BAAV (bovine AAV) | 532 | U.S. Pat. No. 7,427,396 SEQ ID NO: 6 |
| BAAV (bovine AAV) | 533 | U.S. Pat. No. 9,193,769 SEQ ID NO: 7 |
| BAAV (bovine AAV) | 534 | U.S. Pat. No. 9,193,769 SEQ ID NO: 9 |
| BNP61 AAV | 535 | US20150238550 SEQ ID NO |
| BNP61 AAV | 536 | US20150238550 SEQ ID NO: 2 |
| BNP62 AAV | 537 | US20150238550 SEQ ID NO: 3 |
| BNP63 AAV | 538 | US20150238550 SEQ ID NO: 4 |
| caprine AAV | 539 | U.S. Pat. No. 7,427,396 SEQ ID NO: 3 |
| caprine AAV | 540 | U.S. Pat. No. 7,427,396 SEQ ID NO: 4 |
| true type AAV (ttAAV) | 541 | WO2015121501 SEQ ID NO. 2 |
| AAAV (Avian AAV) | 542 | U.S. Pat. No. 9,238,800 SEQ ID NO: 12 |
| AAAV (Avian AAV) | 543 | U.S. Pat. No. 9,238,800 SEQ ID NO: 2 |
| AAAV (Avian AAV) | 544 | U.S. Pat. No. 9,238,800 SEQ ID NO: 6 |
| AAAV (Avian AAV) | 545 | U.S. Pat. No. 9,238,800 SEQ ID NO: 4 |
| AAAV (Avian AAV) | 546 | U.S. Pat. No. 9,238,800 SEQ ID NO: 8 |
| AAAV (Avian AAV) | 547 | U.S. Pat. No. 9,238,800 SEQ ID NO: 14 |
| AAAV (Avian AAV) | 548 | U.S. Pat. No. 9,238,800 SEQ ID NO: 10 |
| AAAV (Avian AAV) | 549 | U.S. Pat. No. 9,238,800 SEQ ID NO: 15 |
| AAAV (Avian AAV) | 550 | U.S. Pat. No. 9,238,800 SEQ ID NO: 5 |
| AAAV (Avian AAV) | 551 | U.S. Pat. No. 9,238,800 SEQ ID NO: 9 |
| AAAV (Avian AAV) | 552 | U.S. Pat. No. 9,238,800 SEQ ID NO: 3 |
| AAAV (Avian AAV) | 553 | U.S. Pat. No. 9,238,800 SEQ ID NO |
| AAAV (Avian AAV) | 554 | U.S. Pat. No. 9,238,800 SEQ ID NO: 11 |
| AAAV (Avian AAV) | 555 | U.S. Pat. No. 9,238,800 SEQ ID NO: 13 |
| AAAV (Avian AAV) | 556 | U.S. Pat. No. 9,238,800 SEQ ID NO: 1 |
| AAV Shuffle 100-1 | 557 | US20160017295 SEQ ID NO: 23 |
| AAV Shuffle 100-1 | 558 | US20160017295 SEQ ID NO: 11 |
| AAV Shuffle 100-2 | 559 | US20160017295 SEQ ID NO: 37 |
| AAV Shuffle 100-2 | 560 | US20160017295 SEQ ID NO: 29 |
| AAV Shuffle 100-3 | 561 | US20160017295 SEQ ID NO: 24 |
| AAV Shuffle 100-3 | 562 | US20160017295 SEQ ID NO: 12 |
| AAV Shuffle 100-7 | 563 | US20160017295 SEQ ID NO: 25 |
| AAV Shuffle 100-7 | 564 | US20160017295 SEQ ID NO: 13 |
| AAV Shuffle 10-2 | 565 | US20160017295 SEQ ID NO: 34 |
| AAV Shuffle 10-2 | 566 | US20160017295 SEQ ID NO: 26 |
| AAV Shuffle 10-6 | 567 | US20160017295 SEQ ID NO: 35 |
| AAV Shuffle 10-6 | 568 | US20160017295 SEQ ID NO: 27 |
| AAV Shuffle 10-8 | 569 | US20160017295 SEQ ID NO: 36 |
| AAV Shuffle 10-8 | 570 | US20160017295 SEQ ID NO: 28 |
| AAV SM 100-10 | 571 | US20160017295 SEQ ID NO: 41 |
| AAV SM 100-10 | 572 | US20160017295 SEQ ID NO: 33 |
| AAV SM 100-3 | 573 | US20160017295 SEQ ID NO: 40 |
| AAV SM 100-3 | 574 | US20160017295 SEQ ID NO: 32 |
| AAV SM 10-1 | 575 | US20160017295 SEQ ID NO: 38 |
| AAV SM 10-1 | 576 | US20160017295 SEQ ID NO: 30 |
| AAV SM 10-2 | 577 | US20160017295 SEQ ID NO: 10 |
| AAV SM 10-2 | 578 | US20160017295 SEQ ID NO: 22 |
| AAV SM 10-8 | 579 | US20160017295 SEQ ID NO: 39 |
| AAV SM 10-8 | 580 | US20160017295 SEQ ID NO: 31 |
| AAVF1/HSC1 | 581 | WO2016049230 SEQ ID NO: 20 |
| AAVF2/HSC2 | 582 | WO2016049230 SEQ ID NO: 21 |
| AAVF3/HSC3 | 583 | WO2016049230 SEQ ID NO: 22 |
| AAVF4/HSC4 | 584 | WO2016049230 SEQ ID NO: 23 |
| AAVF5/HSC5 | 585 | WO2016049230 SEQ ID NO: 25 |
| AAVF6/HSC6 | 586 | WO2016049230 SEQ ID NO: 24 |
| AAVF7/HSC7 | 587 | WO2016049230 SEQ ID NO: 27 |
| AAVF8/HSC8 | 588 | WO2016049230 SEQ ID NO: 28 |
| AAVF9/HSC9 | 589 | WO2016049230 SEQ ID NO: 29 |
| AAVF11/HSC11 | 590 | WO2016049230 SEQ ID NO: 26 |
| AAVF12/HSC12 | 591 | WO2016049230 SEQ ID NO: 30 |
| AAVF13/HSC13 | 592 | WO2016049230 SEQ ID NO: 31 |
| AAVF14/HSC14 | 593 | WO2016049230 SEQ ID NO: 32 |
| AAVF15/HSC15 | 594 | WO2016049230 SEQ ID NO: 33 |
| AAVF16/HSC16 | 595 | WO2016049230 SEQ ID NO: 34 |
| AAVF17/HSC17 | 596 | WO2016049230 SEQ ID NO: 35 |
| AAVF1/HSC1 | 597 | WO2016049230 SEQ ID NO: 2 |

TABLE 6-continued

| | AAV Sequences | |
|---|---|---|
| Serotype | SEQ ID NO: | Reference Information |
| AAVF2/HSC2 | 598 | WO2016049230 SEQ ID NO: 3 |
| AAVF3/HSC3 | 599 | WO2016049230 SEQ ID NO: 5 |
| AAVF4/HSC4 | 600 | WO2016049230 SEQ ID NO: 6 |
| AAVF5/HSC5 | 601 | WO2016049230 SEQ ID NO: 11 |
| AAVF6/HSC6 | 602 | WO2016049230 SEQ ID NO: 7 |
| AAVF7/HSC7 | 603 | WO2016049230 SEQ ID NO: 8 |
| AAVFS/HSC8 | 604 | WO2016049230 SEQ ID NO: 9 |
| AAVF9/HSC9 | 605 | WO2016049230 SEQ ID NO: 10 |
| AAVF11/HSC11 | 606 | WO2016049230 SEQ ID NO: 4 |
| AAVF12/HSC12 | 607 | WO2016049230 SEQ ID NO: 12 |
| AAVF13/HSC13 | 608 | WO2016049230 SEQ ID NO: 14 |
| AAVF14/HSC14 | 609 | WO2016049230 SEQ ID NO: 15 |
| AAVF15/HSC15 | 610 | WO2016049230 SEQ ID NO: 16 |
| AAVF16/HSC16 | 611 | WO2016049230 SEQ ID NO: 17 |
| AAVF17/HSC17 | 632 | WO2016049230 SEQ ID NO: 13 |
| AAV CBr-E1 | 613 | U.S. Pat. No. 8,734,809 SEQ ID NO: 13 |
| AAV CBr-E2 | 614 | U.S. Pat. No. 8,734,809 SEQ ID NO: 14 |
| AAV CBr-E3 | 615 | U.S. Pat. No. 8,734,809 SEQ ID NO: 15 |
| AAV CBr-E4 | 616 | U.S. Pat. No. 8,734,809 SEQ ID NO: 16 |
| AAV CBr-E5 | 617 | U.S. Pat. No. 8,734,809 SEQ ID NO: 17 |
| AAV CBr-e5 | 618 | U.S. Pat. No. 8,734,809 SEQ ID NO: 18 |
| AAV CBr-E6 | 619 | U.S. Pat. No. 8,734,809 SEQ ID NO. 19 |
| AAV CBr-E7 | 620 | U.S. Pat. No. 8,734,809 SEQ ID NO: 20 |
| AAV CBr-E8 | 621 | U.S. Pat. No. 8,734,809 SEQ ID NO: 21 |
| AAV CLv-D1 | 622 | U.S. Pat. No. 8,734,809 SEQ ID NO: 22 |
| AAV CLv-D2 | 623 | U.S. Pat. No. 8,734,809 SEQ ID NO: 23 |
| AAV CLv-D3 | 624 | U.S. Pat. No. 8,734,809 SEQ ID NO: 24 |
| AAV CLv-D4 | 625 | U.S. Pat. No. 8,734,809 SEQ ID NO: 25 |
| AAV CLv-D5 | 626 | U.S. Pat. No. 8,734,809 SEQ ID NO. 26 |
| AAV CLv-D6 | 627 | U.S. Pat. No. 8,734,809 SEQ ID NO: 27 |
| AAV CLv-D7 | 628 | U.S. Pat. No. 8,734,809 SEQ ID NO: 28 |
| AAV CLv-D8 | 629 | U.S. Pat. No. 8,734,809 SEQ ID NO: 29 |
| AAV CLv-E1 | 630 | U.S. Pat. No. 8,734,809 SEQ ID NO: 13 |
| AAV CLv-R1 | 631 | U.S. Pat. No. 8,734,809 SEQ ID NO: 30 |
| AAV CLv-R2 | 632 | U.S. Pat. No. 8,734,809 SEQ ID NO: 31 |
| AAV CLv-R3 | 633 | U.S. Pat. No. 8,734,809 SEQ ID NO: 32 |
| AAV CLv-R4 | 634 | U.S. Pat. No. 8,734,809 SEQ ID NO: 33 |
| AAV CLv-R5 | 635 | U.S. Pat. No. 8,734,809 SEQ ID NO: 34 |
| AAV CLv-R6 | 636 | U.S. Pat. No. 8,734,809 SEQ ID NO: 35 |
| AAV CLv-R7 | 637 | U.S. Pat. No. 8,734,809 SEQ ID NO: 36 |
| AAV CLv-R8 | 638 | U.S. Pat. No. 8,734,809 SEQ ID NO: 37 |
| AAV CLv-R9 | 639 | U.S. Pat. No. 8,734,809 SEQ ID NO: 38 |
| AAV CLg-F1 | 640 | U.S. Pat. No. 8,734,809 SEQ ID NO: 39 |
| AAV CLg-F2 | 641 | U.S. Pat. No. 8,734,809 SEQ ID NO: 40 |
| AAV CLg-F3 | 642 | U.S. Pat. No. 8,734,809 SEQ ID NO: 41 |
| AAV CLg-F4 | 643 | U.S. Pat. No. 8,734,809 SEQ ID NO: 42 |
| AAV CLg-F5 | 644 | U.S. Pat. No. 8,734,809 SEQ ID NO: 43 |
| AAV CLg-F6 | 645 | U.S. Pat. No. 8,734,809 SEQ ID NO: 43 |
| AAV CLg-F7 | 646 | U.S. Pat. No. 8,734,809 SEQ ID NO: 44 |
| AAV CLg-F8 | 647 | U.S. Pat. No. 8,734,809 SEQ ID NO: 43 |
| AAV CSp-1 | 648 | U.S. Pat. No. 8,734,809 SEQ ID NO: 45 |
| AAV CSp-10 | 649 | U.S. Pat. No. 8,734,809 SEQ ID NO: 46 |
| AAV CSp-11 | 650 | U.S. Pat. No. 8,734,809 SEQ ID NO: 47 |
| AAV CSp-2 | 651 | U.S. Pat. No. 8,734,809 SEQ ID NO: 48 |
| AAV CSp-3 | 652 | U.S. Pat. No. 8,734,809 SEQ ID NO: 49 |
| AAV CSp-4 | 653 | U.S. Pat. No. 8,734,809 SEQ ID NO: 50 |
| AAV CSp-6 | 654 | U.S. Pat. No. 8,734,809 SEQ ID NO: 51 |
| AAV CSp-7 | 655 | U.S. Pat. No. 8,734,809 SEQ ID NO: 52 |
| AAV CSp-8 | 656 | U.S. Pat. No. 8,734,809 SEQ ID NO: 53 |
| AAV CSp-9 | 657 | U.S. Pat. No. 8,734,809 SEQ ID NO: 54 |
| AAV CHt-2 | 658 | U.S. Pat. No. 8,734,809 SEQ ID NO: 55 |
| AAV CHt-3 | 659 | U.S. Pat. No. 8,734,809 SEQ ID NO: 56 |
| AAV CKd-1 | 660 | U.S. Pat. No. 8,734,809 SEQ ID NO: 57 |
| AAV CKd-10 | 661 | U.S. Pat. No. 8,734,809 SEQ ID NO: 58 |
| AAV CKd-2 | 662 | U.S. Pat. No. 8,734,809 SEQ ID NO: 59 |
| AAV CKd-3 | 663 | U.S. Pat. No. 8,734,809 SEQ ID NO: 60 |
| AAV CKd-4 | 664 | U.S. Pat. No. 8,734,809 SEQ ID NO: 61 |
| AAV CKd-6 | 665 | U.S. Pat. No. 8,734,809 SEQ ID NO: 62 |
| AAV CKd-7 | 666 | U.S. Pat. No. 8,734,809 SEQ ID NO: 63 |
| AAV CKd-8 | 667 | U.S. Pat. No. 8,734,809 SEQ ID NO: 64 |
| AAV CLv-1 | 668 | U.S. Pat. No. 8,734,809 SEQ ID NO: 65 |
| AAV CLv-12 | 669 | U.S. Pat. No. 8,734,809 SEQ ID NO: 66 |
| AAV CLv-13 | 670 | U.S. Pat. No. 8,734,809 SEQ ID NO: 67 |
| AAV CLv-2 | 671 | U.S. Pat. No. 8,734,809 SEQ ID NO: 68 |

TABLE 6-continued

| | | AAV Sequences |
|---|---|---|
| Serotype | SEQ ID NO: | Reference Information |
| AAV CLv3 | 672 | U.S. Pat. No. 8,734,809 SEQ ID NO: 69 |
| AAV CLv-4 | 673 | U.S. Pat. No. 8,734,809 SEQ ID NO: 70 |
| AAV CLv-6 | 674 | U.S. Pat. No. 8,734,809 SEQ ID NO: 71 |
| AAV CLv-8 | 675 | U.S. Pat. No. 8,734,809 SEQ ID NO: 72 |
| AAV CKd-B1 | 676 | U.S. Pat. No. 8,734,809 SEQ ID NO: 73 |
| AAV CKd-B2 | 677 | U.S. Pat. No. 8,734,809 SEQ ID NO: 74 |
| AAV CKd-B3 | 678 | U.S. Pat. No. 8,734,809 SEQ ID NO: 75 |
| AAV CKd-B4 | 679 | U.S. Pat. No. 8,734,809 SEQ ID NO: 76 |
| AAV CKd-B5 | 680 | U.S. Pat. No. 8,734,809 SEQ ID NO: 77 |
| AAV CKd-B6 | 681 | U.S. Pat. No. 8,734,809 SEQ ID NO: 78 |
| AAV CKd-B7 | 682 | U.S. Pat. No. 8,734,809 SEQ ID NO: 79 |
| AAV CKd-B8 | 683 | U.S. Pat. No. 8,734,809 SEQ ID NO: 80 |
| AAV CKd-H1 | 684 | U.S. Pat. No. 8,734,809 SEQ ID NO: 81 |
| AAV CKd-H2 | 685 | U.S. Pat. No. 8,734,809 SEQ ID NO: 82 |
| AAV CKd-H3 | 686 | U.S. Pat. No. 8,734,809 SEQ ID NO: 83 |
| AAV CKd-H4 | 687 | U.S. Pat. No. 8,734,809 SEQ ID NO: 84 |
| AAV CKd-H5 | 688 | U.S. Pat. No. 8,734,809 SEQ ID NO: 85 |
| AAV CKd-H6 | 689 | U.S. Pat. No. 8,734,809 SEQ ID NO: 77 |
| AAV CHt-1 | 690 | U.S. Pat. No. 8,734,809 SEQ ID NO: 86 |
| AAV CLv1-1 | 691 | U.S. Pat. No. 8,734,809 SEQ ID NO: 171 |
| AAV CLv1-2 | 692 | U.S. Pat. No. 8,734,809 SEQ ID NO: 172 |
| AAV CLv1-3 | 693 | U.S. Pat. No. 8,734,809 SEQ ID NO: 173 |
| AAV CLv1-4 | 694 | U.S. Pat. No. 8,734,809 SEQ ID NO: 174 |
| AAV Clv1-7 | 695 | U.S. Pat. No. 8,734,809 SEQ ID NO: 175 |
| AAV Clv1-8 | 696 | U.S. Pat. No. 8,734,809 SEQ ID NO: 176 |
| AAV Clv1-9 | 697 | U.S. Pat. No. 8,734,809 SEQ ID NO: 177 |
| AAV Clv1-10 | 698 | U.S. Pat. No. 8,734,809 SEQ ID NO: 178 |
| AAV.VR-355 | 699 | U.S. Pat. No. 8,734,809 SEQ ID NO: 181 |
| AAV.hu.48R3 | 700 | U.S. Pat. No. 8,734,809 SEQ ID NO: 183 |
| AAV CBr-E1 | 701 | U.S. Pat. No. 8,734,809 SEQ ID NO: 87 |
| AAV CBr-E2 | 702 | U.S. Pat. No. 8,734,809 SEQ ID NO: 88 |
| AAV CBr-E3 | 703 | U.S. Pat. No. 8,734,809 SEQ ID NO: 89 |
| AAV CBr-E4 | 704 | U.S. Pat. No. 8,734,809 SEQ ID NO: 90 |
| AAV CBr-E5 | 705 | U.S. Pat. No. 8,734,809 SEQ ID NO: 91 |
| AAV CBr-e5 | 706 | U.S. Pat. No. 8,734,809 SEQ ID NO: 92 |
| AAV CBr-E6 | 707 | U.S. Pat. No. 8,734,809 SEQ ID NO: 93 |
| AAV CBr-E7 | 708 | U.S. Pat. No. 8,734,809 SEQ ID NO: 94 |
| AAV CBr-E8 | 709 | U.S. Pat. No. 8,734,809 SEQ ID NO: 95 |
| AAV CLv-D1 | 710 | U.S. Pat. No. 8,734,809 SEQ ID NO: 96 |
| AAV CLv-D2 | 711 | U.S. Pat. No. 8,734,809 SEQ ID NO: 97 |
| AAV CLv-D3 | 712 | U.S. Pat. No. 8,734,809 SEQ ID NO: 98 |
| AAV CLv-D4 | 713 | U.S. Pat. No. 8,734,809 SEQ ID NO: 99 |
| AAV CLv-D5 | 714 | U.S. Pat. No. 8,734,809 SEQ ID NO: 100 |
| AAV CLv-D6 | 715 | U.S. Pat. No. 8,734,809 SEQ ID NO: 101 |
| AAV CLv-D7 | 716 | U.S. Pat. No. 8,734,809 SEQ ID NO: 102 |
| AAV CLv-D8 | 717 | U.S. Pat. No. 8,734,809 SEQ ID NO: 103 |
| AAV CLv-E1 | 718 | U.S. Pat. No. 8,734,809 SEQ ID NO: 87 |
| AAV CLv-R1 | 719 | U.S. Pat. No. 8,734,809 SEQ ID NO: 104 |
| AAV CLv-R2 | 720 | U.S. Pat. No. 8,734,809 SEQ ID NO: 105 |
| AAV CLv-R3 | 721 | U.S. Pat. No. 8,734,809 SEQ ID NO: 106 |
| AAV CLv-R4 | 722 | U.S. Pat. No. 8,734,809 SEQ ID NO: 107 |
| AAV CLv-R5 | 723 | U.S. Pat. No. 8,734,809 SEQ ID NO: 108 |
| AAV CLv-R6 | 724 | U.S. Pat. No. 8,734,809 SEQ ID NO: 109 |
| AAV CLv-R7 | 725 | U.S. Pat. No. 8,734,809 SEQ ID NO: 110 |
| AAV CLv-R8 | 726 | U.S. Pat. No. 8,734,809 SEQ ID NO: 111 |
| AAV CLv-R9 | 727 | U.S. Pat. No. 8,734,809 SEQ ID NO: 112 |
| AAV CLg-F1 | 728 | U.S. Pat. No. 8,734,809 SEQ ID NO: 113 |
| AAV CLg-F2 | 729 | U.S. Pat. No. 8,734,809 SEQ ID NO: 114 |
| AAV CLg-F3 | 730 | U.S. Pat. No. 8,734,809 SEQ ID NO: 115 |
| AAV CLg-F4 | 731 | U.S. Pat. No. 8,734,809 SEQ ID NO: 116 |
| AAV CLg-F5 | 732 | U.S. Pat. No. 8,734,809 SEQ ID NO: 117 |
| AAV CLg-F6 | 733 | U.S. Pat. No. 8,734,809 SEQ ID NO: 117 |
| AAV CLg-F7 | 734 | U.S. Pat. No. 8,734,809 SEQ ID NO: 118 |
| AAV CLg-F8 | 735 | U.S. Pat. No. 8,734,809 SEQ ID NO: 117 |
| AAV CSp-1 | 736 | U.S. Pat. No. 8,734,809 SEQ ID NO: 119 |
| AAV CSp-10 | 737 | U.S. Pat. No. 8,734,809 SEQ ID NO: 120 |
| AAV CSp-11 | 738 | U.S. Pat. No. 8,734,809 SEQ ID NO: 121 |
| AAV CSp-2 | 739 | U.S. Pat. No. 8,734,809 SEQ ID NO: 122 |
| AAV CSp-3 | 740 | U.S. Pat. No. 8,734,809 SEQ ID NO: 123 |
| AAV CSp-4 | 741 | U.S. Pat. No. 8,734,809 SEQ ID NO: 124 |
| AAV CSp-6 | 742 | U.S. Pat. No. 8,734,809 SEQ ID NO: 125 |
| AAV CSp-7 | 743 | U.S. Pat. No. 8,734,809 SEQ ID NO: 126 |
| AAV CSp-8 | 744 | U.S. Pat. No. 8,734,809 SEQ ID NO: 127 |
| AAV CSp-9 | 745 | U.S. Pat. No. 8,734,809 SEQ ID NO: 128 |

TABLE 6-continued

| | AAV Sequences | |
|---|---|---|
| Serotype | SEQ ID NO: | Reference Information |
| AAV CHt-2 | 746 | U.S. Pat. No. 8,734,809 SEQ ID NO: 129 |
| AAV CHt-3 | 747 | U.S. Pat. No. 8,734,809 SEQ ID NO: 130 |
| AAV CKd-1 | 748 | U.S. Pat. No. 8,734,809 SEQ ID NO: 131 |
| AAV CKd-10 | 749 | U.S. Pat. No. 8,734,809 SEQ ID NO: 132 |
| AAV CKd-2 | 750 | U.S. Pat. No. 8,734,809 SEQ ID NO: 133 |
| AAV CKd-3 | 751 | U.S. Pat. No. 8,734,809 SEQ ID NO: 134 |
| AAV CKd-4 | 752 | U.S. Pat. No. 8,734,809 SEQ ID NO: 135 |
| AAV CKd-6 | 753 | U.S. Pat. No. 8,734,809 SEQ ID NO: 136 |
| AAV CKd-7 | 754 | U.S. Pat. No. 8,734,809 SEQ ID NO: 137 |
| AAV CKd-8 | 755 | U.S. Pat. No. 8,734,809 SEQ ID NO: 138 |
| AAV CLv-1 | 756 | U.S. Pat. No. 8,734,809 SEQ ID NO: 139 |
| AAV CLv-12 | 757 | U.S. Pat. No. 8,734,809 SEQ ID NO: 140 |
| AAV CLv-13 | 758 | U.S. Pat. No. 8,734,809 SEQ ID NO: 141 |
| AAV CLv-2 | 759 | U.S. Pat. No. 8,734,809 SEQ ID NO: 142 |
| AAV CLv-3 | 760 | U.S. Pat. No. 8,734,809 SEQ ID NO: 143 |
| AAV CLv-4 | 761 | U.S. Pat. No. 8,734,809 SEQ ID NO: 144 |
| AAV CLv-6 | 762 | U.S. Pat. No. 8,734,809 SEQ ID NO: 145 |
| AAV CLv-8 | 763 | U.S. Pat. No. 8,734,809 SEQ ID NO: 146 |
| AAV CKd-B1 | 764 | U.S. Pat. No. 8,734,809 SEQ ID NO: 147 |
| AAV CKd-B2 | 765 | U.S. Pat. No. 8,734,809 SEQ ID NO: 148 |
| AAV CKd-B3 | 766 | U.S. Pat. No. 8,734,809 SEQ ID NO: 149 |
| AAV CKd-B4 | 767 | U.S. Pat. No. 8,734,809 SEQ ID NO: 150 |
| AAV CKd-B5 | 768 | U.S. Pat. No. 8,734,809 SEQ ID NO: 151 |
| AAV CKd-B6 | 769 | U.S. Pat. No. 8,734,809 SEQ ID NO: 152 |
| AAV CKd-B7 | 770 | U.S. Pat. No. 8,734,809 SEQ ID NO: 153 |
| AAV CKd-B8 | 771 | U.S. Pat. No. 8,734,809 SEQ ID NO: 154 |
| AAV CKd-H1 | 772 | U.S. Pat. No. 8,734,809 SEQ ID NO: 155 |
| AAV CKd-H2 | 773 | U.S. Pat. No. 8,734,809 SEQ ID NO: 156 |
| AAV CKd-H3 | 774 | U.S. Pat. No. 8,734,809 SEQ ID NO: 157 |
| AAV CKd-H4 | 775 | U.S. Pat. No. 8,734,809 SEQ ID NO: 158 |
| AAV CKd-H5 | 776 | U.S. Pat. No. 8,734,809 SEQ ID NO: 159 |
| AAV CKd-H6 | 777 | U.S. Pat. No. 8,734,809 SEQ ID NO: 151 |
| AAV CHt-1 | 778 | U.S. Pat. No. 8,734,809 SEQ ID NO: 160 |
| AAV CHt-P2 | 779 | WO2016065001 SEQ ID NO: 1 |
| AAV CHt-P5 | 780 | WO2016065001 SEQ ID NO: 2 |
| AAV CHt-P9 | 781 | WO2016065001 SEQ ID NO: 3 |
| AAV CBr-7.1 | 782 | WO2016065001 SEQ ID NO. 4 |
| AAV CBr-7.2 | 783 | WO2016065001 SEQ ID NO. 5 |
| AAV CBr-7.3 | 784 | WO2016065001 SEQ ID NO: 6 |
| AAV CBr-7.4 | 785 | WO2016065001 SEQ ID NO: 7 |
| AAV CBr-7.5 | 786 | WO2016065001 SEQ ID NO: 8 |
| AAV CBr-7.7 | 787 | WO2016065001 SEQ ID NO: 9 |
| AAV CBr-7.8 | 788 | WO2016065001 SEQ ID NO: 10 |
| AAV CBr-7.10 | 789 | WO2016065001 SEQ ID NO: 11 |
| AAV CKd-N3 | 790 | WO2016065001 SEQ ID NO. 12 |
| AAV CKd-N4 | 791 | WO2016065001 SEQ ID NO: 13 |
| AAV CKd-N9 | 792 | WO2016065001 SEQ ID NO: 14 |
| AAV CLv-14 | 793 | WO2016065001 SEQ ID NO: 15 |
| AAV CLv-L5 | 794 | WO2016065001 SEQ ID NO: 16 |
| AAV CLv-L6 | 795 | WO2016065001 SEQ ID NO: 17 |
| AAV CLv-K1 | 796 | WO2016065001 SEQ ID NO: 18 |
| AAV CLv-K3 | 797 | WO2016065001 SEQ ID NO. 19 |
| AAV CLv-K6 | 798 | WO2016065001 SEQ ID NO: 20 |
| AAV CLv-M1 | 799 | WO2016065001 SEQ ID NO: 21 |
| AAV CLv-M11 | 800 | WO2016065001 SEQ ID NO: 22 |
| AAV CLv-M2 | 801 | WO2016065001 SEQ ID NO: 23 |
| AAV CLv-M5 | 802 | WO2016065001 SEQ ID NO: 24 |
| AAV CLv-M6 | 803 | WO2016065001 SEQ ID NO: 25 |
| AAV CLv-M7 | 804 | WO2016065001 SEQ ID NO: 26 |
| AAV CLv-MB | 805 | WO2016065001 SEQ ID NO: 27 |
| AAV CLv-M9 | 806 | WO2016065001 SEQ ID NO: 28 |
| AAV CHt-P1 | 807 | WO2016065001 SEQ ID NO: 29 |
| AAV CHt-P | 808 | WO2016065001 SEQ ID NO: 30 |
| AAV CHt-P8 | 809 | WO2016065001 SEQ ID NO: 31 |
| AAV CHt-6.1 | 810 | WO2016065001 SEQ ID NO: 32 |
| AAV CHt-6.10 | 811 | WO2016065001 SEQ ID NO: 33 |
| AAV CHt-6.5 | 812 | WO2016065001 SEQ ID NO: 34 |
| AAV CHt-6.6 | 813 | WO2016065001 SEQ ID NO: 35 |
| AAV CHt-6.7 | 814 | WO2016065001 SEQ ID NO: 36 |
| AAV CHt-6.8 | 815 | WO2016065001 SEQ ID NO: 37 |
| AAV CSp-8.10 | 816 | WO2016065001 SEQ ID NO: 38 |
| AAV CSp-8.2 | 817 | WO2016065001 SEQ ID NO: 39 |
| AAV CSp-8.4 | 818 | WO2016065001 SEQ ID NO: 40 |
| AAV CSp-8.5 | 819 | WO2016065001 SEQ ID NO: 41 |

TABLE 6-continued

| | | |
|---|---|---|
| | AAV Sequences | |

| Serotype | SEQ ID NO: | Reference Information |
|---|---|---|
| AAV CSp-8.6 | 820 | WO2016065001 SEQ ID NO: 42 |
| AAV CSp-8.7 | 821 | WO2016065001 SEQ ID NO: 43 |
| AAV CSp-8.8 | 822 | WO2016065001 SEQ ID NO: 44 |
| AAV CSp-8.9 | 823 | WO2016065001 SEQ ID NO: 45 |
| AAV CBr-B7.3 | 824 | WO2016065001 SEQ ID NO: 46 |
| AAV CBr-B7.4 | 825 | WO2016065001 SEQ ID NO: 47 |
| AAV3B | 826 | WO2016065001 SEQ ID NO: 48 |
| AAV4 | 827 | WO2016065001 SEQ ID NO: 49 |
| AAV5 | 828 | WO2016065001 SEQ ID NO: 50 |
| AAV CHt-P2 | 829 | WO2016065001 SEQ ID NO: 51 |
| AAV CHt-P5 | 830 | WO2016065001 SEQ ID NO: 52 |
| AAV CHt-P9 | 831 | WO2016065001 SEQ ID NO: 53 |
| AAV CBr-7.1 | 832 | WO2016065001 SEQ ID NO: 54 |
| AAV CBr-7.2 | 833 | WO2016065001 SEQ ID NO: 55 |
| AAV CBr-7.3 | 834 | WO2016065001 SEQ ID NO: 56 |
| AAV CBr-7.4 | 835 | WO2016065001 SEQ ID NO: 57 |
| AAV CBr-7.5 | 836 | WO2016065001 SEQ ID NO: 58 |
| AAV CBr-7.7 | 837 | WO2016065001 SEQ ID NO: 59 |
| AAV CBr-7.8 | 838 | WO2016065001 SEQ ID NO: 60 |
| AAV CBr-7.10 | 839 | WO2016065001 SEQ ID NO: 61 |
| AAV CKd-N3 | 840 | WO2016065001 SEQ ID NO: 62 |
| AAV CKd-N4 | 841 | WO2016065001 SEQ ID NO: 63 |
| AAV CKd-N9 | 842 | WO2016065001 SEQ ID NO: 64 |
| AAV CLv-L4 | 843 | WO2016065001 SEQ ID NO: 65 |
| AAV CLv-L5 | 844 | WO2016065001 SEQ ID NO: 66 |
| AAV CLv-L6 | 845 | WO2016065001 SEQ ID NO: 67 |
| AAV CLv-K1 | 846 | WO2016065001 SEQ ID NO: 68 |
| AAV CLv-K3 | 847 | WO2016065001 SEQ ID NO: 69 |
| AAV CLv-K6 | 848 | WO2016065001 SEQ ID NO: 70 |
| AAV CLv-M1 | 849 | WO2016065001 SEQ ID NO: 71 |
| AAV CLv-M1 | 850 | WO2016065001 SEQ ID NO: 72 |
| AAV CLv-M2 | 851 | WO2016065001 SEQ ID NO: 73 |
| AAV CLv-M5 | 852 | WO2016065001 SEQ ID NO: 74 |
| AAV CLv-M6 | 853 | WO2016065001 SEQ ID NO: 75 |
| AAV CLv-M7 | 854 | WO2016065001 SEQ ID NO: 76 |
| AAV CLv-M8 | 855 | WO2016065001 SEQ ID NO: 77 |
| AAV CLv-M9 | 856 | WO2016065001 SEQ ID NO: 78 |
| AAV CHt-P1 | 857 | WO2016065001 SEQ ID NO: 79 |
| AAV CHt-P6 | 858 | WO2016065001 SEQ ID NO: 80 |
| AAV CHt-P8 | 859 | WO2016065001 SEQ ID NO: 81 |
| AAV CHt-6.1 | 860 | WO2016065001 SEQ ID NO: 82 |
| AAV CHt-6.10 | 861 | WO2016065001 SEQ ID NO: 83 |
| AAV CHt-6.5 | 862 | WO2016065001 SEQ ID NO: 84 |
| AAV CHt-6.6 | 863 | WO2016065001 SEQ ID NO: 85 |
| AAV CHt-6.7 | 864 | WO2016065001 SEQ ID NO: 86 |
| AAV CHt-6.8 | 865 | WO2016065001 SEQ ID NO: 87 |
| AAV CSp-8.10 | 866 | WO2016065001 SEQ ID NO: 88 |
| AAV CSp-8.2 | 867 | WO2016065001 SEQ ID NO: 89 |
| AAV CSp-8.4 | 868 | WO2016065001 SEQ ID NO: 90 |
| AAV CSp-8.5 | 869 | WO2016065001 SEQ ID NO: 91 |
| AAV CSp-8.6 | 870 | WO2016065001 SEQ ID NO: 92 |
| AAV CSp-8.7 | 871 | WO2016065001 SEQ ID NO: 93 |
| AAV CSp-8.8 | 872 | WO2016065001 SEQ ID NO: 94 |
| AAV CSp-8.9 | 873 | WO2016065001 SEQ ID NO: 95 |
| AAV CBr-B7.3 | 874 | WO2016065001 SEQ ID NO: 96 |
| AAV CBr-B7.4 | 875 | WO2016065001 SEQ ID NO: 97 |
| AAV3B | 876 | WO2016065001 SEQ ID NO: 98 |
| AAV4 | 877 | WO2016065001 SEQ ID NO: 99 |
| AAV5 | 878 | WO2016065001 SEQ ID NO: 100 |
| GPV | 879 | U.S. Pat. No. 9,624,274 B2 SEQ ID NO: 192 |
| B19 | 880 | U.S. Pat. No. 9,624,274 B2 SEQ ID NO: 193 |
| MVM | 881 | U.S. Pat. No. 9,624,274 B2 SEQ ID NO: 194 |
| FPV | 882 | U.S. Pat. No. 9,624,274 B2 SEQ ID NO: 195 |
| CPV | 883 | U.S. Pat. No. 9,624,274 B2 SEQ ID NO: 196 |
| AAV6 | 884 | U.S. Pat. No. 9,546,112 B2 SEQ ID NO: 5 |
| AAV6 | 885 | U.S. Pat. No. 9,457,103 B2 SEQ ID NO: 1 |
| AAV2 | 886 | U.S. Pat. No. 9,457,103 B2 SEQ ID NO: 2 |
| ShH10 | 887 | U.S. Pat. No. 9,457,103 B2 SEQ ID NO: 3 |
| ShH10 | 888 | U.S. Pat. No. 9,457,103 B2 SEQ ID NO: 4 |
| ShH10 | 889 | U.S. Pat. No. 9,457,103 B2 SEQ ID NO: 5 |
| ShH10 | 890 | U.S. Pat. No. 9,457,103 B2 SEQ ID NO: 6 |
| ShH10 | 891 | U.S. Pat. No. 9,457,103 B2 SEQ ID NO: 7 |
| ShH10 | 892 | U.S. Pat. No. 9,457,103 B2 SEQ ID NO: 8 |
| ShH10 | 893 | U.S. Pat. No. 9,457,103 B2 SEQ ID NO: 9 |

TABLE 6-continued

| | | |
|---|---|---|
| | | AAV Sequences |

| Serotype | SEQ ID NO: | Reference Information |
|---|---|---|
| rh74 | 894 | U.S. Pat. No. 9,434,928 B2 SEQ ID NO: 1, US2015023924A1 SEQ ID NO: 2 |
| rh74 | 895 | U.S. Pat. No. 9,434,928 B2 SEQ ID NO: 2, US2015023924A1 SEQ ID NO: 1 |
| AAV8 | 896 | U.S. Pat. No. 9,434,928 B2 SEQ ID NO: 4 |
| rh74 | 897 | U.S. Pat. No. 9,434,928 B2 SEQ ID NO: 5 |
| rh74 (RHM4-1) | 898 | US2015023924A1 SEQ ID NO: 5, US20160375110A1 SEQ ID NO: 4 |
| rh74 (RHM15-1) | 899 | US2015023924A1 SEQ ID NO: 6, US2016037510A1 SEQ ID NO: 5 |
| rh74 (RHM15-2) | 900 | US2015023924A1 SEQ ID NO: 7, US20160375110A1 SEQ ID NO: 6 |
| rh74 (RHM15-3/RHM15-5) | 901 | US2015023924A1 SEQ ID NO: 8, US20160375110A1 SEQ ID NO: 7 |
| rh74 (RHM15-4) | 902 | US2015023924A1 SEQ ID NO: 9, US20160375110A1 SEQ ID NO: 8 |
| rh74 (RHM15-6) | 903 | US2015023924A1 SEQ ID NO: 10, US20160375110A1 SEQ ID NO: 9 |
| rh74 (RHM4-1) | 904 | US2015023924A1 SEQ ID NO: 11 |
| rh74 (RHM15-1) | 905 | US2015023924A1 SEQ ID NO: 12 |
| rh74 (RHM15-2) | 906 | US2015023924A1 SEQ ID NO: 13 |
| rh74 (RBM15-3/RHM15-5) | 907 | US2015023924A1 SEQ ID NO. 14 |
| rh74 (RHM15-4) | 908 | US2015023924A1 SEQ ID NO: 15 |
| rh74 (RHM15-6) | 909 | US2015023924A1 SEQ ID NO: 16 |
| AAV2 (comprising lung specific polypeptide) | 910 | US20160175389A1 SEQ ID NO: 9 |
| AAV2 (comprising lung specific polypeptide) | 911 | US20160175389A1 SEQ ID NO: 10 |
| Anc80 | 912 | US20170051257A1 SEQ ID NO: 1 |
| Anc80 | 913 | US20170051257A1 SEQ ID NO: 2 |
| Anc81 | 914 | US20170051257A1 SEQ ID NO: 3 |
| Anc80 | 915 | US20170051257A1 SEQ ID NO: 4 |
| Anc82 | 916 | US20170051257A1 SEQ ID NO: 5 |
| Anc82 | 917 | US20170051257A1 SEQ ID NO: 6 |
| Anc83 | 918 | US20170051257A1 SEQ ID NO: 7 |
| Anc83 | 919 | US20170051257A1 SEQ ID NO: 8 |
| Anc84 | 920 | US20170051257A1 SEQ ID NO: 9 |
| Anc84 | 921 | US20170051257A1 SEQ ID NO: 10 |
| Anc94 | 922 | US20170051257A1 SEQ ID NO: 11 |
| Anc94 | 923 | US20170051257A1 SEQ ID NO: 12 |
| Anc113 | 924 | US20170051257A1 SEQ ID NO: 13 |
| Anc113 | 925 | US20170051257A1 SEQ ID NO: 14 |
| Anc126 | 926 | US20170051257A1 SEQ ID NO: 15 |
| Anc126 | 927 | US20170051257A1 SEQ ID NO: 16 |
| Anc127 | 928 | US20170051257A1 SEQ ID NO: 17 |
| Anc127 | 929 | US20170051257A1 SEQ ID NO: 18 |
| Anc80L27 | 930 | US20170051257A1 SEQ ID NO: 19 |
| Anc80L59 | 931 | US20170051257A1 SEQ ID NO: 20 |
| Anc80L60 | 932 | US20170051257A1 SEQ ID NO: 21 |
| Anc80L62 | 933 | US20170051257A1 SEQ ID NO: 22 |
| Anc80L65 | 934 | US20170051257A1 SEQ ID NO: 23 |
| Anc80L33 | 935 | US20170051257A1 SEQ ID NO: 24 |
| Anc80L36 | 936 | US20170051257A1 SEQ ID NO: 25 |
| Anc80L44 | 937 | US20170051257A1 SEQ ID NO: 26 |
| Anc80L1 | 938 | US20170051257A1 SEQ ID NO: 35 |
| Anc80L1 | 939 | US20170051257A1 SEQ ID NO: 36 |
| AAV-X1 | 940 | U.S. Pat. No. 8,283,151 B2 SEQ ID NO: 11 |
| AAV-X1b | 941 | U.S. Pat. No. 8,283,151 B2 SEQ ID NO: 12 |
| AAV-X5 | 942 | U.S. Pat. No. 8,283,151 B2 SEQ ID NO: 13 |
| AAV-X19 | 943 | U.S. Pat. No. 8,283,151 B2 SEQ ID NO: 14 |
| AAV-X21 | 944 | U.S. Pat. No. 8,283,151 B2 SEQ ID NO: 15 |
| AAV-X22 | 945 | U.S. Pat. No. 8,283,151 B2 SEQ ID NO: 16 |
| AAV-X23 | 946 | U.S. Pat. No. 8,283,151 B2 SEQ ID NO: 17 |
| AAV-X24 | 947 | U.S. Pat. No. 8,283,151 B2 SEQ ID NO: 18 |
| AAV-X25 | 948 | U.S. Pat. No. 8,283,151 B2 SEQ ID NO: 19 |
| AAV-X26 | 949 | U.S. Pat. No. 8,283,151 B2 SEQ ID NO: 20 |
| AAV-X1 | 950 | U.S. Pat. No. 8,283,151 B2 SEQ ID NO: 21 |
| AAV-X1b | 951 | U.S. Pat. No. 8,283,151 B2 SEQ ID NO: 22 |
| AAV-X5 | 952 | U.S. Pat. No. 8,283,151 B2 SEQ ID NO: 23 |
| AAV-X19 | 953 | U.S. Pat. No. 8,283,151 B2 SEQ ID NO: 24 |
| AAV-X21 | 954 | U.S. Pat. No. 8,283,151 B2 SEQ ID NO: 25 |
| AAV-X22 | 955 | U.S. Pat. No. 8,283,151 B2 SEQ ID NO: 26 |
| AAV-X23 | 956 | U.S. Pat. No. 8,283,151 B2 SEQ ID NO: 27 |
| AAV-X24 | 957 | U.S. Pat. No. 8,283,151 B2 SEQ ID NO: 28 |

TABLE 6-continued

AAV Sequences

| Serotype | SEQ ID NO: | Reference Information |
|---|---|---|
| AAV-X25 | 958 | U.S. Pat. No. 8,283,151 B2 SEQ ID NO: 29 |
| AAV-X26 | 959 | U.S. Pat. No. 8,283,151 B2 SEQ ID NO: 30 |
| AAVrh8 | 960 | WO2016054554A1 SEQ ID NO: 8 |
| AAVrh8VP2FC5 | 961 | WO2016054554A1 SEQ ID NO: 9 |
| AAVrh8VP2FC44 | 962 | WO2016054554A1 SEQ ID NO: 10 |
| AAVrh8VP2ApoB100 | 963 | WO2016054554A1 SEQ ID NO: 11 |
| AAVrh8VP2RVG | 964 | WO2016054554A1 SEQ ID NO: 12 |
| AAVrhVPAngiopep-2 VP2 | 965 | WO2016054554A1 SEQ ID NO: 13 |
| AAV9.47VP1.3 | 966 | WO2016054554A1 SEQ ID NO: 14 |
| AAV9.47VP2ICAMg3 | 967 | WO2016054554A1 SEQ ID NO: 15 |
| AAV9.47VP2RVG | 968 | WO2016054554A1 SEQ ID NO: 16 |
| AAV9.47VP2Angiopep-2 | 969 | WO2016054554A1 SEQ ID NO: 17 |
| AAV9.47VP2A-string | 970 | WO2016054554A1 SEQ ID NO: 18 |
| AAVrh8VP2FC5 VP2 | 971 | WO2016054554A1 SEQ ID NO: 19 |
| AAVrh8VP2FC44 VP2 | 972 | WO2016054554A1 SEQ ID NO: 20 |
| AAVrh8VP2ApoB100 VP2 | 973 | WO2016054554A1 SEQ ID NO: 21 |
| AAVrh8VP2RVG VP2 | 974 | WO2016054554A1 SEQ ID NO: 22 |
| AAVrh8VP2Angiopep-2 VP2 | 975 | WO2016054554A1 SEQ ID NO: 23 |
| AAV9.47VP2ICAMg3 VP2 | 976 | WO2016054554A1 SEQ ID NO: 24 |
| AAV9.47VP2RVG VP2 | 977 | WO2016054554A1 SEQ ID NO: 25 |
| AAV9.47VP2Angiopep-2 VP2 | 978 | WO2016054554A1 SEQ ID NO: 26 |
| AAV9.47VP2A-string VP2 | 979 | WO2016054554A1 SEQ ID NO: 27 |
| rAAV-B1 | 980 | WO2016054557A1 SEQ ID NO: 1 |
| rAAV-B2 | 981 | WO2016054557A1 SEQ ID NO: 7 |
| rAAV-B3 | 982 | WO2016054557A1 SEQ ID NO: 3 |
| rAAV-B4 | 983 | WO2016054557A1 SEQ ID NO: 4 |
| rAAV-B1 | 984 | WO2016054557A1 SEQ ID NO: 5 |
| rAAV-B2 | 985 | WO2016054557A1 SEQ ID NO: 6 |
| rAAV-B3 | 986 | WO2016054557A1 SEQ ID NO: 7 |
| rAAV-B4 | 987 | WO2016054557A1 SEQ ID NO: 8 |
| rAAV-L1 | 988 | WO2016054557A1 SEQ ID NO: 9 |
| rAAV-L2 | 989 | WO2016054557A1 SEQ ID NO: 10 |
| rAAV-L3 | 990 | WO2016054557A1 SEQ ID NO: 11 |
| rAAV-L4 | 991 | WO2016054557A1 SEQ ID NO: 12 |
| rAAV-L1 | 992 | WO2016054557A1 SEQ ID NO: 13 |
| rAAV-L2 | 993 | WO2016054557A1 SEQ ID NO: 14 |
| rAAV-L3 | 994 | WO2016054557A1 SEQ ID NO: 15 |
| rAAV-L4 | 995 | WO2016054557A1 SEQ ID NO: 16 |
| AAV9 | 996 | WO2016073739A1 SEQ ID NO: 3 |
| rAAV | 997 | WO2016081811A1 SEQ ID NO: 1 |
| rAAV | 998 | WO2016081811A1 SEQ ID NO: 2 |
| rAAV | 999 | WO2016081811A1 SEQ ID NO: 3 |
| rAAV | 1000 | WO2016081811A1 SEQ ID NO: 4 |
| rAAV | 1001 | WO2016081811A1 SEQ ID NO: 5 |
| rAAV | 1002 | WO2016081811A1 SEQ ID NO: 6 |
| rAAV | 1003 | WO2016081811A1 SEQ ID NO: 7 |
| rAAV | 1004 | WO2016081811A1 SEQ ID NO: 8 |
| rAAV | 1005 | WO2016081811A1 SEQ ID NO: 9 |
| rAAV | 1006 | WO2016081811A1 SEQ ID NO: 10 |
| rAAV | 1007 | WO2016081811A1 SEQ ID NO: 11 |
| rAAV | 1008 | WO2016081811A1 SEQ ID NO: 12 |
| rAAV | 1009 | WO2016081811A1 SEQ ID NO: 13 |
| rAAV | 1010 | WO2016081811A1 SEQ ID NO: 14 |
| rAAV | 1011 | WO2016081811A1 SEQ ID NO: 15 |
| rAAV | 1012 | WO2016081811A1 SEQ ID NO: 16 |
| rAAV | 1013 | WO2016081811A1 SEQ ID NO: 17 |
| rAAV | 1014 | WO2016081811A1 SEQ ID NO: 18 |
| rAAV | 1015 | WO2016081811A1 SEQ ID NO: 19 |
| rAAV | 1016 | WO2016081811A1 SEQ ID NO: 20 |
| rAAV | 1017 | WO2016081811A1 SEQ ID NO: 21 |
| rAAV | 1018 | WO2016081811A1 SEQ ID NO: 22 |
| rAAV | 1019 | WO2016081811A1 SEQ ID NO: 23 |
| rAAV | 1020 | WO2016081811A1 SEQ ID NO: 24 |
| rAAV | 1021 | WO2016081811A 1 SEQ ID NO: 25 |
| rAAV | 1022 | WO2016081811A1 SEQ ID NO: 26 |
| rAAV | 1023 | WO2016081811A1 SEQ ID NO: 27 |
| rAAV | 1024 | WO2016081811A1 SEQ ID NO: 28 |
| rAAV | 1025 | WO2016081811A1 SEQ ID NO: 29 |
| rAAV | 1026 | WO2016081811A1 SEQ ID NO: 30 |
| rAAV | 1027 | WO2016081811A1 SEQ ID NO: 31 |
| rAAV | 1028 | WO2016081811A1 SEQ ID NO: 32 |
| rAAV | 1029 | WO2016081811A1 SEQ ID NO: 33 |
| rAAV | 1030 | WO2016081811A1 SEQ ID NO: 34 |
| rAAV | 1031 | WO2016081811A1 SEQ ID NO: 35 |

TABLE 6-continued

| AAV Sequences | | |
|---|---|---|
| Serotype | SEQ ID NO: | Reference Information |
| rAAV | 1032 | WO2016081811A1 SEQ ID NO: 36 |
| rAAV | 1033 | WO2016081811A1 SEQ ID NO: 37 |
| rAAV | 1034 | WO2016081811A1 SEQ ID NO: 38 |
| rAAV | 1035 | WO2016081811A1 SEQ ID NO: 39 |
| rAAV | 1036 | WO2016081811A1 SEQ ID NO: 40 |
| rAAV | 1037 | WO2016081811A1 SEQ ID NO: 41 |
| rAAV | 1038 | WO2016081811A1 SEQ ID NO: 42 |
| rAAV | 1039 | WO2016081811A1 SEQ ID NO: 43 |
| rAAV | 1040 | WO2016081811A1 SEQ ID NO: 44 |
| rAAV | 1041 | WO2016081811A1 SEQ ID NO: 45 |
| rAAV | 1042 | WO2016081811A1 SEQ ID NO: 46 |
| rAAV | 1043 | WO2016081811A1 SEQ ID NO: 47 |
| rAAV | 1044 | WO2016081811A1 SEQ ID NO: 48 |
| rAAV | 1045 | WO2016081811A1 SEQ ID NO: 49 |
| rAAV | 1046 | WO2016081811A1 SEQ ID NO: 50 |
| rAAV | 1047 | WO2016081811A1 SEQ ID NO: 51 |
| rAAV | 1048 | WO2016081811A1 SEQ ID NO: 52 |
| rAAV | 1049 | WO2016081811A1 SEQ ID NO: 53 |
| rAAV | 1050 | WO2016081811A1 SEQ ID NO: 54 |
| rAAV | 1051 | WO2016081811A1 SEQ ID NO: 55 |
| rAAV | 1052 | WO2016081811A1 SEQ ID NO: 56 |
| rAAV | 1053 | WO2016081811A1 SEQ ID NO: 57 |
| rAAV | 1054 | WO2016081811A1 SEQ ID NO: 58 |
| rAAV | 1055 | WO2016081811A1 SEQ ID NO: 59 |
| rAAV | 1056 | WO2016081811A1 SEQ ID NO: 60 |
| rAAV | 1057 | WO2016081811A1 SEQ ID NO: 61 |
| rAAV | 1058 | WO2016081811A1 SEQ ID NO: 62 |
| rAAV | 1059 | WO2016081811A1 SEQ ID NO: 63 |
| rAAV | 1060 | WO2016081811A1 SEQ ID NO: 64 |
| rAAV | 1061 | WO2016081811A1 SEQ ID NO: 65 |
| rAAV | 1062 | WO2016081811A1 SEQ ID NO: 66 |
| rAAV | 1063 | WO2016081811A1 SEQ ID NO: 67 |
| rAAV | 1064 | WO2016081811A1 SEQ ID NO: 68 |
| rAAV | 1065 | WO2016081811A1 SEQ ID NO: 69 |
| rAAV | 1066 | WO2016081811A1 SEQ ID NO: 70 |
| rAAV | 1067 | WO2016081811A1 SEQ ID NO: 71 |
| rAAV | 1068 | WO2016081811A1 SEQ ID NO: 72 |
| rAAV | 1069 | WO2016081811A1 SEQ ID NO: 73 |
| rAAV | 1070 | WO2016081811A1 SEQ ID NO: 74 |
| rAAV | 1071 | WO2016081811A1 SEQ ID NO: 75 |
| rAAV | 1072 | WO2016081811A1 SEQ ID NO: 76 |
| rAAV | 1073 | WO2016081811A1 SEQ ID NO: 77 |
| rAAV | 1074 | WO2016081811A1 SEQ ID NO: 78 |
| rAAV | 1075 | WO2016081811A1 SEQ ID NO: 79 |
| rAAV | 1076 | WO2016081811A1 SEQ ID NO: 80 |
| rAAV | 1077 | WO2016081811A1 SEQ ID NO: 81 |
| rAAV | 1078 | WO2016081811A1 SEQ ID NO: 82 |
| rAAV | 1079 | WO2016081811A1 SEQ ID NO: 83 |
| rAAV | 1080 | WO2016081811A1 SEQ ID NO: 84 |
| rAAV | 1081 | WO2016081811A1 SEQ ID NO: 85 |
| rAAV | 1082 | WO2016081811A1 SEQ ID NO: 86 |
| rAAV | 1083 | WO2016081811A1 SEQ ID NO: 87 |
| rAAV | 1084 | WO2016081811A1 SEQ ID NO: 88 |
| rAAV | 1085 | WO2016081811A1 SEQ ID NO: 89 |
| rAAV | 1086 | WO2016081811A1 SEQ ID NO: 90 |
| rAAV | 1087 | WO2016081811A1 SEQ ID NO: 91 |
| rAAV | 1088 | WO2016081811A1 SEQ ID NO: 92 |
| rAAV | 1089 | WO2016081811A1 SEQ ID NO: 93 |
| rAAV | 1090 | WO2016081811A1 SEQ ID NO: 94 |
| rAAV | 1091 | WO2016081811A1 SEQ ID NO: 95 |
| rAAV | 1092 | WO2016081811A1 SEQ ID NO: 96 |
| rAAV | 1093 | WO2016081811A1 SEQ ID NO: 97 |
| rAAV | 1094 | WO2016081811A1 SEQ ID NO: 98 |
| rAAV | 1095 | WO2016081811A1 SEQ ID NO: 99 |
| rAAV | 1096 | WO2016081811A1 SEQ ID NO: 100 |
| rAAV | 1097 | WO2016081811A1 SEQ ID NO: 101 |
| rAAV | 1098 | WO2016081811A1 SEQ ID NO: 102 |
| rAAV | 1099 | WO2016081811A1 SEQ ID NO: 103 |
| rAAV | 1100 | WO2016081811A1 SEQ ID NO: 104 |
| rAAV | 1101 | WO2016081811A1 SEQ ID NO: 105 |
| rAAV | 1102 | WO2016081811A1 SEQ ID NO: 106 |
| rAAV | 1103 | WO2016081811A1 SEQ ID NO: 107 |
| rAAV | 1104 | WO2016081811A1 SEQ ID NO: 108 |
| rAAV | 1105 | WO2016081811A1 SEQ ID NO: 109 |

TABLE 6-continued

| | SEQ ID NO: | |
|---|---|---|
| Serotype | | Reference Information |
| rAAV | 1106 | WO2016081811A1 SEQ ID NO: 110 |
| rAAV | 1107 | WO2016081811A1 SEQ ID NO: 111 |
| rAAV | 1108 | WO2016081811A1 SEQ ID NO: 112 |
| rAAV | 1109 | WO2016081811A1 SEQ ID NO: 113 |
| rAAV | 1110 | WO2016081811A1 SEQ ID NO: 114 |
| rAAV | 1111 | WO2016081811A1 SEQ ID NO: 115 |
| rAAV | 1112 | WO2016081811A1 SEQ ID NO: 116 |
| rAAV | 1113 | WO2016081811A1 SEQ ID NO: 117 |
| rAAV | 1114 | WO2016081811A1 SEQ ID NO: 118 |
| rAAV | 1115 | WO2016081811A1 SEQ ID NO: 119 |
| rAAV | 1116 | WO2016081811A1 SEQ ID NO: 120 |
| rAAV | 1117 | WO2016081811A1 SEQ ID NO: 121 |
| rAAV | 1118 | WO2016081811A1 SEQ ID NO: 122 |
| rAAV | 1119 | WO2016081811A1 SEQ ID NO: 123 |
| rAAV | 1120 | WO2016081811A1 SEQ ID NO: 124 |
| rAAV | 1121 | WO2016081811A1 SEQ ID NO: 125 |
| rAAV | 1122 | WO2016081811A1 SEQ ID NO: 126 |
| rAAV | 1123 | WO2016081811A1 SEQ ID NO: 127 |
| rAAV | 1124 | WO2016081811A1 SEQ ID NO: 128 |
| AAV8 E532K | 1125 | WO2016081811A1 SEQ ID NO: 133 |
| AAV8 E532K | 1126 | WO2016081811A1 SEQ ID NO: 134 |
| rAAV4 | 1127 | WO2016115382A1 SEQ ID NO: 2 |
| rAAV4 | 1128 | WO2016115382A1 SEQ ID NO: 3 |
| rAAV4 | 1129 | WO2016115382A1 SEQ ID NO: 4 |
| rAAV4 | 1130 | WO2016115382A1 SEQ ID NO: 5 |
| rAAV4 | 1131 | WO2016115382A1 SEQ ID NO: 6 |
| rAAV4 | 1132 | WO2016115382A1 SEQ ID NO: 7 |
| rAAV4 | 1133 | WO2016115382A1 SEQ ID NO: 8 |
| rAAV4 | 1134 | WO2016115382A1 SEQ ID NO: 9 |
| rAAV4 | 1135 | WO2016115382A1 SEQ ID NO: 10 |
| rAAV4 | 1136 | WO2016115382A1 SEQ ID NO: 11 |
| rAAV4 | 1137 | WO2016115382A1 SEQ ID NO: 12 |
| rAAV4 | 1138 | WO2016115382A1 SEQ ID NO: 13 |
| rAAV4 | 1139 | WO2016115382A1 SEQ ID NO: 14 |
| rAAV4 | 1140 | WO2016115382A1 SEQ ID NO: 15 |
| TAAV4 | 1141 | WO2016115382A1 SEQ ID NO: 16 |
| rAAV4 | 1142 | WO2016115382A1 SEQ ID NO: 17 |
| rAAV4 | 1143 | WO2016115382A1 SEQ ID NO: 18 |
| rAAV4 | 1144 | WO2016115382A1 SEQ ID NO: 19 |
| rAAV4 | 1145 | WO2016115382A1 SEQ ID NO: 20 |
| rAAV4 | 1146 | WO2016115382A1 SEQ ID NO: 21 |
| AAV11 | 1147 | WO2016115382A1 SEQ ID NO: 22 |
| AAV12 | 1148 | WO2016115382A1 SEQ ID NO: 23 |
| rh32 | 1149 | WO2016115382A1 SEQ ID NO: 25 |
| rh33 | 1150 | WO2016115382A1 SEQ ID NO: 26 |
| rh34 | 1151 | WO2016115382A1 SEQ ID NO: 27 |
| rAAV4 | 1152 | WO2016115382A1 SEQ ID NO: 28 |
| rAAV4 | 1153 | WO2016115382A1 SEQ ID NO: 29 |
| rAAV4 | 1154 | WO2016115382A1 SEQ ID NO: 30 |
| rAAV4 | 1155 | WO2016115382A1 SEQ ID NO: 31 |
| rAAV4 | 1156 | WO2016115382A1 SEQ ID NO: 32 |
| rAAV4 | 1157 | WO2016115382A1 SEQ ID NO: 33 |
| AAV2/8 | 1158 | WO2016131981A1 SEQ ID NO: 47 |
| AAV2/8 | 1159 | WO2016131981A1 SEQ ID NO: 48 |
| ancestral AAV | 1160 | WO2016154344A1 SEQ ID NO: 7 |
| ancestral AAV variant C4 | 1161 | WO2016154344A1 SEQ ID NO: 13 |
| ancestral AAV variant C7 | 1162 | WO2016154344A1 SEQ ID NO: 14 |
| ancestral AAV variant G4 | 1163 | WO2016154344A1 SEQ ID NO: 15 |
| consensus amino acid sequence of ancestral AAV variants, C4, C7 and G4 | 1164 | WO2016154344A1 SEQ ID NO: 16 |
| consensus amino acid sequence of ancestral AAV variants, C4 and C7 | 1165 | WO2016154344A1 SEQ ID NO: 17 |
| AAV8 (with a AAV2 phospholipase domain) | 1166 | WO2016150403A1 SEQ ID NO: 13 |
| AAV VR-942n | 1167 | US20160289275A1 SEQ ID NO: 10 |
| AAV5-A (M569V) | 1168 | US20160289275A1 SEQ ID NO: 13 |
| AAV5-A (M569V) | 1169 | US20160289275A1 SEQ ID NO: 14 |
| AAV5-A (Y585V) | 1170 | US20160289275A1 SEQ ID NO: 16 |
| AAV5-A (Y585V) | 1171 | US20160289275A1 SEQ ID NO: 17 |
| AAV5-A (L587T) | 1172 | US20160289275A1 SEQ ID NO: 19 |
| AAV5-A (L587T) | 1173 | US20160289275A1 SEQ ID NO: 20 |
| AAV5-A (Y585V/L587T) | 1174 | US20160289275A1 SEQ ID NO: 22 |

TABLE 6-continued

| | | AAV Sequences |
| --- | --- | --- |
| Serotype | SEQ ID NO: | Reference Information |
| AAV5-A (Y585V/L587T) | 1175 | US20160289275A1 SEQ ID NO: 23 |
| AAV5-B (D652A) | 1176 | US20 160289275A1 SEQ ID NO: 25 |
| AAV5-B (D652A) | 1177 | US20160289275A1 SEQ ID NO: 26 |
| AAV5-B (T362M) | 1178 | US20160289275A1 SEQ ID NO: 28 |
| AAV5-B (T362M) | 1179 | US20160289275A1 SEQ ID NO: 29 |
| AAV5-B (Q359D) | 1180 | US20160289275A1 SEQ ID NO: 31 |
| AAV5-B (Q359D) | 1181 | US20160289275A1 SEQ ID NO: 32 |
| AAV5-B (E3500) | 1182 | US20160289275A1 SEQ ID NO: 34 |
| AAV5-B (E350Q) | 1183 | US20 160289275A1 SEQ ID NO: 35 |
| AAV5-B (P533S) | 1184 | US20160289275A1 SEQ ID NO: 37 |
| AAV5-B (P533S) | 1185 | US20160289275A1 SEQ ID NO: 38 |
| AAV5-B (P533G) | 1186 | US20160289275A1 SEQ ID NO: 40 |
| AAV5-B (P533G) | 1187 | US20160289275A1 SEQ ID NO: 41 |
| AAV5-mutation in loop VII | 1188 | US20160289275A1 SEQ ID NO: 43 |
| AAV5-mutation in loop VII | 1189 | US20160289275A1 SEQ ID NO: 44 |
| AAV8 | 1190 | US20160289275A1 SEQ ID NO: 47 |
| MutA (LK03/AAV8) | 1191 | WO2016181123A1 SEQ ID NO: 1 |
| Mut B (LK03/AAV5) | 1192 | WO2016181123A1 SEQ ID NO: 2 |
| Mut C (AAVB/AAV3B) | 1193 | WO2016181123A1 SEQ ID NO: 3 |
| Mut D (AAV5/AAV3B) | 1194 | WO2016181123A1 SEQ ID NO: 4 |
| Mut E (AAV8/AAV3B) | 1195 | WO2016181123A1 SEQ ID NO: 5 |
| Mut F (AAV3B/AAV8) | 1196 | WO2016181123A1 SEQ ID NO: 6 |
| AAV44.9 | 1197 | WO2016183297A1 SEQ ID NO: 4 |
| AAV44.9 | 1198 | WO2016183297A1 SEQ ID NO: 5 |
| AAVrh8 | 1199 | WO2016183297A1 SEQ ID NO: 6 |
| AAV44.9 (S470N) | 1200 | WO2016183297A1 SEQ ID NO: 9 |
| rh74 VPI | 1201 | US20160375110A1 SEQ ID NO: 1 |
| AAV-LK03 (L125I) | 1202 | WO2017015102A1 SEQ ID NO: 5 |
| AAV3B (S663V + T492V) | 1203 | WO2017015102A1 SEQ ID NO: 6 |
| Anc80 | 1204 | WO2017019994A2 SEQ ID NO: 1 |
| Anc80 | 1205 | WO2017019994A2 SEQ ID NO: 2 |
| Anc81 | 1206 | WO2017019994A2 SEQ ID NO: 3 |
| Anc81 | 1207 | WO2017019994A2 SEQ ID NO: 4 |
| Anc82 | 1208 | WO2017019994A2 SEQ ID NO: 5 |
| Anc82 | 1209 | WO2017019994A2 SEQ ID NO: 6 |
| Anc83 | 1210 | WO2017019994A2 SEQ ID NO: 7 |
| Anc83 | 1211 | WO2017019994A2 SEQ ID NO: 8 |
| Anc84 | 1212 | WO2017019994A2 SEQ ID NO: 9 |
| Anc84 | 1213 | WO2017019994A2 SEQ ID NO: 10 |
| Anc94 | 1214 | WO2017019994A2 SEQ ID NO: 11 |
| Anc94 | 1215 | WO2017019994A2 SEQ ID NO: 12 |
| Anc113 | 1216 | WO2017019994A2 SEQ ID NO: 13 |
| Anc113 | 1217 | WO2017019994A2 SEQ ID NO: 14 |
| Anc126 | 1218 | WO2017019994A2 SEQ ID NO: 15 |
| Anc126 | 1219 | WO2017019994A2 SEQ ID NO: 16 |
| Anc127 | 1220 | WO2017019994A2 SEQ ID NO: 17 |
| Anc127 | 1221 | WO2017019994A2 SEQ ID NO: 18 |
| Anc80L27 | 1222 | WO2017019994A2 SEQ ID NO: 19 |
| Anc80L59 | 1223 | WO2017019994A2 SEQ ID NO: 20 |
| Anc80L60 | 1224 | WO2017019994A2 SEQ ID NO: 21 |
| Anc80L62 | 1225 | WO2017019994A2 SEQ ID NO: 22 |
| Anc80L65 | 1226 | WO2017019994A2 SEQ ID NO: 23 |
| Anc80L33 | 1227 | WO2017019994A2 SEQ ID NO: 24 |
| Anc80L36 | 1228 | WO2017019994A2 SEQ ID NO: 25 |
| Anc80L44 | 1229 | WO2017019994A2 SEQ ID NO: 26 |
| Anc80L1 | 1230 | WO2017019994A2 SEQ ID NO: 35 |
| Anc80L1 | 1231 | WO2017019994A2 SEQ ID NO: 36 |
| AAVrh10 | 1232 | WO2017019994A2 SEQ ID NO: 41 |
| Anc110 | 1233 | WO2017019994A2 SEQ ID NO: 42 |
| Anc110 | 1234 | WO2017019994A2 SEQ ID NO: 43 |
| AAVrh32.33 | 1235 | WO2017019994A2 SEQ ID NO: 45 |
| AAVrh74 | 1236 | WO2017049031A1 SEQ ID NO: 1 |
| AAV2 | 1237 | WO2017053629A2 SEQ ID NO: 49 |
| AAV2 | 1238 | WO2017053629A2 SEQ ID NO: 50 |
| AAV2 | 1239 | WO2017053629A2 SEQ ID NO: 82 |
| Parvo-like virus | 1240 | WO2017070476A2 SEQ ID NO: 1 |
| Parvo-like virus | 1241 | WO2017070476A2 SEQ ID NO: 2 |
| Parvo-like virus | 1242 | WO2017070476A2 SEQ ID NO: 3 |
| Parvo-like virus | 1243 | WO2017070476A2 SEQ ID NO: 4 |
| Parvo-like virus | 1244 | WO2017070476A2 SEQ ID NO: 5 |
| Parvo-like virus | 1245 | WO2017070476A2 SEQ ID NO: 6 |
| AAVrh.10 | 1246 | WO2037070516A1 SEQ ID NO: 7 |
| AAVrh.10 | 1247 | WO2017070516A1 SEQ ID NO: 14 |
| AAV2YF | 1248 | WO2017070491A1 SEQ ID NO: 1 |

TABLE 6-continued

AAV Sequences

| Serotype | SEQ ID NO: | Reference Information |
|---|---|---|
| AAV-SPK | 1249 | WO2017075619A1 SEQ ID NO:28 |
| AAV2.5 | 1250 | US20170128528A1 SEQ ID NO |
| AAV1.1 | 1251 | US20170128528A1 SEQ ID NO: 15 |
| AAV6.1 | 1252 | US20170128528A1 SEQ ID NO: 17 |
| AAV6.3.1 | 1253 | US20170128528A3 SEQ ID NO: 18 |
| AAV2i8 | 1254 | US20170128528A1 SEQ ID NO: 28 |
| AAV2i8 | 1255 | US20170128528A1 SEQ ID NO: 29 |
| ttAAV | 1256 | US20170128528A1 SEQ ID NO: 30 |
| ttAAV-S312N | 1257 | US20170128528A1 SEQ ID NO: 32 |
| ttAAV-S312N | 1258 | US20170128528A1 SEQ ID NO: 33 |
| AAV6 (Y705, Y731, and T492) | 1259 | WO2016134337A1 SEQ ID NO: 24 |
| AAV2 | 1260 | WO2016134375A1 SEQ ID NO: 9 |
| AAV2 | 1261 | WO2016134375A1 SEQ ID NO: 10 |

Each of the patents, applications and or publications listed in Table 6 are hereby incorporated by reference in their entirety.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in International Patent Publication WO2015038958, the contents of which are herein incorporated by reference in their entirety, such as, but not limited to, AAV9 (SEQ ID NO: 2 and 11 of WO2015038958 or SEQ ID NO: 138 and 137 respectively herein), PHP.B (SEQ ID NO: 8 and 9 of WO2015038958, herein SEQ ID NO: 5 and 6), G2B-13 (SEQ ID NO: 12 of WO2015038958, herein SEQ ID NO: 7), G2B-26 (SEQ ID NO: 13 of WO2015038958, herein SEQ ID NO: 5), TH1.1-32 (SEQ ID NO: 14 of WO2015038958, herein SEQ ID NO: 8), TH1.1-35 (SEQ ID NO: 15 of WO2015038958, herein SEQ ID NO: 9) or variants thereof.

In some embodiments, the AAV capsid polypeptide, e.g., AAV capsid variant, or the parent AAV capsid described herein does not comprise an insert sequence present immediately subsequent to position 586, 588, or 589 numbered relative to SEQ ID NO: 138, having at least 5 consecutive amino acids corresponding to positions 586 to 594 numbered relative to SEQ ID NO: 138, of any of the following amino acid sequences, TLAVPFK (SEQ ID NO: 1262), KFPVALT (SEQ ID NO: 1263), LAVPFK (SEQ ID NO: 1264), AVPFK (SEQ ID NO: 1265), VPFK (SEQ ID NO: 1266), TLAVPF (SEQ ID NO: 1267), TLAVP (SEQ ID NO: 1268), TLAV (SEQ ID NO: 1269), SVSKPFL (SEQ ID NO: 1270), FTLTTPK (SEQ ID NO: 1271), MNATKNV (SEQ ID NO: 1272), QSSQTPR (SEQ ID NO: 1273), ILGTGTS (SEQ ID NO: 1274), TRTNPEA (SEQ ID NO: 1275), NGGTSSS (SEQ ID NO: 1276), or YTLSQGW (SEQ ID NO: 1277); or encoded by a nucleotide sequence of any of SEQ ID NO: 1278, SEQ ID NO: 1279, SEQ ID NO: 1280, SEQ ID NO: 1281, SEQ ID NO: 1282, SEQ ID NO: 1283, SEQ ID NO: 1284, SEQ ID NO: 1285, SEQ ID NO: 1286, or SEQ ID NO: 1287.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in International Patent Publication WO2017100671, the contents of which are herein incorporated by reference in their entirety, such as, but not limited to, AAV9 (SEQ ID NO: 11), PHP.N (SEQ ID NO: 4), PHP.S (SEQ ID NO: 10), or variants thereof.

In some embodiments, the AAV capsid polypeptide, e.g., AAV capsid variant, or the parent AAV capsid described herein does not comprise an insert sequence present immediately subsequent to position 586, 588, or 589 numbered relative to SEQ ID NO: 138, having at least 5 consecutive amino acids corresponding to positions 586 to 594 numbered relative to SEQ ID NO: 138, of the targeting peptides or amino acid inserts described in WO2017100671.

In some embodiments, the AAV capsid polypeptide, e.g., AAV capsid variant, or the parent AAV capsid described herein does not comprise an insert sequence present immediately subsequent to position 586, 588, or 589 numbered relative to SEQ ID NO: 138, having at least 5 consecutive amino acids corresponding to positions 586 to 594 numbered relative to SEQ ID NO: 138, of any of the following amino acid sequences, AQTLAVPFKAQ (SEQ ID NO: 1288), AQSVSKPFLAQ (SEQ ID NO: 1289), AQFTLTTPKAQ (SEQ ID NO: 1290), DGTLAVPFKAQ (SEQ ID NO: 1291), ESTLAVPFKAQ (SEQ ID NO: 1292), GGTLAVPFKAQ (SEQ ID NO: 1293), AQTLATPFKAQ (SEQ ID NO: 1294), ATTLATPFKAQ (SEQ ID NO: 1295), DGTLATPFKAQ (SEQ ID NO: 1296), GGTLATPFKAQ (SEQ ID NO: 1297), SGSLAVPFKAQ (SEQ ID NO: 1298), AQTLAQPFKAQ (SEQ ID NO: 1299), AQTLQQPFKAQ (SEQ ID NO: 1300), AQTLSNPFKAQ (SEQ ID NO: 1301), AQTLAVPFSNP (SEQ ID NO: 1302), QGTLAVPFKAQ (SEQ ID NO: 1303), NQTLAVPFKAQ (SEQ ID NO: 1304), EGSLAVPFKAQ (SEQ ID NO: 1305), SGN-LAVPFKAQ (SEQ ID NO: 1306), EGTLAVPFKAQ (SEQ ID NO: 1307), DSTLAVPFKAQ (SEQ ID NO: 1308), AVTLAVPFKAQ (SEQ ID NO: 1309), AQTLSTPFKAQ (SEQ ID NO: 1310), AQTLPQPFKAQ (SEQ ID NO: 1311), AQTLSQPFKAQ (SEQ ID NO: 1312), AQTLQLPFKAQ (SEQ ID NO: 1313), AQTLTMPFKAQ (SEQ ID NO: 1314), AQTLTTPFKAQ (SEQ ID NO: 1315), AQYTLSQGWAQ (SEQ ID NO: 1316), AQMNATKNVAQ (SEQ ID NO: 1317), AQVSGGHHSAQ (SEQ ID NO: 1318), AQTLTAPFKAQ (SEQ ID NO: 1319), AQTL-SKPFKAQ (SEQ ID NO: 1320), QAVRTSL (SEQ ID NO: 1321), YTLSQGW (SEQ ID NO: 1277), LAKERLS (SEQ ID NO: 1322), TLAVPFK (SEQ ID NO: 1262), SVSKPFL (SEQ ID NO: 1270), FTLTTPK (SEQ ID NO: 1271), MNSTKNV (SEQ ID NO: 1323), VSGGHHS (SEQ ID NO: 1324), SAQTLAVPFKAQAQ (SEQ ID NO: 1325), SXXXLAVPFKAQAQ (wherein X may be any amino acid;

SEQ ID NO: 1326), SAQXXXVPFKAQAQ (wherein X may be any amino acid; SEQ ID NO: 1327), SAQTLXXXFKAQAQ (wherein X may be any amino acid; SEQ ID NO: 1328), SAQTLAVXXXAQAQ (wherein X may be any amino acid; SEQ ID NO: 1329), SAQT-LAVPFXXXAQ (wherein X may be any amino acid; SEQ ID NO: 1330), TNHQSAQ (SEQ ID NO: 1331), AQAQTGW (SEQ ID NO: 1332), DGTLATPFK (SEQ ID NO: 1333), DGTLATPFKXX (wherein X may be any amino acid; SEQ ID NO: 1334), LAVPFKAQ (SEQ ID NO: 1335), VPFKAQ (SEQ ID NO: 1336), FKAQ (SEQ ID NO: 1337), AQTLAV (SEQ ID NO: 1338), AQTLAVPF (SEQ ID NO: 1339), QAVR (SEQ ID NO: 1340), AVRT (SEQ ID NO: 1341), VRTS (SEQ ID NO: 1342), RTSL (SEQ ID NO: 1343), QAVRT (SEQ ID NO: 1344), AVRTS (SEQ ID NO: 1345), VRTSL (SEQ ID NO: 1346), QAVRTS (SEQ ID NO: 1347), or AVRTSL (SEQ ID NO: 1348); or encoded by a nucleotide sequence of any of SEQ ID NO: 1349, SEQ ID NO: 1350, SEQ ID NO: 1351, SEQ ID NO: 1352, SEQ ID NO: 1353, SEQ ID NO: 1354, SEQ ID NO: 1355, SEQ ID NO: 1356, SEQ ID NO: 1357, SEQ ID NO: 1358 (wherein N may be A, C, T, or G), SEQ ID NO: 1359 (wherein N may be A. C. T, or G), SEQ ID NO: 1360 (wherein N may be A, C, T, or G), SEQ ID NO: 1361 (wherein N may be A, C, T, or G), SEQ ID NO: 1362 (wherein N may be A, C, T, or G), SEQ ID NO: 1279, SEQ ID NO: 1280, SEQ ID NO: 1281, SEQ ID NO: 1287, or SEQ ID NO: 1363.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in U.S. Pat. No. 9,624,274, the contents of which are herein incorporated by reference in their entirety, such as, but not limited to, AAV1 (SEQ ID NO: 181 of U.S. Pat. No. 9,624,274), AAV6 (SEQ ID NO: 182 of U.S. Pat. No. 9,624,274), AAV2 (SEQ ID NO: 183 of U.S. Pat. No. 9,624,274), AAV3b (SEQ ID NO: 184 of U.S. Pat. No. 9,624,274), AAV7 (SEQ ID NO: 185 of U.S. Pat. No. 9,624,274), AAV8 (SEQ ID NO: 186 of U.S. Pat. No. 9,624,274), AAV10 (SEQ ID NO: 187 of U.S. Pat. No. 9,624,274), AAV4 (SEQ ID NO: 188 of U.S. Pat. No. 9,624,274), AAV11 (SEQ ID NO: 189 of U.S. Pat. No. 9,624,274), bAAV (SEQ ID NO: 190 of U.S. Pat. No. 9,624,274), AAV5 (SEQ ID NO: 191 of U.S. Pat. No. 9,624,274), GPV (SEQ ID NO: 192 of U.S. Pat. No. 9,624,274; herein SEQ ID NO: 879), B19 (SEQ ID NO: 193 of U.S. Pat. No. 9,624,274; herein SEQ ID NO: 880), MVM (SEQ ID NO: 194 of U.S. Pat. No. 9,624,274; herein SEQ ID NO: 881), FPV (SEQ ID NO: 195 of U.S. Pat. No. 9,624,274; herein SEQ ID NO: 882), CPV (SEQ ID NO: 196 of U.S. Pat. No. 9,624,274; herein SEQ ID NO: 883) or variants thereof.

In some embodiments, the AAV capsid polypeptide, e.g., AAV capsid variant, or the parent AAV capsid described herein does not comprise an insert sequence present imme-diately subsequent to position 586, 588, or 589 numbered relative to SEQ ID NO: 138, having at least 5 consecutive amino acids corresponding to positions 586 to 594 num-bered relative to SEQ ID NO: 138, of any of the structural protein inserts described in U.S. Pat. No. 9,624,274 or any of the following amino acid sequences, VNLTWSRASG (SEQ ID NO: 1364), EFCINHRGYWVCGD (SEQ ID NO: 1365), EDGQVMDVDLS (SEQ ID NO: 1366), EKQRNGTLT (SEQ ID NO: 1367), TYQCRVTHPHL-PRALMR (SEQ ID NO: 1368), RHSTTQPRKTKGSG (SEQ ID NO: 1369), DSNPRGVSAYLSR (SEQ ID NO: 1370), TITCLWDLAPSK (SEQ ID NO: 1371), KTKGSGFFVF (SEQ ID NO: 1372), THPHLPRALMRS (SEQ ID NO: 1373), GETYQCRVTHPHLPRALMRSTTK (SEQ ID NO: 1374), LPRALMRS (SEQ ID NO: 1375), INHRGYWV (SEQ ID NO: 1376), CDAGSVRTNAPD (SEQ ID NO: 1377), AKAVSNLTESRSESLQS (SEQ ID NO: 1378), SLTGDEFKKVLET (SEQ ID NO: 1379), REAVAYRFEED (SEQ ID NO: 1380), INPEIITLDG (SEQ ID NO: 1381), DISVTGAPVITATYL (SEQ ID NO: 1382), DISVTGAPVITA (SEQ ID NO: 1383), PKTVSNLTESSS-ESVQS (SEQ ID NO: 1384), SLMGDEFKAVLET (SEQ ID NO: 1385), QHSVAYTFEED (SEQ ID NO: 1386), INPEIITRDG (SEQ ID NO: 1387), DISLTGDPVITASYL (SEQ ID NO: 1388), DISLTGDPVITA (SEQ ID NO: 1389), DQSIDFEIDSA (SEQ ID NO: 1390), KNVSEDLPLPTFSPTLLGDS (SEQ ID NO: 1391), KNVSEDLPLPT (SEQ ID NO: 1392), CDSGRVRTDAPD (SEQ ID NO: 1393), FPEHLLVDFLQSLS (SEQ ID NO: 1394), DAEFRHDSG (SEQ ID NO: 1395), HYAAAQWDFGNTMCQL (SEQ ID NO: 1396), YAAQWDFGNTMCQ (SEQ ID NO: 1397), RSQKEG-LHYT (SEQ ID NO: 1398), SSRTPSDKPVAHWANPQAE (SEQ ID NO: 1399), SRTPSDKPVAHWANP (SEQ ID NO: 1400), SSRTPSDKP (SEQ ID NO: 1401), NADGNVDYHMNSVP (SEQ ID NO: 1402), DGNVDYHMNSV (SEQ ID NO: 1403), RSFKEFLQSSL-RALRQ (SEQ ID NO: 1404); FKEFLQSSLRA (SEQ ID NO: 1405), or QMWAPQWGPD (SEQ ID NO: 1406).

In some embodiments, the AAV serotype, the parent AAV capsid polypeptide, or the AAV capsid variant may be or have, at a position other than 5 consecutive amino acids corresponding to positions 586 to 594 numbered relative to SEQ ID NO: 138, a sequence as described in U.S. Pat. No. 9,475,845, the contents of which are herein incorporated by reference in their entirety.

In some embodiments, the AAV capsid polypeptide, e.g., AAV capsid variant, or the parent AAV capsid described herein does not comprise an insert sequence present imme-diately subsequent to position 586, 588, or 589 numbered relative to SEQ ID NO: 138, having at least 5 consecutive amino acids corresponding to positions 586 to 594 num-bered relative to SEQ ID NO: 138, of any of the amino acid sequences of RGNRQA (SEQ ID NO: 1407), SSSTDP (SEQ ID NO: 1408), SSNTAP (SEQ ID NO: 1409), SNSNLP (SEQ ID NO: 1410), SSTTAP (SEQ ID NO: 1411), AAN-TAA (SEQ ID NO: 1412), QQNTAP (SEQ ID NO: 1413), SAQAQA (n SEQ ID NO: 1414), QANTGP (SEQ ID NO: 1415), NATTAP (SEQ ID NO: 1416), SSTAGP (SEQ ID NO: 1417), QQNTAA (SEQ ID NO: 1418), PSTAGP (SEQ ID NO: 1419), NONTAP (SEQ ID NO: 1420), QAANAP (SEQ ID NO: 1421), SIVGLP (SEQ ID NO: 1422), AASTAA (SEQ ID NO: 1423), SQNTTA (SEQ ID NO: 1424), QQDTAP (SEQ ID NO: 1425), QTNTGP (SEQ ID NO: 1426), QTNGAP (SEQ ID NO: 1427), QQNAAP (SEQ ID NO: 1428), or AANTQA (SEQ ID NO: 1429).

In some embodiments, the AAV capsid polypeptide, e.g., AAV capsid variant, or the parent AAV capsid described herein may further comprise an amino acid modification, e.g., a substitution or insertion, at amino acid positions 262 through 265, numbered according to the AAV2 capsid protein or the corresponding position in the capsid protein of another AAV with a targeting sequence, e.g., of any of the amino acid sequences of, NGRAHA (SEQ ID NO: 1430), QPEHSST (SEQ ID NO: 1431), VNTANST (SEQ ID NO: 1432), HGPMQKS (SEQ ID NO: 1433), PHKPPLA (SEQ ID NO: 1434), IKNNEMW (SEQ ID NO: 1435), RNLDTPM (SEQ ID NO: 1436), VDSHRQS (SEQ ID NO: 1437), YDSKTKT (SEQ ID NO: 1438), SQLPHQK (SEQ ID NO: 1439), STMQQNT (SEQ ID NO: 1440), TERYMTQ (SEQ ID NO: 1441), DASLSTS (SEQ ID NO: 1442), DLPNKKT (SEQ ID NO: 1443), DLTAARL (SEQ ID NO: 1444), EPHQFNY (SEQ ID NO: 1445), EPQSNHT (SEQ ID NO: 1446), MSSWPSQ (SEQ ID NO: 1447), NPKHNAT (SEQ ID NO: 1448), PDGMRTT (SEQ ID NO: 1449), PNNNKTT (SEQ ID NO: 1450), QSTTHDS (SEQ ID NO: 1451), TGSKQKQ (SEQ ID NO: 1452), SLKHQAL (SEQ ID NO: 1453), SPIDGEQ (SEQ ID NO: 1454), WIFPWIQL (SEQ ID NO: 1455), CDCRGDCFC (SEQ ID NO: 1456), CNGRC (SEQ ID NO: 1457), CPRECES (SEQ ID NO: 1458), CTTHWGFTLC (SEQ ID NO: 1459), CGR-RAGGSC (SEQ ID NO: 1460), CKGGRAKDC (SEQ ID NO: 1461), CVPELGHEC (SEQ ID NO: 1462), CRRE-TAWAK (SEQ ID NO: 1463), VSWFSHRYSPFAVS (SEQ ID NO: 1464), GYRDGYAGPILYN (SEQ ID NO: 1465), XXXXXXX (SEQ ID NO: 1466), YXNW (SEQ ID NO: 1467), RPLPPLP (SEQ ID NO: 1468), APPLPPR (SEQ ID NO: 1469), DVFYPYPYASGS (SEQ ID NO: 1470), MYWYPY (SEQ ID NO: 1471), DITWDQLWDLMK (SEQ ID NO: 1472), CWDDXWLC (SEQ ID NO: 1473), EWC-EYLGGYLRCYA (SEQ ID NO: 1474), YXCXXGPXTWXCXP (SEQ ID NO: 1475), IEGPTLRQWLAARA (SEQ ID NO: 1476), LWXXX (SEQ ID NO: 1477), XFXXYLW (SEQ ID NO: 1478), SSI-ISHFRWGLCD (SEQ ID NO: 1479), MSRPACPPNDKYE (SEQ ID NO: 1480), CLRSGRGC (SEQ ID NO: 1481), CHWMFSPWC (SEQ ID NO: 1482), WXXF (SEQ ID NO: 1483), CSSRLDAC (SEQ ID NO: 1484), CLPVASC (SEQ ID NO: 1485), CGFECVRQCPERC (SEQ ID NO: 1486), CVALCREACGEGC (SEQ ID NO: 1487), SWCEPGWCR (SEQ ID NO: 1488), YSGKWGW (SEQ ID NO: 1489), GLSGGRS (SEQ ID NO: 1490), LMLPRAD (SEQ ID NO: 1491), CSCFRDVCC (SEQ ID NO: 1492), CRDVVSVIC (SEQ ID NO: 1493), MARSGL (SEQ ID NO: 1494), MARAKE (SEQ ID NO: 1495), MSRTMS (SEQ ID NO: 1496, KCCYSL (SEQ ID NO: 1497), MYWGDSH-WLQYWYE (SEQ ID NO: 1498), MQLPLAT (SEQ ID NO: 1499), EWLS (SEQ ID NO: 1500), SNEW (SEQ ID NO: 1501), TNYL (SEQ ID NO: 1502), WDLAWMFRLPVG (SEQ ID NO: 1503), CTVALPG-GYVRVC (SEQ ID NO: 1504), CVAYCIEHHCWTC (SEQ ID NO: 1505), CVFAHNYDYLVC (SEQ ID NO: 1506), CVFTSNYAFC (SEQ ID NO: 1507), VHSPNKK (SEQ ID NO: 1508), CRGDGWC (SEQ ID NO: 1509), XRGCDX (SEQ ID NO: 1510), PXXX (SEQ ID NO: 1511), SGKGPRQITAL (SEQ ID NO: 1512), AAAAAAAAAXXXXX (SEQ ID NO: 1513), VYMSPF (SEQ ID NO: 1514), ATWLPPR (SEQ ID NO: 1515), HTMYYHHYQHHL (SEQ ID NO: 1516), SEVGCRAG-PLQWLCEKYFG (SEQ ID NO: 1517), CGLLPVGRPDRNVWRWLC (SEQ ID NO: 1518), CKGQCDRFKGLPWEC (SEQ ID NO: 1519), SGRSA (SEQ ID NO: 1520), WGFP (SEQ ID NO: 1521), AEPMPHSLNFSQYLWYT (SEQ ID NO: 1522), WAYXSP (SEQ ID NO: 1523), IELLQAR (SEQ ID NO: 1524), AYTKCSRQWRTCMTTH (SEQ ID NO: 1525), PQNSKIPGPTFLDPH (SEQ ID NO: 1526), SMEPAL-PDWWWKMFK (SEQ ID NO: 1527), ANTPCGPY-THDCPVKR (SEQ ID NO: 1528), TACHQHVRMVRP (SEQ ID NO: 1529), VPWMEPAYQRFL (SEQ ID NO: 1530), DPRATPGS (SEQ ID NO: 1531), FRPNRAQ-DYNTN (SEQ ID NO: 1532), CTKNSYLMC (SEQ ID NO: 1533), CXXTXXXGXGC (SEQ ID NO: 1534), CPIE-DRPMC (SEQ ID NO: 1535), HEWSYLAPYPWF (SEQ ID NO: 1536), MCPKHPLGC (SEQ ID NO: 1537), RMWPSSTVNLSAGRR (SEQ ID NO: 1538), SAK-TAVSQRVWLPSHRGGEP (SEQ ID NO: 1539), KSREHVNNSACPSKRITAAL (SEQ ID NO: 1540), EGFR (SEQ ID NO: 1541), AGLGVR SEQ ID NO: 1542), GTRQGHTMRLGVSDG (SEQ ID NO: 1543), IAGLATPGWSHWLAL (SEQ ID NO: 1544), SMSIARL (SEQ ID NO: 1545), HTFEPGV (SEQ ID NO: 1546), NTSLKRISNKRIRRK (SEQ ID NO: 1547), LRIKRKRRKRKKTRK (SEQ ID NO: 1548), GGG, GFS, LWS, EGG, LLV, LSP, LBS, AGG, GRR, GGH and GTV.

In some embodiments, the AAV capsid polypeptide, e.g., AAV capsid variant, or the parent AAV capsid may be or have, at a position other than 5 consecutive amino acids corresponding to positions 586 to 594 numbered relative to SEQ ID NO: 138, a sequence as described in United States Publication No. US20160369298, the contents of which are herein incorporated by reference in their entirety, such as, but not limited to, site-specific mutated capsid protein of AAV2 (SEQ ID NO: 97 of US20160369298; herein SEQ ID NO: 1549) or variants thereof, wherein the specific site is at least one site selected from sites R447, G453, and/or S662 of a VP1 or a fragment thereof.

In some embodiments, the AAV capsid polypeptide, e.g., AAV capsid variant, or the parent AAV capsid may further comprise any of the mutated sequences described in US 20160369298, e.g., any of the following sequences SDS-GASN (SEQ ID NO: 1550), SPSGASN (SEQ ID NO: 1551), SHSGASN (SEQ ID NO: 1552), SRSGASN (SEQ ID NO: 1553), SKSGASN (SEQ ID NO: 1554), SNSGASN (SEQ ID NO: 1555), SGSGASN (SEQ ID NO: 1556), SASGASN (SEQ ID NO: 1557), SESGTSN (SEQ ID NO: 1558), STTGGSN (SEQ ID NO: 1559), SSAGSTN (SEQ ID NO: 1560), NNDSQA (SEQ ID NO: 1561), NNRNQA (SEQ ID NO: 1562), NNNKQA (SEQ ID NO: 1563), NAKRQA (SEQ ID NO: 1564), NDEHQA (SEQ ID NO: 1565), NTSQKA (SEQ ID NO: 1566), YYLSRTNTPSGTDTQSRLVFSQAGA (SEQ ID NO: 1567), YYLSRTNTDSGTETQSGLDFSQAGA (SEQ ID NO: 1568), YYLSRTNTESGTPTQSALEFSQAGA (SEQ ID NO: 1569), YYLSRTNTHSGTHTQSPLHFSQAGA (SEQ ID NO: 1570), YYLSRTNTSSGTITISHLIFSQAGA (SEQ ID NO: 1571), YYLSRTN-TRSGIMTKSSLMFSQAGA (SEQ ID NO: 1572), YYLSRTNTKSGRKTLSNLSFSQAGA (SEQ ID NO: 1573), YYLSRTNDGSGPVTPSKLRFSQRGA (SEQ ID NO: 1574), YYLSRTNAASGHATHSDLKFSQPGA (SEQ ID NO: 1575), YYLSRTNGQAGSLTMSELGFSQVGA (SEQ ID NO: 1576), YYLSRTNSTGGNQTTSQLLF-SQLSA (SEQ ID NO: 1577), YFLSRTNNNTGLNTN-STLNFSQGRA (SEQ ID NO: 1578), SKTGADNNNSEY-SWTG (SEQ ID NO: 1579), SKTDADNNNSEYSWTG (SEQ ID NO: 1580), SKTEADNNNSEYSWTG (SEQ ID NO: 1581), SKTPADNNNSEYSWTG (SEQ ID NO: 1582), SKTHADNNNSEYSWTG (SEQ ID NO: 1583), SKTQADNNNSEYSWTG SEQ ID NO: 1584), SKTIADNNNSEYSWTG (SEQ ID NO: 1585), SKT-MADNNNSEYSWTG (SEQ ID NO: 1586), SKTRADNNNSEYSWTG (SEQ ID NO: 1587), SKT-NADNNNSEYSWTG (SEQ ID NO: 1588), SKTVGRNNNSEYSWTG (SEQ ID NO: 1589), SKTADRNNNSEYSWTG (SEQ ID NO: 1590), SKKLSQNNNSKYSWQG (SEQ ID NO: 1591), SKPTTGNNNSDYSWPG (SEQ ID NO: 1592), STQK-NENNNSNYSWPG (SEQ ID NO: 1593), HKDDEGKF (SEQ ID NO: 1594), HKDDNRKF (SEQ ID NO: 1595), HKDDTNKF (SEQ ID NO: 1596), HEDSDKNF (SEQ ID NO: 1597), HRDGADSF (SEQ ID NO: 1598), HGDNKSRF (SEQ ID NO: 1599), KQGSEKTNVDFEEV (SEQ ID NO: 1600), KQGSEKTNVDSEEV (SEQ ID NO: 1601), KQGSEKTNVDVEEV (SEQ ID NO: 1602), KQGSDKTNVDDAGV (SEQ ID NO: 1603), KQGSSKTNVDPREV (SEQ ID NO: 1604), KQGSRKTNVDHKQV (SEQ ID NO: 1605), KQGSKGG-NVDTNRV (SEQ ID NO: 1606), KQGSGEANVDNGDV (SEQ ID NO: 1607), KQDAAADNIDYDHV (SEQ ID NO: 1608), KQSGTRSNAAASSV (SEQ ID NO: 1609), KENTNTNDTELTNV (SEQ ID NO: 1610), QRGNN-VAATADVNT (SEQ ID NO: 1611), QRGNNEAATAD-VNT (SEQ ID NO: 1612), QRGNNPAATADVNT (SEQ ID NO: 1613), QRGNNHAATADVNT (SEQ ID NO: 1614), QEENNIAATPGVNT (SEQ ID NO: 1615), QPPNN-MAATHEVNT (SEQ ID NO: 1616), QHHNNSAATTIVNT (SEQ ID NO: 1617), QTTNNRAAFNMVET (SEQ ID NO: 1618), QKKNNNAASKKVAT (SEQ ID NO: 1619), QGG-NNKAADDAVKT (SEQ ID NO: 1620), QAAKGGAADD-AVKT (SEQ ID NO: 1621), QDDRAAAANESVDT (SEQ ID NO: 1622), QQQHDDAAYQRVHT (SEQ ID NO: 1623), QSSSSLAAVSTVQT (SEQ ID NO: 1624), QNNQT-TAAIRNVTT (SEQ ID NO: 1625), NYNKKSDNVDFT (SEQ ID NO: 1626), NYNKKSENVDFT (SEQ ID NO: 1627), NYNKKSLNVDFT (SEQ ID NO: 1628), NYNKK-SPNVDFT (SEQ ID NO: 1629), NYSKKSHCVDFT (SEQ ID NO: 1630), NYRKTIYVDFT (SEQ ID NO: 1631), NYKEKKDVHFT (SEQ ID NO: 1632), NYGHRAIVQFT (SEQ ID NO: 1633), NYANHQFVVCT (SEQ ID NO: 1634), NYDDDPTGVLLT (SEQ ID NO: 1635), NYDD-PTGVLLT (SEQ ID NO: 1636), NFEQQNSVEWT (SEQ ID NO: 1637), SQSGASN (SEQ ID NO: 1638), NNGSQA (SEQ ID NO: 1639), YYLSRTNTPSGTTTWSRLQFSQAGA (SEQ ID NO: 1640), SKTSADNNNSEYSWTG (SEQ ID NO: 1641), HKDDEEKF (SEQ ID NO: 1642), KQGSEKTNVDIEEV (SEQ ID NO: 1643), QRGNNQAATADVNT (SEQ ID NO: 1644), NYNKKSVNVDFT (SEQ ID NO: 1645), SQS-GASNYNTPSGTTTQSRLQFSTSADNNNSEYSWTGAT-KYH (SEQ ID NO: 1646), SAS-GASNFNSEGGSLTQSSLGFSTDGENNNSDFSWTGAT KYH (SEQ ID NO: 1647), SQSGASNYN-TPSGTTTQSRLQFSTDGENNNSDFSWTGATKYH (SEQ ID NO: 1648), SASGASNYNTPSGTTTQSRLQFST-SADNNNSEFSWPGATTYH (SEQ ID NO: 1649), SQS-GASNFNSEGGSLTQSSLGFSTDGENNNSDFSWTGAT-KYH (SEQ ID NO: 1650), SASGASNYNTPSGSLTQSSLGFSTDGENNNSDFSWT-GATKYH (SEQ ID NO: 1651), SQSGASNYN-TPSGTTTQSRLQFSTSADNNNSDFSWTGATKYH (SEQ ID NO: 1652), SGAGASNFNSEGGSLTQSSLGFSTD-GENNNSDFSWTGATKYH (SEQ ID NO: 1653), SGA-GASN (SEQ ID NO: 1654), NSEGGSLTQSSLGFS (SEQ ID NO: 1655), TDGENNNSDFS (SEQ ID NO: 1656), SEFSWPGATT (SEQ ID NO: 1657), TSADNNNSDFSWT (SEQ ID NO: 1658), SQSGASNY (SEQ ID NO: 1659), NTPSGTTTQSRLQFS (SEQ ID NO: 1660), TSADNNN-SEYSWTGATKYH (SEQ ID NO: 1661), SASGASNF (SEQ ID NO: 1662), TDGENNNSDFSWTGATKYH (SEQ ID NO: 1663), SASGASNY (SEQ ID NO: 1664), TSADNNNSEFSWPGATTYH (SEQ ID NO: 1665), NTPSGSLTQSSLGFS (SEQ ID NO: 1666), TSADNNNSDFSWTGATKYH (SEQ ID NO: 1667), SGA-GASNF (SEQ ID NO: 1668), CTCCAGVVSVVSMRSRVCVNSGCAGCTDHCVVSRN-SGTCVMSACACAA (SEQ ID NO: 1669), CTCCAGAGAGGCAACAGACAAGCAGCTACCGCA-GATGTCAACACACAA (SEQ ID NO: 1670), SAAGASN (SEQ ID NO: 1671), YFLSRTNTESGSTTQSTLRFSQAG (SEQ ID NO: 1672), SKTSADNNNSDFS (SEQ ID NO: 1673), KQGSEKTDVDIDKV (SEQ ID NO: 1674), STA-GASN (SEQ ID NO: 1675), YFLSRTNTTSGI-ETQSTLRFSQAG (SEQ ID NO: 1676), SKTD-GENNNSDFS (SEQ ID NO: 1677), KQGAAADDVEIDGV (SEQ ID NO: 1678), SEAGASN (SEQ ID NO: 1679), YYLSRTNTPSGTTTQSRLQFSQAG (SEQ ID NO: 1680), SKTSADNNNSEYS SEQ ID NO: 1681), KQGSEKTNVDIEKV (SEQ ID NO: 1682), YFLSRTNDASGSDTKSTLLFSQAG (SEQ ID NO: 1683), STTPSENNNSEYS (SEQ ID NO: 1684), SAAGATN (SEQ ID NO: 1685), YFLSRTNGEAGSATLSELRFSQAG (SEQ ID NO: 1686), HGDDADRF (SEQ ID NO: 1687), KQGAEKSDVEVDRV (SEQ ID NO: 1688), KQDSGGD-NIDIDQV (SEQ ID NO: 1689), SDAGASN (SEQ ID NO: 1690), YFLSRTNTEGGHDTQSTLRFSQAG (SEQ ID NO: 1691), KEDGGGSDVAIDEV (SEQ ID NO: 1692), SNA-GASN (SEQ ID NO: 1693), and YFLSRTNGEAGS-ATLSELRFSQPG (SEQ ID NO: 1694); or a nucleotide sequence that may encode the amino acid mutated sites of any of the following SEQ ID NO: 1695, SEQ ID NO: 1696, SEQ ID NO: 1697, SEQ ID NO: 1698, SEQ ID NO: 1699, SEQ ID NO: 1700, SEQ ID NO: 1701, SEQ ID NO: 1702, SEQ ID NO: 1703, SEQ ID NO: 1704, SEQ ID NO: 1705, SEQ ID NO: 1706, SEQ ID NO: 1707, SEQ ID NO: 1708, SEQ ID NO: 1709, SEQ ID NO: 1710, SEQ ID NO: 1711, SEQ ID NO: 1712, SEQ ID NO: 1713, SEQ ID NO: 1714, SEQ ID NO: 1715, SEQ ID NO: 1716, and SEQ ID NO: 1717.

In some embodiments, the AAV capsid polypeptide, e.g., AAV capsid variant, or the parent AAV capsid may further comprise an ocular cell targeting peptide, e.g., as described in International Patent Publication WO2016134375, the contents of which are herein incorporated by reference in their entirety, such as, but not limited to SEQ ID NO: 9, and SEQ ID NO: 10 of WO2016134375. Further, any of the ocular cell targeting peptides or amino acids described in WO2016134375, may be inserted into any parent AAV capsid sequence, such as, but not limited to, AAV2 (SEQ ID NO:8 of WO2016134375; herein SEQ ID NO: 1718), or AAV9 (SEQ ID NO: 11 of WO2016134375; herein SEQ ID NO: 1719). The ocular cell targeting peptide may be, but is not limited to, any of the following amino acid sequences, GSTPPPM (SEQ ID NO: 1720), or GETRAPL (SEQ ID NO: 1721).

In some embodiments, the AAV capsid polypeptide, e.g., AAV capsid variant, or the parent AAV capsid may be modified as described in the United States Publication US20170145405 the contents of which are herein incorporated by reference in their entirety. AAV serotypes may include, modified AAV2 (e.g., modifications at Y444F, Y500F, Y730F and/or S662V), modified AAV3 (e.g., modifications at Y705F, Y731F and/or T492V), and modified AAV6 (e.g., modifications at S663V and/or T492V).

In some embodiments, the AAV capsid polypeptide, e.g., AAV capsid variant, or the parent AAV capsid may be modified as described in the International Publication WO2017083722 the contents of which are herein incorporated by reference in their entirety. AAV serotypes may include, AAV1 (Y705+731F+T492V), AAV2 (Y444+500+730F+T491V), AAV3 (Y705+731F), AAV5, AAV 5 (Y436+693+719F), AAV6 (VP3 variant Y705F/Y731F/T492V), AAV8 (Y733F), AAV9, AAV9 (VP3 variant Y731F), and AAV10 (Y733F).

In some embodiments, the AAV capsid polypeptide, e.g., AAV capsid variant, or the parent AAV capsid may comprise, as described in International Patent Publication WO2017015102, the contents of which are herein incorporated by reference in their entirety, an engineered epitope comprising the amino acids SPAKFA (SEQ ID NO: 24 of WO2017015102; herein SEQ ID NO: 1722) or NKDKLN (SEQ ID NO:2 of WO2017015102; herein SEQ ID NO: 1723). The epitope may be inserted in the region of amino acids 665 to 670 based on the numbering of the VP1 capsid of AAV8 (SEQ ID NO: 3 of WO2017015102) and/or residues 664 to 668 of AAV3B (SEQ ID NO: 3).

In some embodiments, the AAV capsid polypeptide, e.g., AAV capsid variant, or the parent AAV capsid may be, or may have a sequence as described in International Patent Publication WO2017058892, the contents of which are herein incorporated by reference in their entirety, such as, but not limited to, AAV variants with capsid proteins that may comprise a substitution at one or more (e.g., 2, 3, 4, 5, 6, or 7) of amino acid residues 262-268, 370-379, 451-459, 472-473, 493-500, 528-534, 547-552, 709-710, 716-722 of AAV1, in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV. The amino acid substitution may be, but is not limited to, any of the amino acid sequences described in WO2017058892. In some embodiments, the AAV may comprise an amino acid substitution at residues 256L, 258K, 259Q, 261S, 263A, 264S, 265T, 266G, 272H, 385S, 386Q, S472R, V473D, N500E 547S, 709A, 710N, 716D, 717N, 718N, 720L, A456T, Q457T, N458Q, K459S, T492S, K493A, S586R, S587G, S588N, T589R and/or 722T of AAV1 (SEQ ID NO: 1 of WO2017058892) in any combination, 244N, 246Q, 248R, 249E, 250I, 251K, 252S, 253G, 254S, 255V, 256D, 263Y, 377E, 378N, 453L, 456R, 532Q, 533P, 535N, 536P, 537G, 538T, 539T, 540A, 541T, 542Y, 543L, 546N, 653V, 654P, 656S, 697Q, 698F, 704D, 705S, 706T, 707G, 708E, 709Y and/or 710R of AAV5 (SEQ ID NO:5 of WO2017058892) in any combination, 248R, 316V, 317Q, 318D, 319S, 443N, 530N, 531S, 532Q 533P, 534A, 535N, 540A, 541 T, 542Y, 543L, 545G, 546N, 697Q, 704D, 706T, 708E, 709Y and/or 710R of AAV5 (SEQ ID NO: 5 of WO2017058892) in any combination, 264S, 266G, 269N, 272H, and/or 457Q, of AAV6 (SEQ ID NO:6 of WO2017058892) in any combination, 457T, 459N, 496G, 499N, and/or 500N, of AAV8 (SEQ ID NO: 8 of WO2017058892) in any combination, 4511, 452N, 453G, 454S, 455G, 456Q, 457N and/or 458Q of AAV9 (SEQ ID NO: 9 of WO2017058892) in any combination.

In some embodiments, the AAV capsid polypeptide, e.g., AAV capsid variant, or the parent AAV capsid may include a sequence of amino acids at positions 155, 156 and 157 of VP1 or at positions 17, 18, 19 and 20 of VP2, as described in International Publication No. WO 2017066764, the contents of which are herein incorporated by reference in their entirety. The sequences of amino acid may be, but not limited to, N-S-S, S-X-S, S-S-Y, N-X-S, N-S-Y, S-X-Y and N-X-Y, where N, X and Y are, but not limited to, independently non-serine, or non-threonine amino acids, wherein the AAV may be, but not limited to AAV1, AAV2, AAV3, AAV4, AAV5, AAV6, AAV7, AAV8, AAV9, AAV10, AAV11 and AAV12. In some embodiments, the AAV may include a deletion of at least one amino acid at positions 156, 157 or 158 of VP1 or at positions 19, 20 or 21 of VP2, wherein the AAV may be, but not limited to AAV1, AAV2, AAV3, AAV4, AAV5, AAV6, AAV7, AAV8, AAV9, AAV10, AAV11 and AAV12.

In some embodiments, the AAV capsid polypeptide, e.g., AAV capsid variant, or the parent AAV capsid further comprise one or more components generated by Cre-recombination-based AAV targeted evolution (CREATE) as described by Deverman et al., (Nature Biotechnology 34 (2): 204-209 (2016)), the contents of which are herein incorporated by reference in their entirety. In some embodiments, AAV serotypes generated in this manner have improved CNS transduction and/or neuronal and astrocytic tropism, as compared to other AAV serotypes.

Promoters

In some embodiments, an AAV particle comprising a novel capsid of the present disclosure, which may hereinafter also be referred to as an AAV particle comprising an AAV capsid polypeptide, e.g., AAV capsid variant (e.g., a TRACER™ AAV particle), comprises at least one element to enhance target specificity and expression (See e.g., Powell et al. Viral Expression Cassette Elements to Enhance Transgene Target Specificity and Expression in Gene Therapy, 2015; the contents of which are herein incorporated by reference in its entirety). Non-limiting examples of an element to enhance the target specificity and expression include promoters, endogenous miRNAs, post-transcriptional regulatory elements (PREs), polyadenylation (PolyA) signal sequences and upstream enhancers (USEs), CMV enhancers and introns.

A person skilled in the art may recognize that expression of the polypeptides in a target cell may require a specific promoter, including but not limited to, a promoter that is species specific, inducible, tissue-specific, or cell cycle-specific (Parr et al., *Nat. Med.* 3:1145-9 (1997); the contents of which are herein incorporated by reference in their entirety).

In some embodiments, the promoter is deemed to be efficient when it drives expression of the polypeptide(s) encoded by AAV capsid mRNA described herein. In some embodiments, the promoter is deemed to be efficient when it drives expression of the polypeptide(s) encoded by viral genomes encapsulated within a capsid described herein.

In some embodiments, the promoter drives expression of the polypeptides (e.g., AAV capsid polypeptides) for a period of time in targeted tissues. Expression driven by a promoter may be for a period of 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years or more than 10 years. Expression may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years, or 5-10 years.

In some embodiments, the promoter drives expression of the polypeptides (e.g., AAV capsid polypeptides) for at least 1 month, 2 months, 3 months, 4 months, 5 months, 6 months, 7 months, 8 months, 9 months, 10 months, 11 months, 1 year, 2 years, 3 years 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, 55 years, 60 years, 65 years, or more than 65 years.

Promoters may be naturally occurring or non-naturally occurring. Non-limiting examples of promoters include viral promoters, plant promoters and mammalian promoters. In some embodiments, the promoters may be human promoters. In some embodiments, the promoter may be truncated.

Promoters which drive or promote expression in most tissues include, but are not limited to, human elongation factor 1α-subunit (EF1α), cytomegalovirus (CMV) immediate-early enhancer and/or promoter, chicken β-actin (CBA; such as, but not limited to, a CBA promotor as described in Miyazaki et al. (Gene. 1989 Jul. 15; 79 (2): 269-77, the contents of which are herein incorporated by reference in its entirety)) and its derivative CAG, β glucuronidase (GUSB), or ubiquitin C (UBC). Tissue-specific expression elements can be used to restrict expression to certain cell types such as, but not limited to, muscle specific promoters, B cell promoters, monocyte promoters, leukocyte promoters, macrophage promoters, pancreatic acinar cell promoters, endothelial cell promoters, lung tissue promoters, astrocyte promoters, or nervous system promoters which can be used to restrict expression to neurons, astrocytes, or oligodendrocytes.

Non-limiting examples of muscle-specific promoters include mammalian muscle creatine kinase (MCK) promoter, mammalian desmin (DES) promoter, mammalian troponin I (TNNI2) promoter, and mammalian skeletal alpha-actin (ASKA) promoter (see, e.g. U.S. Patent Publication US20110212529, the contents of which are herein incorporated by reference in their entirety). Muscle specific promotors may also include Mb promoter, myosin promotor, dystrophin promotor, dMCK and tMCK. As a non-limiting example, the muscle-specific promotor may be used to drive or promote expression in certain cell types, such as, but not limited to, myocytes and muscle stem cells.

Non-limiting examples of blood-specific promoters include B29 promoter, immunoglobulin heavy chain promoter, CD45 promoter, mouse INF-β promoter, CD45 SV40/CD45 promoter, WASP promoter, CD43 promoter, CD43 SV40/CD43 promoter, CD68 promoter, GPIIb promoter, CD14 promoter, and CD2 promoter. As a non-limiting example, the blood-specific promotor may be used to drive or promote expression in certain cell types, such as, but not limited to, in B cells, hematopoietic cells, leukocytes, platelets, macrophages, megakaryocytes, monocytes and/or T cells.

Non-limiting examples of bone-specific promoters include osteocalcin, bone sialoprotein, and OG-2 promoter. As a non-limiting example, the bone-specific promotor may be used to drive or promote expression in certain cell types, such as, but not limited to, osteoblasts and odontoblasts.

Non-limiting examples of eye-specific promoters include Chx10, PrP, Dkk3, Math5, Ptf1a, Pcp2, Nefh, gamma-synuclein gene (SNCG), Grik4, Pdgfra, Chat, Thy1.2, hVmd2, Thy1, Modified αA-crystallin, hRgp, mMo, Opn4, RLBP1, Glast, Foxg1, hVmd2, Trp1, Six3, cx36, Grm6-SV40 eukaryotic promoter, hVmd2, Dct, Rpc65, mRho, Irbp, hRho, Pcp2, Rhodopsin, and mSo, As a non-limiting example, the eye-specific promotor may be used to drive or promote expression in certain cell types, such as, but not limited, to retinal neurons, horizontal cells, bipolar cells, ganglion cells (GCs), ONL Müller cells, amacrine cells, lens cells, S-cone cells, M-cone cells, melanopsin-expressing GCs, neurons, ON bipolar, optic nerve cells, pigmented cells, retinal pigment epithelial cells, rod cells, rod bipolar cells, and rod photoreceptors.

Non-limiting examples of heart-specific promotors include MLC2v promoter, αMHC promoter, rat troponin T (Tnnt2), Tie2, and Tcf21. As a non-limiting example, the heart-specific promotor may be used to drive or promote expression in certain cell types, such as, but not limited to, cardiomyocytes, endothelial cells, and fibroblasts.

Non-limiting examples of kidney-specific promotors include, ECAD, NKCC2, KSPC, NPHS1, and SGLT2. As a non-limiting example, the kidney-specific promotor may be used to drive or promote expression in certain cell types, such as, but not limited to, collecting duct cells, loop of Henle cells, nephron cells, podocytes and proximal tubular cells.

Non-limiting examples of liver-specific promotors include, SV40/bAlb promoter, SV40/hAlb promoter, Hepatitis B virus core promoter, and Alpha fetoprotein. As a non-limiting example, the liver-specific promotor may be used to drive or promote expression in certain cell types, such as, but not limited to, hepatocytes.

Non-limiting examples of lung-specific promotors include Surfactant protein B promoter and Surfactant protein C promoter. As a non-limiting example, the lung-specific promotor may be used to drive or promote expression in certain cell types, such as, but not limited to, AT II cells and Clara cells.

Non-limiting examples of pancreas-specific promotors include elastase-1 promoter, PDX1 promoter, and insulin promoter. As a non-limiting example, the pancreas-specific promotor may be used to drive or promote expression in certain cell types, such as, but not limited to, acinar cells, beta cells, and Langerhans cells.

Non-limiting examples of vascular- or vasculature-specific promotors include Slco1c1, tie, cadherin, ICAM-2, claudin 1, Cldn5, Flt-1 promoter, and Endoglin promoter. As a non-limiting example, the vascular-specific promotor may be used to drive or promote expression in certain cell types, such as, endothelial cells. As a non-limiting example, the endothelial cell is a blood-brain barrier endothelial cell.

Non-limiting examples of tissue-specific expression elements for neurons include neuron-specific enolase (NSE), platelet-derived growth factor (PDGF), platelet-derived growth factor B-chain (PDGF-β), synapsin (Syn or Syn1), methyl-CpG binding protein 2 (MeCP2), $Ca^{2+}$/calmodulin-dependent protein kinase II (CaMKII), metabotropic glutamate receptor 2 (mGluR2), neurofilament light (NFL) or heavy (NFH) chain, β-globin minigene nβ2, preproenkephalin (PPE), enkephalin (Enk), VGF, and excitatory amino acid transporter 2 (EAAT2) promoters. A non-limiting examples of tissue-specific expression elements for neuroectodermal stem cells is nestin.

Non-limiting examples of tissue-specific expression elements for astrocytes include glial fibrillary acidic protein (GFAP, GFabc1D) and EAAT2 promoters. A non-limiting example of a tissue-specific expression element for oligodendrocytes includes the myelin basic protein (MBP) promoter.

In some embodiments, the promoter may be less than 1 kb. The promoter may have a length of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, or more than 800 nucleotides. The promoter may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800, or 700-800.

In some embodiments, the promoter may be a combination of two or more components of the same or different starting or parental promoters such as, but not limited to, CMV and CBA. Each component may have a length of 200, 210, 220, 230, 240, 250, 260, 270, 280, 290, 300, 310, 320, 330, 340, 350, 360, 370, 380, 381, 382, 383, 384, 385, 386, 387, 388, 389, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, or more than 800. Each component may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800. In some embodiments, the promoter is a combination of a 382 nucleotide CMV-enhancer sequence and a 260 nucleotide CBA-promoter sequence.

In some embodiments, the AAV particle comprises a ubiquitous promoter. Non-limiting examples of ubiquitous promoters include CMV, CBA (including derivatives CAG, CB6, CBh, etc.), EF-1a, PGK, UBC, GUSB (hGBp), and UCOE (promoter of HNRPA2B1-CBX3).

Yu et al. (Molecular Pain 2011, 7:63; the contents of which are herein incorporated by reference in their entirety) evaluated the expression of eGFP under the CAG, EFla, PGK and UBC promoters in rat DRG cells and primary DRG cells using lentiviral vectors and found that UBC showed weaker expression than the other 3 promoters and only 10-12% glial expression was seen for all promoters. Soderblom et al. (E. Neuro 2015; the contents of which are herein incorporated by reference in its entirety) evaluated the expression of eGFP in AAV8 with CMV and UBC promoters and AAV2 with the CMV promoter after injection in the motor cortex. Intranasal administration of a plasmid containing a UBC or EF1α promoter showed a sustained airway expression greater than the expression with the CMV promoter (See e.g., Gill et al., Gene Therapy 2001, Vol. 8, 1539-1546; the contents of which are herein incorporated by reference in their entirety). Husain et al. (Gene Therapy 2009; the contents of which are herein incorporated by reference in its entirety) evaluated an HBH construct with a hGUSB promoter, an HSV-1LAT promoter and an NSE promoter and found that the HBH construct showed weaker expression than NSE in mouse brain. Passini and Wolfe (J. Virol. 2001, 12382-12392, the contents of which are herein incorporated by reference in its entirety) evaluated the long-term effects of the HBH vector following an intraventricular injection in neonatal mice and found that there was sustained expression for at least 1 year. Low expression in all brain regions was found by Xu et al. (Gene Therapy 2001, 8, 1323-1332; the contents of which are herein incorporated by reference in their entirety) when NFL and NFH promoters were used as compared to the CMV-lacZ, CMV-luc, EF, GFAP, hENK, nAChR, PPE, PPE+wpre, NSE (0.3 kb), NSE (1.8 kb) and NSE (1.8 kb+wpre). Xu et al. found that the promoter activity in descending order was NSE (1.8 kb), EF, NSE (0.3 kb), GFAP, CMV, hENK, PPE, NFL and NFH. NFL is a 650 nucleotide promoter and NFH is a 920-nucleotide promoter which are both absent in the liver but NFH is abundant in the sensory proprioceptive neurons, brain and spinal cord and NFH is present in the heart. Scn8a is a 470 nucleotide promoter which expresses throughout the DRG, spinal cord and brain with particularly high expression seen in the hippocampal neurons and cerebellar Purkinje cells, cortex, thalamus, and hypothalamus (See e.g., Drews et al. *Identification of evolutionary conserved, functional noncoding elements in the promoter region of the sodium channel gene SCN8A*, Mamm Genome (2007) 18:723-731; and Raymond et al. *Expression of Alternatively Spliced Sodium Channel α-subunit genes*, Journal of Biological Chemistry (2004) 279 (44) 46234-46241; the contents of each of which are herein incorporated by reference in their entireties).

Any of promoters taught by the aforementioned Yu, Soderblom, Gill, Husain, Passini, Xu, Drews, or Raymond may be used in the present disclosures.

In some embodiments, the promoter is ubiquitous. In some embodiments, the promoter is not cell specific.

In some embodiments, the promoter is a ubiquitin c (UBC) promoter. The UBC promoter may have a size of 300-350 nucleotides. As a non-limiting example, the UBC promoter is 332 nucleotides.

In some embodiments, the promoter is a β-glucuronidase (GUSB) promoter. The GUSB promoter may have a size of 350-400 nucleotides. As a non-limiting example, the GUSB promoter is 378 nucleotides.

In some embodiments, the promoter is a neurofilament light (NFL) promoter. The NFL promoter may have a size of 600-700 nucleotides. As a non-limiting example, the NFL promoter is 650 nucleotides.

In some embodiments, the promoter is a neurofilament heavy (NFH) promoter. The NFH promoter may have a size of 900-950 nucleotides. As a non-limiting example, the NFH promoter is 920 nucleotides.

In some embodiments, the promoter is a scn8a promoter. The scn8a promoter may have a size of 450-500 nucleotides. As a non-limiting example, the scn8a promoter is 470 nucleotides.

In some embodiments, the promoter is a phosphoglycerate kinase 1 (PGK) promoter.

In some embodiments, the promoter is a chicken β-actin (CBA) promoter, or a variant thereof.

In some embodiments, the promoter is a CB6 promoter.

In some embodiments, the promoter is a minimal CB promoter.

In some embodiments, the promoter is a P40 promoter. In some embodiments, the P40 promoter is located in the 3' of the AAV capsid REP gene.

In some embodiments, the promoter is a cytomegalovirus (CMV) promoter.

In some embodiments, the CMV promoter is a hybrid CMV enhancer/Chicken beta-actin promoter sequence such as described by Niwa et al., 1991, the contents of which are incorporated herein by reference in their entirety.

In some embodiments, the promoter is a CAG promoter.

In some embodiments, the promoter is a GFAP promoter.

In some embodiments, the promoter is a synapsin (syn or syn1) promoter.

In some embodiments, the promoter is a liver or a skeletal muscle promoter. Non-limiting examples of liver promoters include human a-1-antitrypsin (hAAT) and thyroxine binding globulin (TBG). Non-limiting examples of skeletal muscle promoters include Desmin, MCK or synthetic C5-12.

In some embodiments, the promoter is an RNA pol III promoter. As a non-limiting example, the RNA pol III promoter is U6. As a non-limiting example, the RNA pol III promoter is H1.

In some embodiments, the promoter may be selected depending on the desired tropism. Non-limiting examples of promoters are described in WO2020072683, the contents of which are herein incorporated by reference in their entirety.

In some embodiments, the promoter drives capsid mRNA expression in the absence of helper virus co-infection.

In some embodiments, the AAV particle (e.g., an AAV particle comprising an AAV capsid polypeptide, e.g., an AAV capsid variant described herein) comprises two promoters. As a non-limiting example, the promoters are an P40 promoter and a CMV promoter. As another non-limiting example, the promoters are an P40 promoter and a cell-type specific promoter (e.g. synapsin).

In some embodiments, the AAV particle (e.g., an AAV particle comprising an AAV capsid polypeptide, e.g., an AAV capsid variant described herein) comprises an engineered promoter.

In another embodiment, the AAV particle (e.g., an AAV particle comprising an AAV capsid polypeptide, e.g., AAV capsid variant described herein) comprises a promoter from a naturally expressed protein.

In some embodiments, a portion of the AAV particle (e.g., an AAV particle comprising an AAV capsid polypeptide, e.g., AAV capsid variant described herein) REP gene is deleted to accommodate the promoter insertion. The promoter may be inserted upstream or downstream of the AAV particle CAP gene.

In some embodiments, the AAV particle of the present disclosure (e.g., an AAV particle comprising an AAV capsid polypeptide, e.g., AAV capsid variant described herein) comprises a cell type-specific promoter to drive capsid mRNA expression. As a non-limiting example, the promotor is cell-type specific. The cell-type specific promotor may be synapsin. The cell-type specific promotor may be glial fibrillary acidic protein (GFAP). The AAV particle may comprise a P40 promoter and a cell-type specific promotor.

Figure 5:
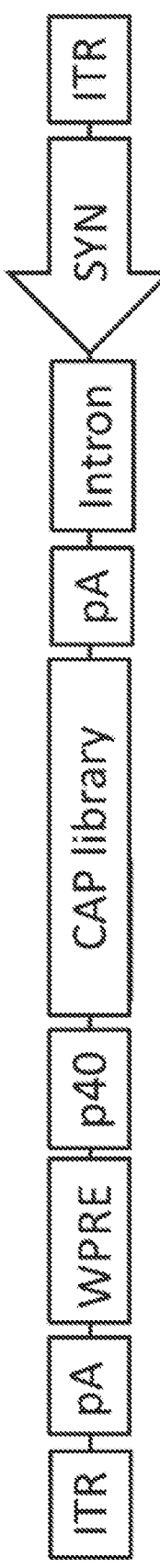
FIG. 5 provides a diagram of an alternative TRACER™ backbone construct.

In some embodiments, the AAV particle of the present disclosure (e.g., an AAV particle comprising an AAV capsid polypeptide, e.g., AAV capsid variant described herein) comprises a structure as shown in FIG. 4. In some embodiments, an alternate backbone may be used for generation of the capsid libraries. In the alternate backbone, the forward version is changed into reverse, which can avoid the expression of capsid proteins and possible immune response to these foreign capsid proteins during in vivo evolution. In some embodiments, one or more additional WPRE elements may also be added to the backbone to improve RNA yield during viral library RNA recovery. In some embodiments, the backbone for the TRACER™ approach is as shown in FIG. 5.

AAV Selection

The present disclosure provides methods of AAV selection for tissue- and/or cell type-specific transduction, whereby AAV particles (e.g., an AAV particle comprising an AAV capsid polypeptide, e.g., an AAV capsid variant, described herein) with high tropism for a tissue(s) and/or cell type(s) are identified and selected for use. In some embodiments, the AAV selection comprises administration of the AAV particles to a cell and/or a subject by standard methods known in the art (e.g. intravenously). In some embodiments, the AAV selection may comprise extraction of polynucleotides, e.g., capsid RNA, encoded by AAV particles, from a specific tissue and/or cell type. In some embodiments, the tissue may be non-nervous system tissue such as, but not limited to, liver, spleen and heart. The cells type may be, e.g., hepatocytes, Islets of Langerhans cells, and cardiomyocytes. In some embodiments, the tissue may be nervous system tissue such as, but not limited to, brain tissue, spinal cord tissue, and dorsal root ganglion tissue. The cell type may be, e.g., neurons, astrocytes, or oligodendrocytes. In some embodiments, the extracted RNA is enriched, reverse transcribed, and/or amplified. In some embodiments, the extracted RNA allows for recovery of full-length capsid "amplicon(s)" from a specific tissue and/or cell type, using various production methods, e.g., reverse transcription polymerase chain reaction (RT-PCR). As used herein, amplicon may refer to any piece of RNA or DNA formed as the product of amplification events, e.g. PCR. In some embodiments, full-length capsid amplicons may be used as templates for next generation sequencing (NGS) library generation. Full-length capsid amplicons may be used for cloning into a DNA library for the generation of AAV TRACER™ particles for any number of additional rounds of AAV selection as described above. In some embodiments, the AAV selection may be performed iteratively, or repeated, any number of times, or rounds. The above-described selection of AAV particles may also be more generally referred to herein as biopanning.

In some embodiments, the AAV selection comprises administration of the AAV particles (e.g., an AAV particle comprising an AAV capsid polypeptide, e.g., AAV capsid variant, described herein) to a cell by standard methods known in the art (e.g. infection). As a non-limiting example, the cell is a HEK293 cell. As another non-limiting example, the cell is a nervous system cell such as, but not limited to, a neuron and/or a glial cell. As yet another non-limiting example, the cell is a brain microvascular endothelial cells (BMVEC). The BMVEC may be a human BMVEC (hBMVEC). The BMVEC may be a non-human primate (NHP) BMVEC.

In some embodiments, the AAV selection comprises administration of the AAV particles (e.g., an AAV particle comprising an AAV capsid polypeptide, e.g., AAV capsid variant, described herein) to a rodent by standard methods known in the art (e.g. intravenously). The rodent may be a transgenic rodent or a non-transgenic (e.g., wild type) rodent. As a non-limiting example, the rodent is a rat or a mouse. Non-limiting examples of rats include Sprague Dawley, Wistar Albino, and Long Evans rats. Non-limiting examples of mice include BALB/C, FVB and C57BL/6 mice.

In some embodiments, the AAV selection comprises administration of the AAV particles (e.g., an AAV particle comprising an AAV capsid polypeptide, e.g., an AAV capsid variant, described herein) to a non-human primate (NHP) by standard methods known in the art (e.g. intravenously). Non-limiting examples of NHPs include rhesus macaques (*Macaca mulatta*) and cynomolgus macaques (*Macaca fascicularis*).

In some embodiments, the AAV selection comprises administration of AAV particles (e.g., an AAV particle comprising an AAV capsid polypeptide, e.g., an AAV capsid variant, described herein) to a rodent, non-human primate, and/or human cells. In some embodiments, the AAV selection comprises administration of AAV particles (e.g., an AAV particle comprising an AAV capsid polypeptide, e.g., an AAV capsid variant, described herein) to a rodent, non-human primate, and/or human subjects.

Figure 1B:
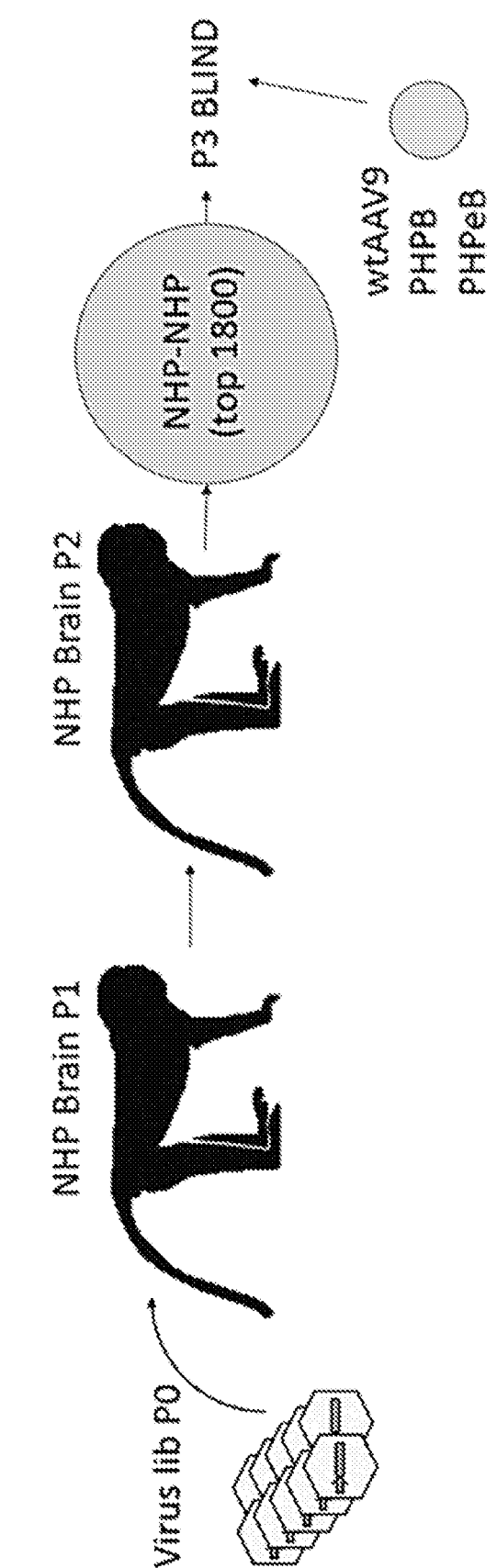

In some embodiments, the AAV selection may be performed iteratively, or repeated, any number of times, or rounds, within a single cell- or subject-type, wherein the single cell- or subject-type may remain unchanged, or the same, across AAV selection rounds. Cell types may be, e.g., HEK293 cells, hBMVECs, and NHP BMVECs. Subject types may be, e.g., Sprague Dawley rats, Wistar Albino rats, Long-Evans rats, BALB/C mice, FVB mice, C57BL/6 mice, rhesus macaques, cynomolgus macaques, and humans. As a non-limiting example, AAV selection is performed across one, two and/or three or more AAV selection rounds in the hBMVEC cell. As a non-limiting example, AAV selection is performed across one, two and/or three or more rounds in a mouse such as, but not limited to, a BALB/C mouse. As a non-limiting example, AAV selection is performed across one, two and/or three or more rounds in an NHP such as, but not limited to, a cynomolgus macaque, as represented in FIG. 1A and FIG. 1B.

AAV selection may be performed iteratively, or repeated, any number of times, or rounds, within any number of cell- and/or subject-types, wherein the cell- and or subject-type may change, or differ, across AAV selection rounds. As a non-limiting example, the AAV selection is performed a first round in a rhesus macaque, and an additional, e.g., subsequent, one, two, and/or or three or more rounds in a Sprague-Dawley rat.

AAV selection may be performed iteratively, or repeated, any number of times, or rounds, within any number of cell- and/or subject-types, and may additionally comprise the combination and/or comparison of any AAV capsid serotype as disclosed herein, or variants or derivatives thereof, with the AAV particle pool, at any AAV selection round. As a non-limiting example, the AAV capsid serotype comprises AAVF7/HSC7 (SEQ ID NO: 8 and 27 of WO2016049230). As another non-limiting example, the AAV capsid serotype comprises AAVF15/HSC15 (SEQ ID NO: 16 and 33 of WO2016049230). As yet another non-limiting example, the AAV capsid serotype AAVF17/HSC17 (SEQ ID NO: 13 and 35 of WO2016049230). The AAV selection round may be the first, second, third, or fourth AAV selection round.

Orthogonal Evolution

Figure 2:
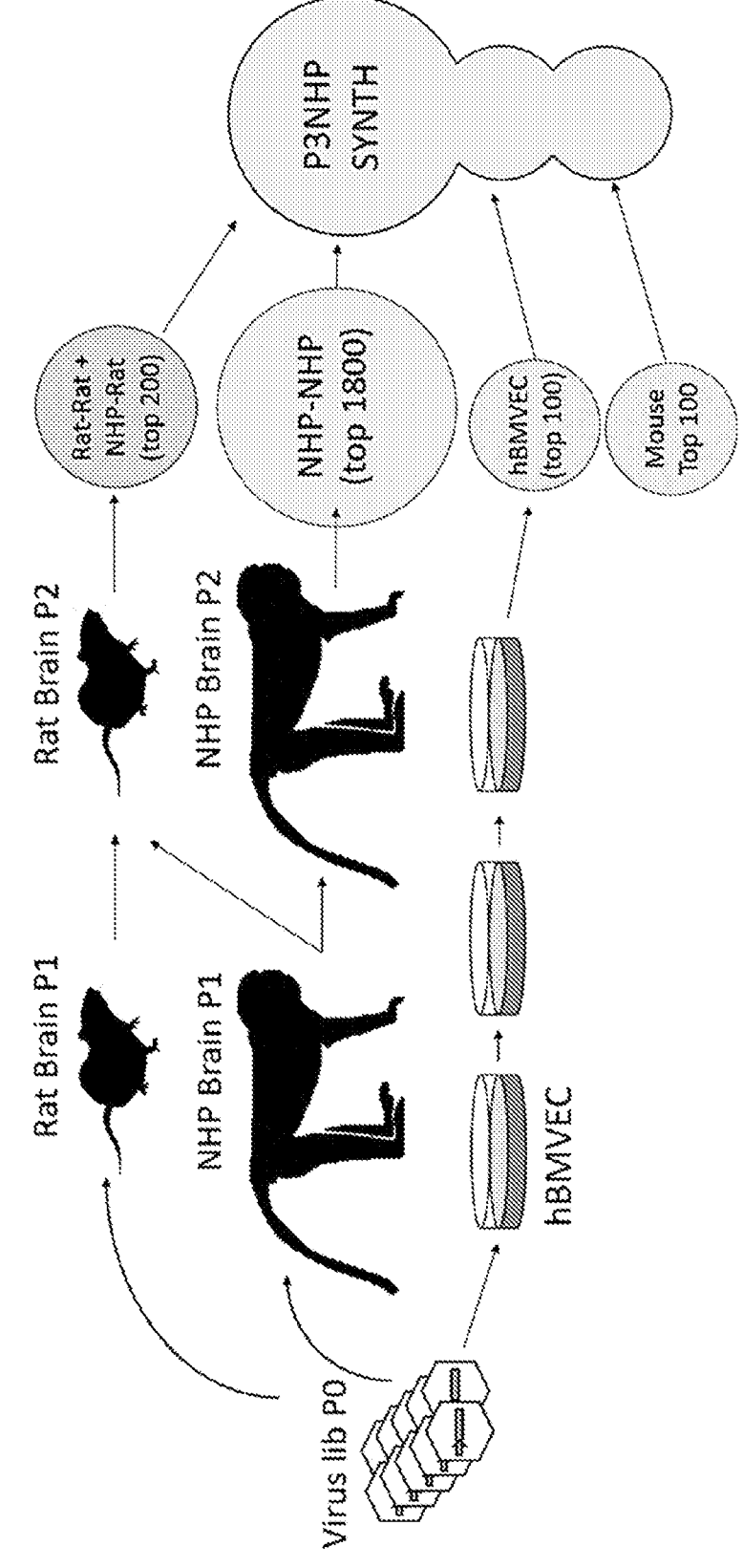
FIG. 2 provides a diagram of orthogonal evolution of TRACER™ AAV capsid libraries.

Methods of AAV selection of the present disclosure may comprise orthogonal evolution. In some embodiments, orthogonal evolution is a method wherein AAV particles are administered for a first round of AAV selection as described herein across a set of any number of cell- and/or subject-types that may be from different species and/or strains, and wherein any number of additional, e.g., subsequent, AAV selection rounds are performed either across a set of any number of cell- and/or subject-types that may be from different species and/or strains, or across a set of any number of cell- and/or subject-types that may be from the same species and/or strains, as represented in FIG. 2. Cell types may be, e.g., HEK293 cells, hBMVECs, and NHP BMVECs. Subject types may be, e.g., Sprague Dawley rats, Wistar Albino rats, Long-Evans rats, BALB/C mice, FVB mice, C57BL/6 mice, rhesus macaques, cynomolgus macaques, and humans.

Viral Genome of the AAV Particle

AAV particle as described herein, comprising a peptide, e.g., a targeting peptide and/or selected by the TRACER™ methods (e.g., an AAV particle comprising an AAV capsid polypeptide, e.g., an AAV capsid polypeptide, e.g., AAV capsid variant, described herein), may be used for the delivery of a viral genome to a tissue, e.g., a target tissue (e.g., CNS, DRG, and/or muscle). In some embodiments, an AAV particle comprising an AAV capsid polypeptide, e.g., an AAV capsid variant, described herein can be used for delivery of a viral genome to a tissue or cell, e.g., CNS, DRG, or muscle cell or tissue. In some embodiments, an AAV particle of the present disclosure is a recombinant AAV particle. In some embodiments, an AAV particle of the present disclosure is an isolated AAV particle.

The viral genome may encode any payload, such as but not limited to a polypeptide (e.g., a therapeutic polypeptide), an antibody, an enzyme, an RNAi agent and/or components of a gene editing system. In one embodiment, the AAV particles described herein are used to deliver a payload to cells of the CNS, after intravenous delivery. In another embodiment, the AAV particles described herein are used to deliver a payload to cells of the DRG, after intravenous delivery. In some embodiments, the AAV particles described herein are used to deliver a payload to cells of a muscle, e.g., a heart muscle, after intravenous delivery.

A viral genome of an AAV particle comprising an AAV capsid polypeptide, e.g., an AAV capsid variant, as described herein, comprises a nucleic acid sequence with at least one payload region encoding a payload, and at least one ITR. A viral genome typically comprises two ITR sequences, one at each of the 5' and 3' ends. Further, a viral genome of the AAV particles described herein may comprise nucleic acid sequences for additional components, such as, but not limited to, a regulatory element (e.g., promoter), untranslated regions (UTR), a polyadenylation sequence (polyA), a filler or stuffer sequence, an intron, and/or a linker sequence for enhanced expression.

These viral genome components can be selected and/or engineered to further tailor the specificity and efficiency of expression of a given payload in a target tissue (e.g., CNS, muscle, or DRG).

Viral Genome Component: Inverted Terminal Repeats (ITRs)

In some embodiments, the AAV particle comprising an AAV capsid polypeptide, e.g., an AAV capsid variant, described herein comprises a viral genome with at least one ITR and a payload region. In one embodiment, the viral genome has two ITRs. These two ITRs flank the payload region at the 5' and 3' ends. The ITRs function as origins of replication comprising recognition sites for replication. ITRs comprise sequence regions which can be complementary and symmetrically arranged. ITRs incorporated into viral genomes as described herein may be comprised of naturally occurring polynucleotide sequences or recombinantly derived polynucleotide sequences.

The ITRs may be derived from the same serotype as the capsid polypeptide, e.g., capsid variant, selected from any of the known serotypes, or a derivative thereof. The ITR may be of a different serotype than the capsid. In one embodiment, the AAV particle has more than one ITR. In a non-limiting example, the AAV particle has a viral genome comprising two ITRs. In one embodiment, the ITRs are of the same serotype as one another. In another embodiment, the ITRs are of different serotypes. Non-limiting examples include zero, one or both of the ITRs having the same serotype as the capsid. In one embodiment both ITRs of the viral genome of the AAV particle are AAV2 ITRs.

Independently, each ITR may be about 100 to about 150 nucleotides in length. An ITR may be about 100-105 nucleotides in length, 106-110 nucleotides in length, 111-115 nucleotides in length, 116-120 nucleotides in length, 121-125 nucleotides in length, 126-130 nucleotides in length, 131-135 nucleotides in length, 136-140 nucleotides in length, 141-145 nucleotides in length or 146-150 nucleotides in length. In one embodiment, the ITRs are 140-142 nucleotides in length. Non-limiting examples of ITR length are 102, 105, 130, 140, 141, 142, 145 nucleotides in length. ITRs encompassed by the present disclosure include those with at least 90% identity, at least 95% identity, at least 98% identity, or at least 99% identity to a known AAV serotype ITR sequence.

Viral Genome Component: Promoters

In one embodiment, the payload region of the viral genome comprises at least one element to enhance the payload target specificity and expression (See e.g., Powell et al. Viral Expression Cassette Elements to Enhance Transgene Target Specificity and Expression in Gene Therapy, 2015; the contents of which are herein incorporated by reference in their entirety). Non-limiting examples of elements to enhance payload target specificity and expression include promoters, endogenous miRNAs, post-transcriptional regulatory elements (PREs), polyadenylation (PolyA) signal sequences and upstream enhancers (USEs), CMV enhancers and introns.

A person skilled in the art may recognize that expression of a payload in a target cell may require a specific promoter, including but not limited to, a promoter that is species specific, inducible, tissue-specific, or cell cycle-specific (Parr et al., *Nat. Med.* 3:1145-9 (1997); the contents of which are herein incorporated by reference in their entirety).

In one embodiment, the promoter is deemed to be efficient when it drives expression of the payload encoded by the viral genome of the AAV particle.

In one embodiment, the promoter is a promoter deemed to be efficient when it drives expression in a cell being targeted.

In one embodiment, the promoter is a promoter having a tropism for a cell being targeted.

In one embodiment, the promoter drives expression of the payload for a period of time in targeted tissues. Expression driven by a promoter may be for a period of 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years or more than 10 years. Expression may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years or 5-10 years. As a non-limiting example, the promoter is a selected for sustained expression of a payload in tissues and/or cells of the central or peripheral nervous system.

Promoters may be naturally occurring or non-naturally occurring. Non-limiting examples of promoters include those derived from viruses, plants, mammals, or humans. In some embodiments, the promoters may be those derived from human cells or systems. In some embodiments, the promoter may be truncated or mutated.

Promoters which drive or promote expression in most tissues include, but are not limited to, the human elongation factor 1α-subunit (EF1α) promoter, the cytomegalovirus (CMV) immediate-early enhancer and/or promoter, the chicken β-actin (CBA) promoter and its derivative CAG, β glucuronidase (GUSB) promoter, or ubiquitin C (UBC) promoter. Tissue-specific promoters can be used to restrict expression to certain cell types such as, but not limited to, cells of the central or peripheral nervous systems, targeted regions within (e.g., frontal cortex), and/or sub-sets of cells therein (e.g., excitatory neurons). As non-limiting examples, cell-type specific promoters may be used to restrict expression of a payload to excitatory neurons (e.g., glutamatergic), inhibitory neurons (e.g., GABA-ergic), neurons of the sympathetic or parasympathetic nervous system, sensory neurons, neurons of the dorsal root ganglia, motor neurons, or supportive cells of the nervous systems such as microglia, astrocytes, oligodendrocytes, and/or Schwann cells.

Cell-type specific promoters also exist for other tissues of the body, with non-limiting examples including, liver promoters (e.g., hAAT, TBG), skeletal muscle specific promoters (e.g., desmin, MCK, C512), B cell promoters, monocyte promoters, leukocyte promoters, macrophage promoters, pancreatic acinar cell promoters, endothelial cell promoters, lung tissue promoters, and/or cardiac or cardiovascular promoters (e.g., αMHC, cTnT, and CMV-MLC2k).

Non-limiting examples of tissue-specific promoters for targeting payload expression to central nervous system tissues and cells include synapsin (Syn), glutamate vesicular transporter (VGLUT), vesicular GABA transporter (VGAT), parvalbumin (PV), sodium channel Na. 1.8, tyrosine hydroxylase (TH), choline acetyltransferase (ChaT), methyl-CpG binding protein 2 (MeCP2), $Ca^{2+}$/calmodulin-dependent protein kinase II (CaMKII), metabotropic glutamate receptor 2 (mGluR2), neurofilament light (NFL) or heavy (NFH), neuron-specific enolase (NSE), β-globin minigene nβ2, preproenkephalin (PPE), enkephalin (Enk) and excitatory amino acid transporter 2 (EAAT2) promoters. Non-limiting examples of tissue-specific expression elements for astrocytes include glial fibrillary acidic protein (GFAP) and EAAT2 promoters. A non-limiting example of a tissue-specific expression element for oligodendrocytes includes the myelin basic protein (MBP) promoter.

In some embodiments, the promoter of the viral genome used to drive expression of the payload in a target tissue may be any of those noted herein for use in AAV particles.

Viral Genome Component: Untranslated Regions (UTRs)

In some embodiments, wild type untranslated regions (UTRs) of a gene are transcribed but not translated. Generally, the 5' UTR starts at the transcription start site and ends at the start codon and the 3' UTR starts immediately following the stop codon and continues until the termination signal for transcription.

Features typically found in abundantly expressed genes of specific target organs (e.g., CNS tissue, muscle, or DRG) may be engineered into UTRs to enhance stability and protein production. As a non-limiting example, a 5' UTR from mRNA normally expressed in the brain (e.g., huntingtin) may be used in the viral genomes of the AAV particles described herein to enhance expression in neuronal cells or other cells of the central nervous system.

While not wishing to be bound by theory, wild-type 5' untranslated regions (UTRs) include features which play roles in translation initiation. Kozak sequences, which are commonly known to be involved in the process by which the ribosome initiates translation of many genes, are usually included in 5' UTRs. Kozak sequences have the consensus CCR (A/G) CCAUGG, where R is a purine (adenine or guanine) three bases upstream of the start codon (ATG), which is followed by another 'G'.

In one embodiment, the 5'UTR in the viral genome includes a Kozak sequence.

In one embodiment, the 5'UTR in the viral genome does not include a Kozak sequence.

While not wishing to be bound by theory, wild-type 3' UTRs are known to have stretches of Adenosines and Uridines embedded therein. These AU rich signatures are particularly prevalent in genes with high rates of turnover. Based on their sequence features and functional properties, the AU rich elements (AREs) can be separated into three classes (Chen et al, 1995, the contents of which are herein incorporated by reference in its entirety): Class I AREs, such as, but not limited to, c-Myc and MyoD, contain several dispersed copies of an AUUUA motif within U-rich regions. Class II ARES, such as, but not limited to, GM-CSF and TNF-a, possess two or more overlapping UUAUUUA (U/A) (U/A) nonamers. Class III ARES, such as, but not limited to, c-Jun and Myogenin, are less well defined. These U rich regions do not contain an AUUUA motif. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of a polynucleotide. When engineering specific polynucleotides, e.g., payload regions of viral genomes, one or more copies of an ARE can be introduced to make polynucleotides less stable and thereby curtail translation and decrease production of the resultant protein. Likewise, AREs can be identified and removed or mutated to increase the intracellular stability and thus increase translation and production of the resultant protein.

In one embodiment, the 3' UTR of the viral genome may include an oligo (dT) sequence for templated addition of a poly-A tail.

In one embodiment, the viral genome may include at least one miRNA seed, binding site or full sequence. microRNAs (or miRNA or miR) are 19-25 nucleotide noncoding RNAs that bind to the sites of nucleic acid targets and down-regulate gene expression either by reducing nucleic acid molecule stability or by inhibiting translation. In some embodiments, a microRNA sequence comprises a seed region, e.g., a sequence in the region of positions 2-8 of the mature microRNA, which has Watson-Crick sequence fully or partially complementarity to the miRNA target sequence of the nucleic acid.

In one embodiment, the viral genome may be engineered to include, alter or remove at least one miRNA binding site, full sequence or seed region.

Any UTR from any gene known in the art may be incorporated into the viral genome of the AAV particle. These UTRs, or portions thereof, may be placed in the same orientation as in the gene from which they were selected or they may be altered in orientation or location. In one embodiment, the UTR used in the viral genome of the AAV particle may be inverted, shortened, lengthened, made with one or more other 5' UTRs or 3' UTRs known in the art. As used herein, the term "altered" as it relates to a UTR, means that the UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides.

In one embodiment, the viral genome of the AAV particle comprises at least one artificial UTR which is not a variant of a wild type UTR.

In one embodiment, the viral genome of the AAV particle comprises UTRs which have been selected from a family of transcripts whose proteins share a common function, structure, feature or property.

Viral Genome Component: Polyadenylation Sequence

The viral genome of the AAV particle described herein (e.g., an AAV particle comprising an AAV capsid polypeptide, e.g., an AAV capsid variant, described herein) may comprise at least one polyadenylation sequence. In one embodiment, the viral genome of the AAV particle (e.g., an AAV particle comprising an AAV capsid polypeptide, e.g., an AAV capsid variant, described herein) comprises a polyadenylation sequence between the 3' end of the payload encoding region and the 5' end of the 3'ITR.

In one embodiment, the polyadenylation sequence or "polyA sequence" may range from absent to about 500 nucleotides in length. In some embodiments, the polyA sequence comprises a length of about 100-600 nucleotides, e.g., about 100-500 nucleotides, about 100-400 nucleotides, about 100-300 nucleotides, about 100-200 nucleotides, about 200-600 nucleotides, about 200-500 nucleotides, about 200-400 nucleotides, about 200-300 nucleotides, about 300-600 nucleotides, about 300-500 nucleotides, about 300-400 nucleotides, about 400-600 nucleotides, about 400-500 nucleotides, or about 500-600 nucleotides. In some embodiments, the polyA signal region comprises a length of about 100 to 150 nucleotides, e.g., about 127 nucleotides. In some embodiments, the polyA sequence comprises a length of about 450 to 500 nucleotides, e.g., about 477 nucleotides. In some embodiments, the polyA sequence comprises a length of about 520 to about 560 nucleotides, e.g., about 552 nucleotides. In some embodiments, the polyA sequence comprises a length of about 127 nucleotides.

Viral Genome Component: Introns

In one embodiment, the viral genome of the AAV particle as described herein (e.g., an AAV particle comprising an AAV capsid polypeptide, e.g., an AAV capsid variant), comprises at least one element to enhance the payload target specificity and expression (See e.g., Powell et al. *Viral Expression Cassette Elements to Enhance Transgene Target Specificity and Expression in Gene Therapy*, Discov. Med, 2015, 19 (102): 49-57; the contents of which are herein incorporated by reference in their entirety) such as an intron. Non-limiting examples of introns include, MVM (67-97 bps), F.IX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

In one embodiment, the intron or intron portion may be 100-500 nucleotides in length. The intron may have a length of 80, 90, 100, 110, 120, 130, 140, 150, 160, 170, 171, 172, 173, 174, 175, 176, 177, 178, 179, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 nucleotides. The intron may have a length between 80-100, 80-120, 80-140, 80-160, 80-180, 80-200, 80-250, 80-300, 80-350, 80-400, 80-450, 80-500, 200-300, 200-400, 200-500, 300-400, 300-500, or 400-500 nucleotides.

Viral Genome Component: Stuffer Sequences

In one embodiment, the viral genome of the AAV particle described herein (e.g., an AAV particle comprising an AAV capsid polypeptide, e.g., an AAV capsid variant), comprises at least one element to improve packaging efficiency and expression, such as a stuffer or filler sequence. Non-limiting examples of stuffer sequences include albumin and/or alpha-1 antitrypsin. Any known viral, mammalian, or plant sequence may be manipulated for use as a stuffer sequence.

In one embodiment, the stuffer or filler sequence may be from about 100-3500 nucleotides in length. The stuffer sequence may have a length of about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900 or 3000 nucleotides.

Viral Genome Component: miRNA

In one embodiment, the viral genome comprises at least one sequence encoding a miRNA to reduce the expression of the payload in an "off-target" tissue. As used herein, "off-target" indicates a tissue or cell-type unintentionally targeted by the AAV particles described herein. miRNAs and their targeted tissues are well known in the art. As an example, an "off-target" tissue or cell when targeting the DRG (dorsal root ganglion), may be neurons of other ganglia, such as those of the sympathetic or parasympathetic nervous system. In some embodiments, a miRNA, e.g., a miR183, a miR182, and/or miR96, may be encoded in the viral genome to modulate, e.g., reduce the expression, of the viral genome in a DRG neuron. As another non-limiting example, a miR-122 miRNA may be encoded in the viral genome to modulate, e.g., reduce, the expression of the viral genome in the liver. In some embodiments, a miRNA, e.g., a miR-142-3p, may be encoded in the viral genome to modulate, e.g., reduce, the expression, of the viral genome in a cell or tissue of the hematopoietic lineage, including for example immune cells (e.g., antigen presenting cells or APC, including dendritic cells (DCs), macrophages, and B-lymphocytes).

Viral Genome Component: miR Binding Site

Tissue- or cell-specific expression of the AAV viral particles of the invention can be enhanced by introducing tissue- or cell-specific regulatory sequences, e.g., promoters, enhancers, microRNA binding sites, e.g., a detargeting site. Without wishing to be bound by theory, it is believed that a miR binding site can modulate, e.g., prevent, suppress, or otherwise inhibit, the expression of a gene of interest on the viral genome of the invention, based on the expression of the corresponding endogenous microRNA (miRNA) or a corresponding controlled exogenous miRNA in a tissue or cell, e.g., a non-targeting cell or tissue. In some embodiments, a miR binding site modulates, e.g., reduces, expression of the payload encoded by a viral genome of an AAV particle described herein in a cell or tissue where the corresponding mRNA is expressed.

In some embodiments, the viral genome of an AAV particle described herein comprises a microRNA binding site, e.g., a detargeting site. In some embodiments, the viral genome of an AAV particle described herein comprises a coding sequence for a miR binding site, a microRNA binding site series (miR BSs), or a reverse complement thereof.

In some embodiments, the miR binding site series or the miR binding site is located in the 3'-UTR region of the viral genome (e.g., 3' relative to the nucleic acid sequence encoding a payload), e.g., before the polyA sequence, 5'-UTR region of the viral genome (e.g., 5' relative to the nucleic acid sequence encoding a payload), or both.

In some embodiments, the miR binding site series comprise at least 1-5 copies, e.g., at least 1-3, 2-4, 3-5, 1, 2, 3, 4, 5 or more copies of a miR binding site (miR BS). In some embodiments, all copies are identical, e.g., comprise the same miR binding site. In some embodiments, the miR binding sites within the miR binding site series are continuous and not separated by a spacer. In some embodiments, the miR binding sites within a miR binding site series are separated by a spacer, e.g., a non-coding sequence. In some embodiments, the spacer is at least about 5 to 10 nucleotides, e.g., about 7-8 nucleotides, nucleotides in length. In some embodiments, the spacer comprises one or more of (i) GGAT; (ii) CACGTG; (iii) GCATGC, or a repeat of one or more of (i)-(iii).

In some embodiments, the miR binding site series comprise at least 1-5 copies, e.g., at least 1-3, 2-4, 3-5, 1, 2, 3, 4, 5 or more copies of a miR binding site (miR BS). In some embodiments, at least 1, 2, 3, 4, 5, or all of the copies are different, e.g., comprise a different miR binding site. In some embodiments, the miR binding sites within the miR binding site series are continuous and not separated by a spacer. In some embodiments, the miR binding sites within a miR binding site series are separated by a spacer, e.g., a non-coding sequence. In some embodiments, the spacer is at least about 5 to 10 nucleotides, e.g., about 7-8 nucleotides, in length. In some embodiments, the spacer comprises one or more of (i) GGAT; (ii) CACGTG; (iii) GCATGC, or a repeat of one or more of (i)-(iii).

In some embodiments, the miR binding site is substantially identical (e.g., at least 70%, 75%, 80%, 85%, 90%, 95%, 99% or 100% identical), to the miR in the host cell. In some embodiments, the miR binding site comprises at least 1, 2, 3, 4, or 5 mismatches or no more than 6, 7, 8, 9, or 10 mismatches to a miR in the host cell. In some embodiments, the mismatched nucleotides are contiguous. In some embodiments, the mismatched nucleotides are non-contiguous. In some embodiments, the mismatched nucleotides occur outside the seed region-binding sequence of the miR binding site, such as at one or both ends of the miR binding site. In some embodiments, the miR binding site is 100% identical to the miR in the host cell.

In some embodiments, a miR binding site or sequence region is at least about 10 to about 125 nucleotides in length, e.g., at least about 10 to 50 nucleotides, 10 to 100 nucleotides, 50 to 100 nucleotides, 50 to 125 nucleotides, or 100 to 125 nucleotides in length. In some embodiments, a miR binding site or sequence region is at least about 7 to about 28 nucleotides in length, e.g., at least about 8-28 nucleotides, 7-28 nucleotides, 8-18 nucleotides, 12-28 nucleotides, 20-26 nucleotides, 22 nucleotides, 24 nucleotides, or 26 nucleotides in length, and optionally comprises at least one consecutive region (e.g., 7 or 8 nucleotides) complementary to the seed sequence of a miRNA (e.g., a miR122, a miR 142, a miR 183).

In some embodiments, the miR binding site is complementary to a miR expressed in liver or hepatocytes, such as miR122. In some embodiments, the miR binding site or miR binding site series comprises a miR 122 binding site sequence. In some embodiments, the miR122 binding site comprises the nucleotide sequence of ACAAACACCAT-TGTCACACTCCA (SEQ ID NO: 3672), or a nucleotide sequence having at least 50%, 55%, 60%, 65%, 70%, 75%, 80%, 85%, 90%, at least 95%, at least 99%, or 100% sequence identity, or having at least one, two, three, four, five, six, or seven modifications but no more than ten modifications to SEQ ID NO: 3672, e.g., wherein the modification can result in a mismatch between the miR binding site and the corresponding miRNA. In some embodiments, the miR122 binding site comprises at least 3, 4, or 5 copies of a miR 122 binding site, optionally comprising the nucleotide sequence of: ACAAACACCATTGT-CACACTCCACACAAACACCATTGTCACACTC-CACACAAACACCATTGTCACACT CCA (SEQ ID NO: 3673), or a sequence having at least 50%, 55%, 60%, 65%, 70%, 75%, 80%, 85%, 90%, at least 95%, at least 99%, or 100% sequence identity, or having at least one, two, three, four, five, six, or seven modifications but no more than ten modifications to SEQ ID NO: 3673, e.g., wherein the modification can result in a mismatch between the miR binding site and the corresponding miRNA. In some embodiments, at least two of the miR122 binding sites are connected directly, e.g., without a spacer. In other embodiments, at least two of the miR122 binding sites are separated by a spacer, e.g., 1, 2, 3, 4, 5, 6, 7, 8, 9, or 10 nucleotides in length, which is located between two or more consecutive miR 122 binding site sequences. In embodiments, the spacer is at least about 5 to 10 nucleotides, e.g., about 7-8, in length. In some embodiments, the spacer comprises one or more of (i) GGAT; (ii) CACGTG; (iii) GCATGC, or repeats thereof. In some embodiments, a miR binding site series comprises at least 3-5 copies, e.g., 4 copies, of a miR 122 binding site, with or without a spacer, wherein the spacer is at least about 5 to 10 nucleotides, e.g., about 7-8 nucleotides, in length.

In some embodiments, the miR binding site is complementary to a miR expressed in hematopoietic lineage, including immune cells (e.g., antigen presenting cells or APC, including dendritic cells (DCs), macrophages, and B-lymphocytes). In some embodiments, the miR binding site complementary to a miR expressed in hematopoietic lineage comprises a nucleotide sequence disclosed, e.g., in US 2018/0066279, the contents of which are incorporated by reference herein in its entirety.

In some embodiments, the miR binding site or miR binding site series comprises a miR-142-3p binding site sequence. In some embodiments, the miR-142-3p binding site comprises the nucleotide sequence of TCCAT-AAAGTAGGAAACACTACA (SEQ ID NO: 3674), a sequence having at least 50%, 55%, 60%, 65%, 70%, 75%, 80%, 85%, 90%, at least 95%, at least 99%, or 100% sequence identity, or having at least one, two, three, four, five, six, or seven modifications but no more than ten modifications to SEQ ID NO: 3674, e.g., wherein the modification can result in a mismatch between the miR binding site and the corresponding miRNA. In some embodiments, the miR-142-3p binding site comprises at least 3, 4, or 5 copies of a miR-142-3p binding site. In some embodiments, a miR binding site series comprises at least 3-5 copies, e.g., 4 copies, of a miR-142-3p binding site, with or without a spacer, wherein the spacer is at least about 5 to 10 nucleotides, e.g., about 7-8 nucleotides, in length.

In some embodiments, the miR binding site is complementary to a miR expressed in a DRG (dorsal root ganglion) neuron, e.g., a miR183, a miR182, and/or miR96 binding site. In some embodiments, the miR binding site complementary to a miR expressed in expressed in a DRG neuron comprises a nucleotide sequence disclosed, e.g., in WO2020/132455, the contents of which are incorporated by reference herein in its entirety.

In some embodiments, the miR binding site or miR binding site series comprises a miR 183 binding site sequence. In some embodiments, the miR 183 binding site comprises the nucleotide sequence of AGTGAATTC- TACCAGTGCCATA (SEQ ID NO: 3675), or a sequence having at least 50%, 55%, 60%, 65%, 70%, 75%, 80%, 85%, 90%, at least 95%, at least 99%, or 100% sequence identity, or having at least one, two, three, four, five, six, or seven modifications but no more than ten modifications to SEQ ID NO: 3675, e.g., wherein the modification can result in a mismatch between the miR binding site and the corresponding miRNA. In some embodiments, the sequence complementary to the seed sequence corresponds to the double underlined of the miR-183 binding site sequence. In some embodiments, the miR183 binding site comprises at least 3, 4, or 5 copies of a miR183 binding site. In some embodiments, a miR binding site series comprises at least 3-5 copies, e.g., 4 copies, of a miR 183 binding site, with or without a spacer, wherein the spacer is at least about 5 to 10 nucleotides, e.g., about 7-8 nucleotides, in length.

In some embodiments, the miR binding site or miR binding site series comprises a miR 182 binding site sequence. In some embodiments, the miR 182 binding site comprises, the nucleotide sequence of AGTGTGAGTTC-TACCATTGCCAAA (SEQ ID NO: 3676), a sequence having at least 50%, 55%, 60%, 65%, 70%, 75%, 80%, 85%, 90%, at least 95%, at least 99%, or 100% sequence identity, or having at least one, two, three, four, five, six, or seven modifications but no more than ten modifications to SEQ ID NO: 3676, e.g., wherein the modification can result in a mismatch between the miR binding site and the corresponding miRNA. In some embodiments, the miR 182 binding site comprises at least 3, 4, or 5 copies of a miR 182 binding site. In some embodiments, a miR binding site series comprises at least 3-5 copies, e.g., 4 copies, of a miR182 binding site, with or without a spacer, wherein the spacer is at least about 5 to 10 nucleotides, e.g., about 7-8 nucleotides, in length.

In certain embodiments, the miR binding site or miR binding site series comprises a miR96 binding site sequence. In some embodiments, the miR96 binding site comprises the nucleotide sequence of AGCAAAAATGTGCTAGTGC-CAAA (SEQ ID NO: 3677), a sequence having at least 50%, 55%, 60%, 65%, 70%, 75%, 80%, 85%, 90%, at least 95%, at least 99%, or 100% sequence identity, or having at least one, two, three, four, five, six, or seven modifications but no more than ten modifications to SEQ ID NO: 3677, e.g., wherein the modification can result in a mismatch between the miR binding site and the corresponding miRNA. In some embodiments, the miR96 binding site comprises at least 3, 4, or 5 copies of a miR96 binding site. In some embodiments, a miR binding site series comprises at least 3-5 copies, e.g., 4 copies, of a miR96 binding site, with or without a spacer, wherein the spacer is at least about 5 to 10 nucleotides, e.g., about 7-8, in length.

In some embodiments, the miR binding site series comprises a miR122 binding site, a miR142 binding site, a miR183 binding site, a miR182 binding site, a miR 96 binding site, or a combination thereof. In some embodiments, the miR binding site series comprises at least 3, 4, or 5 copies of a miR122 binding site, a miR 142 binding site, a miR 183 binding site, a miR182 binding site, a miR 96 binding site, or a combination thereof. In some embodiments, at least two of the miR binding sites are connected directly, e.g., without a spacer. In other embodiments, at least two of the miR binding sites are separated by a spacer, e.g., 1, 2, 3, 4, 5, 6, 7, 8, 9, or 10 nucleotides in length, which is located between two or more consecutive miR binding site sequences. In embodiments, the spacer is at least about 5 to 10 nucleotides, e.g., about 7-8 nucleotides, in length. In some embodiments, the spacer comprises one or more of (i) GGAT; (ii) CACGTG; (iii) GCATGC, or a repeat of one or more of (i)-(iii). In some embodiments, a miR binding site series comprises at least 3-5 copies, e.g., 4 copies, of a combination of at least two, three, four, five, or all of a miR122 binding site, a miR142 binding site, a miR 183 binding site, a miR182 binding site, a miR96 binding site, with or without a spacer, wherein the spacer is at least about 5 to 10 nucleotides, e.g., about 7-8 nucleotides, in length.

Viral Genome Component: Selectable Marker

In some embodiments, the viral genome of the AAV particle described herein (e.g., an AAV particle comprising an AAV capsid polypeptide, e.g., an AAV capsid variant), optionally encodes a selectable marker. The selectable marker may comprise a cell-surface marker, such as any protein expressed on the surface of the cell including, but not limited to receptors, CD markers, lectins, integrins, or truncated versions thereof.

In some embodiments, selectable marker reporter genes are described in International Publication Nos. WO 1996023810 and WO 1996030540; Heim et al., Current Biology 2:178-182 (1996); Heim et al., Proc. Natl. Acad. Sci. USA (1995); or Heim et al., Science 373:663-664 (1995), the contents of each of which are incorporated herein by reference in their entirety.

Genome Size

In one embodiment, the AAV particle described herein (e.g., an AAV particle comprising an AAV capsid polypeptide, e.g., an AAV capsid variant), may comprise a single-stranded or double-stranded viral genome. The size of the viral genome may be small, medium, large or the maximum size. As described above, the viral genome may comprise a promoter and a polyA tail.

In one embodiment, the viral genome may be a small single stranded viral genome. A small single stranded viral genome may be 2.1 to 3.5 kb in size such as, but not limited to, about 2.1, 2.2, 2.3, 2.4, 2.5, 2.6, 2.7, 2.8, 2.9, 3.0, 3.1, 3.2, 3.3, 3.4, and 3.5 kb in size.

In one embodiment, the viral genome may be a small double stranded viral genome. A small double stranded viral genome may be 1.3 to 1.7 kb in size such as, but not limited to, about 1.3, 1.4, 1.5, 1.6, and 1.7 kb in size.

In one embodiment, the viral genome may be a medium single stranded viral genome. A medium single stranded viral genome may be 3.6 to 4.3 kb in size such as, but not limited to, about 3.6, 3.7, 3.8, 3.9, 4.0, 4.1, 4.2 and 4.3 kb in size.

In one embodiment, the viral genome may be a medium double stranded viral genome. A medium double stranded viral genome may be 1.8 to 2.1 kb in size such as, but not limited to, about 1.8, 1.9, 2.0, and 2.1 kb in size.

In one embodiment, the viral genome may be a large single stranded viral genome. A large single stranded viral genome may be 4.4 to 6.0 kb in size such as, but not limited to, about 4.4, 4.5, 4.6, 4.7, 4.8, 4.9, 5.0, 5.1, 5.2, 5.3, 5.4, 5.5, 5.6, 5.7, 5.8, 5.9 and 6.0 kb in size.

In one embodiment, the viral genome may be a large double stranded viral genome. A large double stranded viral genome may be 2.2 to 3.0 kb in size such as, but not limited to, about 2.2, 2.3, 2.4, 2.5, 2.6, 2.7, 2.8, 2.9 and 3.0 kb in size.

Payloads

The AAV particles of the present disclosure (e.g. an AAV particle comprising an AAV capsid polypeptide, e.g., an AAV capsid variant) comprise a viral genome with at least one payload region. In some embodiments, a payload region may be a nucleic acid sequence within the viral genome of an AAV particle described herein, which encodes a payload, wherein the payload is an RNAi agent or a polypeptide. Payloads of the present disclosure may be, but are not limited to, peptides, polypeptides, proteins, antibodies, RNAi agents, etc.

In some embodiments, the payload region may comprise a combination of coding and non-coding nucleic acid sequences. In some embodiments, the payload region may encode a coding or non-coding RNA.

In one embodiment, the AAV particle (e.g., an AAV particle comprising an AAV capsid polypeptide, e.g., an AAV capsid variant, described herein) comprises a viral genome with a payload region encoding more than one payload of interest. In such an embodiment, a viral genome encoding more than one payload may be replicated and packaged into a viral particle. A target cell transduced with a viral particle comprising more than one payload may express each of the payloads in a single cell.

In some embodiments, the AAV particles described herein, e.g., an AAV particle comprising an AAV capsid polypeptide, e.g., an AAV capsid variant, comprises a nucleic acid encoding a payload. In some embodiments, the encoded payload comprises a therapeutic protein, an antibody, an enzyme, one or more components of a genome editing system, and/or an RNAi agent (e.g., a dsRNA, siRNA, shRNA, pre-miRNA, pri-miRNA, miRNA, stRNA, lncRNA, piRNA, or snoRNA). In some embodiments, the encoded payload modulates, e.g., increases or decreases, the presence, level, and/or activity of a gene, mRNA, protein, or a combination thereof, e.g., in a cell or a tissue.

Polypeptides

In some embodiments, the payload of AAV particle comprising an AAV capsid polypeptide, e.g., an AAV capsid variant, described herein comprises a polypeptide, e.g., a polypeptide described herein. Where the payload region encodes a polypeptide, the polypeptide may be a peptide or protein. The payload region may encode a product of any known gene and/or a recombinant version thereof. As a non-limiting example, the payload region may encode at least one allele of apolipoprotein E (APOE) such as, but not limited to ApoE2, ApoE3 and/or ApoE4. In one embodiment, the payload region encodes ApoE2 (cys112, cys158). In one embodiment, the payload region encodes ApoE3 (cys112, arg158). In one embodiment, the payload region of encodes ApoE4 (arg112, arg158). As another non-limiting example, the payload region may encode aromatic L-amin acid decarboxylase (AADC). As another non-limiting example, the payload region may encode an antibody, or a fragment thereof. As another non-limiting example, the payload region may encode human survival of motor neuron (SMN) 1 or SMN2, or fragments or variants thereof. As another non-limiting example, the payload region may encode glucocerebrosidase (GBA1), or a fragment or variant thereof. As another non-limiting example, the payload region may encode granulin precursor or progranulin (GRN), or a fragment or variant thereof. As another non-limiting example, the payload region may encode aspartoacylase (ASPA), or a fragment or variant thereof. As another non-limiting example, the payload region may encode tripeptidyl peptidase I (CLN2), or a fragment or variant thereof. As another non-limiting example, the payload region may encode beta-galactosidase (GLB1), or a fragment or variant thereof. As another non-limiting example, the payload region may encode N-sulphoglucosamine sulphohydrolase (SGSH), or a fragment or variant thereof. As another non-limiting example, the payload region may encode N-acetyl-alpha-glucosaminidase (NA- GLU), or a fragment or variant thereof. As another non-limiting example, the payload region may encode iduronate 2-sulfatase (IDS), or a fragment or variant thereof. As another non-limiting example, the payload region may encode Intracellular cholesterol transporter (NPC1), or a fragment or variant thereof. As another non-limiting example, the payload region may encode gigaxonin (GAN), or a fragment or variant thereof. The AAV viral genomes encoding polypeptides described herein may be useful in the fields of human disease, viruses, infections veterinary applications and a variety of in vivo and in vitro settings.

Amino acid sequences encoded by payload regions of the viral genomes described herein, may be translated as a whole polypeptide, a plurality of polypeptides or fragments of polypeptides, which independently may be encoded by one or more nucleic acids, fragments of nucleic acids or variants of any of the aforementioned.

Antibodies and Antibody Binding Fragments

In some embodiments, the payload of AAV particle comprising an AAV capsid polypeptide, e.g., an AAV capsid variant, described herein comprises an antibody or antibody binding fragment. Where the payload region encodes an antibody, the "antibody" may be a full antibody, a fragment, or any derivative thereof, which forms a "functional antibody", exhibiting the desired biological activity. As non-limiting examples, an antibody may be a native antibody (e.g., with two heavy and two light chains), a heavy chain variable region, a light chain variable region, a heavy chain constant region, a light chain constant region, Fab, Fab', F(ab')$_2$, Fv, or scFv fragments, a diabody, a linear antibody, a single-chain antibody, a multi-specific antibody, an intrabody, one or more heavy chain complementarity determining regions (CDR), one or more light chain CDRs, a bispecific antibody, a monoclonal antibody, a polyclonal antibody, a humanized antibody, an antibody mimetic, an antibody variant, a miniaturized antibody, a unibody, a maxibody, and/or a chimeric antigen receptor.

A payload region of an AAV particle described herein (e.g., an AAV particle comprising an AAV capsid polypeptide, e.g., an AAV capsid variant) may encode a polypeptide that forms or functions as any antibody, including antibodies that are known in the art and/or antibodies that are commercially available. The encoded antibody or antibody binding fragment may be therapeutic, diagnostic, or for research purposes. The encoded antibody or antibody binding fragment may be useful in the treatment of a neurological disease, a neurodegenerative disorder, a muscular disease, a neuromuscular disorder, a neuro-oncological disorder, or any disorder associated with the central and/or peripheral nervous systems.

In some embodiments, the viral genome of the AAV particle (e.g., an AAV particle comprising an AAV capsid polypeptide, e.g., an AAV capsid variant described herein) may comprise a nucleic acid which has been engineered to enable or enhance the expression of an antibody, or antibody binding fragment thereof.

In some embodiments, the encoded antibody of the payload of an AAV particle comprising an AAV capsid polypeptide, e.g., an AAV capsid variant, described herein comprises at least one immunoglobulin variable domain sequence. An antibody may include, for example, full-length, mature antibodies and antigen-binding fragments of an antibody. For example, an antibody can include a heavy (H) chain variable domain sequence (VH), and a light (L) chain variable domain sequence (VL). In another example, an antibody includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments, e.g., an antibody binding fragments, retain the ability to selectively bind with their respective antigen or receptor.

In some embodiments, the antibody binding fragment comprises at least one portion of an intact antibody, or recombinant variants thereof, and refers to the antigen binding domain, for example, an antigenic determining variable region of an intact antibody, that is sufficient to confer recognition and specific binding of the antibody fragment to a target, such as an antigen. Examples of antigen binding fragments include: (i) a Fab fragment, a monovalent fragment consisting of the VL, VH, CL and CH1 domains; (ii) a F(ab') 2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) Science 242:423-426; and Huston et al. (1988) Proc. Natl. Acad. Sci. USA 85:5879-5883); and (viii) a single domain antibody. These antibody fragments are obtained using conventional techniques known to those with skill in the art, and the fragments are screened for utility in the same manner as are intact antibodies. An antibody fragment can also be incorporated into single domain antibodies, maxibodies, minibodies, nanobodies, intrabodies, diabodies, triabodies, tetrabodies, v-NAR and bis-scFv (see, for example, Hollinger and Hudson, Nature Biotechnology 23:1126-1136, 2005).

In some embodiments, the encoded antibody of the payload of an AAV particle described herein comprises a multispecific antibody, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In some embodiments, the first and second epitopes are on the same antigen, e.g., the same protein (or subunit of a multimeric protein). In some embodiments, the first and second epitopes overlap. In some embodiments, the first and second epitopes do not overlap. In some embodiments, the first and second epitopes are on different antigens, e.g., the different proteins (or different subunits of a multimeric protein). In some embodiments, a multispecific antibody comprises a third, fourth or fifth immunoglobulin variable domain. In some embodiments, a multispecific antibody is a bispecific antibody, a trispecific antibody, or tetraspecific antibody.

In some embodiments, an encoded multispecific antibody of the payload of an AAV particle described herein is an encoded bispecific antibody. A bispecific antibody has specificity for no more than two antigens. A bispecific antibody is characterized by a first immunoglobulin variable domain sequence which has binding specificity for a first epitope and a second immunoglobulin variable domain sequence that has binding specificity for a second epitope. In some embodiments, the first and second epitopes are on the same antigen, e.g., the same protein (or subunit of a multimeric protein). In some embodiments, the first and second epitopes overlap. In some embodiments, the first and second epitopes do not overlap. In some embodiments, the first and second epitopes are on different antigens, e.g., the different proteins (or different subunits of a multimeric protein).

An antibody or an antibody binding fragment encoded in a payload region of an AAV particle described herein, may be, but is not limited to, an antibody or antibody fragment that binds to B-amyloid, APOE, tau, SOD1, TDP-43, huntingtin, and/or synuclein. In some embodiments, the encoded payload comprises an antibody or antibody fragment that binds to a neuro-oncology related target, e.g., HER2, EGFR (e.g., EGFRvIII).

Gene Editing System

In some embodiments, the payload of AAV particle comprising an AAV capsid polypeptide, e.g., an AAV capsid variant, described herein comprises a gene editing system or one or more components thereof. In some embodiments, the gene editing system comprises nucleic acid sequences that encode proteins having enzymatic activity to (i) selectively induce double or single stranded breaks in a DNA or RNA sequence, or (ii) substitute, insert or delete a particular base or set of bases of a DNA or RNA sequence in the absence of a double or single stranded break in the DNA or RNA. In some embodiments, the gene editing system includes, but is not limited to a CRISPR-Cas system (including different Cas or Cas-related nucleases), a Zinc finger nuclease, a meganuclease, a TALEN or a base editors. In some embodiments, the gene editing system comprises a chromosomal integration of a transgene, e.g., introduced by a parvovirus vector in the absence of an exogenous nuclease or an enzymatic entity.

RNAi Agents

In some embodiments, the payload of AAV particle comprising an AAV capsid polypeptide, e.g., an AAV capsid variant, described herein comprises an RNAi agent, e.g., an RNAi agent described herein. RNAi (also known as post-transcriptional gene silencing (PTGS), quelling, or co-suppression) is a post-transcriptional gene silencing process in which RNA molecules, in a sequence specific manner, inhibit gene expression, typically by causing the destruction of specific mRNA molecules. RNAi mediated gene silencing can specifically inhibit targeted gene expression. Where the payload region of the viral genome of the AAV particles described herein encodes an RNAi agent, the RNAi agent may be, but is not limited to, dsRNA, siRNA, shRNA, pre-miRNA, pri-miRNA, miRNA, stRNA, lncRNA, piRNA, or snoRNA. Non-limiting examples of a target gene of an RNAi agent include, SOD1, MAPT, APOE, HTT, C9ORF72, TDP-43, APP, BACE, SNCA, ATXN1, ATXN3, ATXN7, SCNIA-SCN5A, or SCN8A-SCN11A.

The AAV particles described herein may comprise viral genomes encoding RNAi agents, wherein the RNAi agent targets the mRNA of a gene of interest to interfere with gene expression and/or protein production. Such AAV particles may be used as a therapeutic, a diagnostic, or for research purposes.

In one embodiment, the RNAi agent may target the gene of interest along any segment of their respective nucleotide sequence.

In one embodiment, the RNAi agent may target the gene of interest at the location of a single-nucleotide polymorphism (SNP) or variant within the nucleotide sequence.

In some embodiments, a nucleic acid sequence encoding an RNAi agent, or a single strand of an RNAi agent, is inserted into the viral genome of the AAV particle and introduced into cells, specifically cells in the central nervous system or cells of the DRG.

The RNAi agent may be an siRNA duplex, wherein the siRNA duplex contains an antisense strand (guide strand) and a sense strand (passenger strand) hybridized together forming a duplex structure, wherein the antisense strand is complementary to the nucleic acid sequence of the targeted gene, and wherein the sense strand is homologous to the nucleic acid sequence of the targeted gene. In some aspects, the 5'end of the antisense strand has a 5' phosphate group and the 3'end of the sense strand contains a 3'hydroxyl group. In other aspects, there are none, one or 2 nucleotide overhangs at the 3'end of each strand.

Each strand of an siRNA duplex targeting a gene of interest may be about 19 to 25, 19 to 24 or 19 to 21 nucleotides in length, preferably about 19 nucleotides, 20 nucleotides, 21 nucleotides, 22 nucleotides, 23 nucleotides, 24 nucleotides, or 25 nucleotides in length.

In one embodiment, an siRNA or dsRNA includes at least two sequences that are complementary to each other. The dsRNA includes a sense strand having a first sequence and an antisense strand having a second sequence. The antisense strand includes a nucleotide sequence that is substantially complementary to at least part of an mRNA encoding the target gene, and the region of complementarity is 30 nucleotides or less, and at least 15 nucleotides in length. Generally, the dsRNA is 19 to 25, 19 to 24 or 19 to 21 nucleotides in length. In some embodiments, the dsRNA is from about 15 to about 25 nucleotides in length, and in other embodiments the dsRNA is from about 25 to about 30 nucleotides in length. In some embodiments, the dsRNA is about 15 nucleotides in length, 16 nucleotides in length, 17 nucleotides in length, 18 nucleotides in length, 19 nucleotides, 20 nucleotides, 21 nucleotides, 22 nucleotides, 23 nucleotides, 24 nucleotides, 25 nucleotides in length, 26 nucleotides in length, 27 nucleotides in length, 28 nucleotides in length, 29 nucleotides in length, or 30 nucleotides in length.

The dsRNA, whether directly administered or encoded in a viral genome in an AAV particle, upon contacting with a cell expressing the target protein, inhibits the expression of the protein by at least 10%, at least 20%, at least 25%, at least 30%, at least 35% or at least 40% or more, such as when assayed by a method known in the art.

In one embodiment, the RNAi agent may be used to reduce the expression of target protein by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of target protein expression may be reduced 50-90%.

In one embodiment, the RNAi agent may be used to reduce the expression of target mRNA by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of target mRNA expression may be reduced 50-90%.

In one embodiment, RNAi agent may be used to reduce the expression of target protein and/or mRNA in at least one region of the CNS. The expression of target protein and/or mRNA is reduced by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in at least one region of the CNS. As a non-limiting example, the expression of target protein and mRNA in neurons (e.g., cortical neurons) is reduced by 50-90%. As a non-limiting example, the expression of target protein and mRNA in neurons (e.g., cortical neurons) is reduced by 40-50%.

In some embodiments, the AAV particle described herein, comprising a viral genome encoding at least one RNAi agent targeting a gene of interest is administered to a subject in need for treating and/or ameliorating a disease, e.g., a neurological disorder of any disease associated with the central or peripheral nervous systems.

In one embodiment, the RNAi agent is an siRNA.

Design of siRNA

An AAV particle described herein (e.g., an AAV particle comprising an AAV capsid polypeptide, e.g., an AAV capsid variant described herein) may comprise a viral genome encoding one or more siRNA molecules (e.g., siRNA duplexes or encoded dsRNA) that are specifically designed to target a gene of interest and suppress target gene expression and protein production. In some aspects, the siRNA molecules are designed and used to selectively "knock out" target gene variants in cells, e.g., transcripts that are identified in neurological disease. In some aspects, the siRNA molecules are designed and used to selectively "knock down" target gene variants in cells.

In some embodiments, siRNA molecules targeting a gene of interest may be designed using any available design tools.

Some guidelines for designing siRNAs (for insertion into a viral genome of the AAV particles described herein) have been proposed in the art. These guidelines generally recommend generating a 19-nucleotide duplexed region, symmetric 2-3 nucleotide 3' overhangs, 5-phosphate and 3-hydroxyl groups targeting a region in the gene to be silenced. Other rules that may govern siRNA sequence preference include, but are not limited to, (i) A/U at the 5' end of the antisense strand; (ii) G/C at the 5' end of the sense strand; (iii) at least five A/U residues in the 5' terminal one-third of the antisense strand; and (iv) the absence of any GC stretch of more than 9 nucleotides in length. In accordance with such considerations, together with the specific sequence of a target gene, highly effective siRNA molecules essential for suppressing mammalian target gene expression may be readily designed.

In one embodiment, the sense and/or antisense strand is designed based on the method and rules outlined in European Patent Publication No. EP1752536, the contents of which are herein incorporated by reference in their entirety. As a non-limiting example, the 3'-terminal base of the sequence is adenine, thymine or uracil. As a non-limiting example, the 5'-terminal base of the sequence is guanine or cytosine. As a non-limiting example, the 3'-terminal sequence comprises seven bases rich in one or more bases of adenine, thymine and uracil.

In one embodiment, an siRNA molecule comprises a sense strand and a complementary antisense strand in which both strands are hybridized together to form a duplex structure. The antisense strand has sufficient complementarity to the target mRNA sequence to direct target-specific RNAi, e.g., the siRNA molecule has a sequence sufficient to trigger the destruction of the target mRNA by the RNAi machinery or process.

In some embodiments, the antisense strand and target mRNA sequences have 100% complementarity. The antisense strand may be complementary to any part of the target mRNA sequence. Neither the identity of the sense sequence nor the homology of the antisense sequence need be 100% complementary to the target.

In other embodiments, the antisense strand and target mRNA sequences comprise at least one mismatch. As a non-limiting example, the antisense strand and the target mRNA sequence have at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementary.

The siRNA molecule may have a length from about 10-50 or more nucleotides, e.g., each strand comprising 10-50 nucleotides (or nucleotide analogs). Preferably, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementary to a target region. In one embodiment, the siRNA molecule has a length from about 19 to 25, 19 to 24 or 19 to 21 nucleotides.

In some embodiments, the siRNA molecule can be a synthetic RNA duplex comprising about 19 nucleotides to about 25 nucleotides, and two overhanging nucleotides at the 3'-end.

The siRNA molecule may comprise an antisense sequence and a sense sequence, or a fragment or variant thereof. As a non-limiting example, the antisense sequence and the sense sequence have at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementary.

The sense and antisense sequences may be completely complementary across a substantial portion of their length. In other embodiments, the sense sequence and antisense sequence may be at least 70, 80, 90, 95 or 99% complementary across independently at least 50, 60, 70, 80, 85, 90, 95, or 99% of the length of the strands.

In some embodiments, the sense and antisense strands of a siRNA duplex are linked by a short spacer sequence leading to the expression of a stem-loop structure termed short hairpin RNA (shRNA). The hairpin is recognized and cleaved by Dicer, thus generating mature siRNA molecules.

In some embodiments, the siRNA molecules, as well as associated spacer and/or flanking regions once designed, can be encoded by the viral genome of the AAV particles described herein, for delivery to a cell.

Molecular Scaffold

In some embodiments, the siRNA molecules may be encoded in a modulatory polynucleotide which also comprises a molecular scaffold.

In some embodiments, the modulatory polynucleotide which comprises the payload (e.g., siRNA, miRNA or other RNAi agent described herein) includes a molecular scaffold which comprises at least one 5' flanking sequence which may be of any length and may be derived in whole or in part from wild type microRNA sequence or be completely artificial. A 3' flanking sequence may mirror the 5' flanking sequence in size and origin. Either flanking sequence may be absent. In one embodiment, both the 5' and 3' flanking sequences are absent. The 3' flanking sequence may optionally contain one or more CNNC motifs, where "N" represents any nucleotide.

In some embodiments the 5' and 3' flanking sequences are the same length.

In some embodiments the 5' flanking sequence is from 1-10 nucleotides in length, from 5-15 nucleotides in length, from 10-30 nucleotides in length, from 20-50 nucleotides in length, greater than 40 nucleotides in length, greater than 50 nucleotides in length, greater than 100 nucleotides in length or greater than 200 nucleotides in length.

In some embodiments, the 5' flanking sequence may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 nucleotides in length.

In one embodiment, the molecular scaffold comprises at least one 3' flanking region. As a non-limiting example, the 3' flanking region may comprise a 3' flanking sequence which may be of any length and may be derived in whole or in part from wild type microRNA sequence or be a completely artificial sequence.

In some embodiments the 3' flanking sequence is from 1-10 nucleotides in length, from 5-15 nucleotides in length, from 10-30 nucleotides in length, from 20-50 nucleotides in length, greater than 40 nucleotides in length, greater than 50 nucleotides in length, greater than 100 nucleotides in length or greater than 200 nucleotides in length.

In some embodiments, the 3' flanking sequence may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 nucleotides in length.

In some embodiments the 5' and 3' flanking sequences are the same sequence. In some embodiments they differ by 2%, 3%, 4%, 5%, 10%, 20% or more than 30% when aligned to each other.

Forming the stem of a stem loop structure is a minimum of at least one payload sequence. In some embodiments, the payload sequence comprises at least one nucleic acid sequence which is in part complementary or will hybridize to the target sequence. In some embodiments, the payload is an siRNA molecule or fragment of an siRNA molecule.

In some embodiments, the 5' arm of the stem loop comprises a sense sequence.

In some embodiments, the 3' arm of the stem loop comprises an antisense sequence. The antisense sequence, in some instances, comprises a "G" nucleotide at the 5' most end.

In other embodiments, the sense sequence may reside on the 3' arm while the antisense sequence resides on the 5' arm of the stem of the stem loop structure.

Separating the sense and antisense sequence of the stem loop structure is a loop (also known as a loop motif). The loop may be of any length, between 4-30 nucleotides, between 4-20 nucleotides, between 4-15 nucleotides, between 5-15 nucleotides, between 6-12 nucleotides, 6 nucleotides, 7, nucleotides, 8 nucleotides, 9 nucleotides, 10 nucleotides, 11 nucleotides, and/or 12 nucleotides.

In some embodiments, the loop comprises at least one UGUG motif. In some embodiments, the UGUG motif is located at the 5' terminus of the loop.

Spacer regions may be present in the modulatory polynucleotide to separate one or more modules from one another. There may be one or more such spacer regions present.

In one embodiment, a spacer region of between 8-20, e.g., 8, 9, 10, 11, 12, 13, 14, 15, 16, 17, 18, 19, or 20 nucleotides may be present between the sense sequence and a flanking sequence.

In one embodiment, the spacer is 13 nucleotides and is located between the 5' terminus of the sense sequence and a flanking sequence. In one embodiment, a spacer is of sufficient length to form approximately one helical turn of the sequence.

In one embodiment, a spacer region of between 8-20, e.g., 8, 9, 10, 11, 12, 13, 14, 15, 16, 17, 18, 19, or 20 nucleotides may be present between the antisense sequence and a flanking sequence.

In one embodiment, the spacer sequence is between 10-13, e.g., 10, 11, 12 or 13 nucleotides and is located between the 3' terminus of the antisense sequence and a flanking sequence. In one embodiment, a spacer is of sufficient length to form approximately one helical turn of the sequence.

In one embodiment, the modulatory polynucleotide comprises in the 5' to 3' direction, a 5' flanking sequence, a 5' arm, a loop motif, a 3' arm and a 3' flanking sequence. As a non-limiting example, the 5' arm may comprise a sense sequence and the 3' arm comprises the antisense sequence. In another non-limiting example, the 5' arm comprises the antisense sequence and the 3' arm comprises the sense sequence.

In one embodiment, the 5' arm, payload (e.g., sense and/or antisense sequence), loop motif and/or 3' arm sequence may be altered (e.g., substituting 1 or more nucleotides, adding nucleotides and/or deleting nucleotides). The alteration may cause a beneficial change in the function of the construct (e.g., increase knock-down of the target sequence, reduce degradation of the construct, reduce off target effect, increase efficiency of the payload, and reduce degradation of the payload).

In one embodiment, the molecular scaffold of the modulatory polynucleotides is aligned in order to have the rate of excision of the guide or antisense strand be greater than the rate of excision of the passenger or sense strand. The rate of excision of the guide or passenger strand may be, independently, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more than 99%. As a non-limiting example, the rate of excision of the guide strand is at least 80%. As another non-limiting example, the rate of excision of the guide strand is at least 90%.

In one embodiment, the rate of excision of the guide strand is greater than the rate of excision of the passenger strand. In one aspect, the rate of excision of the guide strand may be at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more than 99% greater than the passenger strand.

In one embodiment, the efficiency of excision of the guide strand is at least 60%, 65%, 70%, 75%, 80%, 85%, 90%, 95%, 99% or more than 99%. As a non-limiting example, the efficiency of the excision of the guide strand is greater than 80%.

In one embodiment, the efficiency of the excision of the guide strand is greater than the excision of the passenger strand from the molecular scaffold. The excision of the guide strand may be 2, 3, 4, 5, 6, 7, 8, 9, 10 or more than 10 times more efficient than the excision of the passenger strand from the molecular scaffold.

In one embodiment, the molecular scaffold comprises a dual-function targeting modulatory polynucleotide.

In one embodiment, the molecular scaffold may comprise one or more linkers known in the art. The linkers may separate regions or one molecular scaffold from another. As a non-limiting example, the molecular scaffold may be polycistronic.

In one embodiment, the modulatory polynucleotide is designed using at least one of the following properties: loop variant, seed mismatch/bulge/wobble variant, stem mismatch, loop variant and basal stem mismatch variant, seed mismatch and basal stem mismatch variant, stem mismatch and basal stem mismatch variant, seed wobble and basal stem wobble variant, or a stem sequence variant.

AAV Production

Viral production disclosed herein describes processes and methods for producing AAV particles (with enhanced, improved and/or increased tropism for a target tissue), e.g., an AAV particle comprising an AAV capsid polypeptide, e.g., an AAV capsid variant, that may be used to contact a target cell to deliver a payload.

In some embodiments, disclosed herein is a method of making AAV particle of the present disclosure, e.g., an AAV particle comprising an AAV capsid polypeptide, e.g., an AAV capsid variant, the method comprising: (i) providing a host cell comprising a viral genome described herein and (ii) incubating the host cell under conditions suitable to enclose the viral genome in an AAV capsid variant, e.g., an AAV capsid variant described herein (e.g., an AAV capsid variant listed in Tables 3, 4, or 5), thereby making the AAV particle. In some embodiments, the method comprises prior to step (i), introducing a first nucleic acid comprising the viral genome into a cell. In some embodiments, the host cell comprises a second nucleic acid encoding the AAV capsid variant. In some embodiments, the second nucleic acid is introduced into the host cell prior to, concurrently with, or after the first nucleic acid molecule. In some embodiments, the AAV particle described herein is an isolated AAV particle. In some embodiments, the AAV particle described herein is a recombinant AAV particle.

The present disclosure provides methods for the generation of an AAV particle comprising a peptide, e.g., a targeting peptide, (e.g., an AAV particle comprising an AAV capsid polypeptide, e.g., an AAV capsid variant, described herein). In some embodiments, the AAV particles are prepared by viral genome replication in a viral replication cell. Any method known in the art may be used for the preparation of AAV particles. In some embodiments, AAV particles are produced in mammalian cells (e.g., HEK293). In another embodiment, AAV particles are produced in insect cells (e.g., Sf9).

Methods of making AAV particles are well known in the art and are described in e.g., U.S. Pat. Nos. U.S. Pat. Nos. 6,204,059, 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508, 5,064,764, 6,194,191, 6,566,118, 8,137,948; or International Publication Nos. WO1996039530, WO1998010088, WO1999014354, WO1999015685, WO1999047691, WO2000055342, WO2000075353 and WO2001023597; Methods In Molecular Biology, ed. Richard, Humana Press, NJ (1995); O'Reilly et al., Baculovirus Expression Vectors, A Laboratory Manual, Oxford Univ. Press (1994); Samulski et al., *J. Vir.* 63:3822-8 (1989); Kajigaya et al., *Proc. Nat'l. Acad. Sci. USA* 88:4646-50 (1991); Ruffing et al., *J. Vir.* 66:6922-30 (1992); Kimbauer et al., *Vir.,* 219:37-44 (1996); Zhao et al., *Vir.* 272:382-93 (2000); the contents of each of which are herein incorporated by reference in their entirety. In some embodiments, the AAV particles are made using the methods described in International Patent Publication WO2015191508, the contents of which are herein incorporated by reference in their entirety.

Therapeutic Applications

The present disclosure provides a method for treating a disease, disorder and/or condition in a mammalian subject, including a human subject, comprising administering to the subject an AAV particle described herein, e.g., an AAV particle comprising an AAV capsid polypeptide, e.g., an AAV capsid variant (e.g., an AAV capsid variant described herein), or administering to the subject any of the described compositions, including a pharmaceutical composition, described herein.

In some embodiments, the AAV particle of the present disclosure (e.g., an AAV particle comprising an AAV capsid polypeptide, e.g., an AAV capsid variant) are administered to a subject prophylactically, to prevent on-set of disease. In another embodiment, the AAV particle (e.g., an AAV particle comprising an AAV capsid variant) of the present disclosure are administered to treat (lessen the effects of) a disease or symptoms thereof. In yet another embodiment, the AAV particle of the present disclosure (e.g., an AAV particle comprising an AAV capsid polypeptide, e.g., an AAV capsid variant) are administered to cure (eliminate) a disease. In another embodiment, the AAV particle (e.g., an AAV particle comprising an AAV capsid polypeptide, e.g., an AAV capsid variant) of the present disclosure are administered to prevent or slow progression of disease. In yet another embodiment, the AAV particle (e.g., an AAV particle comprising an AAV capsid polypeptide, e.g., an AAV capsid variant) of the present disclosure are used to reverse the deleterious effects of a disease. Disease status and/or progression may be determined or monitored by standard methods known in the art.

In some embodiments, provided herein is method for treating a neurological disorder and/or neurodegenerative disorder in a subject, comprising administering to the subject an effective amount of a pharmaceutical composition described herein or an AAV particle, e.g., a plurality of particles, comprising an AAV capsid variant described herein. In some embodiments, treatment of a neurological disorder and/or neurodegenerative disorder comprises prevention of said neurological disorder and/or neurological disorder.

In some embodiments, the AAV particle (e.g., an AAV particle comprising an AAV capsid polypeptide, e.g., an AAV capsid variant) of the disclosure is useful in the field of medicine for the treatment, prophylaxis, palliation or amelioration of neurological diseases and/or disorders.

In some embodiments, the AAV particle of the disclosure (e.g., an AAV particle comprising an AAV capsid polypeptide, e.g., an AAV capsid variant) is useful in the field of medicine for the treatment, prophylaxis, palliation or amelioration of tauopathy.

In some embodiments, the AAV particle of the disclosure (e.g., an AAV particle comprising an AAV capsid polypeptide, e.g., an AAV capsid variant) is useful in the field of medicine for the treatment, prophylaxis, palliation or amelioration of Alzheimer's Disease.

In some embodiments, the AAV particle of the disclosure (e.g., an AAV particle comprising an AAV capsid polypeptide, e.g., an AAV capsid variant) is useful in the field of medicine for the treatment, prophylaxis, palliation or amelioration of Friedreich's ataxia, or any disease stemming from a loss or partial loss of frataxin protein.

In some embodiments, the AAV particle of the disclosure (e.g., an AAV particle comprising an AAV capsid polypeptide, e.g., an AAV capsid variant) is useful in the field of medicine for the treatment, prophylaxis, palliation or amelioration of Parkinson's Disease.

In some embodiments, the AAV particle of the disclosure (e.g., an AAV particle comprising an AAV capsid polypeptide, e.g., an AAV capsid variant) is useful in the field of medicine for the treatment, prophylaxis, palliation or amelioration of Amyotrophic lateral sclerosis.

In some embodiments, the AAV particle of the disclosure (e.g., an AAV particle comprising an AAV capsid polypeptide, e.g., an AAV capsid variant) is useful in the field of medicine for the treatment, prophylaxis, palliation or amelioration of Huntington's Disease.

In some embodiments, the AAV particle of the disclosure (e.g., an AAV particle comprising an AAV capsid polypeptide, e.g., an AAV capsid variant) is useful in the field of medicine for the treatment, prophylaxis, palliation or amelioration of chronic or neuropathic pain.

In some embodiments, the AAV particle of the disclosure (e.g., an AAV particle comprising an AAV capsid polypeptide, e.g., an AAV capsid variant) is useful in the field of medicine for treatment, prophylaxis, palliation or amelioration of a disease associated with the central nervous system.

In some embodiments, the AAV particle of the disclosure (e.g., an AAV particle comprising an AAV capsid polypeptide, e.g., an AAV capsid variant) is useful in the field of medicine for treatment, prophylaxis, palliation or amelioration of a disease associated with the peripheral nervous system.

In some embodiments, the AAV particle of the present disclosure (e.g., an AAV particle comprising an AAV capsid polypeptide, e.g., an AAV capsid variant) is administered to a subject having at least one of the diseases or symptoms described herein. In some embodiments, an AAV particle of the present disclosure is administered to a subject having or diagnosed with having a disease or disorder described herein.

In some embodiments, provided herein is a method for treating a muscular disorder and/or neuromuscular disorder in a subject, comprising administering to the subject an effective amount of a pharmaceutical composition described herein or an AAV particle, e.g., a plurality of particles, comprising an AAV capsid variant described herein. In some embodiments, treatment of a muscular disorder and/or neuromuscular disorder comprises prevention of said muscular disorder and/or neuromuscular disorder.

In some embodiments, provided herein is a method for treating a neuro-oncological disorder in a subject, comprising administering to the subject an effective amount of a pharmaceutical composition described herein or an AAV particle, e.g., a plurality of particles, comprising an AAV capsid variant described herein. In some embodiments, treatment of a neuro-oncological disorder comprises prevention of said neuro-oncological disorder. In some embodiments, a neuro-oncological disorder comprises a cancer of a primary CNS origin (e.g., a CNS cell, a tissue, or a region), or a metastatic cancer in a CNS cell, tissue, or region.

Any neurological disease or disorder, neurodegenerative disorder, muscular disorder, neuromuscular disorder, and/or neuro-oncological disorder may be treated with the AAV particles of the disclosure, or pharmaceutical compositions thereof, including but not limited to, Absence of the Septum Pellucidum, Acid Lipase Disease, Acid Maltase Deficiency, Acquired Epileptiform Aphasia, Acute Disseminated Encephalomyelitis, Attention Deficit-Hyperactivity Disorder (ADHD), Adie's Pupil, Adie's Syndrome, Adrenoleukodystrophy, Agenesis of the Corpus Callosum, Agnosia, Aicardi Syndrome, Aicardi-Goutieres Syndrome Disorder, AIDS-Neurological Complications, Alexander Disease, Alpers' Disease, Alternating Hemiplegia, Alzheimer's Disease, Amyotrophic Lateral Sclerosis (ALS), Anencephaly, Aneurysm, Angelman Syndrome, Angiomatosis, Anoxia, Antiphospholipid Syndrome, Aphasia, Apraxia, Arachnoid Cysts, Arachnoiditis, Arnold-Chiari Malformation, Arteriovenous Malformation, Asperger Syndrome, Ataxia, Ataxia Telangiectasia, Ataxias and Cerebellar or Spinocerebellar Degeneration, Atrial Fibrillation and Stroke, Attention Deficit-Hyperactivity Disorder, Autism Spectrum Disorder, Autonomic Dysfunction, Back Pain, Barth Syndrome, Batten Disease, Becker's Myotonia, Bechet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors, Brain Aneurysm, Brain Injury, Brown-Sequard Syndrome, Bulbar palsy, Bulbospinal Muscular Atrophy, Cerebral Autosomal Dominant Arteriopathy with Sub-cortical Infarcts and Leukoencephalopathy (CADASIL), Canavan Disease, Carpal Tunnel Syndrome, Causalgia, Cavernomas, Cavernous Angioma, Cavernous Malformation, Central Cervical Cord Syndrome, Central Cord Syndrome, Central Pain Syndrome, Central Pontine Myelinolysis, Cephalic Disorders, Ceramidase Deficiency, Cerebellar Degeneration, Cerebellar Hypoplasia, Cerebral Aneurysms, Cerebral Arteriosclerosis, Cerebral Atrophy, Cerebral Beriberi, Cerebral Cavernous Malformation, Cerebral Gigantism, Cerebral Hypoxia, Cerebral Palsy, Cerebro-Oculo-Facio-Skeletal Syndrome (COFS), Charcot-Marie-Tooth Disease, Chiari Malformation, Cholesterol Ester Storage Disease, Chorea, Choreoacanthocytosis, Chronic Inflammatory Demyelinating Polyneuropathy (CIDP), Chronic Orthostatic Intolerance, Chronic Pain, Cockayne Syndrome Type II, Coffin Lowry Syndrome, Colpocephaly, Coma, Complex Regional Pain Syndrome, Concentric sclerosis (Baló's sclerosis), Congenital Facial Diplegia, Congenital Myasthenia, Congenital Myopathy, Congenital Vascular Cavernous Malformations, Corticobasal Degeneration, Cranial Arteritis, Craniosynostosis, Cree encephalitis, Creutzfeldt-Jakob Disease, Chronic progressive external ophtalmoplegia, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, De Morsier's Syndrome, Dejerine-Klumpke Palsy, Dementia, Dementia-Multi-Infarct, Dementia-Semantic, Dementia-Subcortical, Dementia With Lewy Bodies, Demyelination diseases, Dentate Cerebellar Ataxia, Dentatorubral Atrophy, Dermatomyositis, Developmental Dyspraxia, Devic's Syndrome, Diabetic Neuropathy, Diffuse Sclerosis, Distal hereditary motor neuronopathies, Dravet Syndrome, Dysautonomia, Dysgraphia, Dyslexia, Dysphagia, Dyspraxia, Dyssynergia Cerebellaris Myoclonica, Dyssynergia Cerebellaris Progressiva, Dystonias, Early Infantile Epileptic Encephalopathy, Empty Sella Syndrome, Encephalitis, Encephalitis Lethargica, Encephaloceles, Encephalomyelitis, Encephalopathy, Encephalopathy (familial infantile), Encephalotrigeminal Angiomatosis, Epilepsy, Epileptic Hemiplegia, Episodic ataxia, Erb's Palsy, Erb-Duchenne and Dejerine-Klumpke Palsies, Essential Tremor, Extrapontine Myelinolysis, Faber's disease, Fabry Disease, Fahr's Syndrome, Fainting, Familial Dysautonomia, Familial Hemangioma, Familial Idiopathic Basal Ganglia Calcification, Familial Periodic Paralyses, Familial Spastic Paralysis, Farber's Disease, Febrile Seizures, Fibromuscular Dysplasia, Fisher Syndrome, Floppy Infant Syndrome, Foot Drop, Friedreich's Ataxia, Frontotemporal Dementia, Gaucher Disease, Generalized Gangliosidoses (GM1, GM2), Gerstmann's Syndrome, Gerstmann-Straussler-Scheinker Disease, Giant Axonal Neuropathy, Giant Cell Arteritis, Giant Cell Inclusion Disease, Globoid Cell Leukodystrophy, Glossopharyngeal Neuralgia, Glycogen Storage Disease, Guillain-Barré Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated Myelopathy, Hughes Syndrome, Huntington's Disease, Hurler syndrome, Hydranencephaly, Hydrocephalus, Hydrocephalus-Normal Pressure, Hydromyelia, Hypercortisolism, Hypersomnia, Hypertonia, Hypotonia, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathies, Iniencephaly, Intestinal Lipodystrophy, Intracranial Cysts, Intracranial Hypertension, Isaacs' Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Klüver-Bucy Syndrome, Korsakoff's Amnesic Syndrome, Krabbe Disease, Kugelberg-Welander Disease, Kuru, Lambert-Eaton Myasthenic Syndrome, Landau-Kleffner Syndrome, Lateral Femoral Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lichtheim's disease, Lipid Storage Diseases, Lipoid Proteinosis, Lissencephaly, Locked-In Syndrome, Lou Gehrig's Disease, Lupus-Neurological Sequelae, Lyme Disease-Neurological Complications, Lysosomal storage disorders, Machado-Joseph Disease, Macrencephaly, Megalencephaly, Melkersson-Rosenthal Syndrome, Meningitis, Meningitis and Encephalitis, Menkes Disease, Meralgia Paresthetica, Metachromatic Leukodystrophy, Microcephaly, Migraine, Miller Fisher Syndrome, Mini Stroke, Mitochondrial Myopathy, Mitochondrial DNA depletion syndromes, Moebius Syndrome, Monomelic Amyotrophy, Morvan Syndrome, Motor Neuron Diseases, Moyamoya Disease, Mucolipidoses, Mucopolysaccharidoses, Multi-Infarct Dementia, Multifocal Motor Neuropathy, Multiple Sclerosis, Multiple System Atrophy, Multiple System Atrophy with Orthostatic Hypotension, Muscular Dystrophy, Myasthenia-Congenital, Myasthenia Gravis, Myelinoclastic Diffuse Sclerosis, Myelitis, Myoclonic Encephalopathy of Infants, Myoclonus, Myoclonus epilepsy, Myopathy, Myopathy-Congenital, Myopathy-Thyrotoxic, Myotonia, Myotonia Congenita, Narcolepsy, NARP (neuropathy, ataxia and retinitis pigmentosa), Neuroacanthocytosis, Neurodegeneration with Brain Iron Accumulation, Neurodegenerative disease, Neurofibromatosis, Neuroleptic Malignant Syndrome, Neurological Complications of AIDS, Neurological Complications of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid Lipofuscinosis, Neuronal Migration Disorders, Neuropathic pain, Neuropathy-Hereditary, Neuropathy, Neurosarcoidosis, Neurosyphilis, Neurotoxicity, Nevus Cavernosus, Niemann-Pick Disease, O'Sullivan-McLeod Syndrome, Occipital Neuralgia, Ohtahara Syndrome, Olivopontocerebellar Atrophy, Opsoclonus Myoclonus, Orthostatic Hypotension, Overuse Syndrome, Pain-Chronic, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Peroneal muscular atrophy, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Post-Polio Syndrome, Postherpetic Neuralgia, Postinfectious Encephalomyelitis, Postural Hypotension, Postural Orthostatic Tachycardia Syndrome, Postural Tachycardia Syndrome, Primary Dentatum Atrophy, Primary Lateral Sclerosis, Primary Progressive Aphasia, Prion Diseases, Progressive bulbar palsy, Progressive Hemifacial Atrophy, Progressive Locomotor Ataxia, Progressive Multifocal Leukoencephalopathy, Progressive Muscular Atrophy, Progressive Sclerosing Poliodystrophy, Progressive Supranuclear Palsy, Prosopagnosia, Pseudobulbar palsy, Pseudo-Torch syndrome, Pseudotoxoplasmosis syndrome, Pseudotumor Cerebri, Psychogenic Movement, Ramsay Hunt Syndrome I, Ramsay Hunt Syndrome II, Rasmussen's Encephalitis, Reflex Sympathetic Dystrophy Syndrome, Refsum Disease, Refsum Disease-Infantile, Repetitive Motion Disorders, Repetitive Stress Injuries, Restless Legs Syndrome, Retrovirus-Associated Myelopathy, Rett Syndrome, Reye's Syndrome, Rheumatic Encephalitis, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Severe Myoclonic Epilepsy of Infancy (SMEI), Shaken Baby Syndrome, Shingles, Shy-Drager Syndrome, Sjögren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Ataxia, Spinocerebellar Atrophy, Spinocerebellar Degeneration, Sporadic ataxia, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, Short-lasting, Unilateral, Neuralgiform (SUNCT) Headache, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Troyer Syndrome, Tuberous Sclerosis, Vascular Erectile Tumor, Vasculitis Syndromes of the Central and Peripheral Nervous Systems, Vitamin B12 deficiency, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson Disease, Wolman's Disease, X-Linked Spinal and Bulbar Muscular Atrophy.

Pharmaceutical Composition and Formulations

According to the present disclosure, an AAV particle comprising an AAV capsid polypeptide, e.g., an AAV capsid variant described herein may be prepared as a pharmaceutical composition. In some embodiments, the pharmaceutical composition comprises at least one active ingredients. In some embodiments, the pharmaceutical composition comprises a pharmaceutically acceptable excipient.

In some embodiments, an AAV particle of the present disclosure (e.g., an AAV particle comprising an AAV capsid polypeptide, e.g., an AAV capsid polypeptide, e.g., an AAV capsid variant) can be formulated using an excipient to: (1) increase stability; (2) increase cell transfection or transduction; (3) permit the sustained or delayed expression of the payload; (4) alter the biodistribution (e.g., target the viral particle to specific tissues or cell types); (5) increase the translation of encoded protein; (6) alter the release profile of encoded protein; and/or (7) allow for regulatable expression of the payload. Formulations of the present disclosure can include, without limitation, saline, liposomes, lipid nanoparticles, polymers, peptides, proteins, cells transfected with viral vectors (e.g., for transfer or transplantation into a subject) and combinations thereof.

In some embodiments, the relative amount of the active ingredient (e.g. an AAV particle described herein), a pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, the pharmaceutical composition comprising an AAV particle described herein may comprise an AAV capsid polypeptide, e.g., an AAV capsid variant and a viral genome encoding a payload, e.g., a payload described herein, with or without a pharmaceutically acceptable excipient.

The present disclosure also provides in some embodiments, a pharmaceutical composition suitable for administration to a subject, e.g., a human. In some embodiments, the pharmaceutical composition is administered to a subject, e.g., a human.

Administration

In some embodiments, an AAV particle disclosed herein (e.g., an AAV particle comprising an AAV capsid polypeptide, e.g., an AAV capsid variant) may be administered by a to a subject by a delivery route, e.g., a localized delivery route or a systemic delivery route. In some embodiments, the AAV particle is administered to a subject by a delivery route which results in therapeutically effective outcome.

In some embodiments, an AAV particle described herein (e.g., an AAV particle comprising an AAV capsid polypeptide, e.g., an AAV capsid variant) may be administered via such a route that it is able to cross the blood-brain barrier, vascular barrier, or other epithelial barrier. In some embodiments, an AAV particle of the present disclosure (e.g., an AAV particle comprising an AAV capsid polypeptide, e.g., an AAV capsid variant) may be administered in any suitable form, either as a liquid solution or suspension, as a solid form suitable for liquid solution or suspension in a liquid solution. In some embodiments, an AAV particle (e.g., an AAV particle comprising an AAV capsid polypeptide, e.g., an AAV capsid variant) may be formulated with any appropriate and pharmaceutically acceptable excipient.

In some embodiments, the AAV particle described herein (e.g., an AAV particle comprising, an AAV capsid polypeptide, e.g., an AAV capsid variant) is administered intramuscularly, intravenously, intracerebrally, intrathecally, intracerebroventricularly, via intraparenchymal administration, or via intra-cisterna magna injection (ICM).

In some embodiments, an AAV particle of the present disclosure (e.g., an AAV particle comprising an AAV capsid polypeptide, e.g., an AAV capsid variant) may be delivered to a subject via a single route administration. In some embodiments, an AAV particle of the present disclosure may be delivered to a subject via a multi-site route of administration. In some embodiments, a subject may be administered at 2, 3, 4, 5, or more than 5 sites.

In some embodiments, an AAV particle of the present disclosure (e.g., an AAV particle comprising, an AAV capsid polypeptide, e.g., an AAV capsid variant) is administered via a bolus infusion. In some embodiments, an AAV particle of the present disclosure is administered via sustained delivery over a period of minutes, hours, or days. In some embodiments, the infusion rate may be changed depending on the subject, distribution, formulation, and/or another delivery parameter. In some embodiments, an AAV particle of the present disclosure is administered using a controlled release, e.g., a release profile that conforms to a particular pattern of release to effect a therapeutic outcome. In some embodiments, an AAV particle of the present disclosure is administered using a sustained release, e.g., a release profile that conforms to a release rate over a specific period of time.

In some embodiments, an AAV particle (e.g., an AAV particle comprising an AAV capsid polypeptide, e.g., an AAV capsid variant) may be delivered by more than one route of administration. As non-limiting examples of combination administrations, an AAV particle may be delivered by intrathecal and intracerebroventricular, or by intravenous and intraparenchymal administration.

Intravenous Administration

In some embodiments, an AAV particle described herein (e.g., an AAV particle comprising an AAV capsid polypeptide, e.g., an AAV capsid variant) may be administered to a subject by systemic administration. In some embodiments, the systemic administration is intravenous administration. In another embodiment, the systemic administration is intraarterial administration. In some embodiments, an AAV particle of the present disclosure may be administered to a subject by intravenous administration. In some embodiments, the intravenous administration may be achieved by subcutaneous delivery. In some embodiments, the AAV particle is administered to the subject via focused ultrasound (FUS), e.g., coupled with the intravenous administration of microbubbles (FUS-MB) or MRI-guided FUS coupled with intravenous administration, e.g., as described in Terstappen et al. (Nat Rev Drug Discovery, https://doi.org/10.1038/s41573-021-00139-y (2021)), the contents of which are incorporated herein by reference in its entirety. In some embodiments, the AAV particle is administered to the subject intravenously. In some embodiments, the subject is a human.

Administration to the CNS

In some embodiments, an AAV particle described herein (e.g., an AAV particle comprising an AAV capsid polypeptide, e.g., an AAV capsid variant) may be delivered by direct injection into the brain. As a non-limiting example, the brain delivery may be by intrahippocampal administration. In some embodiments, an AAV particle of the present disclosure may be administered to a subject by intraparenchymal administration. In some embodiments, the intraparenchymal administration is to tissue of the central nervous system. In some embodiments, an AAV particle of the present disclosure may be administered to a subject by intracranial delivery (See, e.g., U.S. Pat. No. 8,119,611; the content of which is incorporated herein by reference in its entirety). In some embodiments, an AAV particle described herein may be delivered by injection into the CSF pathway. Non-limiting examples of delivery to the CSF pathway include intrathecal and intracerebroventricular administration.

In some embodiments, an AAV particle of the present disclosure (e.g., an AAV particle comprising an AAV capsid polypeptide, e.g., an AAV capsid variant) may be delivered to the brain by systemic delivery. As a non-limiting example, the systemic delivery may be by intravascular administration. As a non-limiting example, the systemic or intravascular administration may be intravenous.

In some embodiments, an AAV particle of the present disclosure may be delivered by an intraocular delivery route. A non-limiting example of an intraocular administration includes an intravitreal injection.

Intramuscular Administration

In some embodiments, an AAV particle described herein (e.g., an AAV particle comprising an AAV capsid polypeptide, e.g., an AAV capsid variant) may be delivered by intramuscular administration. Without wishing to be bound by theory, it is believed in some embodiments, that the multi-nucleated nature of muscle cells provides an advantage to gene transduction subsequent to AAV delivery. In some embodiments, cells of the muscle are capable of expressing recombinant proteins with the appropriate post-translational modifications. Without wishing to be bound by theory, it is believed in some embodiments, the enrichment of muscle tissue with vascular structures allows for transfer to the blood stream and whole-body delivery. Examples of intramuscular administration include systemic (e.g., intravenous), subcutaneous or directly into the muscle. In some embodiments, more than one injection is administered. In some embodiments, an AAV particle of the present disclosure may be delivered by an intramuscular delivery route. (See, e.g., U.S. Pat. No. 6,506,379; the content of which is incorporated herein by reference in its entirety). Non-limiting examples of intramuscular administration include an intravenous injection or a subcutaneous injection.

In some embodiments, an AAV particle of the present disclosure (e.g., an AAV particle comprising an AAV capsid polypeptide, e.g., an AAV capsid variant) is administered to a subject and transduces the muscle of a subject. As a non-limiting example, an AAV particle is administered by intramuscular administration. In some embodiments, an AAV particle of the present disclosure may be administered to a subject by subcutaneous administration. In some embodiments, the intramuscular administration is via systemic delivery. In some embodiments, the intramuscular administration is via intravenous delivery. In some embodiments, the intramuscular administration is via direct injection to the muscle.

In some embodiments, the muscle is transduced by administration, e.g., intramuscular administration. In some embodiments, an intramuscular delivery comprises administration at one site. In some embodiments, an intramuscular delivery comprises administration at more than one site. In some embodiments, an intramuscular delivery comprises administration at two, three, four, or more sites. In some embodiments, intramuscular delivery is combined with at least one other method of administration.

In some embodiments, an AAV particle pf the present disclosure (e.g., an AAV particle comprising an AAV capsid polypeptide, e.g., an AAV capsid variant) may be administered to a subject by peripheral injections. Non-limiting examples of peripheral injections include intraperitoneal, intramuscular, intravenous, conjunctival, or joint injection. It was disclosed in the art that the peripheral administration of AAV vectors can be transported to the central nervous system, for example, to the motor neurons (e.g., U.S. Patent Publication Nos. US20100240739 and US20100130594; the content of each of which is incorporated herein by reference in their entirety).

In some embodiments, an AAV particle of the present disclosure (e.g., an AAV particle comprising an AAV capsid polypeptide, e.g., an AAV capsid variant) may be administered to a subject by intraparenchymal administration. In some embodiments, the intraparenchymal administration is to muscle tissue. In some embodiments, an AAV particle of the present disclosure is delivered as described in Bright et al 2015 (Neurobiol Aging. 36 (2): 693-709), the contents of which are herein incorporated by reference in their entirety. In some embodiments, an AAV particle of the present disclosure is administered to the gastrocnemius muscle of a subject. In some embodiments, an AAV particle of the present disclosure is administered to the bicep femorii of the subject. In some embodiments, an AAV particles of the present disclosure is administered to the tibialis anterior muscles. In some embodiments, an AAV particle of the present disclosure is administered to the soleus muscle.

Depot Administration

As described herein, in some embodiments, a pharmaceutical composition and/or an AAV particle of the present disclosure (e.g., an AAV particle comprising an AAV capsid polypeptide, e.g., an AAV capsid variant) are formulated in depots for extended release. Generally, specific organs or tissues are targeted for administration.

In some embodiments, a pharmaceutical composition and/or an AAV particle of the present disclosure (e.g., an AAV particle comprising an AAV capsid polypeptide, e.g., an AAV capsid variant) are spatially retained within or proximal to target tissues. Provided are methods of providing a pharmaceutical composition, an AAV particle, to target tissues of mammalian subjects by contacting target tissues (which comprise one or more target cells) with the pharmaceutical composition and/or the AAV particle, under conditions such that they are substantially retained in target tissues, e.g., such that at least 10, 20, 30, 40, 50, 60, 70, 80, 85, 90, 95, 96, 97, 98, 99, 99.9, 99.99 or greater than 99.99% of the composition is retained in the target tissues. In some embodiments, retention is determined by measuring the amount of pharmaceutical composition and/or AAV particle, that enter a target cell or a plurality of target cells. For example, at least 1%, 5%, 10%, 20%, 30%, 40%, 50%, 60%, 70%, 80%, 85%, 90%, 95%, 96%, 97%, 98%, 99%, 99.9%, 99.99%, or greater than 99.99% of a pharmaceutical composition and/or an AAV particle, administered to a subject are present intracellularly at a period of time following administration. For example, intramuscular injection to a subject may be performed using aqueous compositions comprising a pharmaceutical composition and/or an AAV particle of the present disclosure and a transfection reagent, and retention is determined by measuring the amount of the pharmaceutical composition and/or the AAV particle, present in the muscle cell or plurality of muscle cells.

In some embodiments, disclosed herein are methods of providing a pharmaceutical composition and/or an AAV particle of the present disclosure (e.g., an AAV particle comprising an AAV capsid polypeptide, e.g., an AAV capsid variant) to a tissue of a subject, by contacting the tissue (comprising a cell, e.g., a plurality of cells) with the pharmaceutical composition and/or the AAV particle under conditions such that they are substantially retained in the tissue. In some embodiments, a pharmaceutical composition and/or AAV particle described herein comprise a sufficient amount of an active ingredient such that the effect of interest is produced in at least one cell. In some embodiments, a pharmaceutical composition and/or an AAV particle generally comprise one or more cell penetration agents. In some embodiments, the disclosure provides a naked formulations (such as without cell penetration agents or other agents), with or without pharmaceutically acceptable carriers.

Methods of Treatment

AAV Particles Encoding Protein Payloads

Provided in the present disclosure are methods for introducing the AAV particles of the present disclosure (e.g., an AAV particle comprising an AAV capsid polypeptide, e.g., an AAV capsid variant) into cells, the method comprising introducing into said cells any of the vectors in an amount sufficient to modulate, e.g., increase, the production of a target mRNA and/or protein. In some aspects, the cells may be neurons such as but not limited to, motor, hippocampal, entorhinal, thalamic, cortical, sensory, sympathetic, or parasympathetic neurons, and glial cells such as astrocytes, microglia, and/or oligodendrocytes. In other aspects, the cells may be a muscle cell, e.g., a cell of a diaphragm, a quadriceps, or a heart (e.g., a heart atrium or a heart ventricle).

Disclosed in the present disclosure are methods for treating a neurological disease/disorder or a neurodegenerative disorder, a muscular or neuromuscular disorder, or a neurooncological disorder associated with aberrant, e.g., insufficient or increased, function/presence of a protein, e.g., a target protein in a subject in need of treatment. The method comprises administering to the subject a therapeutically effective amount of a composition comprising AAV particles of the present disclosure. As a non-limiting example, the AAV particles can increase target gene expression, increase target protein production, and thus reduce one or more symptoms of neurological disease in the subject such that the subject is therapeutically treated.

In some embodiments, the composition comprising the AAV particles of the present disclosure is administered to the central nervous system of the subject via systemic administration. In some embodiments, the systemic administration is intravenous (IV) injection. In some embodiments, the AAV particle described herein or a pharmaceutical composition comprising an AAV particle described herein is administered by focused ultrasound (FUS), e.g., coupled with the intravenous administration of microbubbles (FUS-MB) or MRI-guided FUS coupled with intravenous administration.

In some embodiments, the composition comprising the AAV particle of the present disclosure (e.g., an AAV particle comprising an AAV capsid polypeptide, e.g., an AAV capsid variant) is administered to the central nervous system of the subject via intraventricular administration. In some embodiments, the intraventricular administration is intra-cisterna magna injection (ICM).

In some embodiments, the composition comprising an AAV particle of the present disclosure (e.g., an AAV particle comprising an AAV capsid polypeptide, e.g., an AAV capsid variant) is administered to the central nervous system of the subject via intraventricular injection and intravenous injection.

In some embodiments, the composition comprising the AAV particle of the present disclosure (e.g., an AAV particle comprising an AAV capsid polypeptide, e.g., an AAV capsid variant) is administered to the central nervous system of the subject via ICM injection and intravenous injection at a specific dose per subject. As a non-limiting example, the AAV particles are administered via ICM injection at a dose of $1 \times 10^4$ VG per subject. As a non-limiting example, the AAV particles are administered via IV injection at a dose of $2 \times 10^{13}$ VG per subject.

In some embodiments, the composition comprising the AAV particle of the present disclosure (e.g., an AAV particle comprising an AAV capsid polypeptide, e.g., an AAV capsid variant) is administered to the central nervous system of the subject. In other embodiments, the composition comprising the AAV particles of the present disclosure is administered to a CNS tissue of a subject (e.g., putamen, thalamus or cortex of the subject).

In some embodiments, the composition comprising the AAV particle of the present disclosure (e.g., an AAV particle comprising an AAV capsid polypeptide, e.g., an AAV capsid variant) is administered to the central nervous system of the subject via intraparenchymal injection. Non-limiting examples of intraparenchymal injections include intraputamenal, intracortical, intrathalamic, intrastriatal, intrahippocampal or into the entorhinal cortex.

In some embodiments, the composition comprising the AAV particle of the present disclosure (e.g., an AAV particle comprising an AAV capsid polypeptide, e.g., an AAV capsid variant) is administered to the central nervous system of the subject via intraparenchymal injection and intravenous injection.

In some embodiments, the composition comprising the AAV particle of the present disclosure (e.g., an AAV particle comprising an AAV capsid polypeptide, e.g., an AAV capsid variant) is administered to the central nervous system of the subject via intraventricular injection, intraparenchymal injection and intravenous injection.

In some embodiments, the composition comprising an AAV particle (e.g., an AAV particle comprising an AAV capsid polypeptide, e.g., an AAV capsid variant) of a plurality of particles of the present disclosure is administered to a muscle of the subject via intravenous injection. In some embodiments, the composition comprising an AAV particle of a plurality of particles of the present disclosure is administered to a muscle of the subject via intramuscular injection.

In some embodiments, an AAV particle of the present disclosure (e.g., an AAV particle comprising an AAV capsid polypeptide, e.g., an AAV capsid variant) may be delivered into specific types of targeted cells, including, but not limited to, thalamic, hippocampal, entorhinal, cortical, motor, sensory, excitatory, inhibitory, sympathetic, or parasympathetic neurons; glial cells including oligodendrocytes, astrocytes and microglia; and/or other cells surrounding neurons such as T cells. In some embodiments, an AAV particle of the present disclosure may be delivered into a muscle cell, e.g., a cell of the quadriceps, diaphragm, liver, and/or heart.

In some embodiments, an AAV particle (e.g., an AAV particle comprising an AAV capsid polypeptide, e.g., an AAV capsid variant), e.g., a plurality of particles, of the present disclosure may be delivered to neurons in the putamen, thalamus and/or cortex.

In some embodiments, an AAV particle (e.g., an AAV particle comprising an AAV capsid polypeptide, e.g., an AAV capsid variant), e.g., a plurality of particles, of the present disclosure may be used as a therapy for neurological disease.

In some embodiments, an AAV particle (e.g., an AAV particle comprising an AAV capsid polypeptide, e.g., an AAV capsid variant), e.g., a plurality of particles, of the present disclosure may be used as a therapy for tauopathies.

In some embodiments, an AAV particle (e.g., an AAV particle comprising an AAV capsid polypeptide, e.g., an AAV capsid variant), e.g., a plurality of particles, of the present disclosure may be used as a therapy for Alzheimer's Disease.

In some embodiments, an AAV particle (e.g., an AAV particle comprising an AAV capsid polypeptide, e.g., an AAV capsid variant), e.g., a plurality of particles, of the present disclosure may be used as a therapy for Amyotrophic Lateral Sclerosis.

In some embodiments, an AAV particle (e.g., an AAV particle comprising an AAV capsid polypeptide, e.g., an AAV capsid variant), e.g., a plurality of particles, of the present disclosure may be used as a therapy for Huntington's Disease.

In some embodiments, an AAV particle (e.g., an AAV particle comprising an AAV capsid polypeptide, e.g., an AAV capsid variant), e.g., a plurality of particles, of the present disclosure may be used as a therapy for Parkinson's Disease.

In some embodiments, an AAV particle (e.g., an AAV particle comprising an AAV capsid polypeptide, e.g., an AAV capsid variant), e.g., a plurality of particles, of the present disclosure may be used as a therapy for Friedreich's Ataxia.

In some embodiments, an AAV particle (e.g., an AAV particle comprising an AAV capsid polypeptide, e.g., an AAV capsid variant), e.g., a plurality of particles, of the present disclosure may be used as a therapy for chronic or neuropathic pain.

In some embodiments, an AAV particle (e.g., an AAV particle comprising an AAV capsid polypeptide, e.g., an AAV capsid variant), e.g., a plurality of particles, of the present disclosure may be used as a therapy for a muscular disorder or a neuromuscular disorder.

In some embodiments, an AAV particle (e.g., an AAV particle comprising an AAV capsid polypeptide, e.g., an AAV capsid variant) e.g., a plurality of particles, of the present disclosure may be used as a therapy for a neuro-oncological disorder. In some embodiments, the neuro-oncological disorder is a cancer of primary CNS origin (e.g., a cancer of a CNS cell and/or CNS tissue). In some embodiments, the neuro-oncological disorder is metastatic cancer in a CNS cell, CNS region, and/or a CNS tissue.

In some embodiments, administration of the AAV particle described herein (e.g., an AAV particle comprising an AAV capsid polypeptide, e.g., an AAV capsid variant) to a subject may increase target protein levels in a subject. The target protein levels may be increased by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS, or a muscle, a region of a muscle, or a cell of a muscle, of a subject. As a non-limiting example, the AAV particles may increase the protein levels of a target protein by at least 50%. As a non-limiting example, the AAV particles may increase the proteins levels of a target protein by at least 40%. As a non-limiting example, a subject may have an increase of 10% of target protein. As a non-limiting example, the AAV particles may increase the protein levels of a target protein by fold increases over baseline. In some embodiments, AAV particles lead to 5-6 times higher levels of a target protein.

In some embodiments, administration of the AAV particle described herein (e.g., an AAV particle comprising an AAV capsid polypeptide, e.g., an AAV capsid variant) to a subject may increase the expression of a target protein in a subject. The expression of the target protein may be increased by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS or a muscle, a region of a muscle, or a cell of a muscle of a subject. As a non-limiting example, the AAV particles may increase the expression of a target protein by at least 50%. As a non-limiting example, the AAV particles may increase the expression of a target protein by at least 40%.

In some embodiments, intravenous administration of the AAV particles described herein (e.g., an AAV particle comprising an AAV capsid polypeptide, e.g., an AAV capsid variant) to a subject may increase the CNS expression or expression in a muscle, of a target protein in a subject. The expression of the target protein may be increased by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS or a muscle, a region of a muscle, or a cell of a muscle of a subject. As a non-limiting example, the AAV particles may increase the expression of a target protein in the CNS by at least 50%. As a non-limiting example, the AAV particles may increase the expression of a target protein in the CNS by at least 40%. In some embodiments, the AAV particle may increase expression of a target protein in a muscle by at least 50%. In some embodiments, the AAV particle may increase expression of a target protein in a muscle by at least 50%.

In some embodiments, the AAV particles of the present disclosure (e.g., an AAV particle comprising, an AAV capsid polypeptide, e.g., an AAV capsid variant) may be used to increase target protein expression in astrocytes in order to treat a neurological disease. Target protein in astrocytes may be increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles (e.g., an AAV particle comprising an AAV capsid polypeptide, e.g., an AAV capsid variant) may be used to increase target protein in microglia. The increase of target protein in microglia may be, independently, increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5- 70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles (e.g., an AAV particle comprising an AAV capsid polypeptide, e.g., an AAV capsid variant) may be used to increase target protein in cortical neurons. The increase of target protein in the cortical neurons may be, independently, increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles (e.g., an AAV particle comprising an AAV capsid polypeptide, e.g., an AAV capsid variant) may be used to increase target protein in hippocampal neurons. The increase of target protein in the hippocampal neurons may be, independently, increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles (e.g., an AAV particle comprising an AAV capsid polypeptide, e.g., an AAV capsid variant) may be used to increase target protein in DRG and/or sympathetic neurons. The increase of target protein in the DRG and/or sympathetic neurons may be, independently, increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles of the present disclosure (e.g., an AAV particle comprising an AAV capsid polypeptide, e.g., an AAV capsid variant) may be used to increase target protein in sensory neurons in order to treat neurological disease. Target protein in sensory neurons may be increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles of the present disclosure (e.g., an AAV particle comprising an AAV capsid polypeptide, e.g., an AAV capsid variant) may be used to increase target protein and reduce symptoms of neurological disease in a subject. The increase of target protein and/or the reduction of symptoms of neurological disease may be, independently, altered (increased for the production of target protein and reduced for the symptoms of neurological disease) by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles of the present disclosure (e.g., an AAV particle comprising an AAV capsid polypeptide, e.g., an AAV capsid variant) may be used to reduce the decline of functional capacity and activities of daily living as measured by a standard evaluation system such as, but not limited to, the total functional capacity (TFC) scale.

In some embodiments, the AAV particles of the present disclosure (e.g., an AAV particle comprising an AAV capsid polypeptide, e.g., an AAV capsid variant) may be used to improve performance on any assessment used to measure symptoms of neurological disease. Such assessments include, but are not limited to ADAS-cog (Alzheimer Disease Assessment Scale-cognitive), MMSE (Mini-Mental State Examination), GDS (Geriatric Depression Scale), FAQ (Functional Activities Questionnaire), ADL (Activities of Daily Living), GPCOG (General Practitioner Assessment of Cognition), Mini-Cog, AMTS (Abbreviated Mental Test Score), Clock-drawing test, 6-CIT (6-item Cognitive Impairment Test), TYM (Test Your Memory), MoCa (Montreal Cognitive Assessment), ACE-R (Addenbrookes Cognitive Assessment), MIS (Memory Impairment Screen), BADLS (Bristol Activities of Daily Living Scale), Barthel Index, Functional Independence Measure, Instrumental Activities of Daily Living, IQCODE (Informant Questionnaire on Cognitive Decline in the Elderly), Neuropsychiatric Inventory, The Cohen-Mansfield Agitation Inventory, BEHAVE-AD, EuroQol, Short Form-36 and/or MBR Caregiver Strain Instrument, or any of the other tests as described in Sheehan B (Ther Adv Neurol Disord. 5 (6): 349-358 (2012)), the contents of which are herein incorporated by reference in their entirety.

In some embodiments, the present composition is administered as a solo therapeutic or as combination therapeutic for the treatment of a neurological disease/disorder or a neurodegenerative disorder, a muscular disorder or neuromuscular disorder, and/or a neuro-oncological disorder.

The AAV particles (e.g., an AAV particle comprising an AAV capsid polypeptide, e.g., an AAV capsid variant) encoding the target protein may be used in combination with one or more other therapeutic agents. In some embodiments, compositions can be administered concurrently with, prior to, or subsequent to, one or more other desired therapeutics or medical procedures. In general, each agent will be administered at a dose and/or on a time schedule determined for that agent.

Therapeutic agents that may be used in combination with the AAV particles of the present disclosure (e.g., an AAV particle comprising an AAV capsid polypeptide, e.g., an AAV capsid variant) can be small molecule compounds which are antioxidants, anti-inflammatory agents, anti-apoptosis agents, calcium regulators, anti-glutamatergic agents, structural protein inhibitors, compounds involved in muscle function, and compounds involved in metal ion regulation. As a non-limiting example, the combination therapy may be in combination with one or more neuroprotective agents such as small molecule compounds, growth factors and hormones which have been tested for their neuroprotective effect on motor neuron degeneration.

Compounds tested for treating neurological disease which may be used in combination with the AAV particles described herein include, but are not limited to, cholinesterase inhibitors (donepezil, rivastigmine, galantamine), NMDA receptor antagonists such as memantine, anti-psychotics, anti-depressants, anti-convulsants (e.g., sodium valproate and levetiracetam for myoclonus), secretase inhibitors, amyloid aggregation inhibitors, copper or zinc modulators, BACE inhibitors, inhibitors of tau aggregation, such as Methylene blue, phenothiazines, anthraquinones, n-phenylamines or rhodamines, microtubule stabilizers such as NAP, taxol or paclitaxel, kinase or phosphatase inhibitors such as those targeting GSK3β (lithium) or PP2A, immunization with Aβ peptides or tau phospho-epitopes, anti-tau or anti-amyloid antibodies, dopamine-depleting agents (e.g., tetrabenazine for chorea), benzodiazepines (e.g., clonazepam for myoclonus, chorea, dystonia, rigidity, and/or spasticity), amino acid precursors of dopamine (e.g., levodopa for rigidity), skeletal muscle relaxants (e.g., baclofen, tizanidine for rigidity and/or spasticity), inhibitors for acetylcholine release at the neuromuscular junction to cause muscle paralysis (e.g., botulinum toxin for bruxism and/or dystonia), atypical neuroleptics (e.g., olanzapine and quetiapine for psychosis and/or irritability, risperidone, sulpiride and haloperidol for psychosis, chorea and/or irritability, clozapine for treatment-resistant psychosis, aripiprazole for psychosis with prominent negative symptoms), selective serotonin reuptake inhibitors (SSRIs) (e.g., citalopram, fluoxetine, paroxetine, sertraline, mirtazapine, venlafaxine for depression, anxiety, obsessive compulsive behavior and/or irritability), hypnotics (e.g., xopiclone and/or zolpidem for altered sleep-wake cycle), anticonvulsants (e.g., sodium valproate and carbamazepine for mania or hypomania) and mood stabilizers (e.g., lithium for mania or hypomania).

Neurotrophic factors may be used in combination therapy with the AAV particles of the present disclosure (e.g., an AAV particle comprising an AAV capsid polypeptide, e.g., an AAV capsid variant) for treating neurological disease. Generally, a neurotrophic factor is defined as a substance that promotes survival, growth, differentiation, proliferation and/or maturation of a neuron, or stimulates increased activity of a neuron. In some embodiments, the present methods further comprise delivery of one or more trophic factors into the subject in need of treatment. Trophic factors may include, but are not limited to, IGF-I, GDNF, BDNF, CTNF, VEGF, Colivelin, Xaliproden, Thyrotrophin-releasing hormone and ADNF, and variants thereof.

In one aspect, the AAV particle described herein (e.g., an AAV particle comprising an AAV capsid polypeptide, e.g., an AAV capsid variant) may be co-administered with AAV particles expressing neurotrophic factors such as AAV-IGF-I (See e.g., Vincent et al., *Neuromolecular medicine,* 2004, 6, 79-85; the contents of which are incorporated herein by reference in their entirety) and AAV-GDNF (See e.g., Wang et al., *J Neurosci.,* 2002, 22, 6920-6928; the contents of which are incorporated herein by reference in their entirety).

In some embodiments, administration of the AAV particles (e.g., an AAV particle comprising an AAV capsid polypeptide, e.g., an AAV capsid variant) to a subject will modulate, e.g., increase or decrease, the expression of a target protein in a subject and the modulation, e.g., increase or decrease of the presence, level, activity, and/or expression of the target protein will reduce the effects and/or symptoms of a neurological disease/disorder or a neurodegenerative disorder, a muscular disorder or neuromuscular disorder, and/or a neuro-oncological disorder in a subject.

As a non-limiting example, the target protein may be a therapeutic protein or functional variant, or an antibody or antibody binding fragment thereof.

AAV Particles Comprising RNAi Agents or Modulatory Polynucleotides

Provided in the present disclosure are methods for introducing the AAV particles of the disclosure (e.g., an AAV particle comprising an AAV capsid polypeptide, e.g., an AAV capsid variant), comprising a viral genome with a nucleic acid sequence encoding a payload comprising a siRNA molecule into cells, the method comprising introducing into said cells any of the vectors in an amount sufficient for degradation of a target mRNA to occur, thereby activating target-specific RNAi in the cells. In some aspects, the cells may be neurons such as but not limited to, motor, hippocampal, entorhinal, thalamic, cortical, sensory, sympathetic, or parasympathetic neurons, and glial cells such as astrocytes, microglia, and/or oligodendrocytes. In other aspects, the cells may be a muscle cell, e.g., a cell of a diaphragm, a quadriceps, or a heart (e.g., a heart atrium or a heart ventricle).

Disclosed in the present disclosure are methods for treating a neurological disease/disorder or a neurodegenerative disorder, a muscular or neuromuscular disorder, or a neurooncological disorder associated with dysfunction and/or aberrant, e.g., increased or decreased expression of a target protein in a subject in need of treatment. The method comprises administering to the subject a therapeutically effective amount of a composition comprising AAV particles (e.g., an AAV particle comprising an AAV capsid polypeptide, e.g., an AAV capsid variant) comprising a viral genome with a nucleic acid sequence encoding one or more siRNA molecules. As a non-limiting example, the siRNA molecules can silence target gene expression, inhibit target protein production, and reduce one or more symptoms of neurological disease in the subject such that the subject is therapeutically treated.

In some embodiments, the composition comprising the AAV particles of the present disclosure (e.g., an AAV particle comprising an AAV capsid polypeptide, e.g., an AAV capsid variant) comprising a viral genome encoding one or more siRNA molecules comprise an AAV capsid that allows for enhanced transduction of CNS and/or PNS cells after intravenous administration.

In some embodiments, the composition comprising the AAV particles of the present disclosure (e.g., an AAV particle comprising an AAV capsid polypeptide, e.g., an AAV capsid variant) with a viral genome encoding at least one siRNA molecule is administered to the central nervous system of the subject. In other embodiments, the composition comprising the AAV particles of the present disclosure is administered to a tissue of a subject (e.g., putamen, thalamus or cortex of the subject).

In some embodiments, the composition comprising the AAV particles of the disclosure (e.g., an AAV particle comprising an AAV capsid polypeptide, e.g., an AAV capsid variant), comprising a viral genome with a nucleic acid sequence encoding one or more siRNA molecules is administered to the central nervous system of the subject via systemic administration. In some embodiments, the systemic administration is intravenous injection. In some embodiments, the AAV particle described herein or a pharmaceutical composition comprising an AAV particle described herein is administered by focused ultrasound (FUS), e.g., coupled with the intravenous administration of microbubbles (FUS-MB) or MRI-guided FUS coupled with intravenous administration.

In some embodiments, the composition comprising the AAV particles of the disclosure (e.g., an AAV particle comprising an AAV capsid polypeptide, e.g., an AAV capsid variant) comprising a viral genome with a nucleic acid sequence encoding one or more siRNA molecules is administered to the central nervous system of the subject via intraparenchymal injection. Non-limiting examples of intraparenchymal injections include intraputamenal, intracortical, intrathalamic, intrastriatal, intrahippocampal or into the entorhinal cortex.

In some embodiments, the composition comprising the AAV particles (e.g., an AAV particle comprising an AAV capsid polypeptide, e.g., an AAV capsid variant) comprising a viral genome with a nucleic acid sequence encoding one or more siRNA molecules is administered to the central nervous system of the subject via intraparenchymal injection and intravenous injection.

In some embodiments, the composition comprising an AAV particle (e.g., an AAV particle comprising an AAV capsid polypeptide, e.g., an AAV capsid variant) of a plurality of particles of the present disclosure is administered to a muscle of the subject via intravenous injection. In some embodiments, the composition comprising an AAV particle of a plurality of particles of the present disclosure is administered to a muscle of the subject via intramuscular injection.

In some embodiments, the AAV particles (e.g., an AAV particle comprising an AAV capsid polypeptide, e.g., an AAV capsid variant) comprising a viral genome with a nucleic acid sequence encoding one or more siRNA molecules may be delivered into specific types or targeted cells, including, but not limited to, thalamic, hippocampal, entorhinal, cortical, motor, sensory, excitatory, inhibitory, sympathetic, or parasympathetic neurons; glial cells including oligodendrocytes, astrocytes and microglia; and/or other cells surrounding neurons such as T cells. In some embodiments, an AAV particle of the present disclosure may be delivered into a muscle cell, e.g., a cell of the quadriceps, diaphragm, liver, and/or heart.

In some embodiments, an AAV particle (e.g., an AAV particle comprising an AAV capsid polypeptide, e.g., an AAV capsid variant), e.g., a plurality of particles, comprising a viral genome with a nucleic acid sequence encoding one or more siRNA molecules may be delivered to neurons in the putamen, thalamus, and/or cortex.

In some embodiments, an AAV particle (e.g., an AAV particle comprising an AAV capsid polypeptide, e.g., an AAV capsid variant), e.g., a plurality of particles, comprising a viral genome with a nucleic acid sequence encoding one or more siRNA molecules may be used as a therapy for neurological disease.

In some embodiments, an AAV particle (e.g., an AAV particle comprising an AAV capsid polypeptide, e.g., an AAV capsid variant), e.g., a plurality of particles, comprising a viral genome with a nucleic acid sequence encoding one or more siRNA molecules may be used as a therapy for tauopathies.

In some embodiments, an AAV particle (e.g., an AAV particle comprising an AAV capsid polypeptide, e.g., an AAV capsid variant), e.g., a plurality of particles, comprising a viral genome with a nucleic acid sequence encoding one or more siRNA molecules may be used as a therapy for Alzheimer's Disease.

In some embodiments, an AAV particle (e.g., an AAV particle comprising an AAV capsid polypeptide, e.g., an AAV capsid variant), e.g., a plurality of particles, comprising a viral genome with a nucleic acid sequence encoding one or more siRNA molecules may be used as a therapy for Amyotrophic Lateral Sclerosis.

In some embodiments, an AAV particle (e.g., an AAV particle comprising an AAV capsid polypeptide, e.g., an AAV capsid variant), e.g., a plurality of particles, comprising a viral genome with a nucleic acid sequence encoding one or more siRNA molecules may be used as a therapy for Huntington's Disease.

In some embodiments, an AAV particle (e.g., an AAV particle comprising an AAV capsid polypeptide, e.g., an AAV capsid variant), e.g., a plurality of particles, comprising a viral genome with a nucleic acid sequence encoding one or more siRNA molecules may be used as a therapy for Parkinson's Disease.

In some embodiments, an AAV particle (e.g., an AAV particle comprising an AAV capsid polypeptide, e.g., an AAV capsid variant), e.g., a plurality of particles, comprising a viral genome with a nucleic acid sequence encoding one or more siRNA molecules may be used as a therapy for Friedreich's Ataxia.

In some embodiments, an AAV particle (e.g., an AAV particle comprising an AAV capsid polypeptide, e.g., an AAV capsid variant), e.g., a plurality of particles, comprising a viral genome with a nucleic acid sequence encoding one or more siRNA molecules may be used as a therapy for a muscular disorder or a neuromuscular disorder.

In some embodiments, an AAV particle (e.g., an AAV particle comprising an AAV capsid polypeptide, e.g., an AAV capsid variant), e.g., a plurality of particles, comprising a viral genome with a nucleic acid sequence encoding one or more siRNA molecules may be used as a therapy for a neuro-oncological disorder. In some embodiments, the neuro-oncological disorder is a cancer of primary CNS origin (e.g., a cancer of a CNS cell and/or CNS tissue). In some embodiments, the neuro-oncological disorder is metastatic cancer in a CNS cell, a CNS region, and/or a CNS tissue.

In some embodiments, the administration of AAV particles (e.g., an AAV particle comprising an AAV capsid polypeptide, e.g., an AAV capsid variant) comprising a viral genome with a nucleic acid sequence encoding one or more siRNA molecules to a subject may lower target protein levels in a subject. The target protein levels may be lowered by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS, or a muscle, a region of a muscle, or a cell of a muscle, of a subject. As a non-limiting example, the AAV particles may lower the protein levels of a target protein by at least 50%. As a non-limiting example, the AAV particles may lower the proteins levels of a target protein by at least 40%.

In some embodiments, the administration of AAV particles (e.g., an AAV particle comprising an AAV capsid polypeptide, e.g., an AAV capsid variant) comprising a viral genome with a nucleic acid sequence encoding one or more siRNA molecules to a subject may lower the expression of a target protein in a subject. The expression of a target protein may be lowered by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS, or a muscle, a region of a muscle, or a cell of a muscle, of a subject. As a non-limiting example, the AAV particles may lower the expression of a target protein by at least 50%. As a non-limiting example, the AAV particles may lower the expression of a target protein by at least 40%.

In some embodiments, the administration of AAV particles (e.g., an AAV particle comprising an AAV capsid polypeptide, e.g., an AAV capsid variant) comprising a viral genome with a nucleic acid sequence encoding one or more siRNA molecules to a subject may lower the expression of a target protein in the CNS of a subject. The expression of a target protein may be lowered by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS, or a muscle, a region of a muscle, or a cell of a muscle, of a subject. As a non-limiting example, the AAV particles may lower the expression of a target protein by at least 50%. As a non-limiting example, the AAV particles may lower the expression of a target protein by at least 40%.

In some embodiments, the AAV particles (e.g., an AAV particle comprising an AAV capsid polypeptide, e.g., an AAV capsid variant) comprising a viral genome with a nucleic acid sequence encoding one or more siRNA molecules may be used to suppress a target protein in astrocytes in order to treat neurological disease. Target protein in astrocytes may be suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. Target protein in astrocytes may be reduced may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-75%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles (e.g., an AAV particle comprising an AAV capsid polypeptide, e.g., an AAV capsid variant) comprising a viral genome with a nucleic acid sequence encoding one or more siRNA molecules may be used to suppress a target protein in microglia. The suppression of the target protein in microglia may be, independently, suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. The reduction may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles (e.g., an AAV particle comprising an AAV capsid polypeptide, e.g., an AAV capsid variant) comprising a viral genome with a nucleic acid sequence encoding one or more siRNA molecules may be used to suppress target protein in cortical neurons. The suppression of a target protein in cortical neurons may be, independently, suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. The reduction may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles (e.g., an AAV particle comprising an AAV capsid polypeptide, e.g., an AAV capsid variant) comprising a viral genome with a nucleic acid sequence encoding one or more siRNA molecules may be used to suppress a target protein in hippocampal neurons. The suppression of a target protein in the hippocampal neurons may be, independently, suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. The reduction may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles (e.g., an AAV particle comprising an AAV capsid polypeptide, e.g., an AAV capsid variant) comprising a viral genome with a nucleic acid sequence encoding one or more siRNA molecules may be used to suppress a target protein in DRG and/or sympathetic neurons. The suppression of a target protein in the DRG and/or sympathetic neurons may be, independently, suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. The reduction may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles (e.g., an AAV particle comprising an AAV capsid polypeptide, e.g., an AAV capsid variant) comprising a viral genome with a nucleic acid sequence encoding one or more siRNA molecules may be used to suppress a target protein in sensory neurons in order to treat neurological disease. Target protein in sensory neurons may be suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. Target protein in the sensory neurons may be reduced may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles (e.g., an AAV particle comprising an AAV capsid polypeptide, e.g., an AAV capsid variant) comprising a viral genome with a nucleic acid sequence encoding one or more siRNA molecules may be used to suppress a target protein and reduce symptoms of neurological disease in a subject. The suppression of target protein and/or the reduction of symptoms of neurological disease may be, independently, reduced or suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles (e.g., an AAV particle comprising an AAV capsid polypeptide, e.g., an AAV capsid variant) comprising a viral genome with a nucleic acid sequence encoding one or more siRNA molecules may be used to reduce the decline of functional capacity and activities of daily living as measured by a standard evaluation system such as, but not limited to, the total functional capacity (TFC) scale.

In some embodiments, the present composition is administered as a solo therapeutic or as combination therapeutic for the treatment of a neurological disease/disorder or a neurodegenerative disorder, a muscular disorder or neuro-muscular disorder, and/or a neuro-oncological disorder.

The AAV particles (e.g., an AAV particle comprising an AAV capsid polypeptide, e.g., an AAV capsid variant) comprising a viral genome with a nucleic acid sequence encoding one or more siRNA molecules may be used in combination with one or more other therapeutic agents. In some embodiments, compositions can be administered concurrently with, prior to, or subsequent to, one or more other desired therapeutics or medical procedures. In general, each agent will be administered at a dose and/or on a time schedule determined for that agent.

Therapeutic agents that may be used in combination with the AAV particles (e.g., an AAV particle comprising an AAV capsid polypeptide, e.g., an AAV capsid variant) comprising a viral genome with a nucleic acid sequence encoding one or more siRNA molecules can be small molecule compounds which are antioxidants, anti-inflammatory agents, anti-apoptosis agents, calcium regulators, antiglutamatergic agents, structural protein inhibitors, compounds involved in muscle function, and compounds involved in metal ion regulation.

Compounds tested for treating neurological disease which may be used in combination with the AAV particles comprising a viral genome with a nucleic acid sequence encoding one or more siRNA molecules include, but are not limited to, cholinesterase inhibitors (donepezil, rivastig-mine, galantamine), NMDA receptor antagonists such as memantine, anti-psychotics, anti-depressants, anti-convulsants (e.g., sodium valproate and levetiracetam for myoclonus), secretase inhibitors, amyloid aggregation inhibitors, copper or zinc modulators, BACE inhibitors, inhibitors of tau aggregation, such as Methylene blue, phenothiazines, anthraquinones, n-phenylamines or rhodamines, microtubule stabilizers such as NAP, taxol or paclitaxel, kinase or phosphatase inhibitors such as those targeting GSK3β (lithium) or PP2A, immunization with Aβ peptides or tau phospho-epitopes, anti-tau or anti-amyloid antibodies, dopamine-depleting agents (e.g., tetrabenazine for chorea), benzodiazepines (e.g., clonazepam for myoclonus, chorea, dystonia, rigidity, and/or spasticity), amino acid precursors of dopamine (e.g., levodopa for rigidity), skeletal muscle relaxants (e.g., baclofen, tizanidine for rigidity and/or spasticity), inhibitors for acetylcholine release at the neuromuscular junction to cause muscle paralysis (e.g., botulinum toxin for bruxism and/or dystonia), atypical neuroleptics (e.g., olanzapine and quetiapine for psychosis and/or irritability, risperidone, sulpiride and haloperidol for psychosis, chorea and/or irritability, clozapine for treatment-resistant psychosis, aripiprazole for psychosis with prominent negative symptoms), selective serotonin reuptake inhibitors (SSRIs) (e.g., citalopram, fluoxetine, paroxetine, sertraline, mirtazapine, venlafaxine for depression, anxiety, obsessive compulsive behavior and/or irritability), hypnotics (e.g., xopiclone and/or zolpidem for altered sleep-wake cycle), anticonvulsants (e.g., sodium valproate and carbamazepine for mania or hypomania) and mood stabilizers (e.g., lithium for mania or hypomania).

Neurotrophic factors may be used in combination therapy with the AAV particles (e.g., an AAV particle comprising an AAV capsid polypeptide, e.g., an AAV capsid variant) comprising a viral genome with a nucleic acid sequence encoding one or more siRNA molecules for treating neurological disease. Generally, a neurotrophic factor is defined as a substance that promotes survival, growth, differentiation, proliferation and/or maturation of a neuron, or stimulates increased activity of a neuron. In some embodiments, the present methods further comprise delivery of one or more trophic factors into the subject in need of treatment. Trophic factors may include, but are not limited to, IGF-I, GDNF, BDNF, CTNF, VEGF, Colivelin, Xaliproden, Thyrotrophin-releasing hormone and ADNF, and variants thereof.

In one aspect, the AAV particle (e.g., an AAV particle comprising an AAV capsid polypeptide, e.g., an AAV capsid variant) encoding the nucleic acid sequence for the at least one siRNA duplex targeting the gene of interest may be co-administered with AAV particles expressing neurotrophic factors such as AAV-IGF-I (See e.g., Vincent et al., *Neuro-molecular medicine,* 2004, 6, 79-85; the content of which is incorporated herein by reference in its entirety) and AAV-GDNF (See e.g., Wang et al., *J Neurosci.,* 2002, 22, 6920-6928; the contents of which are incorporated herein by reference in their entirety).

In some embodiments, administration of the AAV particles (e.g., an AAV particle comprising an AAV capsid polypeptide, e.g., an AAV capsid variant) to a subject will modulate, e.g., reduce the presence, level, activity, and/or expression of a target gene, mRNA, and/or protein in a subject and the reduction of expression of the target protein will reduce the effects and/or symptoms of a neurological disease/disorder or a neurodegenerative disorder, a muscular disorder or neuromuscular disorder, and/or a neuro-oncological disorder in a subject.

DEFINITIONS

Unless defined otherwise, all technical and scientific terms used herein have the same meaning as commonly understood by one of ordinary skill in the art to which the invention pertains.

Articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" and "consisting essentially thereof" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

Adeno-associated virus: As used herein, the term "adeno-associated virus" or "AAV" refers to members of the dependovirus genus or a variant, e.g., a functional variant, thereof. In some embodiments, the AAV is wildtype, or naturally occurring. In some embodiments, the AAV is recombinant.

AAV Particle: As used herein, an "AAV particle" refers to a particle or a virion comprising an AAV capsid, e.g., an AAV capsid variant, and a polynucleotide, e.g., a viral genome or a vector genome. In some embodiments, the viral genome of the AAV particle comprises at least one payload region and at least one ITR. In some embodiments, an AAV particle of the disclosure is an AAV particle comprising an AAV capsid polypeptide, e.g., a parent capsid sequence with at least one peptide, e.g., targeting peptide, insert. In some embodiments, the AAV particle is capable of delivering a nucleic acid, e.g., a payload region, encoding a payload to cells, typically, mammalian, e.g., human, cells. In some embodiments, an AAV particle of the present disclosure may be produced recombinantly. In some embodiments, an AAV particle may be derived from any serotype, described herein or known in the art, including combinations of serotypes (e.g., "pseudotyped" AAV) or from various genomes (e.g., single stranded or self-complementary). In some embodiments, the AAV particle may be replication defective and/or targeted. In some embodiments, the AAV particle may comprises a peptide, e.g., targeting peptide, present, e.g., inserted into, the capsid to enhance tropism for a desired target tissue. It is to be understood that reference to the AAV particle of the disclosure also includes pharmaceutical compositions thereof, even if not explicitly recited.

Administering: As used herein, the term "administering" refers to providing a pharmaceutical agent or composition to a subject.

Amelioration: As used herein, the term "amelioration" or "ameliorating" refers to a lessening of severity of at least one indicator of a condition or disease. For example, in the context of neurodegeneration disorder, amelioration includes the reduction of neuron loss.

Amplicon: As used herein, "amplicon" may refer to any piece of RNA or DNA formed as the product of amplification events, e.g. PCR. In some embodiments, full-length capsid amplicons may be used as templates for next generation sequencing (NGS) library generation. Full-length capsid amplicons may be used for cloning into a DNA library for any number of additional rounds of AAV selection as described herein.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically engineered animal, or a clone.

Antisense strand: As used herein, the term "the antisense strand" or "the first strand" or "the guide strand" of a siRNA molecule refers to a strand that is substantially complementary to a section of about 10-50 nucleotides, e.g., about 15-30, 16-25, 18-23 or 19-22 nucleotides of the mRNA of a gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biopanning: As used herein, the term "biopanning" refers to an AAV capsid library selection process comprising administration of an AAV particle with enhanced tissue-and/or cell type-specific transduction to a cell and/or subject; extraction of nucleotides encoded by said AAV particle from said transduced tissue- and/or cell type-specific; and, use of the extracted nucleotides for cloning into a nucleotide library for the generation of AAV particles for subsequent rounds of the same.

Capsid: As used herein, the term "capsid" refers to the exterior, e.g., a protein shell, of a virus particle, e.g., an AAV particle, that is substantially (e.g., >50%, >60%, >70%, >80%, >90%, >95%, >99%, or 100%) protein. In some embodiments, the capsid is an AAV capsid comprising an AAV capsid protein described herein, e.g., a VP1, VP2, and/or VP3 polypeptide. The AAV capsid protein can be a wild-type AAV capsid protein or a variant, e.g., a structural and/or functional variant from a wild-type or a reference capsid protein, referred to herein as an "AAV capsid variant." In some embodiments, the AAV capsid variant described herein has the ability to enclose, e.g., encapsulate, a viral genome and/or is capable of entry into a cell, e.g., a mammalian cell. In some embodiments, the AAV capsid variant described herein may have modified tropism compared to that of a wild-type AAV capsid, e.g., the corresponding wild-type capsid.

Complementary and substantially complementary: As used herein, the term "complementary" refers to the ability of polynucleotides to form base pairs with one another. Base pairs are typically formed by hydrogen bonds between nucleotide units in antiparallel polynucleotide strands. Complementary polynucleotide strands can form base pairs in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenine. However, when a U is denoted in the context of the present disclosure, the ability to substitute a T is implied, unless otherwise stated. Perfect complementarity or 100% complementarity refers to the situation in which each nucleotide unit of one polynucleotide strand can form a hydrogen bond with a nucleotide unit of a second polynucleotide strand. Less than perfect complementarity refers to the situation in which some, but not all, nucleotide units of two strands can form hydrogen bond with each other. For example, for two 20-mers, if only two base pairs on each strand can form a hydrogen bond with each other, the polynucleotide strands exhibit 10% complementarity. In the same example, if 18 base pairs on each strand can form hydrogen bonds with each other, the polynucleotide strands exhibit 90% complementarity. The term "complementary" as used herein can encompass fully complementary, partially complementary, or substantially complementary. As used herein, the term "substantially complementary" means that the siRNA has a sequence (e.g., in the antisense strand) which is sufficient to bind the desired target mRNA, and to trigger the RNA silencing of the target mRNA. "Fully complementary", "perfect complementarity", or "100% complementarity" refers to the situation in which each nucleotide unit of one polynucleotide or oligonucleotide strand can base-pair with a nucleotide unit of a second polynucleotide or oligonucleotide strand.

Control Elements: As used herein, "control elements", "regulatory control elements" or "regulatory sequences" refers to promoter regions, polyadenylation signals, transcription termination sequences, upstream regulatory domains, origins of replication, internal ribosome entry sites ("IRES"), enhancers, and the like, which provide for the replication, transcription and translation of a coding sequence in a recipient cell. Not all of these control elements need always be present as long as the selected coding sequence is capable of being replicated, transcribed and/or translated in an appropriate host cell.

Delivery: As used herein, "delivery" refers to the act or manner of delivering an AAV particle, a compound, substance, entity, moiety, cargo or payload.

Element: As used herein, the term "element" refers to a distinct portion of an entity. In some embodiments, an element may be a polynucleotide sequence with a specific purpose, incorporated into a longer polynucleotide sequence.

Encapsulate: As used herein, the term "encapsulate" means to enclose, surround or encase. As an example, a capsid protein, e.g., an AAV capsid variant, often encapsulates a viral genome. In some embodiments, encapsulate within a capsid, e.g., an AAV capsid variant, encompasses 100% coverage by a capsid, as well as less than 100% coverage, e.g., 95%, 90%, 85%, 80%, 70%, 60% or less. For example, gaps or discontinuities may be present in the capsid so long as the viral genome is retained in the capsid, e.g., prior to entry into a cell.

Engineered: As used herein, embodiments of the disclosure are "engineered" when they are designed to have a feature or property, whether structural or chemical, that varies from a starting point, wild type or native molecule.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Formulation: As used herein, a "formulation" includes at least one AAV particle (active ingredient) and an excipient, and/or an inactive ingredient.

Fragment: A "fragment," as used herein, refers to a portion. For example, an antibody fragment may comprise a CDR, or a heavy chain variable region, or a scFv, etc.

Functional: As used herein, a "functional" biological molecule is a biological molecule in a form in which it exhibits a property and/or activity.

Dual-function targeting: As used herein, a "dual-function targeting" modulatory polynucleotide is a polynucleotide where both the guide and passenger strands knock down the same target or the guide and passenger strands knock down different targets.

Gene expression: The term "gene expression" refers to the process by which a nucleic acid sequence undergoes transcription and/or translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA, mRNA, polypeptides and peptides are known in the art.

Homology: As used herein, the term "homology" refers to the overall relatedness between polymeric molecules, e.g. between polynucleotide molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the disclosure, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the disclosure, two protein sequences are considered to be homologous if the proteins are at least about 50%, 60%, 70%, 80%, or 90% identical for at least one stretch of at least about 20 amino acids.

Identity: As used herein, the term "identity" refers to the overall relatedness between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; the contents of each of which are incorporated herein by reference in their entirety. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12 (1), 387 (1984)), BLASTP, BLASTN, and FASTA Altschul, S. F. et al., *J. Molec. Biol.,* 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically, a reduction in the level of an mRNA results in a reduction in the level of a polypeptide translated therefrom. The level of expression may be determined using standard techniques for measuring mRNA or protein.

Insert: As used herein the term "insert," when referring to a polypeptide, refers to the addition of one or more amino acids, e.g., a peptide, e.g., targeting peptide, sequence to an amino acid sequence, e.g., a parent AAV capsid sequence. In some embodiments, an insertion may result in the replacement of one or more amino acids of the amino acid sequence, e.g., the parent AAV capsid sequence. In some embodiments, an insertion may result in no changes to the amino acid sequence, e.g., parent AAV capsid sequence, beyond the addition of the one or more amino acids, e.g., a peptide, e.g., targeting peptide sequence.

Inverted terminal repeat: As used herein, the term "inverted terminal repeat" or "ITR" refers to a cis-regulatory element for the packaging of polynucleotide sequences into viral capsids.

Isolated: As used herein, the term "isolated" refers to a substance or entity that is altered or removed from the natural state, e.g., altered or removed from at least some of component with which it is associated in the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell. Such polynucleotides could be part of a vector and/or such polynucleotides or polypeptides could be part of a composition, and still be isolated in that such vector or composition is not part of the environment in which it is found in nature. In some embodiments, an isolated nucleic acid is recombinant, e.g., incorporated into a vector.

Library: As used herein, the term "library" refers to a diverse collection of linear polypeptides, polynucleotides, viral particles, or viral vectors. As examples, a library may be a DNA library or an AAV capsid library.

Molecular scaffold: As used herein a "molecular scaffold" is a framework or starting molecule that forms the sequence or structural basis against which to design or make a subsequent molecule.

Neurological disease: As used herein, a "neurological disease" is any disease associated with the central or peripheral nervous system and components thereof (e.g., neurons).

Naturally Occurring: As used herein, "naturally occurring" or "wild-type" refers to a substance or entity that has not been altered, e.g., structurally altered, or removed from the natural state, e.g., removed from at least some of component with which it is associated in the natural state. In some embodiments, a naturally occurring when referring to sequence refers to a sequence identical to a wild-type sequence or a naturally occurring variant thereof.

Orthogonal evolution: As used herein, the term "orthogonal evolution" refers to a method wherein AAV particles are administered for a first round of AAV selection as described herein across a set of any number of cell- and/or subject-types that may be from different species and/or strains, and wherein any number of additional, i.e., subsequent, AAV selection rounds are performed either across a set of any number of cell- and/or subject-types that may be from different species and/or strains, or across a set of any number of cell- and/or subject-types that may be from the same species and/or strain.

Open reading frame: As used herein, "open reading frame" or "ORF" refers to a sequence which does not contain a stop codon in a given reading frame.

Parent sequence: As used herein, a "parent sequence" is a nucleic acid or amino acid sequence from which a variant is derived. In some embodiments, a parent sequence is a sequence into which a heterologous sequence is inserted. In other words, a parent sequence may be considered an acceptor or recipient sequence. In some embodiments, a parent sequence is an AAV capsid sequence into which a targeting sequence is inserted.

Particle: As used herein, a "particle" is a virus comprised of at least two components, a protein capsid and a polynucleotide sequence enclosed within the capsid.

Patient: As used herein, "patient" refers to a subject who may seek or be in need of treatment, requires treatment, is receiving treatment, will receive treatment, or a subject who is under care by a trained professional for a particular disease or condition.

Payload region: As used herein, a "payload region" is any nucleic acid sequence (e.g., within the viral genome) which encodes one or more "payloads" of the disclosure. As non-limiting examples, a payload region may be a nucleic acid sequence within the viral genome of an AAV particle, which encodes a payload, wherein the payload is an RNAi agent or a polypeptide. Payloads of the present disclosure may be, but are not limited to, peptides, polypeptides, proteins, antibodies, RNAi agents, etc.

Polypeptide: As used herein, "polypeptide" means a polymer of amino acid residues (natural or unnatural) linked together most often by peptide bonds. The term, as used herein, refers to proteins, polypeptides, and peptides of any size, structure, or function. In some instances, the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multimolecular complex such as a dimer, trimer or tetramer. They may also comprise single chain or multichain polypeptides and may be associated or linked. The term polypeptide may also apply to amino acid polymers in which one or more amino acid residues are an artificial chemical analogue of a corresponding naturally occurring amino acid.

Polypeptide variant: The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. In some embodiments, a variant comprises a sequence having at least about 50%, at least about 80%, or at least about 90%, identical (homologous) to a native or a reference sequence.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Preventing: As used herein, the term "preventing" or "prevention" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease.

Region: As used herein, the term "region" refers to a zone or general area. In some embodiments, when referring to a protein or protein module, a region may comprise a linear sequence of amino acids along the protein or protein module or may comprise a three-dimensional area, an epitope and/or a cluster of epitopes. In some embodiments, regions comprise terminal regions. As used herein, the term "terminal region" refers to regions located at the ends or termini of a given agent. When referring to proteins, terminal regions may comprise N- and/or C-termini.

In some embodiments, when referring to a polynucleotide, a region may comprise a linear sequence of nucleic acids along the polynucleotide or may comprise a three-dimensional area, secondary structure, or tertiary structure. In some embodiments, regions comprise terminal regions. As used herein, the term "terminal region" refers to regions located at the ends or termini of a given agent. When referring to polynucleotides, terminal regions may comprise 5' and/or 3' termini.

RNA or RNA molecule: As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally, e.g., by DNA replication and transcription of DNA, respectively; or be chemically synthesized. DNA and RNA can be single-stranded (i.e., ssRNA or ssDNA, respectively) or multi-stranded (e.g., double stranded, i.e., dsRNA and dsDNA, respectively). The term "mRNA" or "messenger RNA", as used herein, refers to a single stranded RNA that encodes the amino acid sequence of one or more polypeptide chains.

RNA interfering or RNAi: As used herein, the term "RNA interfering" or "RNAi" refers to a sequence specific regulatory mechanism mediated by RNA molecules which results in the inhibition or interfering or "silencing" of the expression of a corresponding protein-coding gene. RNAi has been observed in many types of organisms, including plants, animals and fungi. RNAi occurs in cells naturally to remove foreign RNAs (e.g., viral RNAs). Natural RNAi proceeds via fragments cleaved from free dsRNA which direct the degradative mechanism to other similar RNA sequences. RNAi is controlled by the RNA-induced silencing complex (RISC) and is initiated by short/small dsRNA molecules in cell cytoplasm, where they interact with the catalytic RISC component argonaute. The dsRNA molecules can be introduced into cells exogenously. Exogenous dsRNA initiates RNAi by activating the ribonuclease protein Dicer, which binds and cleaves dsRNAs to produce double-stranded fragments of 21-25 base pairs with a few unpaired overhang bases on each end. These short double stranded fragments are called small interfering RNAs (siRNAs).

RNAi agent: As used herein, the term "RNAi agent" refers to an RNA molecule, or its derivative, that can induce inhibition, interfering, or "silencing" of the expression of a target gene and/or its protein product. An RNAi agent may knock-out (virtually eliminate or eliminate) expression, or knock-down (lessen or decrease) expression. The RNAi agent may be, but is not limited to, dsRNA, siRNA, shRNA, pre-miRNA, pri-miRNA, miRNA, stRNA, lncRNA, piRNA, or snoRNA.

miR binding site: As used herein, a "miR binding site" comprises a nucleic acid sequence (whether RNA or DNA, e.g., differ by "U" of RNA or "T" in DNA) that is capable of binding, or binds, in whole or in part to a microRNA (miR) through complete or partial hybridization. Typically, such binding occurs between the miR and the miR binding site in the reverse complement orientation. In some embodiments, the miR binding site is transcribed from the AAV vector genome encoding the miR binding site.

In some embodiments, a miR binding site may be encoded or transcribed in series. Such a "miR binding site series" or "miR BSs" may include two or more miR binding sites having the same or different nucleic acid sequence.

Spacer: As used here, a "spacer" is generally any selected nucleic acid sequence of, e.g., 1, 2, 3, 4, 5, 6, 7, 8, 9, or 10 nucleotides in length, which is located between two or more consecutive miR binding site sequences. Spacers may also be more than 10 nucleotides in length, e.g., 20, 30, 40, or 50 or more than 50 nucleotides.

Sample: As used herein, the term "sample" or "biological sample" refers to a subset of its tissues, cells, nucleic acids, or component parts (e.g. body fluids, including but not limited to blood, serum, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Self-complementary viral particle: As used herein, a "self-complementary viral particle" is a particle comprised of at least two components, a protein capsid and a self-complementary viral genome enclosed within the capsid.

Sense Strand: As used herein, the term "the sense strand" or "the second strand" or "the passenger strand" of a siRNA molecule refers to a strand that is complementary to the antisense strand or first strand. The antisense and sense strands of a siRNA molecule are hybridized to form a duplex structure. As used herein, a "siRNA duplex" includes a siRNA strand having sufficient complementarity to a section of about 10-50 nucleotides of the mRNA of the gene targeted for silencing and a siRNA strand having sufficient complementarity to form a duplex with the other siRNA strand.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Short interfering RNA or siRNA: As used herein, the terms "short interfering RNA," "small interfering RNA" or "siRNA" refer to an RNA molecule (or RNA analog) comprising between about 5-60 nucleotides (or nucleotide analogs) which is capable of directing or mediating RNAi. Preferably, a siRNA molecule comprises between about 15-30 nucleotides or nucleotide analogs, such as between about 16-25 nucleotides (or nucleotide analogs), between about 18-23 nucleotides (or nucleotide analogs), between about 19-22 nucleotides (or nucleotide analogs) (e.g., 19, 20, 21 or 22 nucleotides or nucleotide analogs), between about 19-25 nucleotides (or nucleotide analogs), and between about 19-24 nucleotides (or nucleotide analogs). The term "short" siRNA refers to a siRNA comprising 5-23 nucleotides, preferably 21 nucleotides (or nucleotide analogs), for example, 19, 20, 21 or 22 nucleotides. The term "long" siRNA refers to a siRNA comprising 24-60 nucleotides, preferably about 24-25 nucleotides, for example, 23, 24, 25 or 26 nucleotides. Short siRNAs may, in some instances, include fewer than 19 nucleotides, e.g., 16, 17 or 18 nucleotides, or as few as 5 nucleotides, provided that the shorter siRNA retains the ability to mediate RNAi. Likewise, long siRNAs may, in some instances, include more than 26 nucleotides, e.g., 27, 28, 29, 30, 35, 40, 45, 50, 55, or even 60 nucleotides, provided that the longer siRNA retains the ability to mediate RNAi or translational repression absent further processing, e.g., enzymatic processing, to a short siRNA. siRNAs can be single stranded RNA molecules (ss-siRNAs) or double stranded RNA molecules (ds-siR-NAs) comprising a sense strand and an antisense strand which hybridized to form a duplex structure called an siRNA duplex.

Subject: As used herein, the term "subject" or "patient" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Targeting peptide: As used herein, a "targeting peptide" refers to a peptide of 3-20 amino acids in length. These targeting peptides may be inserted into, or attached to, a parent amino acid sequence to alter the characteristics (e.g., tropism) of the parent protein. As a non-limiting example, the targeting peptide can be inserted into an AAV capsid sequence for enhanced targeting to a desired cell-type, tissue, organ or organism. It is to be understood that a targeting peptide is encoded by a targeting polynucleotide which may similarly be inserted into a parent polynucleotide sequence. Therefore, a "targeting sequence" refers to a peptide or polynucleotide sequence for insertion into an appropriate parent sequence (amino acid or polynucleotide, respectively).

Target Cells: As used herein, "target cells" or "target tissue" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition. In some embodiments, a therapeutically effective amount is provided in a single dose.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Variant: As used herein, the term "variant" refers to a polypeptide or polynucleotide that has an amino acid or a nucleotide sequence that is substantially identical, e.g., having at least 70%, 75%, 80%, 85%, 90%, 95% or 99% sequence identity to a reference sequence. In some embodiments, the variant is a functional variant.

Functional Variant: As used herein, the term "functional variant" refers to a polypeptide variant or a polynucleotide variant that has at least one activity of the reference sequence.

Insertional Variant: "Insertional variants" when referring to polypeptides are those with one or more amino acids inserted, e.g., immediately adjacent or subsequent, to a position in an amino acid sequence. "Immediately adjacent" or "immediately subsequent" to an amino acid means connected to either the alpha-carboxy or alpha-amino functional group of the amino acid.

Deletional Variant: "Deletional variants" when referring to polypeptides, are those with one or more amino acids in deleted from a reference protein.

Vector: As used herein, the term "vector" refers to any molecule or moiety which transports, transduces or otherwise acts as a carrier of a heterologous molecule. In some embodiments, vectors may be plasmids. In some embodiments, vectors may be viruses. An AAV particle is an example of a vector. Vectors of the present disclosure may be produced recombinantly and may be based on and/or may comprise adeno-associated virus (AAV) parent or reference sequences. The heterologous molecule may be a polynucleotide and/or a polypeptide.

Viral Genome: As used herein, the terms "viral genome" or "vector genome" refer to the nucleic acid sequence(s) encapsulated in an AAV particle. A viral genome comprises a nucleic acid sequence with at least one payload region encoding a payload and at least one ITR.

EQUIVALENTS AND SCOPE

The disclosures of each and every patent, patent application, and publication cited herein are hereby incorporated herein by reference in their entirety. Those skilled in the art will recognize or be able to ascertain using no more than routine experimentation, many equivalents to the specific embodiments in accordance with the disclosure described herein. The scope of the present disclosure is not intended to be limited to the above Description, but rather is as set forth in the appended claims.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the disclosure in its broader aspects.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

The present disclosure is further illustrated by the following non-limiting examples.

EXAMPLES

Example 1. Peptide Display Capsid Library Configuration

Peptide display capsid libraries are configured by insertion of randomized n-mer amino acids such as, but not limited to, 5-mer, 6-mer, 7-mer and/or 9-mer amino acids, into the surface-exposed hypervariable loop I, loop IV, loop VI, and/or loop VIII region of any AAV capsid serotype, including AAV5, AAV6, or AAV-DJ8, as well as AAV9 capsids, and/or variants thereof. The genes encoding the peptide display capsid library are under the control of any promotor, depending on the desired tropism, e.g., a neuron-specific synapsin promoter (SYN or Syn), or an astrocyte-specific GFAP promoter.

Peptide display capsid libraries are further configured such that the n-mer peptide insertion(s) follows a contiguous (or continuous) design and/or a noncontiguous (or noncontinuous), or split design, or combination thereof, with insertion position(s) mapped using a sliding window algorithm. As a non-limiting example, the peptide insertion may be an AAV9 6-mer contiguous peptide insertion with a sliding window originating at any amino acid position, e.g., amino acids 454-461. As another non-limiting example, the peptide insertion may be an AAV9 3-mer peptide split design or contiguous peptide insertion with a sliding window originating at any amino acid position, e.g., amino acids 586-588. As yet another non-limiting example, the peptide insertion may be an AAV9 6-mer and/or 7-mer peptide contiguous peptide insertion with a sliding window originating at any amino acid position, e.g., amino acids 585-590.

Any number of such configured peptide display capsid libraries may be pooled in a cell and/or subject, including a non-human primate (NHP) cell and/or subject, and administered to any tissue (e.g., central nervous system tissue) via any route, including but not limited to IV and/or ICM injection, at any VG/cell and/or VG/subject dose. As a non-limiting example, six configured peptide display capsid libraries are pooled and administered to the central nervous system of an NHP via intravenous administration of dose $1\times10^{14}$ VG/NHP. As another non-limiting example, six libraries are pooled and administered to the central nervous system of NHP via an intraventricular administration, such as, but not limited intraventricular administration that is an intra-cisterna magna injection (ICM) of dose $2\times10^{13}$ a VG/NHP.

Example 2. Identification and Design of Non-Human Primate AAV Capsid Libraries A TRACER™ RNA-driven library selection for increased nervous system tissue transduction in a non-human primate (NHP) is developed and carried out in accordance with methods similar, or equivalent, to those described in WO2020072683, the contents of which are herein incorporated by reference in their entirety, particularly as pertains to the TRACER™ method.

AAV libraries, e.g., AAV9 libraries, generated are administered by any route to NHPs at a given VG dose(s) per animal. A number of groups of NHPs are administered promoter-driven (e.g., SYN-driven or GFAP-driven) libraries derived from wild-type AAV9 flanking sequences, while other groups receive pooled libraries containing wild-type, PHP.eB-derived, or other AAV serotype sequences. After a period, RNA is extracted from a tissue, such as but not limited to spinal cord and brain tissue. The RNA preparation is subjected to mRNA enrichment. The enriched mRNA is reverse transcribed to cDNA. The cDNA is amplified. This method allows recovery of abundant amplicons from tissue samples.

Full-length capsid amplicons are used as templates for NGS library generation, as well as cloning into a DNA library for the next, or subsequent, round(s) of biopanning (FIG. 1A and FIG. 1B). Any number of rounds of AAV selection may be performed. The total number of unique capsid variants may drop by a fold amount across AAV selection rounds. Capsid libraries may be pooled or combined at any step with any other capsid libraries described herein.

Following RNA recovery and PCR amplification, a systematic enrichment analysis by NGS is performed. Capsids enrichment ratio including comparison to a benchmark and sequence convergence is evaluated.

Peptide library candidates are evaluated and optimized using any of the methods described herein and are carried out, e.g., using methods similar, or equivalent, to those described in WO2020072683, the contents of which are herein incorporated by reference in their entirety, particularly the subject matter of Examples, 8, 9, and 10. The top-ranking peptide variants are generated and transduction efficacy evaluated as described in WO2020072683, the contents of which are herein incorporated by reference in their entirety, particularly the subject matter of Examples 10, 12 and 13.

Example 3. Identification and Design of Orthogonal Evolution AAV Capsid Libraries This study involves the use of orthogonal evolution wherein AAV particles may be administered for a first round of AAV selection across a set of any number of cell- and/or subject-types that may be from different species and/or strains; and, wherein any number of additional, i.e., subsequent, AAV selection rounds are performed either across a set of any number of cell- and/or subject-types that may be from different species and/or strains, or across a set of any number of cell- and/or subject-types that may be from the same species and/or strains, as represented in FIG. 2.

A TRACER™ based RNA-driven library selection for increased nervous system tissue transduction a set of any number of cell- and/or subject-types that may be from different species and/or strain is developed and carried out in accordance with methods similar, or equivalent, to those described in WO2020072683, the contents of which are herein incorporated by reference in their entirety, particularly the subject matter of Example 7. AAV libraries, e.g., AAV9 libraries, generated are administered for a first round of AAV selection (biopanning) by any route to a non-human primate (NHP), a rodent (e.g., a rat), and/or a cell (e.g., a human brain microvascular endothelial cell, or hBMVEC) at a given VG dose(s) per subject and/or cell. A number of groups of NHPs, rodents, and/or cells are administered promoter-driven (e.g., SYN-driven or GFAP-driven) libraries derived from wild-type AAV9 sequences, while other groups receive pooled libraries containing wild-type, PHP.eB-derived, or other AAV serotype sequences. After a period, RNA is extracted from a tissue, such as but not limited to spinal cord and brain tissue. The RNA preparation is subjected to mRNA enrichment. The enriched mRNA is reverse transcribed to cDNA. The cDNA is amplified. This method allows recovery of abundant amplicons from tissue samples.

Full-length capsid amplicons are used as templates for NGS library generation, as well as cloning into DNA libraries for the next, or subsequent round(s) of biopanning. Subsequent rounds of biopanning are performed either across a set of any number of cell- and/or subject-types that may be from different species and/or strain as used in the above-described first round, or across a set of any number of cell- and/or subject-types that may be from the same species and/or strain as used in the above-described first round. Any number of rounds of selection is performed. The total number of unique capsid variants may drop by a fold amount across AAV selection rounds. Capsid libraries may be pooled or combined at any step with any other capsid libraries described herein (FIG. 2)

Following RNA recovery and PCR amplification, a systematic enrichment analysis by NGS is performed. Capsids enrichment ratio including comparison to a benchmark and sequence convergence is evaluated.

Peptide library candidates are evaluated and optimized using any of the methods described herein and are carried out, e.g., using methods similar, or equivalent, to those described in WO2020072683, the contents of which are herein incorporated by reference in their entirety. The top-ranking peptide variants are generated and transduction efficacy evaluated as in WO2020072683.

Example 4. NHP High-Throughput Screen of TRACER™ AAV Libraries

Figure 3:
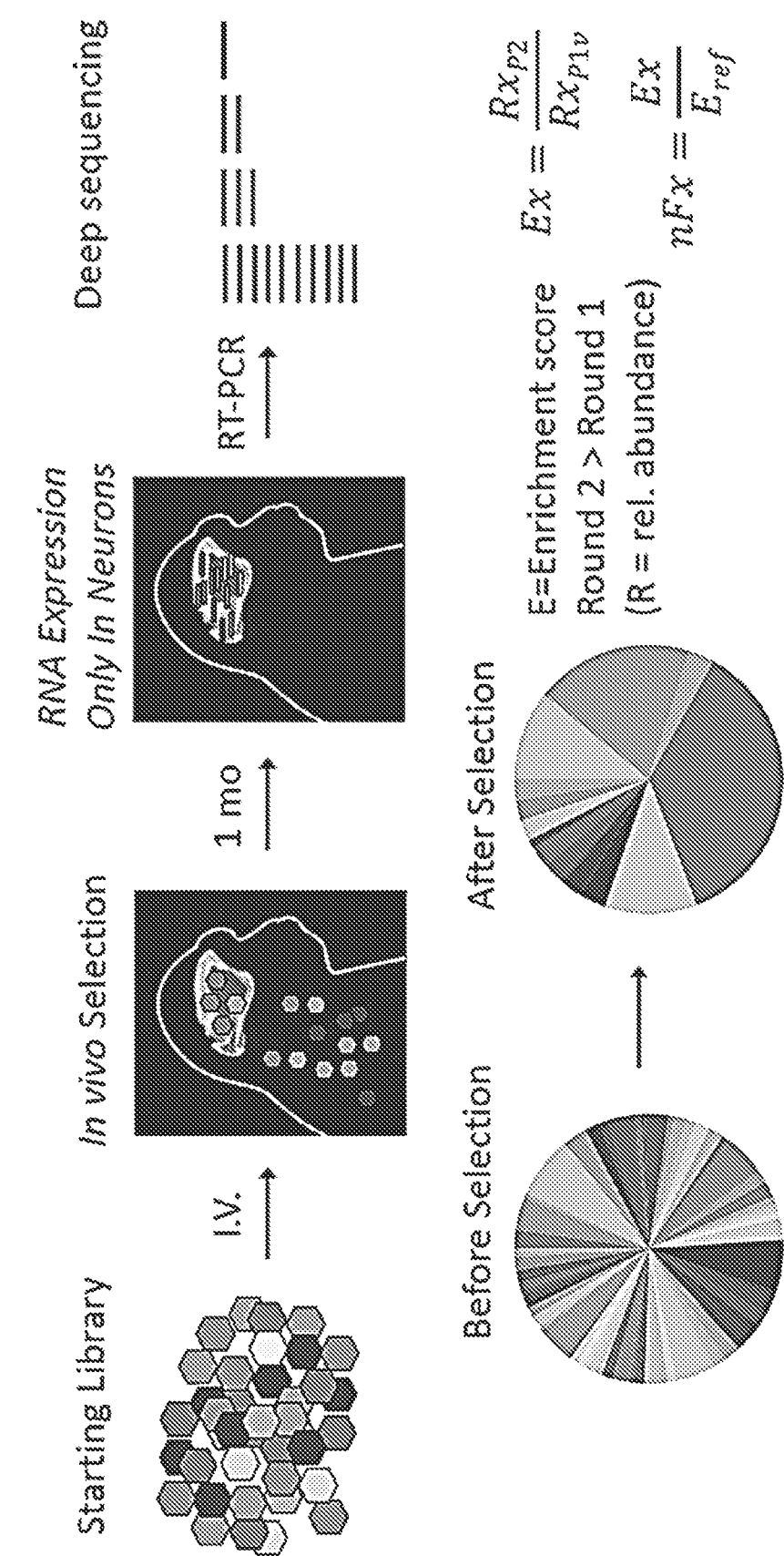
FIG. 3 provides a diagram of high-throughput screening by next-generation sequencing in non-human primate.

A TRACER™ based method as described in WO2020072683, the contents of which are herein incorporated by reference in their entirety, was adapted for use in non-human primates (NHP). An orthogonal evolution approach as exemplified in FIG. 2 (e.g., NHP and BMVEC) was combined with a high throughput screening by NGS in NHP as shown in FIG. 3. Briefly, AAV9/AAV5 starting libraries, driven by synapsin or GFAP promoters as shown in FIG. 4 were administered to non-human primate (NHP) intravenously for in vivo AAV selection (biopanning), performed iteratively. All libraries were injected intravenously at a dose of 1e14VG per animal (approximately 3e13 VG/kg). Orthogonally, biopanning was conducted in hBMVEC cells using the same starting libraries. In the second round of biopanning in NHP, only libraries driven by the synapsin promoter were used. After a period, (e.g., 1 month) RNA was extracted from nervous tissue, e.g., brain and spinal cord. Following RNA recovery and RT-PCR amplification, a systematic NGS enrichment analysis was performed and the targeting peptides shown in Table 1 identified. Capsids enrichment ratio, including calculating the ratio of, e.g., P2/P1 reads and comparison to a benchmark (e.g., AAV9) was evaluated.

Candidate library enrichment data in P3 NHP brain for the targeting peptides of Table 1, over benchmark AAV9, are shown in Table 7. Data are provided as fold enrichment. Fifty-one variants showed greater than 10-fold enrichment over AAV9. Variants with 0.0 enrichment over AAV9 are not included in Table 7.

TABLE 7

NHP NGS AAV9 ENRICHMENT

| Peptide Sequence | SEQ ID NO: | Fold enrichment over AAV9 |
|---|---|---|
| PLNGAVHLYA | 1725 | 473.7 |
| AQARDSPKGW | 1726 | 214 |
| LINGAVRDRP | 1727 | 134.4 |
| VQAFTHDSRG | 1728 | 88.6 |
| AQAYSTDVRM | 1729 | 84.8 |
| AQAYSTDVRI | 1730 | 83.8 |
| AQAFTAAERM | 1731 | 74.9 |
| AQTHLQIGVA | 1732 | 54.6 |
| AQSNAVISLA | 1733 | 51.6 |
| AQAYSTDERM | 1734 | 41.4 |
| AQAYSTDVRL | 1735 | 31.7 |
| AQATVSTLRM | 1736 | 31.5 |
| AQAYSTDERK | 1737 | 31.2 |

TABLE 7-continued

NHP NGS AAV9 ENRICHMENT

| Peptide Sequence | SEQ ID NO: | Fold enrichment over AAV9 |
|---|---|---|
| AQAYSTDMRM | 1738 | 30.4 |
| VVNGAVLHVA | 1739 | 29.8 |
| AQAYSTDVTM | 1740 | 29.7 |
| AQAHLQIGVA | 1741 | 23 |
| FLDPAVSSKA | 1742 | 22.6 |
| AQAYVSTLRM | 1743 | 21.9 |
| AQAQTGPPLK | 1744 | 20.1 |
| EQASRLPTPG | 1745 | 20 |
| AQASVSTMRM | 1746 | 19.7 |
| TDYSAVRLGA | 1747 | 18 |
| TQAYSTDVRM | 1748 | 17.9 |
| AQALPSNERL | 1749 | 17.4 |
| AQAYSTDVRT | 1750 | 16.4 |
| AQSSLPEMVA | 1751 | 16.2 |
| AQAGEQSTRL | 1752 | 16.1 |
| AQASNDVGRA | 1753 | 15.4 |
| AQATFTASEY | 1754 | 15.3 |
| AKAHAGTIYS | 1755 | 14.9 |
| AQARTIDQCC | 1756 | 14.8 |
| AQEYNSNPKA | 1757 | 14.5 |
| AQVVDNSTHA | 1758 | 14.5 |
| AQATLSVPLK | 1759 | 14.4 |
| AQIVMNSLKA | 1760 | 12.5 |
| AQATMSQTMA | 1761 | 12.5 |
| AQALTQDERW | 1762 | 12 |
| AQAQLSTLRP | 1763 | 11.6 |
| AQVVMGISVA | 1764 | 11.4 |
| AQAYTTDVRM | 1765 | 11.4 |
| AQHIDSMRPP | 1766 | 11.3 |
| AQASTGTLRL | 1767 | 11.1 |
| AQHRALDYYA | 1768 | 11 |
| AQARESPRGL | 1769 | 10.9 |
| AQALLAGTRV | 1770 | 10.7 |
| TKIQAVPWNA | 1771 | 10.7 |
| AQASLSSTRP | 1772 | 10.6 |
| AQAMGSRSDQ | 1773 | 10.4 |
| AQAAQGTYRG | 1774 | 10.3 |

TABLE 7-continued

| | | | NHP NGS AAV9 ENRICHMENT | | | |
|---|---|---| |---|---|---|

| Peptide Sequence | SEQ ID NO: | Fold enrichment over AAV9 |
|---|---|---|
| SQENAVFSKA | 1775 | 10.3 |
| AQALSLSTRP | 1776 | 9.8 |
| AQAAAGTLRD | 1777 | 9.7 |
| AQASRLPTPG | 1778 | 9.5 |
| AQAGSLSERG | 1779 | 9.5 |
| AQSKGDGFTA | 1780 | 9.4 |
| GAGTAVTATA | 1781 | 9.3 |
| AQAQGSSSVG | 1782 | 8.8 |
| AQAYSTDARM | 1783 | 8.8 |
| ERAHAVTGLA | 1784 | 8.5 |
| AQAYGLPKGP | 1785 | 8.4 |
| AQAYSTEVRM | 1786 | 8.4 |
| AQAGVSTALH | 1787 | 8.2 |
| AQSYSTDVRM | 1788 | 8.1 |
| AQPLMSHTDA | 1789 | 7.9 |
| AQAAALASRP | 1790 | 7.9 |
| AQAAITSTIS | 1791 | 7.8 |
| AQPANDGLRA | 1792 | 7.5 |
| AQDYSTDVRM | 1793 | 7.4 |
| AQATLGYSTA | 1794 | 7.4 |
| AQATLGTIRV | 1795 | 7.3 |
| AQAGASDMVH | 1796 | 7 |
| AQAVSGTVRS | 1797 | 6.9 |
| GGTLAVVSLA | 1798 | 6.9 |
| AQAYSADVRM | 1799 | 6.8 |
| AQAFAMPKGL | 1800 | 6.6 |
| AQALVSTSRP | 1801 | 6.6 |
| AQASFQQAST | 1802 | 6.6 |
| AQAMTGNDRS | 1803 | 6.3 |
| AQASTQSPPG | 1804 | 6.1 |
| NARSAVESLA | 1805 | 6.1 |
| AQITVSHTTA | 1806 | 6 |
| AQALAGYDKA | 1807 | 6 |
| AQSTSHDTRA | 1808 | 5.9 |
| AQAIQDRTVV | 1809 | 5.8 |
| AQSKTTLTLA | 1810 | 5.7 |
| AQASMGTVRL | 1811 | 5.7 |

TABLE 7-continued

| | | | NHP NGS AAV9 ENRICHMENT | | | |
|---|---|---| |---|---|---|

| Peptide Sequence | SEQ ID NO: | Fold enrichment over AAV9 |
|---|---|---|
| AQHSDTLTRA | 1812 | 5.5 |
| AQKEMYTSVA | 1813 | 5.5 |
| AQASPSQPLL | 1814 | 5.4 |
| AQAYAGTIYS | 1815 | 5.3 |
| AQARSLEPVI | 1816 | 5.3 |
| TQAGVSTAVH | 1817 | 5.2 |
| AQNTLSLSLA | 1818 | 5.2 |
| AQAYVSSVKM | 1819 | 5.2 |
| AQAATSPRLG | 1820 | 5.1 |
| GYLTAVQPQA | 1821 | 5 |
| LNNLAVGMTA | 1822 | 5 |
| AQTVSVHVRA | 1823 | 5 |
| AQINGLVTTA | 1824 | 4.9 |
| AQAAITTTIS | 1825 | 4.8 |
| AQASTFVTTI | 1826 | 4.7 |
| AQALYDNVPL | 1827 | 4.6 |
| AQAAAGTWKG | 1828 | 4.6 |
| AQATTGTLRS | 1829 | 4.6 |
| GQYAADSSYA | 1830 | 4.5 |
| AQAGIATVRT | 1831 | 4.5 |
| AQALGHELRA | 1832 | 4.5 |
| AQAREAIPQG | 1833 | 4.4 |
| AQAMSGTLRM | 1834 | 4.4 |
| AQAVDRVRPP | 1835 | 4.4 |
| AQAPVNNDRG | 1836 | 4.3 |
| AQAQQVAGTM | 1837 | 4.3 |
| AQAEPRDTRA | 1838 | 4.3 |
| AQRLSEQGVA | 1839 | 4.2 |
| AQASEGIQLS | 1840 | 4.1 |
| AQRQGPDPLA | 1841 | 4.1 |
| AQVTLGSAKA | 1842 | 4.1 |
| AQAGASLGLA | 1843 | 4 |
| AQAFTQDERW | 1844 | 4 |
| AQASQTTVRS | 1845 | 4 |
| AQARVSSNGV | 1846 | 3.9 |
| AQGPLSGLRA | 1847 | 3.9 |
| AQAYGGQSLG | 1848 | 3.9 |

TABLE 7-continued

NHP NGS AAV9 ENRICHMENT

| Peptide Sequence | SEQ ID NO: | Fold enrichment over AAV9 |
|---|---|---|
| AQANLGTVRQ | 1849 | 3.9 |
| AQARSDTRGL | 1850 | 3.8 |
| AQAGSDGPRL | 1851 | 3.8 |
| TDGAAVVMRA | 1852 | 3.8 |
| SGITAVPLHA | 1853 | 3.8 |
| AQAAAVGHLP | 1854 | 3.7 |
| AQRVEPKWIA | 1855 | 3.7 |
| AQAVASSPYA | 1856 | 3.7 |
| TQYGAVEGQD | 1857 | 3.7 |
| AQAKSHTLEG | 1858 | 3.6 |
| AQTHLQIVVA | 1859 | 3.6 |
| AQKNEHGMLA | 1860 | 3.6 |
| AQITVSHTRA | 1861 | 3.6 |
| AQARLAPKGL | 1862 | 3.6 |
| KTPGAVSTTA | 1863 | 3.6 |
| AQAFSGTIKS | 1864 | 3.6 |
| PLNGAVNLYA | 1865 | 3.5 |
| AQALTQDERC | 1866 | 3.5 |
| AQATAQVQRS | 1867 | 3.4 |
| AQTPALINLA | 1868 | 3.4 |
| AQASDRSPLL | 1869 | 3.4 |
| AQITVSHTMA | 1870 | 3.3 |
| AQATGTHLMG | 1871 | 3.3 |
| LDGGAVVVTA | 1872 | 3.3 |
| LTNGAVRDRA | 1873 | 3.2 |
| AQARGSDLRD | 1874 | 3.2 |
| AQATFGTQRI | 1875 | 3.2 |
| AQALPQTNRP | 1876 | 3.1 |
| AQARSNDPVL | 1877 | 3.1 |
| AQAYLAVONG | 1878 | 3.1 |
| AQATQSTLRP | 1879 | 3.1 |
| AQALGGFGPQ | 1880 | 3.1 |
| LVGQAVGSRA | 1881 | 3.1 |
| AQSIANVVVA | 1882 | 3 |
| AQASPSVSRP | 1883 | 3 |
| AQTVVVSTTA | 1884 | 3 |
| VKEQAVSVMA | 1885 | 3 |

TABLE 7-continued

NHP NGS AAV9 ENRICHMENT

| Peptide Sequence | SEQ ID NO: | Fold enrichment over AAV9 |
|---|---|---|
| AQQATGTFRA | 1886 | 3 |
| AQAQGSSSGG | 1887 | 3 |
| AQAHAVGPQG | 1888 | 3 |
| AQRLETKETA | 1889 | 3 |
| AQLAQGIGVA | 1890 | 3 |
| AQAVQSSFTI | 1891 | 3 |
| AQATYTASEY | 1892 | 2.9 |
| AQTSSQNLKA | 1893 | 2.9 |
| AQLVPSVAMA | 1894 | 2.9 |
| AQASPSAFAG | 1895 | 2.9 |
| AQALALVSAS | 1896 | 2.9 |
| AQASVGTTYT | 1897 | 2.9 |
| AQARVSSSGT | 1898 | 2.9 |
| NSMGAVLGAA | 1899 | 2.9 |
| AQHTDTLTRA | 1900 | 2.9 |
| AQPNLQPRGA | 1901 | 2.8 |
| AQADRHSSIV | 1902 | 2.8 |
| SPSVAVPSQA | 1903 | 2.8 |
| AQPGIVSTIA | 1904 | 2.8 |
| AQAQHSVGLP | 1905 | 2.7 |
| AQTNSGAILA | 1906 | 2.7 |
| AQDSYDVGRA | 1907 | 2.7 |
| EQAQGSSSVG | 1908 | 2.7 |
| AQAGVSTAVQ | 1909 | 2.7 |
| AQARDMLPLQ | 1910 | 2.7 |
| AQAMVGTLRG | 1911 | 2.7 |
| AQPNVVSTLA | 1912 | 2.7 |
| AQAGHVVTSD | 1913 | 2.7 |
| AQAYTTDERM | 1914 | 2.7 |
| TAVSAVQVMA | 1915 | 2.6 |
| AQAAAGTLRV | 1916 | 2.6 |
| VSNEAVHARA | 1917 | 2.6 |
| AQVLPQSLSA | 1918 | 2.6 |
| AQASVSTLRM | 1919 | 2.6 |
| AQAGLLLSVA | 1920 | 2.5 |
| AQANLVTGPL | 1921 | 2.5 |
| AQASQHSSMA | 1922 | 2.5 |

TABLE 7-continued

| | | | |
|---|---|---|---|
| NHP NGS AAV9 ENRICHMENT | | | |
| Peptide Sequence | SEQ ID NO: | Fold enrichment over AAV9 | |
| GYSSAVSSVA | 1923 | 2.5 | |
| AQVGVSPAVA | 1924 | 2.5 | |
| DGTLAVPFKA | 1925 | 2.5 | |
| AQAPPTSTAM | 1926 | 2.5 | |
| AQATPANVRG | 1927 | 2.5 | |
| AQAGSSNFLS | 1928 | 2.5 | |
| AQLLAQDIRA | 1929 | 2.5 | |
| AQPSSDGYRA | 1930 | 2.5 | |
| AQALIGTLRT | 1931 | 2.5 | |
| SVHGAVGILA | 1932 | 2.5 | |
| AQPYVVSGAA | 1933 | 2.4 | |
| AQWTHNITAA | 1934 | 2.4 | |
| PTNAAVRTNA | 1935 | 2.4 | |
| AHAYSTDVRM | 1936 | 2.4 | |
| PLAAAVGMKA | 1937 | 2.4 | |
| AQARDNSVML | 1938 | 2.4 | |
| AQAQFPRNGG | 1939 | 2.4 | |
| GALNAVNGVA | 1940 | 2.4 | |
| AQASHQQGVP | 1941 | 2.4 | |
| SYQSAVVPQA | 1942 | 2.3 | |
| AQSIMGTIRA | 1943 | 2.3 | |
| AQAYVSQAQG | 1944 | 2.3 | |
| AQATGNQAHF | 1945 | 2.3 | |
| AQVTVGTPIA | 1946 | 2.3 | |
| AQAQTSTFRG | 1947 | 2.3 | |
| SVHMAVTVSA | 1948 | 2.2 | |
| AQAQSTLNLG | 1949 | 2.2 | |
| AQDQTGPPLK | 1950 | 2.2 | |
| HLAHAVSTAA | 1951 | 2.2 | |
| AQALARDSSF | 1952 | 2.2 | |
| AQLLSGTLKA | 1953 | 2.2 | |
| AQASLLPTPG | 1954 | 2.2 | |
| AQPMAGQSTA | 1955 | 2.2 | |
| AQARSLEPDI | 1956 | 2.2 | |
| AQFVTGNQDA | 1957 | 2.2 | |
| AQATFKTSVP | 1958 | 2.1 | |
| LNARAVEGPA | 1959 | 2.1 | |

TABLE 7-continued

| | | |
|---|---|---|
| NHP NGS AAV9 ENRICHMENT | | |
| Peptide Sequence | SEQ ID NO: | Fold enrichment over AAV9 |
| AQALPNSGRP | 1960 | 2.1 |
| AQALNGSPEA | 1961 | 2.1 |
| AQATSLHPLP | 1962 | 2 |
| AQAVQPPLKN | 1963 | 2 |
| AQAMLSGTRI | 1964 | 2 |
| AQHVDLASKA | 1965 | 2 |
| AQASFATMRP | 1966 | 2 |
| AQAMPLNARS | 1967 | 2 |
| AQALVGQMRG | 1968 | 2 |
| VVNGAVLHLA | 1969 | 2 |
| AQAQTAPPLK | 1970 | 2 |
| AQGHGDLHRA | 1971 | 2 |
| AQAADRSPVH | 1972 | 2 |
| GALNAVTGVA | 1973 | 2 |
| AQAERMASLG | 1974 | 1.9 |
| AQAPPTTTRL | 1975 | 1.9 |
| AQAAVGQTLA | 1976 | 1.9 |
| AQSLGTGMHA | 1977 | 1.9 |
| AQSLGSPALA | 1978 | 1.9 |
| AQASVSVTRP | 1979 | 1.9 |
| AQATMSHTMA | 1980 | 1.9 |
| AQAVQSLTVG | 1981 | 1.9 |
| AQSQTGTYRA | 1982 | 1.9 |
| AQSLASVYAA | 1983 | 1.9 |
| STKLAVHEQA | 1984 | 1.9 |
| AQSHLFPTPA | 1985 | 1.9 |
| AQGTWSSSEA | 1986 | 1.9 |
| AQTPQGLTKA | 1987 | 1.9 |
| AQVSLGTQYA | 1988 | 1.9 |
| AQDSRLPTPG | 1989 | 1.8 |
| ASIQAVGVKA | 1990 | 1.8 |
| AQATMSEQRL | 1991 | 1.8 |
| TAQAAVQGMA | 1992 | 1.8 |
| AQAFNAAERM | 1993 | 1.8 |
| AQINFLSGVA | 1994 | 1.8 |
| PQHLAVSSEA | 1995 | 1.8 |
| AQALGNFPAV | 1996 | 1.8 |

TABLE 7-continued

| | | | |
|---|---|---|---|
| | NHP NGS AAV9 ENRICHMENT | | |
| Peptide Sequence | SEQ ID NO: | Fold enrichment over AAV9 | |
| AQANASTVRV | 1997 | 1.8 | |
| AQRIVDLTTA | 1998 | 1.8 | |
| VRQVAVEGVA | 1999 | 1.8 | |
| AQAPASSQKL | 2000 | 1.8 | |
| AQQIDSMRPA | 2001 | 1.7 | |
| AQAHGTSSLF | 2002 | 1.7 | |
| AQVNSGIALA | 2003 | 1.7 | |
| AQLHLAETRA | 2004 | 1.7 | |
| AQALTHDERW | 2005 | 1.7 | |
| NTVRAVIMEA | 2006 | 1.7 | |
| AQAYVAGSRP | 2007 | 1.7 | |
| AQDRAFVVSA | 2008 | 1.7 | |
| AQAQEKQVFS | 2009 | 1.7 | |
| AQACVSTAVH | 2010 | 1.7 | |
| AQAFTHDSRG | 2011 | 1.7 | |
| AQASHQGTVG | 2012 | 1.7 | |
| AQAVLVTEQG | 2013 | 1.7 | |
| AQAVVSTAVH | 2014 | 1.7 | |
| AQATSRETKG | 2015 | 1.7 | |
| YQQPAVSSRA | 2016 | 1.6 | |
| AQANMGLSLS | 2017 | 1.6 | |
| AQWTSSMSEA | 2018 | 1.6 | |
| AQASISIMST | 2019 | 1.6 | |
| AQASVAPLTC | 2020 | 1.6 | |
| AQLVTVEKQA | 2021 | 1.6 | |
| AQAATAGEKL | 2022 | 1.6 | |
| AQALSHGPGG | 2023 | 1.6 | |
| AQSNAHIEIA | 2024 | 1.6 | |
| AQARSSSTGI | 2025 | 1.6 | |
| AQAVGGDVTR | 2026 | 1.6 | |
| AQAPRTVYQG | 2027 | 1.6 | |
| AQALHNLGPA | 2028 | 1.6 | |
| VRMGAVSDNA | 2029 | 1.6 | |
| AQAFRTSQFT | 2030 | 1.6 | |
| AQSSATMQRA | 2031 | 1.5 | |
| AQTLAETYRA | 2032 | 1.5 | |
| AQANGSIVLN | 2033 | 1.5 | |

TABLE 7-continued

| | | |
|---|---|---|
| NHP NGS AAV9 ENRICHMENT | | |
| Peptide Sequence | SEQ ID NO: | Fold enrichment over AAV9 |
| AQARVADQLP | 2034 | 1.5 |
| AQAVKQGLYE | 2035 | 1.5 |
| AQAFSDGLKS | 2036 | 1.5 |
| AQVSVTPVKA | 2037 | 1.5 |
| VNGRAVSMMA | 2038 | 1.5 |
| SLVGAVAQMA | 2039 | 1.5 |
| AQARVSPVGL | 2040 | 1.5 |
| AQSNTTLTLA | 2041 | 1.5 |
| AQTSTEHLRA | 2042 | 1.5 |
| AQAGMGINLP | 2043 | 1.5 |
| AQANAHSLTL | 2044 | 1.5 |
| AQARFTTTEM | 2045 | 1.5 |
| AQLGYQEVKA | 2046 | 1.4 |
| AQAGQHASVF | 2047 | 1.4 |
| AQATGSNPRG | 2048 | 1.4 |
| AQAPVSPSIP | 2049 | 1.4 |
| AQTTLGVGTA | 2050 | 1.4 |
| AQASHLVSLA | 2051 | 1.4 |
| AQAPLTGLSV | 2052 | 1.4 |
| AQVSTSTLRA | 2053 | 1.4 |
| AQVQLGTLKA | 2054 | 1.4 |
| AQAHVSVSER | 2055 | 1.4 |
| AQLLLSGQTA | 2056 | 1.4 |
| TTSSAVLTPA | 2057 | 1.4 |
| AQFGADTVNA | 2058 | 1.4 |
| AQTFSSDNLA | 2059 | 1.4 |
| AQIHPANSRA | 2060 | 1.4 |
| AQSIGQFPVA | 2061 | 1.3 |
| AQVISPENLA | 2062 | 1.3 |
| AQALSAISAT | 2063 | 1.3 |
| AQAGVSASQM | 2064 | 1.3 |
| AQASTKTPLP | 2065 | 1.3 |
| AQAPPSTTAM | 2066 | 1.3 |
| AQAVSSDRMH | 2067 | 1.3 |
| AQAGSVTMRL | 2068 | 1.3 |
| AQAVLLGGAV | 2069 | 1.3 |
| AQAQRDMVTT | 2070 | 1.3 |


TABLE 7-continued

| NHP NGS AAV9 ENRICHMENT | | |
| --- | --- | --- |
| Peptide Sequence | SEQ ID NO: | Fold enrichment over AAV9 |
| AQAHHGSSLG | 2071 | 1.3 |
| VLSSAVGQRA | 2072 | 1.3 |
| AQAAGSVLLG | 2073 | 1.3 |
| AQAYPTDVRM | 2074 | 1.3 |
| AQWSRDAQSA | 2075 | 1.3 |
| AQQGLDMGRA | 2076 | 1.3 |
| AQAAQNHALV | 2077 | 1.3 |
| AQRSQIVEVA | 2078 | 1.3 |
| AQMSDVSGRA | 2079 | 1.3 |
| AKALTQDERW | 2080 | 1.3 |
| AQAVSSSTLT | 2081 | 1.3 |
| AQPSRLPTPG | 2082 | 1.3 |
| RTSTAVLDFA | 2083 | 1.3 |
| AQDLSSSIRA | 2084 | 1.3 |
| AQLLDGLTSA | 2085 | 1.3 |
| AQALIGLSKP | 2086 | 1.3 |
| AQASGTVRPP | 2087 | 1.2 |
| AQLLDTRYKA | 2088 | 1.2 |
| AQAPNTSFTA | 2089 | 1.2 |
| AQTHLQIGVD | 2090 | 1.2 |
| AQRLDTSQVA | 2091 | 1.2 |
| AQRTQDTLSA | 2092 | 1.2 |
| AQADIQSHAL | 2093 | 1.2 |
| PNMNAVGIKA | 2094 | 1.2 |
| AQAGVSTAVH | 2095 | 1.2 |
| AQASGKTFIG | 2096 | 1.2 |
| AQAGVQSTRL | 2097 | 1.2 |
| AQAQGAYPLV | 2098 | 1.2 |
| AQPYSTDVRM | 2099 | 1.2 |
| SSSVAVVTLA | 2100 | 1.2 |
| AQTYNGLNKA | 2101 | 1.2 |
| AQASVSKLRM | 2102 | 1.2 |
| AQRGSENEKA | 2103 | 1.2 |
| PITNAVLKTA | 2104 | 1.2 |
| TNSYAVSSPA | 2105 | 1.2 |
| PYQTAVAGAA | 2106 | 1.1 |
| GPALAVLGRA | 2107 | 1.1 |

TABLE 7-continued

| NHP NGS AAV9 ENRICHMENT | | |
| --- | --- | --- |
| Peptide Sequence | SEQ ID NO: | Fold enrichment over AAV9 |
| LSISAVPAKA | 2108 | 1.1 |
| AQTLGPLPHA | 2109 | 1.1 |
| AQAQQPLAHV | 2110 | 1.1 |
| AQTDGAWSKA | 2111 | 1.1 |
| AQALSGPPSI | 2112 | 1.1 |
| AQASSPSTRG | 2113 | 1.1 |
| AQASLASNRP | 2114 | 1.1 |
| AQNMALSTVA | 2115 | 1.1 |
| AQHSDTMTRA | 2116 | 1.1 |
| AQAMPRYPPL | 2117 | 1.1 |
| AQHIDSMSPA | 2118 | 1.1 |
| AQALPGTSRV | 2119 | 1.1 |
| AQAKSTQDVQ | 2120 | 1.1 |
| AQPLVSASKA | 2121 | 1.1 |
| AQAMSGTLRK | 2122 | 1.1 |
| AQTLILGAHA | 2123 | 1.1 |
| AQAGQARSQG | 2124 | 1.1 |
| AQRKDLSLVA | 2125 | 1.1 |
| AQALSAPMSL | 2126 | 1.1 |
| TNSLAVGMRA | 2127 | 1.1 |
| AQAPIGTVRP | 2128 | 1.1 |
| FIQAAVSSSA | 2129 | 1.1 |
| AQAEKPTHLL | 2130 | 1.1 |
| AQALSGDTTR | 2131 | 1.1 |
| AQAYIASGGT | 2132 | 1.1 |
| QLNQAVGTLA | 2133 | 1.1 |
| AQASGALDRP | 2134 | 1.1 |
| AQAQDTALRA | 2135 | 1.1 |
| AQAQAGMARG | 2136 | 1.1 |
| AQAQGSSAVG | 2137 | 1.1 |
| AQLLRDIGPA | 2138 | 1.1 |
| VDRGAVTQMA | 2139 | 1.1 |
| AQAVNVSKGS | 2140 | 1.1 |
| SVNTAVESLA | 2141 | 1.1 |
| AQARLPHTSS | 2142 | 1.1 |
| AQRNGSEVVA | 2143 | 1.1 |
| AQATDRVDRP | 2144 | 1.1 |

TABLE 7-continued

NHP NGS AAV9 ENRICHMENT

| Peptide Sequence | SEQ ID NO: | Fold enrichment over AAV9 |
|---|---|---|
| AQASLSRERT | 2145 | 1.1 |
| AQAYSTHVRM | 2146 | 1.1 |
| AQHLSAGPTA | 2147 | 1.1 |
| LNGGAVSLRA | 2148 | 1 |
| AQAYGVSSVT | 2149 | 1 |
| AQFGSAVQLA | 2150 | 1 |
| AQAPPTSTRL | 2151 | 1 |
| AQVSTNWPKA | 2152 | 1 |
| AQTSTDLSRA | 2153 | 1 |
| AQAHSTDVRM | 2154 | 1 |
| AQATLTGHVS | 2155 | 1 |
| AQATTQGALT | 2156 | 1 |
| AQAAKASDRT | 2157 | 1 |
| AQGNEHGGRA | 2158 | 1 |
| AQALSTSLLL | 2159 | 1 |
| AQASLGSTYL | 2160 | 1 |
| AQAFSTVGAV | 2161 | 1 |
| AQLNGLVTTA | 2162 | 1 |
| AQASVRTLRM | 2163 | 1 |
| AQATMSRPWQ | 2164 | 1 |
| AQSSLPAMVA | 2165 | 1 |
| RETVAVGQYA | 2166 | 1 |
| AQAFGSEGRS | 2167 | 1 |
| SSGTAVEHRA | 2168 | 1 |
| FGTNAVIPRA | 2169 | 1 |
| AQAGQARSLG | 2170 | 1 |
| AQSISSDNMA | 2171 | 1 |
| AQMNGLTGKA | 2172 | 1 |
| AQQNGKQHLA | 2173 | 1 |
| AQHIDSIRPA | 2174 | 1 |
| AQAADRLSTL | 2175 | 1 |
| AQFGLKDIRA | 2176 | 1 |
| AQAHQGGATL | 2177 | 1 |
| AQATYNSPKP | 2178 | 1 |
| AQAMSNMLRN | 2179 | 0.9 |
| VPISAVMSTA | 2180 | 0.9 |
| AQHSLGNTVA | 2181 | 0.9 |

TABLE 7-continued

NHP NGS AAV9 ENRICHMENT

| Peptide Sequence | SEQ ID NO: | Fold enrichment over AAV9 |
|---|---|---|
| AQATSALSRL | 2182 | 0.9 |
| AQADRQTFPV | 2183 | 0.9 |
| AQAVNSMSIG | 2184 | 0.9 |
| AQALAIVSKN | 2185 | 0.9 |
| AQGQLQERFA | 2186 | 0.9 |
| AQFNGASAHA | 2187 | 0.9 |
| AQLGGQSPVA | 2188 | 0.9 |
| AQANGAYTDN | 2189 | 0.9 |
| AQNLSSSEPA | 2190 | 0.9 |
| AQSAIVLTTA | 2191 | 0.9 |
| ITRSAVPDVA | 2192 | 0.9 |
| GALKAVTGVA | 2193 | 0.9 |
| AQAVGQDYLR | 2194 | 0.9 |
| AQVTLNTPLA | 2195 | 0.9 |
| AQALTQDDRW | 2196 | 0.9 |
| AQAYSTNVRM | 2197 | 0.9 |
| AQAVAAPASL | 2198 | 0.9 |
| AQANPVSIMS | 2199 | 0.9 |
| AQASMQAVKD | 2200 | 0.9 |
| AQAVGGHSVA | 2201 | 0.9 |
| AQAVAASTRL | 2202 | 0.9 |
| GGTHAVSSFA | 2203 | 0.9 |
| AQAADSSGFR | 2204 | 0.9 |
| AQQSHVPQTA | 2205 | 0.9 |
| AQARVGNTNV | 2206 | 0.9 |
| AQTVSYSDLA | 2207 | 0.9 |
| AQAEHGLARS | 2208 | 0.9 |
| AQASNYPVAA | 2209 | 0.9 |
| VLLSAVGMAA | 2210 | 0.9 |
| AQALSGQNRG | 2211 | 0.9 |
| AQAWGQETRQ | 2212 | 0.9 |
| AQGYSTDVRM | 2213 | 0.9 |
| AQAGSVMSRE | 2214 | 0.8 |
| AQAGSLSARG | 2215 | 0.8 |
| AQATALAPKS | 2216 | 0.8 |
| AQAIRQNGSS | 2217 | 0.8 |
| AQLQDNLQLA | 2218 | 0.8 |

TABLE 7-continued

| Peptide Sequence | SEQ ID NO: | Fold enrichment over AAV9 |
|---|---|---|
| NHP NGS AAV9 ENRICHMENT | | |
| AKAYSTDVRM | 2219 | 0.8 |
| AQSVDRTLLA | 2220 | 0.8 |
| AQAGQNSRLP | 2221 | 0.8 |
| AQTNLQPRGA | 2222 | 0.8 |
| PNTIAVGQRA | 2223 | 0.8 |
| AQAHATLSLS | 2224 | 0.8 |
| NHLRAVGSPA | 2225 | 0.8 |
| AQETDRNLRA | 2226 | 0.8 |
| AQARAETSGS | 2227 | 0.8 |
| AQHRELDSYA | 2228 | 0.8 |
| AQRHTSDVLA | 2229 | 0.8 |
| AQVGQTSSWA | 2230 | 0.8 |
| AQANSAALLM | 2231 | 0.8 |
| AQAIIERTAT | 2232 | 0.8 |
| AQSSRYEEKA | 2233 | 0.8 |
| QATGAVNPRA | 2234 | 0.8 |
| AQASYSVSVG | 2235 | 0.8 |
| AQQGHTVNNA | 2236 | 0.8 |
| AQASLPISTR | 2237 | 0.8 |
| AQHIDSMRPT | 2238 | 0.8 |
| AQAQDTENMR | 2239 | 0.8 |
| RTGAAVTGAA | 2240 | 0.8 |
| AQASSVRGMG | 2241 | 0.8 |
| AQPGIESTIA | 2242 | 0.8 |
| AQHVDLDSKA | 2243 | 0.8 |
| AQATTVPALG | 2244 | 0.8 |
| AQVNPTPQKA | 2245 | 0.8 |
| AQAGYISSAS | 2246 | 0.8 |
| AQTLILGDPA | 2247 | 0.8 |
| AQAASGLTMM | 2248 | 0.8 |
| AQALERPPSG | 2249 | 0.8 |
| TTYDAVHSKA | 2250 | 0.8 |
| AQAMLDSANG | 2251 | 0.7 |
| AQAMHQTDKF | 2252 | 0.7 |
| KSTVAVQSVA | 2253 | 0.7 |
| AQATAGTLIG | 2254 | 0.7 |
| GLKSAVTHVA | 2255 | 0.7 |

TABLE 7-continued

| Peptide Sequence | SEQ ID NO: | Fold enrichment over AAV9 |
|---|---|---|
| NHP NGS AAV9 ENRICHMENT | | |
| AQAHSAYQGA | 2256 | 0.7 |
| AQSFSSDNLA | 2257 | 0.7 |
| AQLNMAASVA | 2258 | 0.7 |
| AQFSQAYNAA | 2259 | 0.7 |
| AQHLTAGLRA | 2260 | 0.7 |
| AQAHTVSPHL | 2261 | 0.7 |
| GILGAVLPRA | 2262 | 0.7 |
| AQHNSSSLLA | 2263 | 0.7 |
| AQAPQVAGTM | 2264 | 0.7 |
| AQHQDSRPMA | 2265 | 0.7 |
| AQRFQETGLA | 2266 | 0.7 |
| AQLTVSHTRA | 2267 | 0.7 |
| AQANLRTTMG | 2268 | 0.7 |
| AQAGLRDPRM | 2269 | 0.7 |
| AQHLLHGTAA | 2270 | 0.7 |
| RNQGAVASLA | 2271 | 0.7 |
| AQAGSSSVTW | 2272 | 0.7 |
| AQPHLQIGVA | 2273 | 0.7 |
| AQANSGAVLA | 2274 | 0.7 |
| AQLLGDAVKA | 2275 | 0.7 |
| SSGNAVSSLA | 2276 | 0.7 |
| AQVSVTMALA | 2277 | 0.7 |
| AQYHTRGFAA | 2278 | 0.7 |
| AQSTTKGTLA | 2279 | 0.7 |
| AQAQPPSARY | 2280 | 0.7 |
| AQAGLQGTAA | 2281 | 0.7 |
| AQPQGSSTFA | 2282 | 0.7 |
| TQYRAVEGQA | 2283 | 0.7 |
| AQAISTQLAG | 2284 | 0.7 |
| AQLGSNISHA | 2285 | 0.7 |
| AQTGLSGTVA | 2286 | 0.7 |
| AQRVDSSGRA | 2287 | 0.7 |
| AQAGLALNPN | 2288 | 0.7 |
| AQFYSDNSLA | 2289 | 0.7 |
| AQAVGAPQRL | 2290 | 0.7 |
| AQASYDDGRA | 2291 | 0.7 |
| SSFAAVATAA | 2292 | 0.6 |

TABLE 7-continued

| | NHP NGS AAV9 ENRICHMENT | |
|---|---|---|
| Peptide Sequence | SEQ ID NO: | Fold enrichment over AAV9 |
| AQSTLSMPLA | 2293 | 0.6 |
| AQASLHAPRP | 2294 | 0.6 |
| HAVAAVSYPA | 2295 | 0.6 |
| AQTSPVMVQA | 2296 | 0.6 |
| AQADITSTIS | 2297 | 0.6 |
| AQAAGVAMLY | 2298 | 0.6 |
| AQASVSTLRK | 2299 | 0.6 |
| MDLKAVSSRA | 2300 | 0.6 |
| AQASLSTLRM | 2301 | 0.6 |
| AQPRSPLPMA | 2302 | 0.6 |
| GQYADVSSYA | 2303 | 0.6 |
| LVGGAVVVPA | 2304 | 0.6 |
| AQAQSARPLA | 2305 | 0.6 |
| AQSLHPSTTA | 2306 | 0.6 |
| AQFQTDLSRA | 2307 | 0.6 |
| RTELAVGLSA | 2308 | 0.6 |
| AQVVDNSPLA | 2309 | 0.6 |
| AQAVSSDSMH | 2310 | 0.6 |
| AQASPALHTL | 2311 | 0.6 |
| GQYAAVASYA | 2312 | 0.6 |
| AQLWQSRVDA | 2313 | 0.6 |
| GTFSAVQSTA | 2314 | 0.6 |
| AQAILSTIEV | 2315 | 0.6 |
| AQNVVSTLRA | 2316 | 0.6 |
| AQAMLAVSPG | 2317 | 0.6 |
| AQATDSLVAR | 2318 | 0.6 |
| AQASPQSSHG | 2319 | 0.6 |
| AQATPVHDTL | 2320 | 0.6 |
| LRSSAVGTAA | 2321 | 0.6 |
| MGRGAVLDTA | 2322 | 0.6 |
| AQSHLIPTPA | 2323 | 0.6 |
| AQAVLKAPIN | 2324 | 0.6 |
| AQKIAPAFLA | 2325 | 0.6 |
| AGNVAVLPHA | 2326 | 0.6 |
| AQSLGTGLHD | 2327 | 0.6 |
| AQAHAMSSRP | 2328 | 0.6 |
| AQQGKFDMRA | 2329 | 0.6 |

TABLE 7-continued

| | NHP NGS AAV9 ENRICHMENT | |
|---|---|---|
| Peptide Sequence | SEQ ID NO: | Fold enrichment over AAV9 |
| AQALSGDGTR | 2330 | 0.6 |
| AQTHLQIAVA | 2331 | 0.6 |
| AQRTQGSSWA | 2332 | 0.6 |
| AIGSAVDLRA | 2333 | 0.6 |
| AQAQLASGTL | 2334 | 0.6 |
| AQALVSAGAL | 2335 | 0.6 |
| AQATESVPLK | 2336 | 0.6 |
| AQVYNSNPKA | 2337 | 0.6 |
| AQRTTYPSSA | 2338 | 0.6 |
| AQAMFQQAST | 2339 | 0.6 |
| AQPDALVIRA | 2340 | 0.6 |
| AQARDISMRG | 2341 | 0.6 |
| AQMSFGSTLA | 2342 | 0.6 |
| RLLSAVDQQA | 2343 | 0.6 |
| AQTTRSIENA | 2344 | 0.6 |
| AQVSDFSSRA | 2345 | 0.5 |
| AQAHSRVNTE | 2346 | 0.5 |
| AQAYSTDLRM | 2347 | 0.5 |
| AQALNGSAYS | 2348 | 0.5 |
| TQYGAVEAQA | 2349 | 0.5 |
| AQAHAGTIYS | 2350 | 0.5 |
| AQDPHSMRPA | 2351 | 0.5 |
| AQASANIHSS | 2352 | 0.5 |
| AQASLQAVSM | 2353 | 0.5 |
| AQSSHPAMVA | 2354 | 0.5 |
| AQANLQPRGA | 2355 | 0.5 |
| AQAVGSSPRG | 2356 | 0.5 |
| AQTSAPSALA | 2357 | 0.5 |
| AQAVQLQNRG | 2358 | 0.5 |
| AQAQGSGMVS | 2359 | 0.5 |
| AQAYPSSKSG | 2360 | 0.5 |
| AQAVSDYGRG | 2361 | 0.5 |
| AQMSLGATRA | 2362 | 0.5 |
| AQAFLNSASA | 2363 | 0.5 |
| AQALPSNARL | 2364 | 0.5 |
| AQANVSVRRE | 2365 | 0.5 |
| AQAGASVMVH | 2366 | 0.5 |

TABLE 7-continued

| | | | |
|---|---|---|---|
| NHP NGS AAV9 ENRICHMENT | | | |
| Peptide Sequence | SEQ ID NO: | Fold enrichment over AAV9 | |
| AQSLAKDQSA | 2367 | 0.5 | |
| AQILSALSSA | 2368 | 0.5 | |
| AQSVHLSLAA | 2369 | 0.5 | |
| AQALSASSFL | 2370 | 0.5 | |
| AQTSQLNQTA | 2371 | 0.5 | |
| AQSNLFPTPA | 2372 | 0.5 | |
| AQAHGRSFDT | 2373 | 0.5 | |
| AQLGSNTILA | 2374 | 0.5 | |
| AQASMNSAKA | 2375 | 0.5 | |
| AQRQAVEQSA | 2376 | 0.5 | |
| AQASTGTLRH | 2377 | 0.5 | |
| AQGPTYPNVA | 2378 | 0.5 | |
| AQAGPTTSKA | 2379 | 0.5 | |
| AQATTYRGMA | 2380 | 0.5 | |
| AQVTNRGMPA | 2381 | 0.5 | |
| AQAISGQAAW | 2382 | 0.5 | |
| AQAFRGEDKG | 2383 | 0.5 | |
| AQQSMPRFVA | 2384 | 0.5 | |
| AQAGVKSTRL | 2385 | 0.5 | |
| AQATGSILLA | 2386 | 0.5 | |
| AQASGHSSFS | 2387 | 0.5 | |
| AQTANDGLRA | 2388 | 0.5 | |
| AQASQLALLA | 2389 | 0.5 | |
| AQLVDRVPRA | 2390 | 0.5 | |
| AQHSNGYVHA | 2391 | 0.5 | |
| AQAAPSSSDS | 2392 | 0 5 | |
| AQAMQRSSSA | 2393 | 0.5 | |
| AQAASGRPTC | 2394 | 0.5 | |
| AQPRPGDSRA | 2395 | 0.5 | |
| AQRDRANGIA | 2396 | 0.5 | |
| AQVLAISLSA | 2397 | 0.5 | |
| AQAGMRDPRM | 2398 | 0.5 | |
| AQASSNSSRA | 2399 | 0.5 | |
| MHRDAVSGVA | 2400 | 0.5 | |
| AQAEMKNMPP | 2401 | 0.5 | |
| AQSGSLLASA | 2402 | 0.5 | |
| AQAFASQSRG | 2403 | 0.5 | |

TABLE 7-continued

| | | | |
|---|---|---|---|
| NHP NGS AAV9 ENRICHMENT | | | |
| Peptide Sequence | SEQ ID NO: | Fold enrichment over AAV9 | |
| AQALHLPTLQ | 2404 | 0.5 | |
| AQAKTGGMNT | 2405 | 0.5 | |
| ISLNAVSGKA | 2406 | 0.5 | |
| AQGVHGHYVA | 2407 | 0.5 | |
| AQAYSKDVRM | 2408 | 0.5 | |
| VPSIAVSSHA | 2409 | 0.5 | |
| AQSSRHDDLA | 2410 | 0.5 | |
| AQANGSGSRG | 2411 | 0.5 | |
| AQVGIADRRA | 2412 | 0.5 | |
| AQARGMESML | 2413 | 0.5 | |
| AQAGVSTAGH | 2414 | 0.5 | |
| AQVSTRNLIA | 2415 | 0.5 | |
| AQAVPRLTAG | 2416 | 0.5 | |
| AQRHMELQEA | 2417 | 0.5 | |
| SQSRAVVWEA | 2418 | 0.5 | |
| QSHTAVSSLA | 2419 | 0.5 | |
| AKASVSTLRM | 2420 | 0.5 | |
| AQASGSSQWA | 2421 | 0.5 | |
| AQPNAQYMKA | 2422 | 0.5 | |
| AQAMGTGSSL | 2423 | 0.5 | |
| AQAFSTSQLT | 2424 | 0.5 | |
| AQAKDQSQRL | 2425 | 0.4 | |
| AQVGGNGSRA | 2426 | 0.4 | |
| AQANGASRAV | 2427 | 0.4 | |
| QVNKAVLDFA | 2428 | 0.4 | |
| AQETLSSTRA | 2429 | 0.4 | |
| GVYGAVHSSA | 2430 | 0.4 | |
| AQTITIENVA | 2431 | 0.4 | |
| AQALMKIADG | 2432 | 0.4 | |
| AQANVSLQAA | 2433 | 0.4 | |
| AQSTTSHLRA | 2434 | 0.4 | |
| AQLSNLVSVA | 2435 | 0.4 | |
| AQANSTPTRQ | 2436 | 0.4 | |
| AQQRGDRAAA | 2437 | 0.4 | |
| AQARLGQSVG | 2438 | 0.4 | |
| AQQLTYGSSA | 2439 | 0.4 | |
| AQPAEKQYSA | 2440 | 0.4 | |

TABLE 7-continued

| NHP NGS AAV9 ENRICHMENT | | |
| --- | --- | --- |
| Peptide Sequence | SEQ ID NO: | Fold enrichment over AAV9 |
| AQAMPRSRGD | 2441 | 0.4 |
| AQGLSGRALA | 2442 | 0.4 |
| AQARVTAVDA | 2443 | 0.4 |
| AQVGVSTAVA | 2444 | 0.4 |
| AQTGVTSAQA | 2445 | 0.4 |
| AQALVTSSEK | 2446 | 0.4 |
| AQASPHSSMA | 2447 | 0.4 |
| AQALTQDEMW | 2448 | 0.4 |
| AQAFSTQQRL | 2449 | 0.4 |
| AQAGSQVTQA | 2450 | 0.4 |
| AQQSTLALKA | 2451 | 0.4 |
| AQALNGSHAA | 2452 | 0.4 |
| AQATEGHLRS | 2453 | 0.4 |
| AQPMANMLMA | 2454 | 0.4 |
| PSTSAVSQKA | 2455 | 0.4 |
| AQAPPSSTEM | 2456 | 0.4 |
| AQRERVDLAA | 2457 | 0.4 |
| AQASVTLPRT | 2458 | 0.4 |
| AQAYPSSSKA | 2459 | 0.4 |
| AQAHSGSAIP | 2460 | 0.4 |
| AQSPSQSLKA | 2461 | 0.4 |
| AQATPPATSP | 2462 | 0.4 |
| CLGAAVNQCA | 2463 | 0.4 |
| VLGQAVRDKA | 2464 | 0.4 |
| AQAQKANNVG | 2465 | 0.4 |
| AQTLLPVNGA | 2466 | 0.4 |
| AQAHGTIQRG | 2467 | 0.4 |
| TVYTAVGVSA | 2468 | 0.4 |
| LGRGAVLDMA | 2469 | 0.4 |
| AQANVRSDQM | 2470 | 0.4 |
| AQARDSQKGW | 2471 | 0.4 |
| AQTPGSRSAA | 2472 | 0.4 |
| AQALPSNARQ | 2473 | 0.4 |
| AQASATSVVH | 2474 | 0.4 |
| AQINLGTMRA | 2475 | 0.4 |
| AQVYNNTSAA | 2476 | 0.4 |
| AQASANLTRG | 2477 | 0.4 |

TABLE 7-continued

| NHP NGS AAV9 ENRICHMENT | | |
| --- | --- | --- |
| Peptide Sequence | SEQ ID NO: | Fold enrichment over AAV9 |
| AQLRTDYTRA | 2478 | 0.4 |
| AQAYSTDVKM | 2479 | 0.4 |
| AQTSQLYQPA | 2480 | 0.4 |
| AQALTQEERW | 2481 | 0.4 |
| LPNGAVRDRA | 2482 | 0.4 |
| VTGSAVAGIA | 2483 | 0.4 |
| AQAFSTDVRM | 2484 | 0.4 |
| AQAHGPTSGV | 2485 | 0.4 |
| AQAGVGLPIA | 2486 | 0.4 |
| AQVNSGQARA | 2487 | 0.4 |
| AQAQTGPPMK | 2488 | 0.4 |
| AQARLAPVAC | 2489 | 0.3 |
| LSIGAVASMA | 2490 | 0.3 |
| AQAQDLGVMR | 2491 | 0.3 |
| PTGLAVTSPA | 2492 | 0.3 |
| AQSASTSWSA | 2493 | 0.3 |
| AQNGSNVRNA | 2494 | 0.3 |
| AQASISSSAT | 2495 | 0.3 |
| AQNSHAHLAA | 2496 | 0.3 |
| AQAVGVKQFF | 2497 | 0.3 |
| AQAHLSPTHA | 2498 | 0.3 |
| AQPAYGSSYA | 2499 | 0.3 |
| AQAHQARSGS | 2500 | 0.3 |
| AQAHTSPTQR | 2501 | 0.3 |
| AQAATPSSSR | 2502 | 0.3 |
| AQAHNSYPKV | 2503 | 0.3 |
| AQSSLGSSLA | 2504 | 0.3 |
| AQALSRSNVG | 2505 | 0.3 |
| AQASLSSLSG | 2506 | 0.3 |
| AQHGSSEFTA | 2507 | 0.3 |
| AQSALVAGVA | 2508 | 0.3 |
| AQASSSSLRP | 2509 | 0.3 |
| AQTARDTGFA | 2510 | 0.3 |
| KSVQAVRDPA | 2511 | 0.3 |
| AQAGSHSSVS | 2512 | 0.3 |
| VRAHAVTGLA | 2513 | 0.3 |
| ASHTAVGEFA | 2514 | 0.3 |

TABLE 7-continued

| | | |
|---|---|---|
| NHP NGS AAV9 ENRICHMENT | | |
| Peptide Sequence | SEQ ID NO: | Fold enrichment over AAV9 |
| AQIRSEWRDA | 2515 | 0.3 |
| AQQLARVSGA | 2516 | 0.3 |
| AQAAITSTNS | 2517 | 0.3 |
| AQARDAVQLP | 2518 | 0.3 |
| AQAKELVSTS | 2519 | 0.3 |
| AQGIAETLSA | 2520 | 0.3 |
| AQLGSGFSTA | 2521 | 0.3 |
| AQNAKELERA | 2522 | 0.3 |
| AQTHLQNGVA | 2523 | 0.3 |
| SGNLAVGTPA | 2524 | 0.3 |
| AQPSPGTSVA | 2525 | 0.3 |
| AQSSAAAGRA | 2526 | 0.3 |
| AQAGISAAIM | 2527 | 0.3 |
| AQALGYHQTG | 2528 | 0.3 |
| NAGQAVAARA | 2529 | 0.3 |
| AQPFGGSGYA | 2530 | 0.3 |
| AQAGSPSRLC | 2531 | 0.3 |
| AQARTIGTIA | 2532 | 0.3 |
| AQVVSVSSRA | 2533 | 0.3 |
| AQAGQARSMG | 2534 | 0.3 |
| AQATRGVTAG | 2535 | 0.3 |
| AQQSNGYGRA | 2536 | 0.3 |
| AQASLAPLKS | 2537 | 0.3 |
| AQPGANHNGA | 2538 | 0.3 |
| LGRGAVPDTA | 2539 | 0.3 |
| AQHFQTASLA | 2540 | 0.3 |
| AQAPAGHHTR | 2541 | 0.3 |
| AQPSVQNSMA | 2542 | 0.3 |
| AQAKLSGHVS | 2543 | 0.3 |
| AQFGTSSPSA | 2544 | 0.3 |
| AQASHISSVR | 2545 | 0.3 |
| AQALSRNGIG | 2546 | 0.3 |
| AQASAQVQRS | 2547 | 0.3 |
| AQGGPHLQAA | 2548 | 0.3 |
| AQAQSDSAFR | 2549 | 0.3 |
| AQTYSTDVRM | 2550 | 0.3 |
| LARGAVLDTA | 2551 | 0.3 |

TABLE 7-continued

| | | |
|---|---|---|
| NHP NGS AAV9 ENRICHMENT | | |
| Peptide Sequence | SEQ ID NO: | Fold enrichment over AAV9 |
| AQASPHTLRS | 2552 | 0.3 |
| AQHSDTQTRA | 2553 | 0.3 |
| AQATPSPSAS | 2554 | 0.3 |
| AQNQVTYSKA | 2555 | 0.3 |
| AQHTSVVYGA | 2556 | 0.3 |
| AQAQVSQMSH | 2557 | 0.3 |
| SFLRAVKNDA | 2558 | 0.3 |
| AQAYSTDVGM | 2559 | 0.3 |
| AKTPALINLA | 2560 | 0.3 |
| VSTAAVSSAA | 2561 | 0.3 |
| AQAPITSTIS | 2562 | 0.3 |
| AQTNLQTRGA | 2563 | 0.3 |
| AQATRLPTPG | 2564 | 0.3 |
| PQHLAVSSAA | 2565 | 0.2 |
| AQASPHPSRP | 2566 | 0.2 |
| AQAQPAGQRG | 2567 | 0.2 |
| AQPQRQGVQA | 2568 | 0.2 |
| AQHVAGSSNA | 2569 | 0.2 |
| AQVPIQMGVA | 2570 | 0.2 |
| AQATVSVPLK | 2571 | 0.2 |
| AQISVSHTRA | 2572 | 0.2 |
| SLVGPVAQMA | 2573 | 0.2 |
| AQPRLNLTEA | 2574 | 0.2 |
| AQASQEYSRL | 2575 | 0.2 |
| AQKSLAFDSA | 2576 | 0.2 |
| AQALGHSHHC | 2577 | 0.2 |
| AQAAQTGRPI | 2578 | 0.2 |
| AQASGTSVRQ | 2579 | 0.2 |
| AQAMGTASYC | 2580 | 0.2 |
| AQISHNHPQA | 2581 | 0.2 |
| AQAYSTYVRM | 2582 | 0.2 |
| AQVGKLDIRA | 2583 | 0.2 |
| AQLKQGGINA | 2584 | 0.2 |
| AQASAHFREP | 2585 | 0.2 |
| AQALDTVLSA | 2586 | 0.2 |
| GAGTAVGNIA | 2587 | 0.2 |
| AQANGSATYA | 2588 | 0.2 |

TABLE 7-continued

| | NHP NGS AAV9 ENRICHMENT | |
| --- | --- | --- |
| Peptide Sequence | SEQ ID NO: | Fold enrichment over AAV9 |
| AQTQLAQQKA | 2589 | 0.2 |
| AQYVTTVSPA | 2590 | 0.2 |
| SQFSAVTVTA | 2591 | 0.2 |
| AQAASDSFRY | 2592 | 0.2 |
| AQASPASVTR | 2593 | 0.2 |
| AQARDSGMFL | 2594 | 0.2 |
| AQSKTTLTLS | 2595 | 0.2 |
| AQLVQESLSA | 2596 | 0.2 |
| AQAALKSLAG | 2597 | 0.2 |
| AQAVPNQGQK | 2598 | 0.2 |
| AQALSRSSLG | 2599 | 0.2 |
| AQAGSVMSRV | 2600 | 0.2 |
| AQMATVTPMA | 2601 | 0.2 |
| AQARTASGID | 2602 | 0.2 |
| SHSSAVSHPA | 2603 | 0.2 |
| AQADRMRTTA | 2604 | 0.2 |
| AQNAQNRALA | 2605 | 0.2 |
| AQAASNAYSS | 2606 | 0.2 |
| AQATFQQAST | 2607 | 0.2 |
| AQVYTISTPA | 2608 | 0.2 |
| AQTVIAVGVA | 2609 | 0.2 |
| LARGAVPPTA | 2610 | 0.2 |
| AQMLQTSVLA | 2611 | 0.2 |
| AQARQVSPLL | 2612 | 0.2 |
| AQAGQMSNAR | 2613 | 0.2 |
| AQTPALIKLA | 2614 | 0.2 |
| AQAYTTDVRK | 2615 | 0.2 |
| VVKGAVLHVA | 2616 | 0.2 |
| AQDTVSVPLK | 2617 | 0.2 |
| AQKGAPSLQA | 2618 | 0.2 |
| AQASYDVGRA | 2619 | 0.2 |
| AQGPLSGMRA | 2620 | 0.2 |
| AQALGTSVPA | 2621 | 0.2 |
| AQVNKGASTA | 2622 | 0.2 |
| AQLTRTSPVA | 2623 | 0.2 |
| AQADAALRFS | 2624 | 0.2 |
| AQVQLVVSPA | 2625 | 0.2 |

TABLE 7-continued

| | NHP NGS AAV9 ENRICHMENT | |
| --- | --- | --- |
| Peptide Sequence | SEQ ID NO: | Fold enrichment over AAV9 |
| AQAYSSDVRM | 2626 | 0.2 |
| AQARSGLSLP | 2627 | 0.2 |
| AQNGHKFTAA | 2628 | 0.2 |
| AQGLSSATKA | 2629 | 0.2 |
| AQGTWSTVKA | 2630 | 0.2 |
| AQASGVGGRI | 2631 | 0.2 |
| AQTSYPAQKA | 2632 | 0.2 |
| AQNAVPTHSA | 2633 | 0.2 |
| AQSYPEITRA | 2634 | 0.2 |
| AQTGLSTSSA | 2635 | 0.2 |
| AQYDTHNFAA | 2636 | 0.2 |
| AQAVLSSVIQ | 2637 | 0.2 |
| AQDSAVALMA | 2638 | 0.2 |
| AQATGKGALP | 2639 | 0.2 |
| AQNSRSGHDA | 2640 | 0.2 |
| AQAFQKEPSV | 2641 | 0.2 |
| AQAGSTSGKM | 2642 | 0.2 |
| AQRDQAHSQA | 2643 | 0.2 |
| AQAASALSGR | 2644 | 0.2 |
| AQARHSSLLP | 2645 | 0.2 |
| AQGPGTSYLA | 2646 | 0.2 |
| FLAPAVSSKA | 2647 | 0.2 |
| AQAGPQCSSC | 2648 | 0.2 |
| AQALTQHERW | 2649 | 0.2 |
| AQAIRSSERV | 2650 | 0.2 |
| AQAVHSSSVY | 2651 | 0.2 |
| AQSSRTALAA | 2652 | 0.2 |
| AQITFSHTRA | 2653 | 0.2 |
| AQALTLSGGL | 2654 | 0.2 |
| AQAGKTLSVL | 2655 | 0.2 |
| AQASRSNLDN | 2656 | 0.2 |
| AQGSLSTHTA | 2657 | 0.2 |
| AQQSVAYNVA | 2658 | 0.2 |
| AQHTLRLSSA | 2659 | 0.2 |
| AQAGGTPNKL | 2660 | 0.2 |
| AQAFQSLTLA | 2661 | 0.2 |
| AQAVALSHQE | 2662 | 0.2 |

301

TABLE 7-continued

| | NHP NGS AAV9 ENRICHMENT | |
|---|---|---|
| Peptide Sequence | SEQ ID NO: | Fold enrichment over AAV9 |
| AQMLASGIPA | 2663 | 0.2 |
| AQNRALDSYA | 2664 | 0.2 |
| AQASGSTTRN | 2665 | 0.2 |
| AQARGDGYVA | 2666 | 0.2 |
| DARVAVLDFA | 2667 | 0.2 |
| AQAVASQVSR | 2668 | 0.2 |
| AQARGPSPAT | 2669 | 0.2 |
| AQHRALDSYD | 2670 | 0.2 |
| AQLIDSTSRA | 2671 | 0.2 |
| AQAQTLSRGS | 2672 | 0.2 |
| AQFRSAITSA | 2673 | 0.2 |
| AQANMTKQSL | 2674 | 0.2 |
| AQNAGSTSRA | 2675 | 0.2 |
| VLGSAVTGRA | 2676 | 0.2 |
| AQPMLQSSSA | 2677 | 0.2 |
| AQLGTPSLSA | 2678 | 0.2 |
| AQATAHTGVP | 2679 | 0.2 |
| AQAVGRDNRL | 2680 | 0.2 |
| AQATSASVWA | 2681 | 0.2 |
| AQAGSEASLR | 2682 | 0.2 |
| AQANQNRTAF | 2683 | 0.2 |
| AQASAQVKRS | 2684 | 0.2 |
| AQATSGVHHP | 2685 | 0.2 |
| AQTHMQIGVA | 2686 | 0.2 |
| AQSHIFPTPA | 2687 | 0.2 |
| AQLFHTGSPA | 2688 | 0.2 |
| LASRAVVGTA | 2689 | 0.2 |
| AQALLRVGVG | 2690 | 0.2 |
| AQITLPSGTA | 2691 | 0.2 |
| AQAEKSLGRQ | 2692 | 0.2 |
| AQTSNTTIRA | 2693 | 0.2 |
| AQAHTQASYM | 2694 | 0.2 |
| AQERGASSSA | 2695 | 0.2 |
| AQATPSSTAM | 2696 | 0.2 |
| AQSTVNRTYA | 2697 | 0.2 |
| AQAGHGPSTR | 2698 | 0.2 |
| AQLSLVPLQA | 2699 | 0.2 |

302

TABLE 7-continued

| | NHP NGS AAV9 ENRICHMENT | |
|---|---|---|
| Peptide Sequence | SEQ ID NO: | Fold enrichment over AAV9 |
| AQLHSPIPSA | 2700 | 0.2 |
| AQSLARDGLA | 2701 | 0.2 |
| AQAPPSSPAM | 2702 | 0.2 |
| TQYGAVERQA | 2703 | 0.1 |
| AQAGQARSLA | 2704 | 0.1 |
| AQPVGRVPPA | 2705 | 0.1 |
| AQAREQRGPV | 2706 | 0.1 |
| AQKTSLLWEA | 2707 | 0.1 |
| AQGSGKNLIA | 2708 | 0.1 |
| AQASEGHQLS | 2709 | 0.1 |
| AQALHAGHHP | 2710 | 0.1 |
| AQSKRDDPSA | 2711 | 0.1 |
| AQTSRELRMA | 2712 | 0.1 |
| AQALPASGAR | 2713 | 0.1 |
| AQSNALLSLA | 2714 | 0.1 |
| AQASPVVGVS | 2715 | 0.1 |
| AQARGDSYMA | 2716 | 0.1 |
| AQAGASSLTV | 2717 | 0.1 |
| AQALRPVNGT | 2718 | 0.1 |
| AQVRSGPTLA | 2719 | 0.1 |
| AQFPPLSRSA | 2720 | 0.1 |
| AQVARGTVQA | 2721 | 0.1 |
| AQTSTQSPPG | 2722 | 0.1 |
| AQARDGMNVR | 2723 | 0.1 |
| AQAVSRNVVV | 2724 | 0.1 |
| AQHTATRSVA | 2725 | 0.1 |
| AQAVREDGHA | 2726 | 0.1 |
| TNSSAVAASA | 2727 | 0.1 |
| AQATFQLAST | 2728 | 0.1 |
| AQAHHQQTSL | 2729 | 0.1 |
| AQGQHAHMMA | 2730 | 0.1 |
| AQATSSLHVL | 2731 | 0.1 |
| AQAPNSGLAM | 2732 | 0.1 |
| SASRAVLDFA | 2733 | 0.1 |
| AQARGEQRFV | 2734 | 0.1 |
| AQTHLQIRVA | 2735 | 0.1 |
| AQAPPSSKAM | 2736 | 0.1 |

TABLE 7-continued

| | NHP NGS AAV9 ENRICHMENT | |
|---|---|---|
| Peptide Sequence | SEQ ID NO: | Fold enrichment over AAV9 |
| AQIVSKAMPA | 2737 | 0.1 |
| AQASVRNNPS | 2738 | 0.1 |
| AQAESRVAAL | 2739 | 0.1 |
| LTNGAVRDRT | 2740 | 0.1 |
| AQGRLAGSLA | 2741 | 0.1 |
| AQAGQDSARR | 2742 | 0.1 |
| AQAASRLGAV | 2743 | 0.1 |
| AQALARGMAS | 2744 | 0.1 |
| AQASRGLSMG | 2745 | 0.1 |
| AQAQASSYGS | 2746 | 0.1 |
| AKASRLPTPG | 2747 | 0.1 |
| AQSLSRASTA | 2748 | 0.1 |
| AQASTFVQTI | 2749 | 0.1 |
| AQASSKVVAA | 2750 | 0.1 |
| AQAYRNGEAA | 2751 | 0.1 |
| AQAYSTGVRM | 2752 | 0.1 |
| AQAVSSRSMG | 2753 | 0.1 |
| AQARGGLATP | 2754 | 0.1 |
| AQAGHSGVRA | 2755 | 0.1 |
| AQPSYHGGAA | 2756 | 0.1 |
| AQRVNQVSTA | 2757 | 0.1 |
| AQAAFQQAST | 2758 | 0.1 |
| AQAVPGSPRA | 2759 | 0.1 |
| AQLSLSPLAA | 2760 | 0.1 |
| AQANMTVRVS | 2761 | 0.1 |
| AQATRSSGDP | 2762 | 0.1 |
| AQVASNATRA | 2763 | 0.1 |
| AQTNQQPRGA | 2764 | 0.1 |
| AQRLQNDHLA | 2765 | 0.1 |
| AQAPVQLGRP | 2766 | 0.1 |
| AQRQGPDTLA | 2767 | 0.1 |
| AQHTLSNHMA | 2768 | 0.1 |
| AQLSGMVNRA | 2769 | 0.1 |
| AQDRQVSSRA | 2770 | 0.1 |
| AQRQLSTSLA | 2771 | 0.1 |
| AQQRPTVSFA | 2772 | 0.1 |
| AQAKPHSQLD | 2773 | 0.1 |

TABLE 7-continued

| | NHP NGS AAV9 ENRICHMENT | |
|---|---|---|
| Peptide Sequence | SEQ ID NO: | Fold enrichment over AAV9 |
| AQAGRVNHPP | 2774 | 0.1 |
| AQAINSQSMR | 2775 | 0.1 |
| AQYSTAVMSA | 2776 | 0.1 |
| SQARAVERSA | 2777 | 0.1 |
| AQAYKSSSVG | 2778 | 0.1 |
| AQASTPGLYP | 2779 | 0.1 |
| AQSRTSMLAA | 2780 | 0.1 |
| AQLFSSNMPA | 2781 | 0.1 |
| AQAYCTDVRM | 2782 | 0.1 |
| AQTMSRGFVA | 2783 | 0.1 |
| AQALNGYPAA | 2784 | 0.1 |
| AQAQTGHPLK | 2785 | 0.1 |
| AQASSNSQYR | 2786 | 0.1 |
| AQAAIKSTIS | 2787 | 0.1 |
| AQSTLNLRPA | 2788 | 0.1 |
| AQATLSPGSG | 2789 | 0.1 |
| AQANGSGTGR | 2790 | 0.1 |
| STSLAVAGRA | 2791 | 0.1 |
| AQASNLSAYR | 2792 | 0.1 |
| AQASRQVLVA | 2793 | 0.1 |
| NEVRAVFFEA | 2794 | 0.1 |
| AKAQGSSSVG | 2795 | 0.1 |
| ARGSAVQSQA | 2796 | 0.1 |
| AVRVAVSSSA | 2797 | 0.1 |
| AQAFSTSQFK | 2798 | 0.1 |
| AQGTSSQRTA | 2799 | 0.1 |
| AQATMSQTIA | 2800 | 0.1 |
| AQSANRSTLA | 2801 | 0.1 |
| AQRDLAHSKA | 2802 | 0.1 |
| AQASKVGLYA | 2803 | 0.1 |
| AQAYYTDVRM | 2804 | 0.1 |
| AQAGLRDPRA | 2805 | 0.1 |
| AQAFSQATGA | 2806 | 0.1 |
| AQVAGMSVRA | 2807 | 0.1 |
| AQAGQSSFTI | 2808 | 0.1 |
| AQKEMRSQGA | 2809 | 0.1 |
| AQNYSSGVRA | 2810 | 0.1 |

TABLE 7-continued

NHP NGS AAV9 ENRICHMENT

| Peptide Sequence | SEQ ID NO: | Fold enrichment over AAV9 |
|---|---|---|
| AQITVSYTRA | 2811 | 0.1 |
| AQAQQPRSSI | 2812 | 0.1 |
| WTSGAVPGKA | 2813 | 0.1 |
| AQFKPSQVIA | 2814 | 0.1 |
| RQGQAVGSSA | 2815 | 0.1 |
| AQSISPHYAA | 2816 | 0.1 |
| AQARSLNEYK | 2817 | 0.1 |
| AQAASSRIMA | 2818 | 0.1 |
| AQAYSTDGRM | 2819 | 0.1 |
| AQASVPRVMG | 2820 | 0.1 |
| AQGQMPRYPA | 2821 | 0.1 |
| AQASSGMKPC | 2822 | 0.1 |
| AQPLRSSLSA | 2823 | 0.1 |
| AQNSASQSQA | 2824 | 0.1 |
| AQGHLSGLRA | 2825 | 0.1 |
| AQRAQSGVAA | 2826 | 0.1 |
| AQANPRLQDK | 2827 | 0.1 |
| AQAPRTATLG | 2828 | 0.1 |
| AQRTASLSQA | 2829 | 0.1 |
| AQGNPGLLRA | 2830 | 0.1 |
| MSSHAVGNRA | 2831 | 0.1 |
| AQLAPKASPA | 2832 | 0.1 |
| AQTTQGRERA | 2833 | 0.1 |
| AQASGKSTSS | 2834 | 0.1 |
| AQAPHQHSMK | 2835 | 0.1 |

A subset of the targeting peptide variants from the NHP biopanning showed a very strong and consistent enrichment over AAV9 and PHP.B controls. Further, the targeting peptide of SEQ ID NO: 1725 not only showed a strong enrichment over AAV9 in the brain, but also in the spinal cord, as it led to a 125.6 fold enrichment over AAV9 in the spinal cord. Following the removal of the least reliable variants, a set of 22 variants with enrichment factors ranging from 7-fold to >400-fold over AAV9 was identified. These were cross-referenced to a non-synthetic PCR-amplified library screened in parallel and 12 candidates showed reliable enrichment and high consistency in both assays. Of these, 5 candidates with the highest enrichment scores in both assays and the highest consistency across animals and tissues were retained for individual evaluation. Candidate capsids were labeled TTD-001, TTD-002, TTD-003, TTD-004 and TTD-005 as shown in Table 3 above.

After 3 rounds of screening of AAV9 peptide insertion library in NHP, many capsids outperformed their parental capsid AAV9 in penetration of the blood brain barrier (BBB). Some of the capsids comprising a targeting peptide showed high enrichment scores and high consistency both across different brain tissue samples from the same animal and across different animals. Consistency in both NNK and NNM codons was also observed. 22 capsid variants exhibited enrichment factors ranging from 7-fold to >400-fold over AAV9 in the brain tissues. A majority of these variants also demonstrated high enrichment factors up to 125-fold over AAV9 in the spinal cord. Of these, 5 candidates with diverse inserted sequences were selected for further evaluation as individual capsids.

Example 5. Individual Capsid Characterization

The goal of these experiments was to determine the transduction level and the spatial distribution of each of the 5 capsid candidates selected from the study described in Example 4 relative to AAV9 following intravascular infusion in NHPs (cynomolgus macaque). The 5 selected capsid candidates were TTD-001 (SEQ ID NO: 3623 and 3636, comprising targeting peptide SEQ ID NO: 1725 or 3648), TTD-002 (SEQ ID NO: 3623, 3625, and 3637, comprising targeting peptide SEQ ID NO: 1726 or 3649), TTD-003 (SEQ ID NO: 3626 and 3638, comprising targeting peptide SEQ ID NO: 1729 or 3650), TTD-004 (SEQ ID NO: 3627 and 3639, comprising targeting peptide SEQ ID NO: 1760 or 3651) and TTD-005 (SEQ ID NO: 3629 and 3641, comprising targeting peptide SEQ ID NO: 1769 or 3652) as outlined in Table 3 above.

AAV particles were generated with each of these 5 capsids encapsulating a transgene encoding a payload fused to an HA tag (payload-HA) and driven by a full-length CMV/chicken beta actin promoter by triple transfection in HEK293T cells and formulated in a pharmaceutically acceptable solution.

Each test capsid and AAV9 control were tested by intravenously providing two (2) NHP females the AAV particle formulation at a dose of 2e13 VG/kg. The in-life period was 14 days and then a battery of CNS and peripheral tissues were collected for quantification of transgene mRNA, transgene protein and viral DNA (biodistribution). Samples were also collected, fixed and paraffin embedded for immunohistochemical stainings.

Figure 6A:
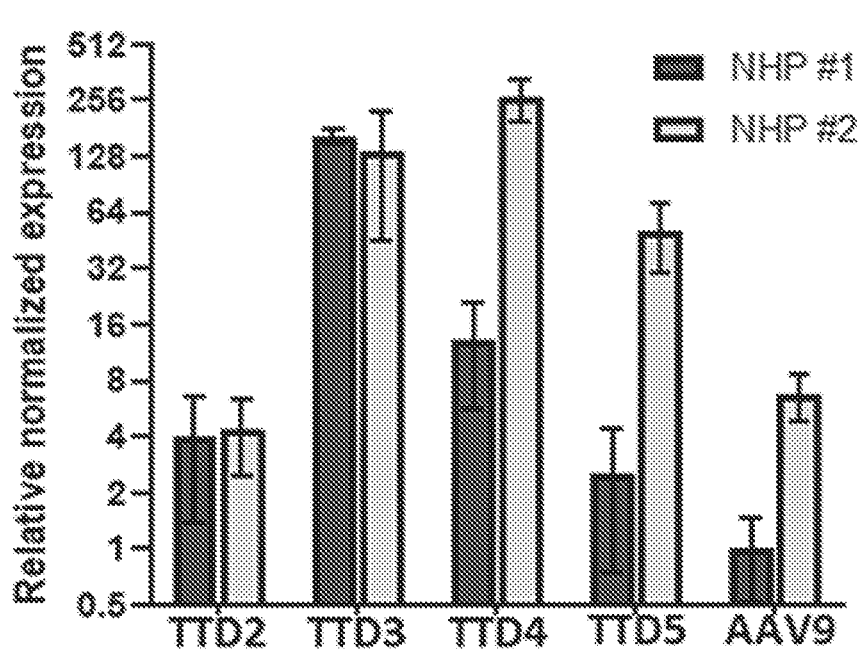
FIG. 6A, FIG. 6B, and FIG. 6C show mRNA quantification of AAV particle transduction in NHP tissues using qRT-PCR.
Figure 6A:
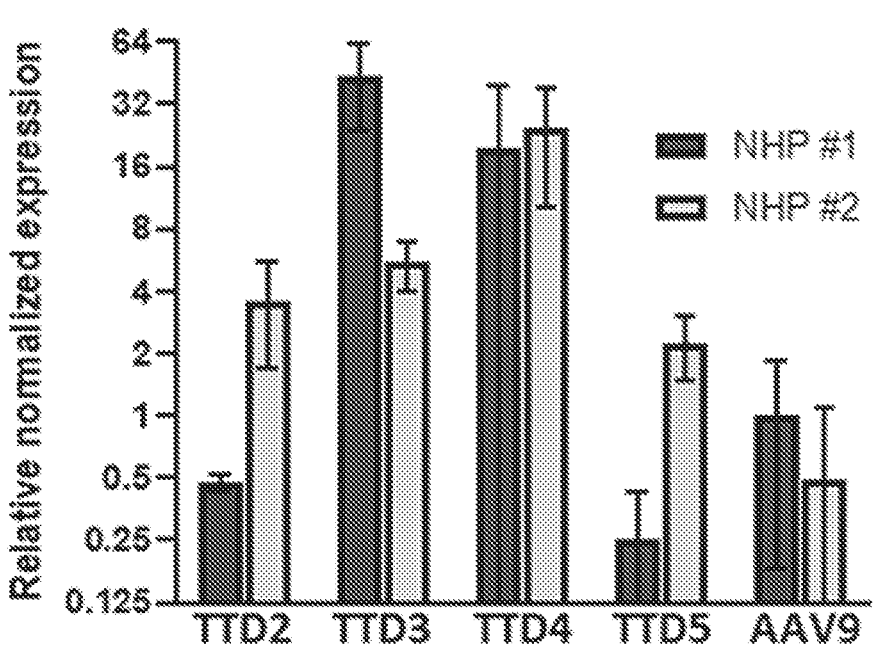
Figure 6B:
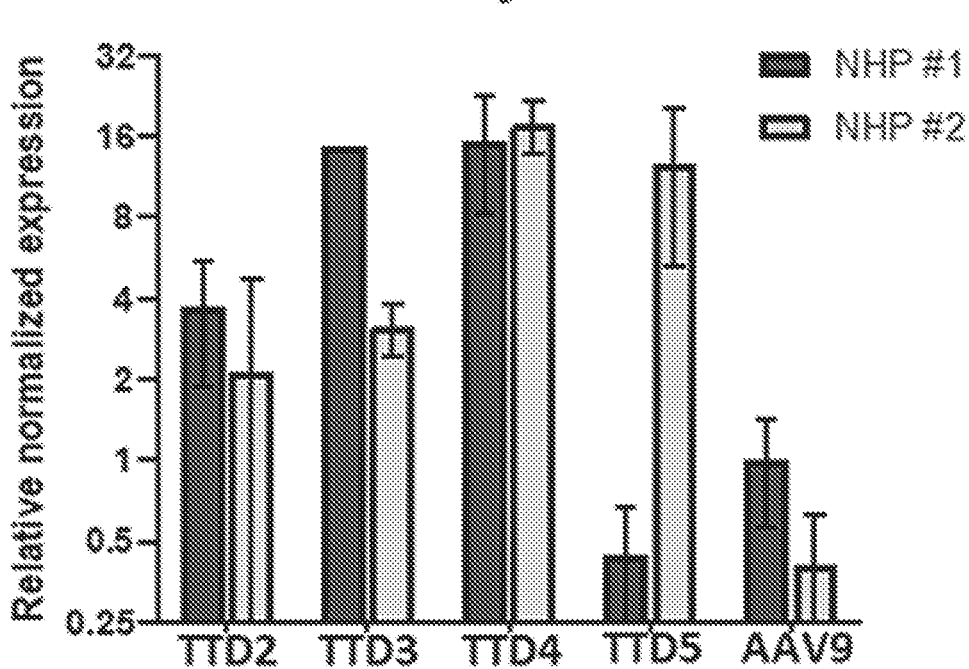
Figure 6B:
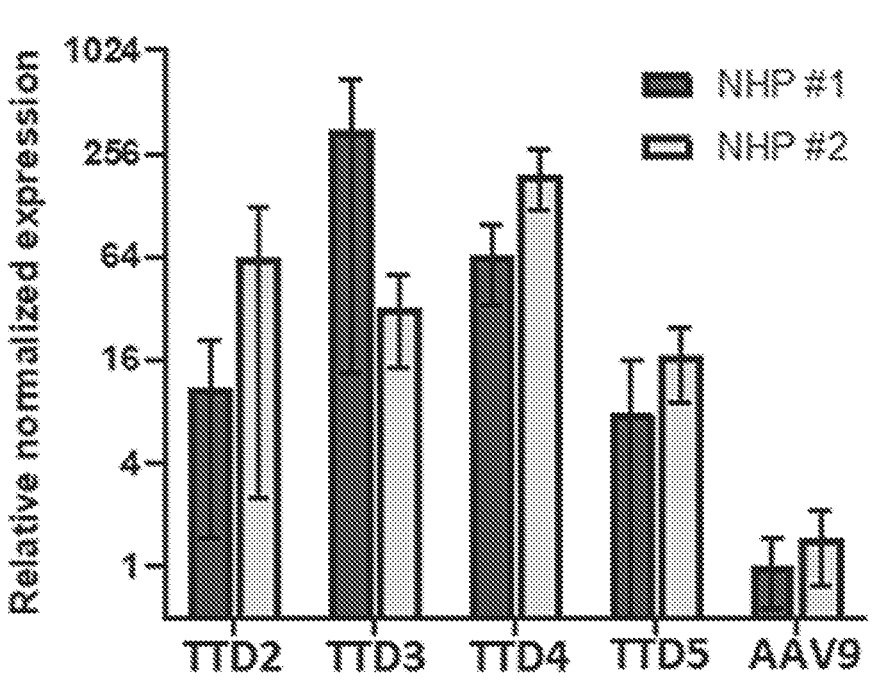
Figure 6C:
Figure 6C:
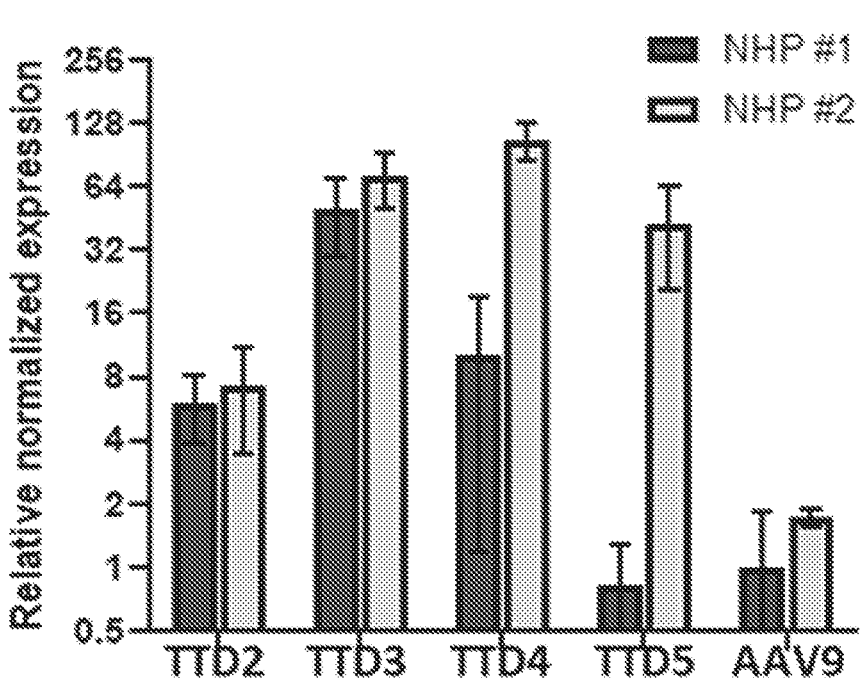
Figure 6C:
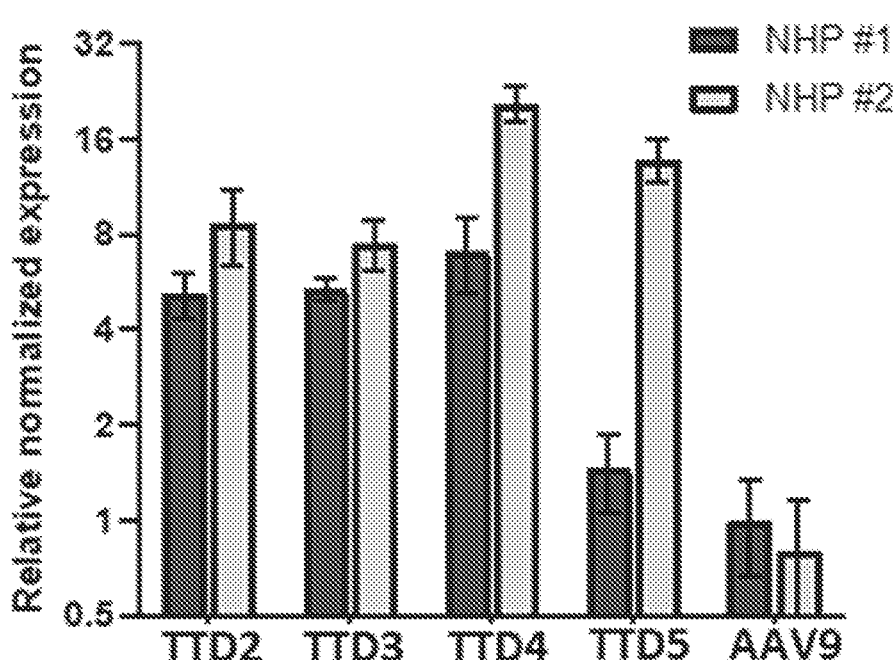

In a first pass screening of RNA quantification by qRT-PCR and RT-ddPCR, total RNA was extracted from 3-mm punches from various areas of the brain (cortex, striatum, hippocampus, cerebellum), spinal cord sections, liver and heart, and analyzed by qRT-PCR using a proprietary TAQMAN™ set specific for the synthetic CAG exon-exon junction. Cynomolgus TBP (TATA box-binding protein) was used as a housekeeping gene. Data are shown in FIG. 6A, FIG. 6B, and FIG. 6C.

Figure 7:
FIG. 7 shows mRNA quantification of AAV particle transduction in NHP tissues using ddPCR.

TRACER™ capsids showed an increase in RNA expression in all brain regions relative to AAV9 in at least one animal. The highest and most consistent increase in brain transduction was observed with capsids TTD-003 and TTD-004 (8- to 200-fold depending in various anatomical locations). In this initial screening TTD-001 was not assessed due to staggered animal dosing. An approximate 10- to 12-fold increase was consistently observed in whole brain slices (equivalent to an average of multiple regions), which was consistent with the values indicated in a next-generation sequencing (NGS) assay. In order to increase data robustness, droplet digital RT-PCR (ddPCR) was performed in parallel to qRT-PCR and confirmed the trends indicated by the qPCR data as shown in FIG. 7.

Figure 8:
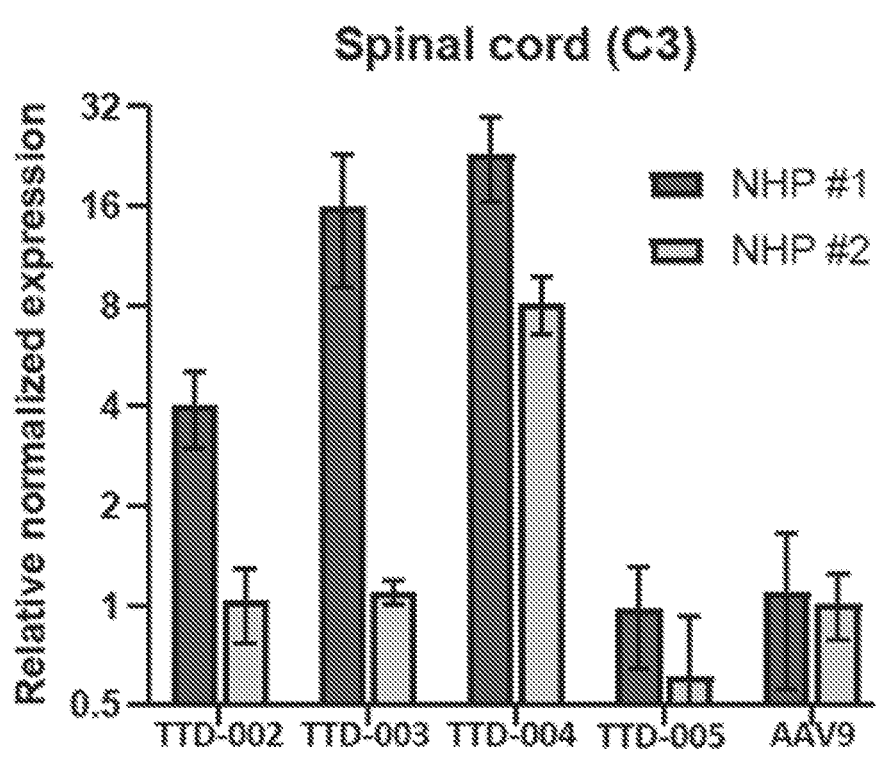
FIG. 8 shows mRNA quantification of AAV particle transduction in the spinal cord and dorsal root ganglia of NHP.
Figure 8:
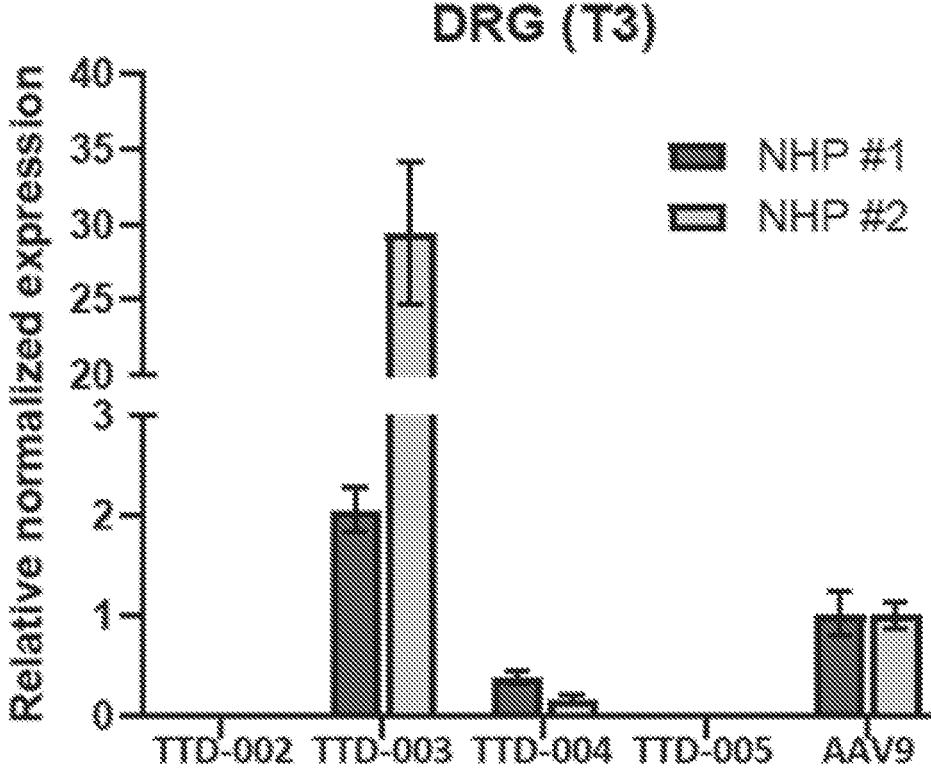
Figure 9A:
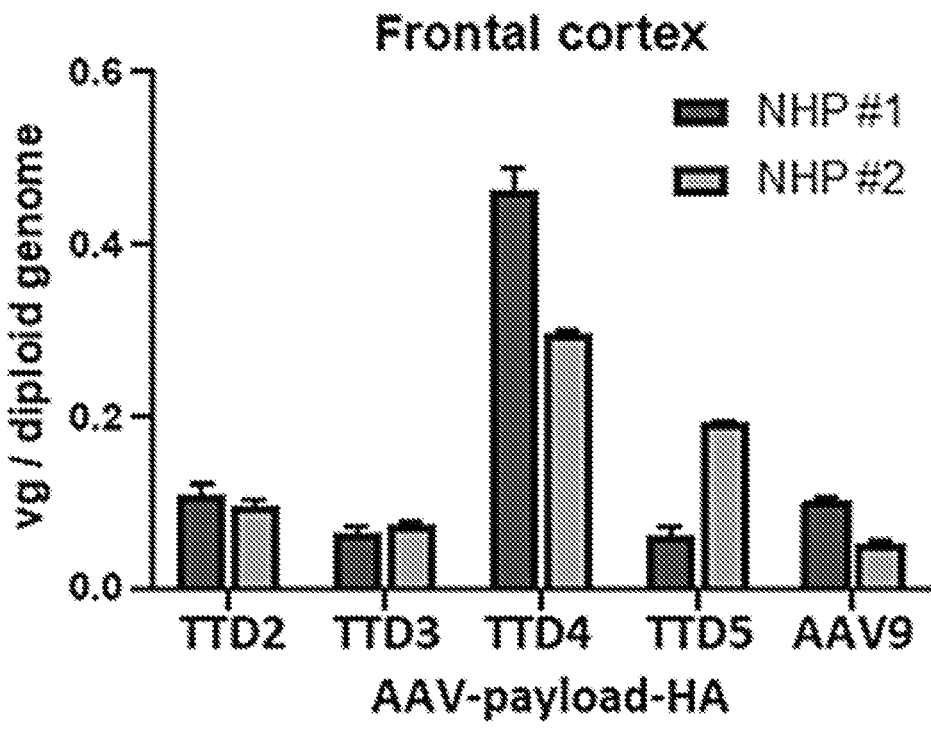
FIG. 9A, FIG. 9B, FIG. 9C, and FIG. 9D show viral genome quantification in NHP tissues.
Figure 9A:
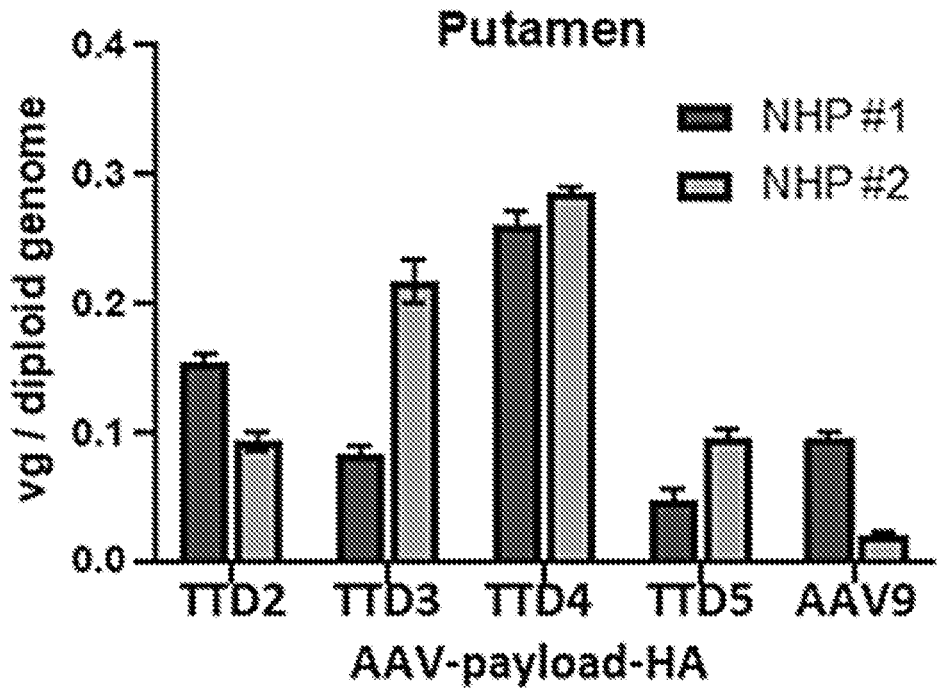
Figure 9B:
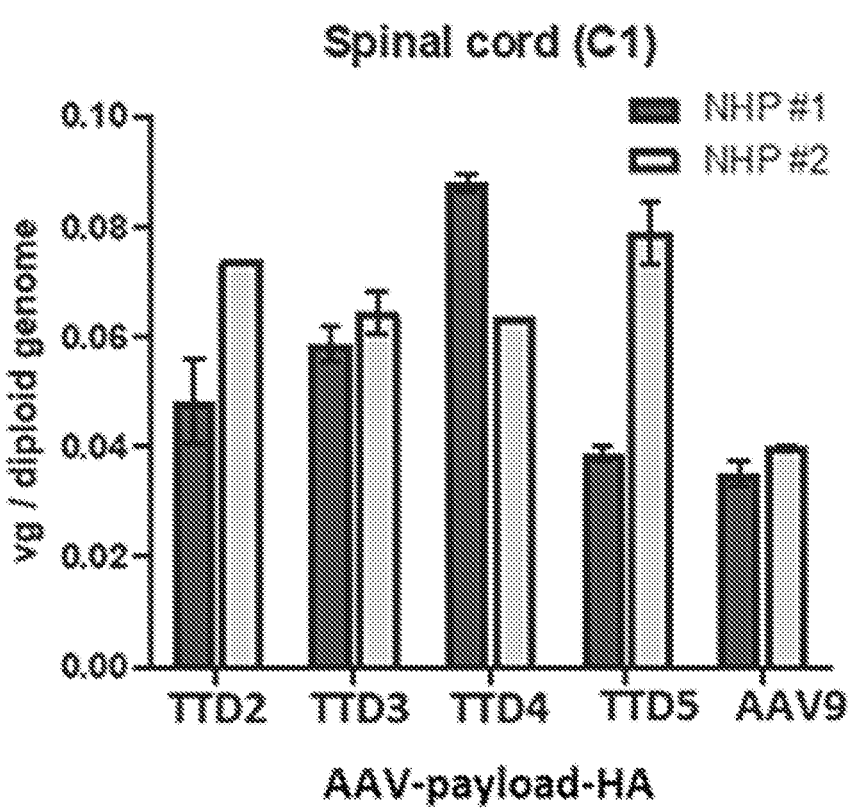
Figure 9B:
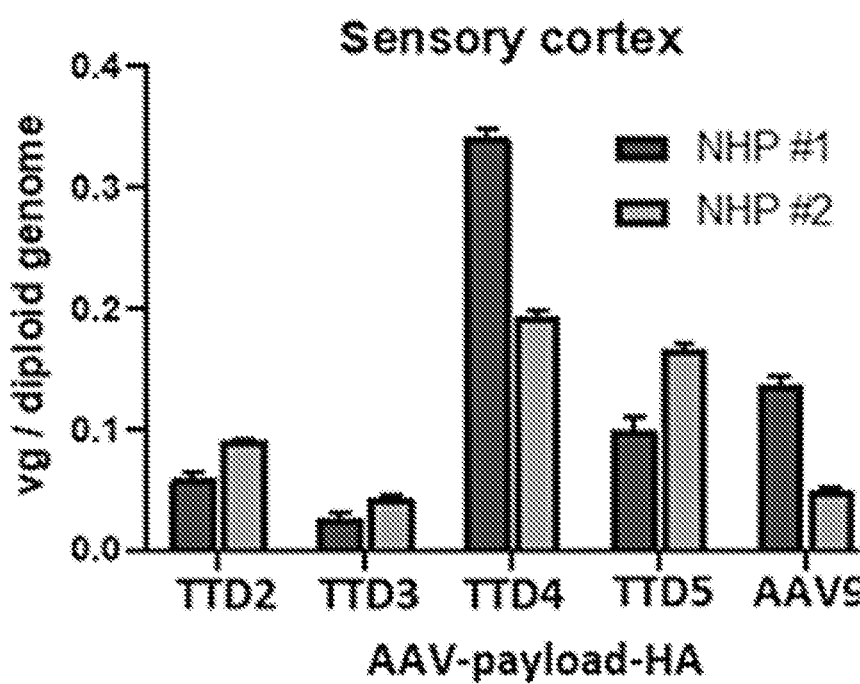
Figure 9C:
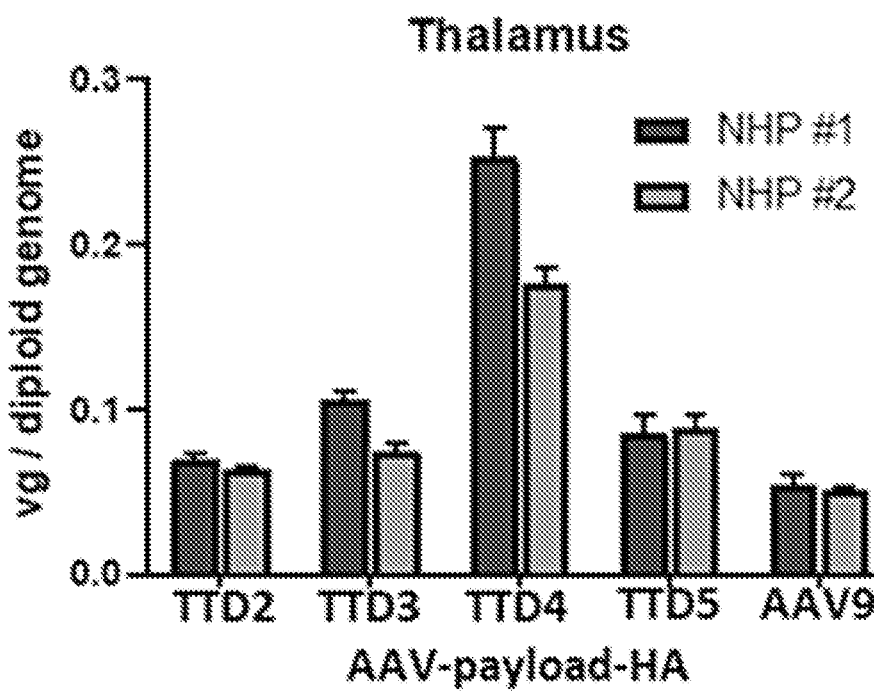
Figure 9C:
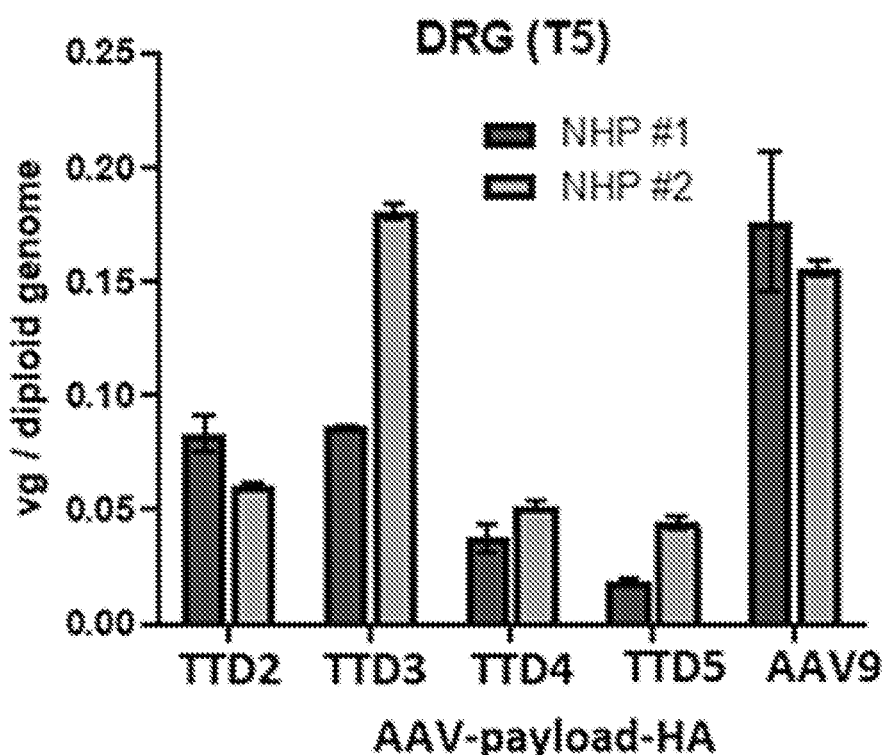
Figure 9D:
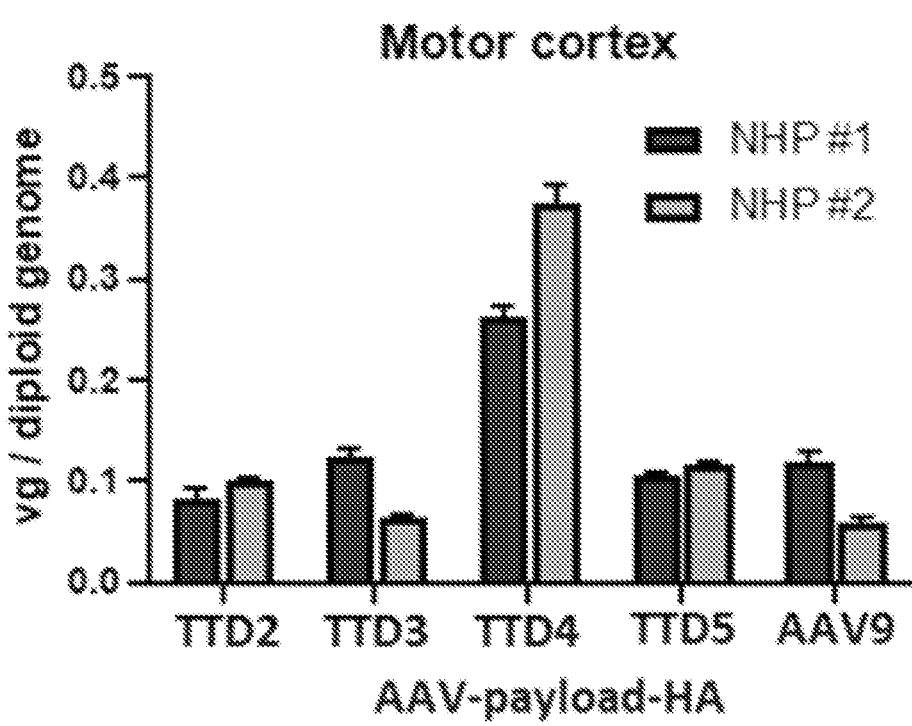
Figure 9D:
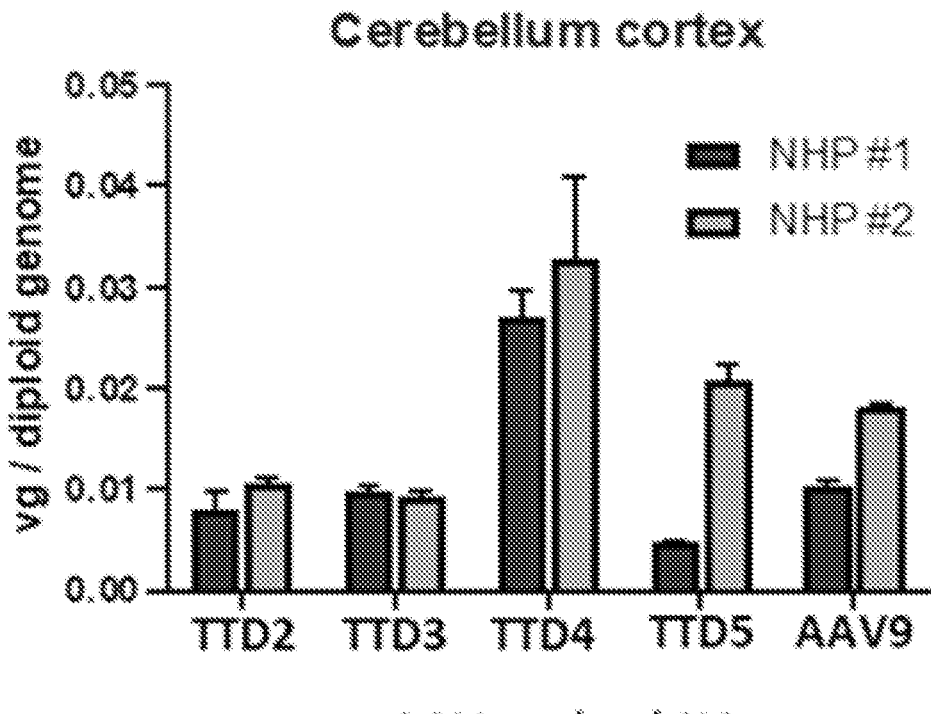

Interestingly, RNA quantification performed in the spinal cord and dorsal root ganglia indicated important differences between the capsid variants. The spinal cord transduction profile was consistent with the brain, with a strong and consistent increase with TTD-003 and TTD-004 capsids, but interestingly the DRG transduction suggested a substantial detargeting of the TTD-004 capsid, whereas the TTD-003 capsid showed a strongly increased RNA expression as shown in FIG. 8.

Total DNA was extracted from the same brain tissues as RNA, and biodistribution was measured by ddPCR using a TAQMAN™ set specific for the CMV promoter sequence. The RNAseP gene was used as a copy number reference. Vector genome (VG) per cell values were determined both by qPCR and ddPCR. Increased biodistribution was observed for the TTD-004 capsid in most brain regions, but surprisingly none of the other candidates showed a significant increase by comparison with AAV9. This apparent contradiction with the RNA quantification data could suggest that some capsids may present improved properties over AAV9 in post-attachment mechanisms rather than strict vector translocation in CNS parenchyma. Interestingly, DNA analysis confirmed the substantial detargeting of TTD-004 capsid from the DRG (FIG. 9A-9D).

Figure 10A:
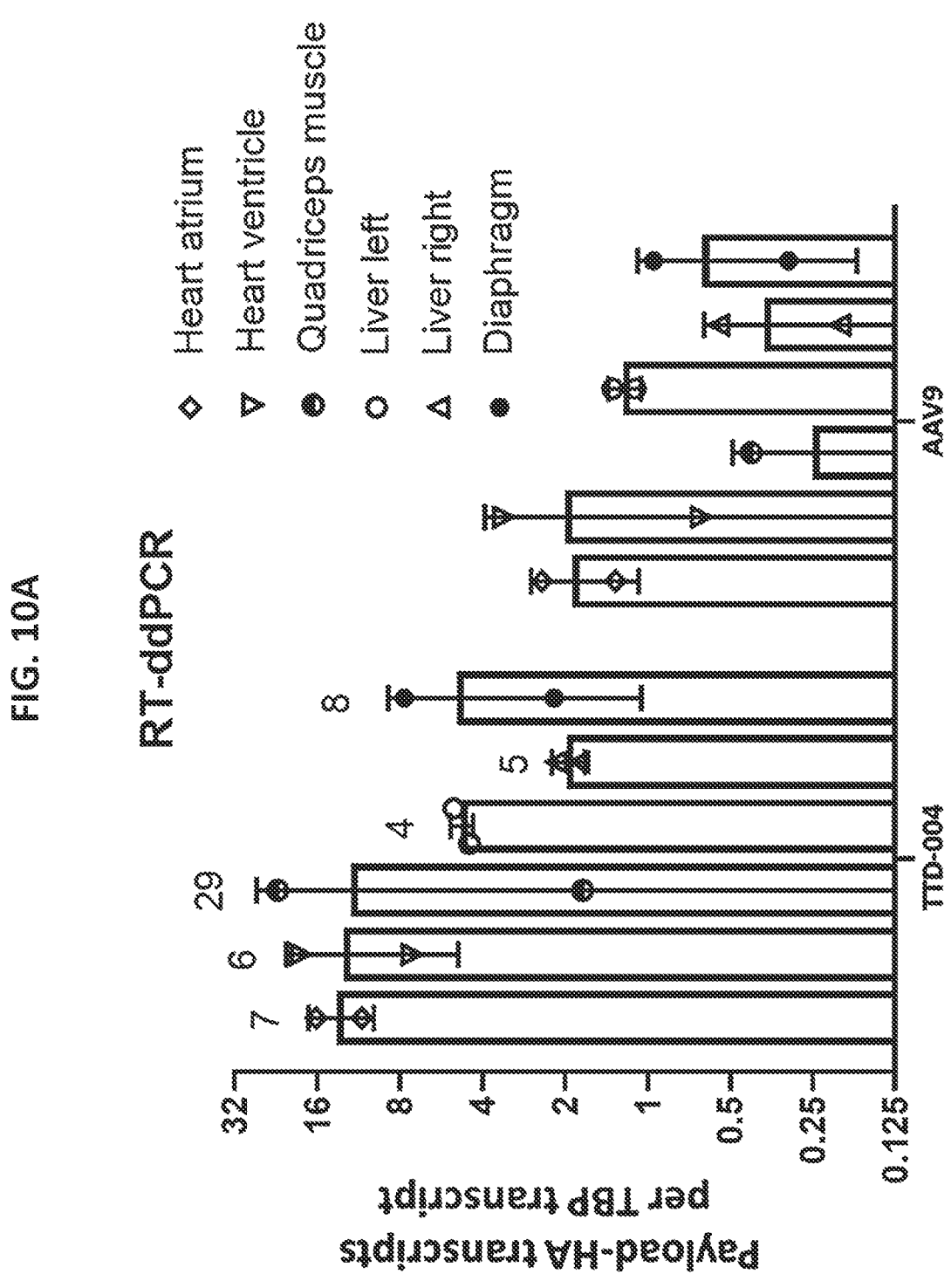
FIG. 10A and FIG. 10B show payload-HA quantification in peripheral tissues following AAV particle transduction as fold over TBP transcript (FIG. 10A) and as fold over AAV9 (FIG. 10B).
Figure 10B:
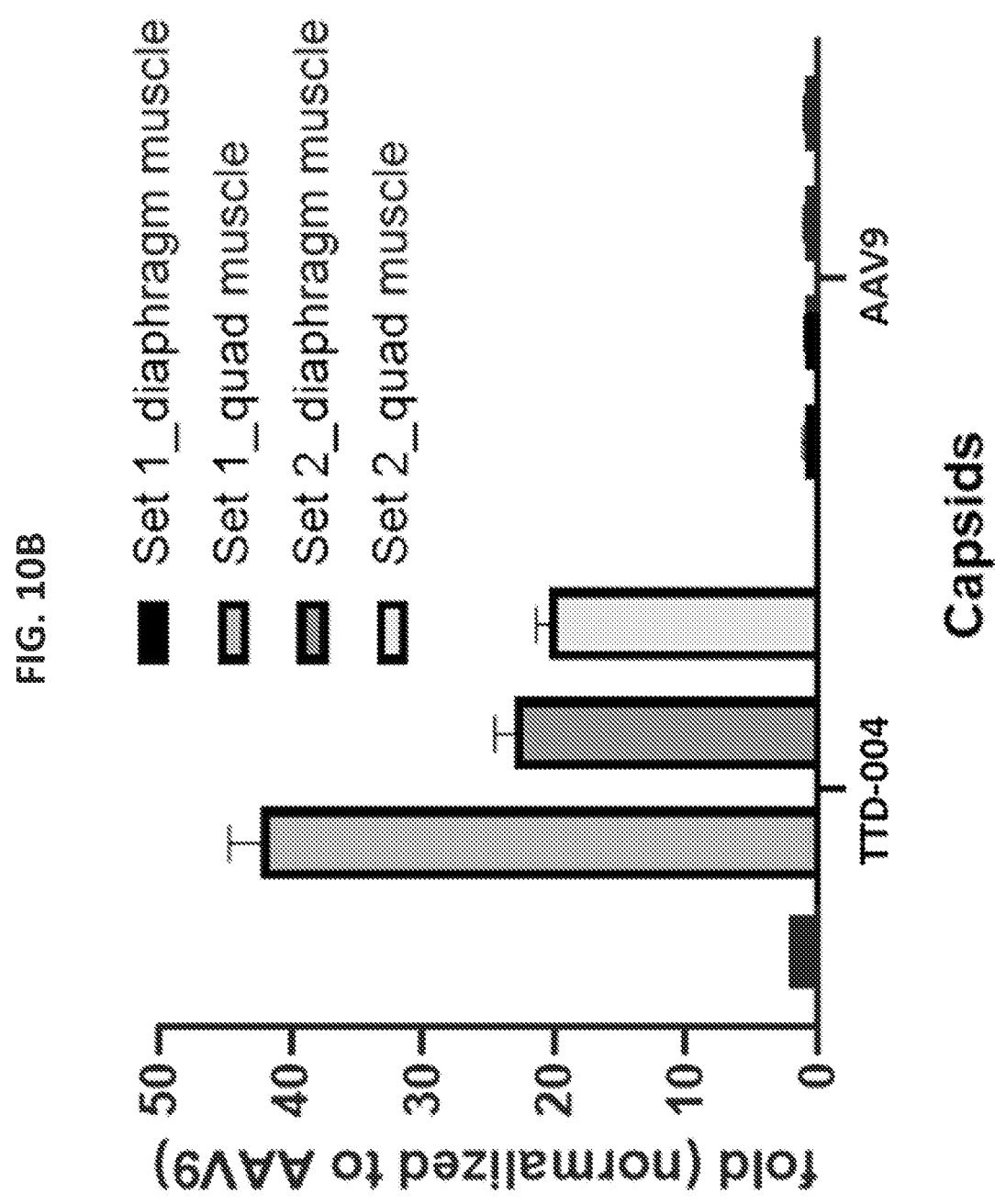
Figure 11A:
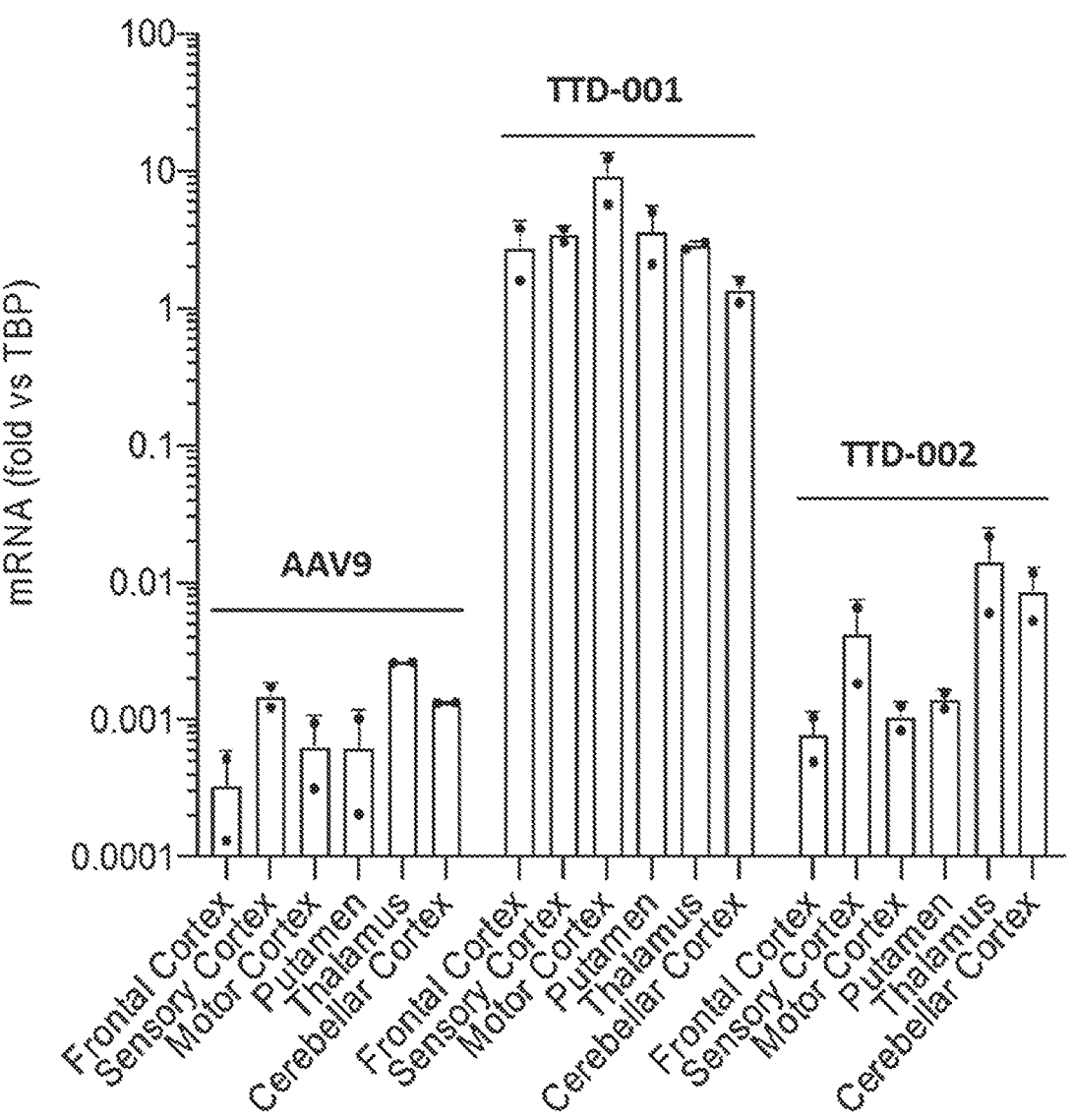
FIG. 11A and FIG. 11B show brain transgene mRNA expression (RT-ddPCR) as fold over TBP (housekeeping gene).
Figure 11B:
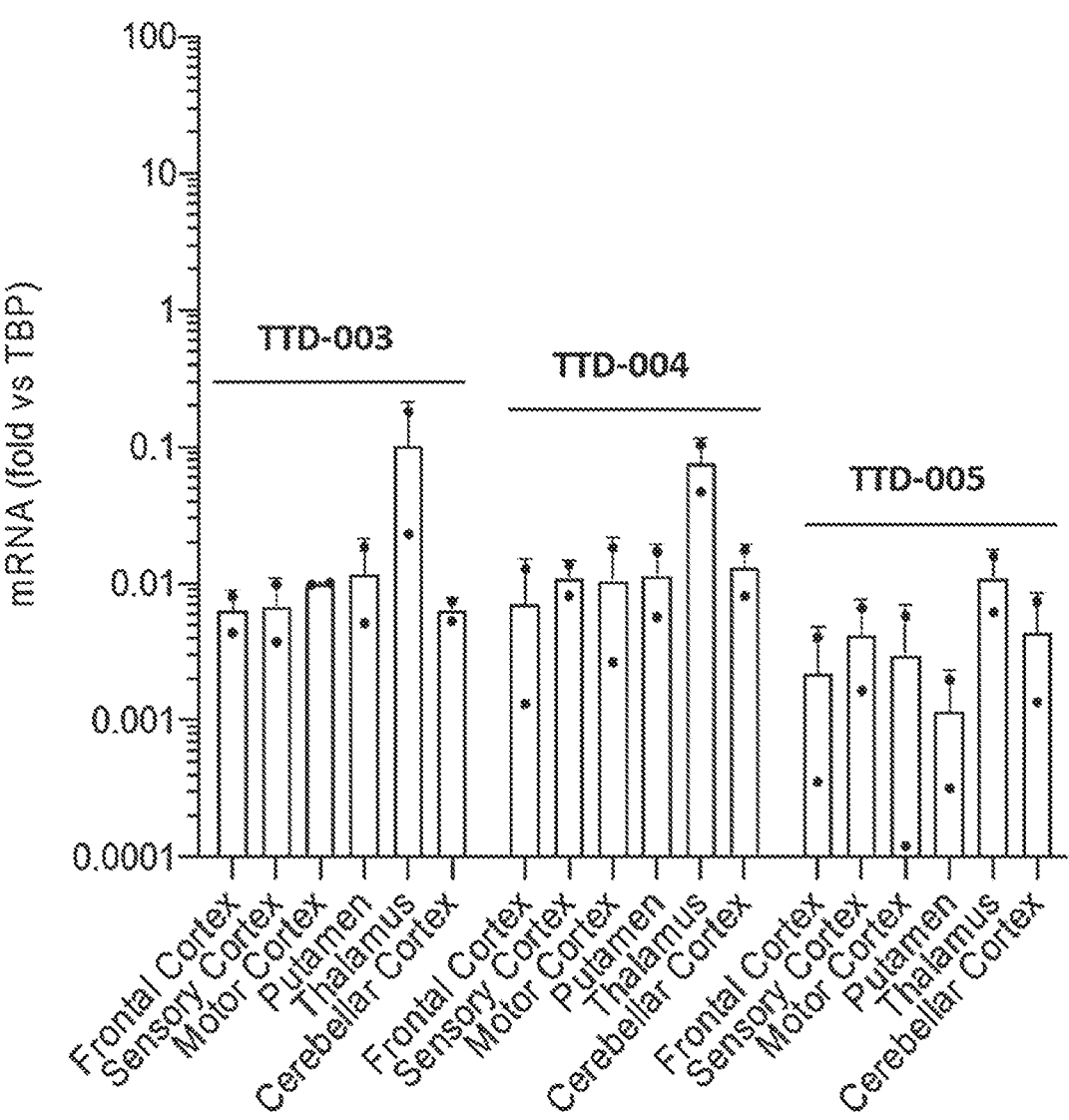
Figure 12A:
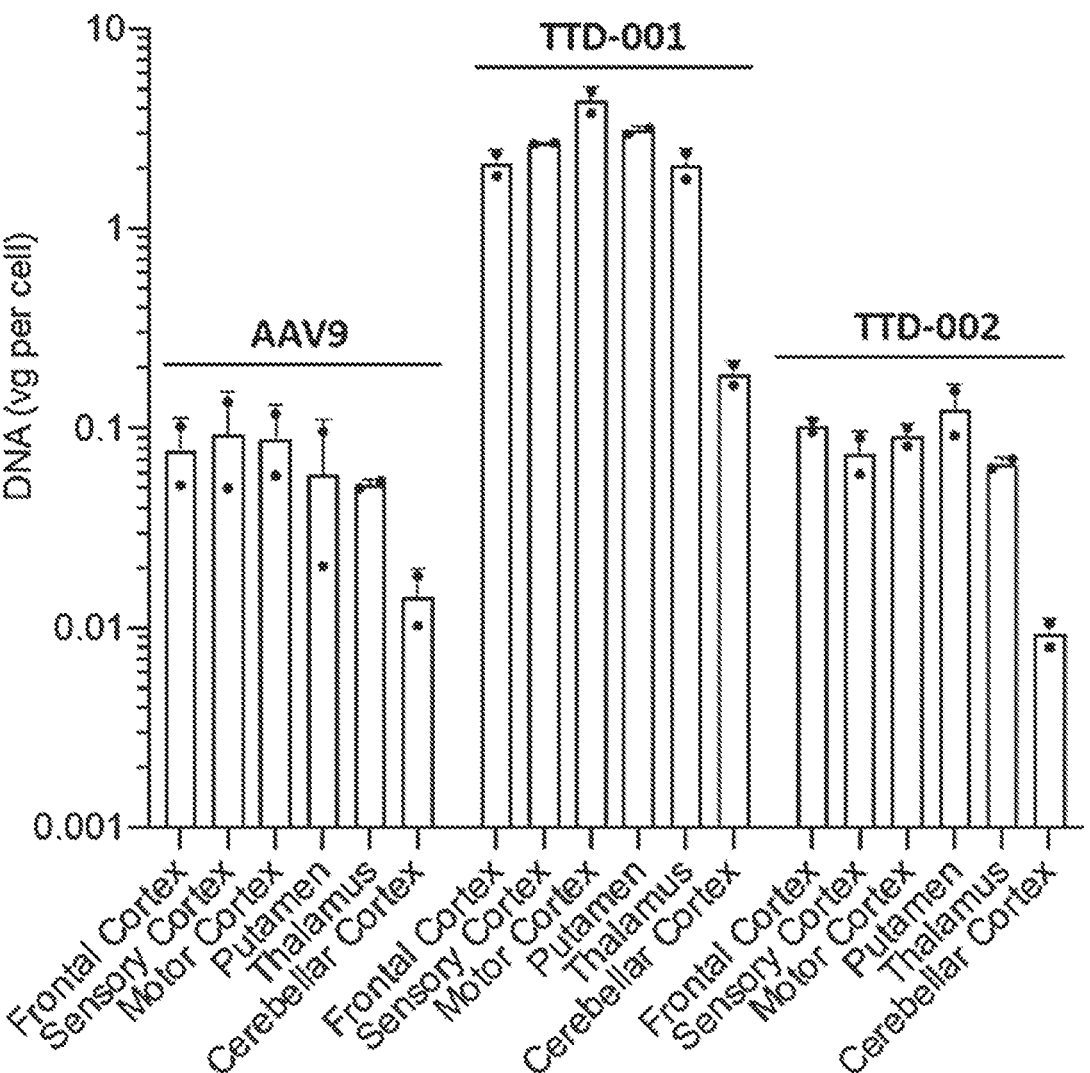
FIG. 12A and FIG. 12B show brain viral DNA biodistribution (ddPCR) as vector genomes per cell.
Figure 12B:
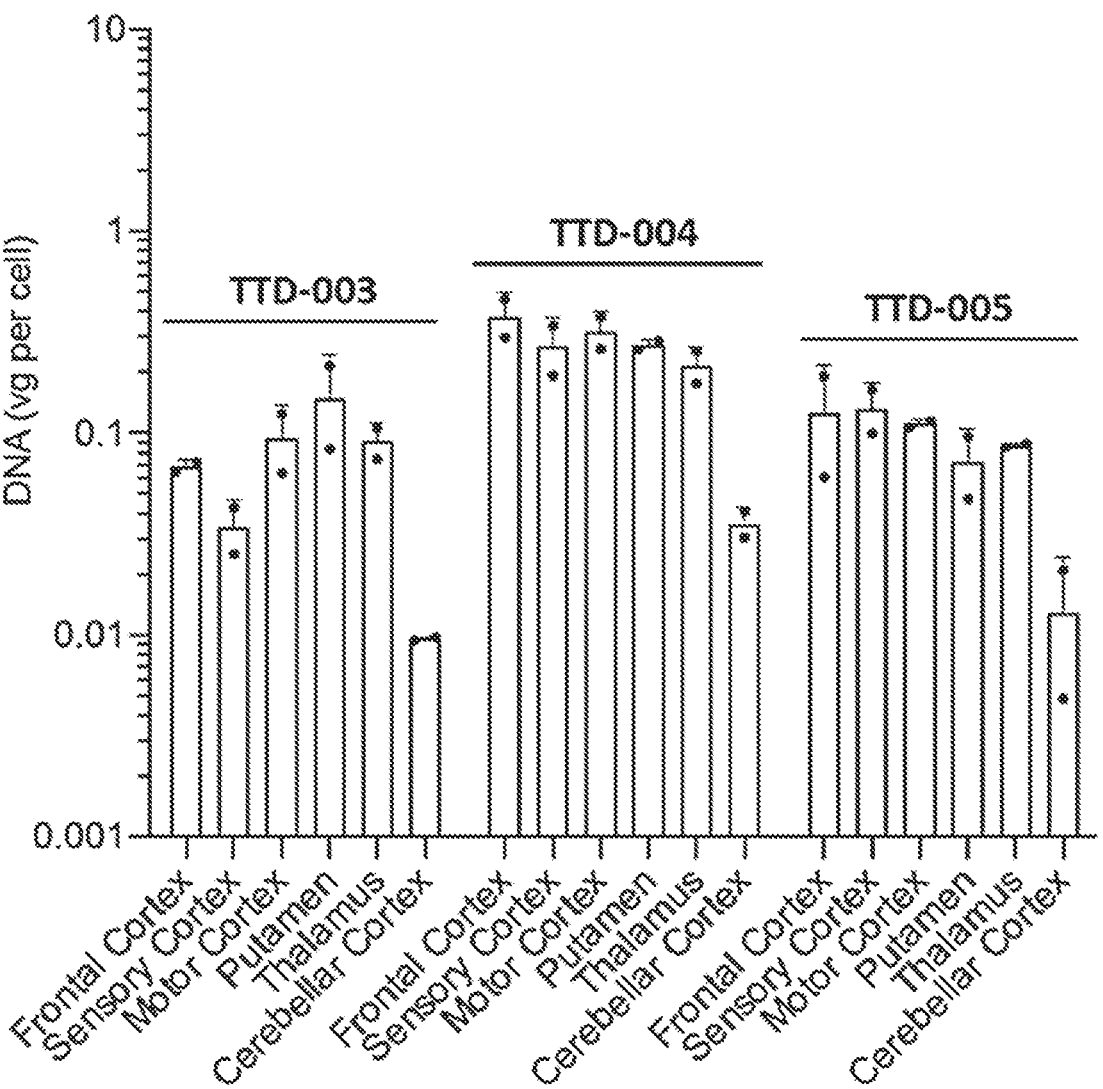
Figure 13A:
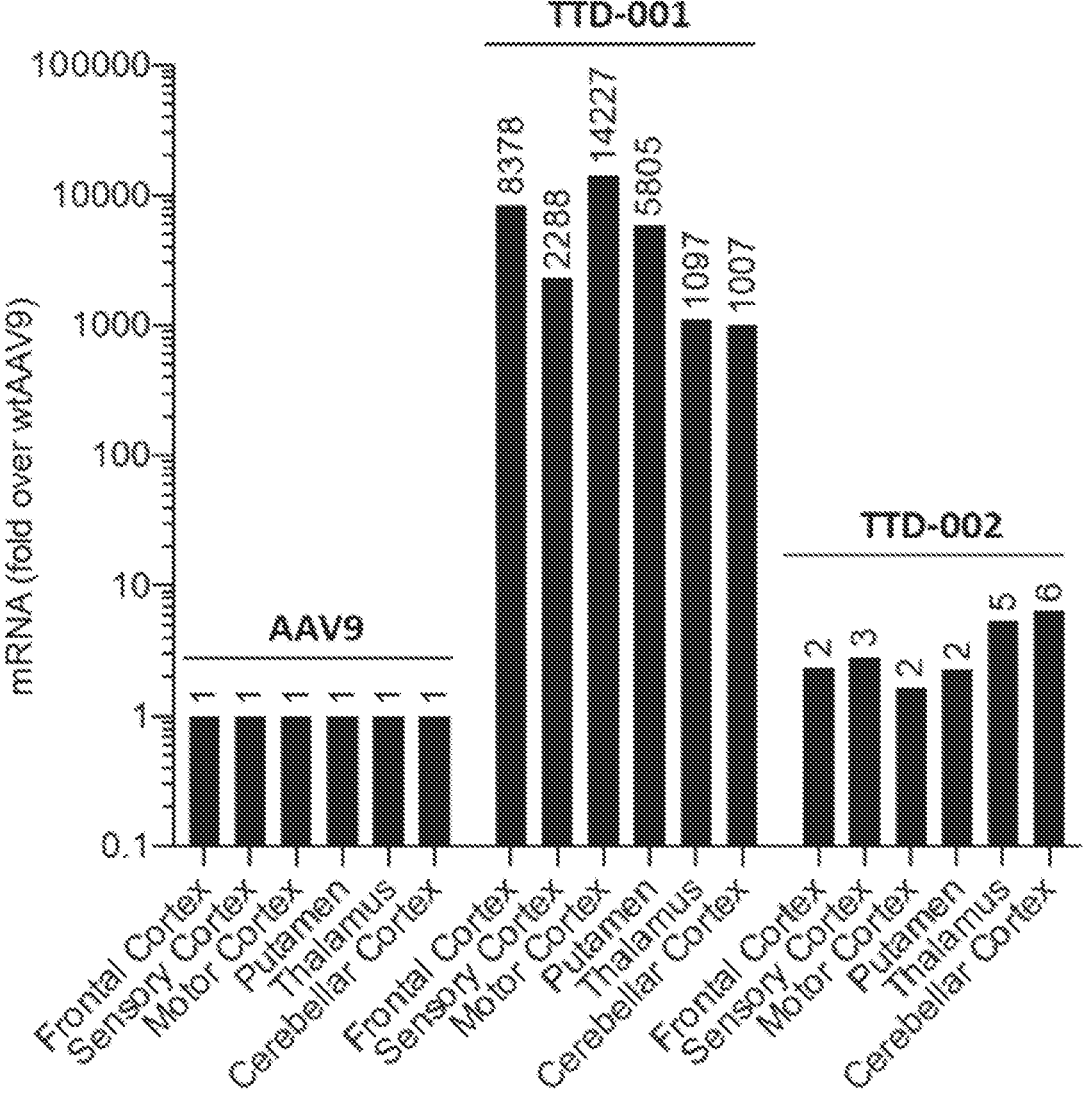
FIG. 13A and FIG. 13B show brain transgene mRNA expression (RT-ddPCR) as fold over AAV9.
Figure 13B:
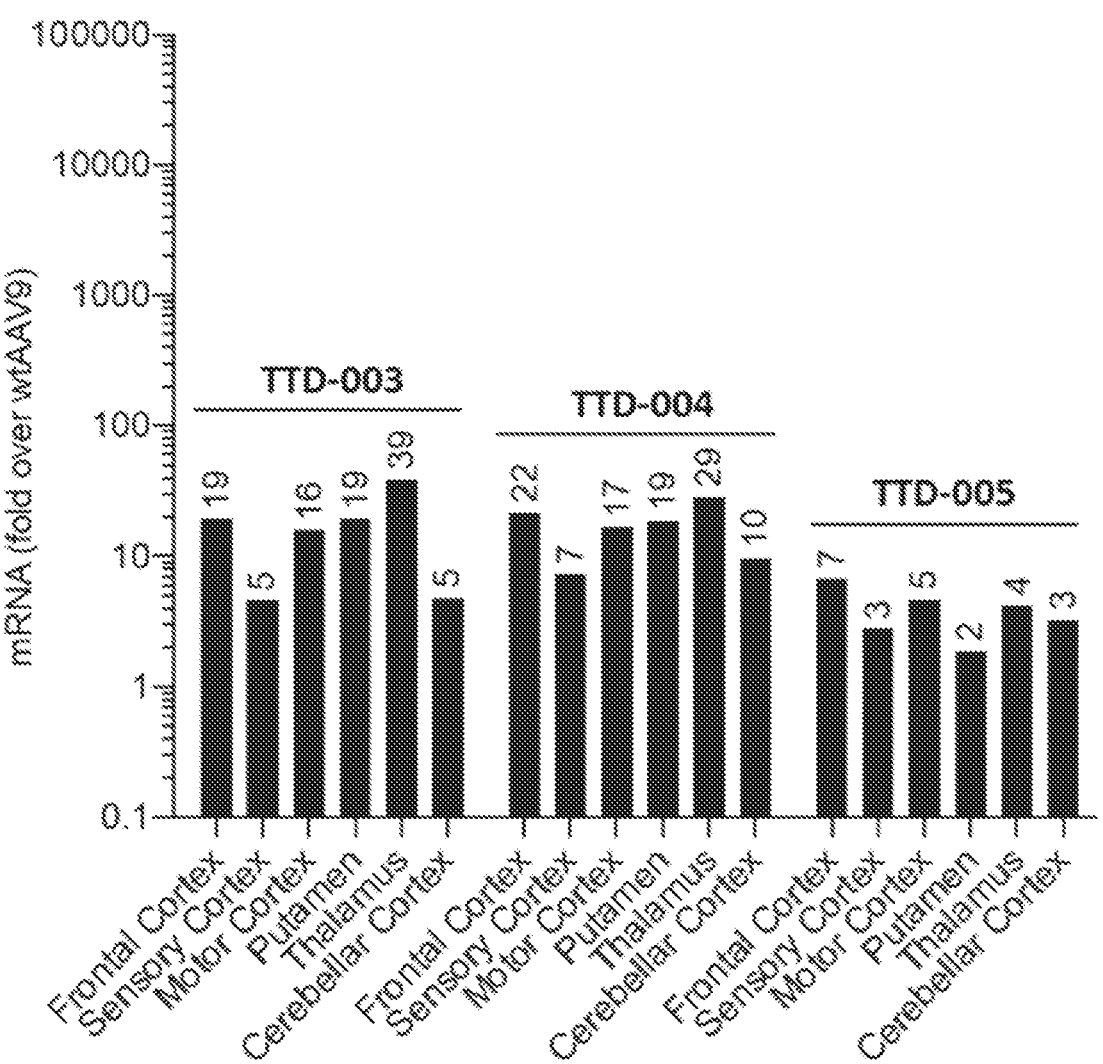
Figure 14A:
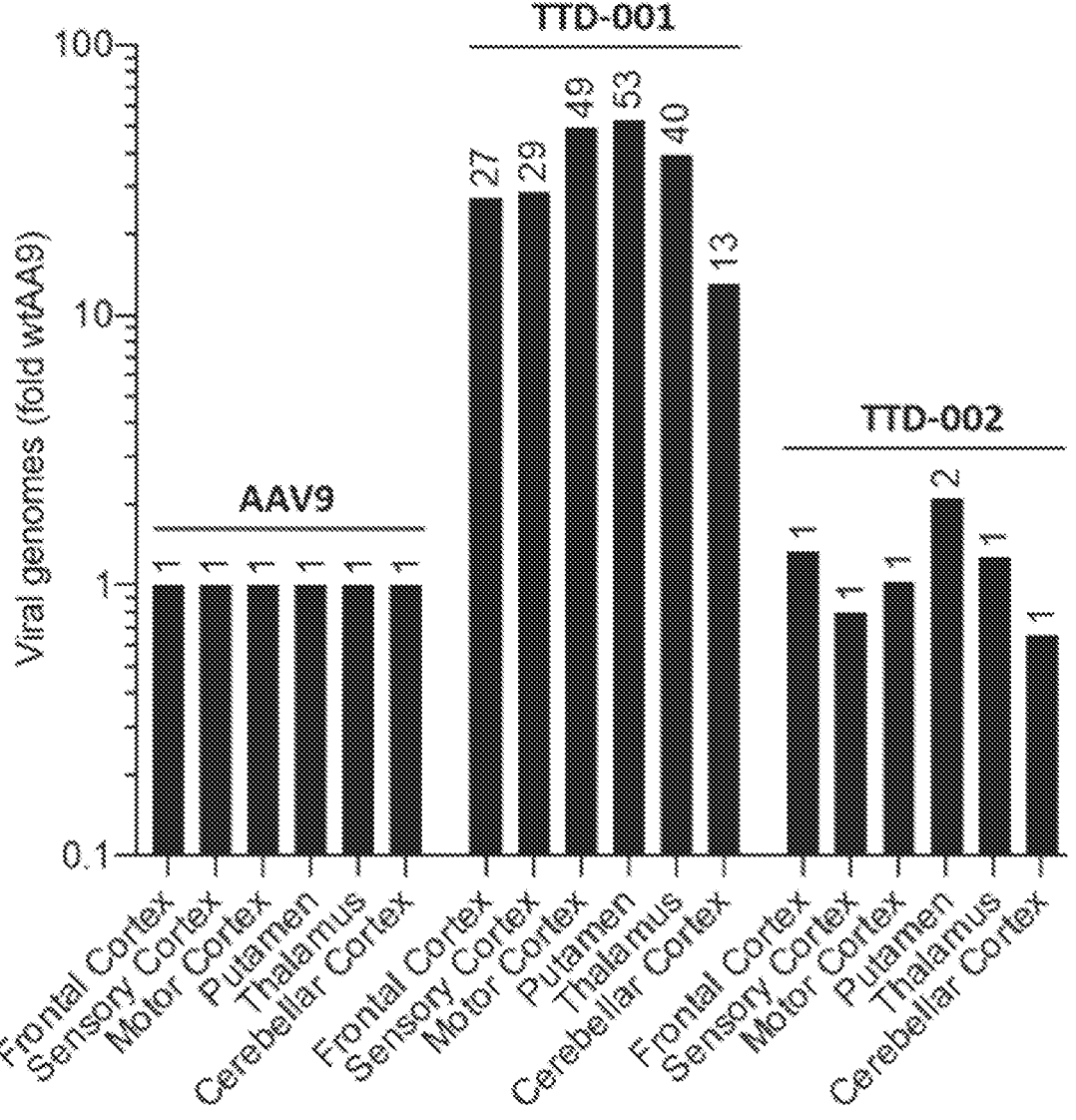
FIG. 14A and FIG. 14B show brain viral DNA biodistribution (ddPCR) as fold over AAV9.
Figure 14B:
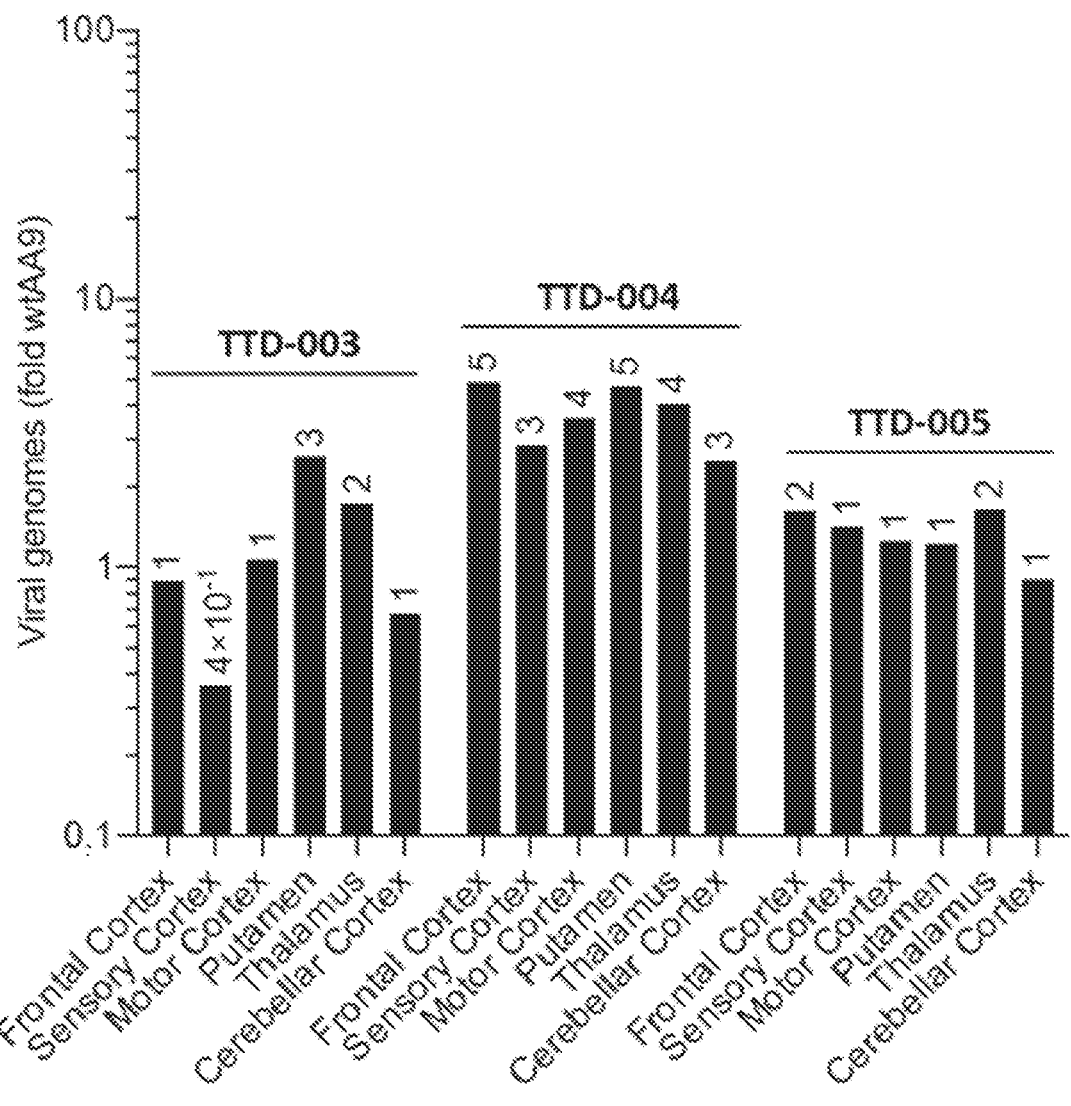
Figure 15A:
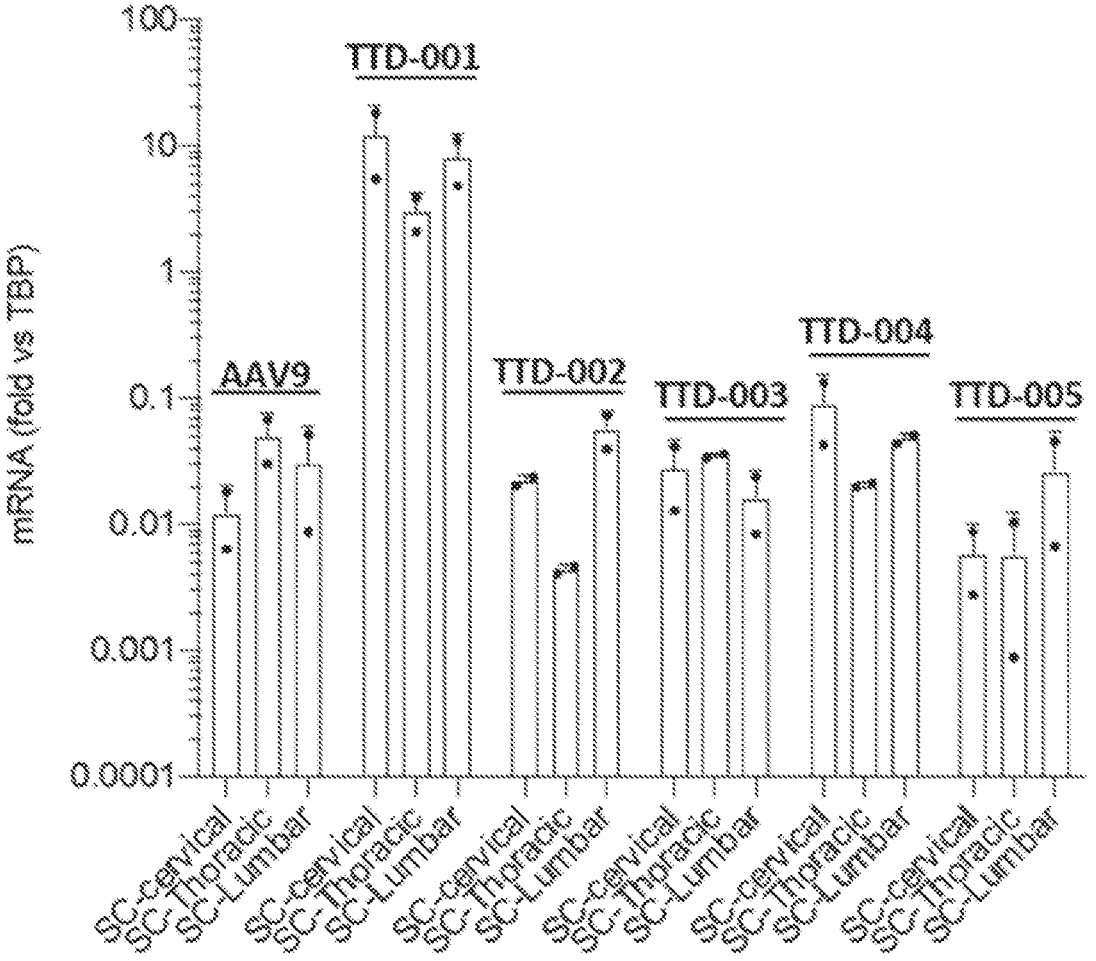
FIG. 15A and FIG. 15B show spinal cord (FIG. 15A) and DRG (FIG. 15B) transgene mRNA expression as fold over TATA box binding protein.
Figure 15B:
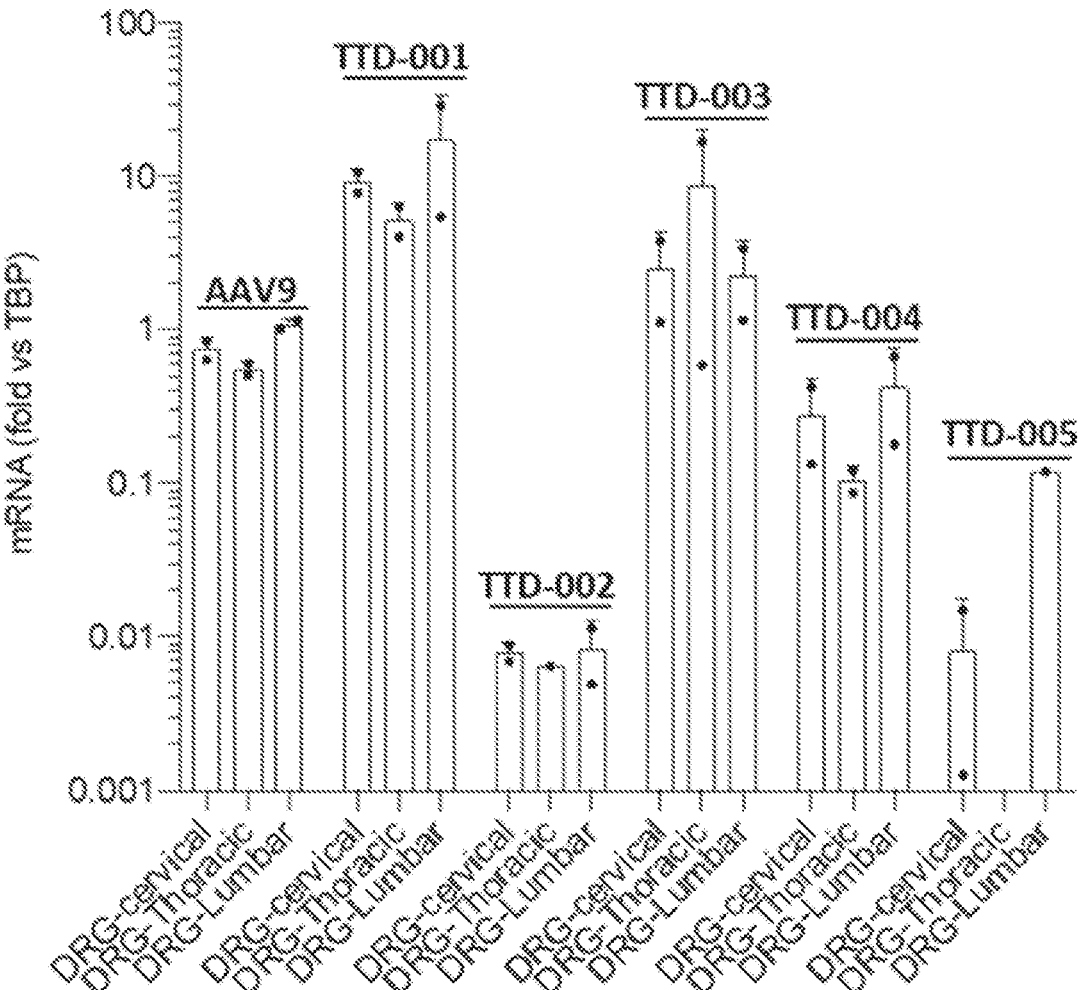
Figure 16A:
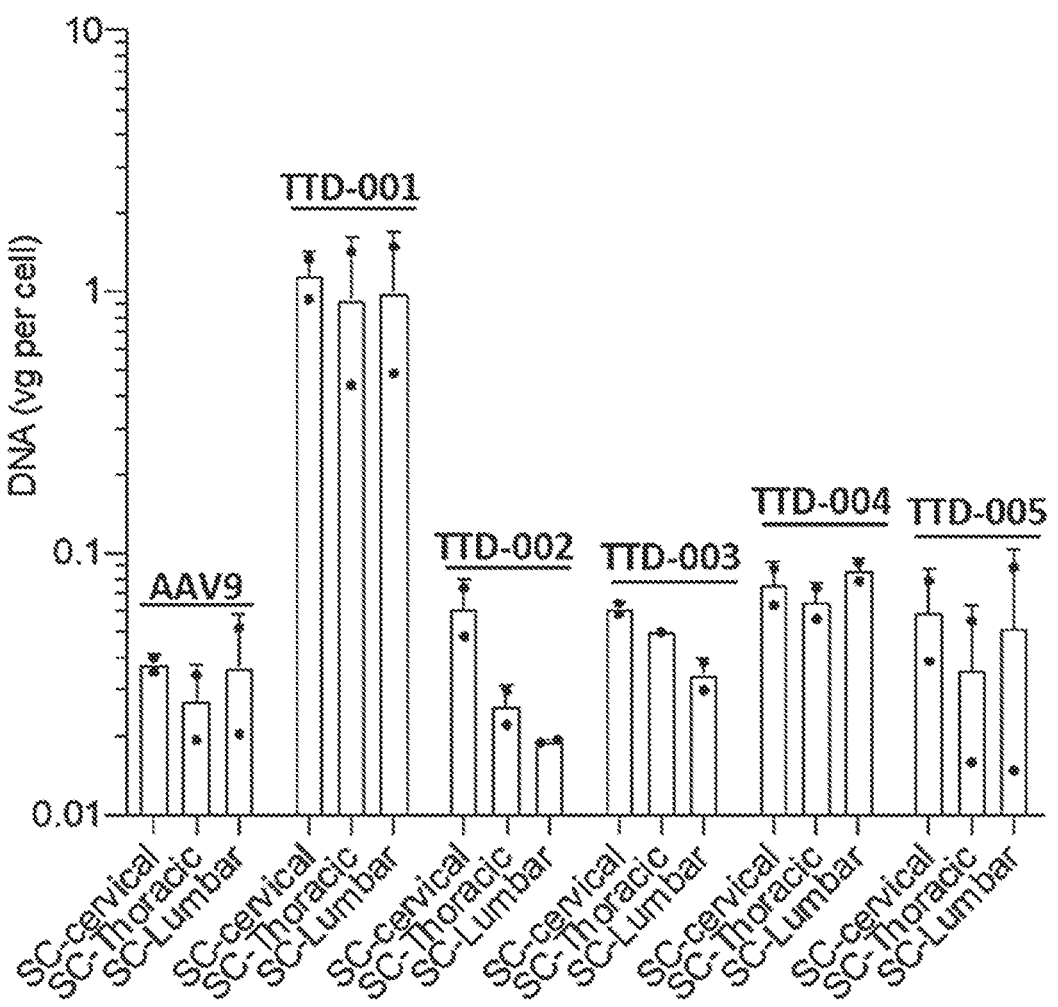
FIG. 16A and FIG. 16B show spinal cord (FIG. 16A) and DRG (FIG. 16B) viral genome biodistribution as vector genomes per cell.
Figure 16B:
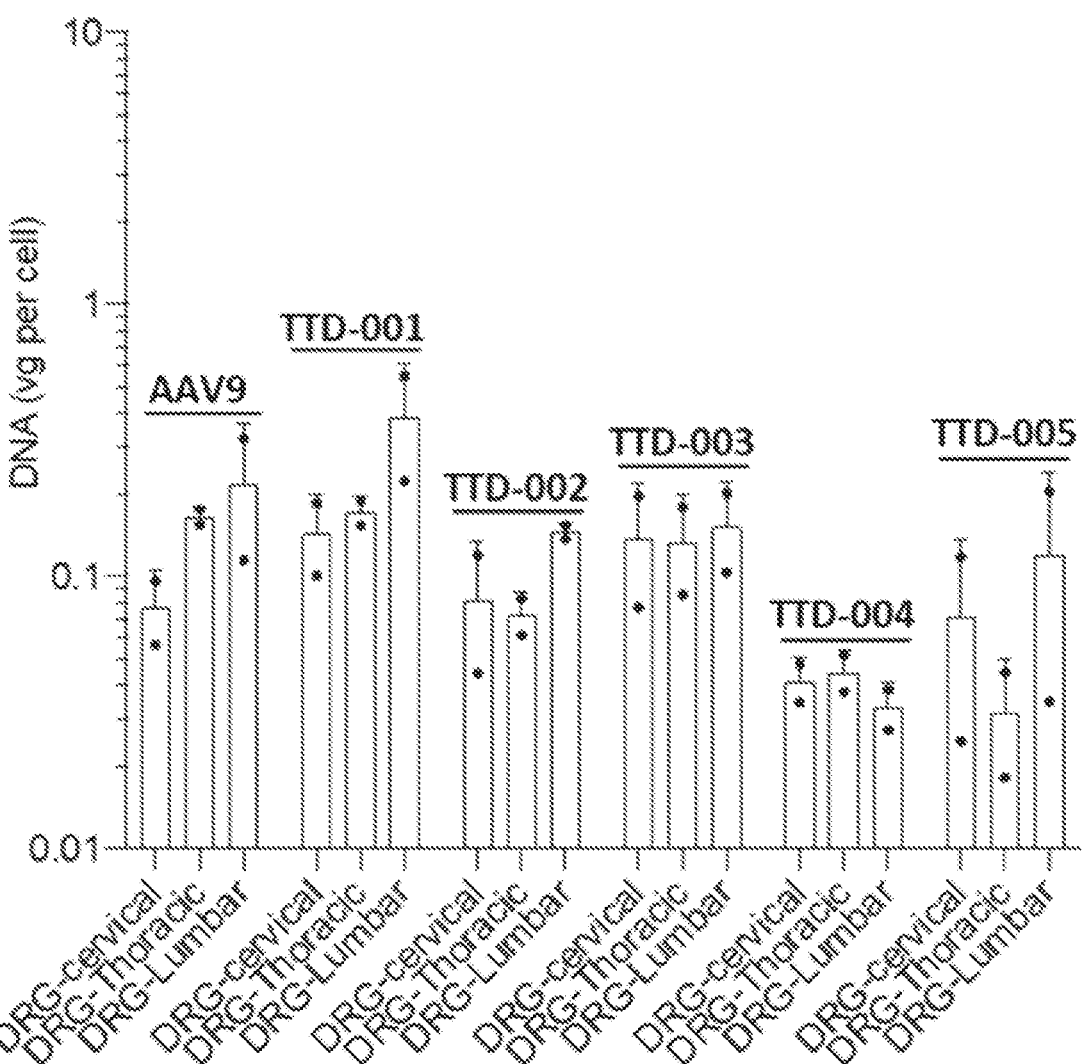
Figure 17A:
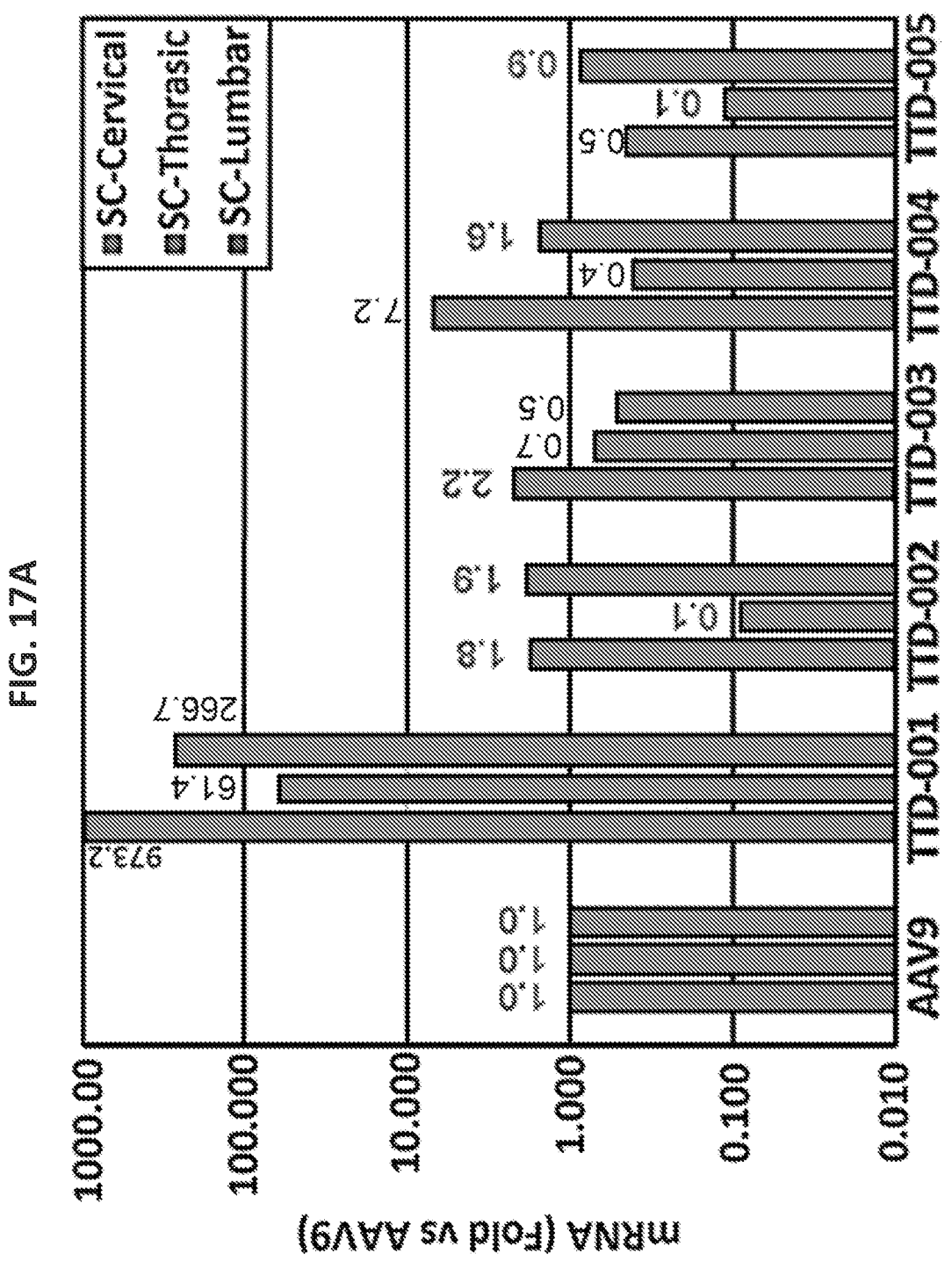
Figure 18B:
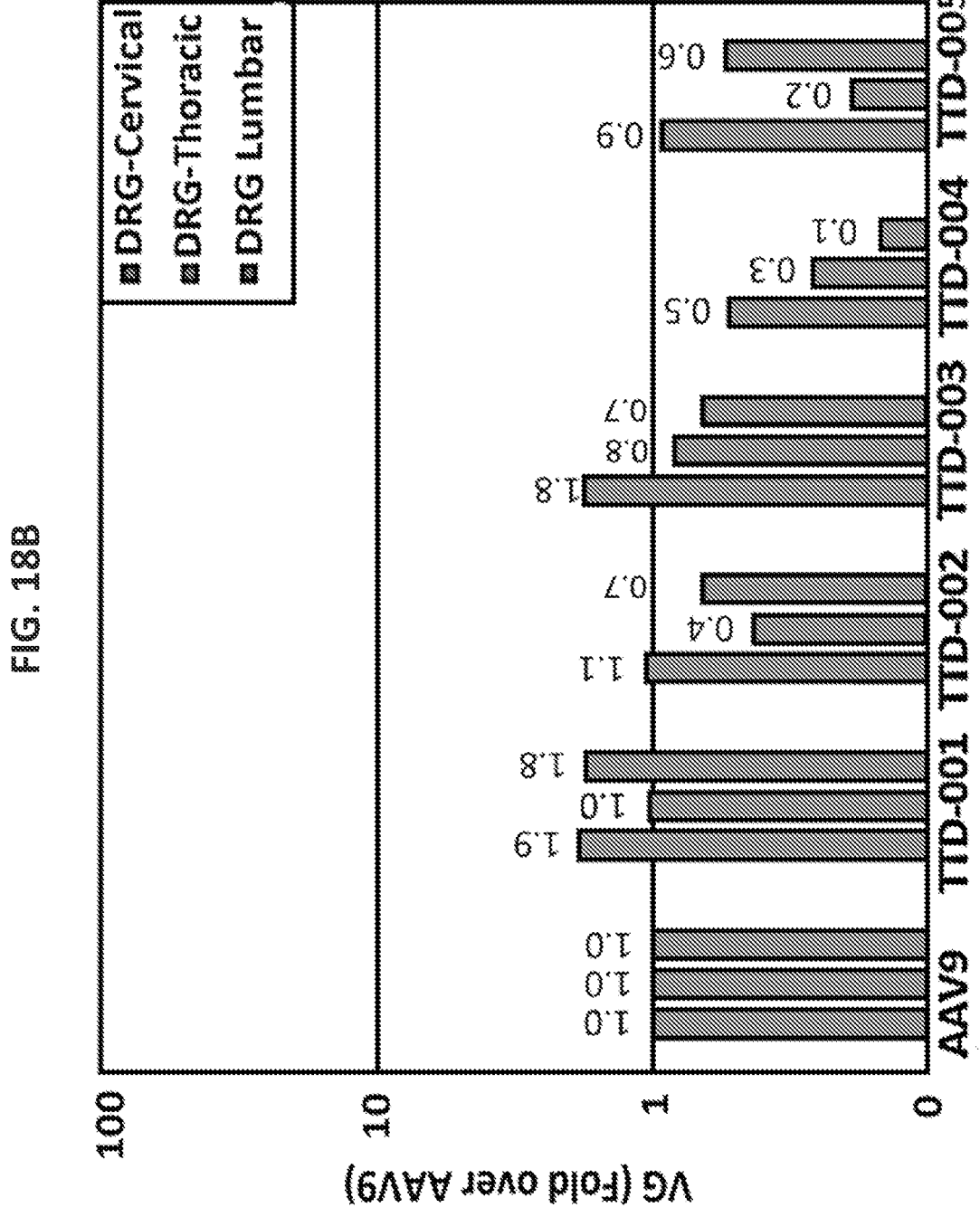
Figure 19B:
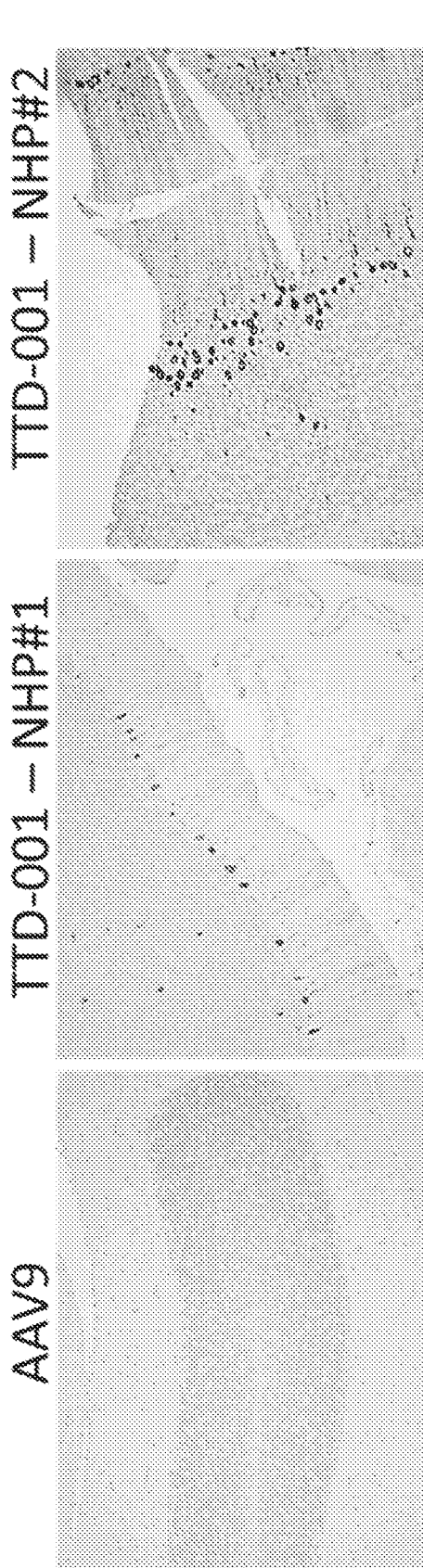
Figure 19C:
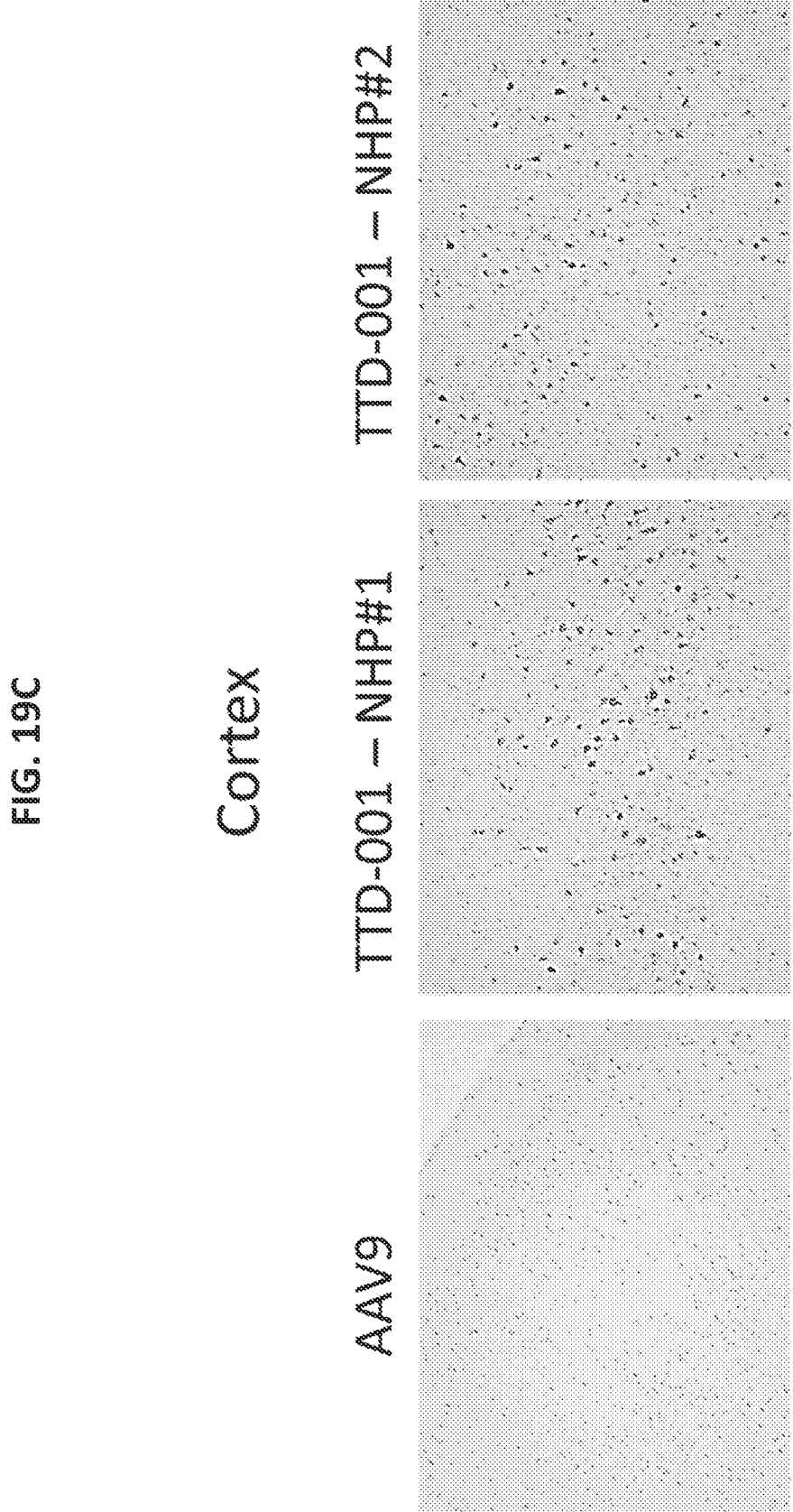
Figure 19D:
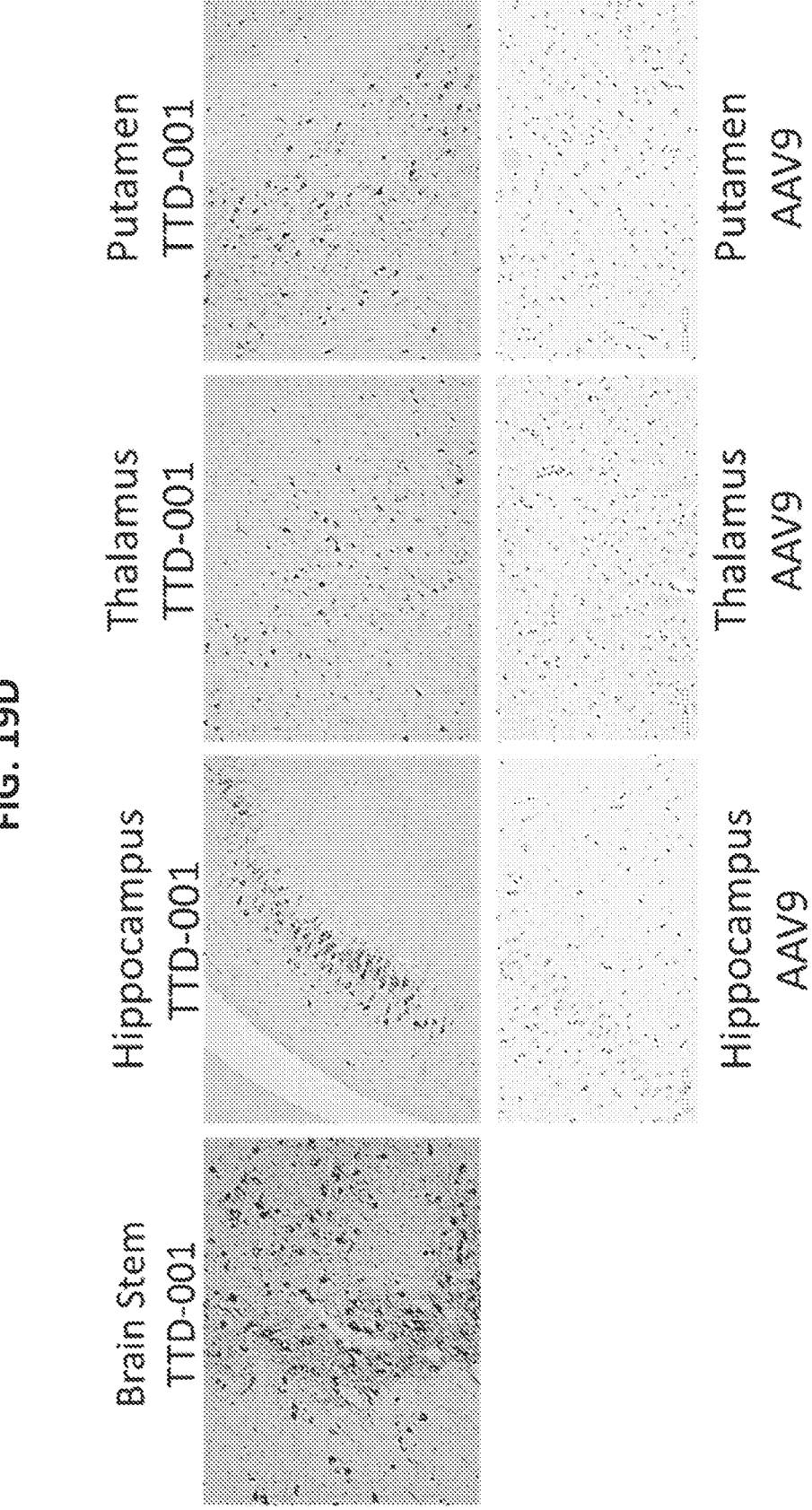
Figure 19E:
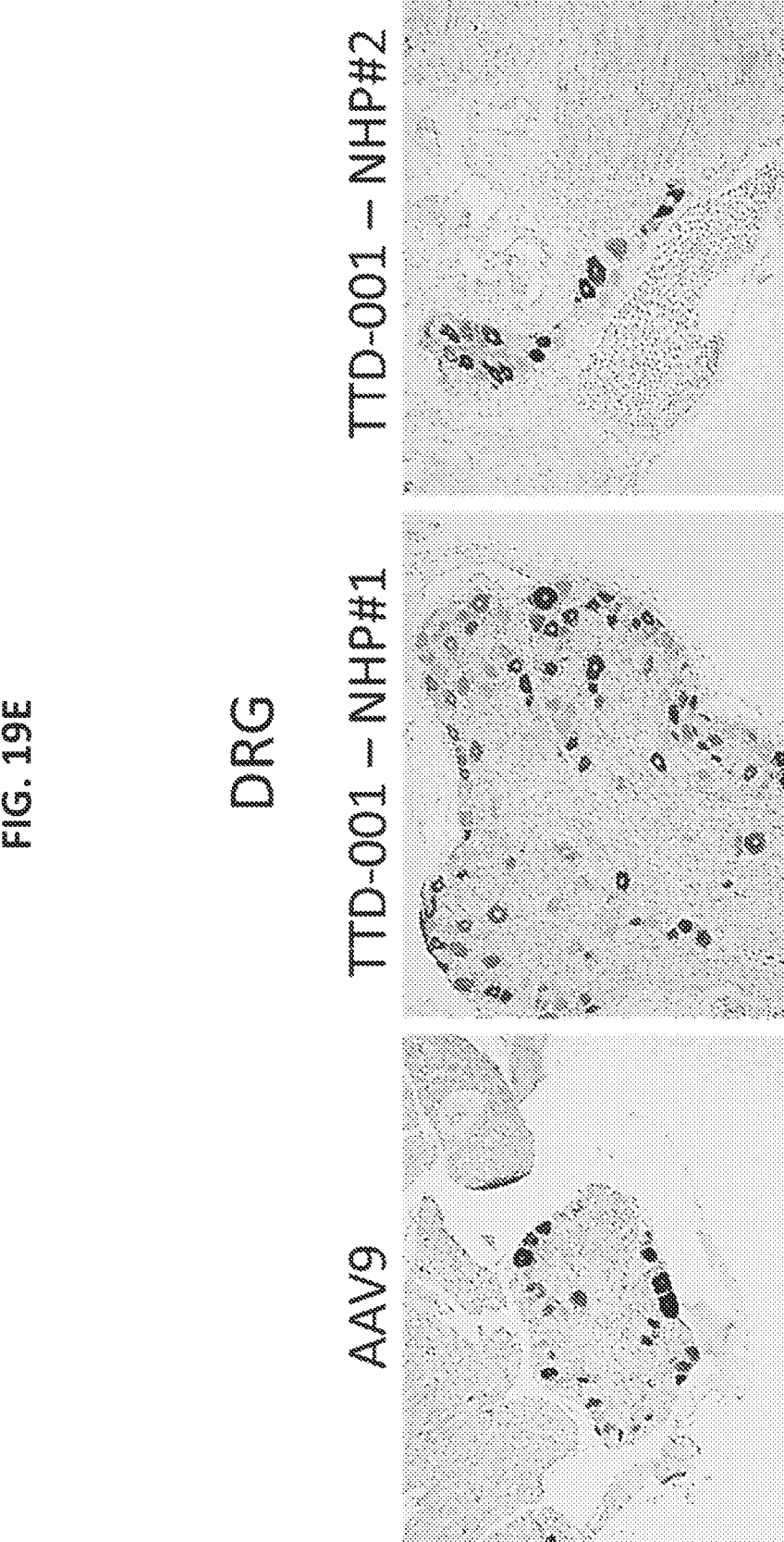

To further explore the behavior of capsid variant TTD-004, viral genome (VG) quantification was completed from tissues collected from heart atrium, heart ventricle, quadriceps muscle, liver (left and right) and diaphragm and compared to vector genome presence as delivered by AAV9 in the same tissues. The data are shown in FIGS. 10A and B.

For TTD-003 and TTD-004 initial immunohistochemical analyses demonstrated the presence of payload-HA to a greater extent than seen with AAV9 delivery in cerebellar tissue, including in the dentate nucleus. Immunohistochemistry confirmed the de-targeting of the dorsal root ganglia for capsid variant TTD-004 as compared to TTD-003 and AAV9.

Data for each of the variants were compiled as an average mRNA (fold over TBP) or DNA (VG per cell) quantification per capsid variant per tissue as shown in Table 8 below and FIG. 11A-11B and FIG. 12A-12B, respectively.

TABLE 8

| | | | | Characterization of exemplary capsid variants | | | |
|---|---|---|---|---|---|---|---|
| Measure | Tissue | AAV9 | TTD-001 | TTD-002 | TTD-003 | TTD-004 | TTD-005 |
| mRNA | Frontal Cortex | 0.000325065 | 2.7232575 | 0.000768179 | 0.006268831 | 0.007076252 | 0.002204024 |
| mRNA | Sensory Cortex | 0.001486245 | 3.400055 | 0.00417739 | 0.006788644 | 0.010976612 | 0.004139604 |
| mRNA | Motor Cortex | 0.00063318 | 9.00819 | 0.001050247 | 0.009954825 | 0.010522399 | 0.002942249 |
| mRNA | Putamen | 0.000612759 | 3.557205 | 0.001395549 | 0.011832671 | 0.011476176 | 0.001150153 |
| mRNA | Thalamus | 0.002610992 | 2.863635 | 0.013937891 | 0.101411445 | 0.07565653 | 0.01100289 |
| mRNA | Cerebellar Cortex | 0.00133497 | 1.3439 | 0.008517779 | 0.006396677 | 0.012964181 | 0.004382119 |
| mRNA | Dentate Nucleus | 0.001364954 | 0.963955 | — | — | — | — |
| mRNA | Caudate | 0.000352281 | 1.3026 | — | 0.003259804 | 0.00634117 | — |
| mRNA | Hippocampus | 0.000311824 | 0.407015 | — | — | — | — |
| mRNA | SC-cervical | 0.012205449 | 11.877762 | 0.022004264 | 0.026994764 | 0.088316491 | 0.005773054 |
| mRNA | SC-Thoracic | 0.048833465 | 2.9974295 | 0.004360318 | 0.035118928 | 0.020543776 | 0.005629959 |
| mRNA | SC-Lumbar | 0.029887407 | 7.969603 | 0.056231995 | 0.016033388 | 0.047713563 | 0.026324154 |
| mRNA | DRG-cervical | 0.74570895 | 9.274951 | 0.007897714 | 2.47872652 | 0.280868887 | 0.008122233 |
| mRNA | DRG-Thoracic | 0.5559061 | 5.22606 | 0.006456564 | 8.721845271 | 0.104701895 | — |
| mRNA | DRG-Lumbar | 1.089758 | 17.308436 | 0.008247771 | 2.271300217 | 0.426704698 | 0.119974244 |
| mRNA | Lung | 0.004807149 | 0.000546842 | — | — | 0.013744781 | — |
| mRNA | Pancreas | — | — | — | — | — | — |
| mRNA | Colon | 0.017962678 | 0.005041385 | — | — | 0.183862903 | — |
| mRNA | Kidney | 0.043825993 | 0.006649157 | — | — | 0.041234576 | — |
| mRNA | Liver | 0.674478605 | 0.253188648 | — | — | 2.578654807 | — |
| mRNA | Adrenal | — | — | — | — | — | — |
| mRNA | Spleen | 0.014066875 | 0.000955981 | — | — | 0.013435626 | — |
| mRNA | Heart | 1.323389668 | 0.132477314 | — | — | 5.587929805 | — |
| mRNA | Quadriceps | 0.116623509 | — | — | — | 4.527799743 | — |
| mRNA | Diaphragm | 0.250001109 | — | — | — | 1.936435215 | — |
| DNA | Frontal Cortex | 0.07713 | 2.104843 | 0.10252 | 0.068367 | 0.380429 | 0.1257545 |
| DNA | Sensory Cortex | 0.093003 | 2.679886 | 0.07443 | 0.034016 | 0.2670975 | 0.132503 |
| DNA | Motor Cortex | 0.08796 | 4.3437625 | 0.0913085 | 0.094401 | 0.318999 | 0.1110695 |
| DNA | Putamen | 0.0581365 | 3.07904 | 0.12326 | 0.1497635 | 0.2731175 | 0.0715295 |
| DNA | Thalamus | 0.0524055 | 2.076863 | 0.0664225 | 0.090511 | 0.214999 | 0.086863 |
| DNA | Cerebellar Cortex | 0.014238 | 0.186361 | 0.0092915 | 0.009578 | 0.0356345 | 0.0128655 |
| DNA | Dentate Nucleus | 0.025042 | 0.1861975 | 0.210238 | 0.041906 | 0.106107 | 0.055287 |
| DNA | Caudate | 0.079294 | 3.9433175 | — | 0.0529005 | 0.2451035 | — |
| DNA | Hippocampus | 0.095436 | 1.760891 | 0.205433 | 0.368645 | 1.335324 | 0.432829 |
| DNA | SC-cervical | 0.0376 | 1.143863 | 0.061085 | 0.061535 | 0.07573 | 0.05885 |
| DNA | SC-Thoracic | 0.02692 | 0.933734 | 0.025955 | 0.05011 | 0.064915 | 0.0355 |
| DNA | SC-Lumbar | 0.03615 | 0.992728 | 0.019125 | 0.034175 | 0.085165 | 0.051475 |

TABLE 8-continued

| | | | | Characterization of exemplary capsid variants | | |
| Measure | Tissue | AAV9 | TTD-001 | TTD-002 | TTD-003 | TTD-004 | TTD-005 |
|---|---|---|---|---|---|---|---|
| DNA | DRG-cervical | 0.0765 | 0.14319 | 0.08196 | 0.13722 | 0.04115 | 0.071625 |
| DNA | DRG-Thoracic | 0.165865 | 0.172363 | 0.07202 | 0.133455 | 0.04444 | 0.03139 |
| DNA | DRG-Lumbar | 0.218725 | 0.385712 | 0.146115 | 0.153205 | 0.032875 | 0.12034 |
| DNA | Lung | 1.085639916 | 3.72 | 0.958576278 | 0.700015423 | 1.22442329 | 0.919823152 |
| DNA | Pancreas | 0.256670617 | 20.535 | 0.320558325 | 0.240633195 | 0.067860607 | 0.004802583 |
| DNA | Colon | 0.053867646 | 3.405 | 1.179065405 | 0.348969617 | 0.116867365 | 0.015288464 |
| DNA | Kidney | 0.896656371 | 26.635 | 4.861362029 | 0.532746958 | 0.386522209 | 7.973793288 |
| DNA | Liver | 207.332334 | 217.64 | 111.910319 | 193.8349405 | 448.5980021 | 213.0317219 |
| DNA | Adrenal | 1.647725996 | 0.69 | 1.561129869 | 1.871878 | 1.269473156 | 0.847293047 |
| DNA | Spleen | 14.93815481 | 20.43565 | 51.70294001 | 22.79095714 | 6.514778227 | 45.91987284 |
| DNA | Heart | 2.012377817 | 14.49 | 0.757528914 | 1.780956673 | 3.814571986 | 0.44694144 |
| DNA | Quadriceps | 0.724278943 | 1.285 | 0.476250457 | 1.366015493 | 5.611203726 | 0.646197937 |
| DNA | Diaphragm | — | 1.06 | — | — | — | — |

When calculated as fold over AAV9 the data were as shown in Table 9 below and FIG. 13A-13B and FIG. 14A-14B.

TABLE 9

| | | | | Characterization of exemplary capsid variants | | |
| Measure | Tissue | AAV9 | TTD-001 | TTD-002 | TTD-003 | TTD-004 | TTD-005 |
|---|---|---|---|---|---|---|---|
| mRNA | Frontal Cortex | 1.0 | 8378 | 2.4 | 19.3 | 21.8 | 6.8 |
| mRNA | Sensory Cortex | 1.0 | 2288 | 2.8 | 4.6 | 7.4 | 2.8 |
| mRNA | Motor Cortex | 1.0 | 14227 | 1.7 | 15.7 | 16.6 | 4.6 |
| mRNA | Putamen | 1.0 | 5805 | 2.3 | 19.3 | 18.7 | 1.9 |
| mRNA | Thalamus | 1.0 | 1097 | 5.3 | 38.8 | 29.0 | 4.2 |
| mRNA | Cerebellar Cortex | 1.0 | 1007 | 6.4 | 4.8 | 9.7 | 3.3 |
| mRNA | Dentate Nucleus | 1.0 | 706 | — | — | — | — |
| mRNA | Caudate | 1.0 | 3698 | — | — | — | — |
| mRNA | Hippocampus | 1.0 | 1305 | — | — | — | — |
| mRNA | SC-cervical | 1.0 | 973 | 1.8 | 2.2 | 7.2 | 0.5 |
| mRNA | SC-Thoracic | 1.0 | 61 | 0.1 | 0.7 | 0.4 | 0.1 |
| mRNA | SC-Lumbar | 1.0 | 267 | 1.9 | 0.5 | 1.6 | 0.9 |
| mRNA | DRG-cervical | 1.0 | 12 | 0.0 | 3.3 | 0.4 | 0.0 |
| mRNA | DRG-Thoracic | 1.0 | 9 | 0.0 | 15.7 | 0.2 | — |
| mRNA | DRG-Lumbar | 1.0 | 16 | 0.0 | 2.1 | 0.4 | 0.1 |
| mRNA | Lung | 1.0 | 0.11 | — | — | 2.9 | — |
| mRNA | Pancreas | — | — | — | — | — | — |
| mRNA | Colon | 1.0 | 0.28 | — | — | 10.2 | — |
| mRNA | Kidney | 1.0 | 0.15 | — | — | 0.9 | — |
| mRNA | Liver | 1.0 | 0.38 | — | — | 3.8 | — |
| mRNA | Adrenal | — | — | — | — | — | — |
| mRNA | Spleen | 1.0 | 0.07 | — | — | 1.0 | — |
| mRNA | Heart | 1.0 | 0.10 | — | — | 4.2 | — |
| mRNA | Quadriceps | 1.0 | — | — | — | 38.8 | — |
| mRNA | Diaphragm | 1.0 | — | — | — | 7.7 | — |
| DNA | Frontal Cortex | 1.0 | 27.29 | 1.3 | 0.9 | 4.9 | 1.6 |
| DNA | Sensory Cortex | 1.0 | 28.82 | 0.8 | 0.4 | 2.9 | 1.4 |
| DNA | Motor Cortex | 1.0 | 49.38 | 1.0 | 1.1 | 3.6 | 1.3 |
| DNA | Putamen | 1.0 | 52.96 | 2.1 | 2.6 | 4.7 | 1.2 |
| DNA | Thalamus | 1.0 | 39.63 | 1.3 | 1.7 | 4.1 | 1.7 |
| DNA | Cerebellar Cortex | 1.0 | 13.09 | 0.7 | 0.7 | 2.5 | 0.9 |
| DNA | Dentate Nucleus | 1.0 | 7.44 | 8.4 | 1.7 | 4.2 | 2.2 |
| DNA | Caudate | 1.0 | 49.73 | — | 0.7 | 3.1 | — |
| DNA | Hippocampus | 1.0 | 18.45 | 2.2 | 3.9 | 14.0 | 4.5 |
| DNA | SC-cervical | 1.0 | 30.42 | 1.6 | 1.6 | 2.0 | 1.6 |
| DNA | SC-Thoracic | 1.0 | 34.69 | 1.0 | 1.9 | 2.4 | 1.3 |
| DNA | SC-Lumbar | 1.0 | 27.46 | 0.5 | 0.9 | 2.4 | 1.4 |
| DNA | DRG-cervical | 1.0 | 1.87 | 1.1 | 1.8 | 0.5 | 0.9 |
| DNA | DRG-Thoracic | 1.0 | 1.04 | 0.4 | 0.8 | 0.3 | 0.2 |
| DNA | DRG-Lumbar | 1.0 | 1.76 | 0.7 | 0.7 | 0.2 | 0.6 |
| DNA | Lung | 1.0 | 3.43 | 0.9 | 0.6 | 1.1 | 0.8 |
| DNA | Pancreas | 1.0 | 80.01 | 1.2 | 0.9 | 0.3 | 0.0 |

TABLE 9-continued

| | | | | Characterization of exemplary capsid variants | | | |
| Measure | Tissue | AAV9 | TTD-001 | TTD-002 | TTD-003 | TTD-004 | TTD-005 |
| --- | --- | --- | --- | --- | --- | --- | --- |
| DNA | Colon | 1.0 | 63.21 | 21.9 | 6.5 | 2.2 | 0.3 |
| DNA | Kidney | 1.0 | 29.70 | 5.4 | 0.6 | 0.4 | 8.9 |
| DNA | Liver | 1.0 | 1.05 | 0.5 | 0.9 | 2.2 | 1.0 |
| DNA | Adrenal | 1.0 | 0.42 | 0.9 | 1.1 | 0.8 | 0.5 |
| DNA | Spleen | 1.0 | 1.37 | 3.5 | 1.5 | 0.4 | 3.1 |
| DNA | Heart | 1.0 | 7.20 | 0.4 | 0.9 | 1.9 | 0.2 |
| DNA | Quadriceps | 1.0 | 1.77 | 0.7 | 1.9 | 7.7 | 0.9 |
| DNA | Diaphragm | — | — | — | — | — | — |

Capsid variant TTD-001 showed greater than 5,000 fold increase in payload-HA levels delivered to the brain as compared to AAV9 and measured by qRT-PCR and normalized to TBP. In all CNS tissues measured, TTD-001 showed dramatically enhanced delivery of payload-HA as compared to AAV9.

Graphical representations of the spinal cord and dorsal root ganglia measurements outlined in Tables 8 and 9 are shown in FIG. 15A-15B, FIG. 16A-16B, FIG. 17A-17B, and FIG. 18A-18B.

Immunohistochemistry of fixed brain tissues revealed dramatic transduction in both NHP tested by TTD-001 of the dentate nucleus, cerebellar cortex, cerebral cortex, brain stem, hippocampus, thalamus and putamen. AAV9 transduction of the dentate nucleus, cerebellar cortex, cerebral cortex, hippocampus, thalamus and putamen appeared negligible in comparison. TTD-001 therefore demonstrated broad and robust expression and distribution in the brain following intravenous administration in NHPs. In the dorsal root ganglia, both TTD-001 and AAV9 showed similar IHC patterns. Images of these stainings are shown in FIG. 19A-19E.

Figure 20A:
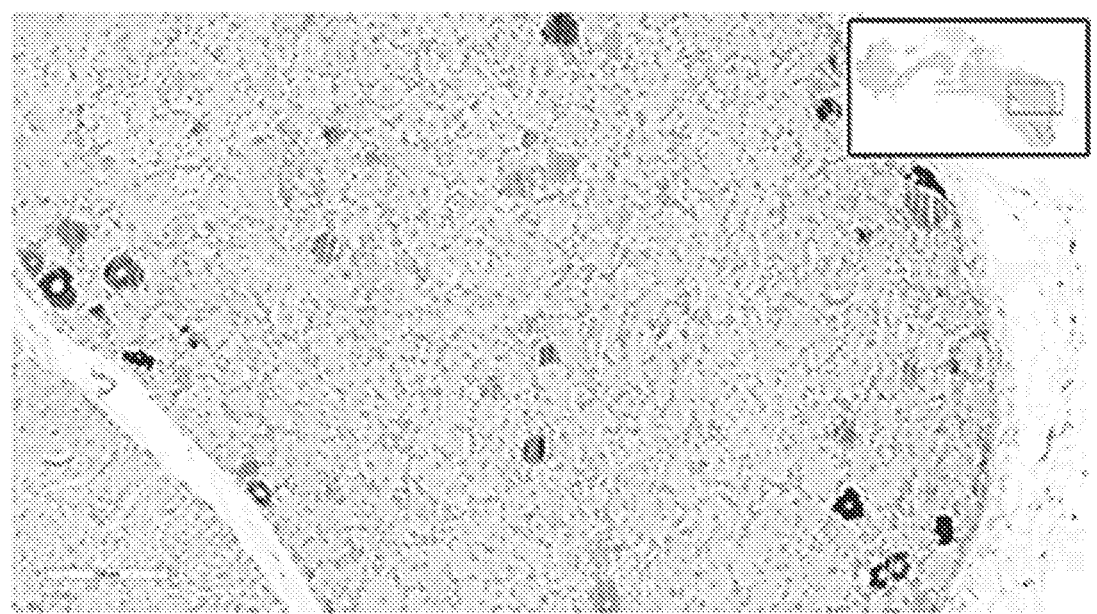
FIG. 20A and FIG. 20B show immunohistochemistry images of the DRG de-targeting characteristic of capsid variant TTD-004, compared to AAV9.
Figure 20A:
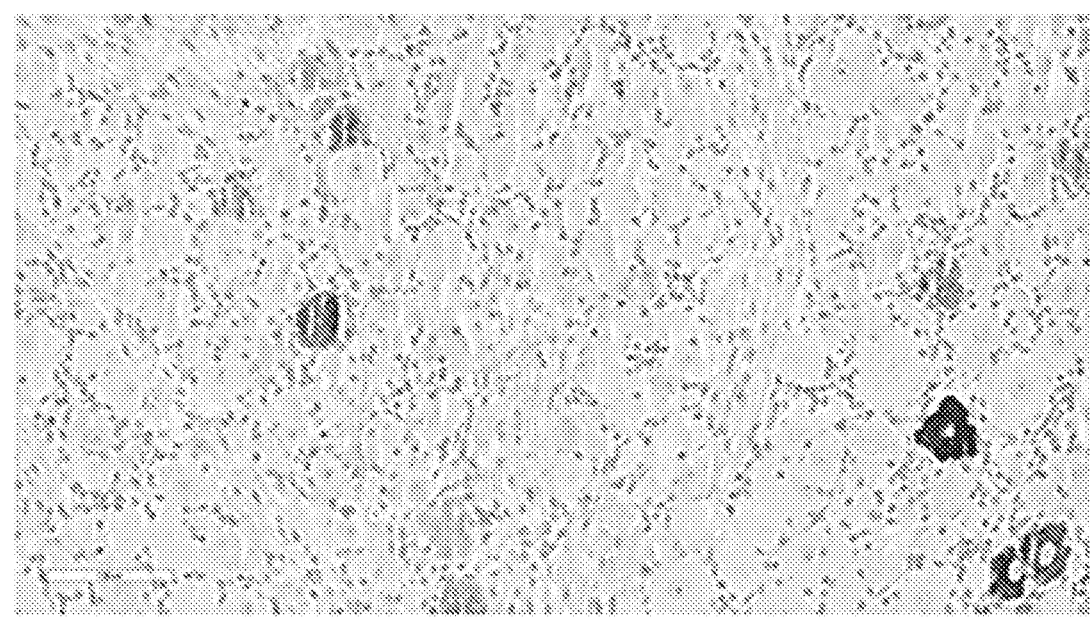
Figure 20B:
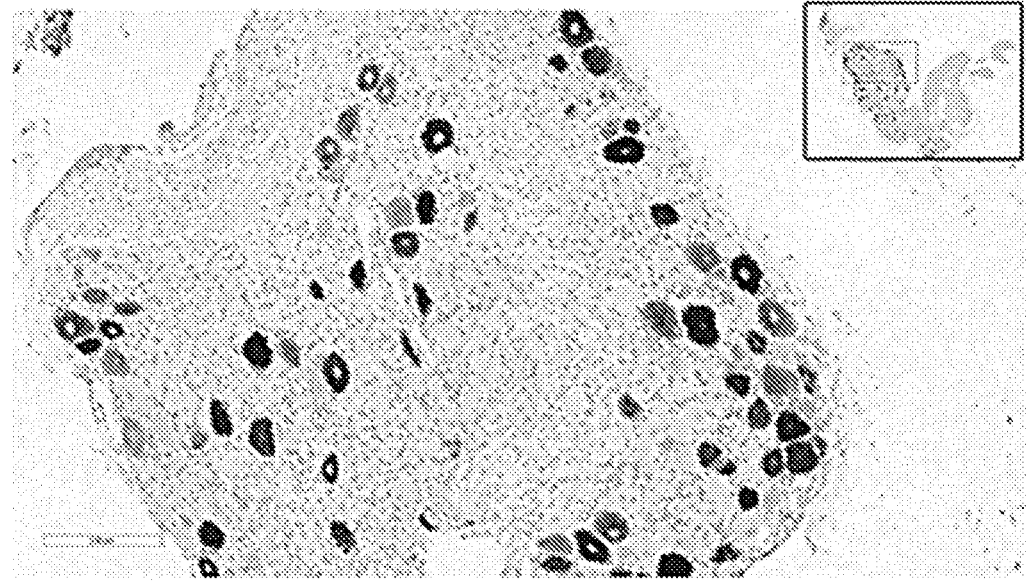
Figure 20B:
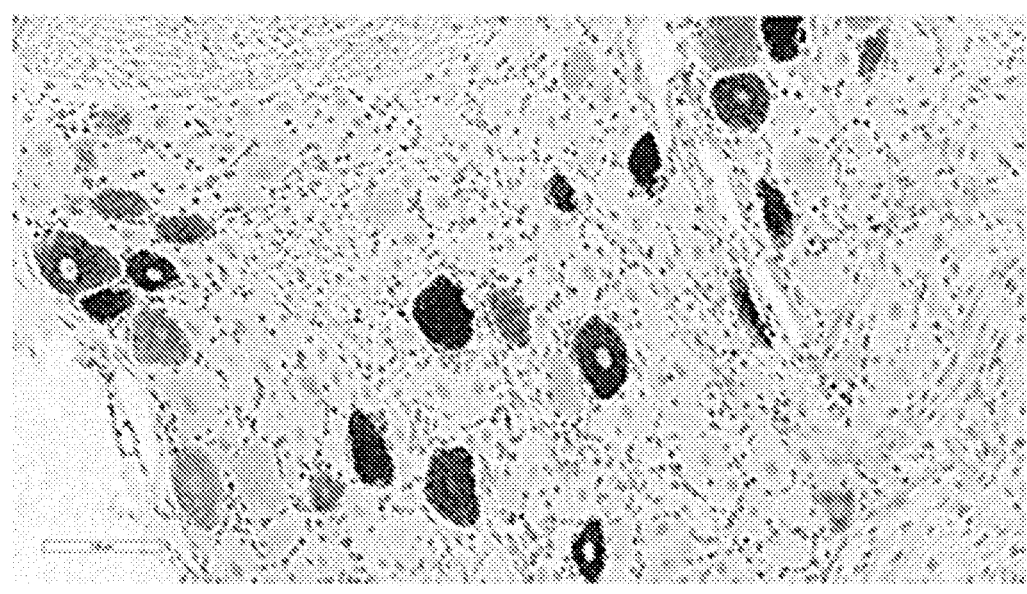

Immunohistochemical support for the DRG de-targeting nature of capsid variant TTD-004 (as noted above) is shown in FIG. 20A-20B.

Figure 21A:
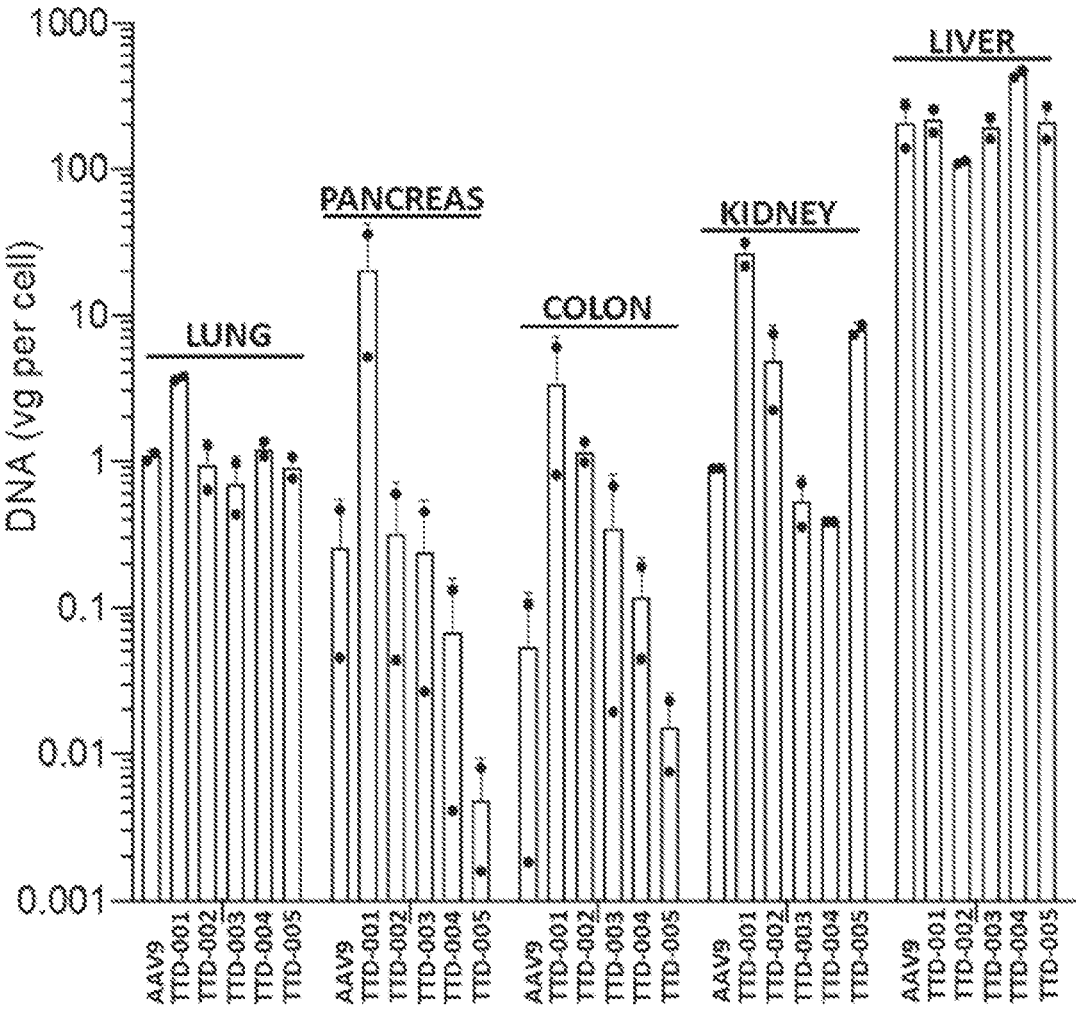
FIG. 21A and FIG. 21B show viral genome biodistribution in peripheral tissues quantified as vector genomes per cell.
Figure 21B:
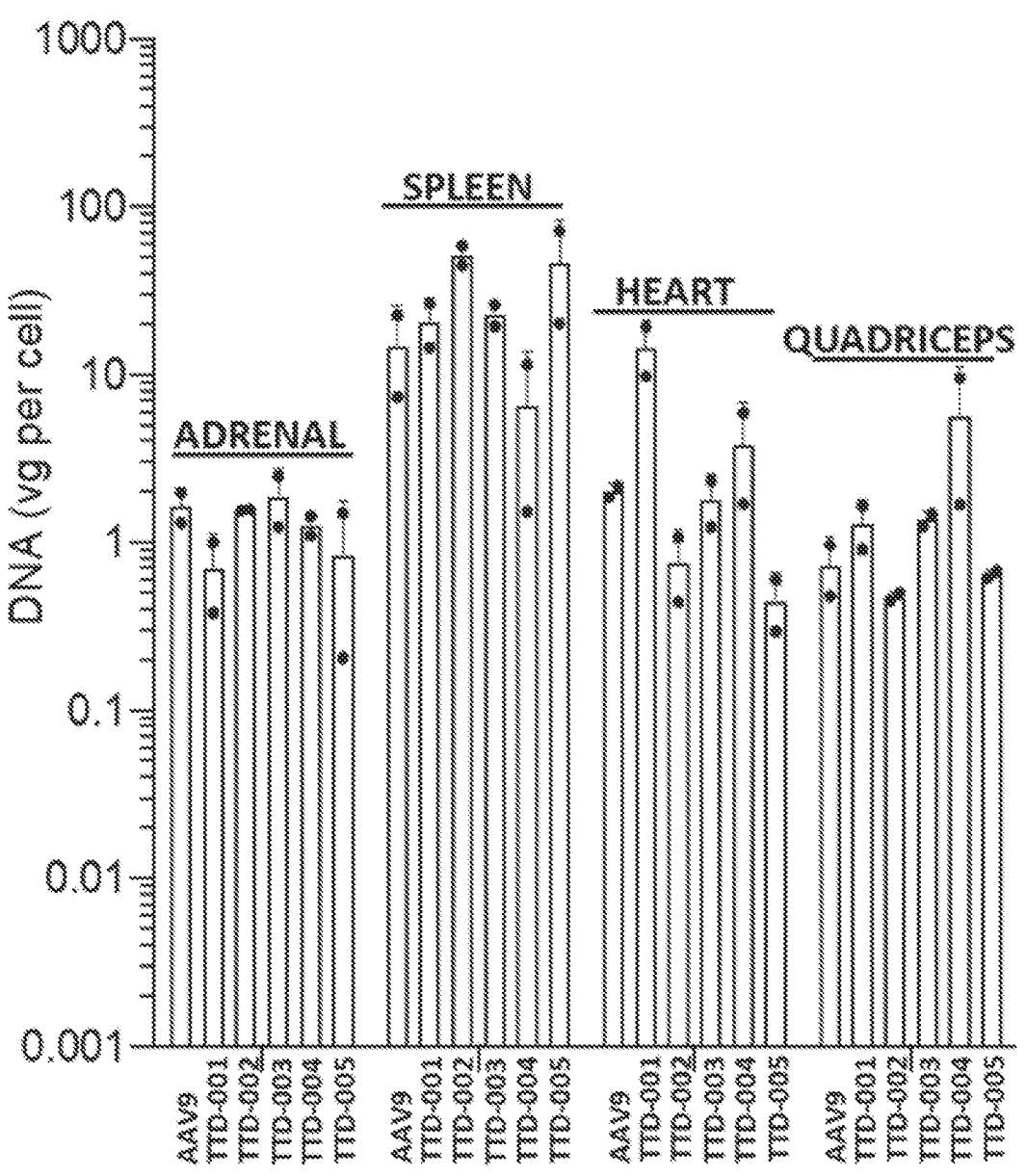

Graphical representations of the biodistribution of viral genomes delivered by variant capsids or AAV9 to peripheral tissues is shown in FIG. 21A-21B.

Example 6. Individual Capsid Characterization in the Heart

This Example characterized the transduction level and the spatial distribution the TTD-001 (SEQ ID NO: 3623 and 3636, comprising targeting peptide SEQ ID NO: 1725 or 3648) and TTD-004 (SEQ ID NO: 3627 and 3639, comprising targeting peptide SEQ ID NO: 1760 or 3651) capsid variants in the heart muscle.

AAV particles were generated with each of a TTD-001 and TTD-004 capsid variant or a wild-type AAV9 capsid polypeptide control, encapsulating a transgene encoding a payload fused to an HA tag (payload-HA) and driven by a full-length CMV/chicken beta actin promoter. The AAV particles comprising the TTD-001 or TTD-004 capsid variant or the wild-type AAV9 capsid control, were administered intravenously to 2 female NHPs at a dose of 2e13 VG/kg. At day 14 post-administration of the AAV particles, the heart tissue was collected, fixed, and paraffin embedded for immunohistochemical staining. An anti-HA antibody (Cell Signal Technology) was used for staining the heart tissue for visualization of the transduction and distribution of the AAV capsid variants investigated. Both left and right heart ventricle samples were collected and analyzed.

Figure 22A:
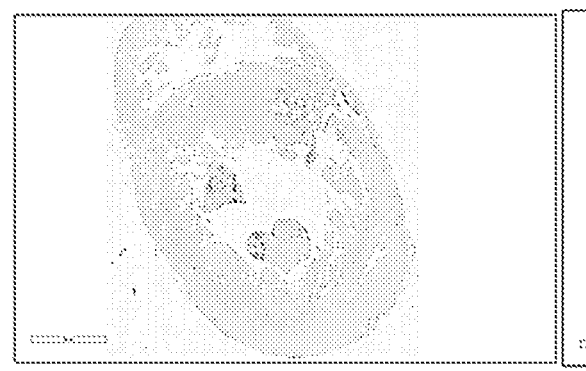
FIG. 22A, FIG. 22B, and FIG. 22C show immunohistochemistry images of the heart of a female NHP at day 14 post-intravenous administration of AAV particles comprising a TTD-001 capsid variant, a TTD-004 capsid variant, or a wild-type AAV9 control capsid polypeptide.
Figure 22A:
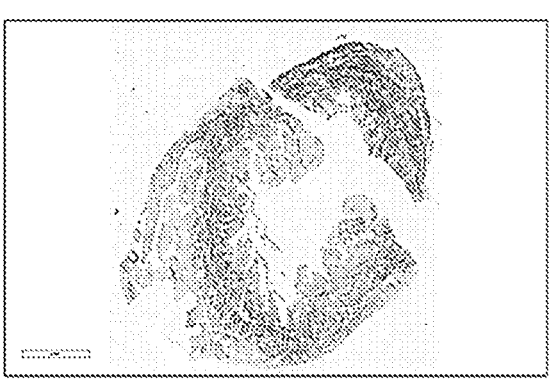
Figure 22A:
Figure 22B:
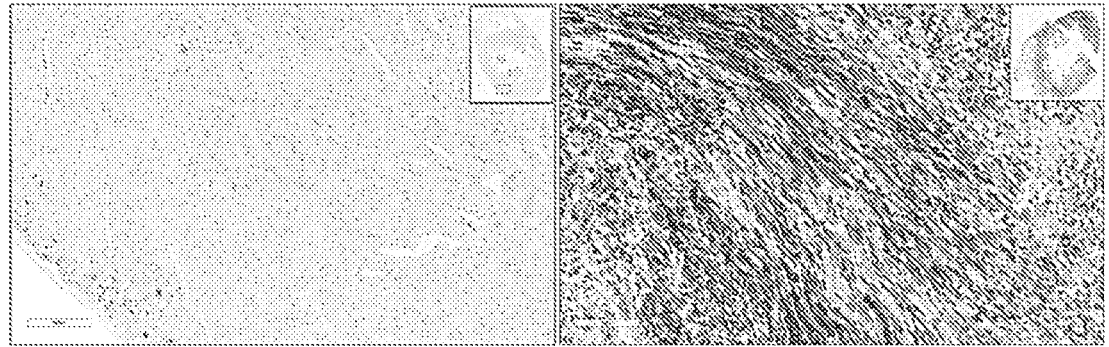
Figure 22C:
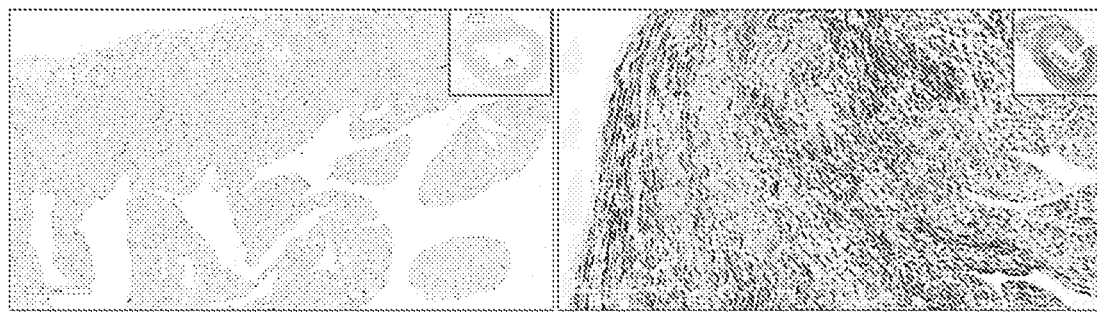
Figure 22C:
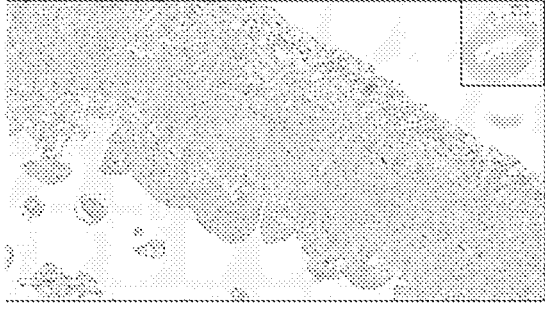

As shown in FIG. 22A-22C, immunohistochemistry of the fixed heart tissue and cardiomyocytes, demonstrated transduction by both TTD-001 and TTD-004, in the left ventricle (FIG. 22B) and right ventricle (FIG. 22C). However, TTD-004 led to the greatest transduction in the left and right ventricle regions of the heart (FIG. 22B-22C), as compared to TTD-001 and the wild-type AAV9 control, as evidenced by increased IHC staining. TTD-001 and the wild-type AAV9 control demonstrated similar levels of transduction in both regions of the heart, as evidenced by similar IHC staining patterns. These data demonstrate that both the TTD-001 and TTD-004 capsid variants can be utilized to transduce and/or deliver a payload, e.g., a payload described herein, to a heart muscle.

SEQUENCE LISTING

The patent contains a lengthy sequence listing. A copy of the sequence listing is available in electronic form from the USPTO web site (https://seqdata.uspto.gov/docdetail?docId=US12630842B2). An electronic copy of the sequence listing will also be available from the USPTO upon request and payment of the fee set forth in 37 CFR 1.19(b)(3).

We claim:

*kel2q*1. A method of delivering a payload to a cell or tissue, comprising administering an adeno-associated virus (AAV) particle comprising an AAV capsid variant and a payload, wherein the AAV capsid variant comprises an amino acid sequence at least 95% identical to amino acids 203-743 of SEQ ID NO: 3636, wherein the amino acid sequence comprises:

(a) the amino acid sequence of PLNGAVHLY (SEQ ID NO: 3648); or (b) an amino acid sequence comprising at least 5 consecutive amino acids from the amino acid sequence of PLNGAVHLY (SEQ ID NO: 3648).

2. The method of claim 1, wherein the cell or tissue is a cell or tissue of a brain region or a spinal cord region.

3. The method of claim 1, wherein the AAV capsid variant comprises an amino acid sequence comprising at least 6, 7, or 8 consecutive amino acids from the amino acid sequence of PLNGAVHLY (SEQ ID NO: 3648).

4. The method of claim 1, wherein the AAV capsid variant comprises the amino acid sequence of PLNGAVHLY (SEQ ID NO: 3648).

5. The method of claim 4, wherein the amino acid sequence of PLNGAVHLY (SEQ ID NO: 3648) is present in hypervariable loop VIII of the AAV capsid variant.

6. The method of claim 4, wherein the amino acid sequence of PLNGAVHLY (SEQ ID NO: 3648) is present immediately subsequent to amino acid 586, numbering according to SEQ ID NO: 3636.

7. The method of claim 1, wherein the AAV capsid variant comprises an amino acid sequence at least 98% identical to amino acids 203-743 of SEQ ID NO: 3636.

8. The method of claim 1, wherein the AAV capsid variant comprises the amino acid sequence of amino acids 203-743 of SEQ ID NO: 3636.

9. The method of claim 1, wherein the AAV capsid variant comprises an amino acid sequence at least 95% identical to amino acids 138-743 of SEQ ID NO: 3636.

10. The method of claim 1, wherein the AAV capsid variant comprises an amino acid sequence at least 98% identical to amino acids 138-743 of SEQ ID NO: 3636.

11. The method of claim 1, wherein the AAV capsid variant comprises the amino acid sequence of amino acids 138-743 of SEQ ID NO: 3636.

12. The method of claim 1, wherein the AAV capsid variant comprises an amino acid sequence at least 95% identical to the amino acid sequence of SEQ ID NO: 3636.

13. The method of claim 1, wherein the AAV capsid variant comprises an amino acid sequence at least 98% identical to the amino acid sequence of SEQ ID NO: 3636.

14. The method of claim 1, wherein the AAV capsid variant comprises the amino acid sequence of SEQ ID NO: 3636.

15. The method of claim 1, wherein the nucleotide sequence encoding the AAV capsid variant comprises the nucleotide sequence of SEQ ID NO: 3623, or a nucleotide sequence at least 90% identical thereto.

16. The method of claim 1, wherein the payload comprises a protein, an antibody, an enzyme, or an inhibitory RNA.

17. The method of claim 1, wherein the AAV particle comprises a nucleotide sequence encoding the payload.

18. The method of claim 17, wherein the AAV particle further comprises:

(i) a promoter operably linked to the nucleotide sequence encoding the payload;
(ii) a 5' inverted terminal repeat (ITR) and a 3' ITR;
(iii) an enhancer;
(iv) an intron;
(v) an exon;
(vi) a nucleotide sequence encoding at least one microRNA (miR) binding site; and/or
(vii) a polyadenylation (polyA) sequence.

19. The method of claim 1, wherein the AAV particle is comprised in a pharmaceutical composition comprising the AAV particle and a pharmaceutically acceptable excipient.

20. The method of claim 1, wherein the cell or tissue is a cell or tissue of the frontal cortex, sensory cortex, motor cortex, caudate, dentate nucleus, cerebellar cortex, cerebral cortex, brain stem, hippocampus, thalamus, putamen, cervical spinal cord region, thoracic spinal cord region, lumbar spinal cord region, or a combination thereof.

21. The method of claim 1, wherein the cell is a neuron or an astrocyte.

22. The method of claim 1, wherein the cell is in a subject.

23. The method of claim 22, wherein the subject has, has been diagnosed with having, or is at risk of having a neurological disorder, a neurodegenerative disorder, or a neuro-oncological disorder.

24. The method of claim 22, wherein the AAV particle is administered intravenously to the subject.

25. The method of claim 22, wherein the AAV particle is administered via intra-cisterna magna injection (ICM), intracerebrally, intrathecally, intracerebroventricularly, via intraparenchymal administration, or intramuscularly to the subject.

* * * * *